US012115217B2

(12) United States Patent
McGee et al.

(10) Patent No.: US 12,115,217 B2
(45) Date of Patent: Oct. 15, 2024

(54) SELF-REPLICATING RNA AND USES THEREOF

(71) Applicant: Trustees of Boston University, Boston, MA (US)

(72) Inventors: Joshua Edward McGee, Watertown, MA (US); Jack Rainier Kirsch, Cambridge, MA (US); Eric Bressler, Boston, MA (US); Mark W. Grinstaff, Brookline, MA (US); Wilson Wong, Brookline, MA (US); Lidya Yidnekachew Sertse, Boston, MA (US); Kexin Li, Boston, MA (US)

(73) Assignee: Trustees of Boston University

( * ) Notice: Subject to any disclaimer, the term of this patent is extended or adjusted under 35 U.S.C. 154(b) by 0 days.

(21) Appl. No.: 18/512,730

(22) Filed: Nov. 17, 2023

(65) Prior Publication Data

US 2024/0197860 A1 Jun. 20, 2024

Related U.S. Application Data

(60) Provisional application No. 63/538,540, filed on Sep. 15, 2023, provisional application No. 63/460,506, filed on Apr. 19, 2023, provisional application No. 63/426,597, filed on Nov. 18, 2022.

(51) Int. Cl.

| | |
|---|---|
| ***A61K 39/00*** | (2006.01) |
| ***A61K 39/02*** | (2006.01) |
| ***A61K 39/12*** | (2006.01) |
| ***A61K 39/155*** | (2006.01) |
| ***A61K 39/215*** | (2006.01) |
| ***A61P 31/04*** | (2006.01) |
| ***A61P 37/04*** | (2006.01) |
| ***C07K 14/005*** | (2006.01) |
| ***C07K 14/575*** | (2006.01) |
| ***C07K 16/28*** | (2006.01) |
| ***C07K 16/32*** | (2006.01) |
| ***C12N 15/86*** | (2006.01) |

(52) U.S. Cl.

CPC ........ *A61K 39/215* (2013.01); *A61K 39/4631* (2023.05); *A61P 37/04* (2018.01); *C07K 14/005* (2013.01); *C07K 14/575* (2013.01); *C07K 16/2803* (2013.01); *C07K 16/32* (2013.01); *C12N 15/86* (2013.01); *A61K 2039/53* (2013.01); *A61K 2239/23* (2023.05); *C12N 2770/20022* (2013.01); *C12N 2770/36143* (2013.01); *C12N 2830/002* (2013.01); *C12N 2830/50* (2013.01); *C12N 2840/203* (2013.01)

(58) Field of Classification Search

CPC ............ A61K 2039/53; A61K 2039/54; A61K 2039/545; A61K 2039/552; C07K 16/28

See application file for complete search history.

(56) References Cited

U.S. PATENT DOCUMENTS

| | | | |
|---|---|---|---|
| 10,487,332 | B2 | 11/2019 | Geall |
| 10,532,067 | B2 | 1/2020 | Geall |
| 11,058,762 | B2 | 7/2021 | Geall |
| 11,059,864 | B2 | 7/2021 | Ngo |
| 11,530,252 | B2 | 12/2022 | Wong |
| 2011/0300205 | A1 | 12/2011 | Geall |
| 2014/0271829 | A1 | 9/2014 | Lilja |
| 2020/0283497 | A1 | 9/2020 | Oehm |
| 2020/0299724 | A1 | 9/2020 | Beissert |
| 2021/0347828 | A1 | 11/2021 | Dehart |
| 2021/0363543 | A1 | 11/2021 | Garban |
| 2022/0192997 | A1 | 6/2022 | Geall |
| 2022/0313815 | A1 | 10/2022 | Horton |
| 2023/0203538 | A1 | 6/2023 | Parhiz |

FOREIGN PATENT DOCUMENTS

| | | | |
|---|---|---|---|
| WO | 2022/069577 | A1 | 4/2022 |
| WO | 2022137128 | A2 | 6/2022 |
| WO | 2022/150712 | A1 | 7/2022 |
| WO | 2022/157153 | A2 | 7/2022 |

OTHER PUBLICATIONS

Pepini et al., "Induction of an IFN-Mediated antiviral response by a self-amplifying RNA vaccine: Implications for vaccine design", The Journal of Immunology, 2017:4012-4024.*

Aliahmad et al., Next generation self-replicating RNA vectors for vaccines and immunotherapies. Cancer Gene Therapy 30(6): 785-793 (Feb. 22, 2022).

Beissert et al., A Trans-amplifying RNA Vaccine Strategy for Induction of Potent Protective Immunity. Mol Ther 28(1): 119-128 (2020).

Blakney et al., Effects of cationic adjuvant formulation particle type, fluidity and immunomodulators on delivery and immunogenicity of saRNA. J Control Release 304: 65-74 (2019).

Blakney et al., Innate Inhibiting Proteins Enhance Expression and Immunogenicity of Self-Amplifying RNA. Mol Ther. 29(3): 1174-1185 (2021).

Bloom et al., Self-amplifying RNA vaccines for infectious diseases. Gene Ther. 28(3-4): 117-129 (2021).

Davis, Stabilization of RNA stacking by pseudouridine. Nucleic Acids Res. 23(24): 5020-5026 (1995).

Deering et al., Nucleic acid vaccines: prospects for non-viral delivery of mRNA vaccines. Expert Opin Drug Deliv. 11 (6): 885-899 (2014).

Dinnon et al., A mouse-adapted model of SARS-CoV-2 to test COVID-19 countermeasures. Nature 586(7830): 560-566 (2020).

(Continued)

*Primary Examiner* — Barry A Chestnut

(74) *Attorney, Agent, or Firm* — NIXON PEABODY LLP; Ronald I. Eisenstein; Alissa R. Young

(57) ABSTRACT

The technology described herein is directed to compositions and methods for modifying and controlling the activity of cells by expression of proteins from self-amplifying RNA (saRNA). Also described herein are compositions and methods for modifying and controlling the activity of cells by expression of proteins from self-amplifying RNA that is substituted with chemically modified nucleotides.

30 Claims, 122 Drawing Sheets

Specification includes a Sequence Listing.

(56) References Cited

OTHER PUBLICATIONS

Erasmus et al., Intramuscular Delivery of Replicon RNA Encoding ZIKV-117 Human Monoclonal Antibody Protects against Zika Virus Infection. Mol Ther Methods Clin Dev 18: 402-414 (2020).
Geall et al. Vaccines on demand, part II: future reality. Expert Opinion on Drug Discovery 18(2): 119-127 (Nov. 23, Nov. 23, 2022).
Harcourt et al., Chemical and structural effects of base modifications in messenger RNA. Nature, 541(7637): 339-346 (2017).
Helm, Post-transcriptional nucleotide modification and alternative folding of RNA. Nucleic Acids Res. 34(2): 721-733 (2006).
Hyde et al., The 5' and 3' ends of alphavirus RNAs—Non-coding is not non-functional, Virus Research 206: 99-107 (2015).
Kairuz et al., Advancing mRNA technologies for therapies and vaccines: An African context. Front Immunol. 13: 1018961 (Oct. 24, 2022).
Kairuz et al., Production, Characterization, and Assessment of Permanently Cationic and Ionizable Lipid Nanoparticles for Use in the Delivery of Self-Amplifying RNA Vaccines. Pharmaceutics 15(4): 1173 (Apr. 7, 2023).
Karikó et al. Incorporation of pseudouridine into mRNA yields superior nonimmunogenic vector with increased translational capacity and biological stability. Molecular Therapy 16(11): 1833-1840 (2008).
Karikó et al. Suppression of RNA recognition by Toll-like receptors: the impact of nucleoside modification and the evolutionary origin of RNA. Immunity 23(2): 165-175 (2005).
Kenney et al., Humanized mice reveal a macrophage-enriched gene signature defining human lung tissue protection during SARS-CoV-2 infection. Cell Rep. 39(3): 110714 (Apr. 4, 2022).
Kierzek et al., Secondary structure prediction for RNA sequences including N(6)-methyladenosine. Nat Commun. 13 (1): 1271. (Mar. 11, 2022).
Kimura et al., A localizing nanocarrier formulation enables multi-target immune responses to multivalent replicating RNA with limited systemic inflammation. Mol Ther. 31(8): 2360-2375 (Aug. 8, 2023).
Kormann et al. Expression of therapeutic proteins after delivery of chemically modified mRNA in mice, Nature Biotechnology 29(2): 154-157 (2011).
Li et al. High-performance multiplex drug-gated CAR circuits. Cancer Cell 40, 1-12 (Sep. 8, 2022) .
Li et al. KIR-based inhibitory CARs overcome CAR-NK cell trogocytosis-mediated fratricide and tumor escape. Nat Med. 28(10): 2133-2144 (Sep. 29, 2022).
Li et al., In vitro evolution of enhanced RNA replicons for immunotherapy. Sci Rep. 9(1): 6932 (2019).
Low et al., A phase I/II randomized, double-blinded, placebo-controlled trial of a self-amplifying Covid-19 mRNA vaccine. NPJ Vaccines 7(1): 161 (Dec. 13, 2022).
Lundstrom, Self-Replicating RNA Viruses for Vaccine Development against Infectious Diseases and Cancer, Vaccines 9(10): 1187 (2021).
Minnaert et al., Strategies for controlling the innate immune activity of conventional and self-amplifying mRNA therapeutics: Getting the message across. Adv Drug Deliv Rev. 176: 113900 (2021).
Ong et al., Immune gene expression analysis indicates the potential of a self- amplifying Covid-19 mRNA vaccine. NPJ Vaccines 7(1): 154 (Nov. 28, 2022).
Papukashvili et al., Self-Amplifying RNA Approach for Protein Replacement Therapy. Int J Mol Sci. 23(21): 12884 (Oct. 25, 2022).
Perkovic et al., A trans-amplifying RNA simplified to essential elements is highly replicative and robustly immunogenic in mice. Molecular Therapy 31(6): 1636-1646 (Jun. 2023).
Pollock et al., Safety and immunogenicity of a self-amplifying RNA vaccine against COVID-19: COVAC1, a phase I, dose-ranging trial. EClinicalMedicine 44: 101262 (Jan. 14, 2022).
Rurik et al., "Car T cells produced in vivo to treat cardiac injury." Science 375(6576): 91-96 (Jan. 7, 2022).
Tong et al., The Emerging Role of RNA Modifications in the Regulation of Antiviral Innate Immunity. Front Microbiol, 13: 845625 (Feb. 3, 2022).
Voigt et al., A self-amplifying RNA vaccine against COVID-19 with long-term room-temperature stability. NPJ Vaccines 7(1): 136 (Nov. 2, 2022).
Zhong et al., Corticosteroids and cellulose purification improve, respectively, the in vivo translation and vaccination efficacy of sa-mRNAs. Mol Ther. 29(4): 1370-1381 (2021).
Zhong et al., Immunogenicity and Protection Efficacy of a Naked Self-Replicating mRNA-Based Zika Virus Vaccine. Vaccines 7(3): 96 (2019).
Zhong et al. mRNA therapeutics deliver a hopeful message, Nano Today: 16-39 (2018).

* cited by examiner

Fig. 88
26S Subgenomic Promoter
mRNA 5'UTR
Kozak
Shine-Dalgarno sequence
51 nt CSE
T7 promoter
pBR322ori-F
Amp-R
Mini-PolyA,AmpR promoter
VEEV 3'UTR

SELF-REPLICATING RNA AND USES THEREOF

CROSS-REFERENCE TO RELATED APPLICATIONS

This application claims benefit under 35 U.S.C. § 119(e) of U.S. Provisional Application No. 63/538,540 filed Sep. 15, 2023, U.S. Provisional Application No. 63/460,506 filed Apr. 19, 2023, and U.S. Provisional Application No. 63/426,597 filed Nov. 18, 2022, the contents of each of which are incorporated herein by reference in their entireties.

GOVERNMENT SUPPORT

This invention was made with government support under Contract No. CA265713-02 and Grant No. R01 AR079489 awarded by the National Institutes of Health. The government has certain rights in the invention.

SEQUENCE LISTING

The instant application contains a Sequence Listing which has been submitted in XML format via Patent Center and is hereby incorporated by reference in its entirety. Said XML copy, created on Nov. 27, 2023, is named 701586-000105USPT_SL.xml and is 74,509 bytes in size.

TECHNICAL FIELD

The technology described herein relates to methods and compositions for the modification and control of cell activity via self-replicating RNA.

The technology described herein relates to methods of use and compositions of self-amplifying RNA that is highly or fully substituted with chemically modified nucleotides.

BACKGROUND

Adoptive cell therapy represents a promising strategy for the treatment of a variety of cancers. Today, five approved adoptive cell therapies exist in for the treatment of leukemia, lymphoma, and multiple myeloma. Additionally, applications of adoptive cell therapy are being explored beyond oncology. Although the clinical outcomes of the approved therapies are promising, many challenges associated with ex vivo cell engineering remain. The isolation of cells, genetic engineering, and expansion protocols are costly and time consuming. Additionally, the genetic modification of cells poses the risk of off-target genomic editing. An attractive alternative is to reprogram cells either ex vivo or in vivo with messenger RNA (mRNA). In the context of oncology, the use of mRNA programmed immune cells has shown efficacy in a limited number of cancer models. However, some challenges with the level of expression and duration of expression were reported. As a result, repeat dosing is often required to achieve a functional benefit. By contrast, self-replicating RNA can be used to express therapeutic programs at a higher level and over a longer duration. Moreover, self-replicating RNA systems can be utilized for the ex vivo or in vivo modification of cells.

To ensure safety and improve the activity of engineered cell therapies, control is desired. Control is often accomplished by including components that can be externally controlled to turn activity on or off A common example of control in cell therapy is a kill switch that can be included in engineered cells. If the engineered cells pose risks, they can be killed off by the infusion of a small molecule that activates the kill switch present in the engineered cells. There are additional strategies to control the activity of engineered cells by utilizing engineered proteins with externally controlled behavior. In the context of oncology, a series of drug-regulated chimeric antigen receptors exist. The resulting activity of CAR-T cells manufactured with drug-controlled receptors is dependent on the dose of the control molecule that is administered. An additional strategy to control the activity of cells is to utilize logic computation. By including components that interact with one another, circuits that sense a variety of signals and logically respond can be created. This results in the ability to create therapies with enhanced specificity by requiring combinations of input signals to be satisfied before the therapeutic activity is conducted. The complexity of such logic computation circuits is often limited by the size capacity of genetic engineering methods. The development of methods to modify cells with controllable activity in a rapid, scar-free manner with self-replicating RNA is highly desired.

Furthermore, the original discovery of how modified nucleotides enable mRNA to evade the immune system by Karikó and Weissman paved the way for the field of mRNA therapeutics (Karikó, K. Immunity, 2005. PMID: 16111635) (Karikó, K. Molecular Therapy, 2008. PMID: 18797453). mRNA containing chemically modified nucleotides are significantly less immunogenic (Karikó, K. Molecular Therapy, 2008. PMID: 18797453)(Kormann, M. Nature Biotechnology, 2011. PMID: 21217696)(Karikó, K. Immunity, 2005. PMID: 16111635). Currently, the clinical-gold standard in mRNA therapeutics is the complete substitution of uridine for N1-methylpseudouridine (mlP) which has the greatest impact on the suppression of the type I interferon (IFN) response traditionally elicited by dsRNA and ssRNA (Karikó, K. Immunity, 2005. PMID: 16111635). On a molecular level, modified nucleotides alter the stability or accessibility of specific base pairs, change hydrogen bonding patterns, and shift RNA hydrophobicity. Along with altering RNA stability, some of these new interactions change RNA primary or secondary structure such that RNA-protein interactions are either stabilized or inhibited (Kierzek, E. Nature Communications, 2022. PMID: 35277476)(Harcourt, E. Nature, 2017. PMID: 28102265)(Davis, D. Nucleic Acids Research, 1995. PMID: 8559660). It is in part through these mechanisms that modified nucleotides imbue RNA with immune evasion properties. However, these same RNA-RNA and RNA-protein interactions are essential for self-amplifying RNA (saRNA) function.

saRNA is a type of RNA which has the ability to replicate and amplify itself, in situ. This is accomplished by encoding both an RNA dependent RNA polymerase (RdRp) as well as the protein of interest (Bloom, K. Gene Therapy, 2021. PMID: 33093657). Some of the advantages of saRNA include increased potency per g RNA compared to non-replicating mRNA (nrRNA) and extended duration of action (Minnaert, K. Advanced Drug Delivery Reviews, 2021. PMID: 34324884)(Geall, A. Expert Opinion on Drug Discovery, 2022. PMID: 36384351). The RdRp encoded by saRNA recognizes conserved secondary structures and sequences, referred to as the conserved sequence elements and sub genomic promoter (SGP), which allow for transcription of both negative and positive strand saRNA as well as the mRNA encoding the cargo of interest. The current understanding of the saRNA field is that the incorporation of modified nucleotides into saRNA results in inactivation of replicase activity and the abrogation of downstream efficacy (Geall, A. Expert Opinion on Drug Discovery, 2022. PMID:

36384351)(Voigt, E. NPJ vaccines, 2022. PMID: 36323666) (Novartis AG, 12/831,252)(Kairuz, D. Frontiers in Immunology, 2022. PMID: 36353641)(Minnaert, K. Advanced Drug Delivery Reviews, 2021. PMID: 34324884). These works teach that incorporation of modified nucleotides at >25% substitution results an saRNA that does not produce sufficient antigen to be therapeutically effective.

There have been 10+ clinical trials employing saRNA since 2015 and though preclinical evidence is promising, human data has demonstrated lower seroconversion, lower neutralizing antibodies levels, and decreased production of antibodies after booster compared to non-replicating mRNA (Geall, A. Expert Opinion on Drug Discovery, 2022. PMID: 36384351). One hypothesized reason for this, is the early and intense activation of the innate immune response by saRNA containing unmodified nucleotides, which hinders both saRNA replication and the launch of cargo from the saRNA SGP. In knockout mice deficient for type I IFN a and p receptor subunit 1, saRNA resulted in higher IgG specific antibody titers and seroconversion compared to WT mice (Pepini, T. The Journal of Immunology, 2017. PMID: 28416600)(Zhong, Z. Nano Today, 2018. DOI: 10.1016/J.NANTOD.2018.10.005). Recently, corticosteroid immune suppression was explored as a co-therapy to minimize innate immune response, but ended up suppressing seroconversion. This same study did demonstrate that removal of dsRNA contaminants, which activate TLR3 and stimulate type I IFN expression, increased vaccine immunogenicity (Zhong, Z. Molecular Therapy, 2021. PMID: 33484964). A Type I IFN suppression of saRNA is further supported by the fact that IM is the optimal delivery route for saRNA, as intradermal injection has been shown to elicit higher type I IFN response than IM (Zhong, Z. Vaccines, 2019. PMID: 31450775). In sum, previous research points towards the potential for substantially increased saRNA efficacy if the early interferon response could be overcome. Part of what makes saRNA so potent as a vaccine candidate is that it acts as its own adjuvant. However, to achieve a balance between adjuvancy and IFN-mediated suppression of saRNA launch, controlling the early IFN response is essential (Zhong, Z. Nano Today, 23. (2018) DOI: 10.1016/J.NANTOD.2018.10.005). Without a mechanism to evade early recognition during endosomal escape and preliminary expression, saRNA may continue to falter in the clinic.

Although considerable efforts have been made to develop self-amplifying RNAs as therapeutics, there still remains a need to increase the stability and efficacy of self-amplifying RNAs to achieve this objective.

SUMMARY

The technology described herein is directed to self-replicating RNA systems. In particular, described herein are methods and compositions for utilizing self-replicating RNA to modify cells and introduce elements that can be controlled externally or establish logic computation control. Self-replicating RNA is comprised of sequences derived from an RNA virus and additional cargo sequences. The external control is established by utilizing cargo protein domains that are responsive to external inputs (e.g., small molecules, light, proteins). Logic computation control is established by including components that sense external or internal inputs and interact with each other directly or indirectly to perform logic operations.

Described herein are general frameworks for modifying cells and equipping them with controllable behavior via self-replicating RNA: (1) expression of cargo protein(s) in cells; (2) external control of cell behavior by administration of external factors that increase or decrease activity of cargo protein(s); (3) internal control of cell behavior by logic computation circuits that sense inputs and perform logic computation.

In some embodiments, self-replicating RNA is created by utilizing sequences derived from the viral elements capable of copying and generating additional RNA. Exemplary viruses include alphaviruses, flaviviruses, measles viruses, and rhabdoviruses. In particular embodiments, self-replicating RNA is created by utilizing sequences derived from Venezuela Equine Encephalitis Virus (VEEV), Semliki Forest Virus (SFV), Sindbis Virus (SIN), Kunjin Virus (KUN), Measles virus (MV), Rabies virus (RABV), and Vesicular Stomatitis virus (VSV). In a specific embodiment, the replication can be the result of inclusion of conserved noncoding sequence elements on the 5' and 3' ends of the RNA strand in addition to the inclusion of coding sequences for the proteins nsp1, nsp2, nsp3, and nsp4. The expression of any genetically encodable protein is enabled by placing the coding sequence after a subgenomic promoter sequence or an internal ribosome entry site (IRES) sequence.

In one aspect, described herein is a self-amplifying RNA (saRNA) comprising from 5' to 3': (a) a 5' cap; (b) non-structural protein 1 (nsp1), non-structural protein 2 (nsp2), non-structural protein 3 (nsp3), and/or non-structural protein 4 (nsp4), each derived from at least one virus; (c) a subgenomic promoter (SGP) derived from at least one virus; (d) a 5' untranslated region (UTR) derived from at least one virus; (e) at least one cargo of interest; (f) a 3' untranslated region (UTR) derived from at least one virus; and (g) a poly-A tail.

In one embodiment of any aspect herein, the self-replicating RNA is generated by in vitro transcription. In other embodiments, the self-replicating RNA is delivered to cells as plasmid DNA that is transcribed into RNA and contains the necessary sequences for replication.

In one embodiment of any aspect herein, the RNA contains a 5' cap structure.

In one embodiment of any aspect herein, the RNA contains a 3' poly-A tail.

In one embodiment of any aspect herein, the RNA contains a 5' UTR, a 3' UTR, or a combination of both.

In one embodiment of any aspect herein, the inclusion of sequence elements from the VEEV virus results in enhanced expression of a functional protein over a longer duration than conventional mRNA.

In one embodiment of any aspect herein, a functional protein is expressed from self-replicating RNA that contains the protein coding sequence downstream of a subgenomic promoter.

In one embodiment of any aspect herein, a functional protein is expressed from self-replicating RNA that contains the protein coding sequence downstream of an internal ribosome entry site (IRES) sequence.

In one embodiment of any aspect herein, the functional protein is a chimeric antigen receptor.

In one embodiment of any aspect herein, the functional protein is a chimeric antigen receptor with a protease domain that is responsive to a protease inhibitor.

In one embodiment of any aspect herein, the functional protein is a chimeric antigen receptor with a domain that interacts with a small molecule. The stability of the receptor is modulated by known and unknown mechanisms in the presence of the small molecule.

Another aspect details a method, wherein the activity of the functional protein is dependent on the concentration of an administered small molecule.

Another aspect details a method, wherein the activity of the functional protein is dependent on the concentration of multiple administered small molecules.

In one embodiment of any aspect herein, the functional protein is a chimeric antigen receptor with a domain that interacts with a protein. The stability of the receptor is modulated by known and unknown mechanisms in the presence of the protein.

Another aspect details a method, wherein the activity of the functional protein is dependent on the concentration of an administered protein.

Another aspect details a method, wherein the activity of the functional protein is dependent on the concentration of multiple administered proteins.

In one embodiment of any aspect herein, the level of expression of the functional protein is equal to or greater than levels of expression resulting from other methods to establish constitutive expression of a protein.

In one embodiment of any aspect herein, multiple proteins are expressed from the same self-replicating RNA strand by inclusion of an IRES sequence between the coding sequences of each protein.

In one embodiment of any aspect herein, multiple proteins are expressed from the same self-replicating RNA strand by inclusion of a 2A sequence between the coding sequences of each protein.

In one embodiment of any aspect herein, the expression level of multiple proteins expressed from the same self-replicating RNA are equal to or greater than levels of expression resulting from other methods to establish constitutive expression of multiple proteins.

In one embodiment of any aspect herein, multiple chimeric antigen receptors with opposing functions are expressed from the same self-replicating RNA strand.

Another aspect details a method, wherein the activity of the resulting cell is dependent on external signals that are sensed by multiple proteins with differing functions. The resulting activity conducted by the cell is dependent on the presence or lack of the sensed external signals. In some embodiments, small molecules are administered as the external signal. Non-limiting examples of other external signals that can be used to control activity include light, ultrasound, proteins, ligands, antibodies, antibody fragments etc.

In one embodiment of any aspect herein, a functional protein with expression enhancing ability either by known or unknown mechanisms is used to enhance the level and duration of expression is co-expressed.

In one embodiment of any aspect herein, self-replicating RNA is delivered to cells via electroporation.

In one embodiment of any aspect herein, self-replicating RNA is delivered to cells via nucleofection.

In one embodiment of any aspect herein, RNA is delivered to cells via lipid nanoparticles.

In one embodiment of any aspect herein, RNA is delivered to cells via nanoparticles.

In one embodiment of any aspect herein, RNA is delivered to a specified cell type by delivery with a lipid nanoparticle containing an antibody on the nanoparticle surface.

In one embodiment of any aspect herein, the function of the chimeric antigen receptor is to activate immune cells.

In one embodiment of any aspect herein, the function of the chimeric antigen receptor is to inhibit immune cells.

In one embodiment of any aspect herein, a reporter protein is co-expressed along with cargo protein to measure the levels of expression resulting from the self-replicating RNA.

In one embodiment of any aspect herein, multiple cell types are modified with self-replicating RNA.

In one embodiment of any aspect herein, one or more cell types are modified with self-replicating RNA.

In one embodiment of any aspect herein, one or more cell types are modified with self-replicating RNA prior to administration to a patient.

In one embodiment of any aspect herein, one or more cell types are modified with self-replicating RNA where the cells are in the patient.

In one embodiment of any aspect herein, one or more cell types modified with self-replicating RNA are administrated to a patient via intraosseous (10), intraperitoneal (IP), subcutaneous (SC), intravenous (IV), intramuscular (IM), and intraarticular or via inhalation or topical.

Previous studies have suggested that the level of substitution of SaRNAs with modified nucleotides should be less than 25% otherwise the expression of transgenes encoded by SaRNAs expression decreases relative to comparable SaRNAs without such modifications (see, e.g., Voigt, E. NPJ vaccines, 7. (2022) (U.S. Ser. No. 12/831,252) (WO2011005799) (U.S. Ser. No. 10/532,067B2), (U.S. Ser. No. 11/291,682B2), (US20220054525A1), (U.S. Ser. No. 10/487,332B2), (US20200048636A1), (US20220056449A1), (EP3964584A1), (WO2012006376), (US20220192997A1), (U.S. Ser. No. 11/058,762B2), (US20210290755A1), (US20140242152), (US20220313815A1), (US20210347828A1), (WO2022137128A2), (US20140271829A1). For example, U.S. Ser. No. 12/831,252 teaches that incorporation of 0.01%-25% modified nucleotide is the optimal substitution ratio that maintains expression of a transgene cargo, either reporter construct or vaccine antigen. At higher substitution ratios, expression of the transgene cargo is decreased.

The invention is based, in part, upon the discovery that certain modified nucleotides can be incorporated into saRNA at levels above 25%, including greater than 50%, 60%, 70%, 80%, 90%, 95%, 96%, 97%, 98%, 99%, 99.1%-100% or even 100%, and that the resulting saRNA can still express cargo or cargos of interested encoded on the saRNA. Furthermore, under certain circumstances, the level of expression of transgenes encoded by the saRNA can even be higher than the level of expression of comparable saRNA without such modifications. These specific modifications allow for maintenance of self-amplifying function of the saRNA as well as maintaining expression of the cargo protein encoded by one or more cargos.

Described herein are general frameworks for expressing cargo from self-amplifying RNA that comprises modified nucleotides at greater than 25% substation and is able to maintain or increase expression capabilities compared to unmodified saRNA. This enables expressing vaccine antigen, protein replacement therapies, antibodies, enzymes, or modifying cells and equipping them with controllable behavior via modified self-replicating RNA: (1) expression of cargo protein(s) in cells; (2) external control of cell behavior by administration of external factors that increase or decrease activity of cargo protein(s); (3) internal control of cell behavior by logic computation circuits that sense inputs and perform logic computation.

Disclosed herein are self-amplifying RNAs containing greater than 25% substitution of a given nucleotide with modified nucleotides. These highly-substituted saRNA are not only capable of maintaining saRNA functionality, but confer suppression of innate immune activation. Additionally, these highly-substituted saRNA are more efficacious, increasing cargo expression and transfection efficiency. The saRNA described herein have the potential to unlock the next frontier in RNA therapeutics that has been hampered by the inherent immunogenicity of the constructs; this work provides a blueprint for the modification and potentiation of saRNA therapeutics as vaccines, long-lasting cell therapies, protein replacement therapies, and any other conceived embodiment of RNA therapeutics.

In some embodiments, self-replicating RNA is created by utilizing sequences derived from the viral elements capable of copying and generating additional RNA. Exemplary viruses include alphaviruses, flaviviruses, measles viruses, coronaviruses and rhabdoviruses. In particular embodiments, self-replicating RNA is created by utilizing sequences derived from Venezuela Equine Encephalitis Virus (VEEV), Semliki Forest Virus (SFV), Sindbis Virus (SIN), Kunjin Virus (KUN), Measles virus (MV), Rabies virus (RABV), and Vesicular Stomatitis virus (VSV). In a specific embodiment, the replication can be the result of inclusion of conserved noncoding sequence elements on the 5' and 3' ends of the RNA strand in addition to the inclusion of coding sequences for the proteins nsp1, nsp2, nsp3, and nsp4. The expression of any genetically encodable protein is enabled by placing the coding sequence after a subgenomic promoter sequence or an internal ribosome entry site (IRES) sequence. In addition, noncoding RNA can be transcribed by placement of a microRNA or siRNA sequence after the subgenomic promoter.

In one aspect, described herein is a self-amplifying RNA (saRNA) comprising at least 25% modified nucleotides, wherein the modified nucleotides comprise a pyrimidine nucleoside phosphate with a moiety on carbon 5 of the pyrimidine, wherein the moiety is selected from the group consisting of methyl, ethyl, propyl, trifluoromethyl, hydroxymethyl, hydroxyethyl, and hydroxypropyl functional groups, and at least one cargo of interest.

In some embodiments of any of the aspects, the modified nucleotides comprise 5-methylcytidine, 5-methyluridine, 5-hydroxymethyluridine, 5-hydroxymethylcytidine or a combination thereof.

In some embodiments of any of the aspects, the saRNA expresses the cargo at a level greater than or equal to that of a corresponding saRNA with less than 25% modified nucleotides.

In one embodiment of any aspect herein, the self-amplifying RNA is comprised of nucleotides wherein one or more of the unmodified nucleotides comprising cytidine, adenosine, uridine, and guanosine, is replace with a percentage of modified analog to the corresponding base, where the percentage is at least 25%, e.g., 25-100%, 30-100%, 40-100%, 50-100%, 60-100%, 70-100%, 80-100% or 90-100%, 25-95%, 30-95%, 40-95%, 50-95%, 60-95%, 70-95%, 80-95%, 25-90%, 30-90%, 40-90%, 50-90%, 60-90%, 70-90%, or 80-90%, 25-30%; 30-35%; 40-45%; 45-50%; 50-55%; 55-60%; 60-65%; 65-70%; 70-75%; 75-80%; 80-85%, 85-90%, 90-95%, 95-99%, 99%-100%, or 100%. In some embodiments of any of the aspects, the level of substitution of the modified nucleotides is: 25%-50%; 51%-75%; 75%-99%; 99.1%-99.9%; or 100%.

In one embodiment of any aspect herein, a self-amplifying RNA (saRNA) encodes a cargo of interest, wherein the saRNA comprises a level of substitution of a given nucleotide with a modified nucleotide greater than 25%, where the modified nucleotide is selected from the group consisting of 5-methylcytidine, 5-methyluridine, and 5-hydroxymethylcytidine, and optionally the saRNA expresses the cargo at a level greater than or equal to that of the same saRNA without the modified nucleotide.

In one embodiment of any aspect herein, a self-amplifying RNA (saRNA) encodes a cargo of interest, wherein the saRNA comprises a level of substitution of a given nucleotide with a modified nucleotide greater than 25%, where the modified nucleotide is selected from the group consisting of 5-methylcytidine, 5-methyluridine, 5-hydroxymethyluridine, and 5-hydroxymethylcytidine, and optionally the saRNA expresses the cargo at a level greater than or equal to that of the same saRNA without the modified nucleotide.

In one embodiment of any aspect herein, a self-amplifying RNA (saRNA) encodes a cargo of interest, wherein the saRNA comprises a level of substitution of a given nucleotide with a modified nucleotide greater than 25%, where the modified nucleotide is comprised of a pyrimidine nucleoside triphosphate with a moiety on the 5 carbon, wherein the moiety is selected from a list comprising methyl, ethyl, propyl, trifluoromethyl, hydroxymethyl, hydroxyethyl, or hydroxypropyl functional groups, and optionally the saRNA expresses the cargo at a level greater than or equal to that of the same saRNA without the modified nucleotide.

In one embodiment of any aspect herein, the substitution with 5-methyluridine and one or both, 5-methylcytidine and 5-hydroxymethylcytidine, occurs in the same saRNA molecule.

In one embodiment of any aspect herein, the substitution with 5-methyluridine or 5-hydroxymethyluridine, and one or both of 5-methylcytidine and 5-hydroxymethylcytidine, occurs in the same saRNA molecule.

In one embodiment of any aspect herein, the initiating nucleotide, the nucleotide directly proximal to the 5' cap, is an adenosine or adenosine analog.

In one embodiment of any aspect herein, the initiating nucleotide, the nucleotide directly proximal to the 5' cap, is a guanosine or guanosine analog.

In one embodiment of any aspect herein, the initiating nucleotide, and optionally the subsequent nucleotide, of the saRNA is methylated at the 2'O position of the ribose.

In some embodiments of any of the aspects, the initiating nucleotide comprises: (a) an adenosine or adenosine analog, and the initiating nucleotide of the saRNA is methylated at the 2'O position of the ribose (Cap 1); (b) an adenosine or adenosine analog, and the initiating nucleotide and the subsequent nucleotide of the saRNA are both methylated at the 2'O position of the ribose (Cap2); (c) a guanosine or guanosine analog, and the initiating nucleotide of the saRNA is methylated at the 2'O position of the ribose (Cap 1); or (d) a guanosine or guanosine analog, and the initiating nucleotide and the subsequent nucleotide of the saRNA are both methylated at the 2'O position of the ribose (Cap2).

In one embodiment of any aspect herein, the saRNA contains components derived from the Venezuela Equine Encephalitis Virus (VEEV), Semliki Forest Virus (SFV), Sindbis Virus (SIN), Kunjin Virus (KUN), Measles virus (MV), Coronavirus (CoV), Rabies virus (RABV), or Vesicular Stomatitis virus (VSV).

In some embodiments of any of the aspects, the saRNA comprises from 5' to 3': (a) a 5' cap; (b) non-structural protein 1 (nsp1), non-structural protein 2 (nsp2), non-structural protein 3 (nsp3), and/or non-structural protein 4 (nsp4), each derived from at least one virus; (c) a subgenomic promoter (SGP) derived from at least one virus; (d) 5' untranslated region (UTR) derived from at least one virus;

(e) the at least one cargo of interest; (f) a 3' untranslated region (UTR) derived from at least one virus; and (g) a poly-A tail.

In some embodiments of any of the aspects, the saRNA further comprises at least one 5' conserved sequence element (CSE) and/or 3' at least one conserved sequence element (CSE) derived from at least one virus.

In some embodiments of any of the aspects, the at least one virus is an alphavirus.

In some embodiments of any of the aspects, the at least one virus is selected from the group consisting of: Venezuela Equine Encephalitis Virus (VEEV), Semliki Forest Virus (SFV), Sindbis Virus (SIN), Chikungunya Virus (CHIKV), Eastern Equine Encephalitis Virus (EEEV), Mayaro Virus (MAYV), Getah Virus (GETV), Ross River Virus (RRV), Una Virus (UNAV), Middleburg Virus (MIDV), O'nyong nyong virus (ONNV), Barmah Forest Virus (BFV), Mucambo Virus (MUCV), Tonate Virus (TONV), Everglades Virus (EVEV), Rio Negro Virus (RNV), Turnip Rosette Virus (TROV), Highlands J Virus (HJV), Western Equine Encephalitis Virus (WEEV), Fig Mosaic Emaravirus (FMV), Aura Virus (AURAV), Kunjin Virus (KUN), Measles virus (MV), Coronavirus (CoV), Rabies virus (RABV), and Vesicular Stomatitis virus (VSV).

In one embodiment of any aspect herein, the saRNA expresses a cargo that is a protein or multiple proteins of viral, bacterial, protozoan, mammalian, or plant in origin.

In some embodiments of any of the aspects, the cargo comprises: a chimeric antigen receptor (CAR) comprising an extracellular domain that specifically binds to an antigen of interest; a ligand, a cell surface receptor, a transcription factor, a cytokine, a chemokine, an enzyme, and/or an antibody or fragment thereof, a bispecific T cell engager (BiTE); at least one non-coding RNA; at least one vaccine-associated antigen comprising at least one protein encoded by a genome of a virus; comprises at least one transcription factor; at least one growth factor and/or cytokine; one or both of Pappalysin-A1 (PAPPA1) and Pappalysin-A2 (PAPPA2); at least one interleukin and/or a cognate receptor(s) of the interleukin and/or receptor sub-units for the interleukin; at least one enzyme with antioxidant activity; glucagon-like peptide-1 (GLP-1) or a fragment thereof.

In one embodiment of any aspect herein, the saRNA expresses a chimeric antigen receptor containing an extracellular domain that senses input signals.

In one embodiment of any aspect herein, the saRNA expresses a ligand, a cell surface receptor, a transcription factor, a cytokine, a chemokine, an enzyme, an antibody, or other protein with biological activity.

In one embodiment of any aspect herein, the saRNA expresses cargo or cargos of interest comprising a domain or domains responsive to an external input.

In one embodiment of any aspect herein, the saRNA transcribes one or multiple non-coding RNA selected from a list comprising siRNA, shRNA, or microRNA.

In one embodiment of any aspect herein, the cargo of interest is one or multiple vaccine associated antigens, wherein the vaccine associated antigen is one or multiple proteins encoded on the genomes of viruses selected from a list comprising respiratory syncytial virus, hemagglutinin virus, human immunodeficiency virus, influenza virus, zika virus, sudden acute respiratory syndrome coronavirus 2, human papillomavirus, herpes virus, rotavirus, chicken pox, dengue virus, hepatitis A virus, hepatitis virus B, rubella virus, poliovirus, or rabies virus.

In one embodiment of any aspect herein, the cargo or cargos encoded by the saRNA is one or more chimeric antigen receptors selected from the list comprising CD19, CD22, CD30, b-cell maturation antigen (BCMA), disialoganglioside GD2, human estrogen receptor 2 (HER2), GPR87, Fibroblast Activator Protein (FAP), CD20, receptor tyrosine kinase-like orphan receptor 1 (ROR1), carcinoembryonic antigen (CEA), mesothelin (MSLN), prostate-specific membrane antigen (PSMA), EGFRvIII, IL13Rα2, NKG2D.

In one embodiment of any aspect herein, the cargo or cargos encoded by the saRNA is one or more transcription factor, including those selected from the list Oct3/4, Sox2, Klf4, & c-Myc.

In one embodiment of any aspect herein the cargo or cargos encoded by the saRNA is one or more growth factor or cytokine, selected from the list comprising platelet-derived growth factor (PDGF), erythropoietin (EPO), vascular endothelial growth factor (VEGF), transforming growth factor-β1 (TGF-β1), fibroblast growth factor (FGF), human relaxin-2 (RLX2), alpha-melanocyte-stimulating hormone (alpha-MSH), insulin-like growth factor-I (IGF-I), epidermal growth factor (EGF), nerve growth factor (NGF), granulocyte-monocyte colony-stimulating factor (GMCSF), Thrombopoietin (TPO), Bone morphogenic protein (BMP), hepatocyte growth factor (HGF), growth/differentiation factor (GDF), Neurotrophins, migration stimulating factor (MSF), sarcoma growth factor (SGF).

In one embodiment of any aspect herein, the cargo or cargos encoded by the saRNA is one or both Pappalysin-A1 (PAPPA1) and Pappalysin-A2 (PAPPA2).

In one embodiment of any aspect herein, the cargo or cargos encoded by the saRNA is one or more interleukin(s) or their cognate receptors and receptor sub-units, selected from the list comprising IL-2, IL-4, IL-7, IL-10, IL-13, and IL-15.

In one embodiment of any aspect herein, the cargo or cargos encoded by the saRNA is one or more enzyme with antioxidant activity, selected from a list comprising phospholipid hydroperoxide glutathione peroxidase, superoxide dismutase-1, and superoxide dismutase-2; Bruton's tyrosine kinase; adenosine deaminase; ecto-nucleoside triphosphate diphosphydrolase.

In one embodiment of any aspect herein, the invention is pharmaceutical composition comprising a saRNA and a pharmaceutically acceptable carrier.

In one aspect described herein is a method of expressing at least one cargo of interest in a cell, the method comprising contacting a cell with at least one saRNA as described herein. In one embodiment of any aspect herein, a cell is transfected with the described saRNA.

In one embodiment of any aspect herein, the cargo of the described saRNA is expressed in a cell (e.g. a eukaryotic cell).

In one aspect described herein is a method of expressing at least one cargo in a subject in need thereof, the method comprising administering to the subject an effective amount of a pharmaceutical composition comprising or expressing at least one saRNA as described herein. In one embodiment of any aspect herein, one or more preselected cargos are expressed in a subject in need thereof, this embodiment comprising administering to a subject (e.g., a human, a livestock) an effective amount of saRNA.

In one embodiment of any aspect herein, the saRNA maintains or increases initial saRNA replication and cargo expression compared to an unmodified saRNA of the same dose.

In one embodiment of any aspect herein, the expression of the cargo or cargos of interest encoded by a saRNA is equivalent or increased compared to that of an unmodified saRNA.

In one embodiment of any aspect herein, the transfection efficiency of a self-amplifying RNA molecule is increased compared to that of an unmodified saRNA.

In one embodiment of any aspect herein, the early interferon response resulting from introduction of the saRNA is decreased compared to that of unmodified saRNA.

In one embodiment of any aspect herein, the length of time over which cargo is expressed at a detectable level from the saRNA is increased compared to that of unmodified saRNA.

In one embodiment of any aspect herein, the saRNA is delivered to a human cell.

In one embodiment of any aspect herein, the saRNA is administrated to a subject that has cancer.

In one embodiment of any aspect herein, the saRNA is administrated to a subject in need of vaccination.

In one embodiment of any aspect herein, the saRNA is administrated to a subject in need of protein replacement therapy.

In one embodiment of any aspect herein, the saRNA is administrated to a subject in need of antibody therapy.

In one embodiment of any aspect herein, the saRNA permits tissue, organ, or cell-type specific expression of the cargo.

In one embodiment of any aspect herein, the saRNA comprises greater than 50% substitution of uridine with 5-methyluridine to facilitate kidney specific expression of the cargo.

In one embodiment of any aspect herein, the saRNA modulates cellular differentiation of a cell containing the saRNA at a level equivalent to or greater than the level of modulation achieved with the unmodified saRNA at an equivalent dose.

In a preferred embodiment, the self-amplifying RNA highly substituted with modified nucleotides expresses more cargo when compared to an unmodified saRNA.

In a preferred embodiment of any aspect herein, the self-replicating RNA is generated by in vitro transcription.

In one embodiment of any aspect herein, the RNA contains a 5' cap structure.

In a preferred embodiment of any aspect herein, the 5' cap structure is directly upstream of an adenosine nucleotide or analog.

In a preferred embodiment of any aspect herein, the 5' cap structure is directly upstream of an guanosine nucleotide or analog.

In one embodiment of any aspect herein, the RNA contains a 3' poly-A tail.

In one embodiment of any aspect herein, the RNA contains a 5' UTR, a 3' UTR, or a combination of both.

In one embodiment of any aspect herein, the inclusion of select modified nucleotides increases or enhances expression of a cargo protein compared to un-substituted saRNA.

In one embodiment of any aspect herein, the inclusion of select unmodified nucleotides increases or enhances the transfection efficiency of the saRNA into cells of interest.

In one embodiment of any aspect herein, a cargo protein is expressed from self-replicating RNA that contains the protein coding sequence downstream of a subgenomic promoter.

In one embodiment of any aspect herein, a functional protein is expressed from self-replicating RNA that contains the protein coding sequence downstream of an internal ribosome entry site (IRES) sequence.

In one embodiment of any aspect herein, the cargo protein is a chimeric antigen receptor.

In a preferred embodiment, the vaccine associated antigen is a protein encoded on the viral genome of any strain of respiratory syncytial virus, hemagglutinin virus, human immunodeficiency virus, influenza virus, zika virus, sudden acute respiratory syndrome coronavirus 2, human papillomavirus, herpes virus, rotavirus, chicken pox, dengue virus, hepatitis A virus, hepatitis virus B, rubella virus, poliovirus, or rabies virus.

In a preferred embodiment, the vaccine associated antigen is a protein encoded on the genome of any tuberculosis, diptheriae, meningococcal, pneumococcal or *tetani* bacteria.

In one embodiment of any aspect herein, the functional protein is a chimeric antigen receptor.

In one embodiment of any aspect herein, the functional protein is a chimeric antigen receptor with a protease domain that is responsive to a protease inhibitor.

In one embodiment of any aspect herein, the functional protein is a chimeric antigen receptor with a domain that interacts with a small molecule. The stability of the receptor is modulated by known and unknown mechanisms in the presence of the small molecule.

Another aspect details a method, wherein the activity of the functional protein is dependent on the concentration of an administered small molecule.

Another aspect details a method, wherein the activity of the functional protein is dependent on the concentration of multiple administered small molecules.

In one embodiment of any aspect herein, the level of expression of the functional protein from highly substituted saRNA is equal to or greater than levels of expression resulting from un-substituted saRNA.

In one embodiment of any aspect herein, the early immune response elicited by highly substituted saRNA is less than that of un-substituted saRNA.

In one embodiment of any aspect herein, multiple chimeric antigen receptors with opposing functions are expressed from the same highly substituted self-replicating RNA strand.

Another aspect details a method, wherein the activity of the resulting cell is dependent on external signals that are sensed by multiple proteins with differing functions. The resulting activity conducted by the cell is dependent on the presence or lack of the sensed external signals. In some embodiments, small molecules are administered as the external signal. Non-limiting examples of other external signals that can be used to control activity include light, ultrasound, proteins, nucleic acids, ligands, antibodies, antibody fragments etc.

In one embodiment of any aspect herein, a functional protein with expression enhancing ability either by known or unknown mechanisms is used to enhance the level and duration of expression is co-expressed.

In one embodiment of any aspect herein, highly substituted saRNA is delivered to cells via electroporation.

In one embodiment of any aspect herein, highly substituted saRNA is delivered to cells via nucleofection.

In one embodiment of any aspect herein, the highly substituted saRNA is delivered to cells via lipid nanoparticles.

In one embodiment of any aspect herein, the highly substituted saRNA is delivered to a specified cell type by delivery with a lipid nanoparticle with a targeting moiety.

In a preferred embodiment of any aspect herein, the function of the chimeric antigen receptor is to activate immune cells.

In a preferred embodiment of any aspect herein, the function of the chimeric antigen receptor is to inhibit immune cells.

In one embodiment of any aspect herein, a reporter protein is co-expressed along with cargo protein to measure the levels of expression resulting from the highly substituted self-replicating RNA.

In one embodiment of any aspect herein, multiple cell types are modified with highly substituted self-replicating RNA.

In one embodiment of any aspect herein, cell type specific expression is achieved by selection of the proper modified nucleotide for high substitution.

BRIEF DESCRIPTION OF THE DRAWINGS

FIG. 1A shows conventional vs. self-replicating RNA modification of cells. In this figure, immune cells are used as a non-limiting example. The self-replicating RNA results in greater and longer expression of cargo protein(s) due to self-renewal and amplification. Conventional mRNA is subject to degradation and dilution via proliferation. FIG. 1B shows a schematic detailing the use of self-replicating RNA in modifying a cell by expressing protein(s). The delivered protein(s) (e.g., reporter, enzyme, receptor, ligand, transcription factor) can respond to external inputs (e.g., small molecules, light) or perform logic computation to enable control over the modified cell.

FIG. 51A shows representative flow cytometry plots of each treatment condition. FIG. 51B shows representative live-cell fluorescent microscopy images. FIG. 51C shows quantification of flow cytometry data from biological replicate experiments; left-right order of the bars corresponds to top-down order in the legend.

FIG. 53A shows representative flow cytometry plots of each treatment condition. FIG. 53B shows representative live-cell fluorescent microscopy images. FIG. 53C shows quantification of flow cytometry data from biological replicate experiments; left-right order of the bars corresponds to top-down order in the legend.

FIG. 54A shows histograms from these experiments, and FIG. 54B shows time-course line graphs of these experiments.

FIG. 58A shows a schematic illustrating the limitations of unmodified saRNA, NlmΨ modified saRNA, and the advantages of saRNA with compatible modNTPs. FIG. 58B shows a workflow for synthesizing a library of saRNA with complete substitution of modified nucleotides and transfecting the library encoding an mCherry reporter into HEK293 cells using lipofection. FIG. 58C shows flow cytometry results measuring the percentage of expressing cells in HEK293 cells transfected with the library of modified saRNA. Error bars represent the standard deviation of n=3 biological replicates. FIG. 58D shows live-cell fluorescent microscopy images of selected modified nucleotides and representative histograms in HEK293 cells. Error bars represent the standard deviation of n=4 biological replicates. FIG. 58E shows expression levels 24 hours after transfection of 10 ng of RNA encoding a luciferase reporter in HEK293 cells with SM102 LNPs. Luciferase signal is presented as fold-change compared to untransfected mock cells. Error bars represent the standard deviation of n=4 biological replicates. FIG. 58F shows expression levels 24 hours after transfection of 10 ng of RNA encoding a luciferase reporter in C2C12 cells with SM102 LNPs. Luciferase signal is presented as fold-change compared to untransfected mock cells. Error bars represent the standard deviation of n=4 biological replicates. FIG. 58G shows transfection efficiency 24 hours after transfection with 25 ng and 250 ng of RNA encoding an mCherry reporter in Jurkat cells with SM102 LNPs. Error bars represent the standard deviation of n=3 biological replicates. FIG. 58H shows transfection efficiency 24 hours after transfection of 500 ng of RNA encoding an mCherry reporter in CD3+ T cells from two different donors. n=3 biological replicates per group. FIG. 58I shows an expression time course in Jurkat cells using 100 ng of unmodified or 5mC modified saRNA. Error bars represent the standard deviation of n=3 biological replicates. Statistical significance was determined by two-way ANOVA with Tukey's multiple comparisons correction, **$p<0.0001$, $p<0.01$, *$p<0.05$. Left-right order of the bars in each group corresponds to top-down order in the legend in FIG. 58E-58H.

FIG. 59A shows a diagram depicting modified saRNA evading TLR detection, leading to reduced interferon production. FIG. 59B shows an assay for detection of early interferon response from transfection of human PBMCs with unmodified or modified saRNA. FIG. 59C-59E show gene expression analysis of IFN-$\alpha$1 (FIG. 59C), IFN-$\alpha$2, (FIG. 59D) and IFN-$\beta$1 (FIG. 59E) in RNA harvested from unique human PBMCs (n=3) after 6-hour treatment with saRNA. FIG. 59F shows an IFN-$\alpha$ (all-subtype) serum analysis after 6 hours of saRNA treatment in a unique donor. FIG. 59G shows a 6 hour and 24-hour serum analysis of IFN-$\beta$ levels from saRNA treated PBMCs. Error bars represent standard deviation of n=3 biological replicates. Statistical significance was determined by ANOVA, controlling for multiple comparisons using Dunnett's method. *$p<0.001$, $p<0.0001$. n.d. not determined/below limit of detection. Left-right order of the bars in each group corresponds to top-down order in the legend in FIG. 59C-59**G.

FIG. 60A shows a schematic illustrating the different RNA formats for expressing the SARS-CoV-2 Spike protein, compared in vitro and in vivo. This includes non-replicating N1mΨmRNA, wildtype self-amplifying RNA, and 5mC modified self-amplifying RNA. FIG. 60B shows expression of Spike protein 24 hours after transfection with 100 ng of RNA in SM102 LNPs in HEK293 cells. FIG. 60C shows expression of Spike protein 24 hours after transfection with 100 ng of RNA in SM102 LNPs in C2C12 cells. FIG. 60D shows median fluorescence intensity (MFI) of anti-Spike AF647 staining in C2C12 cells. MFI is relative to untreated cells. Error bars represent the standard deviation of n=3 biological replicates. FIG. 60E shows a study design for the SARS-CoV-2 challenge study in C57BL/6 mice. Mice were vaccinated in a prime-boost scheme, serum was collected to analyze interferon response and titers, and mice were challenged with SARS-CoV-2 MA30 on day 35. FIG. 60F shows IFN-$\alpha$1 expression in serum collected 24 hours or 48 hours after initial vaccination with 1000 ng of RNA in LNPs. Error bars represent the standard deviation of n=5 biological replicates. FIG. 60G shows survival of mice after challenge with a lethal challenge of MA30 virus. n=10 mice per group. FIG. 60H shows weight change of mice after challenge with mouse-adapted SARS-CoV-2 MA30 virus. Error bars indicate SEM. Statistical significance was determined by ANOVA, controlling for multiple comparison's using Dunnett's method. $p<0.005$, *$p<0.001$, **$p<0.0001$. For survival study statistics, a log-rank (Matel-Cox) test was used between groups. =$p<0.0001$, *=$p<0.001$. Left-right order of the bars in each group corresponds to top-down order in the legend in FIGS. 60D and 60F.

FIG. 61A shows a comparison of flow cytometry results from modified saRNA screen to a wildtype unmodified control construct. FIG. 61B shows median fluorescence intensity of HEK293 cells transfected with library of modified saRNA. FIG. 61C shows live-cell microscopy images of control samples from FIG. 58D. Wildtype refers to unmodified saRNA. FIG. 61D shows representative histograms of HEK293 cells transfected with modified saRNA synthesized with 3'-O-Me-m7G(5')ppp(5')G (ARCA) (top row) or m7G(5')ppp(5')(2'OMeA)pU (CLEANCAP AU) (bottom row).

FIG. 62A shows a dose response ofHEK293 transfected with SM102 LNPs containing N1mΨmRNA, WT saRNA, or 5mC saRNA encoding luciferase. FIG. 62B shows representative flow plots of Jurkat cells transfected with WT or 5mC saRNA encoding mCherry. FIG. 62C shows live-cell microscopy of Jurkat cells transfected with WT or 5mC saRNA encoding mCherry. FIG. 62D shows expression levels 24 hours after transfection of 250 ng of RNA encoding a luciferase reporter in Jurkat cells with SM102 LNPs. Luciferase signal is presented as fold-change compared to untransfected mock cells. Left-right order of the bars corresponds to top-down order in the legend. FIG. 62E shows MFI of Jurkat cells transfected with WT or 5mC saRNA encoding mCherry over 7 days.

FIG. 63A shows representative flow plots of primary T cells from two different donors transfected with WT or 5mC saRNA encoding mCherry. FIG. 63B shows live cell microscopy of primary T cells transfected with WT or 5mC encoding mCherry.

FIG. 64A shows transfection efficiency 24 hours after transfection of C2C12 with 100 ng of modified Spike encoding mRNA or saRNA. FIG. 64B shows detection of Spike protein by ELISA in lysed C2C12 cells after transfection with 100 ng modified Spike encoding mRNA or saRNA. FIG. 64C shows transfection efficiency 24 hours after transfection of C2C12 with 25 ng of modified HA encoding mRNA or saRNA. FIG. 64D shows median fluorescence intensity (MFI) of anti-HA AF647 staining in C2C12 cells. Left-right order of the bars in each group corresponds to top-down order in the legend in FIG. 64A-64D.

FIG. 65A shows IFN-$\beta$ expression in serum collected 24 hours or 48 hours after initial vaccination with 1000 ng of RNA in LNPs. Error bars represent the standard deviation of n=5 biological replicates. Left-right order of the bars in each group corresponds to top-down order in the legend. FIG. 65B shows survival of mice after challenge with a lethal challenge of MA30 virus. n=10 mice per group. For survival study statistics, a log-rank (Matel-Cox) test was used between groups. ****=$p<^{0}0.0^{001}$.

FIG. 66A shows encapsulation efficiency of post-dialysis spike encoding LNPs used in in vivo study. FIG. 66B shows the size of LNPs used in in vivo study. FIG. 66C shows polydispersity index (PDI) of LNPs used in in vivo study. FIG. 66D shows the RNA concentration in ng/uL. Left-right order of the bars in each group corresponds to top-down order in the legend in FIG. 66A-66D.

FIG. 67A shows a gating strategy used in screening of modNTP saRNA library via HEK293 transfection. FIG. 67B shows a gating strategy used in analysis of transfection efficiency of saRNA LNPs in Jurkat T cells. FIG. 67C shows a gating strategy for determining the expression of SARS-CoV-2 Spike protein in HEK or C2C12 cells. FIG. 67D shows a gating strategy used in analysis of transfection efficiency of saRNA LNPs in primary T cells.

DETAILED DESCRIPTION

Figure 1A:
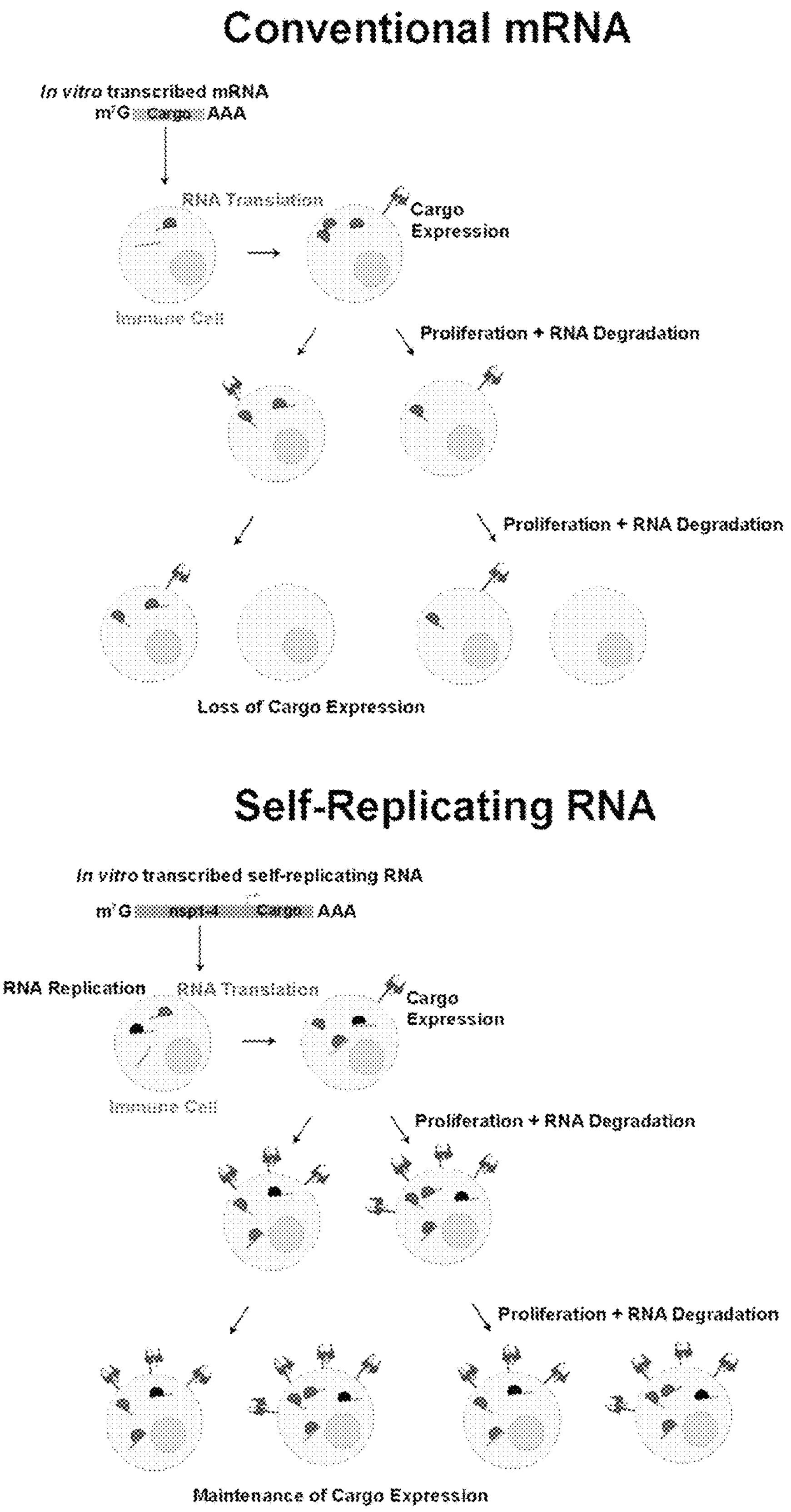
FIG. 1A-1B shows a series of schematics.

The above summary of the present invention is not intended to describe each disclosed embodiment or every implementation of the present invention. The description and examples that follow exemplifies illustrative embodiments. In several places throughout the application, guidance is provided through lists of examples, which can be used in various combinations. In each instance, the recited list serves only as a representative group and should not be interpreted as an exclusive list.

Disclosed herein are methods and compositions for modifying and controlling the activity of cells by expression of proteins from self-replicating RNA. The technology disclosed herein allows for the ability to express proteins at levels comparable to other methods used to establish constitutive protein expression. The protein cargo can be any genetically encodable protein with known or unknown function. The system is modular and allows for the expression of multiple proteins with various functions. Additionally, the activity of the cells transfected with the self-replicating RNA can be controlled by expression of proteins responsive to external inputs or by expression of proteins that that interact with each other to conduct logic computation. The technology is useful for generating cell therapies with controllable activity in a rapid manner without gene editing. Additionally, the technology can be combined with RNA delivery strategies (e.g., lipid nanoparticles) to transfect cells in vivo.

As a clinically relevant, non-limiting example, this disclosure outlines the development of self-replicating RNA systems that are used to modify immune cells to express reporter proteins and chimeric antigen receptors targeting CD19 and HER2. In some embodiments, the activity of the modified cells is controlled externally or by logic computation circuits that are established by the delivered self-replicating RNA.

Disclosed herein are methods and compositions for modifying and controlling the activity of cells by expression of proteins from self-amplifying RNA that is highly substituted with chemically modified nucleotides. The technology disclosed herein allows for highly substituted saRNA to express proteins at levels comparable or greater than unsubstituted self-amplifying RNA. The protein cargo can be any genetically encodable protein with known or unknown function. The system is modular and allows for the expression of multiple proteins with various functions. Additionally, the activity of the cells transfected with the highly substituted self-amplifying RNA can be controlled by expression of proteins responsive to external inputs or by expression of proteins that interacts with each other to conduct logic computation. The technology is useful for generating low dose saRNA based vaccines that express equal or greater cargo compared to an unmodified saRNA. An additional aspect of the invention is the decreased immunogenicity through which highly substituted saRNA are potentiated. The technology is useful for generating vaccines, cell therapies either in situ or ex vivo, and protein replacement therapies. Additionally, the technology can be combined with RNA delivery strategies (e.g., lipid nanoparticles) to transfect cells in vivo.

Self-Amplifying RNAs

Described herein in multiple aspects are self-amplifying RNAs. As used herein, the terms “self-amplifying RNA” or “saRNA” or “self-replicating RNA” or “srRNA” are used interchangeably and refer to an RNA strand capable of undergoing replication activity that results in replicate strands from an original strand.

In multiple aspects described herein is an saRNA comprising: (a) at least one non-structural protein derived from at least one virus; (b) a subgenomic promoter (SGP) derived from at least one virus; and (c) least one cargo of interest. In additional aspects described herein is an saRNA comprising from 5' to 3': (a) at least one non-structural protein derived from at least one virus; (b) a subgenomic promoter (SGP) derived from at least one virus; and (c) least one cargo of interest.

In other aspects described herein is an saRNA comprising: (a) at least one non-structural protein derived from at least one alphavirus; (b) a subgenomic promoter (SGP) derived from at least one alphavirus; and (c) least one cargo of interest. In additional aspects described herein is an saRNA comprising from 5' to 3': (a) at least one non-structural protein derived from at least one alphavirus; (b) a subgenomic promoter (SGP) derived from at least one alphavirus; and (c) least one cargo of interest.

In one aspect described herein is an saRNA comprising: (a) a 5' cap; (b) non-structural protein 1 (nsp1), non-structural protein 2 (nsp2), non-structural protein 3 (nsp3), and/or non-structural protein 4 (nsp4), each derived from at least one virus; (c) a subgenomic promoter (SGP) derived from at least one virus; (d) 5' untranslated region (UTR) derived from at least one virus; (e) the at least one cargo of interest; (f) a 3' untranslated region (UTR) derived from at least one virus; and (g) a poly-A tail.

In one aspect described herein is an saRNA comprising from 5' to 3': (a) a 5' cap; (b) non-structural protein 1 (nsp1), non-structural protein 2 (nsp2), non-structural protein 3 (nsp3), and/or non-structural protein 4 (nsp4), each derived from at least one virus; (c) a subgenomic promoter (SGP) derived from at least one virus; (d) 5' untranslated region (UTR) derived from at least one virus; (e) the at least one cargo of interest; (f) a 3' untranslated region (UTR) derived from at least one virus; and (g) a poly-A tail.

In one aspect described herein is an saRNA comprising: (a) a 5' cap; (b) non-structural protein 1 (nsp1), non-structural protein 2 (nsp2), non-structural protein 3 (nsp3), and/or non-structural protein 4 (nsp4), each derived from at least one alphavirus; (c) a subgenomic promoter (SGP) derived from at least one alphavirus; (d) 5' untranslated region (UTR) derived from at least one alphavirus; (e) the at least one cargo of interest; (f) a 3' untranslated region (UTR) derived from at least one alphavirus; and (g) a poly-A tail.

In one aspect described herein is an saRNA comprising from 5' to 3': (a) a 5' cap; (b) non-structural protein 1 (nsp1), non-structural protein 2 (nsp2), non-structural protein 3 (nsp3), and/or non-structural protein 4 (nsp4), each derived from at least one alphavirus; (c) a subgenomic promoter (SGP) derived from at least one alphavirus; (d) 5' untranslated region (UTR) derived from at least one alphavirus; (e) the at least one cargo of interest; (f) a 3' untranslated region (UTR) derived from at least one alphavirus; and (g) a poly-A tail.

In one aspect described herein is an saRNA comprising: (a) a 5' cap; (b) non-structural protein 1 (nsp1), non-structural protein 2 (nsp2), non-structural protein 3 (nsp3), and/or non-structural protein 4 (nsp4), each derived from at least one virus, wherein the nsP1 comprises at least one conserved 5' sequence element (5' CSE); (c) a subgenomic promoter (SGP) derived from at least one virus; (d) 5' untranslated region (UTR) derived from at least one virus; (e) the at least one cargo of interest; (f) a 3' untranslated region (UTR) derived from at least one virus, wherein the 3' UTR comprises at least one 3'-conserved sequence element (3' CSE); and (g) a poly-A tail.

In one aspect described herein is an saRNA comprising from 5' to 3': (a) a 5' cap; (b) non-structural protein 1 (nsp1), non-structural protein 2 (nsp2), non-structural protein 3 (nsp3), and/or non-structural protein 4 (nsp4), each derived from at least one virus, wherein the nsP1 comprises at least one conserved 5' sequence element (5' CSE); (c) a subgenomic promoter (SGP) derived from at least one virus; (d) 5' untranslated region (UTR) derived from at least one virus; (e) the at least one cargo of interest; (f) a 3' untranslated region (UTR) derived from at least one virus, wherein the 3' UTR comprises at least one 3'-conserved sequence element (3' CSE); and (g) a poly-A tail.

In one aspect described herein is an saRNA comprising: (a) a 5' cap; (b) non-structural protein 1 (nsp1), non-structural protein 2 (nsp2), non-structural protein 3 (nsp3), and/or non-structural protein 4 (nsp4), each derived from at least one alphavirus, wherein the nsP1 comprises at least one conserved 5' sequence element (5' CSE); (c) a subgenomic promoter (SGP) derived from at least one alphavirus; (d) 5' untranslated region (UTR) derived from at least one alphavirus; (e) the at least one cargo of interest; (f) a 3' untranslated region (UTR) derived from at least one alphavirus, wherein the 3' UTR comprises at least one 3'-conserved sequence element (3' CSE); and (g) a poly-A tail.

In one aspect described herein is an saRNA comprising from 5' to 3': (a) a 5' cap; (b) non-structural protein 1 (nsp1), non-structural protein 2 (nsp2), non-structural protein 3 (nsp3), and/or non-structural protein 4 (nsp4), each derived from at least one alphavirus, wherein the nsP1 comprises at least one conserved 5' sequence element (5' CSE); (c) a subgenomic promoter (SGP) derived from at least one alphavirus; (d) 5' untranslated region (UTR) derived from at least one alphavirus; (e) the at least one cargo of interest; (f) a 3' untranslated region (UTR) derived from at least one alphavirus, wherein the 3' UTR comprises at least one 3'-conserved sequence element (3' CSE); and (g) a poly-A tail.

In some embodiments of the aspects, an saRNA as described herein comprises at least one nucleotide modification, as described further herein. In some embodiments of the aspects, an saRNA as described herein does not comprises nucleotide modifications.

In one aspect, described herein is a self-amplifying RNA (saRNA) comprising: (a) at least one non-structural protein derived from at least one virus; (b) a subgenomic promoter (SGP) derived from at least one virus; and (c) at least one cargo of interest; wherein the saRNA comprises at least 25% modified nucleotides, wherein the modified nucleotides are selected from the group consisting of 5-methylcytidine, 5-methyluridine, 5-hydroxymethyluridine, and 5-hydroxymethylcytidine; wherein the initiating nucleotide comprises an adenosine or adenosine analog; and wherein the initiating nucleotide of the saRNA is methylated at the 2'O position of the ribose (Cap 1).

In one aspect, described herein is a self-amplifying RNA (saRNA) comprising: (a) a 5' cap; (b) non-structural protein 1 (nsp1), non-structural protein 2 (nsp2), non-structural protein 3 (nsp3), and/or non-structural protein 4 (nsp4), each derived from at least one virus; (c) a subgenomic promoter (SGP) derived from at least one virus; (d) a 5' untranslated region (UTR) derived from at least one virus; (e) at least one cargo of interest; (f) a 3' untranslated region (UTR) derived from at least one virus; and (g) a poly-A tail; wherein the saRNA comprises at least 25% modified nucleotides, wherein the modified nucleotides are selected from the group consisting of 5-methylcytidine, 5-methyluridine, 5-hydroxymethyluridine, and 5-hydroxymethylcytidine; wherein the initiating nucleotide comprises an adenosine or adenosine analog; and wherein the initiating nucleotide of the saRNA is methylated at the 2'O position of the ribose (Cap 1).

In one aspect, described herein is a self-amplifying RNA (saRNA) comprising from 5' to 3': (a) at least one non-structural protein derived from at least one virus; (b) a subgenomic promoter (SGP) derived from at least one virus; and (c) at least one cargo of interest; wherein the saRNA comprises at least 25% modified nucleotides, wherein the modified nucleotides are selected from the group consisting of 5-methylcytidine, 5-methyluridine, 5-hydroxymethyluridine, and 5-hydroxymethylcytidine; wherein the initiating nucleotide comprises an adenosine or adenosine analog; and wherein the initiating nucleotide of the saRNA is methylated at the 2'O position of the ribose (Cap 1).

In one aspect, described herein is a self-amplifying RNA (saRNA) comprising from 5' to 3': (a) a 5' cap; (b) non-structural protein 1 (nsp1), non-structural protein 2 (nsp2), non-structural protein 3 (nsp3), and/or non-structural protein 4 (nsp4), each derived from at least one virus; (c) a subgenomic promoter (SGP) derived from at least one virus; (d) a 5' untranslated region (UTR) derived from at least one virus; (e) at least one cargo of interest; (f) a 3' untranslated region (UTR) derived from at least one virus; and (g) a poly-A tail; wherein the saRNA comprises at least 25% modified nucleotides, wherein the modified nucleotides are selected from the group consisting of 5-methylcytidine, 5-methyluridine, 5-hydroxymethyluridine, and 5-hydroxymethylcytidine; wherein the initiating nucleotide comprises an adenosine or adenosine analog; and wherein the initiating nucleotide of the saRNA is methylated at the 2'O position of the ribose (Cap 1).

In one aspect, described herein is a self-amplifying RNA (saRNA) comprising from 5' to 3': (a) a 5' cap; (b) non-structural protein 1 (nsp1), non-structural protein 2 (nsp2), non-structural protein 3 (nsp3), and/or non-structural protein 4 (nsp4), each derived from at least one virus, wherein the nsP1 comprises at least one conserved 5' sequence element (5' CSE); (c) a subgenomic promoter (SGP) derived from at least one virus; (d) a 5' untranslated region (UTR) derived from at least one virus; (e) at least one cargo of interest; (f) a 3' untranslated region (UTR) derived from at least one virus, wherein the 3' UTR comprises at least one 3'-conserved sequence element (3' CSE); and (g) a poly-A tail; wherein the saRNA comprises at least 25% modified nucleotides, wherein the modified nucleotides are selected from the group consisting of 5-methylcytidine, 5-methyluridine, 5-hydroxymethyluridine, and 5-hydroxymethylcytidine; wherein the initiating nucleotide comprises an adenosine or adenosine analog; and wherein the initiating nucleotide of the saRNA is methylated at the 2'O position of the ribose (Cap 1).

In one aspect, described herein is a self-amplifying RNA (saRNA) comprising: (a) at least one non-structural protein derived from at least one alphavirus; (b) a subgenomic promoter (SGP) derived from at least one alphavirus; and (c) at least one cargo of interest; wherein the saRNA comprises at least 25% modified nucleotides, wherein the modified nucleotides are selected from the group consisting of 5-methylcytidine, 5-methyluridine, 5-hydroxymethyluridine, and 5-hydroxymethylcytidine; wherein the initiating nucleotide comprises an adenosine or adenosine analog; and wherein the initiating nucleotide of the saRNA is methylated at the 2'O position of the ribose (Cap 1).

In one aspect, described herein is a self-amplifying RNA (saRNA) comprising: (a) a 5' cap; (b) non-structural protein 1 (nsp1), non-structural protein 2 (nsp2), non-structural protein 3 (nsp3), and/or non-structural protein 4 (nsp4), each derived from at least one alphavirus; (c) a subgenomic promoter (SGP) derived from at least one alphavirus; (d) a 5' untranslated region (UTR) derived from at least one alphavirus; (e) at least one cargo of interest; (f) a 3' untranslated region (UTR) derived from at least one alphavirus; and (g) a poly-A tail; wherein the saRNA comprises at least 25% modified nucleotides, wherein the modified nucleotides are selected from the group consisting of 5-methylcytidine, 5-methyluridine, 5-hydroxymethyluridine, and 5-hydroxymethylcytidine; wherein the initiating nucleotide comprises an adenosine or adenosine analog; and wherein the initiating nucleotide of the saRNA is methylated at the 2'O position of the ribose (Cap 1).

In one aspect, described herein is a self-amplifying RNA (saRNA) comprising from 5' to 3': (a) at least one non-structural protein derived from at least one alphavirus; (b) a subgenomic promoter (SGP) derived from at least one alphavirus; and (c) at least one cargo of interest; wherein the saRNA comprises at least 25% modified nucleotides, wherein the modified nucleotides are selected from the group consisting of 5-methylcytidine, 5-methyluridine, 5-hydroxymethyluridine, and 5-hydroxymethylcytidine; wherein the initiating nucleotide comprises an adenosine or adenosine analog; and wherein the initiating nucleotide of the saRNA is methylated at the 2'O position of the ribose (Cap 1).

In one aspect, described herein is a self-amplifying RNA (saRNA) comprising from 5' to 3': (a) a 5' cap; (b) non-structural protein 1 (nsp1), non-structural protein 2 (nsp2), non-structural protein 3 (nsp3), and/or non-structural protein 4 (nsp4), each derived from at least one alphavirus; (c) a subgenomic promoter (SGP) derived from at least one alphavirus; (d) a 5' untranslated region (UTR) derived from at least one alphavirus; (e) at least one cargo of interest; (f) a 3' untranslated region (UTR) derived from at least one alphavirus; and (g) a poly-A tail; wherein the saRNA comprises at least 25% modified nucleotides, wherein the modified nucleotides are selected from the group consisting of 5-methylcytidine, 5-methyluridine, 5-hydroxymethyluridine, and 5-hydroxymethylcytidine; wherein the initiating nucleotide comprises an adenosine or adenosine analog; and wherein the initiating nucleotide of the saRNA is methylated at the 2'O position of the ribose (Cap1).

In one aspect, described herein is a self-amplifying RNA (saRNA) comprising from 5' to 3': (a) a 5' cap; (b) nonstructural protein 1 (nsp1), non-structural protein 2 (nsp2), non-structural protein 3 (nsp3), and/or non-structural protein 4 (nsp4), each derived from at least one alphavirus, wherein the nsP1 comprises at least one conserved 5' sequence element (5' CSE); (c) a subgenomic promoter (SGP) derived from at least one alphavirus; (d) a 5' untranslated region (UTR) derived from at least one alphavirus; (e) at least one cargo of interest; (f) a 3' untranslated region (UTR) derived from at least one alphavirus, wherein the 3' UTR comprises at least one 3'-conserved sequence element (3' CSE); and (g) a poly-A tail; wherein the saRNA comprises at least 25% modified nucleotides, wherein the modified nucleotides are selected from the group consisting of 5-methylcytidine, 5-methyluridine, 5-hydroxymethyluridine, and 5-hydroxymethylcytidine; wherein the initiating nucleotide comprises an adenosine or adenosine analog; and wherein the initiating nucleotide of the saRNA is methylated at the 2'O position of the ribose (Cap 1).

In some embodiments of any of the aspects, a nucleic acid (e.g., DNA) encoding an saRNA as described herein comprises one of SEQ ID NOs: 2 or 5 or a nucleic acid sequence that is at least about 75%, at least about 80%, at least about 85%, at least about 90%, at least about 91%, at least about 92%, at least about 93%, at least about 94%, at least about 95%, at least about 96%, at least about 97%, at least at least about 98%, at least about 99%, or 100%, identical to one of SEQ ID NOs: 2 or 5 that maintains the same function (e.g., self-replication), or a codon-optimized version thereof.

In some embodiments of any of the aspects, at least one cargo is inserted between the AflII and NdeI cut sites of SEQ ID NO: 2. In some embodiments of any of the aspects, at least one cargo is inserted between nucleotides 7627 and 7628 of SEQ ID NO: 2. In some embodiments of any of the aspects, nucleotides 7634 to 8347 of SEQ ID NO: 5, nucleotides 7617 to 8330 of SEQ ID NO: 6, or nucleotides 7617 to 8330 of SEQ ID NO: 7, each corresponding to mCherry, is replaced with at least one cargo of interest, as described further herein.

In some embodiments of any of the aspects, an saRNA as described herein comprises one of SEQ ID NOs: 6-7 or a nucleic acid sequence that is at least about 75%, at least about 80%, at least about 85%, at least about 90%, at least about 91%, at least about 92%, at least about 93%, at least about 94%, at least about 95%, at least about 96%, at least about 97%, at least at least about 98%, at least about 99%, or 100%, identical to one of SEQ ID NOs: 6-7 that maintains the same function (e.g., self-replication), or a codon-optimized version thereof.

Table 6 provides non-limiting examples of domains comprised by exemplary saRNAs, and exemplary template DNAs for saRNAs, as described further herein.

TABLE 6

| Exemplary saRNAs | | | |
|---|---|---|---|
| Domain | SEQ ID NO: 2 (DNA template for saRNA, site for inserting cargo): nucleotides | SEQ ID NO: 5 (DNA template for saRNA with exemplary mCherry cargo) nucleotides | SEQ ID NOs: 6-7 (substituted or unsubstituted saRNA, exemplary mCherry cargo): nucleotides |
| T7 (see e.g., SEQ ID NO: 3) | 1-17 | 1-17 | N/A |
| 5' UTR | 18-61 | 18-61 | 1-44 |
| nsP1-4 (see e.g., SEQ ID NOs: 4, 23) | 62-7543 | 62-7543 | 45-7526 |
| 5' CSE (see e.g., SEQ ID NO: 10) | 149-199 | 149-199 | 132-182 |
| SGP (see e.g., SEQ ID NO: 11) | 7308-7578 | 7308-7578 | 7291-7561 |
| 5' UTR | 7579-7627 | 7579-7627 | 7562-7610 |
| Cargo (see e.g., SEQ ID NOs: 13-16, 22) | Inserted in between 7627 and 7628 | 7634 to 8347 (e.g., mCherry) | 7617 to 8330 (e.g., mCherry) |
| 3' UTR | 7629-7742 | 8348-8462 | 8331-8445 |
| 3' CSE (see e.g., SEQ ID NO: 9) | 7673-7742 | 8393-8462 | 8376-8445 |
| polyA tail | 7743-7768 | 8463-8488 | 8446-8471 |

Nucleic Acid Modifications

In some embodiments of any of the aspects, an saRNA as described herein comprises at least one nucleic acid modification, which can increase the efficacy of the saRNA. In some embodiments of any of the aspects, an saRNA as described herein comprises modified nucleotides, e.g., at least 25% modified nucleotides. In some embodiments of any of the aspects, an saRNA as described herein comprises a specific combination of 5' and initiating nucleotide(s). In some embodiments of any of the aspects, an saRNA as described herein comprises end modifications, backbone modifications, and/or sugar modifications.

Modified Nucleotides

In multiple aspects, described herein are saRNAs comprising modified nucleotides. The term "modified nucleotide" refers to any analog of cytidine, adenosine, guanosine, uridine, or pseudouridine. These analogs can include isomers of the nitrogenous base, as well as inclusion or exclusion of chemical groups, both natural occurring and synthetically introduced, on any aspect of the nitrogenous base. It is explicitly stated herein that modifications to the sugar-phosphate backbone are not included in the definition of the term "modified nucleotide." This exception is not meant to exclude the methylation at the 2'O position of the first and second initiating nucleotides, also referred to as Cap-1 and cap-2 structures.

In some embodiments of any of the aspects, the modified nucleotides comprise a modified pyrimidine nucleoside phosphate. In some embodiments of any of the aspects, the modified nucleotides comprise a pyrimidine nucleoside phosphate with a moiety on carbon 5 of the pyrimidine. In some embodiments of any of the aspects, the moiety on carbon 5 of the pyrimidine is selected from the group consisting of methyl, ethyl, propyl, trifluoromethyl, hydroxymethyl, hydroxyethyl, and hydroxypropyl functional groups. In some embodiments of any of the aspects, the pyrimidine comprises cytidine and/or uridine.

In some embodiments of any of the aspects, the pyrimidine comprises cytidine. In some embodiments of any of the aspects, the pyrimidine comprises cytidine, and the modified nucleotide comprises 5-methylcytidine (see e.g., Formula I). In some embodiments of any of the aspects, the pyrimidine comprises cytidine, and the modified nucleotide comprises 5-hydroxymethylcytidine (see e.g., Formula II). In some embodiments of any of the aspects, the pyrimidine comprises cytidine, and the modified nucleotide comprises 5-methylcytidine and 5-hydroxymethylcytidine.

In some embodiments of any of the aspects, the pyrimidine comprises uridine. In some embodiments of any of the aspects, the pyrimidine comprises uridine, and the modified nucleotide comprises 5-methyluridine (see e.g., Formula III). In some embodiments of any of the aspects, the pyrimidine comprises uridine, and the modified nucleotide comprises 5-hydroxymethyluridine (see e.g., Formula IV). In some embodiments of any of the aspects, the pyrimidine comprises uridine, and the modified nucleotide comprises 5-methyluridine and 5-hydroxymethyluridine.

In some embodiments of any of the aspects, the modified nucleotides are selected from the group consisting of 5-methylcytidine, 5-methyluridine, 5-hydroxymethyluridine, and 5-hydroxymethylcytidine, or any combination thereof. For example, an saRNA described herein can comprise any of the combinations of modified nucleotides shown in Table 4. In some embodiments of any of the aspects, the modified nucleotides are selected from the group consisting of 5-methylcytidine, 5-methyluridine, and 5-hydroxymethylcytidine, or any combination thereof. In some embodiments of any of the aspects, the modified nucleotides are selected from the group consisting of 5-methyluridine, 5-hydroxymethyluridine, and 5-hydroxymethylcytidine, or any combination thereof.

In some embodiments of any of the aspects, the modified nucleotides comprise 5-methyluridine or 5-hydroxymethyluridine, and one or both of 5-methylcytidine and 5-hydroxymethylcytidine, in the same saRNA molecule. In some embodiments of any of the aspects, the modified nucleotides comprise 5-methyluridine and one or both of 5-methylcytidine and 5-hydroxymethylcytidine, in the same saRNA molecule.

In some embodiments of any of the aspects, an saRNA as described herein comprises 5-methylcytidine as a nucleotide modification in combination with at least one of 5-methyluridine, 5-hydroxymethyluridine, and/or 5-hydroxymethylcytidine, or any combination thereof. In some embodiments of any of the aspects, an saRNA as described herein does not comprise 5-methylcytidine as a nucleotide modification. In some embodiments of any of the aspects, an saRNA as described herein does not comprise 5-methylcytidine as the only nucleotide modification.

In some embodiments of any of the aspects, an saRNA as described herein comprises at least 25% modified nucleotides. The percentage of modified nucleotides can be determined by dividing the total number of modified nucleotides in the modified saRNA by the total number of the specific nucleotide in the corresponding unmodified saRNA. For example, if an unmodified saRNA comprises 1000 uridine nucleosides, and the modified saRNA comprises 250 5-methyluridines (5mU) in place of the uridines, then the saRNA comprises 25% modified nucleotides. As another non-limiting example, if an unmodified saRNA comprises 1000 uridine nucleosides, and the modified saRNA comprises 125 5-methyluridines (5mU) and 125 5-hydroxymethyluridine (5OHmU) in place of the uridines, then the saRNA comprises 25% modified nucleotides.

TABLE 4

Exemplary modified nucleotide combinations in saRNAs described herein.

| 5-methylcytidine (5mC)<br>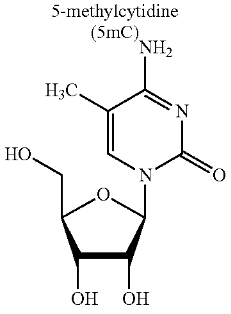<br>(Formula 1) | 5-hydroxymethyl-cytidine (5OHmC)<br>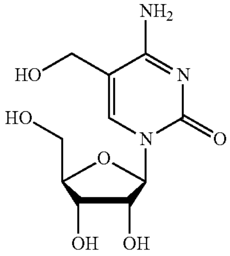<br>(Formula II) | 5-methyluridine (5mU)<br>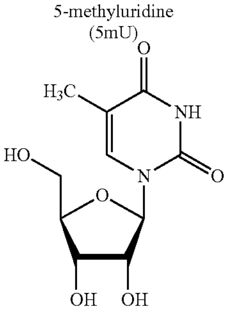<br>(Formula III) | 5-hydroxymethyl-uridine (5oHmU)<br>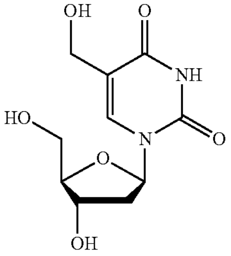<br>Formula (IV) |
|---|---|---|---|
| X | | | |
| | X | | |
| X | X | | |
| | | X | |
| X | | X | |
| | X | X | |
| X | X | X | |
| | | | X |
| X | | | X |
| | X | | X |
| X | X | | X |
| | | X | X |
| X | | X | X |
| | X | X | X |
| X | X | X | X |

In some embodiments of any of the aspects, the percentage of modified nucleotides in the saRNA can be controlled by the mole percentage of modified nucleotides included in the in vitro transcription (IVT) reaction to generate the saRNA from a DNA template. For example, to generate an saRNA comprising 25% 5-methyluridine (5mU), the IVT reaction mixture can comprise 25 mole % 5-methyluridine (5mU) and 75 mole % uridine.

In some embodiments of any of the aspects, an saRNA as described herein comprises at least 25% modified nucleotides and at most 100% modified nucleotides, corresponding to at least one specific nucleotide (e.g., a pyrimidine; e.g., cytidine and/or uridine). In some embodiments of any of the aspects, an saRNA as described herein comprises at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% modified nucleotides, corresponding to at least one specific nucleotide (e.g., a pyrimidine; e.g., cytidine and/or uridine).

In some embodiments of any of the aspects, an saRNA as described herein comprises at most 25%, at most 26%, at most 27%, at most 28%, at most 29%, at most 30%, at most 31%, at most 32%, at most 33%, at most 34%, at most 35%, at most 36%, at most 37%, at most 38%, at most 39%, at most 40%, at most 41%, at most 42%, at most 43%, at most 44%, at most 45%, at most 46%, at most 47%, at most 48%, at most 49%, at most 50%, at most 51%, at most 52%, at most 53%, at most 54%, at most 55%, at most 56%, at most 57%, at most 58%, at most 59%, at most 60%, at most 61%, at most 62%, at most 63%, at most 64%, at most 65%, at most 66%, at most 67%, at most 68%, at most 69%, at most 70%, at most 71%, at most 72%, at most 73%, at most 74%, at most 75%, at most 76%, at most 77%, at most 78%, at most 79%, at most 80%, at most 81%, at most 82%, at most 83%, at most 84%, at most 85%, at most 86%, at most 87%, at most 88%, at most 89%, at most 90%, at most 91%, at most 92%, at most 93%, at most 94%, at most 95%, at most 96%, at most 97%, at most 98%, at most 99%, at most 99.1%, at most 99.2%, at most 99.3%, at most 99.4%, at most 99.5%, at most 99.6%, at most 99.7%, at most 99.8%, at most 99.9%, or at most 100% modified nucleotides, corresponding to at least one specific nucleotide (e.g., a pyrimidine; e.g., cytidine and/or uridine).

In some embodiments of any of the aspects, an saRNA as described herein comprises 25% to 35%, 30% to 40%, 35% to 45%, 40% to 50%, 45% to 55%, 50% to 60%, 55% to 65%, 60% to 70%, 65% to 75%, 70% to 80%, 75% to 85%, 80% to 90%, 85% to 95%, 90% to 100%, 95% to 100%, or 99% to 100% modified nucleotides, corresponding to at least one specific nucleotide (e.g., a pyrimidine; e.g., cytidine and/or uridine).

In some embodiments of any of the aspects, an saRNA as described herein comprises 25%-50% modified nucleotides, corresponding to at least one specific nucleotide (e.g., a pyrimidine; e.g., cytidine and/or uridine). In some embodiments of any of the aspects, an saRNA as described herein comprises 51%-75% modified nucleotides, corresponding to at least one specific nucleotide (e.g., a pyrimidine; e.g., cytidine and/or uridine). In some embodiments of any of the aspects, an saRNA as described herein comprises 75%-99% modified nucleotides, corresponding to at least one specific nucleotide (e.g., a pyrimidine; e.g., cytidine and/or uridine). In some embodiments of any of the aspects, an saRNA as described herein comprises 100% modified nucleotides, corresponding to at least one specific nucleotide (e.g., a pyrimidine; e.g., cytidine and/or uridine).

In some embodiments of any of the aspects, an saRNA as described herein comprises 100% 5-methylcytidine (5mC) substituted for cytidine. In some embodiments of any of the aspects, an saRNA as described herein comprises 100% 5-hydroxymethyl-cytidine (5OHmC) substituted for cytidine. In some embodiments of any of the aspects, an saRNA as described herein comprises 100% 5-methyluridine (5mU) substituted for uridine. In some embodiments of any of the aspects, an saRNA as described herein comprises 100% 5-hydroxymethyl-uridine (5OHmU) substituted for uridine.

In some embodiments of any of the aspects, an saRNA as described herein comprises 100% 5-methylcytidine (5mC) substituted for cytidine and 100% 5-methyluridine (5mU) substituted for uridine. In some embodiments of any of the aspects, an saRNA as described herein comprises 100% 5-methylcytidine (5mC) substituted for cytidine and 100% 5-hydroxymethyl-uridine (5OHmU) substituted for uridine. In some embodiments of any of the aspects, an saRNA as described herein comprises 100% 5-hydroxymethyl-cytidine (5OHmC) substituted for cytidine and 100% 5-methyluridine (5mU) substituted for uridine. In some embodiments of any of the aspects, an saRNA as described herein comprises 100% 5-hydroxymethyl-cytidine (5OHmC) substituted for cytidine and 100% 5-hydroxymethyl-uridine (5OHmU) substituted for uridine.

In some embodiments of any of the aspects, an saRNA comprising at least 25% modified nucleotides expresses at least one cargo at a level greater than or equal to that of a corresponding saRNA with less than 25% modified nucleotides. As used herein, the phrase "corresponding saRNA with less than 25% modified nucleotides" refers to an saRNA with the same base sequence as the RNA comprising at least 25% modified nucleotides, when the base sequence uses adenosine, guanosine, uridine (and analogs thereof), and cytidine (and analogs thereof); modified nucleotides can be classified as analogs of the unmodified nucleotide (e.g., 5-methylcytidine and 5-hydroxymethylcytidine are classified as cytidine analogs; e.g., 5-methyluridine and 5-hydroxymethyluridine are classified as uridine analogs).

In some embodiments of any of the aspects, an saRNA comprising at least 25% modified nucleotides expresses at least one cargo at a level equal to that of a corresponding saRNA with less than 25% modified nucleotides. In some embodiments of any of the aspects, an saRNA comprising at least 25% modified nucleotides expresses at least one cargo at a level that is at least 1%, at least 5%, at least 10%, at least 20%, at least 30%, at least 40%, at least 50%, at least 60%, at least 70%, at least 80%, at least 90%, at least 100%, at least 2-fold, at least 3-fold, at least 4-fold, at least 5-fold, or at least 10-fold, greater, or more, than that of a corresponding saRNA with less than 25% modified nucleotides.

In embodiments wherein the saRNA comprises multiple types of modified nucleotides (e.g., at least two of 5-methylcytidine, 5-methyluridine, 5-hydroxymethyluridine, and 5-hydroxymethylcytidine), the percentage of each modified nucleotide can be the same as each other or can be different from each other. As a non-limiting example, in an saRNA comprising 25% modified cytidines, the saRNA can comprise 0% 5mC and 25% 5OHmC; 1% 5mC and 24% 5OHmC; 2% 5mC and 23% 5OHmC; 3% 5mC and 22% 5OHmC; 4% 5mC and 21% 5OHmC; 5% 5mC and 20% 5OHmC; 6% 5mC and 19% 5OHmC; 7% 5mC and 18% 5OHmC; 8% 5mC and 17% 5OHmC; 9% 5mC and 16% 5OHmC; 10% 5mC and 15% 5OHmC; 11% 5mC and 14% 5OHmC; 12% 5mC and 13% 5OHmC; 12.5% 5mC and 12.5% 5OHmC; 13% 5mC and 12% 5OHmC; 14% 5mC and 11% 5OHmC; 15% 5mC and 10% 5OHmC; 16% 5mC and 9% 5OHmC; 17% 5mC and 8% 5OHmC; 18% 5mC and 7% 5OHmC; 19% 5mC and 6% 5OHmC; 20% 5mC and 5% 5OHmC; 21% 5mC and 4% 5OHmC; 22% 5mC and 3% 5OHmC; 23% 5mC and 2% 5OHmC; 24% 5mC and 1% 5OHmC; or 25% 5mC and 0% 5OHmC.

As a non-limiting example, in an saRNA comprising 25% modified uridines, the saRNA can comprise 0% 5mU and 25% 5OHmU; 1% 5mU and 24% 5OHmU; 2% 5mU and 23% 5OHmU; 3% 5mU and 22% 5OHmU; 4% 5mU and 21% 5OHmU; 5% 5mU and 20% 5OHmU; 6% 5mU and 19% 5OHmU; 7% 5mU and 18% 5OHmU; 8% 5mU and 17% 5OHmU; 9% 5mU and 16% 5OHmU; 10% 5mU and 15% 5OHmU; 11% 5mU and 14% 5OHmU; 12% 5mU and 13% 5OHmU; 12.5% 5mU and 12.5% 5OHmU; 13% 5mU and 12% 5OHmU; 14% 5mU and 11% 5OHmU; 15% 5mU and 10% 5OHmU; 16% 5mU and 9% 5OHmU; 17% 5mU and 8% 5OHmU; 18% 5mU and 7% 5OHmU; 19% 5mU and 6% 5OHmU; 20% 5mU and 5% 5OHmU; 21% 5mU and 4% 5OHmU; 22% 5mU and 3% 5OHmU; 23% 5mU and 2% 5OHmU; 24% 5mU and 1% 5OHmU; or 25% 5mU and 0% 5OHmU.

In some embodiments of any of the aspects, an saRNA as described herein comprises less than 25% modified nucleotides. In some embodiments of any of the aspects, an saRNA as described herein comprises 0%, at most 1%, at most 2%, at most 3%, at most 4%, at most 5%, at most 6%, at most 7%, at most 8%, at most 9%, at most 10%, at most 11%, at most 12%, at most 13%, at most 14%, at most 15%, at most 16%, at most 17%, at most 18%, at most 19%, at most 20%, at most 21%, at most 22%, at most 23%, at most 24%, at most 25% modified nucleotides. In some embodiments of any of the aspects, an saRNA as described herein does not comprise any modified nucleotides.

In some embodiments of any of the aspects, the modified nucleotide is not a modified purine. In some embodiments of any of the aspects, the modified nucleotide is not a modified guanosine or adenosine. In some embodiments of any of the aspects, the modified nucleotide is not 7-Deazaadenosine, N1-Methyladenosine, N6-Methyladenosine, 6-Chloropurineriboside, 2-Amino-6-chloropurineriboside, 2-Aminoadenosine, 5-Methoxycytidine, 5-Formylcytidine, 5-Aminoallylcytidine, 5-Hydroxycytidine, Isoguanosine, Thienoguanosine, 2-Aminopurine-riboside, 8-Oxoguanosine, 5-Carboxymethylesteruridine, Thienouridine, 5-Methoxyuridine, 5-Carboxyuridine, 2-Thiouridine, N1-Propylpseudouridine, N1-Methoxymethylpseudouridine, N1-Ethylpseudouridine, Pseudouridine, or N1-Methylpseudouridine.

In some embodiments of any of the aspects, an saRNA as described herein is substituted using the template of SEQ ID NO: 2 or a nucleic acid sequence that is at least about 75%, at least about 80%, at least about 85%, at least about 90%, at least about 91%, at least about 92%, at least about 93%, at least about 94%, at least about 95%, at least about 96%, at least about 97%, at least at least about 98%, at least about 99%, or 100%, identical to SEQ ID NO: 2 that maintains the same function (e.g., self-replication), or a codon-optimized version thereof. In some embodiments of any of the aspects, at least one cargo is inserted between the AflII and NdeI cut sites of SEQ ID NO: 2. In some embodiments of any of the aspects, at least one cargo is inserted between nucleotides 7627 and 7628 of SEQ ID NO: 2.

In some embodiments of any of the aspects, an saRNA as described herein saRNA is substituted using the template of SEQ ID NO: 5 or a nucleic acid sequence that is at least about 75%, at least about 80%, at least about 85%, at least about 90%, at least about 91%, at least about 92%, at least about 93%, at least about 94%, at least about 95%, at least about 96%, at least about 97%, at least at least about 98%, at least about 99%, or 100%, identical to SEQ ID NO: 5 that maintains the same function (e.g., self-replication), or a codon-optimized version thereof.

In some embodiments of any of the aspects, the pyrimidine comprises cytidine, and the modified nucleotide comprises 5-methylcytidine and/or 5-hydroxymethylcytidine, and the substituted saRNA comprises SEQ ID NO: 6 or a nucleic acid sequence that is at least about 75%, at least about 80%, at least about 85%, at least about 90%, at least about 91%, at least about 92%, at least about 93%, at least about 94%, at least about 95%, at least about 96%, at least about 97%, at least at least about 98%, at least about 99%, or 100%, identical to SEQ ID NO: 6 that maintains the same function (e.g., self-replication), or a codon-optimized version thereof.

In some embodiments of any of the aspects, the pyrimidine comprises uridine, and the modified nucleotide comprises 5-methyluridine and/or 5-hydroxymethyluridine, and the substituted saRNA comprises SEQ ID NO: 7 or a nucleic acid sequence that is at least about 75%, at least about 80%, at least about 85%, at least about 90%, at least about 91%, at least about 92%, at least about 93%, at least about 94%, at least about 95%, at least about 96%, at least about 97%, at least at least about 98%, at least about 99%, or 100%, identical to SEQ ID NO: 7 that maintains the same function (e.g., self-replication), or a codon-optimized version thereof.

Caps and Initiating Nucleotides

In multiple aspects, described herein are saRNAs comprising a 5' cap, which is found on the 5' end of the saRNA molecule. In some embodiments of any of the aspects, the 5' cap is derived from at least one virus. In some embodiments of any of the aspects, the 5' cap is derived from at least one alphavirus. In some embodiments of any of the aspects, the 5' cap is selected from the group consisting of cap-0, cap-1, and cap-2. The 5' cap can be involved in translation, nucleocytoplasmic transport, splicing, and/or stabilization of saRNA against 5' exonucleolytic degradation.

In eukaryotes, the 5' cap, referred to as cap-0, is found on the 5' end of an RNA molecule. Cap-0 consists of a guanine nucleotide connected to mRNA via a 5' to 5' triphosphate linkage. This guanosine is methylated on the 7 position directly after capping in vivo by a methyltransferase. Cap-0 can also be referred to as a 7-methylguanylate cap, abbreviated m7G. In some embodiments of any of the aspects, an saRNA as described herein comprises cap-0. In some embodiments of any of the aspects, an saRNA as described herein comprises a m7G 5' cap. ARCA (Anti-Reverse Cap Analog) consisting of 3'-O-Me-m7G(5')ppp(5')G is a non-limiting example of a reagent for producing an saRNA comprising a 5' Cap0.

In multicellular eukaryotes and some viruses, further 5' cap modifications exist, including the methylation of the 2' hydroxy-groups of the first 2 ribose sugars of the 5' end of the RNA. cap-1 has a methylated 2'-hydroxy group on the first ribose sugar, while cap-2 has methylated 2'-hydroxy groups on the first two ribose sugars. In some embodiments of any of the aspects, the initiating nucleoside of an saRNA as described herein is methylated at the 2'O position of the ribose (Cap 1). In some embodiments of any of the aspects, Cap1 has the following chemical structure: m7GpppNm. CLEANCAP AU consisting of m7G(5')ppp(5')(2'OMeA)pU is a non-limiting example of a reagent for producing an saRNA comprising a 5' Cap1. In some embodiments of any of the aspects, the initiating nucleotide and the subsequent nucleotide of an saRNA as described herein are both methylated at the 2'O position of the ribose (Cap2). In some embodiments of any of the aspects, Cap2 has the following chemical structure: m7GpppNmNm.

In some embodiments of any of the aspects, the initiating nucleotide directly proximal to the 5' cap in an saRNA as described herein comprises an adenosine or adenosine analog. In some embodiments of any of the aspects, the initiating nucleotide directly proximal to the 5' cap in an saRNA as described herein comprises a guanosine or guanosine analog. In some embodiments of any of the aspects, the first two initiating nucleotides directly proximal to the 5' cap in an saRNA as described herein comprises: in position 1 an adenosine or adenosine analog and in position 2 a uridine or a uridine analog. In some embodiments of any of the aspects, the first three initiating nucleotides directly proximal to the 5' cap in an saRNA as described herein comprises: in position 1 a guanosine or guanosine analog, in position 2 an adenosine or adenosine analog, and in position 3 a uridine or a uridine analog.

In some embodiments of any of the aspects, the initiating nucleotide of an saRNA as described herein comprises an adenosine or adenosine analog, and the initiating nucleotide of the saRNA is methylated at the 2'O position of the ribose (Cap1).

In some embodiments of any of the aspects, the initiating nucleotide of an saRNA as described herein comprises an adenosine or adenosine analog, and the initiating nucleotide and the subsequent nucleotide of the saRNA are both methylated at the 2'O position of the ribose (Cap2).

In some embodiments of any of the aspects, the initiating nucleotide of an saRNA as described herein comprises a guanosine or guanosine analog, and wherein the initiating nucleotide of the saRNA is methylated at the 2'O position of the ribose (Cap1).

In some embodiments of any of the aspects, the initiating nucleotide of an saRNA as described herein comprises a guanosine or guanosine analog, and wherein the initiating nucleotide and the subsequent nucleotide of the saRNA are both methylated at the 2'O position of the ribose (Cap2).

In some embodiments of any of the aspects, the initiating nucleotide of an saRNA as described herein comprises an adenosine or adenosine analog, and the 5' cap is a m7G 5' cap-0. In some embodiments of any of the aspects, the initiating nucleotide of an saRNA as described herein comprises a guanosine or guanosine analog, and the 5' cap is a m7G 5' cap-0.

Non-Limiting Examples of Nucleic Acid Modifications

It is further contemplated herein that the nucleic acids described herein (e.g., DNA, saRNA) can be chemically modified to enhance stability or other beneficial characteristics. The nucleic acids described herein can be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) sugar modifications (e.g., at the 2' position or 4' position) or replacement of the sugar, as well as (c) backbone modifications, including modification or replacement of the phosphodiester linkages. Specific examples of nucleic acid compounds useful in the embodiments described herein include, but are not limited, to nucleic acids containing modified backbones or no natural internucleoside linkages. Nucleic acids having modified backbones include, among others, those that do not have a phosphorus atom in the backbone. For the purposes of this specification, and as sometimes referenced in the art, modified nucleic acids that do not have a phosphorus atom in their internucleoside backbone can also be considered to be oligonucleosides. In some embodiments of any of the aspects, the modified nucleic acid can have a phosphorus atom in its internucleoside backbone.

Modified nucleic acid backbones can include, for example, phosphorothioates, chiral phosphorothioates, phosphorodithioates, phosphotriesters, aminoalkylphosphotriesters, methyl and other alkyl phosphonates including 3-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3-5' linkages, 2'-5' linked analogs of these, and those) having inverted polarity wherein the adjacent pairs of nucleoside units are linked 3-5' to 5-3' or 2'-5' to 5'-2'. Various salts, mixed salts and free acid forms are also included. Modified nucleic acid backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and $CH_2$ component parts, and oligonucleosides with heteroatom backbones, and in particular $—CH_2—NH—CH_2—$, $—CH_2—N(CH_3)—O—CH_2—$[known as a methylene (methylimino) or MMI backbone], $—CH_2—O—N(CH_3)—CH_2—$, $—CH_2—N(CH_3)—N(CH_3)—CH_2—$and $—N(CH_3)—CH_2—CH_2—$[wherein the native phosphodiester backbone is represented as $—O—P—O—CH_2—$].

In other nucleic acid mimetics, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

The nucleic acid can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, Or. et al., (2007) Mol. Canc. Ther. 6(3):833-843; Grunweller, A. et al., (2003) Nucleic Acids Research 31(12):3185-3193).

Modified nucleic acids can also contain one or more substituted sugar moieties. The nucleic acids described herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include $O[(CH_2)_nO]$ $mCH_3$, $O(CH_2)$,$OCH_3$, $O(CH_2)_nNH_2$, $O(CH_2)_nCH_3$, $O(CH_2)_nONH_2$, and $O(CH_2)_nON[(CH_2)_nCH_3)]_2$, where n is from 1 to about 10. In some embodiments of any of the aspects, nucleic acids include one of the following at the 2' position: C1 to C10 lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of a nucleic acid, or a group for improving the pharmacodynamic properties of a nucleic acid, and other substituents having similar properties. In some embodiments of any of the aspects, the modification includes a 2' methoxyethoxy (2'-O—$CH_2CH_2OCH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$, also described in examples herein below.

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the nucleic acid, particularly the 3' position of the sugar on the 3' terminal nucleotide or in 2'-5' linked dsRNAs and the 5' position of 5' terminal nucleotide. Nucleic acids may also have sugar mimetics such as cyclobutyl moieties in place of the pentofuranosyl sugar.

The preparation of the modified nucleic acids, backbones, and sugars described above are well known in the art.

Another modification of a nucleic acid featured in the invention involves chemically linking to the nucleic acid to one or more ligands, moieties or conjugates that enhance the activity, cellular distribution, pharmacokinetic properties, or cellular uptake of the nucleic acid. Such moieties include but are not limited to lipid moieties such as a cholesterol moiety (Letsinger et al., Proc. Natl. Acid. Sci. USA, 1989, 86:6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

Exemplary Viral Components

In some embodiments of any of the aspects, at least one component of the saRNAs described herein are derived from at least one virus. As non-limiting examples, at least one non-structural protein, a subgenomic promoter (SGP), 5' conserved sequence element (5' CSE), 5' untranslated region (5' UTR), 3' untranslated region (3' UTR), and/or 3' at least one conserved sequence element (3' CSE) can be derived from at least one virus. For example, in some embodiments, the saRNAs described herein can self-replicate due to inclusion of conserved sequence elements (CSEs) derived from at least one virus, located on the 5' and 3' ends of the RNA in combination with protein machinery (RNA-dependent RNA polymerase or RdRp derived from at least one virus). In some embodiments, the saRNA can also include amplification of a sub-genomic RNA, which can encode the cargo of interest, from a subgenomic promoter (SGP) derived from a virus that is recognized by the RdRp.

As used herein, the term "derived from" refers to the origin or source, and can include naturally occurring, recombinant, unpurified, or purified molecules, such as nucleic acids or polypeptides. In some embodiments of any of the aspects, "derived from" includes mutation and/or maturation of any of the nucleic acids or polypeptides as described herein. As a non-limiting example, at least one of the non-structural proteins (nsp1-4), each derived from at least one virus, can be mutated and/or matured compared to the wild-type sequence(s), e.g., to increase the amount and/or duration of cargo expression. Non-limiting examples of non-structural protein mutations include: nsP2 A1979G (nucleic acid), G656G (amino acid); nsP2 G3936C (nucleic acid), G1309R (amino acid); nsP3 A431IG (nucleic acid), K1434E (amino acid): nsP3 A4758G (nucleic acid), S1583G (amino acid); nsP3 G4796T (nucleic acid), E1595D (amino acid); and/or nsP3 G4944A (nucleic acid), V1645M (amino acid). As another non-limiting example, at least one of the non-coding conserved sequence elements (e.g., 5' UTR, 5' CSE, SGP, 3' CSE, 3' UTR), each derived from at least one virus, can be mutated and/or matured compared to the wild-type sequence(s), e.g., to increase the replication rate of the RNA. For example, at least one of the non-coding conserved sequence elements (e.g., 5' UTR) can be mutated or matured to comprise A-rich regions, which can accelerate RNA replication. See e.g., Li et al., Scientific Reports volume 9, Article number: 6932 (2019); Perkovic et al., Molecular Therapy Volume 31, Issue 6, P1636-1646 (2023); the contents of each of which are incorporated herein by reference in their entireties.

In some embodiments of any of the aspects, an nsp1, nsp2, nsp3, nsp4, SGP, 5' UTR, 3' UTR, 5' CSE, and/or 3' CSE in an saRNA described herein are derived from the same virus. In some embodiments of any of the aspects, at least one of an nsp1, nsp2, nsp3, nsp4, SGP, 5' UTR, 3' UTR, 5' CSE, and/or 3' CSE in an saRNA described herein are derived from different viruses.

In some embodiments of any of the aspects, the component, e.g., RNA or polypeptide, derived from at least one virus, comprises the naturally occurring component, e.g., RNA or polypeptide, in the virus or is at least about 75%, at least about 80%, at least about 85%, at least about 90%, at least about 91%, at least about 92%, at least about 93%, at least about 94%, at least about 95%, at least about 96%, at least about 97%, at least at least about 98%, at least about 99%, or 100%, identical to the naturally occurring component, e.g., RNA or polypeptide, in the virus.

In some embodiments of any of the aspects, the component, e.g., RNA or polypeptide, derived from at least one virus, maintains the function of the naturally occurring component, e.g., RNA or polypeptide, in the virus or maintains at least about 75%, at least about 80%, at least about 85%, at least about 90%, at least about 91%, at least about 92%, at least about 93%, at least about 94%, at least about 95%, at least about 96%, at least about 97%, at least at least about 98%, at least about 99%, or 100%, of the function of to the naturally occurring component, e.g., RNA or polypeptide, in the virus.

The phrase "derived from at least one virus" language can include any virus. Non-limiting examples of such viruses include: Venezuela Equine Encephalitis Virus (VEEV), Semliki Forest Virus (SFV), Sindbis Virus (SIN), Chikungunya Virus (CHIKV), Eastern Equine Encephalitis Virus (EEEV), Mayaro Virus (MAYV), Getah Virus (GETV), Ross River Virus (RRV), Una Virus (UNAV), Middleburg Virus (MIDV), O'nyong nyong virus (ONNV), Barmah Forest Virus (BFV), Mucambo Virus (MUCV), Tonate Virus (TONV), Everglades Virus (EVEV), Rio Negro Virus (RNV), Turnip Rosette Virus (TROV), Highlands J Virus (HJV), Western Equine Encephalitis Virus (WEEV), Fig Mosaic Emaravirus (FMV), Aura Virus (AURAV), Kunjin Virus (KUN), Measles virus (MV), Coronavirus (CoV), Rabies virus (RABV), and Vesicular Stomatitis virus (VSV).

In some embodiments of any of the aspects, at least one component of the saRNAs described herein are derived from at least one alphavirus. Non-limiting examples of such alphaviruses include: Aura Virus (AURAV), Barmah Forest Virus (BFV), Bebaru virus, Caaingua virus, Cabassou virus, Chikungunya Virus (CHIKV), Eastern Equine Encephalitis Virus (EEEV), Eliat virus, Everglades Virus (EVEV), Fort Morgan virus, Getah Virus (GETV), Highlands J Virus (HJV), Madariaga virus, Mayaro Virus (MAYV), Middleburg Virus (MIDV), Mosso das Pedras virus, Mucambo Virus (MUCV), Ndumu virus, O'nyong nyong virus (ONNV), Pixuna virus, Rio Negro Virus (RNV), Ross River Virus (RRV), Salmon pancreas disease virus, Semliki Forest Virus (SFV), Sindbis Virus (SIN), Southern elephant seal virus, Tonate Virus (TONV), Trocara virus, Una Virus (UNAV), Venezuela Equine Encephalitis Virus (VEEV), Western Equine Encephalitis Virus (WEEV), and Whataroa virus. In some embodiments of any of the aspects, at least one component of the saRNAs described herein are derived from Venezuela Equine Encephalitis Virus (VEEV).

Alphavirus is a genus of RNA viruses, the sole genus in the Togaviridae family. Alphaviruses belong to group IV of the Baltimore classification of viruses, with a positive-sense, single-stranded RNA genome. The alphaviruses are small, spherical, enveloped viruses with a genome of a single strand of positive-sense RNA. The total genome length ranges between 11,000 and 12,000 nucleotides, and the genome has a 5' cap and a 3' poly-A tail. The four non-structural protein genes are encoded in the 5' two-thirds of the genome, while the three structural proteins are translated from a subgenomic mRNA colinear with the 3' one-third of the genome. There are two open reading frames (ORFs) in the genome, nonstructural and structural. The first is non-structural and encodes proteins (nsP1-nsP4) necessary for transcription and replication of viral RNA. The second encodes three structural proteins: the core nucleocapsid protein C, and the envelope proteins P62 and E1.

In some embodiments of any of the aspects, the saRNAs described herein do not comprise structural proteins derived from at least one virus. In some embodiments of any of the aspects, the saRNAs described herein do not comprise structural proteins derived from at least one alphavirus. In some embodiments of any of the aspects, the saRNAs described herein do not comprise structural proteins derived from VEEV (e.g., do not comprise C, P62, or E1).

In some embodiments of any of the aspects, the saRNAs described herein do not comprise capsid or envelope proteins derived from at least one virus. In some embodiments of any of the aspects, the saRNAs described herein do not comprise capsid or envelope proteins derived from at least one alphavirus. In some embodiments of any of the aspects, the saRNAs described herein do not comprise capsid or envelope proteins derived from VEEV.

Non-Structural Proteins

In some embodiments of any of the aspects, the saRNAs described herein comprise at least one non-structural protein derived from at least one virus. In some embodiments of any of the aspects, the saRNAs described herein comprise at least one non-structural protein derived from at least one alphavirus. In some embodiments of any of the aspects, the saRNAs described herein comprise at least one non-structural protein derived from VEEV. Alphavirus nonstructural proteins can be selected from the four nonstructural proteins (nsP1-4) which are produced as a single polyprotein constitute the virus' replication machinery. For example, in VEEV and other alphaviruses, nsp1 is a methyl/guanylyl-transferase involved with RNA capping; nsp2 is a cysteine protease, helicase, and NTPase; nsp3 is a polyADP-ribose hydroxylase; and nsp4 is an RNA-dependent RNA polymerase (RdRp). In some embodiments of any of the aspects, the saRNAs described herein comprise at least one non-structural protein that functions as an RNA-dependent RNA polymerase (RdRp) and allows for replication of the saRNA (e.g., +RNA to −RNA to +RNA) and/or production of the subgenomic RNA (e.g., −RNA to sgRNA using the SGP).

In some embodiments of any of the aspects, the saRNAs described herein comprise an nsP1 derived from an alphavirus, an nsP2 derived from an alphavirus, an nsP3 derived from an alphavirus, and/or an nsP4 derived from an alphavirus, or any combination thereof. For example, an saRNA described herein can comprise any of the combinations of non-structural proteins shown in Table 5, each derived from an alphavirus, which can be the same or different species of alphavirus. As a non-limiting example, an saRNA described herein can comprise an nsP1 derived from an alphavirus, an nsP2 derived from an alphavirus, an nsP3 derived from an alphavirus, and an nsP4 derived from an alphavirus. In some embodiments of any of the aspects, an saRNA described herein comprises from 5' to 3': nsP1, nsP2, nsP3, and nsP4, each derived from a species of alphavirus, which each can be the same or different species of alphavirus. In some embodiments of any of the aspects, the 5' region of an saRNA described herein comprises from 5' to 3': nsP1, nsP2, nsP3, and nsP4, each derived from a species of alphavirus, which each can be the same or different species of alphavirus.

TABLE 5

Exemplary non-structural protein combinations in saRNAs described herein

| nsP1 | nsP2 | nsP3 | nsP4 |
|---|---|---|---|
| X | | | |
| | X | | |
| X | X | | |
| | | X | |
| X | | X | |
| | X | X | |
| X | X | X | |
| | | | X |
| X | | | X |
| | X | | X |
| X | X | | X |
| | | X | X |
| X | | X | X |
| | X | X | X |
| X | X | X | X |

In some embodiments of any of the aspects, the saRNAs described herein comprise an nsP1 derived from a strain of VEEV, an nsP2 derived from a strain of VEEV, an nsP3 derived from a strain of VEEV, and/or an nsP4 derived from a strain of VEEV, or any combination thereof. For example, an saRNA described herein can comprise any of the combinations of non-structural proteins shown in Table 5, each derived from a strain of VEEV, which can be the same or different strains of VEEV. As a non-limiting example, an saRNA described herein can comprise an nsP1 derived from a strain of VEEV, an nsP2 derived from a strain of VEEV, an nsP3 derived from a strain of VEEV, and an nsP4 derived from a strain of VEEV. In some embodiments of any of the aspects, an saRNA described herein comprises from 5' to 3': nsP1, nsP2, nsP3, and nsP4, each derived from a strain of VEEV, which each can be the same or different strain of VEEV. In some embodiments of any of the aspects, the 5' region of an saRNA described herein comprises from 5' to 3': nsP1, nsP2, nsP3, and nsP4, each derived from a strain of VEEV, which each can be the same or different strain of VEEV.

In some embodiments of any of the aspects, an saRNA described herein encodes for the amino acid sequence of SEQ ID NO: 4 and/or SEQ ID NO: 23, or an amino acid sequence that is at least about 75%, at least about 80%, at least about 85%, at least about 90%, at least about 91%, at least about 92%, at least about 93%, at least about 94%, at least about 95%, at least about 96%, at least about 97%, at least at least about 98%, at least about 99%, or 100%, identical to SEQ ID NO: 4 and/or SEQ ID NO: 23,, that maintains its function (e.g., at least one nsP1-nsP4 function; e.g., saRNA replication; e.g., an RNA-dependent RNA polymerase).

In some embodiments of any of the aspects, an saRNA described herein comprises nonstructural proteins comprising one of nucleotides 62-7543 of SEQ ID NO: 2 (DNA or the corresponding RNA sequence), nucleotides 62-7543 of SEQ ID NO: 5, nucleotides 45-7526 of SEQ ID NO: 6, nucleotides 45-7526 of SEQ ID NO: 7, or a nucleic acid sequence that is at least about 75%, at least about 80%, at least about 85%, at least about 90%, at least about 91%, at least about 92%, at least about 93%, at least about 94%, at least about 95%, at least about 96%, at least about 97%, at least at least about 98%, at least about 99%, or 100%, identical to one of nucleotides 62-7543 of SEQ ID NO: 2 (DNA or the corresponding RNA sequence), nucleotides 62-7543 of SEQ ID NO: 5, nucleotides 45-7526 of SEQ ID NO: 6, nucleotides 45-7526 of SEQ ID NO: 7, or a corresponding RNA sequence from codon-optimized version thereof.

Conserved Sequence Elements

In some embodiments of any of the aspects, the saRNAs described herein comprise at least one conserved sequence element (CSE) derived from at least one virus. In some embodiments of any of the aspects, the saRNAs described herein comprise at least one conserved sequence element (CSE) derived from at least one alphavirus. In some embodiments of any of the aspects, the conserved sequence element(s) are conserved across multiple species of alphaviruses. In some embodiments of any of the aspects, the saRNAs described herein comprise at least one conserved sequence element (CSE) derived from VEEV. In some embodiments of any of the aspects, the conserved sequence element(s) can interact with the RdRp encoded by the saRNA (e.g., nsP1-4) and allow for replication of the saRNA. In some embodiments of any of the aspects, the conserved sequence element(s) comprise secondary structures (e.g., hairpins) for interaction with the RdRp encoded by the saRNA (e.g., nsP1-4). In some embodiments of any of the aspects, the conserved sequence element(s) are non-coding, i.e., do not encode polypeptides and are not translated.

As a non-limiting example, analysis of alphavirus genome sequences has identified four sequence elements conserved across the genus (CSEs): the 5' untranslated region (UTR), a 51 nt 5' CSE within nsP1, the subgenomic promoter (or junction) region, and a 3' CSE within a 3' UTR. In some embodiments of any of the aspects, an saRNA as described herein comprises at least one of the following conserved sequence elements, each derived from at least one alphavirus: a 5' UTR, a 5' CSE, a SGP, and/or a 3' CSE within a 3' UTR. In some embodiments of any of the aspects, an saRNA as described herein comprises a 5' UTR, a 5' CSE, a SGP, and/or a 3' CSE within a 3' UTR, each derived from at least one alphavirus. In some embodiments of any of the aspects, an saRNA as described herein comprises a 5' UTR, a 5' CSE, a SGP, and/or a 3' CSE within a 3' UTR, each derived from VEEV. See e.g., Hyde et al., "The 5' and 3' ends of alphavirus RNAs—Non-coding is not non-functional," Virus Research 206 (2015): 99-107, the contents of which are incorporated here by reference in their entirety.

In some embodiments of any of the aspects, the saRNAs described herein comprise at least one 5' conserved sequence element (5' CSE) derived from at least one virus. In some embodiments of any of the aspects, the saRNAs described herein comprise at least one 5' conserved sequence element (5' CSE) derived from at least one alphavirus. In some embodiments of any of the aspects, the saRNAs described herein comprise at least one 5' conserved sequence element (5' CSE) derived from VEEV.

The conserved 5' sequence element (5' CSE) can be contained in the nsp1 coding sequence. The conserved 5' sequence element (5' CSE) can be about 51 nucleotides (nt) long, or about 40-60 nt long. The 5' CSE can be dependent on viral machinery (e.g., nsP1-4) used to generate the saRNA. For VEEV, the 5' CSE can comprise: aagcaggtcactgataatgaccatgctaatgccagagcgttttcgcatctg, SEQ ID NO: 10 (see e.g., nucleotides 149-199 of SEQ ID NO: 2, nucleotides 149-199 of SEQ ID NO: 5, nucleotides 132-182 of SEQ ID NOs: 6-7).

In some embodiments of any of the aspects, the saRNAs described herein comprise at least one 3' conserved sequence element (3' CSE) derived from at least one virus. In some embodiments of any of the aspects, the saRNAs described herein comprise at least one 3' conserved sequence element (3' CSE) derived from at least one alphavirus. In some embodiments of any of the aspects, the saRNAs described herein comprise at least one 3' conserved sequence element (3' CSE) derived from VEEV.

The conserved 3'-conserved sequence element (3' CSE) can be encoded in the 3' UTR. The conserved 3' sequence element (3' CSE) can be about 70 nucleotides (nt) long, or about 60-80 nt long. The 3' CSE can be dependent on the viral machinery (e.g., nsP1-4) encoded in the saRNA to replicate itself. For VEEV, the 3' CSE is in the 3' UTR sequence and can comprise: catgccgccttaaaattttattttattttttcttttcttttccgaatcggattttgtttttaatatttc, SEQ ID NO: 9 (see e.g., nucleotides 7673-7742 of SEQ ID NO: 2, nucleotides 8393-8462 of SEQ ID NO: 5, nucleotides 8376-8445 of SEQ ID NOs: 6-7). The 3'CSE, which is highly conserved in at least 27 alphaviral genomes, can comprise an 85% to 90% AU-rich sequence.

In some embodiments of any of the aspects, a conserved sequence element comprises SEQ ID NO: 9, SEQ ID NO: 10 or a nucleic acid sequence that is at least about 75%, at least about 80%, at least about 85%, at least about 90%, at least about 91%, at least about 92%, at least about 93%, at least about 94%, at least about 95%, at least about 96%, at least about 97%, at least at least about 98%, at least about 99%, or 100%, identical to SEQ ID NO: 9 or SEQ ID NO: 10, that maintains its function (e.g., at least one nsP1-nsP4 function; e.g., saRNA replication; e.g., an RNA-dependent RNA polymerase).

In some embodiments of any of the aspects, the saRNAs described herein comprise at least one 5' conserved sequence element (5' CSE) and at least one 3' conserved sequence element (3' CSE), each derived from at least one virus. In some embodiments of any of the aspects, the saRNAs described herein comprise at least one 5' conserved sequence element (5' CSE) and at least one 3' conserved sequence element (3' CSE), each derived from at least one alphavirus. In some embodiments of any of the aspects, the saRNAs described herein comprise at least one 5' conserved sequence element (5' CSE) and at least one 3' conserved sequence element (3' CSE), each derived from VEEV.

In some embodiments of any of the aspects, the saRNAs described herein comprise at least one subgenomic promoter (SGP) derived from at least one virus. In some embodiments of any of the aspects, the SGP is 3' (downstream) of the at least one nonstructural proteins and 5' (upstream) of the 5' UTR and at least one cargo. In some embodiments of any of the aspects, the saRNAs described herein comprise at least one subgenomic promoter (SGP) derived from at least one alphavirus. In some embodiments of any of the aspects, the saRNAs described herein comprise at least one subgenomic promoter (SGP) derived from VEEV.

The subgenomic promoter (SGP) can be located at the end of nsp4 and contains sequences within and after the coding sequence of nsp4. The SGP can be dependent on viral machinery (e.g., nsP1-4; e.g., RdRP) to generate the subgenomic RNA (sgRNA) of the saRNA. The subgenomic promoter controls expression of sgRNA from anti-sense template RNA independently of its genomic length counterpart. In some embodiments of any of the aspects, the strength of the subgenomic promoter (SGP) leads to more copies of the sgRNA compared to the full-length+RNA. In the context of alphaviruses, the higher concentration of the sgRNA compared to the full-length+RNA can allow for a higher concentration of translated structural proteins compared to translated non-structural proteins. In the context of the saRNAs described herein, the higher concentration of the sgRNA compared to the full-length+RNA can allow for a higher concentration of the at least one cargo (which can be a translated protein or a non-coding RNA, as described further herein) compared to translated non-structural proteins.

The sequence for the SGP in VEEV can comprise: SEQ ID NO: 11,

```
                                             SEQ ID NO: 11
agcttggcaaacctctggcagcagacgatgaacatgatgatgacaggag

aagggcattgcatgaagagtcaacacgctggaaccgagtgggtattctt

tcagagctgtgcaaggcagtagaatcaaggtatgaaaccgtaggaactt

ccatcatagttatggccatgactactctagctagcagtgttaaatcatt

cagctacctgagaggggcccctataactctctacggctaacctgaatgg

actacgacatagtctagtccgccaag,
```

(see e.g., nucleotides 7308-IDC-28 DNA M 7578 of SEQ ID NO: 2; see e.g., nucleotides 7308-7578 of SEQ ID NO: 5; see e.g., nucleotides 7291-7561 of SEQ ID NOs: 6-7).

In some embodiments of any of the aspects, a subgenomic promoter (SGP) comprises SEQ ID NO: 11 or a nucleic acid sequence that is at least about 75%, at least about 80%, at least about 85%, at least about 90%, at least about 91%, at least about 92%, at least about 93%, at least about 94%, at least about 95%, at least about 96%, at least about 97%, at least at least about 98%, at least about 99%, or 100%, identical to SEQ ID NO: 11, that maintains its function (e.g., replication of the subgenomic RNA (sgRNA); e.g., replication of the at least one cargo encoded by the saRNA).

In some embodiments of any of the aspects, the saRNAs described herein comprise at least one 5' conserved sequence element (5' CSE), at least one 3' conserved sequence element (3' CSE), and at least one subgenomic promoter (SGP), each derived from at least one virus. In some embodiments of any of the aspects, the saRNAs described herein comprise at least one 5' conserved sequence element (5' CSE), at least one 3' conserved sequence element (3' CSE), and at least one subgenomic promoter (SGP), each derived from at least one alphavirus. In some embodiments of any of the aspects, the saRNAs described herein comprise at least one 5' conserved sequence element (5' CSE), at least one 3' conserved sequence element (3' CSE), and at least one subgenomic promoter (SGP), each derived from VEEV.

In some embodiments of any of the aspects, the saRNAs described herein comprise at least one 5' untranslated region (5' UTR) derived from at least one virus. In some embodiments of any of the aspects, the 5' UTR is 3' (downstream) of the SGP and 5' (upstream) of the at least one SGP. In some embodiments of any of the aspects, the saRNAs described herein comprise at least one 5' untranslated region (5' UTR) derived from at least one alphavirus. In some embodiments of any of the aspects, the saRNAs described herein comprise at least one 5' untranslated region (5' UTR) derived from VEEV.

In some embodiments of any of the aspects, the saRNAs described herein comprise at least one 3' untranslated region (3' UTR) derived from at least one virus. In some embodiments of any of the aspects, the 3' UTR is 3' (downstream) of the at least one cargo and 5' (upstream) of the poly-A tail. In some embodiments of any of the aspects, the saRNAs described herein comprise at least one 3' untranslated region (3' UTR) derived from at least one alphavirus. In some embodiments of any of the aspects, the saRNAs described herein comprise at least one 3' untranslated region (3' UTR) derived from VEEV.

In some embodiments of any of the aspects, the saRNAs described herein comprise at least one 5' untranslated region (5' UTR) and at least one 3' untranslated region (3' UTR) derived from at least one virus. In some embodiments of any of the aspects, the saRNAs described herein comprise at least one 5' untranslated region (5' UTR) and at least one 3' untranslated region (3' UTR) derived from at least one alphavirus. In some embodiments of any of the aspects, the saRNAs described herein comprise at least one 5' untranslated region (5' UTR) and at least one 3' untranslated region (3' UTR) derived from VEEV.

Exemplary Cargos

The saRNAs described herein encode for and express at least one cargo of interest. In some embodiments of any of the aspects, an saRNA as described herein comprises 1, 2, 3, 4, 5, 6, 7, 8, 9, 10, or more cargos. In some embodiments of any of the aspects, the at least one cargo is 3' (downstream) of the subgenomic promoter and 5' untranslated region (UTR) and 5' (upstream) of the 3' untranslated region (UTR) and polyA tail.

In some embodiments of any of the aspects, the cargo comprises at least one cargo protein. In some embodiments of any of the aspects, the cargo comprises at least one cargo peptide. In some embodiments of any of the aspects, the cargo comprises at least one cargo protein and at least one cargo peptide. In some embodiments of any of the aspects, the cargo comprises at least two cargo proteins. Non-limiting examples of ways to separate each cargo protein include: a self-cleaving peptide domain, an internal ribosome entry site (IRES), or a separate promoter (e.g., a subgenomic promoter) between each cargo protein. The self-cleaving peptide domain can be a 2A peptide, for example, selected from the group consisting of P2A, E2A, F2A and T2A. An IRES is an RNA element that allows for translation initiation in a cap-independent manner.

In some embodiments of any of the aspects, the at least one cargo protein is viral, bacterial, protozoan, mammalian, or plant in origin. In some embodiments of any of the aspects, the at least one cargo peptide is viral, bacterial, protozoan, mammalian, or plant in origin.

In some embodiments of any of the aspects, the cargo comprises a chimeric antigen receptor (CAR). In some embodiments of any of the aspects, an saRNA as described herein encodes for and expresses a CAR is selected from the group consisting of: (a) a conventional CAR; (b) an ON-CAR; (c) an OFF-CAR system; (d) an ON/OFF-CAR; (e) an inhibitory CAR; or (f) a split, universal, programmable and reconfigurable (SUPRA) CAR system. For further details concerning such exemplary CARs, see e.g., U.S. patent Ser. Nos. 11/059,864 and 11/530,252; Li et al. Cancer Cell 40, 1-12 (2022); Li et al. Nat Med. 28(10): 2133-2144 (2022); the contents of each of which are incorporated herein by reference in their entireties.

In some embodiments of any of the aspects, an saRNA as described herein encodes for and expresses at least one conventional CAR. In some embodiments of any of the aspects, the conventional CAR comprises (e.g., from 5' to 3', or from N- to C-terminus): (a) an extracellular binding domain; (b) a transmembrane domain; and (c) at least one intracellular signaling domain.

In some embodiments of any of the aspects, an saRNA as described herein encodes for and expresses at least one ON-CAR. In some embodiments of any of the aspects, the ON-CAR comprises (e.g., from 5' to 3', or from N- to C-terminus): (a) an extracellular binding domain; (b) a transmembrane domain; (c) at least one intracellular signaling domain; and (d) a repressible protease domain that cleaves and degrades the ON-CAR in the absence of a protease inhibitor.

In some embodiments of any of the aspects, an saRNA as described herein encodes for and expresses at least one OFF-CAR system, or at least one component thereof. In some embodiments of any of the aspects, the OFF-CAR system comprises: (a) a first polypeptide comprising (e.g., from 5' to 3', or from N- to C-terminus): (i) an extracellular binding domain; (ii) a transmembrane domain; and (iii) a peptide domain; and (b) a second polypeptide comprising (e.g., from 5' to 3', or from N- to C-terminus): (i) a repressible protease domain that can bind specifically to the peptide domain in the absence of a protease inhibitor; and (ii) at least one intracellular signaling domain. In some embodiments of any of the aspects, at least one domain is moved from the first polypeptide to the second polypeptide of the OFF-CAR system, or from the second polypeptide to the first polypeptide of the OFF-CAR system. As a non-limiting example, the first polypeptide can comprise the repressible protease, and the second polypeptide can comprise the peptide domain. In some embodiments of any of the aspects, the second polypeptide further comprises a transmembrane domain.

In some embodiments of any of the aspects, the peptide domain is selected from the group consisting of: K5-66, K5-66-A, K5-66-B, K6-10, K6-10A, K6-10B K5-66-R, CP5-46, CP5-46-4D5E, CP5-46-A, CP5-46A-4D5E, Ant-CP5-46A-4D5E, and apo NS3a reader (ANR) peptides.

In some embodiments of any of the aspects, an saRNA as described herein encodes for and expresses at least one ON/OFF-CAR. In some embodiments of any of the aspects, the ON/OFF-CAR comprises (e.g., from 5' to 3', or from N- to C-terminus): (a) an extracellular binding domain; (b) a transmembrane domain; (c) at least one intracellular signaling domain; (d) a repressible protease domain that cleaves and degrades the ON/OFF-CAR in the absence of a protease inhibitor; and (e) a drug-inducible degron domain.

In some embodiments of any of the aspects, the repressible protease domain comprises hepatitis C virus (HCV) nonstructural protein 3 (NS3). In some embodiments of any of the aspects, the NS3 is catalytically active (e.g., ON-CAR, ON/OFF CAR). In some embodiments of any of the aspects, the NS3 is catalytically inactive (i.e., dead; e.g., OFF-CAR). For NS3, the catalytic triad can comprise His-57, Asp-81, and Ser-139. Accordingly, a catalytically inactive NS3 protease can comprise a nonsynonymous mutation at any one of His-57, Asp-81, and Ser-139, or another inactivating mutation as described herein. In some embodiments of any of the aspects, the catalytically inactive N33 protease comprises an S139A mutation.

In some embodiments of any of the aspects, a CAR as described herein comprises at least one protease cleavage site. As used herein, the term "protease cleavage site" refers to a specific sequence or sequence motif recognized by and cleaved by the repressible protease. A cleavage site for a protease includes the specific amino acid sequence or motif recognized by the protease during proteolytic cleavage and typically includes the surrounding one to six amino acids on either side of the scissile bond, which bind to the active site of the protease and are used for recognition as a substrate. In some embodiments of any of the aspects, the protease cleavage site can be any site specifically bound by and cleaved by the repressible protease. In some embodiments of any of the aspects, a CAR polypeptide as described herein (or the CAR polypeptide system collectively) comprises 1, 2, 3, 4, 5, or more protease cleavage sites. In some embodiments of any of the aspects, the CAR polypeptide comprises two protease cleavage sites. In embodiments comprising multiple protease cleavage sites, the multiple protease cleavage sites can be different individual protease cleavage sites or multiple copies of the same protease cleavage sites, or a combination of the foregoing.

As a non-limiting example, during HCV replication, the NS3-4A serine protease is responsible for the proteolytic cleavage at four junctions of the HCV polyprotein precursor: NS3/NS4A (self-cleavage), NS4A/NS4B, NS4B/NS5A, and NS5A/NS5B. Accordingly, the protease cleavage site of a CAR polypeptide as described herein can be a NS3/NS4A cleavage site, a NS4A/NS4B cleavage site, a NS4B/NS5A cleavage site, or a NS5A/NS5B cleavage site.

In some embodiments of any of the aspects, a CAR polypeptide as described herein is in combination with a protease inhibitor. As used herein, "in combination with" refers to two or more substances being present in the same formulation in any molecular or physical arrangement, e.g., in an admixture, in a solution, in a mixture, in a suspension, in a colloid, in an emulsion. The formulation can be a homogeneous or heterogeneous mixture. In some embodiments of any of the aspects, the active compound(s) can be comprised by a superstructure, e.g., nanoparticles, liposomes, vectors, cells, scaffolds, or the like, said superstructure is which in solution, mixture, admixture, suspension, etc., with the CAR polypeptide or CAR polypeptide system. In some embodiments of any of the aspects, the CAR polypeptide is bound to a protease inhibitor bound to the repressible protease. In some embodiments of any of the aspects, the CAR polypeptide is bound specifically to a protease inhibitor bound to the repressible protease.

In some embodiments of any of the aspects, the CAR polypeptide is in combination with 1, 2, 3, 4, 5, or more protease inhibitors. In some embodiments of any of the aspects, the CAR polypeptide is in combination with one protease inhibitor. In embodiments comprising multiple protease inhibitors, the multiple protease inhibitors can be different individual protease inhibitors or multiple copies of the same protease inhibitor, or a combination of the foregoing.

In some embodiments of any of the aspects, the protease inhibitor is grazoprevir (abbreviated as GZV or GZP; see e.g., PubChem CID: 44603531). In some embodiments of any of the aspects, the protease inhibitor is danoprevir (DNV; see e.g., PubChem CID: 11285588). In some embodiments of any of the aspects, the protease inhibitor is an approved NS3 protease inhibitor, such as but not limited to grazoprevir, danoprevir, simeprevir, asunaprevir, ciluprevir, boceprevir, sovaprevir, paritaprevir, ombitasvir, paritaprevir, ritonavir, dasabuvir, and telaprevir. Additional non-limiting examples of NS3 protease inhibitors are listed in McCauley and Rudd, Hepatitis C virus NS3/4a protease inhibitors, Current Opinion in Pharmacology 2016, 30:84-92; the content of which is incorporated herein by reference in its entirety.

In some embodiments of any of the aspects, the drug-inducible degron domain comprises an IKAROS family zinc finger 3 (IKZF3) domain capable of being bound and activated to degrade the CAR by the drug lenalidomide or pomalidomide.

In some embodiments of any of the aspects, an saRNA as described herein encodes for and expresses at least one inhibitory CAR. In some embodiments of any of the aspects, the inhibitory CAR comprises (e.g., from 5' to 3', or from N- to C-terminus): (a) an extracellular binding domain; (b) a transmembrane domain; and (c) an inhibitory domain.

In some embodiments of any of the aspects, the inhibitory domain comprises a Killer Cell Inhibitory Receptor (KIR) domain. In some embodiments of any of the aspects, the inhibitory domain comprises at least one immunoreceptor tyrosine-based inhibitory motifs (ITIMs). In some embodiments, an ITIM comprises S/I/V/LxYxxI/V/L, SEQ ID NO: 20, where x is any amino acid, Y is a tyrosine residue that can be phosphorylated, S is the amino acid Serine, I is the amino acid Isoleucine, and V is the amino acid Valine). In some embodiments of any of the aspects, the inhibitory domain comprises an inhibitory domain (e.g., an ITIM-comprising domain) from FcγRIIB, CTLA-4, PD-1, BTLA, CD72, NKG2A, CD31, SIGLEC, CD66, ILT, or LIR.

In some embodiments of any of the aspects, an saRNA as described herein encodes for and expresses at least one SUPRA CAR system or at least one component thereof. In some embodiments of any of the aspects, the SUPRA CAR system comprises: (a) a first polypeptide comprising (e.g., from 5' to 3', or from N- to C-terminus): (i) an extracellular binding domain; and (ii) a first member of an extracellular protein interaction domain; and (b) a second polypeptide comprising (e.g., from 5' to 3', or from N- to C-terminus): (i) a second member of the extracellular protein interaction domain that can bind specifically with the first member of the extracellular protein interaction domain of the first polypeptide; (ii) a transmembrane domain; and (iii) at least one intracellular signaling domain.

In some embodiments of any of the aspects, at least one domain is moved from the first polypeptide to the second polypeptide of the SUPRA-CAR system, or from the second polypeptide to the first polypeptide of the SUPRA–CAR system. As a non-limiting example, the first polypeptide can comprise the second member of the extracellular protein interaction domain, and the second polypeptide can comprise the first member of the extracellular protein interaction domain. In some embodiments of any of the aspects, the first and second members of the extracellular protein interaction domain comprise a leucine zipper pair.

In some embodiments of any of the aspects, at least intracellular signaling domain in a CAR as described herein is selected from the group consisting of: TCRC; FcRy; FcRp; CD3zeta; CD3y; CD35; CD3s; CD3C; CD22; CD79a; CD79b; CD66d; CARD11; CD2; CD7; CD27; CD28; CD30; CD40; CD54 (ICAM); CD83; CD134 (OX40); CD137 (4-1BB); CD150 (SLAMFI); CD152 (CTLA4); CD223 (LAG3); CD270 (HVEM); CD273 (PD-L2); CD274 (PD-L1); CD278 (ICOS); DAP10; LAT; KD2C SLP76; TRIM; ZAP70; and 41BB. In some embodiments of any of the aspects, at least intracellular signaling domain in a CAR as described herein is derived from CD28 or CD3zeta.

In some embodiments of any of the aspects, the cargo comprises a CAR and at least one expression-enhancing protein. In some embodiments of any of the aspects, the expression enhancing protein is B18R. In some embodiments of any of the aspects, the expression enhancing protein is E3L.

In some embodiments of any of the aspects, the extracellular binding domain of a CAR as described herein comprises an antigen binding domain from an antibody. In some embodiments of any of the aspects, the extracellular binding domain of a CAR as described herein comprises a single-chain variable fragment (scFv).

In some embodiments of any of the aspects, the cargo comprises at least one domain responsive to an external input. In some embodiments of any of the aspects, the cargo comprises an antibody or fragment thereof. In some embodiments of any of the aspects, the antibody is a bispecific antibody. In some embodiments of any of the aspects, the cargo comprises a bispecific T cell engager (BiTE). In some embodiments of any of the aspects, a BiTE is a fusion protein comprising the extracellular binding domain of two antibodies. For example, one arm of the BiTE comprises an extracellular binding domain specific for a protein found on the surface of cytotoxic T cells (e.g., CD3), and the other arm of the BiTE comprises an extracellular binding domain specific for a specific protein found primarily on tumor cells (e.g., HER2, or other antigens as described herein). When both targets are engaged, the BiTE molecule forms a bridge between a cytotoxic T cell and the tumor cell, which permits the T cell to recognize the tumor cell and fight it through an infusion of toxic molecules.

In some embodiments of any of the aspects, the cargo comprises an extracellular domain that specifically binds to an antigen of interest. In some embodiments of any of the aspects, the antigen of interest is specific to and/or upregulated on certain cancer cells. Non-limiting examples of the antigen of interest for the cargo protein (e.g., CAR, antibody, BiTE, etc.) include: CD19, CD22, CD30, b-cell maturation antigen (BCMA), disialoganglioside GD2, human estrogen receptor 2 (HER2), G protein-coupled receptor 87 (GPR87), Fibroblast Activator Protein (FAP), CD20, receptor tyrosine kinase-like orphan receptor 1 (ROR1), carcinoembryonic antigen (CEA), mesothelin (MSLN), prostate-specific membrane antigen (PSMA), epidermal growth factor receptor variant III (EGFRvIII), Interleukin 13 receptor alpha 2 (IL13Rα2), and natural killer group 2 member D (NKG2D).

Additional non-limiting examples of tumor antigens that can be targeted include EphA2, HER2, AXL, GD2, Glypican-3, 5T4, 8H9, αvβ6 integrin, BCMA, B7-H3, B7-H6, CAIX, CA9, CD19, CD20, CD22, kappa light chain, CD30, CD33, CD38, CD44, CD44v6, CD44v7/8, CD70, CD123, CD138, CD171, CEA, CSPG4, EGFR, EGFRvIII, EGP2, EGP40, EPCAM, ERBB3, ERBB4, ErbB3/4, FAP, FAR, FBP, fetal AchR, Folate Receptor a, GD2, GD3, HLA-AI MAGE A1, HLA-A2, IL1 1Ra, IL13Rα2, KDR, Lambda, Lewis-Y, MCSP, Mesothelin, Muel, Mucl6, NCAM, NKG2D ligands, NY-ESO-1, PRAME, PSCA, PSC1, PSMA, ROR1, SURVIVIN, TAG72, TEM1, TEM8, VEGRR2, carcinoembryonic antigen, HMW-MAA, and VEGF receptors. Other exemplary antigens that can be targeted are antigens that are present with in the extracellular matrix of tumors, such as oncofetal variants of fibronectin, tenascin, or necrotic regions of tumors.

Additional tumor-selective molecules that can be targeted include any membrane protein or biomarker that is expressed or overexpressed in tumor cells including, but not limited to, integrins (e.g., integrin αvβ3, α5β1), EGF Receptor Family (e.g., EGFR2, Erbb2/HER2/neu, Erbb3, Erbb4), proteoglycans (e.g., heparan sulfate proteoglycans), disialogangliosides (e.g., GD2, GD3), B7-H3 (aka CD276), cancer antigen 125 (CA-125), epithelial cell adhesion molecule (EpCAM), vascular endothelial growth factor receptors 1 and 2 (VEGFR-1, VEGFR-2), CD52, carcinoembryonic antigen (CEA), tumor associated glycoproteins (e.g., TAG-72), cluster of differentiation 19 (CD19), CD20, CD22, CD30, CD33, CD40, CD44, CD74, CD152, mucin 1 (MUC1), tumor necrosis factor receptors (e.g., TRAIL-R2), insulin-like growth factor receptors, folate receptor a, transmembrane glycoprotein NMB (GPNMB), C—C chemokine receptors (e.g., CCR4), prostate specific membrane antigen (PSMA), recepteur d'origine nantais (RON) receptor, cytotoxic T-lymphocyte antigen 4 (CTLA4), and other tumor specific receptors or antigens.

Non-limiting examples of tumor antigens include the following: differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90Mac-2 binding protein\cyclophilin C-associated protein, TAAL6, TAG72, TLP, and TPS.

In some embodiments of any of the aspects, the tumor antigen is a tumor antigen described in International Application PCT/US2015/020606 or US Patent Applications US20170209492 or US20170335281, the contents of each of which are herein incorporated by reference in their entireties. In some embodiments, the tumor antigen is chosen from one or more of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fins-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (AbI) (bcr-ab1); tyrosinase; ephrin type-A receptor 2 (EphA2); Fucosyl GMi; sialyl Lewis adhesion molecule (sLe); ganglioside GM3 (aNeu5Ac(2-3)bDGalp(1-4) bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCRI); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-la); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYPIB1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAXS); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1). In some embodiments, the tumor antigen is GFRa4 (see e.g., Spinasanta, "The Endocrine Society's 97th Annual Meeting & Expo: Targeted Therapies in Medullary Thyroid Cancer" Mar. 13, 2015).

In some embodiments of any of the aspects, the extracellular binding domain comprises an anti-Her2 antibody. HER2 (human epidermal growth factor receptor 2) is a gene that plays a role in the development of breast cancer. Cancers that can be HER2 positive include breast, bladder, pancreatic, ovarian, and stomach cancers. Non-limiting examples of anti-Her2 antibodies include G98A, C6.5, ML39, H3B1 (e.g., SEQ ID NOs: 8, 41), scFv800E6, and trastuzumab. See e.g., Rudnick et al., Cancer Res. 2011 Mar. 15, 71(6): 2250-2259; Sommaruga et al. Appl Microbiol Biotechnol. 2011 August, 91(3):613-21; U.S. Pat. Nos. 5,977,322, 8,580,263, 8,703,427, 8,927,694, 10,188,742, 10,239,951, the contents of each of which are incorporated herein by reference in their entireties.

In some embodiments of any of the aspects, the extracellular binding domain comprises an anti-Axl antibody. AXL overexpression has been demonstrated in various cancer types, e.g., breast (Meric et al., Clin. Cancer Res. 8: 361-367, 2002; Berclaz et al., Ann. Oncol. 12: 819-824, 2001), colon (Chen et al., Int. J. Cancer 83: 579-584, 1999; Craven et al., Int. J. Cancer 60: 791-797, 1995), prostate (Jacob et al., Cancer Detect. Prey. 23: 325-332, 1999), lung (Wimmel et al., Eur J Cancer 37: 2264-2274, 2001), gastric (Wu et al., Anticancer Res 22: 1071-1078, 2002), ovarian (Sun et al., Oncology 66: 450-457, 2004), endometrial (Sun et al., Ann. Oncol. 14: 898-906, 2003), renal (Chung et al., DNA Cell Biol. 22: 533-540, 2003), hepatocellular (Tsou et al., Genomics 50:331-340, 1998), thyroid (Ito et al., Thyroid 12:971-975, 2002; Ito et al., Thyroid 9: 563-567, 1999), and esophageal carcinoma (Nemoto et al., 1997), furthermore in CML (Janssen et al., A novel putative tyrosine kinase receptor with oncogenic potential. Oncogene, 6: 2113-2120, 1991; Braunger et al., Oncogene 14:2619-2631 1997; O'Bryan et al., Mol Cell Biol 11:5016-5031, 1991), AML (Rochlitz et al., Leukemia 13: 1352-1358, 1999), osteosarcoma (Nakano et al., J. Biol. Chem. 270:5702-5705, 2003) melanoma (van Ginkel et al., Cancer Res 64:128-134, 2004) and in head and neck squamous cell carcinoma (Green et al., Br J. Cancer. 2006 94:1446-5, 2006). Moreover, AXL has been identified as a metastasis-associated gene that is upregulated in aggressive breast cancer cell lines compared to non-invasive cells. Non-limiting examples of anti-Axl antibodies include 11B7, 11D5, 10D12, and h #1 1B7-T18. See e.g., International Patent Application WO2010130751 or U.S. Pat. No. 8,841,424, the contents of each of which are incorporated herein by reference in their entireties.

In some embodiments of any of the aspects, the extracellular binding domain comprises an anti-CD19 antibody. Since CD19 is a marker of B cells, the protein has been used to diagnose cancers that arise from this type of cell—notably B cell lymphomas, acute lymphoblastic leukemia (ALL), and chronic lymphocytic leukemia (CLL). The majority of B cell malignancies express normal to high levels of CD19. Non-limiting examples of anti-CD19 antibodies include A3B1, FMC63, FMC63-28Z, SEQ ID NO: 94; see e.g., U.S. Pat. No. 10,221,245, 8,906,682, 10,421,810, the contents of each of which are incorporated herein by reference in their entireties.

In some embodiments of any of the aspects, the cargo comprises a ligand, a cell surface receptor, a transcription factor, a cytokine, a chemokine, an enzyme, and/or an antibody. In some embodiments of any of the aspects, the cargo comprises least one ligand. In some embodiments of any of the aspects, the cargo comprises at least one cell surface receptor. In some embodiments of any of the aspects, the cargo comprises least one transcription factor. In some embodiments of any of the aspects, the cargo comprises least one cytokine. In some embodiments of any of the aspects, the cargo comprises least one chemokine. In some embodiments of any of the aspects, the cargo comprises least one enzyme. In some embodiments of any of the aspects, the cargo comprises least one antibody.

In some embodiments of any of the aspects, the cargo comprises at least one non-coding RNA. For example, the non-coding RNA can be selected from the group consisting of short interfering RNA (siRNA), small hairpin RNA (shRNA), and microRNA. In some embodiments of any of the aspects, the cargo comprises at least one siRNA. In some embodiments of any of the aspects, the cargo comprises at least one shRNA. In some embodiments of any of the aspects, the cargo comprises at least one microRNA.

In some embodiments of any of the aspects, the cargo comprises at least one vaccine-associated antigen. As used herein, the term "vaccine-associated antigen" refers to a foreign (e.g., microbial) substance that can illicit an immune response in a subject administered the antigen, e.g., as a vaccination against the foreign substance (e.g., microbe).

In some embodiments of any of the aspects, the vaccine-associated antigen comprises at least one protein encoded by a genome of a virus. Non-limiting examples of viruses expressing such an antigen include: Rift valley fever, Crimean-Congo haemorrhagic fever, Lassa fever, Chikungunya Virus (CHIKV), Nipah Virus (NiV), respiratory syncytial virus (RSV), Ebola virus, Marburg virus, West Nile virus, Venezuela equine encephalitis, yellow fever virus, Japanese encephalitis virus, western equine encephalitis virus, eastern equine encephalitis, cytomegalovirus (CMV), human immunodeficiency virus (HIV), influenza virus, Zika virus, middle eastern respiratory syndrome coronavirus (MERS-CoV), severe acute respiratory syndrome coronavirus (SARS-CoV), severe acute respiratory syndrome coronavirus 2 (SARS-CoV-2), human papillomavirus (HPV), herpes virus, rotavirus, varicella-zoster virus (VZV), dengue virus, hepatitis A virus, hepatitis B virus, rubella virus, poliovirus, and rabies virus.

In some embodiments of any of the aspects, the vaccine-associated antigen comprises an antigen selected from the group consisting of: influenza virus hemagglutinin, Severe acute respiratory syndrome coronavirus 2 (SARS-CoV-2) Spike protein, and Human respiratory syncytial virus (RSV) Fusion glycoprotein.

In some embodiments of any of the aspects, the vaccine-associated antigen comprises one of SEQ ID NOs: 13-16, 22 or an amino acid sequence that is at least about 75%, at least about 80%, at least about 85%, at least about 90%, at least about 91%, at least about 92%, at least about 93%, at least about 94%, at least about 95%, at least about 96%, at least about 97%, at least at least about 98%, at least about 99%, or 100%, identical to one of SEQ ID NOs: 13-16, 22. In some embodiments of any of the aspects, the vaccine-associated antigen is encoded by nucleotides 7599-11384 of SEQ ID NO: 21 or a nucleic acid sequence that is at least about 75%, at least about 80%, at least about 85%, at least about 90%, at least about 91%, at least about 92%, at least about 93%, at least about 94%, at least about 95%, at least about 96%, at least about 97%, at least at least about 98%, at least about 99%, or 100%, identical to nucleotides 7599-11384 of SEQ ID NO: 21. In some embodiments, the vaccine-associated antigen encoded and expressed by the saRNA maintains the same function of the wild-type viral protein (e.g., viral entry into a cell). In some embodiments, the vaccine-associated antigen encoded and expressed by the saRNA has an attenuated or inactive function compared to the function of the wild-type viral protein.

In some embodiments of any of the aspects, the cargo comprises at least one transcription factor. In some embodiments of any of the aspects, the transcription factor is a stem cell transcription factor. In some embodiments of any of the aspects, the transcription factor is selected from the group consisting of Octamer-Binding Transcription Factor 3 (Oct3, Oct4), Sex-Determining Region Y (SRY)-Box Transcription Factor 2 (Sox2), Kruppel-Like Factor 4 (Klf4), and cellular myelocytomatosis oncogene (c-Myc).

In some embodiments of any of the aspects, the cargo comprises at least one growth factor and/or cytokine. In some embodiments of any of the aspects, the growth factor or cytokine is selected from the list consisting of platelet-derived growth factor (PDGF), erythropoietin (EPO), vascular endothelial growth factor (VEGF), transforming growth factor-β1 (TGF-β1), fibroblast growth factor (FGF), human relaxin-2 (RLX2), alpha-melanocyte-stimulating hormone (alpha-MSH), insulin-like growth factor-I (IGF-I), epidermal growth factor (EGF), nerve growth factor (NGF), granulocyte-monocyte colony-stimulating factor (GMCSF), Thrombopoietin (TPO), Bone morphogenic protein (BMP), hepatocyte growth factor (HGF), growth/differentiation factor (GDF), a Neurotrophin, migration stimulating factor (MSF), and sarcoma growth factor (SGF).

In some embodiments of any of the aspects, the cargo comprises one or both Pappalysin-A1 (PAPPA1) and Pappalysin-A2 (PAPPA2).

In some embodiments of any of the aspects, the cargo comprises at least one interleukin. In some embodiments of any of the aspects, the cargo comprises at least one cognate receptor of an interleukin. In some embodiments of any of the aspects, the cargo comprises at least one receptor subunits for an interleukin. In some embodiments of any of the aspects, the interleukin is selected from the group consisting of IL-2, IL-4, IL-7, IL-10, IL-12, IL-13, and IL-15.

In some embodiments of any of the aspects, the cargo comprises at least one enzyme with antioxidant activity. In some embodiments of any of the aspects, the enzyme is selected from the group consisting of phospholipid hydroperoxide glutathione peroxidase, superoxide dismutase-1, superoxide dismutase-2, Bruton's tyrosine kinase, adenosine deaminase, and ecto-nucleoside triphosphate diphosphydrolase.

In some embodiments of any of the aspects, the cargo comprises glucagon-like peptide-1 (GLP-1) or a fragment thereof. As a non-limiting example, a bioactive form of glucagon-like peptide-1 (GLP-1) comprises amino acids 7-37 of GLP-1: HAEGTFTSDVSSYLEGQAAKEFIAWLVRGRG (SEQ ID NO: 17). In some embodiments of any of the aspects, GLP-1 comprises SEQ ID NO: 17 or an amino acid sequence that is at least about 75%, at least about 80%, at least about 85%, at least about 90%, at least about 91%, at least about 92%, at least about 93%, at least about 94%, at least about 95%, at least about 96%, at least about 97%, at least at least about 98%, at least about 99%, or 100%, identical SEQ ID NO: 17, that maintains its function (e.g., stimulate insulin secretion and/or inhibit glucagon secretion).

In some embodiments of any of the aspects, the cargo further comprises an endogenous insulin secretion signal (MALWMRLLPLLALLALWGPDPAAA, SEQ ID NO: 18)

and/or a furin cleavage site (RGRR, SEQ ID NO: 19). In some embodiments of any of the aspects, an saRNA comprising glucagon-like peptide-1 (GLP-1) or a fragment thereof can be used to treat diabetes and/or obesity.

In some embodiments of any of the aspects, at least one cargo is inserted between the AflII and NdeI cut sites of SEQ ID NO: 2. In some embodiments of any of the aspects, at least one cargo is inserted between nucleotides 7627 and 7628 of SEQ ID NO: 2. In some embodiments of any of the aspects, nucleotides 7634 to 8347 of SEQ ID NO: 5, nucleotides 7617 to 8330 of SEQ ID NO: 6, or nucleotides 7617 to 8330 of SEQ ID NO: 7, each corresponding to mCherry, is replaced with at least one cargo of interest, as described further herein.

In some embodiments of any of the aspects, at least one cargo comprises a detectable marker or a reporter molecule, including but not limited to a fluorescent protein or a detectable tag (e.g., c-Myc, HA, VSV-G, HSV, FLAG, V5, HIS, or biotin). In some embodiments of any of the aspects, an saRNA as described herein, especially those that are administered to a subject or those that are part of a pharmaceutical composition, do not encode for or comprise detectable markers that are immunogenic. In some embodiments of any of the aspects, an saRNA as described herein do not comprise or encode for GFP, mCherry, HA1, or any other immunogenic markers. In some embodiments of any of the aspects, an saRNA described herein that comprises a detectable marker can have the detectable marker removed at a later time, e.g., a removable (e.g., cleavable) detectable marker. In some embodiments of any of the aspects, an saRNA described herein that comprises a detectable marker can have the detectable marker replaced with a different detectable marker, as known in the art or described herein, e.g., a replaceable (e.g., interchangeable) detectable marker.

PolyA Tails

In multiple aspects, described herein are saRNAs comprising a polyA tail, which is found on the 3' end of the saRNA molecule. In some embodiments of any of the aspects, the polyA tail is derived from at least one virus. In some embodiments of any of the aspects, the polyA tail is derived from at least one alphavirus. In some embodiments of any of the aspects, the polyA tail is derived from VEEV.

A poly-A (polyadenylation) tail is a long chain of adenine nucleotides that is added to an RNA molecule during RNA processing to increase the stability of the molecule. In some embodiments, the poly-A tail can be between 20 and 30, between 30 and 50, between 50 and 100, or between 100 and 250 residues long. The poly-A tail makes the RNA molecule more stable and prevents its degradation. Additionally, the poly-A tail allows the mature RNA molecule to be exported from the nucleus and/or translated into a protein by ribosomes in the cytoplasm.

In some embodiments of any of the aspects, the saRNA comprises a polyA signal (e.g., AAUAAA) that leads to cleaving of the 3' end of the RNA to free a 3' hydroxyl and recruitment of a poly-A polymerase to add a chain of adenine nucleotides to the RNA. In some embodiments of any of the aspects, the polyA tail is encoded in the saRNA, such as by using a polyT sequence at the 5' end of a negative-strand template for the saRNA.

Nucleic Acids and Vectors

The saRNAs described herein can be encoded and/or expressed by nucleic acids and/or vectors. Accordingly, in one aspect described herein is a nucleic acid encoding or comprising an saRNA as described herein. In another aspect described herein is a vector encoding or comprising an saRNA as described herein.

In some embodiments of any of the aspects, the nucleic acid encoding or comprising an saRNA as described herein comprises DNA. In some embodiments of any of the aspects, the nucleic acid encoding or comprising an saRNA as described herein consists essentially of DNA. In some embodiments of any of the aspects, the nucleic acid encoding or comprising an saRNA as described herein consists of DNA.

In some embodiments of any of the aspects, a DNA molecule encoding an saRNA as described herein comprises one of SEQ ID NOs: 2 or 5 or a nucleic acid sequence that is at least about 75%, at least about 80%, at least about 85%, at least about 90%, at least about 91%, at least about 92%, at least about 93%, at least about 94%, at least about 95%, at least about 96%, at least about 97%, at least at least about 98%, at least about 99%, or 100%, identical to one of SEQ ID NOs: 2 or 5 that maintains the same function (e.g., self-replication), or a codon-optimized version thereof.

In some embodiments of any of the aspects, a DNA molecule encoding an saRNA as described herein comprises at least one regulatory sequence upstream of the encoded saRNA. In some embodiments of any of the aspects, a DNA molecule encoding an saRNA as described herein comprises a promoter for transcription of the saRNA using an RNA polymerase. In some embodiments of any of the aspects, a DNA molecule encoding an saRNA as described herein comprises a T7 promoter (see e.g., SEQ ID NO: 3, SEQ ID NO: 8, SEQ ID NO: 12; see e.g., nucleotides 1-17 of SEQ ID: 2, nucleotides 1-17 of SEQ ID: 5).

When the nucleic acid molecule that encodes any of the saRNAs described herein is expressed in a cell, a variety of transcription control sequences (e.g., promoter/enhancer sequences) can be used to direct its expression. The promoter can be a native promoter, e.g., the promoter of the at least one cargo protein in its endogenous context, which provides normal regulation of expression of the cargo protein. In some embodiments the promoter can be constitutive, i.e., the promoter is unregulated allowing for continual transcription of the saRNA and its associated cargo(s). A variety of conditional promoters also can be used, such as promoters controlled by the presence or absence of a molecule.

The precise nature of the regulatory sequences needed for expression can vary between species or cell types, but in general can include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences can include a promoter region which includes a promoter sequence for transcriptional control of the encoded saRNA. Regulatory sequences can also include enhancer sequences or upstream activator sequences as desired.

As used herein, an saRNA-encoding sequence and regulatory sequences are said to be "operably" joined when they are covalently linked in such a way as to place the expression or transcription of the saRNA-encoding sequence under the influence or control of the regulatory sequences. If it is desired that at least one cargo encoded in the saRNA be translated into a functional protein, two DNA sequences are said to be operably joined if induction of a promoter in the 5' regulatory sequences results in the transcription of the saRNA and if the nature of the linkage between the two DNA sequences does not (1) result in the introduction of a frame-shift mutation, (2) interfere with the ability of the promoter region to direct the transcription of the saRNA, or (3) interfere with the ability of the at least one cargo encoded in the saRNA to be translated into a protein.

A nucleic acid molecule that encodes an saRNA as described herein can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding an saRNA as described herein can also be accomplished by integrating the nucleic acid molecule into the genome.

In some embodiments, one or more of the saRNAs described herein is expressed in a recombinant expression vector or plasmid. FIGS. 81-91 contain schematics of exemplary vectors used for in vitro transcription of exemplary saRNAs. As used herein, the term "vector" refers to a polynucleotide sequence suitable for transferring nucleic acids (e.g., DNA encoding saRNAs as described herein) into a host cell. The vector can encompass any genetic element that is capable of replication when associated with the proper control elements and that can transfer nucleic acid sequences to cells. The term "vector" includes a plasmid, a cloning vector, an expression vector, naked DNA, a mini-chromosome, a chromosome, a transposon, a cosmid, a virus, virion, phage, and the like. See, for example, U.S. Pat. Nos. 4,980,285; 5,631,150; 5,707,828; 5,759,828; 5,888,783 and, 5,919,670, and, Sambrook et al, Molecular Cloning: A Laboratory Manual, 2nd Ed., Cold Spring Harbor Press (1989). One type of vector is a "plasmid," which refers to a circular double stranded DNA loop into which additional DNA segments are ligated. Another type of vector is a viral vector, wherein additional DNA segments are ligated into the viral genome. Certain vectors are capable of autonomous replication in a host cell into which they are introduced (e.g., bacterial vectors having a bacterial origin of replication and episomal mammalian vectors). Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" is used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

A cloning vector is one which is able to replicate autonomously or integrated in the genome in a host cell, and which is further characterized by one or more endonuclease restriction sites at which the vector can be cut in a determinable fashion and into which a desired DNA sequence (e.g., a DNA template for an saRNA as described herein) can be ligated such that the new recombinant vector retains its ability to replicate in the host cell. In the case of plasmids, replication of the desired sequence can occur many times as the plasmid increases in copy number within the host cell such as a host bacterium or just a single time per host before the host reproduces by mitosis. In the case of phage, replication can occur actively during a lytic phase or passively during a lysogenic phase.

An expression vector is one into which a desired DNA sequence (e.g., a DNA template for an saRNA as described herein) can be inserted by restriction and ligation such that it is operably joined to regulatory sequences and can be expressed as an saRNA transcript. Vectors can further contain one or more marker sequences suitable for use in the identification of cells which have or have not been transformed or transformed or transfected with the vector. Markers include, for example, genes encoding proteins which increase or decrease either resistance or sensitivity to antibiotics or other compounds (e.g., ampicillin resistance), genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). In certain embodiments, the vectors used herein are capable of autonomous replication and expression of the saRNAs present in the DNA segments to which they are operably joined. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (or RNA). That heterologous DNA (or RNA) is placed under operable control of transcriptional elements to permit the expression of the heterologous DNA in the host cell.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art. Non-limiting examples of a viral vector of this invention include an AAV vector, an adenovirus vector, a lentivirus vector, a retrovirus vector, a herpesvirus vector, an alphavirus vector, a poxvirus vector, a baculovirus vector, and a chimeric virus vector.

It should be understood that the vectors described herein can, in some embodiments, be combined with other suitable compositions and therapies. In some embodiments, the vector is episomal. The use of a suitable episomal vector provides a means of maintaining the nucleic acid of interest (e.g., encoding an saRNA as described herein) in the subject in high copy number extra chromosomal DNA thereby eliminating potential effects of chromosomal integration.

Compositions and Administration

The saRNAs described herein can be comprised by compositions, such as pharmaceutical compositions, as described further herein. In some embodiments, saRNAs described herein can be comprised by cells, such as eukaryotic cells. In some embodiments of any of the aspects, the cell is a human cell. In some embodiments the cells are immune cells. In some embodiments of any of the aspects, the cells are T cells, NK cells, Macrophages, or B cells. In some embodiments the cells are T lymphocyte cells. In some embodiments the cells are CD4+T lymphocyte cells.

In one aspect described herein is a composition comprising an saRNA as described herein. In one aspect described herein is a composition comprising a nucleic acid or vector comprising or expressing an saRNA as described herein. In one aspect described herein is a composition comprising a cell comprising or expressing an saRNA as described herein.

In one aspect described herein is a pharmaceutical composition comprising an saRNA as described herein and a pharmaceutically acceptable carrier. In one aspect described herein is a pharmaceutical composition comprising a nucleic acid or vector comprising or expressing an saRNA as described herein and a pharmaceutically acceptable carrier. In one aspect described herein is a pharmaceutical composition comprising a cell comprising or expressing an saRNA as described herein and a pharmaceutically acceptable carrier.

In some embodiments of any of the aspects, the saRNA is formulated as lipid nanoparticles (LNP). In some embodiments of any of the aspects, the lipid nanoparticle comprises a targeting moiety, specific for a cell or tissue of interest. As a non-limiting example, the LNP can be conjugated to an antibody, such as an anti-CD3 antibody, which is specific for T cells. In some embodiments, the LNPs are formulated with a lipid:oligonucleotide weight ratio of about 10:1. In some embodiments, the LNPs are formulated with a N:P ratio of about 10. In some embodiments, the LNPs are formulated with a N:P ratio of about 1, about 2, about 3, about 4, about 5, about 6, about 7, about 8, about 9, about 10, about 11, about 12, about 13, about 14, about 15, about 16, about 17, about 18, about 19, or about 20.

In another embodiment, the lipid nanoparticle has an average diameter less than 1000 nm, such as less than 500 nm, less than 300 nm, less than 200 nm, less than 150 nm, less than 100 nm or less than about 50 nm. In another embodiment the diameter ranges from 1000 nm to 50 nm, or from about 500 nm to 50 nm, or from about 300 nm to 50, or from 200 nm to 50, or from 100 nm to 50 nm. In another embodiment, the nanoparticle average diameter is less than about 100 nm.

In another embodiment, the population of the nanoparticle has a polydispersion index (PDI) of about 2 or less, or about 1 or less, or about 0.5 or less, or about 0.25 or less, or about 0.14 or less.

In another embodiment, the lipid nanoparticles possess a positive charge.

In another embodiment, the lipid nanoparticles possess a negative charge.

In another embodiment, the lipid nanoparticles do not possess an overall charge.

In some embodiments, lipids in the LNPs comprise ionizable lipids, cholesterol, phospholipids, and/or polyethylene glycol lipids. Further non-limiting examples of lipids for use in LNP formulations include DSPE, SM-102, DMG-PEG2K, DOPE, and/or cholesterol.

In some embodiments, the lipid nanoparticles can be formulated from one or more of cationic, anionic, neutral, ionizable, and/or zwitterionic lipids, non-limiting examples of which include: phosphatidylcholine, phosphatidylethanolamine, phosphatidylserine, phosphatidylinositol, phosphatidic acid, palmitoyloleryl phosphatidylcholine, lysophosphatidylcholine, lysophosphatidylethanolamine, dipalmitoylphosphatidylcholine, dioleoylphospbatidylcholine, dstearoylphosphatidylcholine dilinoleoylphosphatidylcholine, phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglyeerol (POPG), diacylphosphatidylcholine, diacylphosphatidyletbanolamine, ceramide, sphingomyelin, cephalin, cholesterol, cerebrosides and diacylglycerols, triglycerides, DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)), Trimyristin (DYNASAN 114), Tripalmitin (DYNASAN 116), Tristearin (DYNASAN 118), Mono-, di-, and triglyceride mixtures, Glyceryl stearates (IMWITOR 900), Glyceryl behenates (COMPRITOL 888 ATO), Glyceryl palmitostearates (PRECIROL ATO 5), stearic acid, Palmitic acid, DPPC, MSPC, DSPE-PEG2000, DSPE-PEG2500, Phosphatidylcholine, Soybean phosphatidylcholine, (4-hydroxybutyl)azanediyl bis(hexane-6,1-diyl)bis(2-hexyldecanoate), (2-hexyldecanoate), 2-[(polyethylene glycol)-2000]-N,N-ditetradecylacetamide, 1,2-distearoyl-sn-glycero-3-phosphocholine, cholesterol, heptadecan-9-yl 8-((2-hydroxyethyl)(6-oxo-6-(undecyloxy)hexyl)amino)octanoate, 1,2-dimyristoyl-rac-glycero-3-methoxypolyethylene glycol-2000, ALC-0315, ALC-0159, SM-102, DTOP, DDAB, DOGS, N-(1,2-dimyristyloxyprop-3-yl)-N,N-dimethyl-N-hydmxyethyl ammonium bromide ("DMRIE"), DODAP, DLinDMA, cKK-E12, OF-02, C12-200, MC3, DLinkC2DMA, ICE (Imidazol-based), HGT5000, HGT5001, HGT4003, N,N-dioleyl-N,N-dimethylammonium chloride ("DODAC"), N-(2,3dioleyloxy)propyl)-N,N, Ntrimethylammonium chloride ("DOTMA"), N-(2,3dioleoyloxy)propyl)-N,N,N-trimethylamntonium chloride ("DODAP, N,NdistearylN,N-dimethylammonium bromide ("DDAB"), 3-(N—(N,N-dimethylaminoethane)-carbamoyl) cholesterol ("DC-Chol"), DOSPA, DODMA and DMDMA, DODAC, 1,2-DiLinoleyloxy-N,N-dimethylaminopropane (DLinDMA), DMRIE, CLinDMA, CpLinDMA, DMOBA, DOcarbDAP, DLinDAP, DLincarbDAP, DLinCDAP, KLin-K-DMA, DLin-K-XTC2-DMA, 3-(4-(bis(2-hydroxydodecyl)amino)butyl)-6-(4-((2-hydroxydodecyl)(2-hydroxyundecyl)amino)butyl)-1,4-dioxane-2,5-dione, 4-(2,2-diocta-9,12-dienyl-[1,3]dioxolan-4-ylmethyl)-dimethylamine, DLinKDMA (see e.g., WO 2009/132131 A1, which is hereby incorporated by reference in its entirety), DLin-K-C2-DMA (see e.g., WO2010/042877, which is hereby incorporated by reference in its entirety), DLin-M-C3-DMA (see e.g., WO 2010/146740 and/or WO 2010/105209, which are hereby incorporated by reference in their entireties), 2-{4-[(3p)-cholest-5-en-3-yloxy]butoxy}-N,N-dimethyl-3-[(9Z,12Z)-octadeca-9,12-dienlyloxyl]propan-1-amine) (CLinDMA), 3-(5-(bis(2-hydroxydodecyl)amino)pentan-2-yl)-6-(5-((2-hydroxydodecyl)(2-hydroxyundecyl)amino)pentan-2-yl)-1,4-dioxane-2,5-dione, N1GL, N2GL, V1GL, LIPOFECTIN® (commercially available cationic lipid nanoparticles comprising DOTMA and 1,2dioleoyl-sn-3-phosphoethanolamine ("DOPE")), TRANSFECTAM®, and combinations thereof.

In some embodiments, the LNPs comprise one or more PEG-modified lipids. In some embodiments, the one or more PEG-modified lipids comprise a poly(ethylene) glycol chain of up to 5 kDa in length covalently attached to a lipid with alkyl chain(s) of $C_6$-$C_{20}$ length.

Other compounds lacking in phosphorus, such as sphingolipid, glycosphingolipid families, diacylglycerols and S-acyloxyacids, are also within the group designated as amphipathic lipids, which can be comprised by the LNPs described herein.

In some embodiments, the one or more cationic lipids comprised by the LNPs described herein are amino lipids. Amino lipids suitable for use in the LNPs described herein include those described in WO 2017180917, which is hereby incorporated by reference in its entirety. Exemplary amino lipids in WO 2017180917 include those described at paragraph [0744] such as DLin-MC3-DMA (MC3), (13Z, 16Z)—N,N-dimethyl-3-nonyldocosa-13,16-dien-1-amine (L608), and Compound 18 described in WO 2017180917. Other exemplary amino lipids include Compound 2, Compound 23, Compound 27, Compound 10, or Compound 20 described in WO 2017180917. Further amino lipids suitable for use in the LNPs described herein include those described in WO2017112865, which is hereby incorporated by reference. Exemplary amino lipids in WO 2017112865 include a compound according to one of formulae (I), (Ia1)-(Ia6), (Ib), (II), (IIa), (III), (IIIa), (IV), (17-1), (19-1), (19-11), and (20-1), and compounds of paragraphs [00185], [00201], [0276] in WO 2017112865. In some embodiments, cationic lipids suitable for use in the LNPs described herein include those described in WO2016118725, which is hereby incorporated by reference. Exemplary cationic lipids in WO2016118725 include those such as KL22 and KL25. In some embodiments, cationic lipids suitable for use in the LNPs described herein include those described in WO2016118724, which is hereby incorporated by reference. Exemplary cationic lipids in WO2016118725 include those such as KL10, 1,2-dilinoleyloxy-N,N-dimethylaminopropane (DLin-DMA), and KL25.

In some embodiments, the saRNA is formulated in a polymeric matrix. In some embodiments, the polymeric matrix can comprise one or more polymer, with or without at one or more lipids, to form nanoparticles.

In one embodiment, the polymeric matrix containing the saRNA is a reverse micelle nanoparticle which comprises two or more polymers, such as polyethylenes, polycarbonates, polyanhydrides, polyhydroxyacids, polypropylfumerates, polyglycerols, polycaprolactones, polyamides, polyacetals, polyethers, polyesters, poly(orthoesters), polycyanoacrylates, polyvinyl alcohols, polyurethanes, Poly (O-amino esters), polyphosphazenes, polyacrylates, polymethacrylates, polycyanoacrylates, polyureas, polystyrenes, or polyamines, or combinations thereof. In one embodiment, the polymeric matrix comprises one or more polyesters, polyanhydrides, polyethers, polyurethanes, polymethacrylates, polyacrylates or polycyanoacrylates. In one embodiment, the polymeric matrix comprises a polyalkylene glycol, such as polyethylene glycol. In another embodiment, the polymeric matrix comprises PLGA, PLA, PGA, or a polycaprolactone. In another embodiment, the polymeric matrix comprises a copolymer of two or more polymers, such as a copolymer of PLGA or PLA and PEG. The polymeric matrix can comprise PLGA or PLA and a copolymer of PLGA or PLA and PEG.

In another embodiment, the polymeric matrix comprises a lipid-terminated polyalkylene glycol and a polyester, such as a lipid-terminated PEG and PLGA. The lipid can be one such as 1,2 distearoyl-sn-glycero-3-phosphoethanolamine (DSPE), and salts thereof.

In one embodiment, the reverse micelle comprises an amphipathic lipid, such as lecithin, phosphatidylcholine, lipid A, cholesterol, dolichol, shingosine, sphingomyelin, ceramide, cerebroside, sulfatide, glycosylceramide, phytosphingosine, phosphatidylethanolamine, phosphatidylglycerol, phosphatidylinositol, phosphatidylserine, cardiolipin, phophatidic acid, or lysophophatides, or combinations thereof.

In some embodiments, the technology described herein relates to a pharmaceutical composition comprising an saRNA as described herein, and optionally a pharmaceutically acceptable carrier. In some embodiments, the active ingredients of the pharmaceutical composition comprise an saRNA as described herein. In some embodiments, the active ingredients of the pharmaceutical composition consist essentially of an saRNA as described herein. In some embodiments, the active ingredients of the pharmaceutical composition consist of an saRNA as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21)

polyesters, polycarbonates and/or polyanhydrides; (22) bulking agents, such as polypeptides and amino acids; (23) serum component, such as serum albumin, HDL and LDL; (24) C2-$C_1$ alcohols; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g., an saRNA as described herein.

In some embodiments, the pharmaceutical composition comprising an saRNA as described herein can be a parenteral dose form (i.e., administered or occurring elsewhere in the body than the mouth and alimentary canal). Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of saRNAs as disclosed within are well known to those skilled in the art. Non-limiting examples include, without limitation: sterile water; water for injection USP; saline solution; phosphate-based saline; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Pharmaceutical compositions comprising an saRNA as described herein can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the saRNA, and can be prepared by methods of pharmacy well known to those skilled in the art. See generally, Remington: The Science and Practice of Pharmacy, 21st Ed., Lippincott, Williams, and Wilkins, Philadelphia PA. (2005).

In some embodiments, the methods described herein comprise administering an effective amount of compositions described herein, e.g. an saRNA as described herein to a subject in order to alleviate a symptom of a disease or disorder. As used herein, "alleviating a symptom of a disease or disorder" is ameliorating any condition or symptom associated with the disease or disorder. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art.

In some embodiments of any of the aspects, the saRNA is formulated at a dose of about $5\times10^{-4}$ mg/kg. In some embodiments of any of the aspects, the saRNA is formulated at a dose of about $5\times10^{-3}$ mg/kg. In some embodiments of any of the aspects, the saRNA is formulated at a dose of about $5\times10^{-2}$ mg/kg. In some embodiments of any of the aspects, the saRNA is formulated at a dose of about $5\times10^{-1}$ mg/kg. In some embodiments of any of the aspects, the saRNA is formulated at a dose of about 1 ng. In some embodiments of any of the aspects, the saRNA is formulated at a dose of about 10 ng. In some embodiments of any of the aspects, the saRNA is formulated at a dose of about 100 ng. In some embodiments of any of the aspects, the saRNA is formulated at a dose of about 1000 ng. In some embodiments of any of the aspects, the saRNA is formulated at a dose of about 10,000 ng. In some embodiments of any of the aspects, the saRNA is formulated at a dose of about 2.5 μg. In some embodiments of any of the aspects, the saRNA can be formulated at a dose of about 0.1 μg to about 100 μg. In embodiments with a subject (e.g., human subject) of approximately 70 kg, saRNA can be formulated at a dose of about $1\times10^{-6}$ mg/kg to $1\times10^{-3}$ mg/kg.

For systemic administration, subjects can be administered a therapeutic amount of a composition comprising an saRNA as described herein, such as, e.g., $1\times10^{-6}$ mg/kg, $1\times10^{-5}$ mg/kg, $1\times10^{-4}$ mg/kg, $1\times10^{-3}$ mg/kg, $1\times10^{-2}$ mg/kg, 0.1 mg/kg, 0.5 mg/kg, 1.0 mg/kg or more.

The term "effective amount" as used herein refers to the amount of saRNA needed to alleviate at least one or more symptom of the disease or disorder, and relates to a sufficient amount of pharmacological composition to provide the desired effect. The term "therapeutically effective amount" therefore refers to an amount of saRNA that is sufficient to provide a particular alleviating effect when administered to atypical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the ED50 (the dose therapeutically effective in 50% of the population). The dosage can vary depending upon the dosage form employed and the route of administration utilized. A therapeutically effective dose can be estimated initially from cell culture assays. Also, a dose can be formulated in animal models to achieve a circulating plasma concentration range that includes the IC50 (i.e., the concentration of saRNA, which achieves a half-maximal inhibition of symptoms) as determined in cell culture, or in an appropriate animal model. Levels in plasma can be measured, for example, by PCR. The effects of any particular dosage can be monitored by a suitable bioassay. The dosage can be determined by a physician and adjusted, as necessary, to suit observed effects of the treatment.

The dosage ranges for the administration of the saRNA, according to the methods described herein depend upon, for example, the form of saRNA, its potency, and the extent to which symptoms, markers, or indicators of a condition described herein are desired to be reduced. The dosage should not be so large as to cause adverse side effects, such as an autoimmune reaction. Generally, the dosage will vary with the age, condition, and sex of the patient and can be determined by one of skill in the art. The dosage can also be adjusted by the individual physician in the event of any complication.

The efficacy of the saRNA in, e.g. the treatment of a condition described herein, or to induce a response as described herein can be determined by the skilled clinician. However, a treatment is considered “effective treatment,” as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g., pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters.

Efficacy can be assessed in animal models of a condition described herein or using in vitro assays. When using an experimental animal model or an in vitro assay, efficacy of treatment is evidenced when a statistically significant change in a marker is observed.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen.

In certain embodiments, an effective dose of a composition comprising an saRNA as described herein can be administered to a patient once. In certain embodiments, an effective dose of a composition comprising an saRNA as described herein can be administered to a patient repeatedly.

The dosing schedule can vary from once a week to daily depending on a number of clinical factors, such as the subject's sensitivity to the saRNA. The desired dose or amount can be administered at one time or divided into subdoses, e.g., 2-4 subdoses and administered over a period of time, e.g., at appropriate intervals through the day or other appropriate schedule. In some embodiments, administration can be one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an saRNA as described herein can be administered over a period of time, such as over a 5 minute, 10 minute, 15 minute, 20 minute, or 25 minute period.

In some embodiments, after an initial treatment regimen, the treatments can be administered on a less frequent basis. For example, after treatment biweekly for three months, treatment can be repeated once per month, for six months or a year or longer.

A variety of means for administering the compositions described herein to subjects are known to those of skill in the art. Such methods can include, but are not limited to intraocular, intraosseous (IO), intraperitoneal (IP), subcutaneous (SC), intravenous (IV), intramuscular (IM), intrarectal, intravaginal, intraarticular (IA), inhalation, or topical administration. Further non-limiting administration methods include oral, parenteral, intravenous, intramuscular, transdermal, airway (aerosol), pulmonary, cutaneous, injection, or intratumoral administration. Administration can be local or systemic.

In some embodiments of any of the aspects, an saRNA as described herein is administered as a monotherapy, e.g., another treatment for the disease or disorder is not administered to the subject.

In some embodiments of any of the aspects, the methods described herein can further comprise administering a second agent and/or treatment to the subject, e.g. as part of a combinatorial therapy. Non-limiting examples of a second agent and/or treatment can include a cancer therapy selected from the group consisting of: radiation therapy, surgery, gemcitabine, cisplatin, paclitaxel, carboplatin, bortezomib, AMG479, vorinostat, rituximab, temozolomide, rapamycin, ABT-737, PI-103; alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylmelamines including altretamine, triethylenemelamine, trietylenephosphoramide, triethylenethiophosphoramide and trimethylol melamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin gammalI and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomycins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In addition, the methods of treatment can further include the use of radiation or radiation therapy. Further, the methods of treatment can further include the use of surgical treatments.

The methods described herein can further comprise administering a second agent and/or treatment to the subject, e.g. as part of a combinatorial therapy. By way of non-limiting example, if a subject is to be treated for pain or inflammation according to the methods described herein, the subject can also be administered a second agent and/or treatment known to be beneficial for subjects suffering from pain or inflammation. Examples of such agents and/or treatments include, but are not limited to, non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; or opiates (e.g. endorphins, enkephalins, and dynorphin), steroids, analgesics, barbiturates, oxycodone, morphine, lidocaine, and the like.

In some embodiments of any of the aspects, the saRNAs described herein can be co-administered with synergistic therapeutics. Non-limiting examples of such synergistic therapeutics include RNA (e.g., siRNA, shRNA, miRNA), small-molecules, and/or checkpoint inhibitors. Such co-administration can increase activation, antigen presentation, and/or function of cells, including but not limited to T cells and dendritic cells.

Non-limiting examples of immune checkpoint inhibitors (ICIs) include: pembrolizumab (Keytruda®), nivolumab (Opdivo®), cemiplimab (Libtayo®), spartalizumab, camrelizumab (AiRuiKa™), sintilimab (TYVYT®), tislelizumab, toripalimab (Tuoyi™), dostarlimab (JEMPERLI), INCMGA00012, AMP-224, AMP-514 (MEDI0608), atezolizumab (Tecentriq®), avelumab (Bavencio®), envafolimab (KN035), cosibelimab (CK-301), AUNP12, CA-170, BMS-986189, BMS-936559 (MDX-1105), durvalumab (IMFINZI®), tremelimumab, and ipilimumab (Yervoy®). See e.g., U.S. Pat. Nos. 5,811,097, 5,855,887, 6,051,227, 6,682,736, 6,984,720, 7,595,048, 7,605,238, 7,943,743, 8,008,449, 8,217,149, 8,354,509, 8,383,796, 8,728,474, 8,735,553, 8,779,105, 8,779,108, 8,907,053, 8,900,587, 8,952,136, 9,067,999, 9,073,994, 9,683,048, 9,987,500, 10,160,736, 10,316,089, 10,441,655, 10,590,199, 11,225,522, US Patent Publication US2014341917; Storz et al., MAbs. 2016 January; 8(1): 10-26; the contents of each of which are incorporated herein by reference in their entireties.

Exemplary Uses of saRNAs

Described herein are exemplary uses of the saRNAs described herein. In one aspect, described herein is a method of expressing at least one cargo of interest in a cell, the method comprising contacting the cell with at least one saRNA as described herein. In some embodiments of any of the aspects, the cell is a human cell. In some embodiments, the saRNA is delivered to the cell in situ. In some embodiments, the saRNA is delivered to the cell ex vivo. In some embodiments of any of the aspects, the saRNA is delivered to the cell by electroporation. In some embodiments of any of the aspects, the saRNA is delivered to the cell by lipid nanoparticles. In some embodiments of any of the aspects, a plurality of distinct saRNAs is delivered to a mixture of cells.

In another aspect, described herein is a method of expressing at least one cargo in a subject in need thereof, the method comprising administering to the subject an effective amount of a pharmaceutical composition as described herein, e.g., encoding, expressing, or comprising at least one saRNA as described herein.

As used herein, a "subject" means a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of a disease or disorder. In some embodiments of any of the aspects, the subject is a human. In some embodiments of any of the aspects, the subject is a livestock animal. In some embodiments of any of the aspects, the subject is a domestic or tamed animal, such as a pet, including but not limited to a dog, cat, guinea pig, rabbit, rat, mouse, or hamster. In some embodiments of any of the aspects, the subject is a fish or a bird or a lizard or a snake. A subject can be male or female.

In some embodiments of any of the aspects, the subject has cancer. In some embodiments of any of the aspects, the subject is in need of vaccination for an infectious disease. In some embodiments of any of the aspects, the subject is in need of protein replacement therapy. In some embodiments of any of the aspects, the subject is in need of antibody therapy. In some embodiments of any of the aspects, the subject is in need of treatment for diabetes and/or obesity. In some embodiments of any of the aspects, the subject is in need of BITE therapy.

A subject can be one who has been previously diagnosed with or identified as suffering from or having such a condition in need of treatment or one or more complications related to such a condition, and optionally, have already undergone treatment for such a disease or disorder or the one or more complications related to that disease or disorder. Alternatively, a subject can also be one who has not been previously diagnosed as having that disease or disorder or one or more complications related to the disease or disorder. For example, a subject can be one who exhibits one or more risk factors for the disease or disorder or one or more complications related to the disease or disorder or a subject who does not exhibit risk factors. A "subject in need" of treatment for a particular condition can be a subject having that condition, diagnosed as having that condition, or at risk of developing that condition.

In some embodiments of any of the aspects, an saRNA as described herein increases the level of expression of a cargo protein in a cell, e.g., by at least 1%, at least 5%, at least 10%, at least 20%, at least 30%, at least 40%, at least 50%, at least 60%, at least 70%, at least 80%, at least 90%, at least 100%, at least 2-fold, at least 3-fold, at least 4-fold, at least 5-fold, or at least 10-fold, or more, as compared to a cell that does not comprise the saRNA.

In some embodiments of any of the aspects, use of a modified saRNA (e.g., comprising at least 25% modified nucleotides) has beneficial, unexpected results compared to a corresponding saRNA with less than 25% modified nucleotides.

In some embodiments of any of the aspects, the modified saRNA replicates at a level greater than or equal to that of an equivalent dose of a corresponding saRNA with less than 25% modified nucleotides. In some embodiments of any of the aspects, the modified saRNA replicates at a level equal to that of an equivalent dose of a corresponding saRNA with less than 25% modified nucleotides. In some embodiments of any of the aspects, the modified saRNA replicates at a level that is at least 1%, at least 5%, at least 10%, at least 20%, at least 30%, at least 40%, at least 50%, at least 60%, at least 70%, at least 80%, at least 90%, at least 100%, at least 2-fold, at least 3-fold, at least 4-fold, at least 5-fold, or at least 10-fold, greater, or more, than that of an equivalent dose of a corresponding saRNA with less than 25% modified nucleotides.

In some embodiments of any of the aspects, the modified saRNA expresses the cargo at a level greater than or equal to that of an equivalent dose of a corresponding saRNA with less than 25% modified nucleotides. In some embodiments of any of the aspects, the modified saRNA expresses the cargo at a level equal to that of an equivalent dose of a corresponding saRNA with less than 25% modified nucleotides. In some embodiments of any of the aspects, the modified saRNA expresses the cargo at a level that is at least 1%, at least 5%, at least 10%, at least 20%, at least 30%, at least 40%, at least 50%, at least 60%, at least 70%, at least 80%, at least 90%, at least 100%, at least 2-fold, at least 3-fold, at least 4-fold, at least 5-fold, or at least 10-fold, greater, or more, than that of an equivalent dose of a corresponding saRNA with less than 25% modified nucleotides.

In some embodiments of any of the aspects, the transfection efficiency of the modified saRNA is greater than or equal to that of an equivalent dose of a corresponding saRNA with less than 25% modified nucleotides. In some embodiments of any of the aspects, the transfection efficiency of the modified saRNA is equal to that of an equivalent dose of a corresponding saRNA with less than 25% modified nucleotides. In some embodiments of any of the aspects, the transfection efficiency of the modified saRNA is at a level that is at least 1%, at least 5%, at least 10%, at least 20%, at least 30%, at least 40%, at least 50%, at least 60%, at least 70%, at least 80%, at least 90%, at least 100%, at least 2-fold, at least 3-fold, at least 4-fold, at least 5-fold, or at least 10-fold, greater, or more, than that of an equivalent dose of a corresponding saRNA with less than 25% modified nucleotides.

In some embodiments of any of the aspects, the modified saRNA produces an early interferon response in the subject. In some embodiments of any of the aspects, the early interferon response is decreased compared to an equivalent dose of a corresponding saRNA with less than 25% modified nucleotides. In some embodiments of any of the aspects, the early interferon response is decreased by at least 1%, at least 5%, at least 10%, at least 20%, at least 30%, at least 40%, at least 50%, at least 60%, at least 70%, at least 80%, at least 90%, at least 100%, at least 2-fold, at least 3-fold, at least 4-fold, at least 5-fold, or at least 10-fold, greater, or more, compared to an equivalent dose of a corresponding saRNA with less than 25% modified nucleotides.

In some embodiments of any of the aspects, the cargo is expressed at a detectable level from the modified saRNA for an increased time period compared to an equivalent dose of a corresponding saRNA with less than 25% modified nucleotides. In some embodiments of any of the aspects, the cargo is expressed at a detectable level from the modified saRNA for a time period that is increased that is at least 1%, at least 5%, at least 10%, at least 20%, at least 30%, at least 40%, at least 50%, at least 60%, at least 70%, at least 80%, at least 90%, at least 100%, at least 2-fold, at least 3-fold, at least 4-fold, at least 5-fold, or at least 10-fold, greater, or more, compared to an equivalent dose of a corresponding saRNA with less than 25% modified nucleotides.

In some embodiments of any of the aspects, an saRNA as described herein permits tissue, organ, or cell-type specific expression of the cargo. In some embodiments of any of the aspects, a modified saRNA as described herein permits tissue, organ, or cell-type specific expression of the cargo.

In some embodiments of any of the aspects, the saRNA comprises greater than 50% substitution of uridine with 5-methyluridine. In some embodiments of any of the aspects, the saRNA comprising greater than 50% substitution of uridine with 5-methyluridine has increased kidney specific expression of the cargo compared to an equivalent dose of a corresponding saRNA comprising less than 50% substitution of uridine with 5-methyluridine. In some embodiments of any of the aspects, the kidney specific expression is increased by at least 1%, at least 5%, at least 10%, at least 20%, at least 30%, at least 40%, at least 50%, at least 60%, at least 70%, at least 80%, at least 90%, at least 100%, at least 2-fold, at least 3-fold, at least 4-fold, at least 5-fold, or at least 10-fold, greater, or more.

In some embodiments of any of the aspects, a modified saRNA modulates cellular differentiation of a cell containing the saRNA at a level equivalent to or greater than the level of modulation achieved with an equivalent dose of a corresponding saRNA with less than 25% modified nucleotides. In some embodiments of any of the aspects, a modified saRNA modulates cellular differentiation of a cell containing the saRNA at a level equivalent to the level of modulation achieved with an equivalent dose of a corresponding saRNA with less than 25% modified nucleotides. In some embodiments of any of the aspects, a modified saRNA modulates cellular differentiation of a cell containing the saRNA at a level that is at least 1%, at least 5%, at least 10%, at least 20%, at least 30%, at least 40%, at least 50%, at least 60%, at least 70%, at least 80%, at least 90%, at least 100%, at least 2-fold, at least 3-fold, at least 4-fold, at least 5-fold, or at least 10-fold, greater, or more, than the level of modulation achieved with an equivalent dose of a corresponding saRNA with less than 25% modified nucleotides.

In some embodiments of any of the aspects, a cell is modulated by expression of a stem cell transcription factor encoded by the saRNA. In some embodiments of any of the aspects, a cell is modulated by an saRNA as described herein to become a stem cell.

In some embodiments of any of the aspects, at least one cargo is expressed constitutively (i.e., in an ongoing manner) in the cell. In some embodiments of any of the aspects, at least one cargo is expressed constitutively (i.e., in an ongoing manner) in the subject.

In some embodiments of any of the aspects, the cargo comprises a chimeric antigen receptor. In some embodiments of any of the aspects, the cargo comprises multiple chimeric antigen receptors. In some embodiments of any of the aspects, the saRNA encodes and expresses a plurality of cargo proteins that are capable of interacting with each other. In some embodiments of any of the aspects, the interaction of the plurality of cargo proteins results in conditional activity of the cell transfected by the saRNA. In some embodiments of any of the aspects, the cargo proteins capable of interacting with each other are chimeric antigen receptors with activating and/or inhibitory functions. In some embodiments of any of the aspects, the cargo comprises 1, 2, 3, 4, 5, 6, 7, 8, 9, 10, or more chimeric antigen receptors. In some embodiments of any of the aspects, the cargo comprises a protein comprising a chimeric antigen receptor comprising an extracellular domain that senses at least one input signal. In some embodiments of any of the aspects, the cargo is a protein comprising at least one chimeric antigen receptor, and the input is a small molecule and/or a protein. In some embodiments of any of the aspects, the cargo is a protein comprising at least one domain responsive to an external input. In some embodiments of any of the aspects, the cargo is a protein comprising at least one repressible protease domain that responds to at least one protease inhibitor to regulate activity of the cargo.

In some embodiments of any of the aspects, the activity of the cargo protein expressed by the saRNA is controlled by administration of a small molecule and/or a protein and/or an RNA molecule. In some embodiments of any of the aspects, the RNA molecule is an aptamer. In some embodiments of any of the aspects, the protein is a chimeric antigen receptor (CAR), and the activity of the CAR is regulated by at least one small molecule-responsive domain. In some embodiments of any of the aspects, the activity of the cargo protein expressed by the saRNA is increased and/or decreased by administration of at least one small molecule. In some embodiments of any of the aspects, the at least one small molecule is a protease inhibitor or a molecule capable of interacting with at least one protein domain in the cargo protein.

In some embodiments of any of the aspects, a method as described herein comprises contacting a cell comprising at least one saRNA with at least one input to control the fate or function of the cell. In some embodiments of any of the aspects, a method as described herein comprises administering at least one input to control the fate or function of at least one cell in a subject, wherein the subject has previously been administered at least one saRNA as described herein.

In some embodiments of any of the aspects, the input is endogenous to the environment of the cell comprising the saRNA. In some embodiments of any of the aspects, the input is exogenous to the environment of the cell comprising the saRNA. In some embodiments of any of the aspects, the input comprises a cell, a protein, a small molecule, a specific wavelength or wavelengths of light, a specific temperature, and/or a magnetic field.

In some embodiments of any of the aspects, the input results in inhibition of a repressible protease domain in the cargo encoded by an saRNA as described herein. In some embodiments of any of the aspects, the input results in the activation of a repressible protease domain in the cargo encoded by an saRNA as described herein. In some embodiments of any of the aspects, the input results in oligomerization and a resultant activation of the cargo. In some embodiments of any of the aspects, the input results in oligomerization and a resultant inhibition of the cargo.

In some embodiments of any of the aspects, control of the cell requires the presence of all inputs simultaneously. In some embodiments of any of the aspects, control of the cell requires the presence of any input. In some embodiments of any of the aspects, control of the cell requires both the presence and absence of a distinct combination of inputs.

In some embodiments of any of the aspects, addition or removal of at least one saRNA and/or at least one input results in an altered fate and/or function of at least one cell. In some embodiments of any of the aspects, the fate of the cell (e.g., following adding or removing at least one input) is an altered cell type and/or an altered cell localization. In some embodiments of any of the aspects, the altered function of the cell is lytic. In some embodiments of any of the aspects, the altered function of the cell is stimulatory. In some embodiments of any of the aspects, the altered function of the cell is immunomodulatory. In some embodiments of any of the aspects, the input results in death of the cell comprising at least one saRNA as described herein. In some embodiments of any of the aspects, the input results in increased clearance rate of the cell comprising at least one saRNA as described herein. In some embodiments of any of the aspects, the input results in cell-cycle arrest of the cell comprising at least one saRNA as described herein.

In some embodiments of any of the aspects, the cargo of the saRNA encodes for and expresses at least one cargo protein, at least one protein reporters and/or at least one expression-enhancing protein. In some embodiments of any of the aspects, the cargo of the saRNA encodes for and expresses at least one cargo protein and at least one protein reporter. In some embodiments of any of the aspects, the cargo of the saRNA encodes for and expresses at least one cargo protein and at least one expression-enhancing protein. In some embodiments of any of the aspects, the cargo of the saRNA encodes for and expresses at least one protein reporter and at least one expression-enhancing protein. In some embodiments of any of the aspects, the cargo of the saRNA encodes for and expresses at least one cargo protein, at least one protein reporters and at least one expression-enhancing protein.

In some embodiments of any of the aspects, the cargo protein is a chimeric antigen receptor. In some embodiments of any of the aspects, the expression enhancing protein is B18R. In some embodiments of any of the aspects, the expression enhancing protein is E3L. In some embodiments of any of the aspects, the expression enhancing protein is B18R and E3L.

In some embodiments of any of the aspects, an saRNA as described herein comprises a targeting domain to increase transfection efficiency of the saRNA into a specific cell type. In some embodiments of any of the aspects, a composition comprising an saRNA as described herein further comprises a targeting domain to increase transfection efficiency of the saRNA into a specific cell type.

Definitions

The inventions illustratively described herein may be practiced in the absence of any element or elements, limitation or limitations which is not specifically disclosed herein. Thus, for example, the terms "comprising", "including," containing", etc. shall be read expansively and without limitation. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present inventions have been specifically disclosed by preferred methods, embodiments and optional features, modification and variation of the concepts herein disclosed may be resorted to by those skilled in the art, and that such modifications and variations are considered to be within the scope of the inventions as defined by the embodiments and elsewhere in the invention. In the case of conflict, the specification, including definitions, will control.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

Certain aspects and embodiments of the invention and inventions have been described broadly and generically herein. Each of the narrower species and subgeneric groupings falling within the generic invention also form part of some aspects and embodiments of inventions contemplated herein. This includes the generic description of inventions with a proviso or negative limitation removing any subject matter from the genus, regardless of whether or not the excised material is specifically recited herein.

For convenience, the meaning of some terms and phrases used in the invention, examples, and appended claims, are provided. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

The terms "protein", "cargo", or "protein of interest" refers to any genetically encodable polypeptide or nucleic acid sequence of known or unknown function. Examples of nucleic acid cargos of interest include non-coding RNA, long non-coding RNA, microRNA, and siRNA. Examples of poly peptide cargos of interest include receptors, ligands, enzymes, transmembrane receptors, transcription factors, viral components, etc. These are examples of proteins with known function and should not be interpreted as an exclusive list. Proteins with unknown function can also be genetically encoded.

The term "protein" refers to any genetically encodable polypeptide sequence of known or unknown function. Examples of proteins include receptors, ligands, enzymes, transcription factors, etc. These are examples of proteins with known function and should not be interpreted as an exclusive list. Proteins with unknown function can also be genetically encoded.

The term "cargo" refers to a polypeptide sequence that is encoded by conventional or self-replicating RNA. The polypeptide sequence can represent a polypeptide with known or unknown function. A non-exhaustive list of polypeptides that may be expressed by RNA include fluorescent proteins, enzymes, transcription factors, receptors, ligands, and antibodies.

Chimeric antigen receptors (CARs) combine components or functions of the T cell receptor (TCR) and associated molecules into a single polypeptide. In some embodiments of any of the aspects, the polypeptide described herein is a second or third generation CAR, which comprises an extracellular binding domain, a hinge region, a transmembrane domain, and one or more intracellular signaling domains. The extracellular binding domain typically contains a single-chain variable fragment (scFv) derived from antigen-reactive antibodies that usually have a high specificity to a specific antigen. Most CARs contain the CD3 zeta chain domain as the intracellular signaling domain, which is a primary transmitter of T cell activation signals. In addition to scFvs, non-antibody-based approaches have also been used to direct CAR specificity, usually taking advantage of ligand/receptor pairs that normally bind to each other. In some embodiments of any of the aspects, the polypeptide described herein can comprise cytokines, innate immune receptors, TNF receptors, growth factors, and structural proteins, which have all been successfully used as CAR antigen recognition domains.

The term "self-replicating RNA" refers to RNA strands that are known to undergo replication activity that results in replicate strands from an original strand. Self-replicating RNA is known to exist in the form of RNA viral genomes and artificial self-replicating RNA can be created by utilizing components from RNA viruses along with sequences of interest. The components from RNA viruses can be used in combination or from a particular RNA virus exclusively.

The term "self-amplifying RNA" refers to a polymer of nucleic acids that is capable of replication of the entire nucleic acid polymer in both the negative-strand and positive-strand conformations. It is capable of synthesizing additional self-amplifying RNA in part through production of various non-structural proteins of viral origin capable of acting as, among other activities, an RNA dependent RNA polymerase. Self-amplifying RNA can be created by utilizing components from RNA viruses along with sequence(s) that encode for cargo of interest. An integral aspect of saRNA is the ability for the non-structural proteins to generation both new full length saRNA strands, as well as RNA produced from a sub-genomic promoter. In therapeutic saRNA, the RNA produced by transcription from the sub-genomic protomer encodes for the cargo(s) of interest. Self-amplifying RNA, saRNA, self-replicating RNA, and srRNA may be used interchangeably throughout the entirety of the disclosure of this invention.

The term "expression" refers to the production of protein from an RNA strand. For example, "high expression" may refer to the production of a sufficient or large amount of protein. The level of expression desired is dependent on the application of interest. The terms "high expression" and "low expression" may be used in embodiments to describe observations made between cells of interest.

The term "expression" refers to the production of cargo from an RNA strand. In some embodiments, "expression" may refer to the production of protein to elicit the intended therapeutic effect. In some embodiments, "expression" may refer to the percentage of a cell population that expresses the cargo. In a preferred embodiment, "high expression" refers to over-production of the cargo of interest with respect to total amount. In another preferred embodiment, "high expression" refers to a percentage of a cell population that is equal to or greater than the control that is expressing the cargo of interest. The terms "high expression" and "low expression" may be used in embodiments to compare cargo expression with respect to total amount or percentage of cell expression, between cells of interest.

The term "conventional mRNA" refers to messenger RNA that does not have self-replicating functions. In some embodiments, conventional mRNA is generated by in vitro transcription. In some embodiments, conventional mRNA contains a 5' cap structure and a poly-A tail. In some embodiments, conventional mRNA contains 5' and 3' untranslated regions.

The term "transfection" or "delivery" refers to the introduction of exogenous RNA into the intracellular space of cells. In some embodiments, transfection or delivery occurs by electroporation. In some embodiments, transfection or delivery is by lipid nanoparticles. In some embodiments, transfection or delivery occurs directly, without modification of the RNA or vehicle to carry the RNA. In some embodiments, transfection or delivery occurs through conjugation of cell-reactive or targeting moieties to the RNA.

The term "input" or "inputs" refers to a stimuli that interacts with the cargo of the self-replicating RNA. Input or inputs include, but are not limited to, a cell, a protein, an enzyme, a small molecule, a specific wavelength or wavelengths of light, a thermal stimuli, or application of a magnetic field. Input or inputs include, but are not limited to, a cell, a protein, an enzyme, a small molecule, DNA, RNA, a specific wavelength or wavelengths of light, a thermal stimuli, or application of a magnetic field.

The term "modified nucleotide" refers to any analog of cytidine, adenosine, guanosine, uridine, or pseudouridine. These analogs can include isomers of the nitrogenous base, as well as inclusion or exclusion of chemical groups, both natural occurring and synthetically introduced, on any aspect of the nitrogenous base. It is explicitly stated herein that modifications to the sugar-phosphate backbone are not included in the definition of the term "modified nucleotide." This exception is not meant to exclude the methylation at the 2'O position of the first and second initiating nucleotides, also referred to as Cap-1 and cap-2 structures.

The term "highly substituted" or "high substitution" refers to the replacement of the natural nucleotide with a high percentage of the corresponding analog. Where the high percentage is greater than 25%; where the percentage is greater than 30%, where the percentage is greater than 35%; where the percentage is greater than 40%; where the percentage is greater than 45%; where the percentage is greater than 50%; where the percentage is greater than 55%; where the percentage is greater than 60%; where the percentage is greater than 65%; where the percentage is greater than 70%; where the percentage is greater than 75%; where the percentage is greater than 80%; where the percentage is greater than 85%; where the percentage is greater than 90%; where the percentage is greater than 95%; where the percentage is 100%. Additionally, the terms "100% substitution", "100% replaced", "full substitution", "fully substituted", and "completely replaced" may be used interchangeably throughout the disclosure of this invention. Full substitution means that there is no presence of the given non-modified nucleotide in the synthesis or final product of the self-amplifying RNA. A given percentage of substitution means the fractional mixture of a given nucleotide that is comprised of analog and naturally occurring either cytidine, adenosine, guanosine, or uridine. In a preferred embodiment 50-100%, of one of a combination of 5-methyluridine, 5-methylcytidine, and 5-hydroxymethylcytidine is substituted into the saRNA. In a preferred embodiment, 50%-100% of one of a combination of 5-methyluridine, 5-methylcytidine, 5-hydroxymethyluridine, and 5-hydroxymethylcytidine is substituted into the saRNA. In a preferred embodiment, 100% of cytidine is replace by 5-methylcytidine, and the resulting composition of the fully substituted self-amplifying RNA is comprised entirely of adenosine, guanosine, uridine, and 5-methylcytidine, which expresses cargo at equivalent or greater levels than unmodified saRNA. In another preferred embodiment 100% of cytidine is replace by 5-hydroxymethylcytidine, and the resulting composition of the fully substituted self-amplifying RNA is adenosine, guanosine, uridine, and 5-hydroxymethylcytidine, which expresses cargo at equivalent or greater levels than unmodified saRNA. In another preferred embodiment 100% of uridine is replace by 5-methyluridine, and the resulting composition of the fully substituted self-amplifying RNA is adenosine, guanosine, cytidine, and 5-methyluridine, which expresses cargo at equivalent or greater levels than unmodified saRNA. In another preferred embodiment 100% of uridine is replace by 5-hydroxymethyluridine, and the resulting composition of the fully substituted self-amplifying RNA is adenosine, guanosine, cytidine, and 5-hydroxymethyluridine, which expresses cargo at equivalent or greater levels than unmodified saRNA.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal, e.g., for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, the terms "protein" and "polypeptide" are used interchangeably to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested to confirm that a desired activity, e.g., activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the polypeptide described herein (or a nucleic acid encoding such a polypeptide) can be a functional fragment of one of the amino acid sequences described herein. As used herein, a "functional fragment" is a fragment or segment of a polypeptide which retains at least 50% of the wild-type reference polypeptide's activity. A functional fragment can comprise conservative substitutions of the sequences disclosed herein.

In some embodiments, the polypeptide described herein can be a variant of a polypeptide sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a protein or fragment thereof that retains activity of the native or reference polypeptide. A wide variety of, for example, PCR-based, site-specific mutagenesis approaches are known in the art and can be applied by the ordinarily skilled artisan to generate and test artificial variants.

A variant amino acid or DNA sequence can be at least 80%, at least 85%, at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

A variant amino acid sequence can be at least 50%, at least 60%, at least 70%, at least 80%, at least 90%, at least 91%, at least 92%, at least 93%, at least 94%, at least 95%, at least 96%, at least 97%, at least 98%, at least 99%, or more, similar to a native or reference sequence. As used herein, "similarity" refers to an identical amino acid or a conservatively substituted amino acid, as described herein. Accordingly, the percentage of "sequence similarity" is the percentage of amino acids which is either identical or conservatively changed; e.g., "sequence similarity"=(% sequence identity)+(% conservative changes). It should be understood that a sequence that has a specified percent similarity to a reference sequence necessarily encompasses a sequence with the same specified percent identity to that reference sequence. The skilled person will be aware of various computer programs, using different mathematical algorithms, that are available to determine the identity or similarity between two sequences. For instance, use can be made of a computer program employing the Needleman and Wunsch algorithm (Needleman et al. (1970)); the GAP program in the Accelrys GCG software package (Accelerys Inc., San Diego U.S.A.); the algorithm of E. Meyers and W. Miller (Meyers et al. (1989)) which has been incorporated into the ALIGN program (version 2.0); or more preferably the BLAST (Basic Local Alignment Tool using default parameters); see e.g., U.S. Pat. No. 10,023,890, the content of which is incorporated by reference herein in its entirety.

As used herein, the phrase "maintains the same function", when used in reference to an enzyme, catalyzes the same reaction as a reference enzyme.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. A wide variety of, site-specific mutagenesis approaches, e.g., Kunkel's method, cassette mutagenesis, PCR site-directed mutagenesis (e.g., traditional PCR, primer extension, or inverse PCR), whole plasmid mutagenesis, in vivo site-directed mutagenesis, CRISPR/Cas-guided mutagenesis, are known in the art and can be applied by the ordinarily skilled artisan to introduce mutations into specific nucleic acid loci. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); Braman, Jeff, ed. (2002) In Vitro Mutagenesis Protocols, Methods in Molecular Biology, Vol. 182 (2nd ed.); Khudyakov and Fields (2002), Artificial DNA: Methods and Applications, CRC Press; Hsu et al. (2014), Cell 157 (6): 1262-78; Cerchione et al. (2020) PLOS ONE 15 (4): e0231716; and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., template DNA, plasmid DNA, vector DNA. Suitable RNA can include, e.g., saRNA, mRNA.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (e.g., saRNA, mRNA) or antisense RNA derived from a nucleic acid fragment or fragments and/or to the translation of saRNA or mRNA into a polypeptide.

"Expression products" include RNA transcribed from a gene, and polypeptides obtained by translation of mRNA transcribed from a gene. The term "gene" refers to the nucleic acid sequence which is transcribed (DNA) to RNA in vitro or in vivo when operably linked to appropriate regulatory sequences. The gene may or may not include regions preceding and following a coding region, e.g. 5' untranslated (5'UTR) or "leader" sequences and 3' UTR or "trailer" sequences, as well as intervening sequences (introns) between individual coding segments (exons).

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g., a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in or within nature.

As used herein, the term "administering," refers to the placement of a saRNA, or a nucleic acid or cell or composition comprising an saRNA, as disclosed herein, into a subject by a method or route which results in at least partial delivery of the saRNA, or a nucleic acid or cell or composition comprising an saRNA, at a desired site. Pharmaceutical compositions comprising the saRNA, or a nucleic acid or cell or composition comprising an saRNA, as disclosed herein, can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, transfection, transduction, perfusion, injection, or other delivery method known to one skilled in the art. In some embodiments, contacting comprises physical human activity, e.g., an injection; an act of dispensing, mixing, and/or decanting; and/or manipulation of a delivery device or machine.

In some embodiments of any of the aspects, the cells can be maintained in culture. As used herein, "maintaining" refers to continuing the viability of a cell or population of cells. A maintained population of cells will have at least a subpopulation of metabolically active cells.

As used herein, the term "specific binding" refers to a chemical or physical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third non-target entity. A reagent specific for a given target is one that exhibits specific binding for that target under the conditions of the assay being utilized.

As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in cell biology, immunology, and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Some embodiments of the technology described herein can be defined according to any of the following numbered paragraphs:

1. A method whereby self-replicating RNA is used to express a protein or multiple proteins at a level comparable to other methods used to establish constitutive protein expression.
2. A method of paragraph 1, wherein the self-replicating components are derived from the Venezuela Equine Encephalitis Virus (VEEV), Semliki Forest Virus (SFV), Sindbis Virus (SIN), Kunjin Virus (KUN), Measles virus (MV), Rabies virus (RABV), or Vesicular Stomatitis virus (VSV).
3. A method wherein self-replicating RNA and one or multiple input(s) controls the fate or function of a cell.
4. A method of paragraph 3, wherein the input is endogenous to the environment of the cell containing self-replicating RNA; wherein the input is exogenous to the environment of the cell containing self-replicating RNA.
5. A method of paragraph 3, wherein the input is a cell; wherein the input is a protein; wherein the input is a small molecule; wherein the input is a specific wavelength or wavelengths of light; wherein the input is temperature; wherein the input is application of a magnetic field.
6. A method of paragraph 3, wherein the input results in the death, increased clearance rate, or cell-cycle arrest of a cell containing the self-replicating RNA.
7. A method of paragraph 3, wherein the input results in inhibition of a protease domain comprising an aspect of the cargo; wherein the input results in the activation of a protease domain comprising an aspect of the cargo.
8. A method of paragraph 3, wherein the input results in oligomerization and a resultant activation of the cargo; wherein the input results in oligomerization and a resultant inhibition of the cargo.
9. A method of paragraph 3, wherein the cargo comprises a chimeric antigen receptor; wherein the cargo comprises multiple chimeric antigen receptors.
10. A method of paragraph 3, wherein control of the cell requires the presence of all inputs simultaneously; wherein control of the cell requires the presence of any input; wherein control of the cell requires both the presence and absence of a distinct combination of inputs.
11. A method of paragraph 3, wherein the function alters cell type; wherein the function is localization; wherein the function is lytic; wherein the function is stimulatory; wherein the function is immunomodulatory
12. A self-replicating RNA of paragraph 3, wherein the cargo protein comprises a chimeric antigen receptor that contains an extracellular domain that sense input signals.
13. A self-replicating RNA of paragraph 3, wherein the cargo proteins are chimeric antigen receptors, and the input signal is a small molecule and/or a protein.
14. A self-replicating RNA of paragraph 3, wherein the cargo proteins have a domain or domains responsive to an external input.

15. A self-replicating RNA of paragraph 3, wherein the cargo proteins include protease domains that respond to protease inhibitors to regulate activity.
16. A method of paragraph 3, wherein self-replicating RNA is delivered in situ; wherein the self-replicating RNA is delivered ex vivo.
17. A method whereby self-replicating RNA is used to express cargo proteins along with additional protein reporters or expression enhancing proteins.
18. A self-replicating RNA according to paragraph 17, wherein the cargo protein is a chimeric antigen receptor and the expression enhancing protein is B18R.
19. A self-replicating RNA according to paragraph 17, wherein the cargo protein is a chimeric antigen receptor and the expression enhancing protein is E3L.
20. A method to manufacture cells with controllable activity by delivery of self-replicating RNA by electroporation.
21. A method to manufacture cells with controllable activity by delivery of self-replicating RNA by lipid nanoparticles.
22. A lipid nanoparticle according to paragraph 21, wherein an targeting domain is attached to the surface that has the purpose of increasing transfection efficiency of a desired cell type.
23. A method to increase the level of expression of a cargo protein in a cell by expressing the cargo protein by self-replicating RNA.
24. A method to control the activity of a protein that is expressed by self-replicating RNA by administration of a small molecule and/or protein and/or RNA (aptamer).
25. A self-replicating RNA according to paragraphs 16 and 17, wherein the protein is a chimeric antigen receptor, and the activity is regulated by small molecule responsive domains.
26. A method to increase and decrease the activity of a protein that is expressed by self-replicating RNA by administration of distinct small molecules.
27. A method according to paragraph 19, wherein the small molecules are protease inhibitors or molecules known to interact with specified protein domains.
28. A method for expressing proteins that can interact with each other by self-replicating RNA.
29. A method for expressing proteins that can interact with each other in a manner resulting in conditional activity of the transfected cell by self-replicating RNA.
30. A self-replicating RNA according to paragraph 22, wherein the proteins are chimeric antigen receptors with activating and inhibitory functions.
31. A method for generating cells with controllable functions by delivering multiple distinct self-replicating RNAs to a mixture of cells.
32. A method to administer one or more cell types modified with self-replicating RNA to a patient via intraosseous (IO), intraperitoneal (IP), subcutaneous (SC), intravenous (IV), intramuscular (IM), intrarectal, intravaginal, and intraarticular (IA) or via inhalation or topically.

Some embodiments of the technology described herein can be defined according to any of the following numbered paragraphs:

1. A self-amplifying RNA (saRNA) encoding a cargo of interest, the saRNA comprising a level of substitution of a given nucleotide with a modified nucleotide greater than 25%, where the modified nucleotide is selected from the group consisting of 5-methylcytidine, 5-methyluridine, and 5-hydroxymethylcytidine, and optionally the saRNA expresses the cargo at a level greater than or equal to that of the same saRNA without the modified nucleotide.
2. A self-amplifying RNA (saRNA), encoding a cargo of interest, the saRNA comprising a level of substitution of a given nucleotide with a modified nucleotide greater than 25%, where the modified nucleotide is comprised of a pyrimidine nucleoside triphosphate with a moiety on the 5 carbon, wherein the moiety is selected from a list comprising methyl, ethyl, propyl, trifluoromethyl, hydroxymethyl, hydroxyethyl, or hydroxypropyl functional groups, and optionally the saRNA expresses the cargo at a level greater than or equal to that of the same saRNA without the modified nucleotide.
3. The saRNA of paragraph 1 or 2, wherein the substitution ratio is 25-50%; is 51-75%; is 75-99%; is 100%.
4. The saRNA of paragraph 1, wherein substitution with 5-methyluridine and one or both, 5-methylcytidine and 5-hydroxymethylcytidine, occurs in the same saRNA molecule. A composition of paragraph 1 or 2, wherein the initiating nucleotide, the nucleotide directly proximal to the 5' cap, is an adenosine or adenosine analog.
5. The saRNA of paragraph 1 or 2, wherein the initiating nucleotide, the nucleotide directly proximal to the 5' cap, is a guanosine or guanosine analog.
6. The saRNA of paragraph 1 or 2, wherein the initiating nucleotide, and optionally the subsequent nucleotide, of the saRNA is methylated at the 2'O position of the ribose.
7. The saRNA of paragraph 1 or 2, wherein the saRNA contains components derived from the Venezuela Equine Encephalitis Virus (VEEV), Semliki Forest Virus (SFV), Sindbis Virus (SIN), Kunjin Virus (KUN), Measles virus (MV), Coronavirus (CoV), Rabies virus (RABV), or Vesicular Stomatitis virus (VSV).
8. The saRNA of any one of paragraphs 1-7, wherein the saRNA expresses a cargo that is a protein or multiple proteins of viral, bacterial, protozoan, mammalian, or plant in origin.
9. The saRNA of any one of paragraphs 1-7, wherein the saRNA expresses a chimeric antigen receptor containing an extracellular domain that senses input signals.
10. The saRNA of any one of paragraphs 1-7, wherein the saRNA expresses a ligand, a cell surface receptor, a transcription factor, a cytokine, a chemokine, an enzyme, an antibody, or other protein with biological activity.
11. The saRNA of any one of paragraphs 1-7, wherein the saRNA expresses cargo or cargos of interest comprising a domain or domains responsive to an external input.
12. The saRNA of any one of paragraphs 1-7, wherein the saRNA transcribes one or multiple non-coding RNA selected from a list comprising siRNA, shRNA, or microRNA.
13. The saRNA of any one of paragraphs 1-7, wherein the cargo of interest is one or multiple vaccine associated antigens, wherein the vaccine associated antigen is one or multiple proteins encoded on the genomes of viruses selected from a list comprising respiratory syncytial virus, hemagglutinin virus, human immunodeficiency virus, influenza virus, zika virus, sudden acute respiratory syndrome coronavirus 2, human papillomavirus, herpes virus, rotavirus, chicken pox, dengue virus, hepatitis A virus, hepatitis virus B, rubella virus, poliovirus, or rabies virus.

14. The saRNA of any one of paragraphs 1-7, wherein the cargo or cargos encoded by the saRNA is one or more chimeric antigen receptors selected from the list comprising CD19, CD22, CD30, b-cell maturation antigen (BCMA), disialoganglioside GD2, human estrogen receptor 2 (HER2), GPR87, Fibroblast Activator Protein (FAP), CD20, receptor tyrosine kinase-like orphan receptor 1 (ROR1), carcinoembryonic antigen (CEA), mesothelin (MSLN), prostate-specific membrane antigen (PSMA), EGFRvIII, IL13Rα2, NKG2D.
15. The saRNA of any one of paragraphs 1-7, wherein the cargo or cargos encoded by the saRNA is one or more transcription factor, including those selected from the list Oct3/4, Sox2, Klf4, & c-Myc.
16. The saRNA of any one of paragraphs 1-7, wherein the cargo or cargos encoded by the saRNA is one or more growth factor or cytokine, selected from the list comprising platelet-derived growth factor (PDGF), erythropoietin (EPO), vascular endothelial growth factor (VEGF), transforming growth factor-β1 (TGF-β1), fibroblast growth factor (FGF), human relaxin-2 (RLX2), alpha-melanocyte-stimulating hormone (alpha-MSH), insulin-like growth factor-I (IGF-I), epidermal growth factor (EGF), nerve growth factor (NGF), granulocyte-monocyte colony-stimulating factor (GMCSF), Thrombopoietin (TPO), Bone morphogenic protein (BMP), hepatocyte growth factor (HGF), growth/differentiation factor (GDF), Neurotrophins, migration stimulating factor (MSF), sarcoma growth factor (SGF).
17. The saRNA of any one of paragraphs 1-7, wherein the cargo or cargos encoded by the saRNA is one or both Pappalysin-A1 (PAPPA1) and Pappalysin-A2 (PAPPA2).
18. The saRNA of any one of paragraphs 1-7, wherein the cargo or cargos encoded by the saRNA is one or more interleukin(s) or their cognate receptors and receptor sub-units, selected from the list comprising IL-2, IL-4, IL-7, IL-10, IL-13, and IL-15.
19. The saRNA of any one of paragraphs 1-7, wherein the cargo or cargos encoded by the saRNA is one or more enzyme with antioxidant activity, selected from a list comprising phospholipid hydroperoxide glutathione peroxidase, superoxide dismutase-1, and superoxide dismutase-2; Bruton's tyrosine kinase; adenosine deaminase; ecto-nucleoside triphosphate diphosphydrolase.
20. A pharmaceutical composition comprising a saRNA of any one of paragraphs 1-19 and a pharmaceutically acceptable carrier.
21. A cell transfected with a saRNA of any one of paragraphs 1-19.
22. The method of expressing a cargo encoded on a saRNA, the method comprising expressing in a cell (e.g. a eukaryotic cell) from a saRNA of any one of paragraphs 1-19.
23. The method of expressing one or more preselected cargos in a subject in need thereof, the method comprising administering to a subject (e.g., a human, a livestock) an effective amount of a pharmaceutical composition of paragraph 20.
24. The method of paragraph 22 or 23, wherein the saRNA maintains or increases initial saRNA replication and cargo expression compared to an unmodified saRNA of the same dose.
25. The method of any one of paragraphs 22-24, wherein the expression of the cargo or cargos of interest encoded by a saRNA is equivalent or increased compared to that of an unmodified saRNA.
26. The method of any one of paragraphs 22-25, wherein the transfection efficiency of a self-amplifying RNA molecule is increased compared to that of an unmodified saRNA.
27. The method of any one of paragraphs 22-26, wherein the early interferon response resulting from introduction of the saRNA is decreased compared to that of unmodified saRNA.
28. The method of any one of paragraphs 22-27, wherein the length of time over which cargo is expressed at a detectable level from the saRNA is increased compared to that of unmodified saRNA.
29. The method of any one of paragraphs 22-28, wherein the cell is a human cell.
30. The method of any one of paragraphs 22-29, wherein the subject has cancer.
31. The method of any one of paragraphs 22-29, wherein the subject is in need of vaccination.
32. The method of any one of paragraphs 22-29, wherein the subject is in need of protein replacement therapy.
33. The method of any one of paragraphs 22-29, wherein the subject is in need of antibody therapy.
34. The method of any one of paragraphs 22-33, wherein the saRNA permits tissue, organ, or cell-type specific expression of the cargo.
35. A method of paragraph 34, wherein the saRNA comprises greater than 50% substitution of uridine with 5-methyluridine to facilitate kidney specific expression of the cargo.
36. The method of any one of paragraphs 22-34, wherein the saRNA modulates cellular differentiation of a cell containing the saRNA at a level equivalent to or greater than the level of modulation achieved with the unmodified saRNA at an equivalent dose.
37. The method of paragraph 36, wherein the cell is modulated by expression of a transcription factor encoded by the saRNA to become a stem cell.

Some embodiments of the technology described herein can be defined according to any of the following numbered paragraphs:

1. A self-amplifying RNA (saRNA) comprising at least 25% modified nucleotides, wherein the modified nucleotides comprise a pyrimidine nucleoside phosphate with a moiety on carbon 5 of the pyrimidine, wherein the moiety is selected from the group consisting of methyl, ethyl, propyl, trifluoromethyl, hydroxymethyl, hydroxyethyl, and hydroxypropyl functional groups, and at least one cargo of interest.
2. The saRNA of paragraph 1, wherein the modified nucleotides comprise 5-methylcytidine, 5-methyluridine, 5-hydroxymethyluridine, 5-hydroxymethylcytidine or a combination thereof.
3. The saRNA of paragraph 1, wherein the saRNA expresses the cargo at a level greater than or equal to that of a corresponding saRNA with less than 25% modified nucleotides.
4. The saRNA of paragraph 1, wherein the level of substitution of the modified nucleotides is: 25%-50%; 51%-75%; 75%-99%; 99.1%-99.9%; or 100%.
5. The saRNA of paragraph 1, wherein the initiating nucleotide comprises:
(a) an adenosine or adenosine analog, and wherein the initiating nucleotide of the saRNA is methylated at the 2'O position of the ribose (Cap 1);

(b) an adenosine or adenosine analog, and wherein the initiating nucleotide and the subsequent nucleotide of the saRNA are both methylated at the 2'O position of the ribose (Cap2);
(c) a guanosine or guanosine analog, and wherein the initiating nucleotide of the saRNA is methylated at the 2'O position of the ribose (Cap 1); or
(d) a guanosine or guanosine analog, and wherein the initiating nucleotide and the subsequent nucleotide of the saRNA are both methylated at the 2'O position of the ribose (Cap2).

6. The saRNA of paragraph 1 comprising from 5' to 3':
(a) a 5' cap;
(b) non-structural protein 1 (nsp1), non-structural protein 2 (nsp2), non-structural protein 3 (nsp3), and/or non-structural protein 4 (nsp4), each derived from at least one virus;
(c) a subgenomic promoter (SGP) derived from at least one virus;
(d) 5' untranslated region (UTR) derived from at least one virus;
(e) the at least one cargo of interest;
(f) a 3' untranslated region (UTR) derived from at least one virus; and
(g) a poly-A tail.

7. The saRNA of paragraph 1, further comprising at least one 5' conserved sequence element (CSE) and/or 3' at least one conserved sequence element (CSE) derived from at least one virus.

8. The saRNA of paragraph 6, wherein the at least one virus is an alphavirus.

9. The saRNA of paragraph 6, wherein the at least one virus is selected from the group consisting of: Venezuela Equine Encephalitis Virus (VEEV), Semliki Forest Virus (SFV), Sindbis Virus (SIN), Chikungunya Virus (CHIKV), Eastern Equine Encephalitis Virus (EEEV), Mayaro Virus (MAYV), Getah Virus (GETV), Ross River Virus (RRV), Una Virus (UNAV), Middleburg Virus (MIDV), O'nyong nyong virus (ONNV), Barmah Forest Virus (BFV), Mucambo Virus (MUCV), Tonate Virus (TONV), Everglades Virus (EVEV), Rio Negro Virus (RNV), Turnip Rosette Virus (TROV), Highlands J Virus (HJV), Western Equine Encephalitis Virus (WEEV), Fig Mosaic Emaravirus (FMV), Aura Virus (AURAV), Kunjin Virus (KUN), Measles virus (MV), Coronavirus (CoV), Rabies virus (RABV), and Vesicular Stomatitis virus (VSV).

10. The saRNA of paragraph 1, wherein the cargo comprises a chimeric antigen receptor (CAR) comprising an extracellular domain that specifically binds to an antigen of interest.

11. The saRNA of paragraph 10, wherein the antigen of interest for the CAR is selected from the group consisting of: CD19, CD22, CD30, b-cell maturation antigen (BCMA), disialoganglioside GD2, human estrogen receptor 2 (HER2), G protein-coupled receptor 87 (GPR87), Fibroblast Activator Protein (FAP), CD20, receptor tyrosine kinase-like orphan receptor 1 (ROR1), carcinoembryonic antigen (CEA), mesothelin (MSLN), prostate-specific membrane antigen (PSMA), epidermal growth factor receptor variant III (EGFRvIII), Interleukin 13 receptor alpha 2 (IL13R$\alpha$2), and natural killer group 2 member D (NKG2D).

12. The saRNA of paragraph 10, wherein the CAR is selected from the group consisting of:
(a) a conventional CAR;
(b) an ON-CAR;
(c) an OFF-CAR system;
(d) an ON/OFF-CAR;
(e) an inhibitory CAR; or
(f) a split, universal, programmable and reconfigurable (SUPRA) CAR system.

13. The saRNA of paragraph 1, wherein the cargo comprises a ligand, a cell surface receptor, a transcription factor, a cytokine, a chemokine, an enzyme, and/or an antibody or fragment thereof.

14. The saRNA of paragraph 13, wherein the antibody is a bispecific antibody.

15. The saRNA of paragraph 1, wherein the cargo comprises a bispecific T cell engager (BiTE).

16. The saRNA of paragraph 1, wherein the cargo comprises at least one non-coding RNA selected from the group consisting of siRNA, shRNA, and microRNA.

17. The saRNA of paragraph 1, wherein the cargo comprises at least one vaccine-associated antigen comprising at least one protein encoded by a genome of a virus.

18. The saRNA of paragraph 17, wherein the virus is selected from the group consisting of: Rift valley fever, Crimean-Congo haemorrhagic fever, Lassa fever, Chikungunya Virus (CHIKV), Nipah Virus (NiV), respiratory syncytial virus (RSV), Ebola virus, Marburg virus, West Nile virus, Venezuela equine encephalitis, yellow fever virus, Japanese encephalitis virus, western equine encephalitis virus, eastern equine encephalitis, cytomegalovirus (CMV), human immunodeficiency virus (HIV), influenza virus, Zika virus, middle eastern respiratory syndrome coronavirus (MERS-CoV), severe acute respiratory syndrome coronavirus (SARS-CoV), severe acute respiratory syndrome coronavirus 2 (SARS-CoV-2), human papillomavirus (HPV), herpes virus, rotavirus, varicella-zoster virus (VZV), dengue virus, hepatitis A virus, hepatitis B virus, rubella virus, poliovirus, and rabies virus.

19. The saRNA of paragraph 1, wherein the cargo comprises at least one transcription factor selected from the group consisting of Octamer-Binding Transcription Factor 3 (Oct3, Oct4), Sex-Determining Region Y (SRY)-Box Transcription Factor 2 (Sox2), Kruppel-Like Factor 4 (Klf4), and cellular myelocytomatosis oncogene (c-Myc).

20. The saRNA of paragraph 1, wherein the cargo comprises at least one growth factor and/or cytokine selected from the group consisting of platelet-derived growth factor (PDGF), erythropoietin (EPO), vascular endothelial growth factor (VEGF), transforming growth factor-$\beta$1 (TGF-$\beta$1), fibroblast growth factor (FGF), human relaxin-2 (RLX2), alpha-melanocyte-stimulating hormone (alpha-MSH), insulin-like growth factor-I (IGF-I), epidermal growth factor (EGF), nerve growth factor (NGF), granulocyte-monocyte colony-stimulating factor (GMCSF), Thrombopoietin (TPO), Bone morphogenic protein (BMP), hepatocyte growth factor (HGF), growth/differentiation factor (GDF), a Neurotrophin, migration stimulating factor (MSF), and sarcoma growth factor (SGF); or wherein the cargo comprises one or both of Pappalysin-A1 (PAPPA1) and Pappalysin-A2 (PAPPA2).

21. The saRNA of paragraph 1, wherein the cargo comprises at least one interleukin and/or a cognate receptor(s) of the interleukin and/or receptor sub-units for the interleukin, wherein the interleukin is selected from the group consisting of IL-2, IL-4, IL-7, IL-10, IL-12, IL-13, and IL-15.

22. The saRNA of paragraph 1, wherein the cargo comprises at least one enzyme with antioxidant activity, wherein the enzyme is selected from the group consisting of phospholipid hydroperoxide glutathione peroxidase, superoxide dismutase-1, superoxide dismutase-2, Bruton's tyrosine kinase, adenosine deaminase, and ecto-nucleoside triphosphate diphosphydrolase.
23. The saRNA of paragraph 1, wherein the cargo comprises glucagon-like peptide-1 (GLP-1) or a fragment thereof.
24. A self-amplifying RNA (saRNA) comprising from 5' to 3':
    (a) a 5' cap;
    (b) non-structural protein 1 (nsp1), non-structural protein 2 (nsp2), non-structural protein 3 (nsp3), and/or non-structural protein 4 (nsp4), each derived from at least one virus;
    (c) a subgenomic promoter (SGP) derived from at least one virus;
    (d) a 5' untranslated region (UTR) derived from at least one virus;
    (e) at least one cargo of interest;
    (f) a 3' untranslated region (UTR) derived from at least one virus; and
    (g) a poly-A tail.
25. A nucleic acid, vector, or cell encoding or comprising the saRNA of paragraph 1.
26. A pharmaceutical composition comprising the saRNA of paragraph 1 and a pharmaceutically acceptable carrier.
27. A method of expressing at least one cargo of interest in a cell, the method comprising contacting the cell with the saRNA of paragraph 1.
28. The method of paragraph 27, the method further comprising contacting the cell with at least one input to control the fate or function of the cell.
29. A method of expressing at least one cargo in a subject in need thereof, the method comprising administering to the subject an effective amount of the pharmaceutical composition of paragraph 26.
30. The method of paragraph 29, the method further comprising administering to the subject at least one input to control the fate or function of at least one cell in the subject.

Some embodiments of the technology described herein can be defined according to any of the following numbered paragraphs:

1. A self-amplifying RNA (saRNA) comprising at least 25% modified nucleotides, wherein the modified nucleotides comprise a pyrimidine nucleoside phosphate with a moiety on carbon 5 of the pyrimidine, wherein the moiety is selected from the group consisting of methyl, ethyl, propyl, trifluoromethyl, hydroxymethyl, hydroxyethyl, and hydroxypropyl functional groups, and at least one cargo of interest.
2. The saRNA of paragraph 1, wherein the modified nucleotides comprise 5-methylcytidine, 5-methyluridine, 5-hydroxymethyluridine, 5-hydroxymethylcytidine or a combination thereof.
3. The saRNA of paragraphs 1 or 2, wherein the saRNA expresses the cargo at a level greater than or equal to that of a corresponding saRNA with less than 25% modified nucleotides.
4. The saRNA of any one of paragraphs 1-3, wherein the pyrimidine comprises cytidine, and the modified nucleotide comprises 5-methylcytidine.
5. The saRNA of any one of paragraphs 1-4, wherein the pyrimidine comprises cytidine, and the modified nucleotide comprises 5-hydroxymethylcytidine.
6. The saRNA of any one of paragraphs 1-5, wherein the pyrimidine comprises uridine, and the modified nucleotide comprises 5-methyluridine.
7. The saRNA of any one of paragraphs 1-6, wherein the pyrimidine comprises uridine, and the modified nucleotide comprises 5-hydroxymethyluridine.
8. The saRNA of any one of paragraphs 1-7, wherein the level of substitution of the modified nucleotides is 25%-50%.
9. The saRNA of any one of paragraphs 1-8, wherein the level of substitution of the modified nucleotides is 51%-75%.
10. The saRNA of any one of paragraph 1-9, wherein the level of substitution of the modified nucleotides is 75%-99%.
11. The saRNA of any of paragraphs 1-10, where the level of substitution of the modified nucleotides is 99.1%-99.9%.
12. The saRNA of any one of paragraphs 1-11, wherein the level of substitution of the modified nucleotides is 100%.
13. The saRNA of any one of paragraphs 1-12, wherein the modified nucleotides comprise 5-methyluridine or 5-hydroxymethyluridine, and one or both of 5-methylcytidine and 5-hydroxymethylcytidine, in the same saRNA molecule.
14. The saRNA of any one of paragraphs 1-13, wherein the initiating nucleotide directly proximal to the 5' cap in the saRNA comprises an adenosine or adenosine analog.
15. The saRNA of any one of paragraphs 1-14, wherein the initiating nucleoside directly proximal to the 5' cap in the saRNA comprises a guanosine or guanosine analog.
16. The saRNA of any one of paragraphs 1-15, wherein the initiating nucleoside of the saRNA is methylated at the 2'O position of the ribose (Cap 1).
17. The saRNA of any one of paragraphs 1-16, wherein the initiating nucleotide and the subsequent nucleotide of the saRNA are both methylated at the 2'O position of the ribose (Cap2).
18. The saRNA of any one of paragraphs 1-17, wherein the initiating nucleotide comprises an adenosine or adenosine analog, and wherein the initiating nucleotide of the saRNA is methylated at the 2'O position of the ribose (Cap 1).
19. The saRNA of any one of paragraphs 1-18, wherein the initiating nucleotide comprises an adenosine or adenosine analog, and wherein the initiating nucleotide and the subsequent nucleotide of the saRNA are both methylated at the 2'O position of the ribose (Cap2).
20. The saRNA of any one of paragraphs 1-19, wherein the initiating nucleotide comprises a guanosine or guanosine analog, and wherein the initiating nucleotide of the saRNA is methylated at the 2'O position of the ribose (Cap 1).
21. The saRNA of any one of paragraphs 1-20, wherein the initiating nucleotide comprises a guanosine or guanosine analog, and wherein the initiating nucleotide and the subsequent nucleotide of the saRNA are both methylated at the 2'O position of the ribose (Cap2).
22. The saRNA of any one of paragraphs 1-21, comprising from 5' to 3':

(a) at least one non-structural protein derived from at least one virus;
(b) a subgenomic promoter (SGP) derived from at least one virus; and
(c) the at least one cargo of interest.

23. The saRNA of any one of paragraphs 1-22, comprising from 5' to 3':
(a) a 5' cap;
(b) non-structural protein 1 (nsp1), non-structural protein 2 (nsp2), non-structural protein 3 (nsp3), and/or non-structural protein 4 (nsp4), each derived from at least one virus;
(c) a subgenomic promoter (SGP) derived from at least one virus;
(d) 5' untranslated region (UTR) derived from at least one virus;
(e) the at least one cargo of interest;
(f) a 3' untranslated region (UTR) derived from at least one virus; and
(g) a poly-A tail.

24. The saRNA of any one of paragraphs paragraph 1-23, further comprising at least one 5' conserved sequence element (CSE) and/or 3' at least one conserved sequence element (CSE) derived from at least one virus.

25. The saRNA of any one of paragraphs 1-24, wherein the nsp1, nsp2, nsp3, nsp4, SGP, 5' UTR, 3' UTR, 5' CSE, and/or 3' CSE are derived from the same virus.

26. The saRNA of any one of paragraphs 1-25, wherein at least one of the nsp1, nsp2, nsp3, nsp4, SGP, 5' UTR, 3' UTR, 5' CSE, and/or 3' CSE are derived from different viruses.

27. The saRNA of any one of paragraphs 1-26, wherein the virus is an alphavirus.

28. The saRNA of any one of paragraphs 1-27, wherein the at least one virus is selected from the group consisting of: Venezuela Equine Encephalitis Virus (VEEV), Semliki Forest Virus (SFV), Sindbis Virus (SIN), Chikungunya Virus (CHIKV), Eastern Equine Encephalitis Virus (EEEV), Mayaro Virus (MAYV), Getah Virus (GETV), Ross River Virus (RRV), Una Virus (UNAV), Middleburg Virus (MIDV), O'anyong nyong virus (ONNV), Barmah Forest Virus (BFV), Mucambo Virus (MUCV), Tonate Virus (TONV), Everglades Virus (EVEV), Rio Negro Virus (RNV), Turnip Rosette Virus (TROV), Highlands J Virus (HJV), Western Equine Encephalitis Virus (WEEV), Fig Mosaic Emaravirus (FMV), Aura Virus (AURAV), Kunjin Virus (KUN), Measles virus (MV), Coronavirus (CoV), Rabies virus (RABV), and Vesicular Stomatitis virus (VSV).

29. The saRNA of any one of paragraphs 1-28, wherein the alphavirus is selected from the group consisting of: Venezuela Equine Encephalitis Virus (VEEV), Semliki Forest Virus (SFV), Sindbis Virus (SIN), Chikungunya Virus (CHIKV), Eastern Equine Encephalitis Virus (EEEV), Mayaro Virus (MAYV), Getah Virus (GETV), Ross River Virus (RRV), Una Virus (UNAV), Middleburg Virus (MIDV), O'anyong nyong virus (ONNV), Barmah Forest Virus (BFV), Mucambo Virus (MUCV), Tonate Virus (TONV), Everglades Virus (EVEV), Rio Negro Virus (RNV), Highlands J Virus (HJV), Western Equine Encephalitis Virus (WEEV), and Aura Virus (AURAV).

30. The saRNA of any one of paragraphs 1-29, wherein the saRNA expresses the cargo of interest.

31. The saRNA of any one of paragraphs 1-30, wherein the cargo comprises at least one cargo protein or peptide.

32. The saRNA of any one of paragraphs 1-31, wherein the cargo comprises at least two cargo proteins or peptides.

33. The saRNA of paragraph 1-32, wherein the at least one cargo protein or peptide is viral, bacterial, protozoan, mammalian, or plant in origin.

34. The saRNA of any one of paragraphs 1-33, wherein the cargo comprises a chimeric antigen receptor (CAR) comprising an extracellular domain that specifically binds to an antigen of interest.

35. The saRNA of any one of paragraphs 1-34, wherein the antigen of interest for the CAR is selected from the group consisting of: CD19, CD22, CD30, b-cell maturation antigen (BCMA), disialoganglioside GD2, human estrogen receptor 2 (HER2), G protein-coupled receptor 87 (GPR87), Fibroblast Activator Protein (FAP), CD20, receptor tyrosine kinase-like orphan receptor 1 (ROR1), carcinoembryonic antigen (CEA), mesothelin (MSLN), prostate-specific membrane antigen (PSMA), epidermal growth factor receptor variant III (EGFRvIII), Interleukin 13 receptor alpha 2 (IL13Rα2), and natural killer group 2 member D (NKG2D).

36. The saRNA of any one of paragraphs 1-35, wherein the CAR is selected from the group consisting of:
(a) a conventional CAR;
(b) an ON-CAR;
(c) an OFF-CAR system;
(d) an ON/OFF-CAR;
(e) an inhibitory CAR; or
(f) a split, universal, programmable and reconfigurable (SUPRA) CAR system.

37. The saRNA of paragraph 36, wherein the conventional CAR comprises:
(a) an extracellular binding domain;
(b) a transmembrane domain; and
(c) at least one intracellular signaling domain.

38. The saRNA of paragraph 36, wherein the ON-CAR comprises:
(a) an extracellular binding domain;
(b) a transmembrane domain;
(c) at least one intracellular signaling domain; and
(d) a repressible protease domain that cleaves and degrades the ON-CAR in the absence of a protease inhibitor.

39. The saRNA of paragraph 36, wherein the OFF-CAR system comprises:
(a) a first polypeptide comprising:
  (i) an extracellular binding domain;
  (ii) a transmembrane domain; and
  (iii) a peptide domain; and
(b) a second polypeptide comprising:
  (i) a repressible protease domain that can bind specifically to the peptide domain in the absence of a protease inhibitor; and
  (ii) at least one intracellular signaling domain.

40. The saRNA of paragraph 39, wherein the peptide domain is selected from the group consisting of: K5-66, K5-66-A, K5-66-B, K6-10, K6-10A, K6-10B K5-66-R, CP5-46, CP5-46-4D5E, CP5-46-A, CP5-46A-4D5E, Ant-CP5-46A-4D5E, and apo NS3a reader (ANR) peptides.

41. The saRNA of paragraph 36, wherein the ON/OFF-CAR comprises:

(a) an extracellular binding domain;
(b) a transmembrane domain;
(c) at least one intracellular signaling domain;
(d) a repressible protease domain that cleaves and degrades the ON/OFF-CAR in the absence of a protease inhibitor; and
(e) a drug-inducible degron domain.

42. The saRNA of any one of paragraphs 38, 39, or 41, wherein the repressible protease domain comprises hepatitis C virus (HCV) nonstructural protein 3 (NS3).

43. The saRNA of any one of paragraphs 38, 39, or 41, wherein the protease inhibitor is selected from grazoprevir (GZV), danoprevir, simeprevir, asunaprevir, ciluprevir, boceprevir, sovaprevir, paritaprevir, ombitasvir, paritaprevir, ritonavir, dasabuvir, and telaprevir.

44. The saRNA of paragraph 41, wherein the drug-inducible degron domain comprises an IKAROS family zinc finger 3 (IKZF3) domain capable of being bound and activated to degrade the CAR by the drug lenalidomide or pomalidomide.

45. The saRNA of paragraph 36, wherein the inhibitory CAR comprises:
(a) an extracellular binding domain;
(b) a transmembrane domain; and
(c) an inhibitory domain.

46. The saRNA of paragraph 45, wherein the inhibitory domain comprises a Killer Cell Inhibitory Receptor (KIR) domain.

47. The saRNA of paragraph 36, wherein the SUPRA CAR system comprises:
(a) a first polypeptide comprising:
(i) an extracellular binding domain; and
(ii) a first member of an extracellular protein interaction domain; and
(b) a second polypeptide comprising:
(i) a second member of the extracellular protein interaction domain that can bind specifically with the first member of the extracellular protein interaction domain of the first polypeptide;
(ii) a transmembrane domain; and
(iii) at least one intracellular signaling domain.

48. The saRNA of any one of paragraphs 37-47, wherein the intracellular signaling domain is selected from the group consisting of: TCRC; FcRy; FcRp; CD3zeta; CD3y; CD35; CD3s; CD3C; CD22; CD79a; CD79b; CD66d; CARD11; CD2; CD7; CD27; CD28; CD30; CD40; CD54 (ICAM); CD83; CD134 (OX40); CD137 (4-1BB); CD150 (SLAMFI); CD152 (CTLA4); CD223 (LAG3); CD270 (HVEM); CD273 (PD-L2); CD274 (PD-L1); CD278 (ICOS); DAP10; LAT; KD2C SLP76; TRIM; ZAP70; and 41BB.

49. The saRNA of any one of paragraphs 1-48, wherein the extracellular binding domain comprises an antigen binding domain from an antibody.

50. The saRNA of any one of paragraphs 1-49, wherein the cargo comprises a ligand, a cell surface receptor, a transcription factor, a cytokine, a chemokine, an enzyme, and/or an antibody.

51. The saRNA of any one of paragraphs 1-50, wherein the cargo comprises an antibody or fragment thereof.

52. The saRNA of paragraph 51, wherein the antibody is a bispecific antibody.

53. The saRNA of any one of paragraphs 1-52, wherein the cargo comprises a bispecific T cell engager (BiTE).

54. The saRNA of any one of paragraphs 1-53, wherein the cargo comprises at least one domain responsive to an external input.

55. The saRNA of any one of paragraphs 1-54, wherein the cargo comprises at least one non-coding RNA.

56. The saRNA of paragraph 55, wherein the non-coding RNA is selected from the group consisting of siRNA, shRNA, and microRNA.

57. The saRNA of any one of paragraphs 1-56, wherein the cargo comprises at least one vaccine-associated antigen.

58. The saRNA of paragraph 57, wherein the vaccine-associated antigen comprises at least one protein encoded by a genome of a virus.

59. The saRNA of paragraph 58, wherein the virus is selected from the group consisting of: Rift valley fever, Crimean-Congo haemorrhagic fever, Lassa fever, Chikungunya Virus (CHIKV), Nipah Virus (NiV), respiratory syncytial virus (RSV), Ebola virus, Marburg virus, West Nile virus, Venezuela equine encephalitis, yellow fever virus, Japanese encephalitis virus, western equine encephalitis virus, eastern equine encephalitis, cytomegalovirus (CMV), human immunodeficiency virus (HIV), influenza virus, Zika virus, middle eastern respiratory syndrome coronavirus (MERS-CoV), severe acute respiratory syndrome coronavirus (SARS-CoV), severe acute respiratory syndrome coronavirus 2 (SARS-CoV-2), human papillomavirus (HPV), herpes virus, rotavirus, varicella-zoster virus (VZV), dengue virus, hepatitis A virus, hepatitis B virus, rubella virus, poliovirus, and rabies virus.

60. The saRNA of any one of paragraphs 57-59, wherein the vaccine-associated antigen comprises an antigen selected from the group consisting of: influenza virus hemagglutinin, Severe acute respiratory syndrome coronavirus 2 (SARS-CoV-2) Spike protein, and Human respiratory syncytial virus (RSV) Fusion glycoprotein.

61. The saRNA of any one of paragraphs 57-60, wherein the vaccine-associated antigen comprises one of SEQ ID NOs: 13-16, 22, or an amino acid sequence that is at least 80% identical to one of SEQ ID NOs: 13-16, 22, that maintains the same function.

62. The saRNA of any one of paragraphs 1-61, comprising the sequence of SEQ ID NO: 21 or a nucleic acid sequence that is at least 80% identical to SEQ ID NO: 21 that maintains the same function.

63. The saRNA of any one of paragraphs 1-62, wherein the cargo comprises at least one transcription factor.

64. The saRNA of paragraph 63, wherein the transcription factor is a stem cell transcription factor.

65. The saRNA of paragraph 63 or 64, wherein the transcription factor is selected from the group consisting of Octamer-Binding Transcription Factor 3 (Oct3, Oct4), Sex-Determining Region Y (SRY)-Box Transcription Factor 2 (Sox2), Kruppel-Like Factor 4 (Klf4), and cellular myelocytomatosis oncogene (c-Myc).

66. The saRNA of any one of paragraphs 1-65, wherein the cargo comprises at least one growth factor and/or cytokine.

67. The saRNA of paragraph 66, wherein the growth factor or cytokine is selected from the group consisting of platelet-derived growth factor (PDGF), erythropoietin (EPO), vascular endothelial growth factor (VEGF), transforming growth factor-β1 (TGF-β1), fibroblast growth factor (FGF), human relaxin-2 (RLX2), alpha-melanocyte-stimulating hormone (alpha-MSH), insulin-like growth factor-I (IGF-I), epidermal growth factor (EGF), nerve growth factor (NGF), granulocyte-monocyte colony-stimulating factor (GMCSF), Thrombopoietin (TPO), Bone morphogenic protein (BMP), hepatocyte growth factor (HGF), growth/differentiation factor (GDF), a Neurotrophin, migration stimulating factor (MSF), and sarcoma growth factor (SGF).

68. The saRNA of any one of paragraphs 1-67, wherein the cargo comprises one or both Pappalysin-A1 (PAPPA1) and Pappalysin-A2 (PAPPA2).

69. The saRNA of any one of paragraphs 1-68, wherein the cargo comprises at least one interleukin and/or a cognate receptor(s) of the interleukin and/or receptor sub-units for the interleukin.

70. The saRNA of paragraph 69, wherein the interleukin is selected from the group consisting of IL-2, IL-4, IL-7, IL-10, IL-12, IL-13, and IL-15.

71. The saRNA of any one of paragraphs 1-70, wherein the cargo comprises at least one enzyme with antioxidant activity.

72. The saRNA of paragraph 71, wherein the enzyme is selected from the group consisting of phospholipid hydroperoxide glutathione peroxidase, superoxide dismutase-1, superoxide dismutase-2, Bruton's tyrosine kinase, adenosine deaminase, and ecto-nucleoside triphosphate diphosphydrolase.

73. The saRNA of any one of paragraphs 1-72, wherein the cargo comprises glucagon-like peptide-1 (GLP-1) or a fragment thereof.

74. The saRNA of any one of paragraphs 1-73, wherein the saRNA is substituted using the template of SEQ ID NO: 2 or a nucleic acid sequence that is at least 90% identical to SEQ ID NO: 2 that maintains the same function, and wherein the at least one cargo is inserted between the AflII and NdeI cut sites of SEQ ID NO: 2 or between nucleotides 7627 and 7628 of SEQ ID NO: 2.

75. The saRNA of any one of paragraphs 1-74, wherein the nsp1, nsp2, nsp3, and nsp4 proteins encoded by the saRNA comprise SEQ ID NO: 4 and/or SEQ ID NO: 23 or at least one amino acid sequence that is at least 90% identical to SEQ ID NO: 4 and/or at least 90% identical to SEQ ID NO: 23, that maintains the same function.

76. The saRNA of any one of paragraphs 1-75, wherein the saRNA is substituted using the template of SEQ ID NO: 5 or a nucleic acid sequence that is at least 90% identical to SEQ ID NO: 5 that maintains the same function.

77. The saRNA of any one of paragraphs 1-76, wherein the pyrimidine comprises cytidine, and the modified nucleotide comprises 5-methylcytidine and/or 5-hydroxymethylcytidine, and the substituted saRNA comprises SEQ ID NO: 6 or a nucleic acid sequence that is at least 90% identical to SEQ ID NO: 6 that maintains the same function.

78. The saRNA of any one of paragraphs 1-77, wherein the pyrimidine comprises uridine, and the modified nucleotide comprises 5-methyluridine and/or 5-hydroxymethyluridine, and the substituted saRNA comprises SEQ ID NO: 7 or a nucleic acid sequence that is at least 90% identical to SEQ ID NO: 7 that maintains the same function.

79. The saRNA of any one of paragraphs 1-78, wherein nucleotides 7634 to 8347 of SEQ ID NO: 5, nucleotides 7617 to 8330 of SEQ ID NO: 6, or nucleotides 7617 to 8330 of SEQ ID NO: 7, each corresponding to mCherry, is replaced with at least one alternative cargo of interest.

80. A self-amplifying RNA (saRNA) comprising from 5' to 3':
(a) at least one non-structural protein derived from at least one virus;
(b) a subgenomic promoter (SGP) derived from at least one virus; and
(c) at least one cargo of interest;
wherein the saRNA comprises at least 25% modified nucleotides, wherein the modified nucleotides are selected from the group consisting of 5-methylcytidine, 5-methyluridine, 5-hydroxymethyluridine, and 5-hydroxymethylcytidine;
wherein the initiating nucleotide comprises an adenosine or adenosine analog; and
wherein the initiating nucleotide of the saRNA is methylated at the 2'O position of the ribose (Cap1).

81. A self-amplifying RNA (saRNA) comprising from 5' to 3':
(a) a 5' cap;
(b) non-structural protein 1 (nsp1), non-structural protein 2 (nsp2), non-structural protein 3 (nsp3), and/or non-structural protein 4 (nsp4), each derived from at least one virus;
(c) a subgenomic promoter (SGP) derived from at least one virus;
(d) a 5' untranslated region (UTR) derived from at least one virus;
(e) at least one cargo of interest;
(f) a 3' untranslated region (UTR) derived from at least one virus; and
(g) a poly-A tail;
wherein the saRNA comprises at least 25% modified nucleotides, wherein the modified nucleotides are selected from the group consisting of 5-methylcytidine, 5-methyluridine, 5-hydroxymethyluridine, and 5-hydroxymethylcytidine; wherein the initiating nucleotide comprises an adenosine or adenosine analog; and
wherein the initiating nucleotide of the saRNA is methylated at the 2'O position of
the ribose (Cap 1).

82. The saRNA of paragraph 80 or 81, further comprising at least one 5' conserved sequence element (CSE) and/or at least one 3' conserved sequence element (CSE) derived from at least one virus.

83. A self-amplifying RNA (saRNA) comprising from 5' to 3':
(a) at least one non-structural protein derived from at least one virus;
(b) a subgenomic promoter (SGP) derived from at least one virus; and
(c) at least one cargo of interest.

84. A self-amplifying RNA (saRNA) comprising from 5' to 3':
(a) a 5' cap;
(b) non-structural protein 1 (nsp1), non-structural protein 2 (nsp2), non-structural protein 3 (nsp3), and/or non-structural protein 4 (nsp4), each derived from at least one virus;
(c) a subgenomic promoter (SGP) derived from at least one virus;
(d) a 5' untranslated region (UTR) derived from at least one virus;
(e) at least one cargo of interest;
(f) a 3' untranslated region (UTR) derived from at least one virus; and (g) a poly-A tail.

85. The saRNA of paragraph 83 or 84, further comprising at least one 5' conserved sequence element (CSE) and/or at least one 3' conserved sequence elements (CSE) derived from at least one virus.

86. The saRNA of any one of paragraphs 83-85, wherein the saRNA does not comprise modified nucleotides.

87. The saRNA of any one of paragraphs 83-86, wherein the saRNA comprises less than 25% modified nucleotides.

88. The saRNA of any one of paragraphs 83-87, wherein the cargo comprises a chimeric antigen receptor (CAR) comprising an extracellular domain that specifically binds to an antigen of interest.

89. The saRNA of any one of paragraphs 83-88, wherein the CAR is selected from the group consisting of:

(a) a conventional CAR;

(b) an ON-CAR;

(c) an OFF-CAR system;

(d) an ON/OFF-CAR;

(e) an inhibitory CAR; or (f) a split, universal, programmable and reconfigurable (SUPRA) CAR system.

90. A nucleic acid encoding or comprising the saRNA of any one of paragraphs 1-89.

91. A vector encoding or comprising the saRNA of any one of paragraphs 1-89.

92. A composition comprising the saRNA of any one of paragraphs 1-89.

93. The composition of paragraph 92, wherein the saRNA is formulated at a dose of about $5\times10^{-4}$ mg/kg.

94. The composition of paragraph 92, wherein the saRNA is formulated at a dose of about $5\times10^{-3}$ mg/kg.

95. The composition of paragraph 92, wherein the saRNA is formulated at a dose of about $5\times10^{-2}$ mg/kg.

96. The composition of paragraph 92, wherein the saRNA is formulated at a dose of about $5\times10^{-1}$ mg/kg.

97. The composition of any one of paragraphs 92-96, formulated as lipid nanoparticles.

98. The composition of any one of paragraphs 92-96, formulated in a polymeric matrix.

99. A cell contacted with the saRNA of any one of paragraphs 1-89, the nucleic acid of paragraph 90, the vector of paragraph 91, or the composition of any one of paragraphs 92-98.

100. The cell of paragraph 99, wherein the cell is a eukaryotic cell.

101. A pharmaceutical composition comprising the saRNA of any one of paragraphs 1-89 and a pharmaceutically acceptable carrier.

102. A pharmaceutical composition comprising the nucleic acid of paragraph 90, and a pharmaceutically acceptable carrier.

103. A pharmaceutical composition comprising the vector of paragraph 91, and a pharmaceutically acceptable carrier.

104. A pharmaceutical composition comprising the cell of any one of paragraphs 99-100 and a pharmaceutically acceptable carrier.

105. The pharmaceutical composition of any one of paragraphs 101-104, wherein the saRNA is formulated at a dose of about $5\times10^{-4}$ mg/kg.

106. The pharmaceutical composition of any one of paragraphs 101-104, wherein the saRNA is formulated at a dose of about $5\times10^{-3}$ mg/kg.

107. The pharmaceutical composition of any one of paragraphs 101-104, wherein the saRNA is formulated at a dose of about $5\times10^{-2}$ mg/kg.

108. The pharmaceutical composition of any one of paragraphs 101-104, wherein the saRNA is formulated at a dose of about $5\times10^{-1}$ mg/kg.

109. The pharmaceutical composition of any one of paragraphs 101-108, formulated as lipid nanoparticles.

110. The pharmaceutical composition of any one of paragraphs 101-108, formulated in a polymeric matrix.

111. A method of expressing at least one cargo of interest in a cell, the method comprising contacting the cell with the saRNA of any one of paragraphs 1-89.

112. A method of expressing at least one cargo in a subject in need thereof, the method comprising administering to the subject an effective amount of the pharmaceutical composition any one of paragraphs 101-110.

113. The method of paragraph 112, wherein the subject is a human.

114. The method of paragraph 112, wherein the subject is a livestock animal or a pet.

115. The method of any one of paragraphs 111-114, wherein the saRNA is a modified saRNA comprising at least 25% modified nucleotides.

116. The method of paragraph 115, wherein the modified saRNA replicates at a level greater than or equal to that of an equivalent dose of a corresponding saRNA with less than 25% modified nucleotides.

117. The method of paragraph 115, wherein the modified saRNA expresses the cargo at a level greater than or equal to that of an equivalent dose of a corresponding saRNA with less than 25% modified nucleotides.

118. The method of paragraph 115, wherein the transfection efficiency of the modified saRNA is greater than that of an equivalent dose of a corresponding saRNA with less than 25% modified nucleotides.

119. The method of paragraph 115, the modified saRNA produces an early interferon response in the subject, and wherein the early interferon response is decreased compared to an equivalent dose of a corresponding saRNA with less than 25% modified nucleotides.

120. The method of paragraph 115, wherein the cargo is expressed at a detectable level from the modified saRNA for an increased time period compared to an equivalent dose of a corresponding saRNA with less than 25% modified nucleotides.

121. The method of any one of paragraphs 111-120, wherein the cell is a human cell.

122. The method of any one of paragraphs 111-121, wherein the subject has cancer.

123. The method of any one of paragraphs 111-122, wherein the subject is in need of vaccination for an infectious disease.

124. The method of any one of paragraphs 111-123, wherein the subject is in need of protein replacement therapy.

125. The method of any one of paragraphs 111-124, wherein the subject is in need of antibody therapy.

126. The method of any one of paragraphs 111-125, wherein the subject is in need of treatment for diabetes and/or obesity.

127. The method of any one of paragraphs 111-126, wherein the subject is in need of BITE therapy.

128. The method of any one of paragraphs 111-127, wherein the saRNA permits tissue, organ, or cell-type specific expression of the cargo.

129. The method of paragraph 128, wherein the saRNA comprises greater than 50% substitution of uridine with 5-methyluridine, and the saRNA has increased kidney specific expression of the cargo compared to an equivalent dose of a corresponding saRNA comprising less than 50% substitution of uridine with 5-methyluridine.
130. The method of any one of paragraphs 111-129, wherein the modified saRNA modulates cellular differentiation of a cell containing the saRNA at a level equivalent to or greater than the level of modulation achieved with an equivalent dose of a corresponding saRNA with less than 25% modified nucleotides.
131. The method of paragraph 130, wherein the cell is modulated by expression of a stem cell transcription factor encoded by the saRNA.
132. The method of paragraph 130 or 131, wherein the cell is modulated to become a stem cell.
133. The method of any one of paragraphs 111-132, wherein the at least one cargo is expressed constitutively in the cell.
134. The method of any one of paragraphs 111-133, wherein the at least one cargo is expressed constitutively in the subject.
135. The method of any one of paragraphs 111-134, the method further comprising contacting the cell with at least one input to control the fate or function of the cell.
136. The method of any one of paragraphs 111-135, the method further comprising administering to the subject at least one input to control the fate or function of at least one cell in the subject.
137. The method of any one of paragraphs 135 or 136, wherein the input is endogenous to the environment of the cell comprising the saRNA.
138. The method of any one of paragraphs 135 or 136, wherein the input is exogenous to the environment of the cell comprising the saRNA.
139. The method of any one of paragraphs 135-138, wherein the input is a cell.
140. The method of any one of paragraphs 135-139, wherein the input is a protein.
141. The method of any one of paragraphs 135-140, wherein the input is a small molecule.
142. The method of any one of paragraphs 135-141, wherein the input is a specific wavelength or wavelengths of light.
143. The method of any one of paragraphs 135-142, wherein the input is a specific temperature.
144. The method of any one of paragraphs 135-143, wherein the input is application of a magnetic field.
145. The method of any one of paragraphs 135-144, wherein the input results in death of the cell comprising the saRNA, increased clearance rate of the cell comprising the saRNA, and/or cell-cycle arrest of the cell comprising the saRNA.
146. The method of any one of paragraphs 135-145, wherein the input results in inhibition of a repressible protease domain in the cargo.
147. The method of any one of paragraphs 135-146, wherein the input results in the activation of a repressible protease domain in the cargo.
148. The method of any one of paragraphs 135-147, wherein the input results in oligomerization and a resultant activation of the cargo.
149. The method of any one of paragraphs 135-148, wherein the input results in oligomerization and a resultant inhibition of the cargo.
150. The method of any one of paragraphs 111-149, wherein the cargo comprises a chimeric antigen receptor.
151. The method of any one of paragraphs 111-150, wherein the cargo comprises multiple chimeric antigen receptors.
152. The method of any one of paragraphs 111-151, wherein control of the cell requires the presence of all inputs simultaneously.
153. The method of any one of paragraphs 111-152, wherein control of the cell requires the presence of any input.
154. The method of any one of paragraphs 111-153, wherein control of the cell requires both the presence and absence of a distinct combination of inputs.
155. The method of any one of paragraphs 111-154, wherein the fate of the cell is an altered cell type.
156. The method of any one of paragraphs 111-155, wherein the fate of the cell is an altered cell localization.
157. The method of any one of paragraphs 111-156, wherein the function of the cell is lytic.
158. The method of any one of paragraphs 111-157, wherein the function of the cell is stimulatory.
159. The method of any one of paragraphs 111-158, wherein the function of the cell is immunomodulatory.
160. The method of any one of paragraphs 111-159, wherein the cargo is a protein comprising a chimeric antigen receptor comprising an extracellular domain that senses at least one input signal.
161. The method of any one of paragraphs 111-160, wherein the cargo is a protein comprising at least one chimeric antigen receptor, and the input is a small molecule and/or a protein.
162. The method of any one of paragraphs 111-161, wherein the cargo is a protein comprising at least one domain responsive to an external input.
163. The method of any one of paragraphs 111-162, wherein the cargo is a protein comprising at least one repressible protease domain that responds to at least one protease inhibitor to regulate activity of the cargo.
164. The method of any one of paragraphs 111-163, wherein the saRNA is delivered to the cell in situ.
165. The method of any one of paragraphs 111-164, wherein the saRNA is delivered to the cell ex vivo.
166. The method of any one of paragraphs 111-165, wherein the cargo of the saRNA encodes for and expresses at least one cargo protein, at least one protein reporters and/or at least one expression-enhancing protein.
167. The method of paragraph 166, wherein the cargo protein is a chimeric antigen receptor, and the expression enhancing protein is B18R.
168. The method of paragraph 166, wherein the cargo protein is a chimeric antigen receptor, and the expression enhancing protein is E3L.
169. The method of any one of paragraphs 111-168, wherein the saRNA is delivered to the cell by electroporation.
170. The method of any one of paragraphs 111-169, wherein the saRNA is delivered to the cell by lipid nanoparticles.
171. The method of any one of paragraphs 111-170, wherein the saRNA, or a composition comprising the saRNA, comprises a targeting domain to increase transfection efficiency of the saRNA into a specific cell type.

172. The method of any one of paragraphs 111-171, wherein the saRNA increases the level of expression of a cargo protein in the cell.
173. The method of any one of paragraphs 111-172, wherein the activity of the cargo protein expressed by the saRNA is controlled by administration of a small molecule and/or a protein and/or an RNA molecule.
174. The method of paragraph 173, wherein the RNA molecule is an aptamer.
175. The method of any one of paragraphs 111-174, wherein the protein is a chimeric antigen receptor (CAR), and the activity of the CAR is regulated by at least one small molecule-responsive domain.
176. The method of any one of paragraphs 111-175, wherein the activity of the cargo protein expressed by the saRNA is increased and/or decreased by administration of at least one small molecule.
177. The method of paragraph 176, wherein the at least one small molecule is a protease inhibitor or a molecule capable of interacting with at least one protein domain in the cargo protein.
178. The method of any one of paragraphs 111-177, wherein the saRNA encodes and expresses a plurality of cargo proteins that are capable of interacting with each other.
179. The method of paragraph 178, wherein the interaction of the plurality of cargo proteins results in conditional activity of the cell transfected by the saRNA.
180. The method of paragraph 178 or 179, wherein the cargo proteins capable of interacting with each other are chimeric antigen receptors with activating and/or inhibitory functions.
181. The method of any one of paragraphs 111-180, wherein, a plurality of distinct saRNAs is delivered to a mixture of cells.
182. The method of any one of paragraphs 111-181, wherein the saRNA is administered to the subject via intraocular, intraosseous (IO), intraperitoneal (IP), subcutaneous (SC), intravenous (IV), intramuscular (IM), intrarectal, intravaginal, intraarticular (IA), inhalation, or topical administration.

The technology described herein is further illustrated by the following examples which in no way should be construed as being further limiting.

EXAMPLES

Example 1: Increased Expression of Chimeric Antigen Receptors in Immune Cells for an Extended Duration by Transfection with Self-Replicating RNA Described herein is a system for the delivery and application of self-replicating RNA to permit the modification of cells by expression of cargo proteins. The cargo proteins can be receptors, ligands, transcription factors, reporter proteins, enzymes, or any other genetically encodable protein. Self-replicating RNA delivery confers higher protein expression than that of conventional mRNA and maintains expression for longer duration. This system can be used to simultaneously express multiple proteins at levels comparable to or greater than other methods used to establish constitutive protein expression (e.g., transient DNA transfection, mRNA transfection, lentiviral transduction). Additionally, described herein is a system for enhanced expression, and controlled activity of the cargo either by external means or by in situ logic computation circuits. Such control permits reversible action and conditional activity of the cargo, respectively. As a clinically relevant example of the technology, self-replicating RNA that encode several cargos (e.g., reporter proteins, chimeric antigen receptors (CAR), expression enhancing proteins) can be delivered to T cells. The self-replicating RNAs described herein can be used in any application in which the modification of cells is needed and can be employed to modify cells in vivo by delivery with lipid nanoparticles.

Figure 1B:
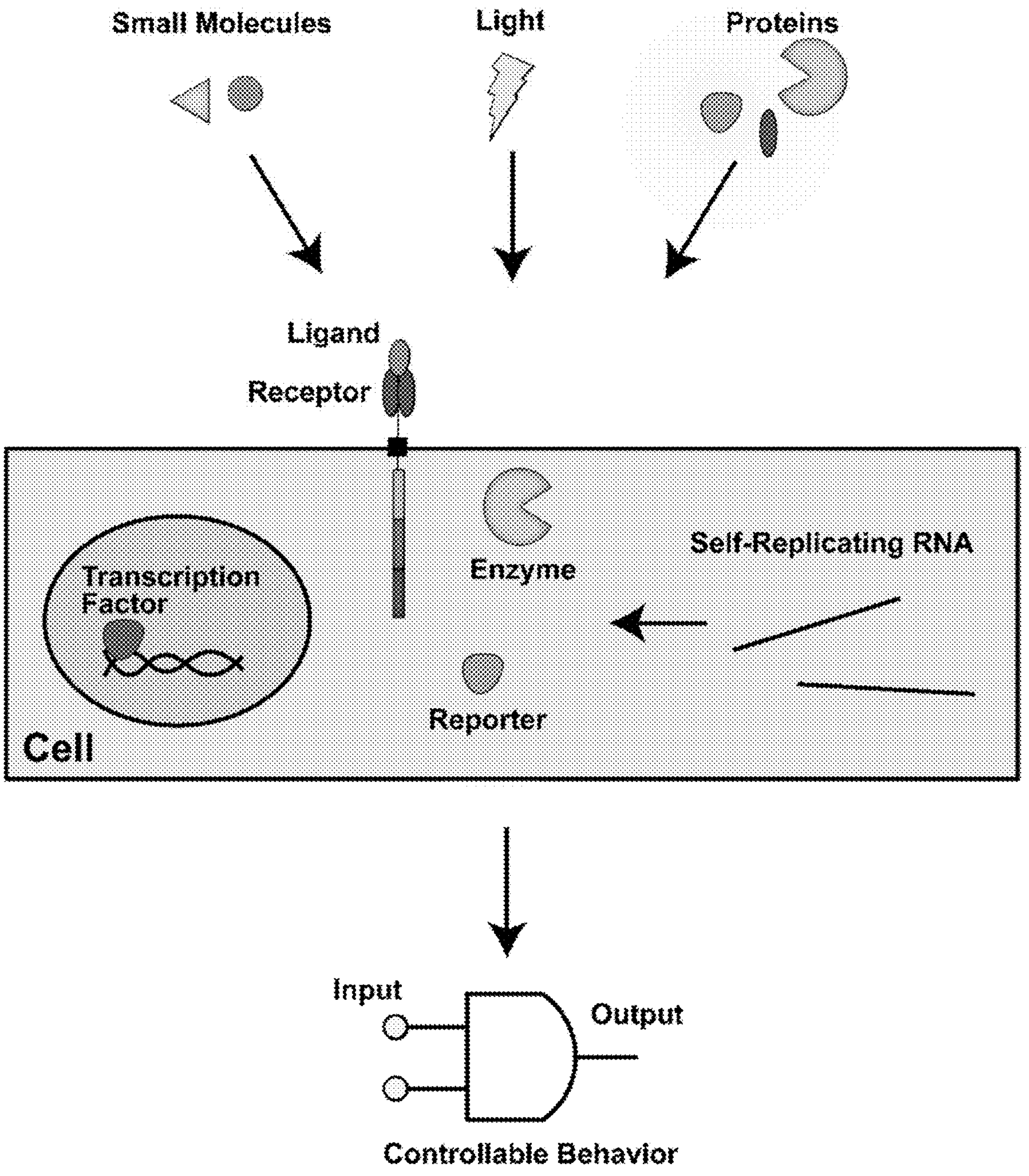

As a non-limiting example, described herein are self-replicating RNA formats to express a range of cargo and reporter proteins (see e.g., FIG. 1A-1B). The examples described herein relate to the use of the self-replicating RNA platform to express functional chimeric antigen receptors in T cells to generate CAR-T cells. There are many challenges associated with ex vivo cell engineering. The isolation of immune cells and subsequent genetic engineering and expansion is costly and time consuming, representing a major bottleneck from a patient and manufacturing perspective. An alternative to this is to reprogram cells in vivo through the delivery of mRNA. Challenges associated with expression level and duration have been reported. As a result, repeat dosing is often required to achieve functional benefit, and efficacy has been shown in a limited number of animal models. By creating self-replicating RNA that combines components from RNA viruses and cargos of interest, greater expression of therapeutic programs can occur over a longer duration. Moreover, self-replicating RNA systems can be delivered in vivo to control immune cells for therapeutically relevant purposes. The CAR-T cells generated from self-replicating RNA have higher levels of CAR expression over a longer period when compared to CAR-T cells generated via mRNA (see e.g., FIG. 1A-1B).

The replication of self-replicating RNA is a result of the inclusion of sequence elements derived from RNA viruses. The replication components can be derived from the Venezuela Equine Encephalitis (VEE) alphavirus as an example, and sequences from other viruses can provide similar function. Upon entrance inside of a cell, the self-replicating RNA is translated to express the four proteins (nsp 1, nsp2, nsp3, nsp4) necessary for the formation of an RNA replication complex. The resulting RNA replication complex can then replicate the full-length RNA strand by interaction with conserved sequence elements at the 5' and 3' ends of the RNA. Additionally, the replication complex can recognize a subgenomic promoter (SGP) sequence to enable amplification of the RNA encoding the cargo. This replication and amplification activity allows for higher levels of expression of delivered cargo over a longer period when compared with conventional mRNA.

Figure 2:
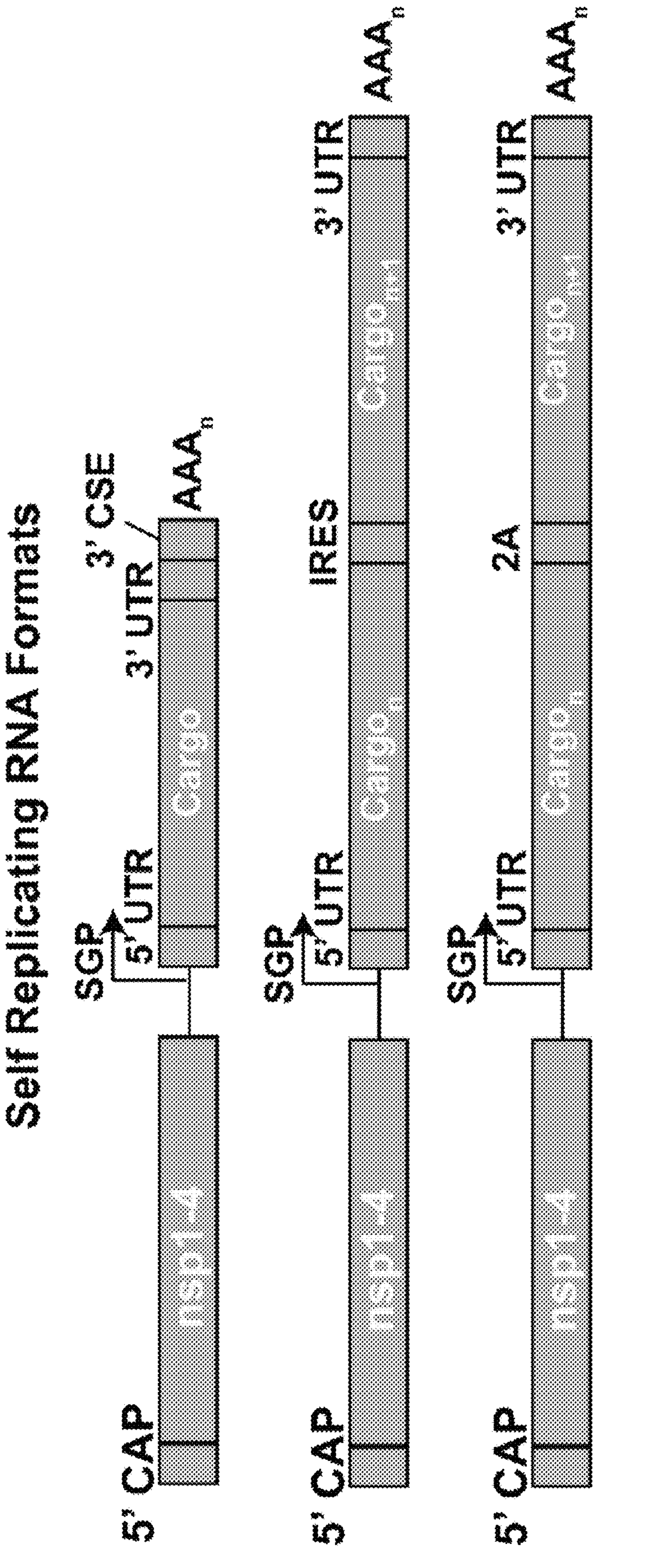
FIG. 2 shows a schematic detailing an exemplary format of self-replicating RNA. The developed self-replicating RNA formats include conserved sequence elements (CSE) derived from RNA viruses (e.g., Venezuela Equine Encephalitis virus) and coding sequences for non-structural proteins (e.g., nsp1, nsp2, nsp3, nsp4). The cargo coding sequence is placed downstream of a subgenomic promoter (SGP) or an internal ribosome entry site (IRES) sequence. Multiple cargo proteins can be co-expressed by separating the coding sequences with IRES or 2A sequences or additional SGP sequences.
Figure 3:
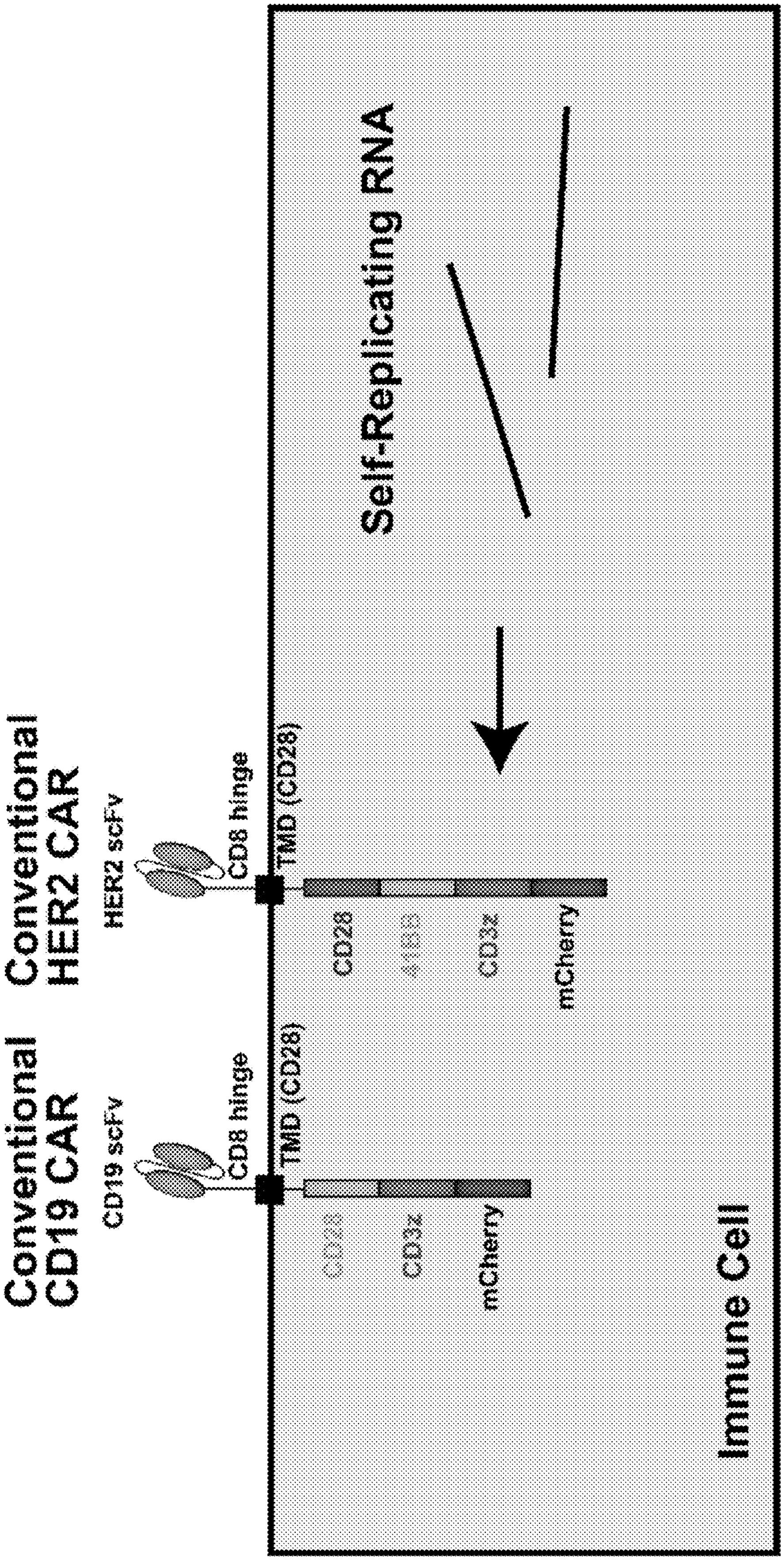
FIG. 3 shows the expression of conventional chimeric antigen receptors via self-replicating RNA. Self-replicating RNA can be used to express a chimeric antigen receptor targeting a variety of antigens.
Figure 4:
FIG. 4 shows a longer duration of expression of a HER2 chimeric antigen receptor from self-replicating RNA (black) compared to convention mRNA (gray). Cells expressing a HER2 CAR tagged with mCherry were analyzed via flow cytometry 48 and 96 hours after transfection. The percentage of cells expressing the receptor was determined by measuring mCherry fluorescence. The bars above the bar chart show the fold change between each time point for the respective conditions.
Figure 5:
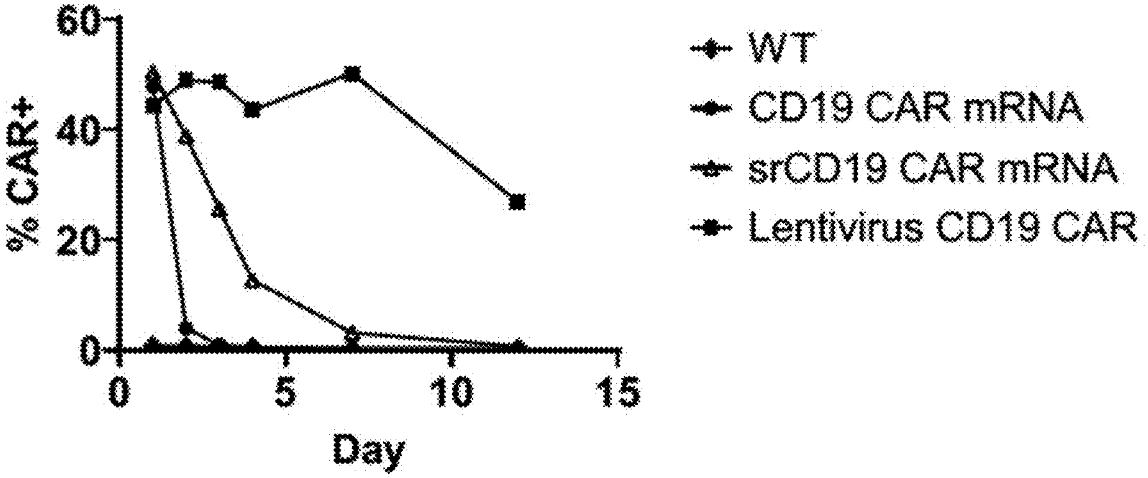
FIG. 5 shows a longer duration of expression of a CD19 chimeric antigen receptor from self-replicating RNA. Cells expressing a CD19 CAR were analyzed via flow cytometry for up to 12 days following transfection. The percentage of cells expressing the receptor was determined by staining the cells with an anti-myc antibody that binds a myc tag on the receptor. Lentivirally transduced cells were used as a control to account for any discrepancies with staining.
Figure 6:
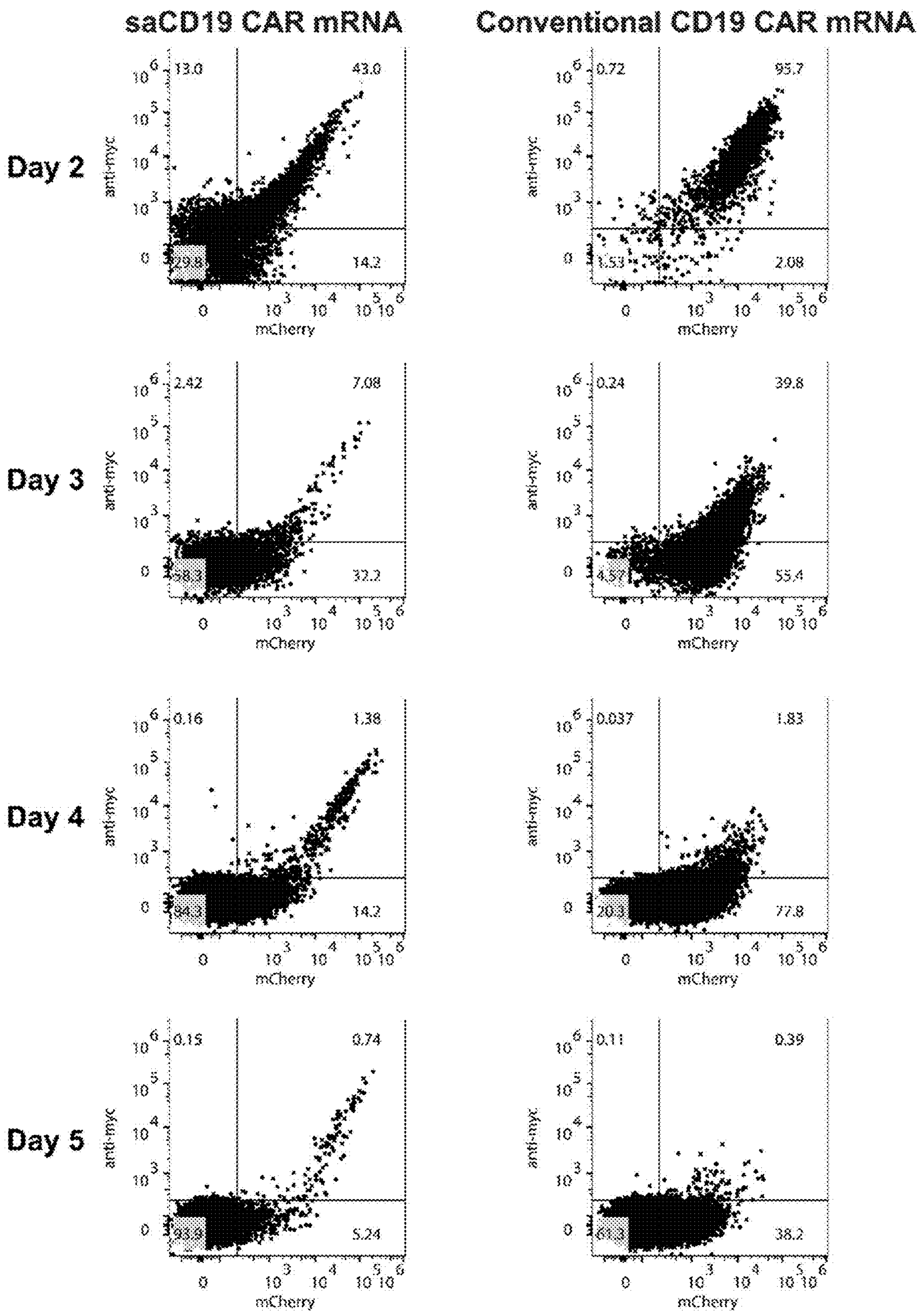
FIG. 6 shows detection of a CD19 chimeric antigen for a longer duration in CD3+ primary T cells transfected with self-replicating RNA. Primary CD3+ T cells were transfected with self-replicating (left) or conventional (right) RNA encoding a CD19 chimeric antigen receptor tagged with intracellular mCherry. The plots show the measurement of mCherry fluorescence (x axis) and an anti-myc stain (y axis) (an anti-myc antibody that binds an extracellular myc tag on the receptor) at multiple time points after transfection.

Self-replicating RNA formats to express a range of proteins and reporter molecules were developed that utilize components from the Venezuela Equine Encephalitis Virus (VEEV) in vanous formats (see e.g., FIG. 2). A series of self-replicating RNA sequences that encode chimeric antigen receptors targeting CD19 and HER2 were developed (see e.g., FIG. 3). The RNA was generated by in vitro transcription. As a control, conventional mRNA (lacking self-replicating components) encoding HER2 and CD19 CARs were synthesized. All RNA species were transfected into Jurkat T cells and the levels of expression were tracked longitudinally by measuring the fluorescence of an mCherry tag placed on the C-terminus of the CARs or by staining with an anti-myc antibody reactive to a myc tag on the extracellular domain of the CAR. After transfection, the cells expressing the HER2 CAR were analyzed at 48 hours and 96 hours. A larger percentage of cells transfected with self-replicating RNA had detectable CAR expression at 96 hours when compared with the conventional mRNA transfected cells (see e.g., FIG. 4). This indicates a greater level of expression at the protein level. The cells transfected with RNA encoding the CD19 CAR were tracked along with cells transduced with lentivirus encoding a CD19 CAR as a control. A larger percentage of cells transfected with the self-replicating RNA encoding the CD19 CAR had detectable CAR expression via staining with an anti-myc antibody (see e.g., FIG. 5). As an additional example, primary CD3+ T cells isolated from a human donor were transfected with self-replicating RNA and conventional mRNA encoding a CD19 chimeric antigen receptor. The expression was measured over time by staining for the receptor with an anti-myc antibody and by measuring the fluorescence of the C-terminal mCherry tag. The expression levels were greater and lasted for a longer time period in cells transfected with the self-replicating RNA (see e.g., FIG. 6). By comparison, cells expressing the receptor at levels detectable by the anti-myc stain were not detected 5 days after transfection with the conventional mRNA. These examples demonstrate the ability to modify cells (e.g., immune cells) to express a cargo protein via transfection with self-replicating RNA. Additionally, the expression is greater than levels resulting from transfection with conventional mRNA and lasts for a longer period of time.

Figure 7:
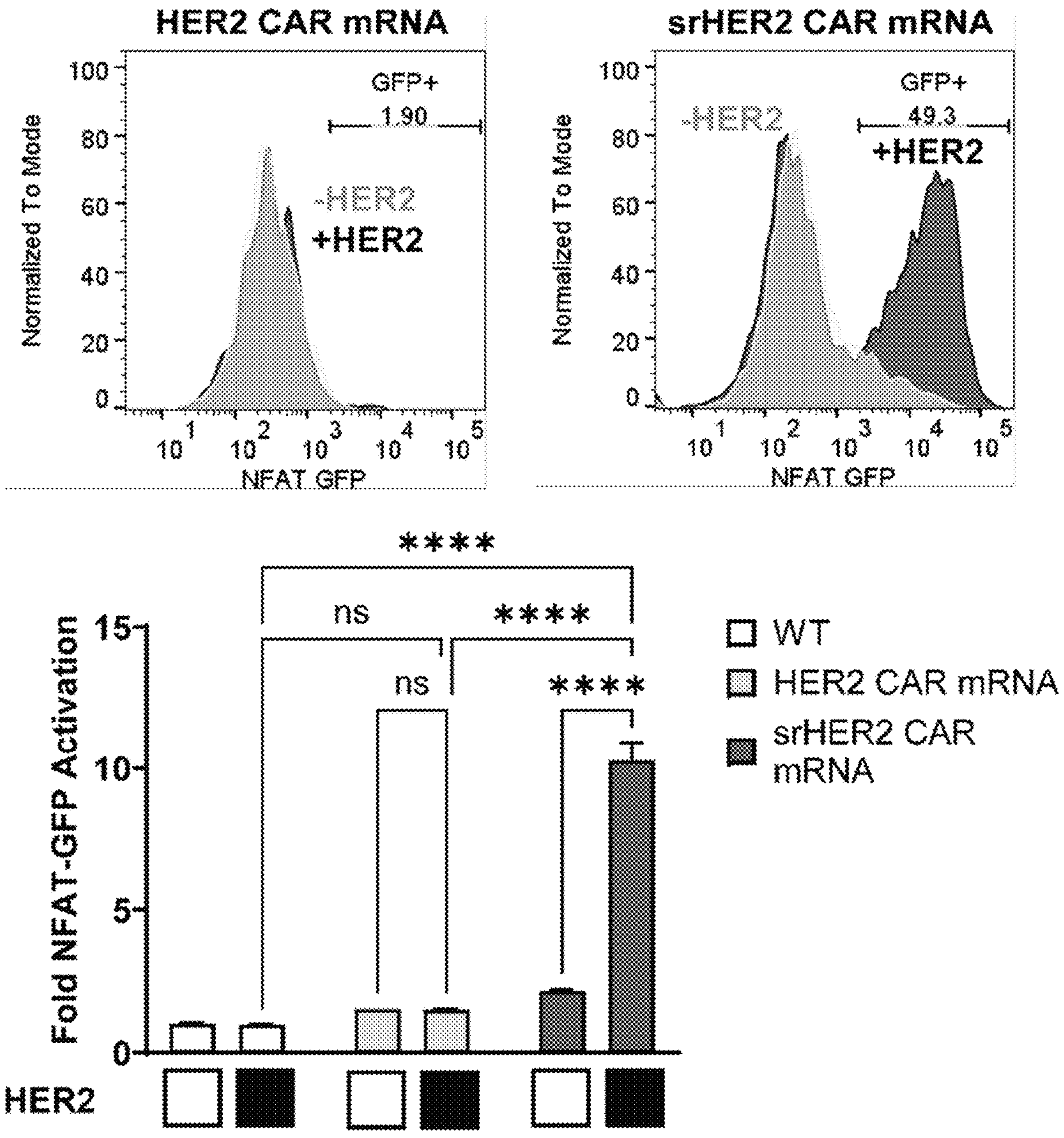
FIG. 7 shows function of a HER2 chimeric antigen receptor for a longer duration after transfection with self-replicating RNA. Activation of Jurkat T cells expressing a HER2 CAR from conventional or self-replicating RNA 72 hours after transfection (top). Cells were cultured on plates with or without HER2 antigen. The activation is measured by the fluorescence of GFP from an NFAT GFP reporter system. Fold activation read out from the mean fluorescence intensity of GFP (bottom). ****=p $<0.0001$. ns=not significant. N=3 independent replicates.

Example 2: Expression of Cargo Proteins in Cells Via Self-Replicating RNA Results in Enhanced Protein Functionality Over a Longer Duration when Compared with Conventional mRNA The self-replicating RNA encoding the HER2 and CD19 chimeric antigen receptors were transfected into Jurkat T cells that contain an NFAT-GFP reporter system, commonly utilized to measure T cell activation under various conditions. When the Jurkat T cells become activated, GFP is expressed. To measure the response of the cells transfected with the HER2 CAR to the HER2 antigen, the cells were cultured on tissue culture plates treated with PBS or HER2 antigen. The cultured cells were incubated overnight, beginning 72 hours after transfection. In the case of cells transfected with the conventional mRNA encoding the HER2 CAR, negligible activation was observed (see e.g., FIG. 7, top and bottom). However, the cells transfected with the self-replicating HER2 CAR RNA displayed robust activation as measured by the mean fluorescence intensity of GFP via flow cytometry (see e.g., FIG. 7, bottom).

Figure 8:
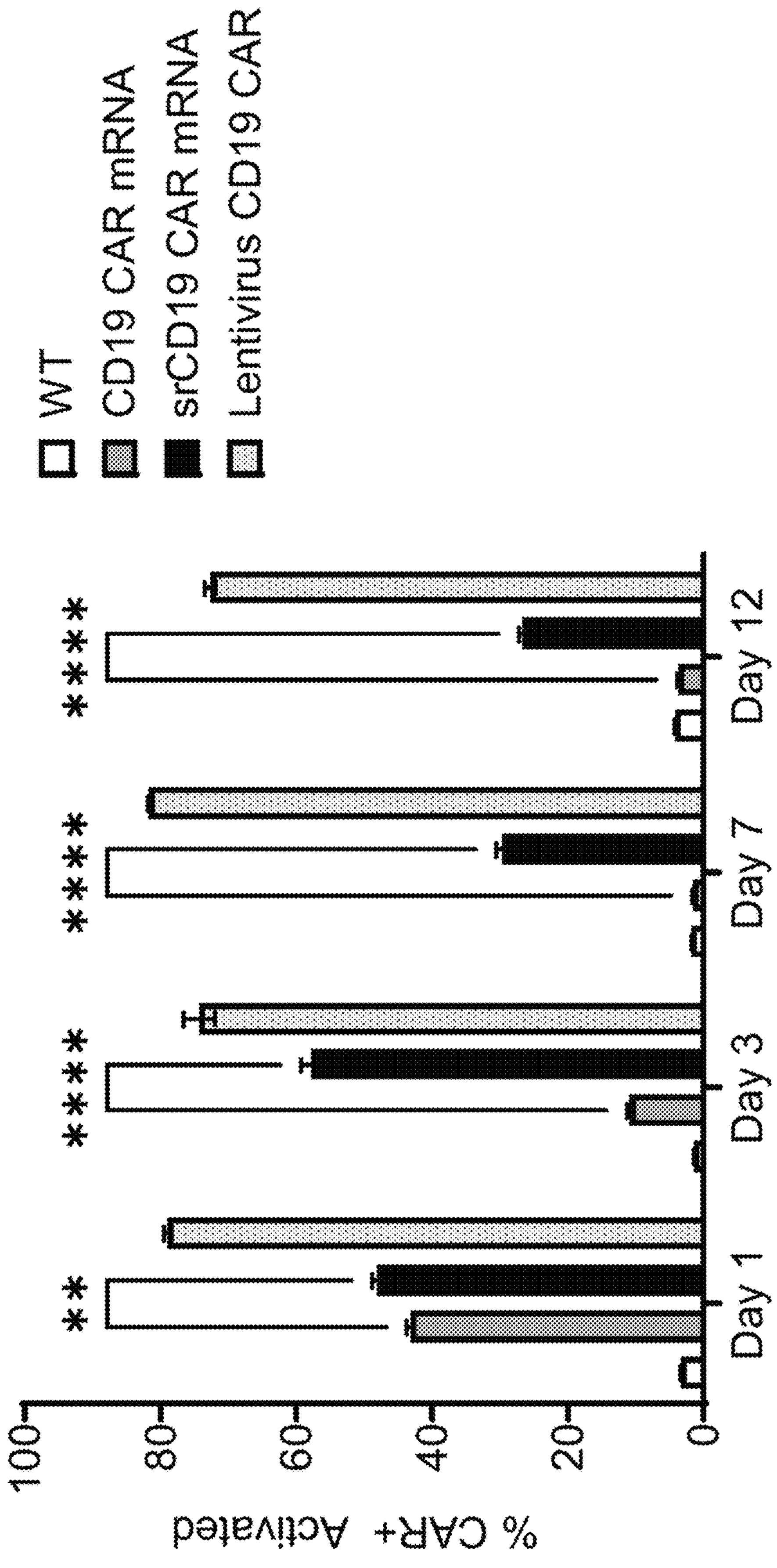
FIG. 8 shows function of a CD19 chimeric antigen receptor for a longer duration after transfection with self-replicating RNA. The percentage of CAR-T cells that were activated during overnight co-culture with CD19 expressing Nalm6 cells was measured by flow cytometry. Activation was measured by the fluorescence of GFP in Jurkat T cells containing an NFAT-GFP reporter system. N=3 independent replicates. =$p<0.001$, =$p<0.0001$

Jurkat T cells transfected with conventional or self-replicating RNA encoding a CD19 CAR were co-cultured with CD19 expressing Nalm6 cells at a series of time points after transfection. The activation of the CAR-T cells was determined by measuring the percentage of CAR expressing NFAT GFP reporter cells that were GFP positive. Cells transfected with conventional mRNA displayed a reduced response on day 3 compared to day 1 and did not respond to the CD19 antigen after 7 days. By comparison, cells transfected with the self-replicating RNA respond at all time points in the assay (see e.g., FIG. 8).

Figure 9:
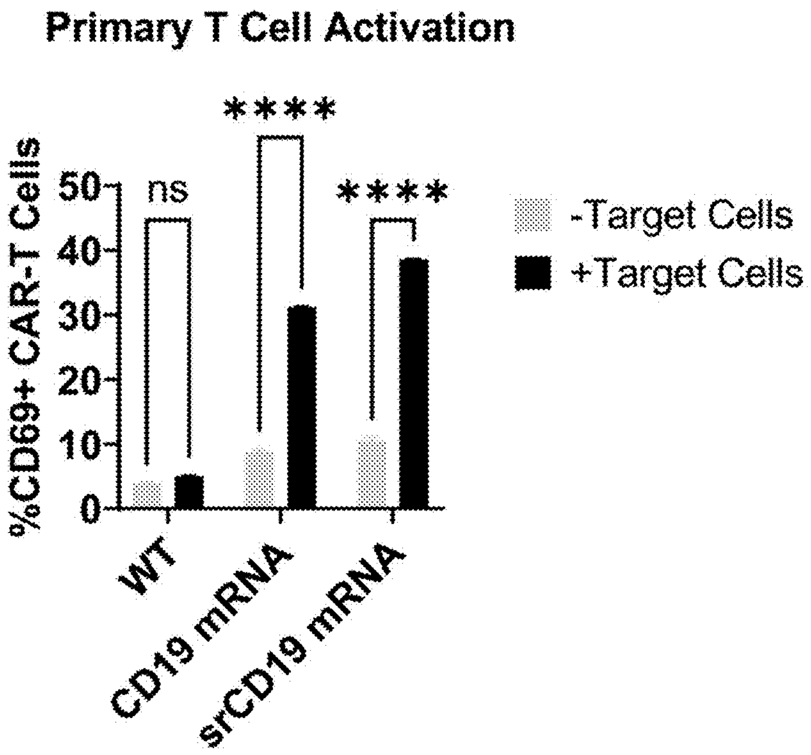
FIG. 9 shows function of a CD19 chimeric antigen receptor in primary CD3+ T cells transfected with self-replicating RNA. The bar graph shows the percentage of CAR-T cells positive for CD69, a marker of early T cell activation. Primary T cells transfected with conventional or self-replicating RNA encoding a CD19 CAR were co-cultured with CD19 expressing Nalm6 cells. N=3 independent replicates. **=$p<0.0001$. ns=not significant.
Figure 10:
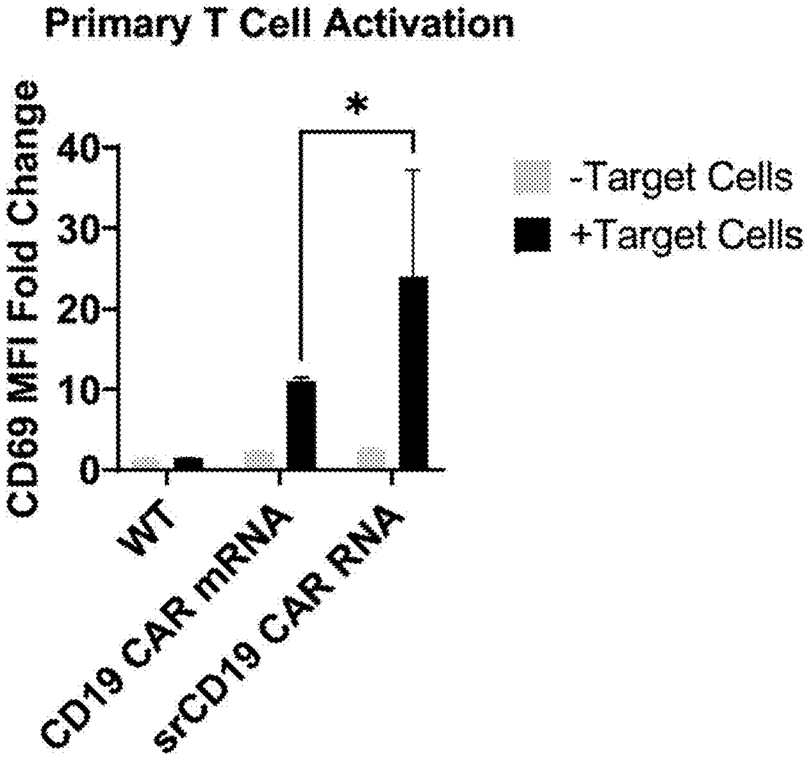
FIG. 10 shows enhanced function of a CD19 chimeric antigen receptor in primary CD3+ T cells transfected with self-replicating RNA. The bar graph shows the fold change in mean fluorescence intensity of CAR-T stained with an antibody targeting CD69 after an overnight co-culture with Nalm6 cells. N=3 independent replicates. *=$p<0.05$.
Figure 11:
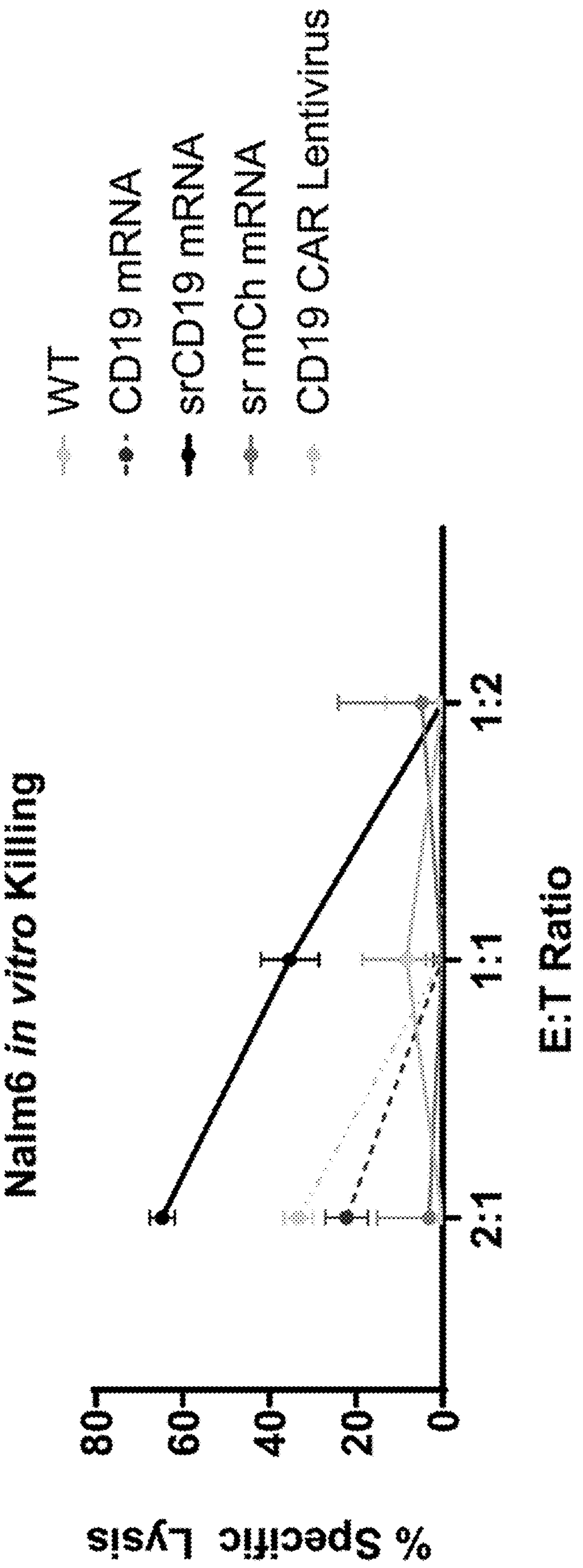
FIG. 11 shows enhanced cytotoxic function of CAR-T cells generated from self-replicating RNA. Target cell killing observed after co-culture of CAR-T cells with Nalm6-Luc cells for a period of 24 hours. The CAR-T cells were primary CD3+ T cells transfected with mRNA or self-replicating RNA 48 hours prior to the assay. N=3 independent replicates.

As an additional example, CAR-T cells were generated from CD3+ human primary T cells by transfection with conventional or self-replicating RNA encoding a CD19 CAR. The resulting cells were co-cultured overnight with Nalm6 cells, beginning 48 hours after transfection. The CAR-T cells were then stained with an antibody targeting CD69, a surface marker for early activation in T cells. The proportion of cells positive for CD69 was quantified via flow cytometry. The CAR-T cells transfected with conventional and self-replicating RNA encoding the CD19 CAR responded to the target cells and expressed CD69 (see e.g., FIG. 9). Additionally, the fold change in mean fluorescence intensity with and without target cells present was quantified. The fold change was greater for the cells transfected with the self-replicating RNA (see e.g., FIG. 10). The CAR-T cells were also co-cultured with CD19 and luciferase expressing Nalm6 cells to measure the cytotoxic function of the CAR-T cells. The co-culture was performed at various effector (CAR-T cells) to target (Nalm6 cells) ratios. The degree of killing was determined by quantifying the signal from the luciferase enzyme expressed by the Nalm6 cells. The CAR-T cells generated via transfection with self-replicating RNA killed the most Nalm6 cells at all E:T ratios tested (see e.g., FIG. 11). The observed increase in activation marker and enhanced killing ability is likely a result of the increased expression of the CD19 CAR expressed from self-replicating RNA. These examples demonstrate the ability to express cargo proteins with enhanced activity that can occur over a longer duration via transfection with self-replicating RNA.

Figure 12:
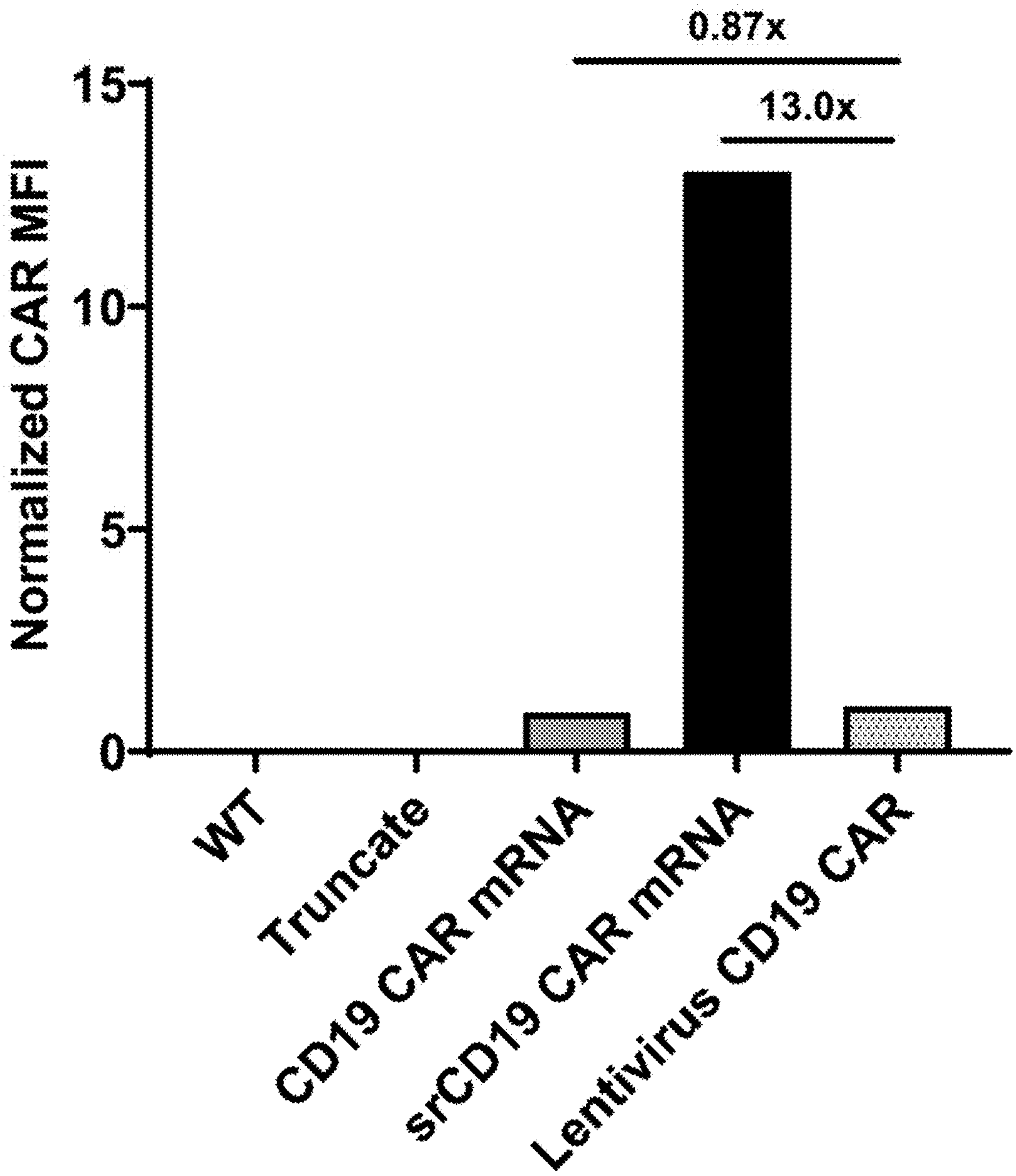
FIG. 12 shows greater levels of expression of a chimeric antigen receptor per cell after transfection with self-replicating RNA. The expression levels of a chimeric antigen receptor were measured by flow cytometry. The bars report the normalized mean fluorescence intensity of a fluorescently labeled anti-myc antibody that binds a myc tag on the receptor. The intensity values are normalized to the intensity of the cells transduced with lentivirus encoding the CD19 CAR. The fold difference is shown above each bar.
Figure 13:
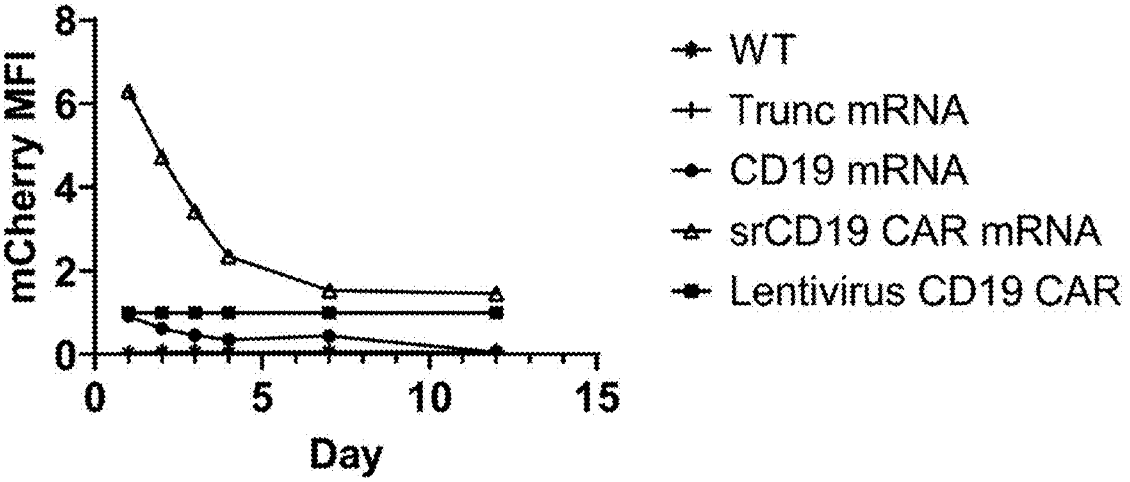
FIG. 13 shows greater levels of expression of a chimeric antigen receptor (tagged with mCherry) per cell for an extended duration after transfection with self-replicating RNA. CAR expression levels over time via measurement of mCherry fluorescence by flow cytometry. The resulting mean fluorescence intensity values were normalized to the value of the obtained for the cells transduced with lentivirus at each time point.
Figure 14:
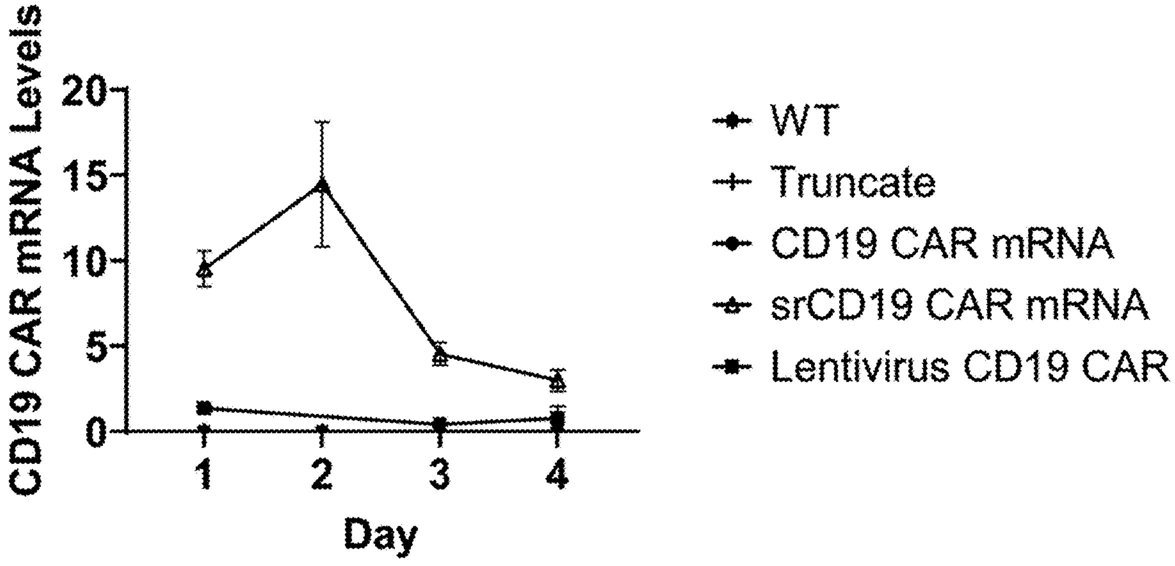
FIG. 14 shows greater amounts of chimeric antigen receptor RNA transcript at multiple time points after transfection. The RNA levels of the CD19 CAR transcript were measured via RT-qPCR. The resulting transcript levels were normalized to the value obtained for the cells transduced with lentivirus. N =3 independent replicates.

Example 3: Transfection of Cells with Self-Replicating RNA Results in Greater Expression Levels of a Protein Per Cell To analyze the levels of expression resulting from the delivery of self-replicating RNA to immune cells, Jurkat T cells were transfected with self-replicating and conventional RNA encoding a CD19 CAR. The resulting CAR-T cells were stained with an anti-myc antibody. The antibody binds the extracellular scFv containing a myc tag. The CAR-T cells generated by self-replicating RNA had approximately 13-fold greater expression of the CAR than CAR-T cells produced via conventional mRNA or by lentiviral transduction (see e.g., FIG. 12). By comparison, the lentivirally transduced cells and cells produced by transfection with conventional mRNA had approximately the same level of expression. The expression levels were tracked over time by measuring the fluorescence from the mCherry tagged CD19 CAR. The CAR was detected on cells transfected with the self-replicating RNA over a 12-day period. In comparison, the receptor was no longer detected after 4 days in the case of conventional mRNA transfection (see e.g., FIG. 13). Overall, CAR expression in cells transfected with self-replicating RNA, measured with mCherry mean fluorescence intensity, is 1.5-6× higher than in lentiviral transduced CAR T cells (see e.g., FIG. 13). Additionally, the amount of mRNA was measured over time via quantitative PCR. It was found that the self-replicating RNA produced transcript levels that were consistently higher than the cells transduced with lentivirus (see e.g., FIG. 14). These examples demonstrate the utility of this invention in expressing cargo proteins at levels equal to or greater than other methods used to establish constitutive protein expression.

Example 4: Self-Replicating RNA can be Utilized to Express Cargo with Externally Controllable Activity in Cells A framework for controlling the activity of cells by expressing proteins with controllable activity by self-replicating RNA was developed (see e.g., FIG. 1). This control is highly desirable in the generation of therapeutic cells so that activity can be precisely modulated. The constructs described herein can be used to express a therapeutic program in situ, without genetic modification, and in a regulated and controllable manner, e.g., to reduce cost and enhance the safety of therapeutic applications.

The activity of the cargo can be controlled externally by including protein domains regulated by small molecules, light, etc. The presence or absence of these factors can modify the cargo activity by increasing or decreasing the desired function. This is often achieved via regulation at the protein level. The expressed protein cargo can be degraded by the addition of factors that result in an enhanced rate of protein degradation. Additionally, multiple components of the protein can be separated and recombined by the addition of external components. An alternative strategy to achieve regulation of the cargo is to regulate at the translational level. The translation of the cargo sequence can be modulated by RNA-binding proteins that recognize sequences included in the design of the self-replicating RNA. The RNA-binding proteins can block translation or result in RNA transcript degradation. To control the activity of the RNA-binding proteins and resulting cargo, the RNA-binding protein function can be controlled by external means as discussed above.

Figure 15:
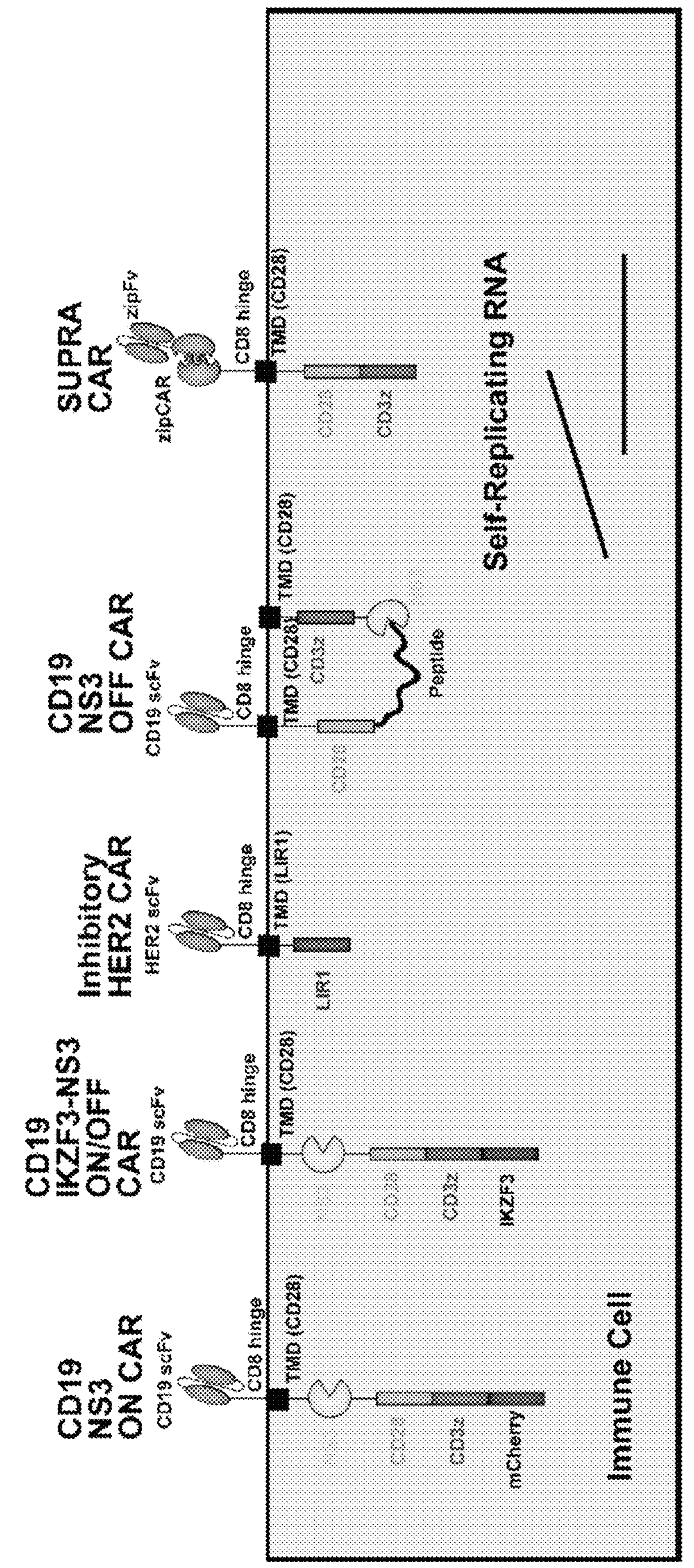
FIG. 15 shows a schematic depicting the expression of exemplary chimeric antigen receptors with external control and logic functions via self-replicating RNA. The schematic shows the structure of chimeric antigen receptors with external control and logic functions. Some of the receptors have domains that are responsive to external molecules to turn function on or off (e.g., ON-CAR, OFF-CAR, ON/OFF CAR). Additionally, some receptors function as activating or inhibitory receptors, allowing for conditional activity depending on the presence or absence of target antigens (e.g., inhibitory CAR, SUPRA CAR).
Figure 16:
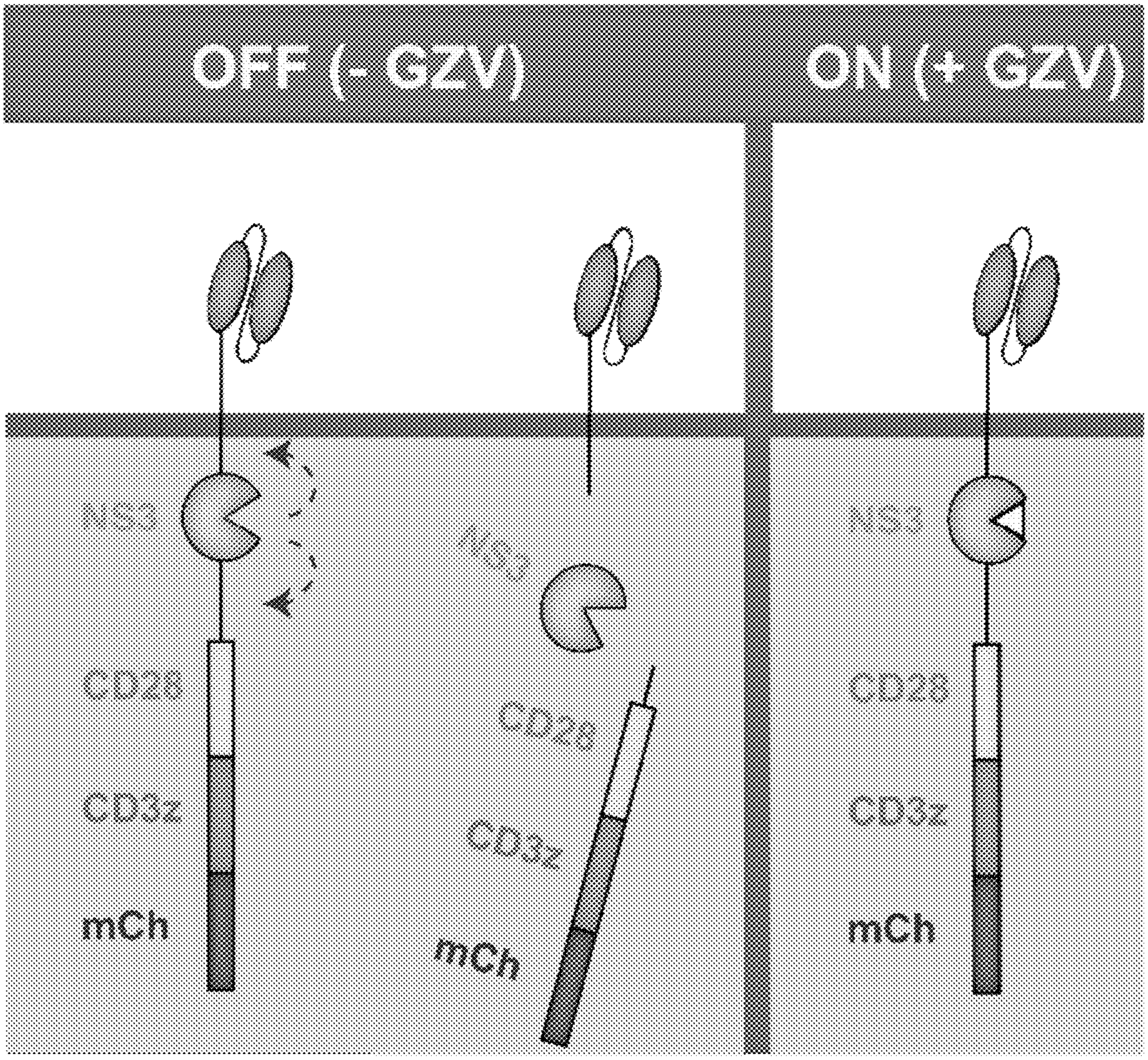
FIG. 16 shows the function of a drug controlled "ON" chimeric antigen receptor ("ON-CAR"). After the CAR is expressed, the NS3 protease domain will cleave flanking cut sites, resulting in detachment of the signaling domains from the extracellular scFv. When an NS3 protease inhibitor (e.g., grazoprevir) is added, the self-cleavage is prevented, and the CAR is able to turn on in the presence of the target antigen.
Figure 17:
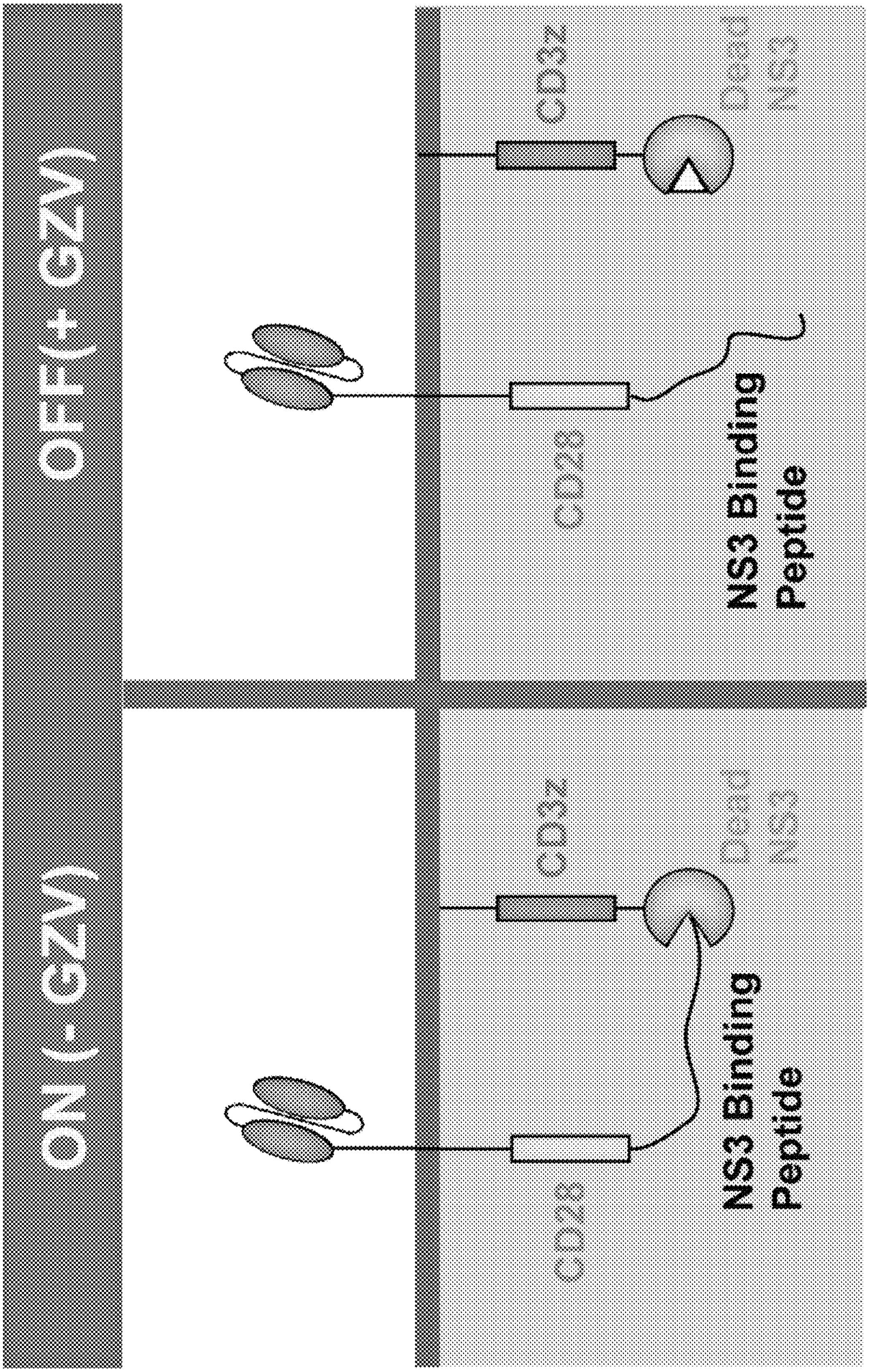
FIG. 17 shows the function of a drug controlled "OFF" chimeric antigen receptor ("OFF-CAR"). After the two components are expressed, the NS3 binding peptide on component 1 will bind the catalytically dead NS3 domain of component 2. This results in CAR activation when the target antigen is bound. If a protease inhibitor (e.g., grazoprevir) is added, the binding peptide is displaced, and the CAR cannot be activated.
Figure 18:
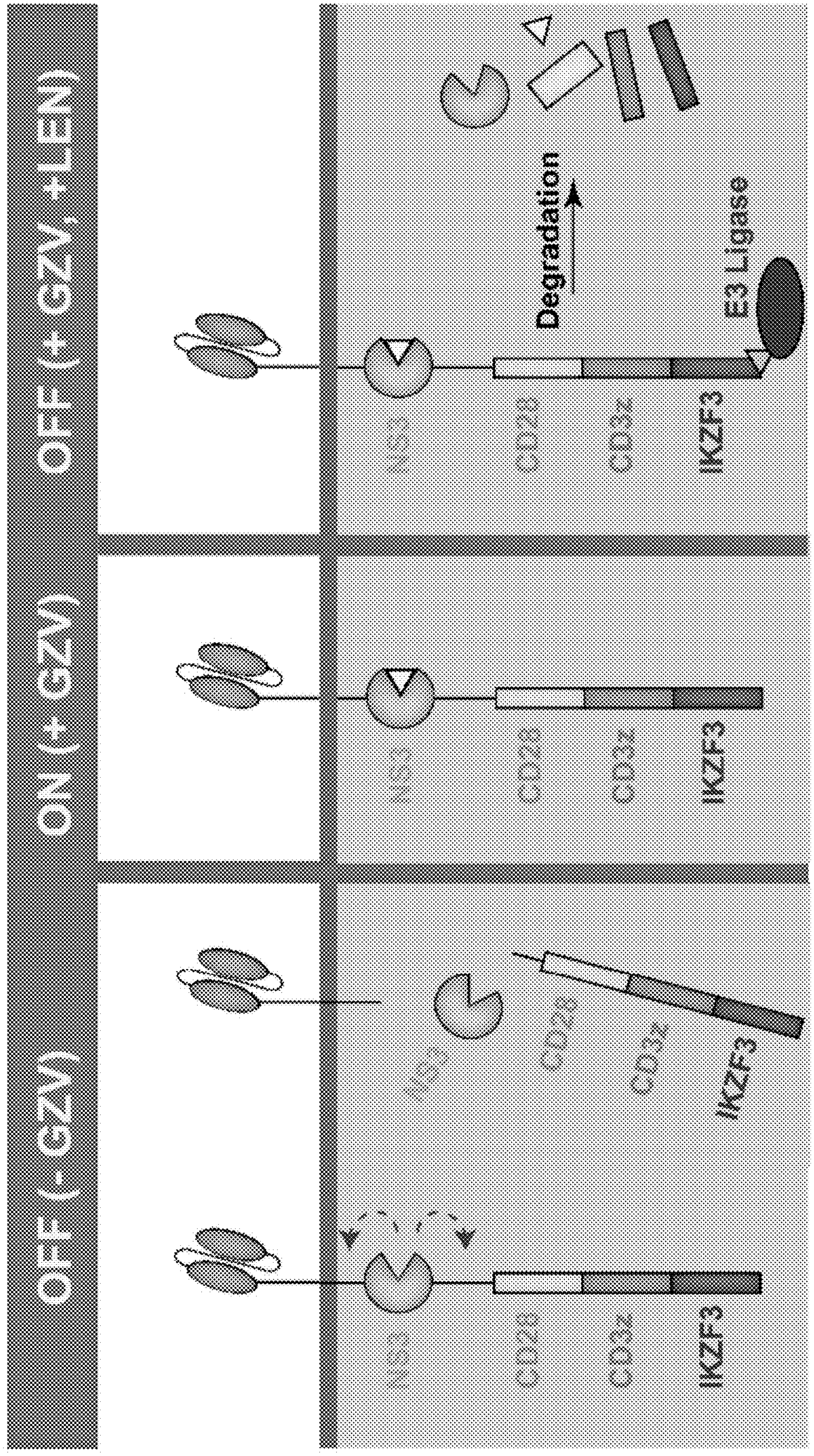
FIG. 18 shows the function of a chimeric antigen receptor with "OFF" and "ON" drug control ("ON/OFF-CAR"). After the CAR is expressed, the NS3 protease domain will cleave flanking cut sites, resulting in detachment of the signaling domains from the extracellular scFv. When an NS3 protease inhibitor (e.g., grazoprevir) is added, the self-cleavage is prevented, and the CAR is functional. If lenalidomide is also added, and E3 ligase is recruited to the IKZF3 domain, and the CAR is degraded.

To demonstrate that the activity of the cargo delivered by the self-replicating RNA, self-replicating RNA encoding externally controlled chimeric antigen receptors were developed (see e.g., FIG. 15). Self-replicating RNA can be used to express an NS3 CAR with externally controllable activity. The NS3 CAR is described in exemplary patents U.S. Ser. No. 11/059,864B2, US20220098246A1, the contents of each of which are incorporated herein by reference in their entireties. As described previously, the NS3 domain self-cleaves and prevents CAR activation in the absence of a protease inhibitor (e.g., grazoprevir, glecaprevir, simeprevir, boceprevir). In this case, the protease inhibitor acts as an "on" switch to control CAR activity (see e.g., FIG. 16). The NS3 domain can also be used in a manner that results in CAR inactivation in the presence of protease inhibitor. As described previously, the NS3 OFF CAR contains two components that are expressed as separate polypeptides. The first component consists of an scFv, transmembrane domain, costimulatory domain, and an NS3 binding peptide. The second component consists of a transmembrane domain, catalytically dead NS3 domain, and an activation domain. In the absence of a protease inhibitor, the NS3 binding peptide binds the catalytically dead NS3 domain, allowing for CAR activation to occur. When a protease inhibitor is added, the NS3 binding peptide is displaced, blocking CAR signaling and activation from occurring (see e.g., FIG. 17). To precisely control CAR activity, it is desirable to have a multi-input control strategy that involves two control modules that individually regulate activity. To demonstrate this, an NS3-IKZF3 CAR that is regulated by a protease inhibitor and by lenalidomide was developed. When a protease inhibitor is added, the cleavage of vital CAR domains are prevented, allowing for activation to occur in the presence of antigen. When lenalidomide is added, an E3 ligase is recruited to the cytoplasmic IKZF3 domain, resulting in ubiquitination and subsequent degradation of the CAR. This additional control element is useful to turn off CAR-T cell activity in the event of over-activation or safety concerns (see e.g., FIG. 18).

Figure 19:
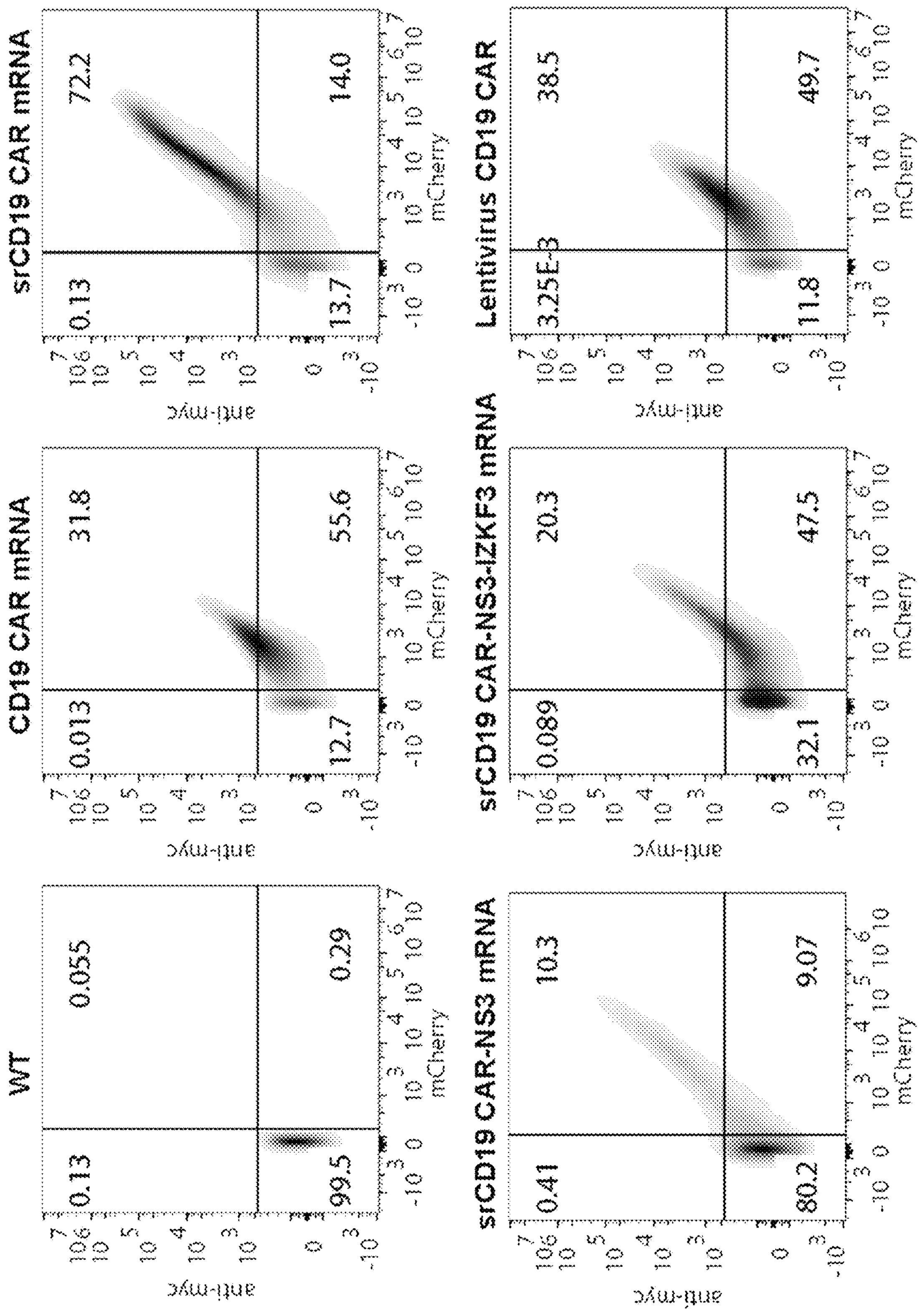
FIG. 19 shows the efficient expression of chimeric antigen receptors with external control functions via self-replicating RNA. Expression level of controllable and conventional CD19 CARs (e.g., ON-CAR, ON/OFF CAR) by self-replicating RNA, conventional mRNA, and lentiviral transduced cells measured via staining with anti-myc antibody and measurement of the fluorescence intensity of a mCherry tag on the receptor.
Figure 20:
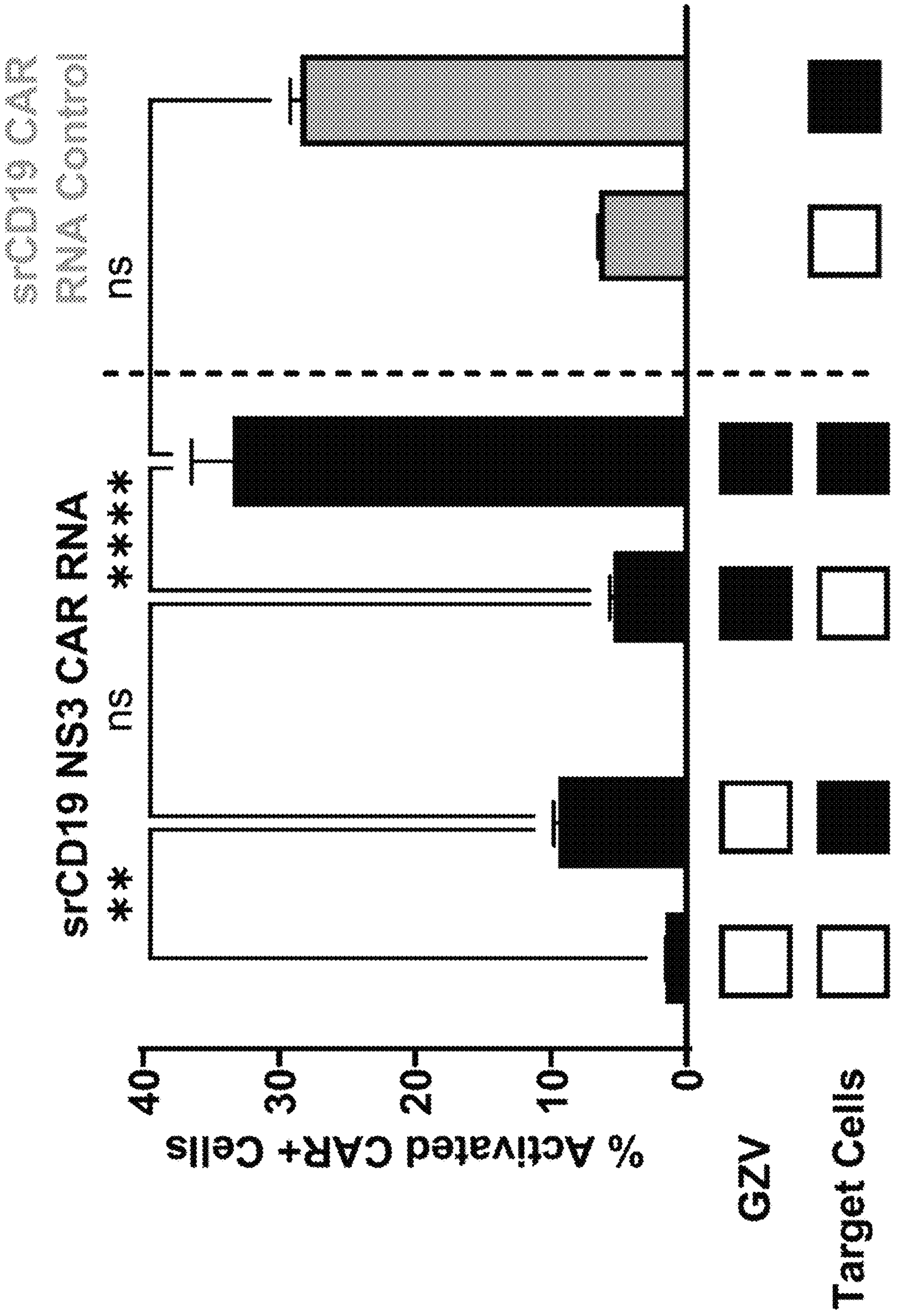
FIG. 20 shows that the activity of a chimeric antigen receptor expressed via self-replicating RNA can be increased by administration of a small molecule. The percentage of activated Jurkat CAR-T cells expressing a CD19 CAR with an NS3 domain (ON-CAR) was measured by flow cytometry. The cells were transfected with self-replicating RNA encoding the receptor 24 hours before the assay. The CAR-T cells were co-cultured overnight with Nalm6 in the absence or presence of grazoprevir at 1 μM. A CD19 CAR without an NS3 domain expressed via self-replicating RNA was included as a control (right). N=3 independent replicates. Ns=not significant. =$p<0.01$. **=$p<0.0001$.
Figure 21:
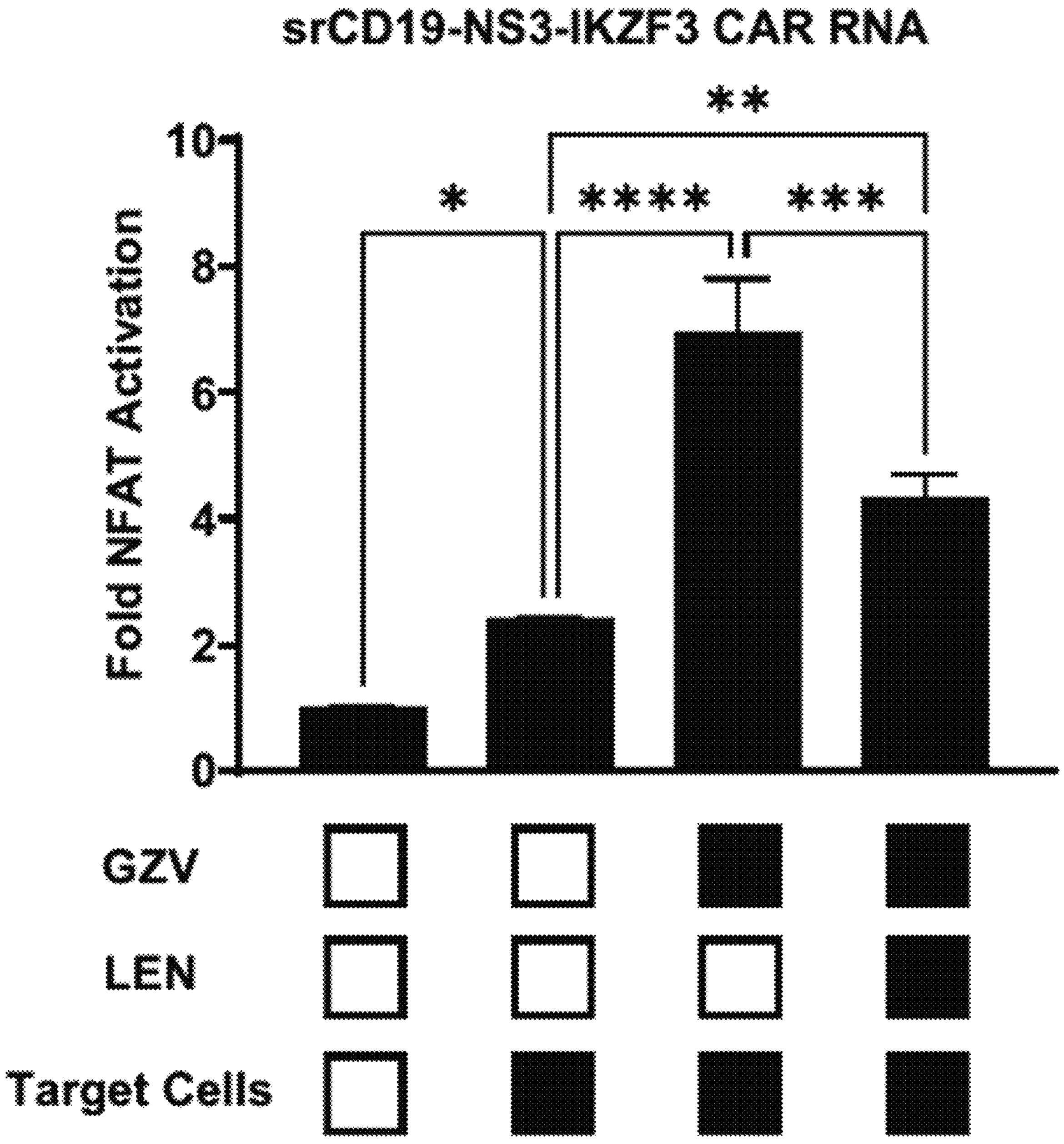
FIG. 21 shows that the activity of a chimeric antigen receptor expressed via self-replicating RNA can be increased or decreased by administration of two distinct small molecules. The degree of activation of Jurkat CAR-T cells expressing a CD19 CAR with NS3 and IKZF3 domains (ON/OFF-CAR) was measured by flow cytometry. The cells were transfected with self-replicating RNA encoding the receptor 24 hours before the assay. The CAR-T cells were co-cultured overnight with Nalm6 without grazoprevir or lenalidomide, with grazoprevir at 1 μM, and 1 μM of grazoprevir with 1 μM of lenalidomide. N=3 independent replicates.

Self-replicating RNAs encoding NS3 and NS3-IKZF3 CARs targeting CD19 were developed. To characterize the controllable nature of the cargo proteins, the self-replicating RNA was transfected into Jurkat T cells with an NFAT-GFP reporter system. The expression of the NS3 and NS3-IKZF3 CARs were measured by staining with an anti-myc antibody and by measuring the fluorescence of an mCherry expression reporter. The controllable CARs had levels of expression equal to or greater than that of a conventional CAR expressed by lentivirus or conventional mRNA (see e.g., FIG. 19). To test the CD19 NS3 CAR "on" behavior, the transfected Jurkat T cells were co-cultured with CD19 expressing Nalm6 cells in the absence or presence of grazoprevir. The degree of NFAT activation was measured by flow cytometry. The administration of grazoprevir permitted CAR-T cell activation in the presence of target cells, with minimal activation in the presence of target cells and the absence of grazoprevir (see e.g., FIG. 20). To test the activity of the NS3-IKZF3 CAR, the transfected Jurkat cells were co-cultured with Nalm6 in the absence of grazoprevir and lenalidomide, in the presence of grazoprevir, and in the presence of grazoprevir and lenalidomide. Activation when grazoprevir was present and reduction in activation when grazoprevir and lenalidomide were present together was observed (see e.g., FIG. 21).

Figure 22:
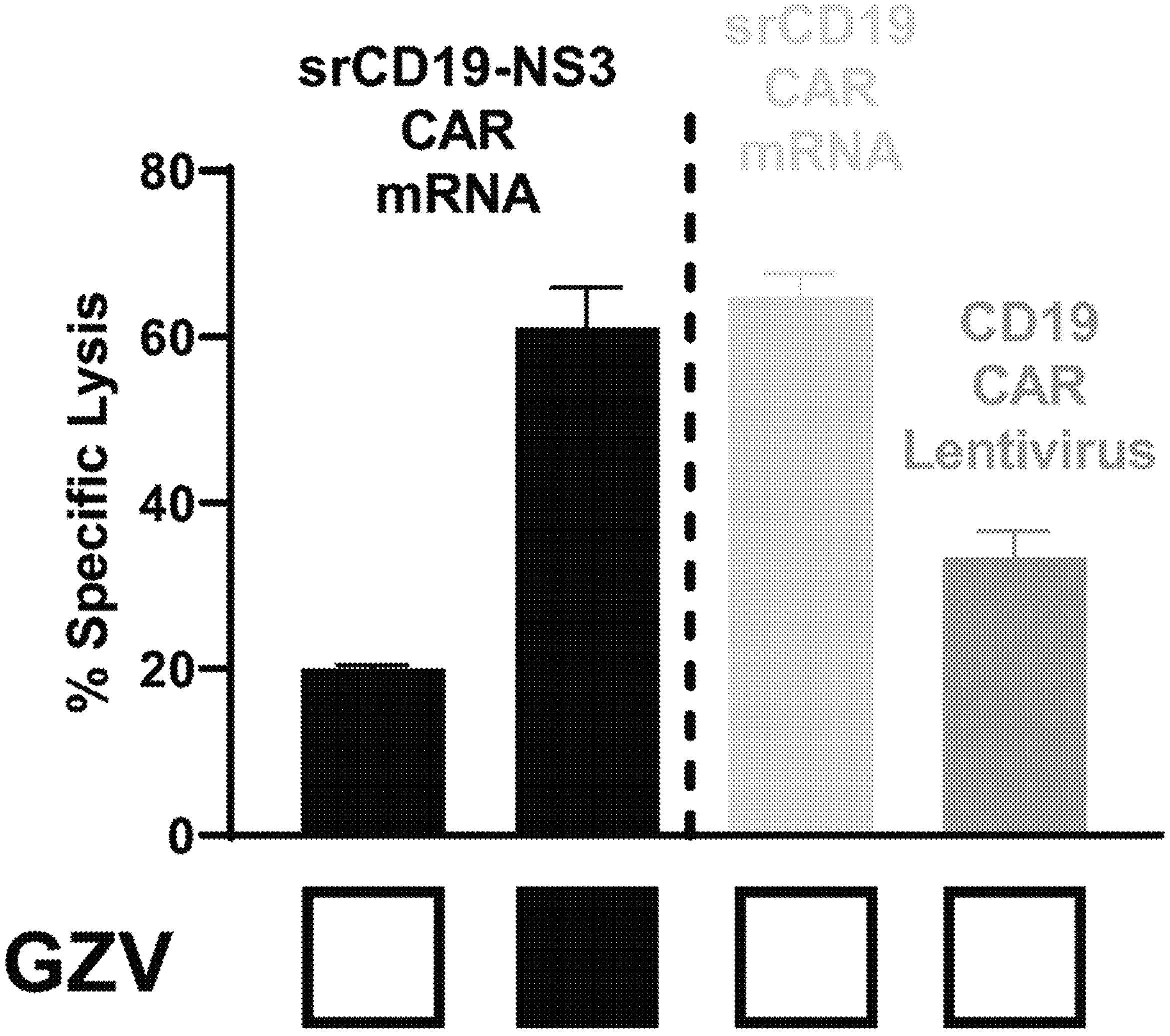
FIG. 22 shows that the activity of a chimeric antigen receptor expressed via self-replicating RNA can be controlled in primary T cells by administration of a small molecule (ON-CAR). The cytotoxicity of CAR-T cells expressing a CD19 CAR with an NS3 domain was measured by co-culture with a Nalm6 luciferase cell line at a 2:1 effector to target ratio. The CAR-T and Nalm6 cells were cultured overnight in the absence or presence of 1 μM GZV. As a control, CD19 CAR-T cells generated with self-replicating RNA were included along with CD19 CAR-T cells generated via lentivirally transduction.

To further characterize the system, CD3+ human primary T cells were transfected with the self-replicating RNA encoding the NS3 CD19 CAR. The resulting CAR-T cells were co-cultured with CD19 and luciferase expressing Nalm6 cells at a 2:1 effector to target cell ratio in the presence or absence of grazoprevir. The in vitro killing of the CAR-T target cells was dependent on grazoprevir (see e.g., FIG. 22). The percentage of cells killed increased from approximately 20% to 60% when grazoprevir was added. Additionally, the killing observed in the presence of grazoprevir was similar to that of cells transfected with self-replicating RNA encoding the conventional CD19 CAR that lacks the NS3 domain. This example demonstrates the ability to deliver a cargo protein with externally controlled activity via self-replicating RNA.

Figure 23:
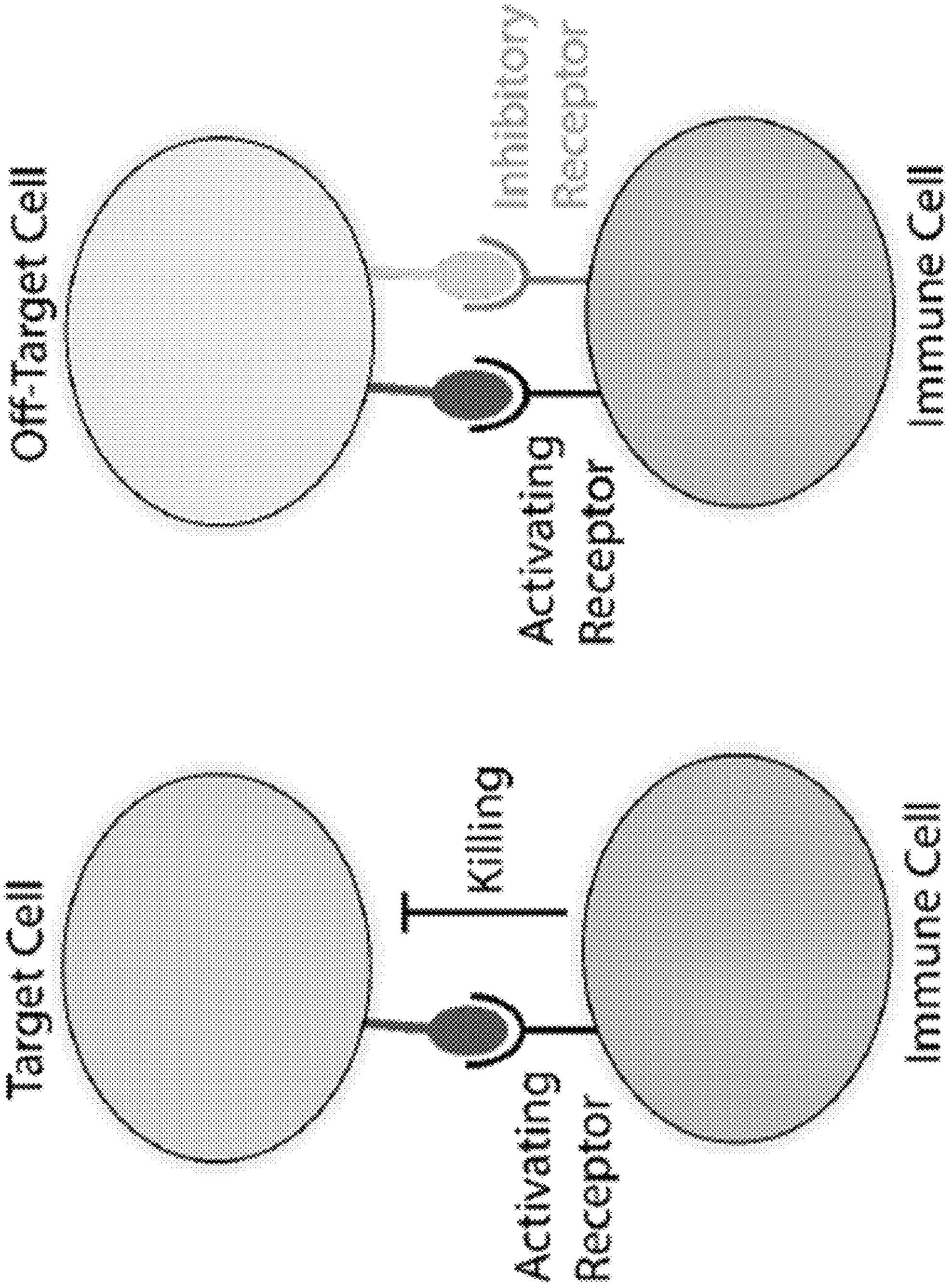
FIG. 23 shows a schematic detailing the function of chimeric antigen receptors with activating or inhibitory functions that can be expressed via self-replicating RNA. An activating receptor binds an antigen on the target cell, resulting in killing of the target cell by the CAR-T cell. An inhibitory receptor binds an antigen expressed on an off-target cell, resulting in inhibition of the killing response. This serves to enhance the specificity of CAR-T therapy by improving the ability of the CAR-T cells to discriminate between target and non-target cells.

Example 5: Self-Replicating RNA can be Utilized to Express Proteins that Result in the Ability to Perform Logic Computation to Control Cell Activity A strategy to control the activity of the cargo by utilizing logic computation was developed. In the context of chimeric antigen receptor therapy, logic computation can be utilized to enhance target specificity and enable conditional activity. This is particularly useful in distinguishing between healthy tissue and tumors with heterogeneous antigen expression. Logic computation enables the ability to produce an output that depends on an input signal or combination of input signals. To demonstrate that logic computation can be used to control the activity of cargo expressed from self-replicating RNA, a polycistronic self-replicating RNA encoding multiple chimeric antigen receptors was developed. As an example, an activating CAR targeting CD19 and an inhibitory CAR targeting HER2 were co-expressed from self-replicating RNA with their coding sequences separated by an internal ribosome entry site (IRES) sequence. The activation of the resulting CAR-T cells is dependent on the expression of two antigens. If the antigen targeted by the activating CAR is present exclusively, maximal activation can occur. If the antigen targeted by the inhibitory CAR is also present, activation is prevented or reduced (see e.g., FIG. 23). In this way, the inhibitory CAR operates as a NOT gate. It is desirable to titrate the ratio of expression of the activating CAR to the inhibitory CAR. For maximal activity of the inhibitory CAR, the expression level should be greater than the expression level of the activating CAR. To accomplish this, the inhibitory CAR coding sequence was inserted after the IRES sequence. It is known that often the gene following the IRES sequence is expressed at an efficiency lower than the gene preceding it. An additional strategy to titer the expression of multiple cargos is to express the cargos from a polycistronic self-replicating RNA containing multiple subgenomic promoters. In this design, each gene is placed downstream of a subgenomic promoter. The sequence of the subgenomic promoter can be modulated to change the resulting expression level.

Figure 24:
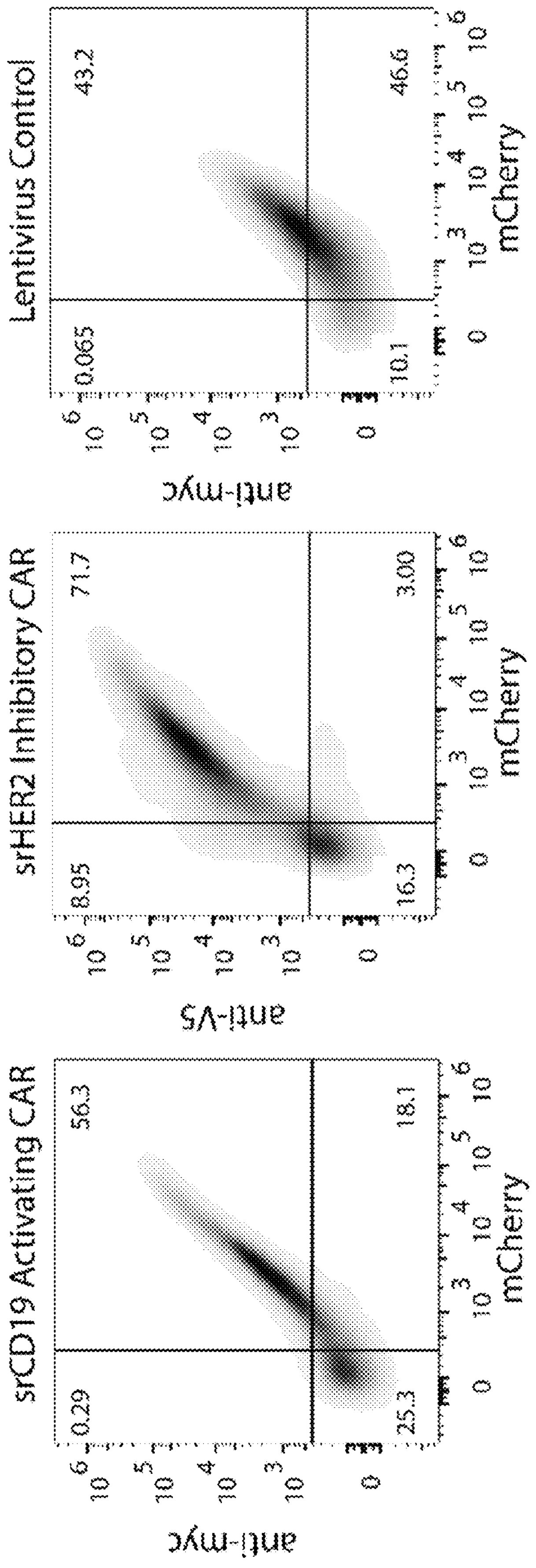
FIG. 24 shows that multiple chimeric antigen receptors with differing functions can be efficiently expressed in the same cell via self-replicating RNA. The flowcharts show expression of a CD19 activating CAR and HER2 inhibitory CAR in Jurkat cells transfected with self-replicating RNA. The CD19 activating CAR expression was measured by staining with an anti-myc antibody. The HER2 inhibitory CAR expression was measured by staining with an anti-V5 antibody. As a control, cells were transduced with a lentivirus encoding an activating CAR targeting CD19.

As an example, the self-replicating RNA encoding the CD19 activating CAR and the HER2 inhibitory CAR was transfected into Jurkat T cells. The resulting expression of both receptors was greater than what is typically observed by constitutive expression of a single receptor (see e.g., FIG. 24). This invention circumvents many of the challenges associated with the high expression of multiple receptors in a single cell. Many of these challenges are a result of maximum cargo capacities imposed by genetic engineering methods. With self-replicating RNA, the cargo capacity is presumably on the order of 10 kilobases–100 kilobases, which is much larger than the limit imposed by many genetic engineering methods commonly used to establish constitutive expression. To measure activity, the resulting dual CAR-T cells were then cultured on plates coated with CD19 antigen alone or CD19 antigen and HER2 antigen. As controls, lentiviral generated CAR-T cells and cells transfected with self-replicating RNA encoding the CD19 activating CAR only were evaluated.

Figure 25:
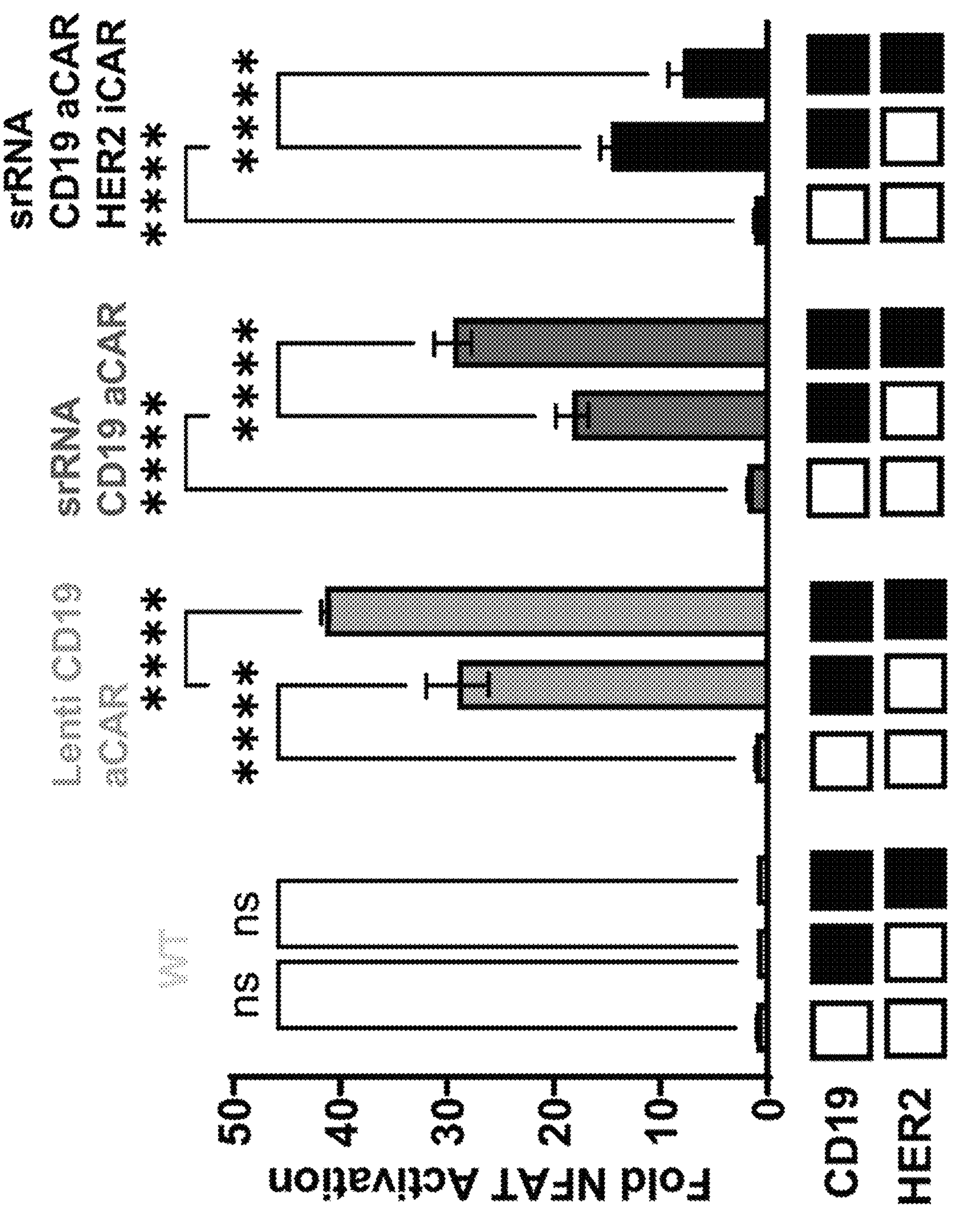
FIG. 25 shows that the expression of multiple chimeric antigen receptors via self-replicating RNA results in the ability to control cell function by logic computation. The activation of Jurkat CAR-T cells expressing a CD19 activating CAR and a HER2 inhibitory CAR via self-replicating RNA was measured by flow cytometry. The CAR-T cells were cultured on plates coated with CD19 antigen alone or CD19 and HER2 antigen together. The degree of NFAT activation was measured via mean fluorescence intensity after gating on CAR+ cells. As controls, cells were transduced with lentivirus or transfected with self-replicating RNA that encode a CD19 activating CAR only. N=3 independent replicates. Ns=not significant. ****=$p<0.0001$.

For the lentiviral transduced CAR-T cells and the activating CAR only cells, a 20-40-fold activation response was observed in the presence of CD19 antigen. When HER2 antigen was added, the activation response increased. This is likely a result of improved binding of the CD19 antigen to the plate when HER2 is added. However, in the case of the cells transfected with the self-replicating RNA encoding the CD19 activating CAR and the HER2 inhibitory CAR, a drastic decrease in activation was observed in the presence of HER2 (see e.g., FIG. 25). In this case, HER2 is acting as a signal to turn off CAR-T activity. This demonstrates the ability to express multiple CARs or cargo proteins simultaneously to generate cells that conduct logic computation to improve specificity of the desired activity.

Figure 26:
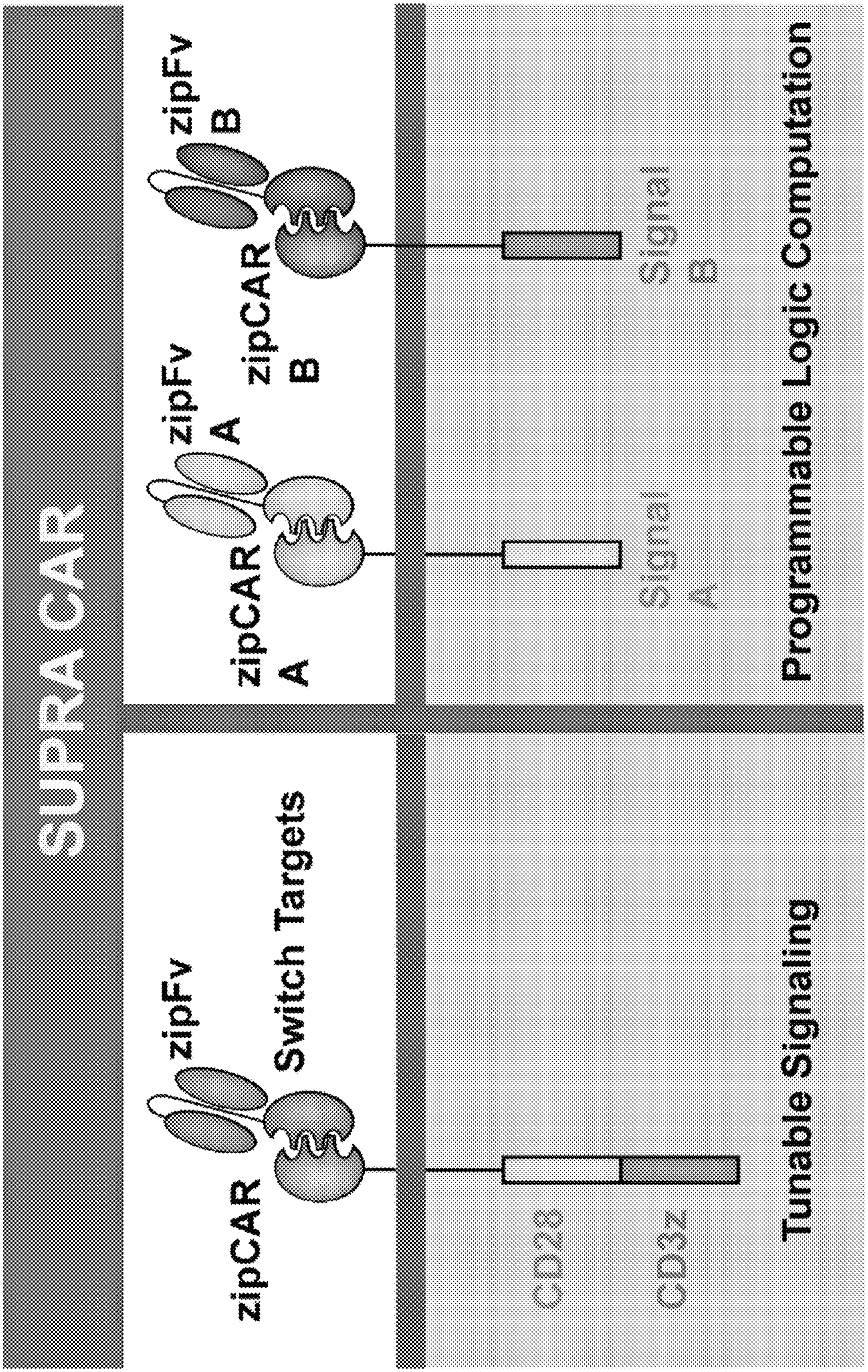
FIG. 26 shows a schematic detailing the split, universal, and programmable (SUPRA) CAR system that can be expressed via self-replicating RNA. The signaling and antigen recognition domains are split into two polypeptide sequences that can interact via a leucine zipper pair. The split nature of the SUPRA CAR system allows for tunable signaling by swapping the signaling domains recognized by a specific recognition domain. Additionally, the SUPRA CAR system can be used to perform logic computation by recognizing multiple antigens and conducting different signaling operations for each.

The example presented here demonstrates the ability of self-replicating RNA to create CAR-T cells that respond to two antigens and conduct a NOT gate operation. The self-replicating RNA platform can also be used to conduct a variety of other logic operations (AND, OR). The AND operation can be conducted by expressing multiple chimeric antigen receptors, one with an activating domain and the other with costimulatory domains. The resulting CAR-T cell activity is maximal only when both antigens are detected by the two receptors. The OR operation can be conducted by expressing multiple conventional chimeric antigen receptors targeting separate antigens. If either of the antigen is detected, CAR-T cell activity can occur. The self-replicating RNA system can be used to express the SUPRA CAR system (see e.g., WO2017091546A1, U.S. Ser. No. 11/530,252B2, the contents of each of which are incorporated herein by reference in their entireties). The SUPRA CAR system consists of a multi-component CAR in which the signaling and recognition portions of the CAR are separated and expressed as separate polypeptides (see e.g., FIG. 26). The recognition portion of the CAR can bind to a cancer cell marker but not activate an immune cell unless combined with the signaling portion of the multi-component CAR. The recognition portion of the CAR can bind to the other CAR component by recognizing an extracellular cognate leucine zipper on the signaling domain portion. This allows for the ability to target multiple antigens from the same CAR-T cell by applying different recognition components. The ability to target multiple antigens allows for logic computation by multiplexing different combinations of signaling and recognition portions of the SUPRA CAR system. The self-replicating RNA system presented here can be utilized to deliver the SUPRA CAR system to conduct complex logic operations including AND, OR, etc.

Figure 27:
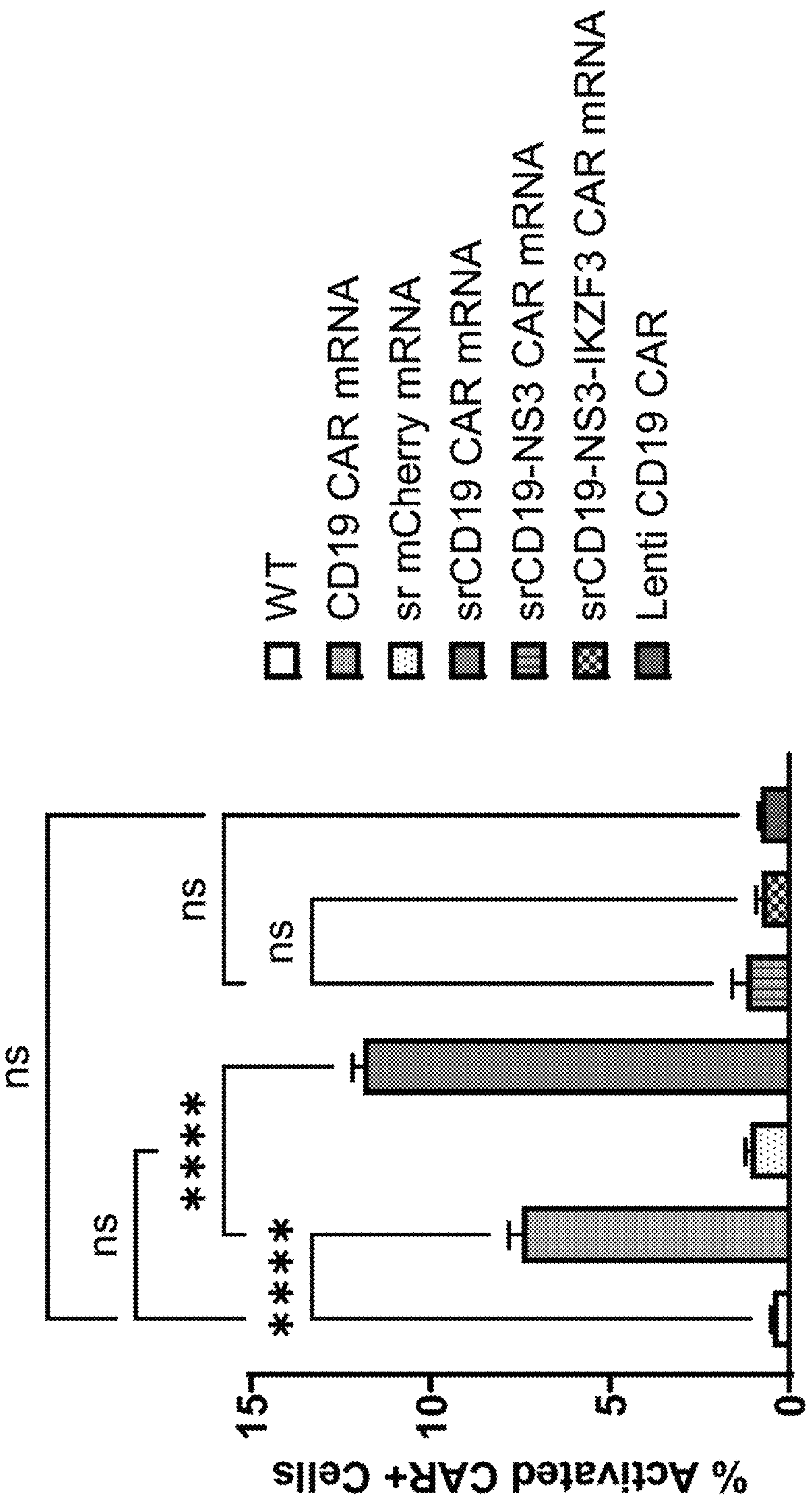
FIG. 27 shows reduced basal activation of T cells expressing a CAR with an a drug-controllable domain via self-replicating RNA (e.g., ON-CAR, ON/OFF-CAR). The bar graphs show the percentage of activated Jurkat CAR-T cells under resting conditions due to tonic signaling. Activation was measured by flow cytometry in Jurkat cells with an NFAT-GFP reporter. N=3 independent replicates. Ns=not significant. ****=$p<0.0001$.
Figure 28:
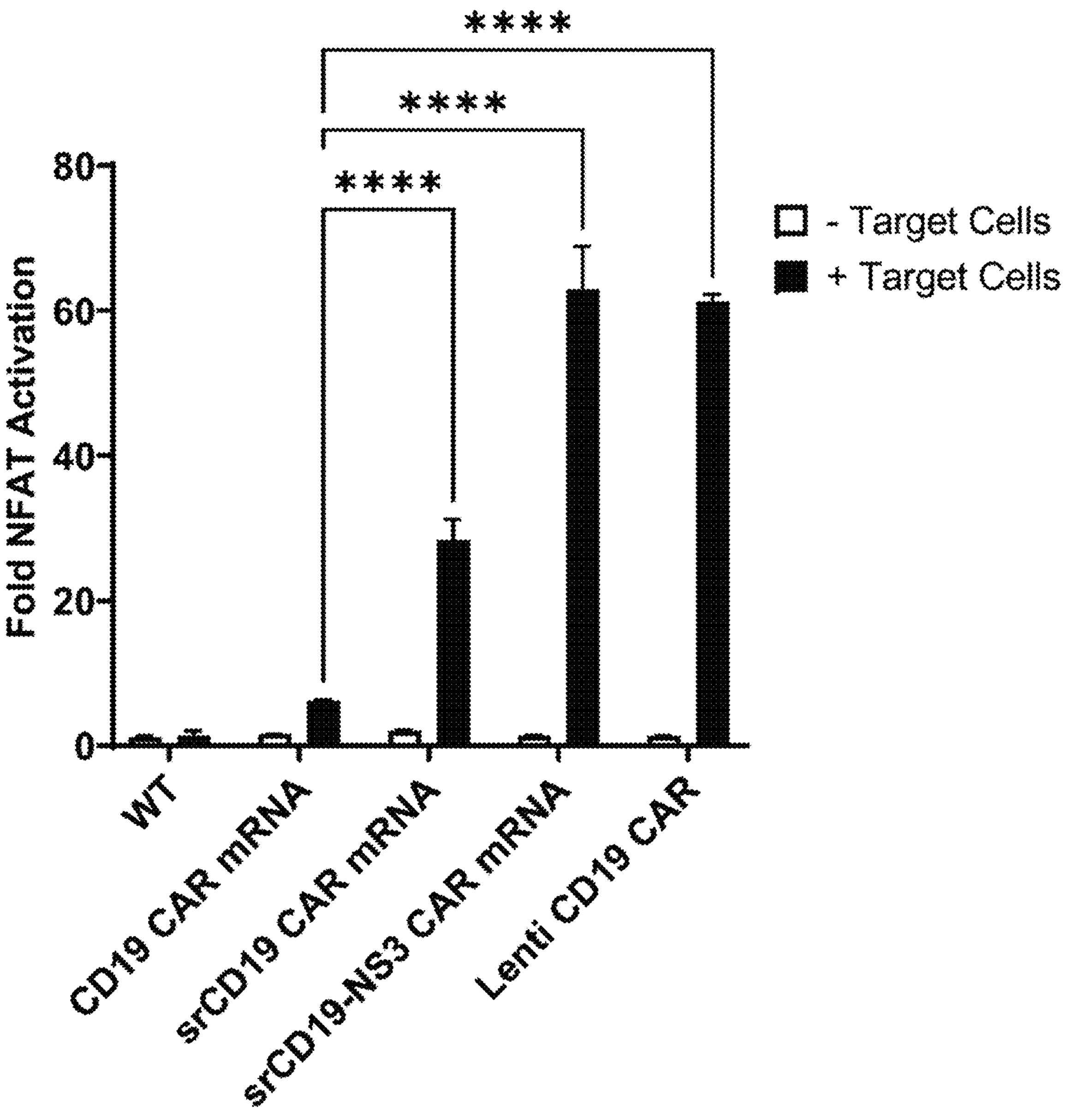
FIG. 28 shows that the activation of T cells expressing a CAR with a drug-controllable domain (e.g., ON-CAR) via self-replicating RNA is comparable to the activation of T cells generated via lentivirus. Degree of NFAT activation was measured in Jurkat CAR-T cells after co-culture with CD19 expressing Nalm6 cells. The fold NFAT activation was determined by measuring the mean fluorescence intensity after gating on CAR+ cells. N=3 independent replicates. ****=$p<0.0001$.

Example 6: Expressing Externally Controlled Cargo Proteins Via Self-Replicating RNA Results in Improved Function There are several advantages of utilizing externally controlled cargo to control the phenotype of the cells modified with self-replicating RNA. To demonstrate this, Jurkat T cells were transfected with the self-replicating RNA encoding the drug controllable CARs containing the NS3 and NS3+IKZF3 domains. High expression of a CAR receptor can trigger ligand-independent activation, a phenomenon often referred to as tonic signaling. To measure tonic signaling, Jurkat NFAT GFP reporter cells were transfected with conventional or self-replicating RNA encoding a CD19 CAR or a CD19 CAR with an NS3 domain. CD19 CAR-T cells with an NS3 domain exhibited low levels of basal activation, indistinguishable from wild-type Jurkat T cells (see e.g., FIG. 27). To measure the response to antigen, the RNA transfected and lentivirally transduced CAR-T cells were co-cultured with Nalm6 cells. For the CAR-T cells containing an NS3 domain, grazoprevir was added to allow for activation to occur. The activation response from the cells transfected with self-replicating RNA encoding the NS3 CD19 CAR was indistinguishable from that of lentivirally transduced CD19 CAR-T cells in a co-culture assay (see e.g., FIG. 28). By comparison, the cells transfected with the self-replicating RNA encoding a conventional CD19 CAR had an activation response that was weaker than the lentivirally transduced cells, but much greater than the cells transfected with the conventional mRNA. This example demonstrates the ability to improve function after transfection with self-replicating RNA by controlling the cargo externally.

Figure 29:
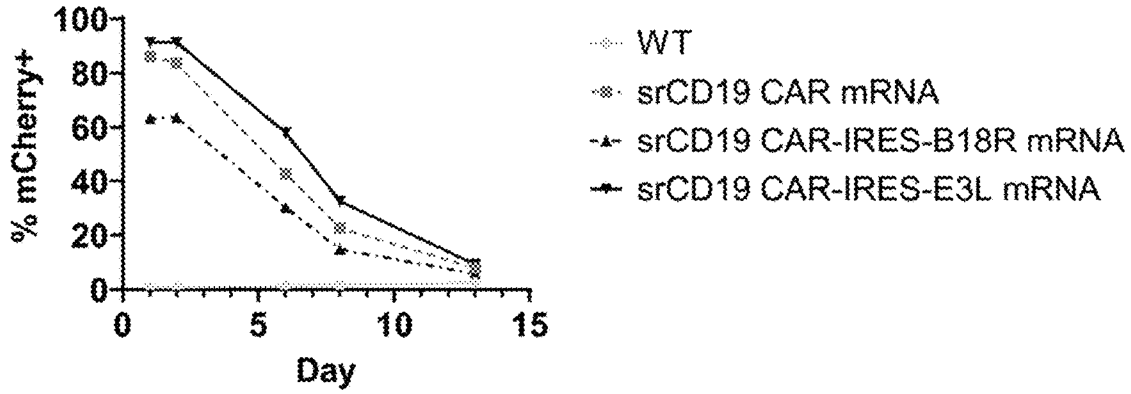
FIG. 29 shows that the expression of a chimeric antigen receptor via self-replicating RNA is enhanced by co-expression of expression enhancing proteins. Jurkat T cells were transfected with self-replicating RNA encoding a CD19 CAR or CD19 CAR and B18R or E3L. The percentage of cells expressing the CAR was tracked longitudinally with flow cytometry by measuring the fluorescence of an mCherry tag on the C-terminus of the CAR.
Figure 30:
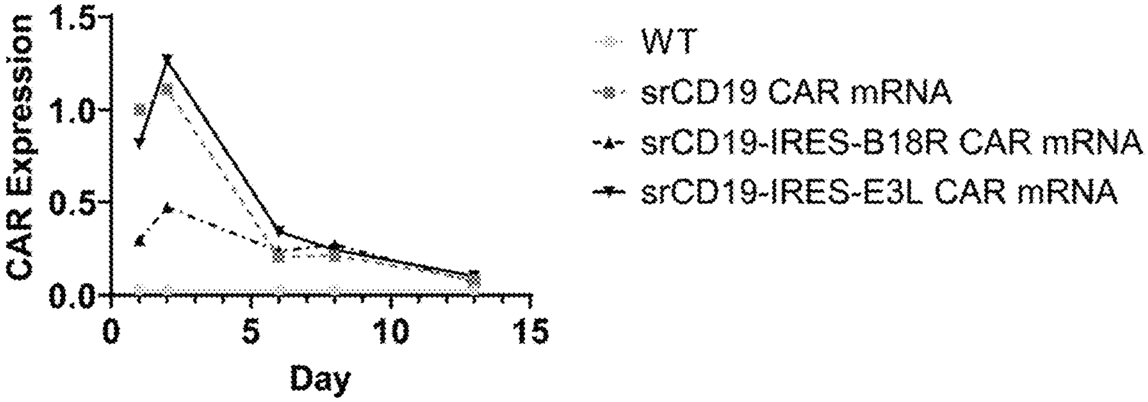
FIG. 30 shows that the expression level over time of a chimeric antigen receptor expressed via self-replicating RNA can be controlled by co-expression of expression enhancing proteins. Jurkat T cells were transfected with self-replicating RNA encoding a CD19 CAR or CD19 CAR and either B18R or E3L. The expression levels of the CAR were tracked longitudinally with flow cytometry by measuring the fluorescence of an mCherry tag on the C-terminus of the CAR. The MFI values were normalized to the MFI for the self-replicating CD19 CAR alone on day 1.

Example 7: Additional Cargo Proteins can be Expressed by the Self-replicatingRNA to Enhance Cargo Protein Expression The entrance of RNA into cells can induce an innate immune response through various pathways. This response can trigger an interferon response known to reduce transfection efficiency and expression duration. To reduce the response and increase transfection efficiency, proteins known to prevent or reduce the interferon response can be delivered in addition to the desired cargo via self-replicating RNA. To demonstrate this, a series of self-replicating RNA systems were developed that deliver a chimeric antigen receptor and one of two proteins, B18R or E3L. The function of B18R is to act as a decoy receptor for type I interferon proteins. The function of E3L is to bind double stranded RNA in order to prevent recognition by host factors. The co-expression of the CAR and either of the expression enhancing proteins can be accomplished by placing an IRES sequence between the two cargos. To characterize the effect of B18R and E3L, self-replicating RNAs encoding a CD19 CAR and either B18R or E3L were transfected into Jurkat T cells with an NFAT-GFP reporter system. The transfection efficiency was higher when the E3L protein was co-expressed (see e.g., FIG. 29). Additionally, the greatest levels of expression over time occurred when the E3L protein was co-expressed (see e.g., FIG. 30).

Figure 31:
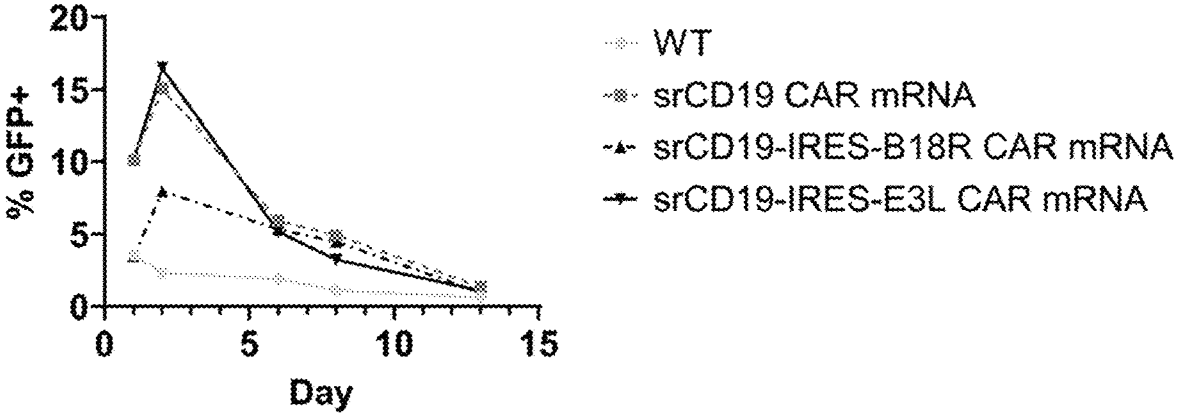
FIG. 31 shows Jurkat T cells with an NFAT-GFP reporter that were transfected with self-replicating RNA encoding a CD19 CAR or CD19 CAR and either B18R or E3L. The activation of the NFAT pathway was measured by analysis of GFP expression in cells that were expressing the constructs.

To assess the activation state of the cells that can be induced by the self-replicating RNA variants, the percentage of GFP+ cells was determined. The cells that co-expressed the B18R protein along with the CAR had lowest levels of GFP expression (see e.g., FIG. 31). This indicates that B18R can reduce an innate immune response against the self-replicating RNA.

Figure 32:
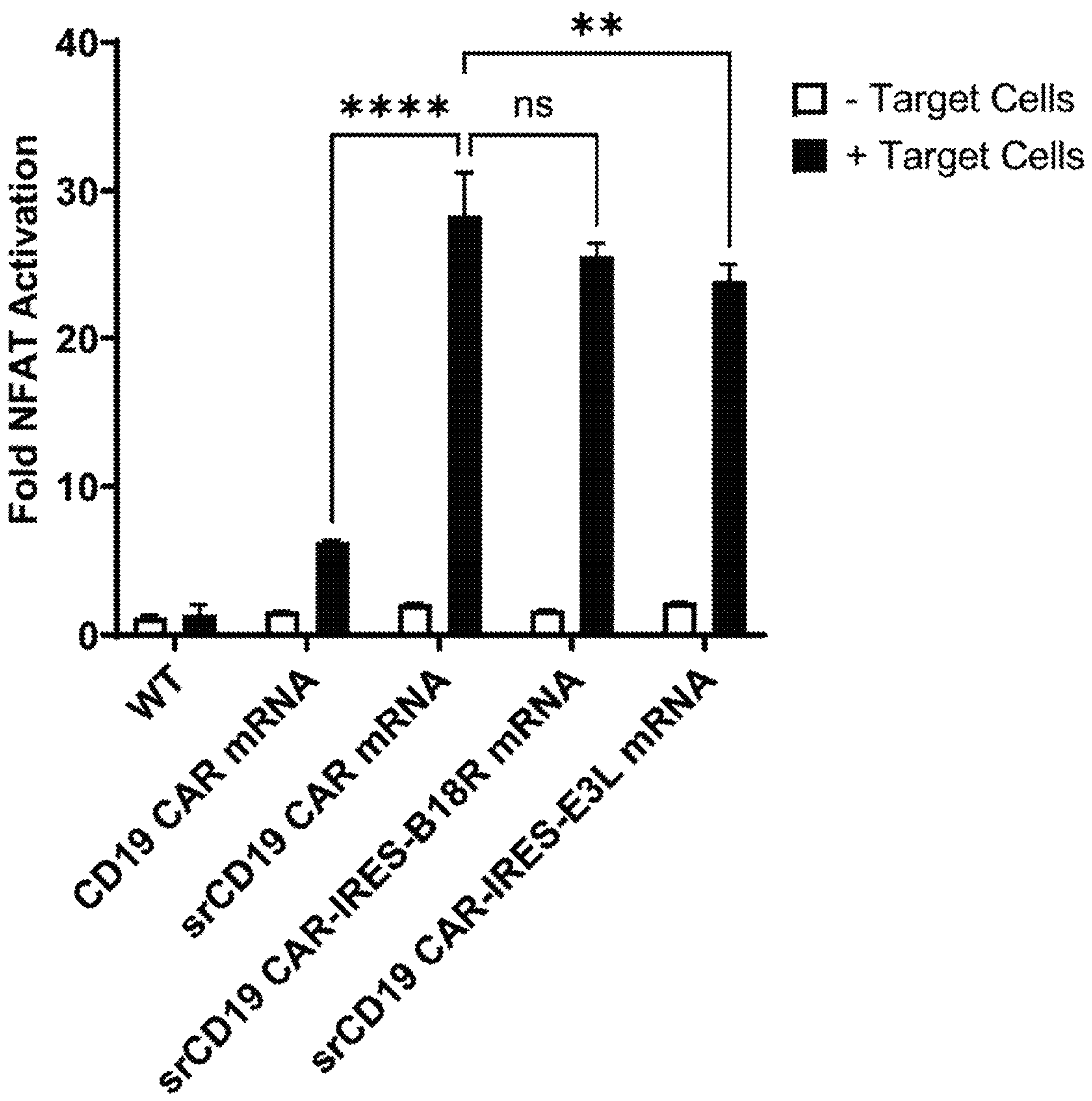
FIG. 32 shows that the co-expression of additional proteins does not impact the activity of the chimeric antigen receptor expressed via self-replicating RNA. Degree ofNFAT activation was measured in Jurkat CAR-T cells after co-culture with CD19 expressing Nalm6 cells. The fold NFAT activation was determined by measuring the mean fluorescence intensity after gating on CAR+ cells. N=3 independent replicates.

Additionally, both proteins can be co-delivered simultaneously along with the cargo to further enhance expression. To assess functionality of the resulting CAR-T cells generated by the self-replicating RNA variants, the cells were co-cultured with CD19 expressing Nalm6 cells. The CAR-T cells co-expressing B18R or E3L were activated to roughly the same degree as CAR-T cells transfected with self-replicating RNA encoding only a CD19 CAR (see e.g., FIG. 32). This example demonstrates the ability to enhance the levels of expression and improve the functionality of the desired cargo via co-expression of additional proteins. The additional proteins are not limited to ones known to reduce the interferon response. They can be transcription factors, receptors, ligands, enzymes, etc. depending on the desired application.

Example 8: Transfection of Cells with mRNA by Lipid Nanoparticle Delivery

Figure 33:
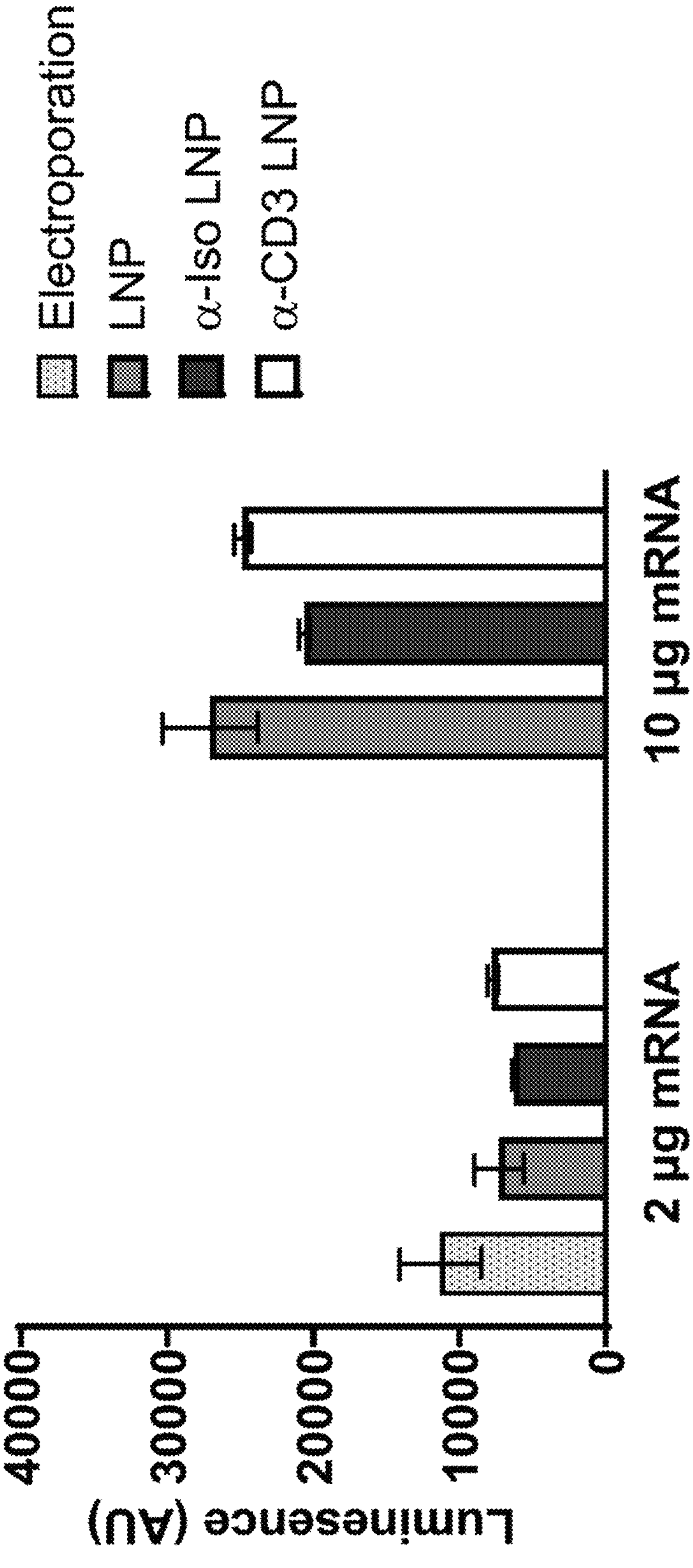
FIG. 33 shows that T cells can be transfected with mRNA containing lipid nanoparticles with or without antibody conjugation on the nanoparticle surface. The bar graphs show luminescence following transfection of luciferase encoding mRNA in Jurkat via Dlin-MC3-PEG-DBCO naked ("LNP"), isotype antibody conjugated ("α-Iso LNP"), or anti-CD3 antibody conjugated ("α-CD3 LNP") lipid nanoparticles. As a positive transfection control, electroporation was performed. Transfection was verified by lysing the cells with a commercial luciferase assay reagent and measuring the emitted light with a plate reader. n=3 independent replicates.

As an example of delivery of the self-replicating RNA platform, lipid nanoparticles were developed to efficiently transfect T cells. Lipid nanoparticles were synthesized via a microfluidic mixing strategy and were composed of an ionizable lipid, helper lipid, cholesterol, PEG lipid linked to a functional group, and encapsulated RNA. After synthesis, the lipid nanoparticles were conjugated to a CD3 targeting antibody via click chemistry. To demonstrate the efficacy of this approach, Jurkat T cells were transfected with lipid nanoparticles containing firefly luciferase mRNA. The transfection was performed with unconjugated lipid nanoparticles or lipid nanoparticles conjugated to an anti-CD3 antibody or an isotype control antibody. To measure transfection efficacy, the cells were lysed with a commercial luciferase reagent and the resulting signal was read with a plate reader. It was observed that the lipid nanoparticles transfected the Jurkat T cells to a level comparable to electroporation (see e.g., FIG. 33).

Figure 34:
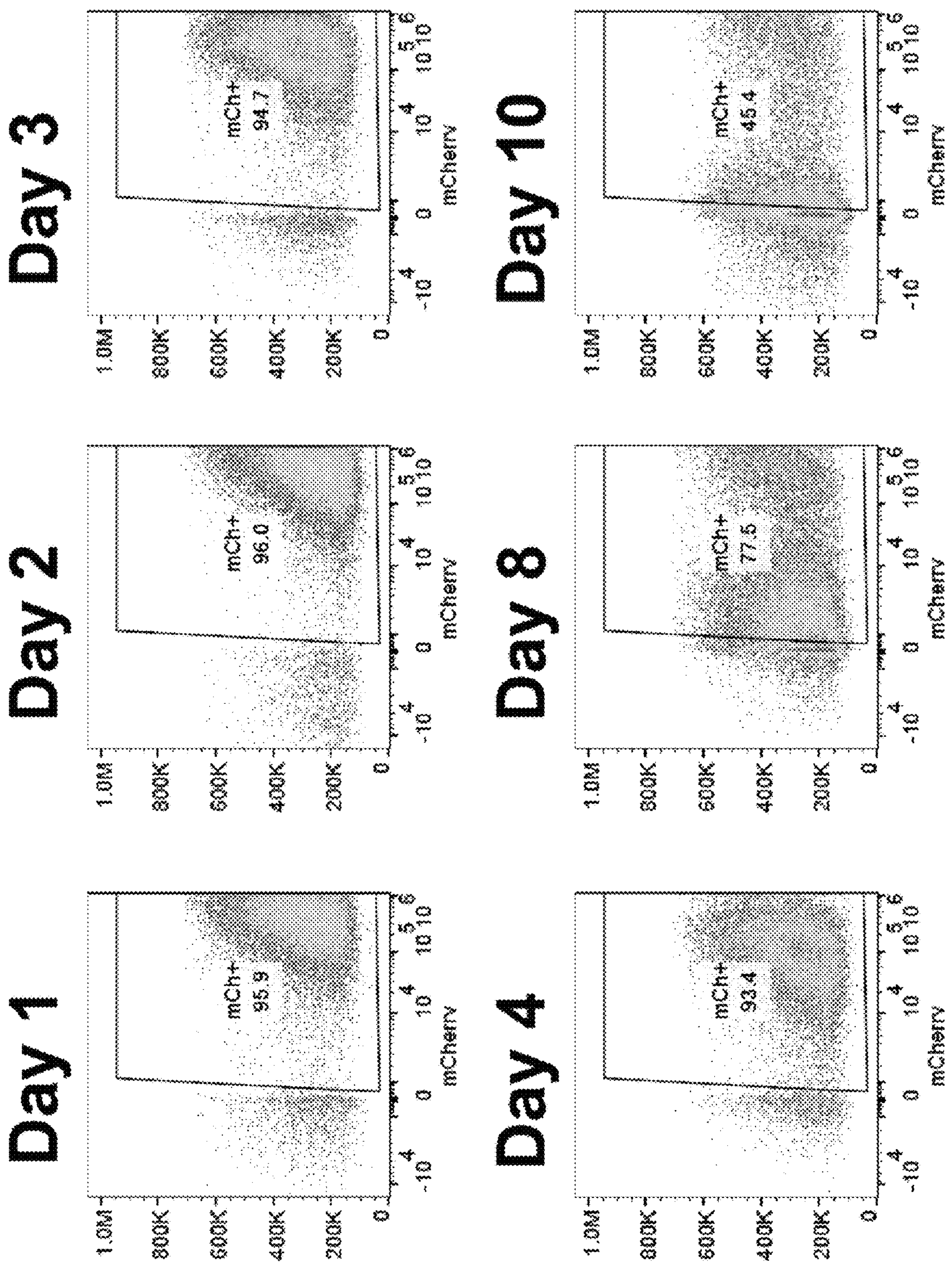
FIG. 34 shows that self-replicating RNA can be used to express a protein and track its activity over an extended duration. The flow plots show expression of mCherry from self-replicating RNA as a model cargo over a period of 10 days in Jurkat T cells.
Figure 35:
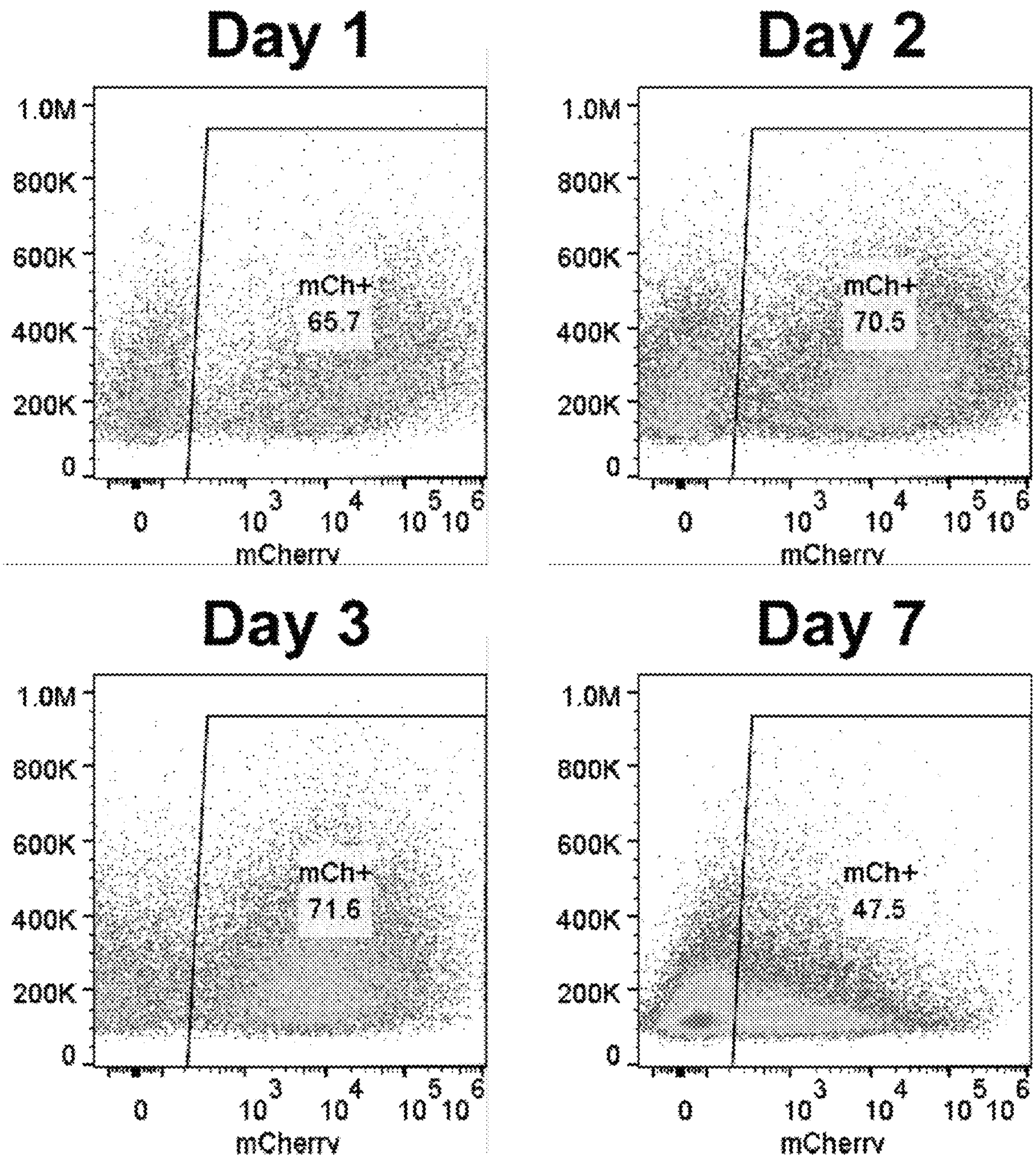
FIG. 35 shows that primary cells can be modified ex vivo to express a protein via self-replicating RNA. The flow plots show expression of mCherry from self-replicating RNA as a model cargo over a period of 7 days in Primary CD3+ T cells.

Example 9: Expression of a Mock Cargo/Reporter Protein in Cells for an Extended Duration without Genetic Modification To demonstrate the versatility of this platform, self-replicating RNA expressing mCherry was developed. In this example, mCherry serves as a model cargo or reporter protein. The actual cargo can be a transcription factor that can result in phenotypic changes. The cargo can also be an enzyme used to modify the genome or transcriptome of the cell. Additionally, the cargo can act on a protein to inhibit or induce its function to alter the activity of the targeted cell. The self-replicating RNA encoding mCherry was transfected into Jurkat T cells. A majority of the cells expressed the mCherry protein at a high level over a period of at least 10 days (see e.g., FIG. 34). To further characterize the system, the self-replicating RNA encoding mCherry was transfected in human CD3+ primary T cells. Most of the cells expressed the mCherry protein at a high level over a period of at least 7 days (see e.g., FIG. 35). This time period is likely sufficient to result in a variety of desirable functions by expression of a cargo protein.

Example 10: In Vitro Transcription Offully Substituted Self-Amplifying RNA

Figure 36:
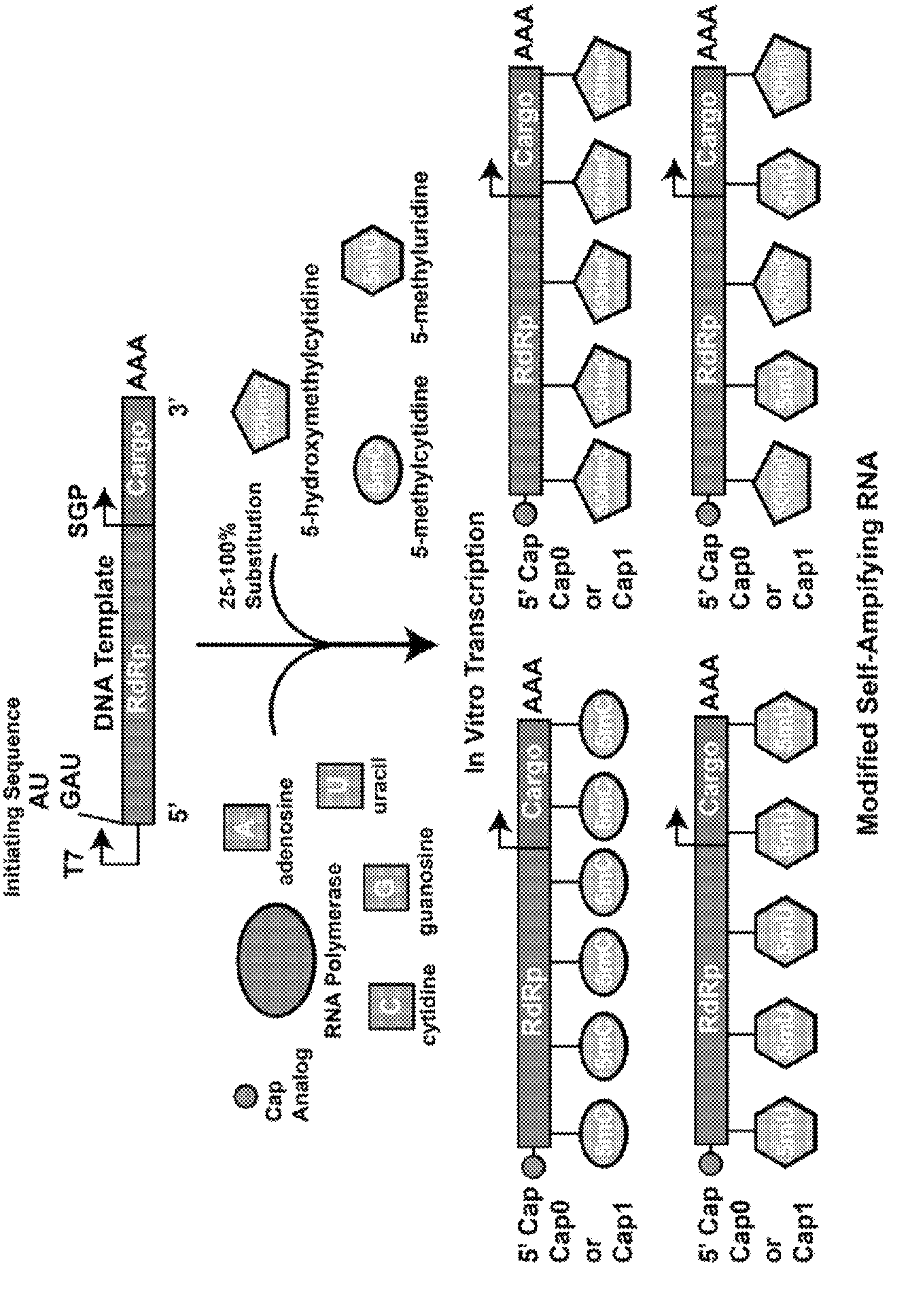
FIG. 36 is a schematic detailing exemplary self-amplifying RNAs (saRNAs) comprising modified nucleotides. A linearized plasmid encoding an RNA Dependent RNA Polymerase (RdRp) as well as a cargo of interest is shown utilized as template for in vitro transcription (IVT). The IVT reaction includes a nucleoside triphosphate (NTP) mixture of 25%-100% modified nucleotides, and can include cap analog for co-transcriptional capping. The resulting composition is an saRNA with 25%-100% substitution of modified nucleotide.
Figure 37:
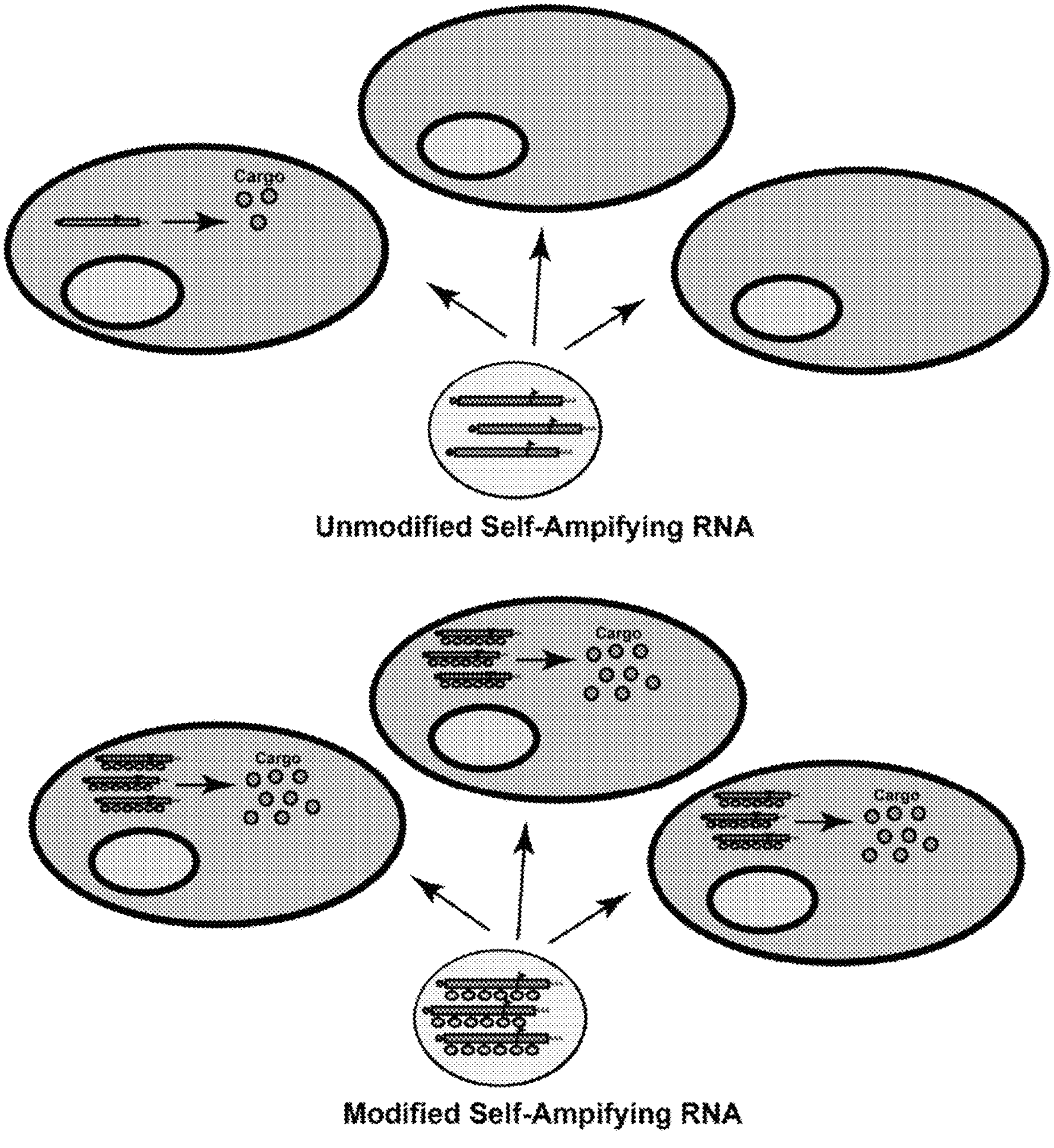
FIG. 37 is a schematic detailing the expression profile of saRNA with >25% substitution of the specified modified nucleotide. The top of the schematic details the result of unmodified saRNA, where a small population of cells uptake the saRNA and express the cargo. Aspects of this disclosure detail the unexpected result that the incorporation of modified nucleotides into the self-amplifying RNA increased both the percentage of transfected cells and the amount of protein expressed in each transfected cell.

Described herein are self-amplifying RNAs (saRNAs) comprising modified nucleotides. This example demonstrates the process for synthesis of fully (i.e., 100%) substituted saRNA (e.g., of a specific pyrimidine for a specific modified nucleotide, as described further herein). This example is schematically depicted in FIG. 36 with the bioactive result of this composition of matter schematically depicted in FIG. 37. In this example, a plasmid containing sequences for the DNA template of an saRNA encoding for NSP1-4 of VEEV and a fluorescent reporter, mCherry, as the cargos of interest was cloned in DH5a *E. coli* and purified using ZymoPURE™ II Plasmid Midiprep Kit (ZYMO RESEARCH). The promoter region was a CLEANCAP AU (TRILINK BIOTECHNOLOGIES) compatible T7 promoter (Promoter seq: TAATACGACTCACTATAAT; SEQ ID NO: 1). Plasmids were linearized with MluI-HF for 3 hours at 37° C., and linearized template was purified using QIAQUICK PCR Purification Kit (QIAGEN). saRNA was synthesized using MEGASCRIPT T7 Transcription kit (Invitrogen™, THERMOFISHER SCIENTIFIC) with 1p g template, co-transcriptional capping using CLEANCAP AU (final conc. 4 mM), and a 3 hour incubation (TRILINK BIOTECHNOLOGIES). The final concentration of all NTPs, either modified or unmodified, was 5 mM. IVT was followed by 10 min DNase treatment and 30 min post-transcriptional poly-adenylation using a Poly(A) Tailing Kit (Invitrogen™, THERMOFISHER SCIENTIFIC). saRNA was purified using MEGAclear™ Transcription Clean-up Kit (Invitrogen™ THERMOFISHER SCIENTIFIC) and eluted in DNase/RNase free $H_2O$ prior to storing at −80° C. The A260 of all modified nucleoside triphosphates (modNTPs) was empirically determined using a NANODROP2000 (THERMOFISHER SCIENTIFIC). The adjusted factor for each modNTP was used to calculate RNA concentration to ensure consistent delivery between modNTPs. As a result, this example demonstrates that saRNA was successfully synthesized at 100% incorporation of modified nucleotides using established and common synthesis methods.

Figure 38:
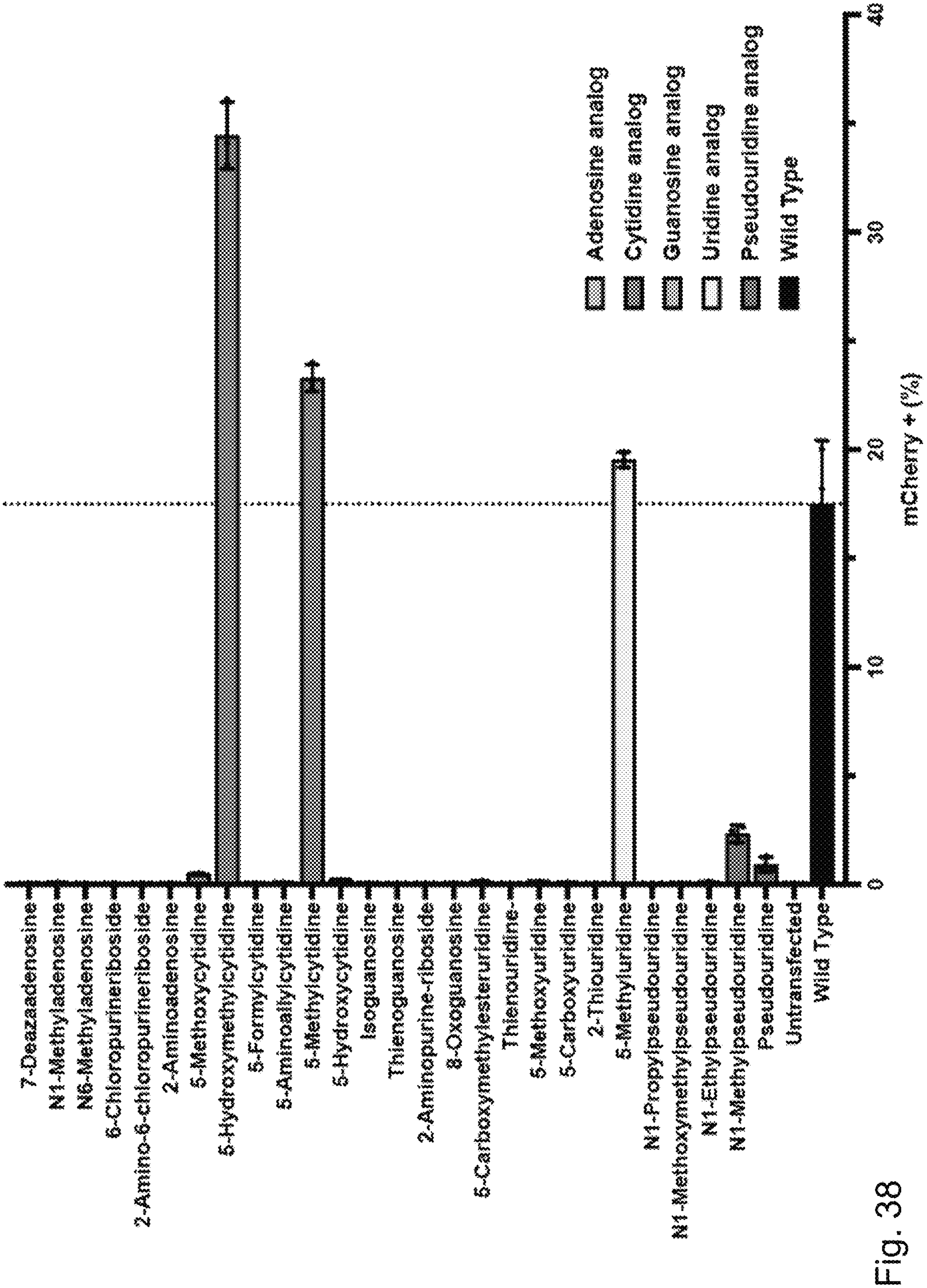
FIG. 38 depicts the transfection efficiency of a library of self-amplifying RNA encoding for mCherry with individual, full substitution by 28 modified nucleotides in HEK293T cells. This IVT was performed using a template with a T7 promoter using m7G(5')ppp(5')(2'OMeA)pU (CLEANCAP AU) as the 5' Cap.
Figure 39:
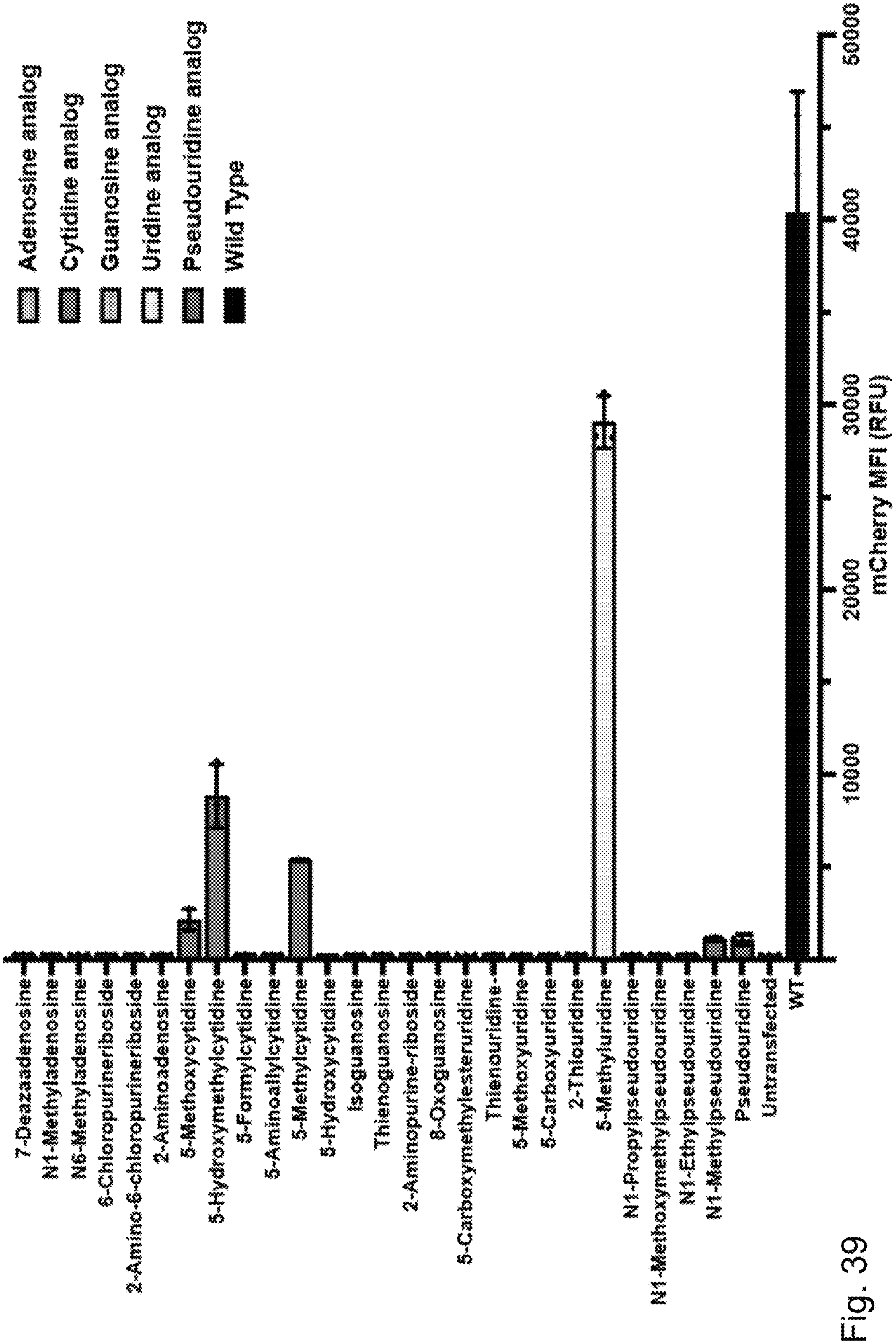
FIG. 39 depicts the median expression intensity of a library of self-amplifying RNA encoding for mCherry with individual, full substitution by 28 modified nucleotides in HEK293T cells. This IVT was performed using a template with a T7 promoter using m7G(5')ppp(5')(2'OMeA)pU (CLEANCAP AU) as the 5' Cap.

Example 11: A Screen of 100% Substitution with Commercially Available Modified Nucleotides This example demonstrates the unexpected result that specific nucleotides are capable of maintaining saRNA function when substituted at 100%. Individual IVT reactions were carried out to generate saRNA encoding a mCherry fluorescent reporter, produced as detailed in Example 10, with 100% substitution of a specific nucleotide (e.g., adenosine, cytosine, guanosine, or uridine) for each of the following modified nucleotides: 7-Deazaadenosine, N1-Methyladenosine, N6-Methyladenosine, 6-Chloropurineriboside, 2-Amino-6-chloropurineriboside, 2-Aminoadenosine, 5-Methoxycytidine, 5-Hydroxymethylcytidine, 5-Formylcytidine, 5-Aminoallylcytidine, 5-Methylcytidine, 5-Hydroxycytidine, Isoguanosine, Thienoguanosine, 2-Aminopurine-riboside, 8-Oxoguanosine, 5-Carboxymethylesteruridine, Thienouridine, 5-Methoxyuridine, 5-Carboxyuridine, 2-Thiouridine, 5-Methyluridine, N1-Propylpseudouridine, N1-Methoxymethylpseudouridine, N1-Ethylpseudouridine, N1-Methylpseudouridine, and Pseudouridine. All modified nucleotides were purchased from TRILINK BIOTECHNOLOGIES. HEK293T cells were plated at 80,000 cells/$cm^2$ and allowed to adhere overnight. Cells were transfected with 100 ng saRNA using MESSENGERMAX reagent; lipoplexes were prepared according to manufacturer's protocol (THERMO FISHER SCIENTIFIC). After 24 hours, cells were gently dissociated and fluorescence was assessed via flow cytometry. Unexpectedly, 5-methylcytidine, 5-hydroxymethylcytidine, and 5-methyluridine displayed equivalent or greater transfection efficiency compared to unmodified saRNA, while construct expression was maintained at appreciable levels (see e.g., FIG. 38 & FIG. 39). Without wishing to be bound by theory, given that 5-hydroxymethylcytidine and 5-methylcytidine both function similarly, it is expected that 5-methyluridine and 5-hydroxymethyluridine have similar functions, and that 5-hydroxymethyluridine can be used to substitute uridine in saRNA to increase transfection efficiency compared to unmodified saRNA. As a result, this example demonstrates that saRNA with 100% incorporation of modified nucleotides are capable of maintaining biological activity, an expected result.

Figure 40:
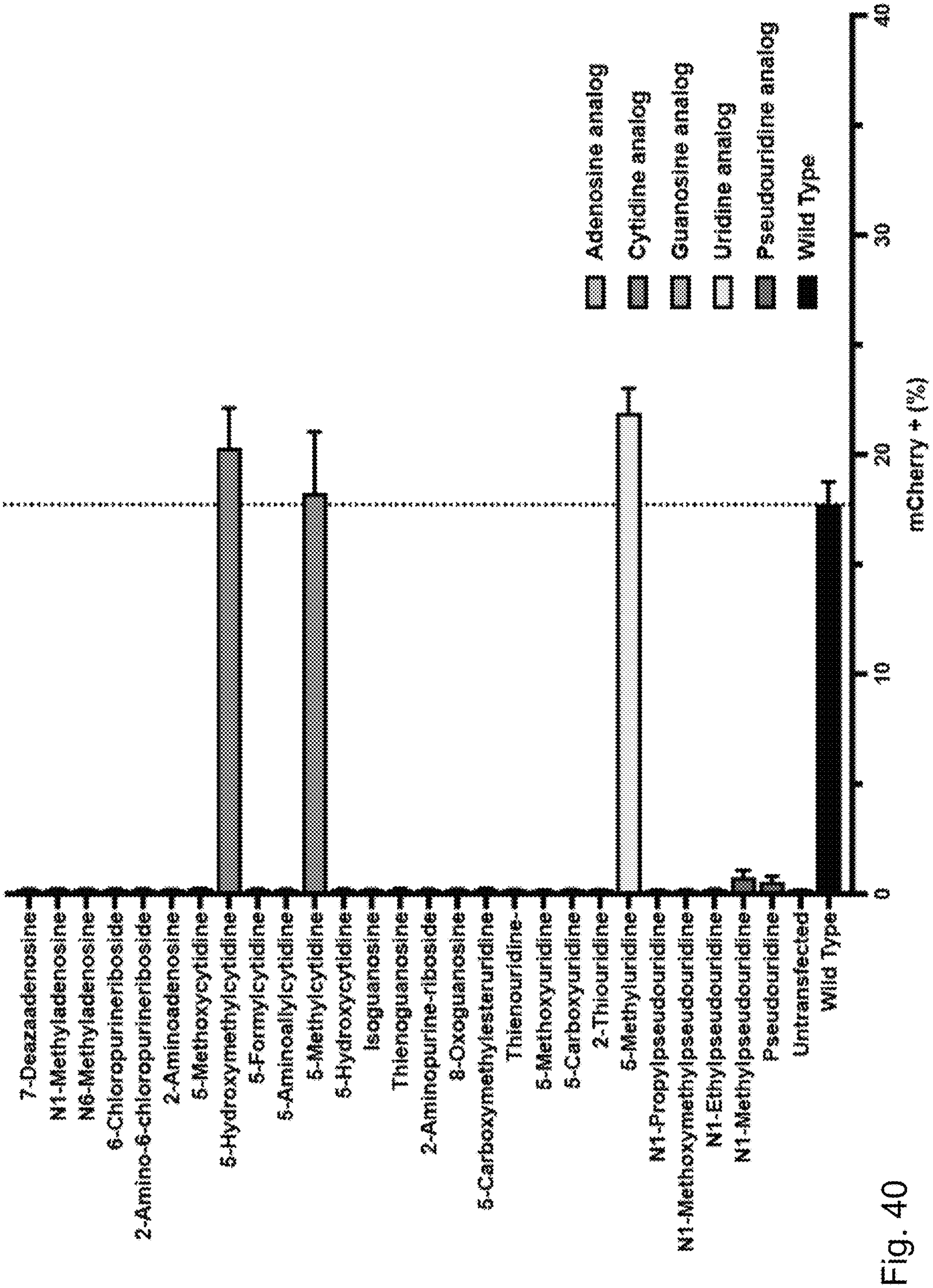
FIG. 40 depicts the transfection efficiency of a library of self-amplifying RNA encoding for mCherry with individual, full substitution by 28 modified nucleotides in HEK293T cells. This IVT was performed using a template with a T7 promoter using 3'-O-Me-m7G(5')ppp(5')G (ARCA) as the 5' Cap.
Figure 41:
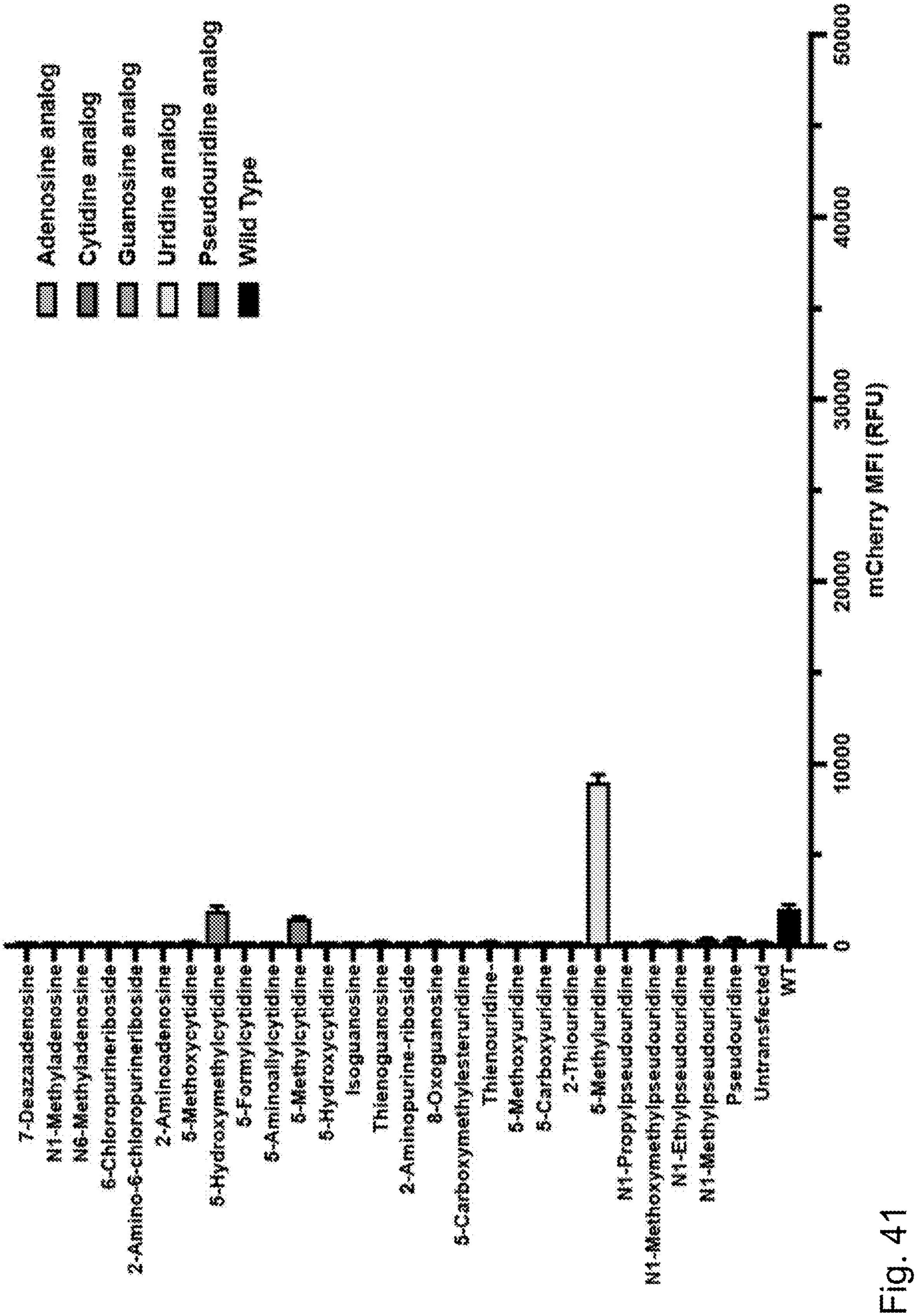
FIG. 41 depicts the median expression intensity of a library of self-amplifying RNA encoding for mCherry with individual, full substitution by 28 modified nucleotides in HEK293T cells. This IVT was performed using a template with a T7 promoter using 3'-O-Me-m7G(5')ppp(5')G (ARCA) as the 5' Cap.
Figure 42:
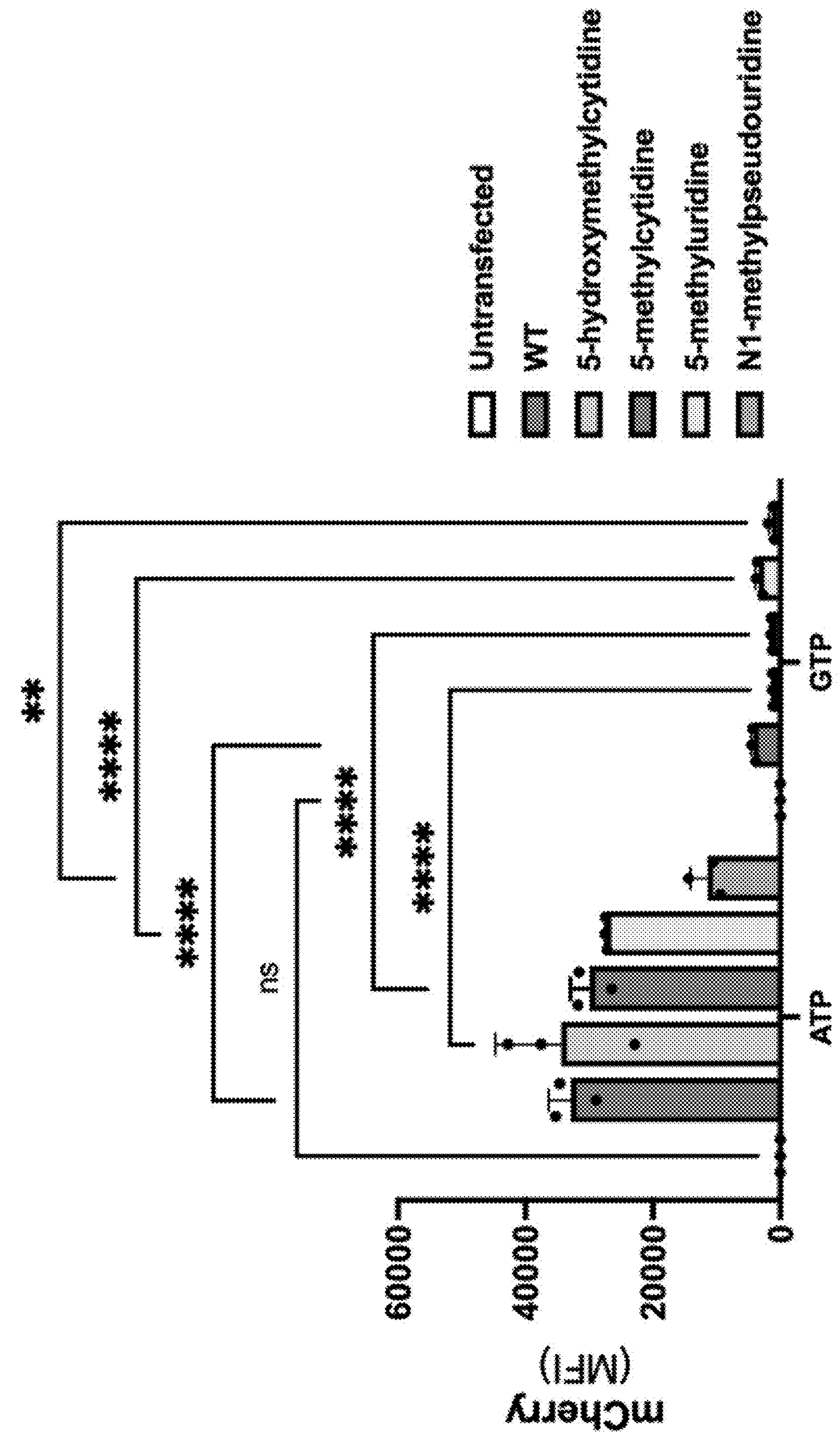
FIG. 42 depicts relative expression of a cargo protein, as measured by MFI of mCherry, from self-amplifying RNA with differing initiation nucleotides. This figure shows the Cap 0 structure in HEK293T cells. Left-right order of the bars in each group corresponds to top-down order in the legend.
Figure 43:
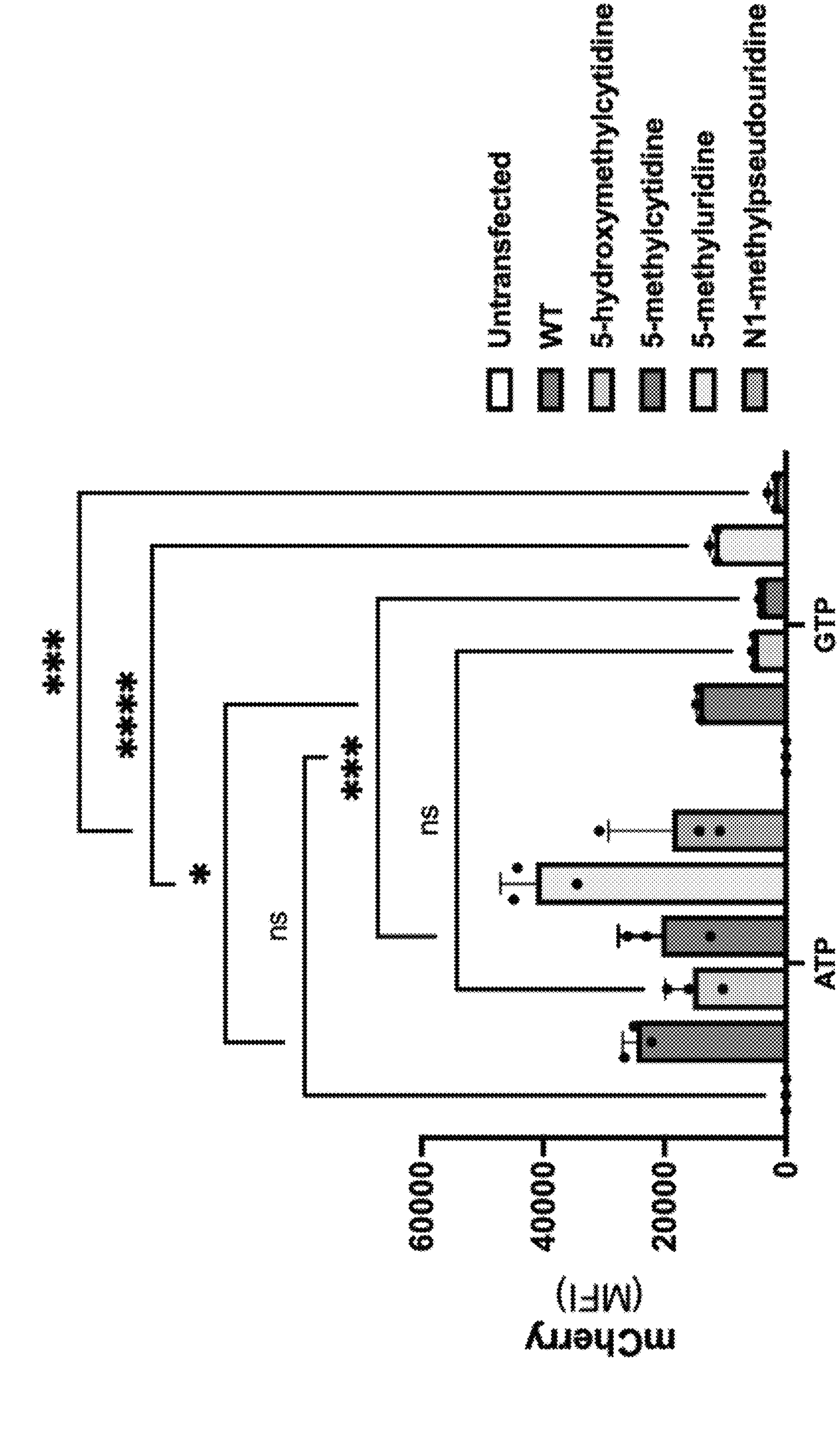
FIG. 43 depicts relative expression of a cargo protein, as measured by MFI of mCherry, from self-amplifying RNA with differing initiation nucleotides. This figure shows the Cap 1 structure in HEK293T cells. Left-right order of the bars in each group corresponds to top-down order in the legend.
Figure 44:
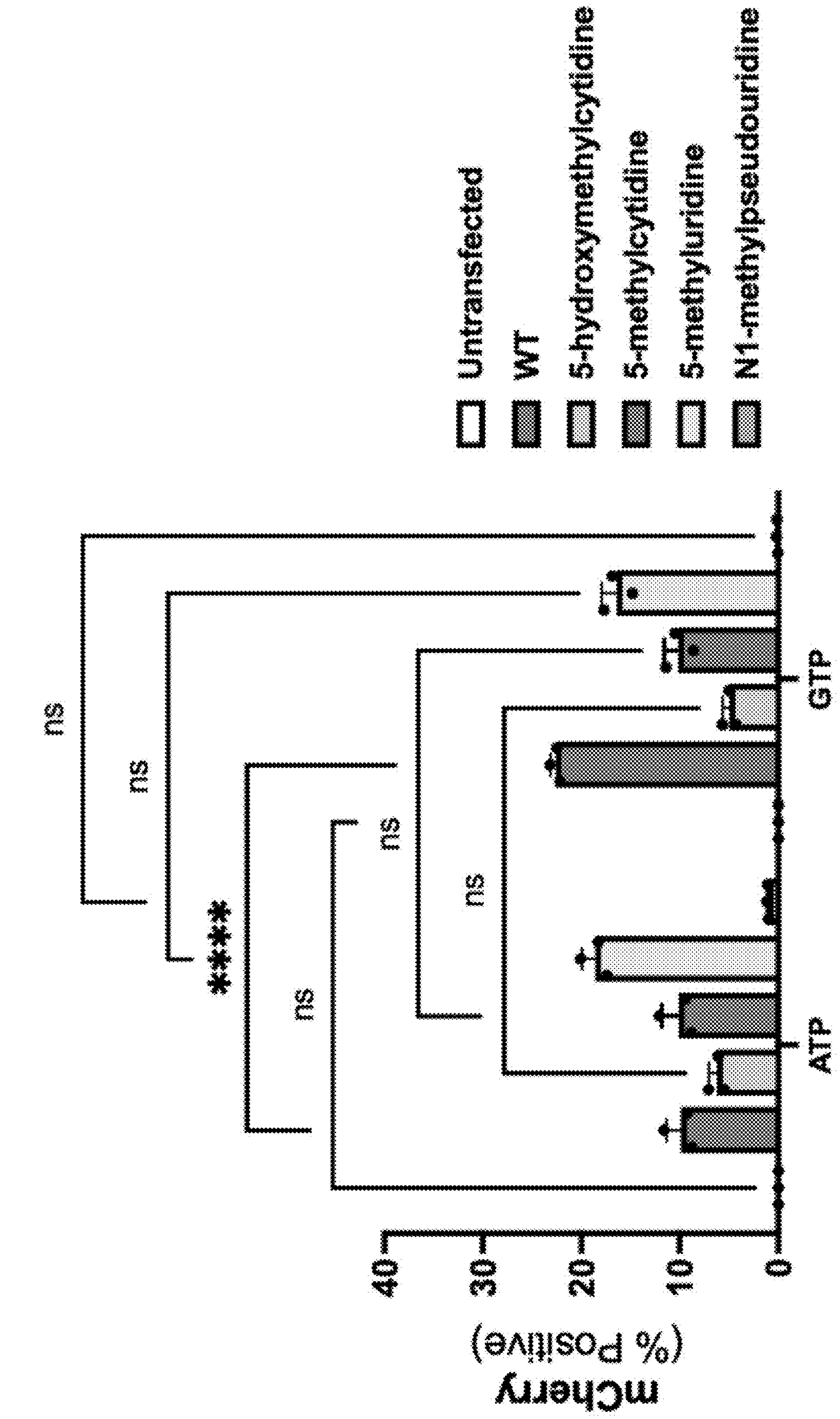
FIG. 44 depicts relative expression of a cargo protein, as measured by percent positive mCherry expression, from self-amplifying RNA with differing initiation nucleotides. This figure shows the Cap 0 structure in HEK293T cells. Left-right order of the bars in each group corresponds to top-down order in the legend.
Figure 45:
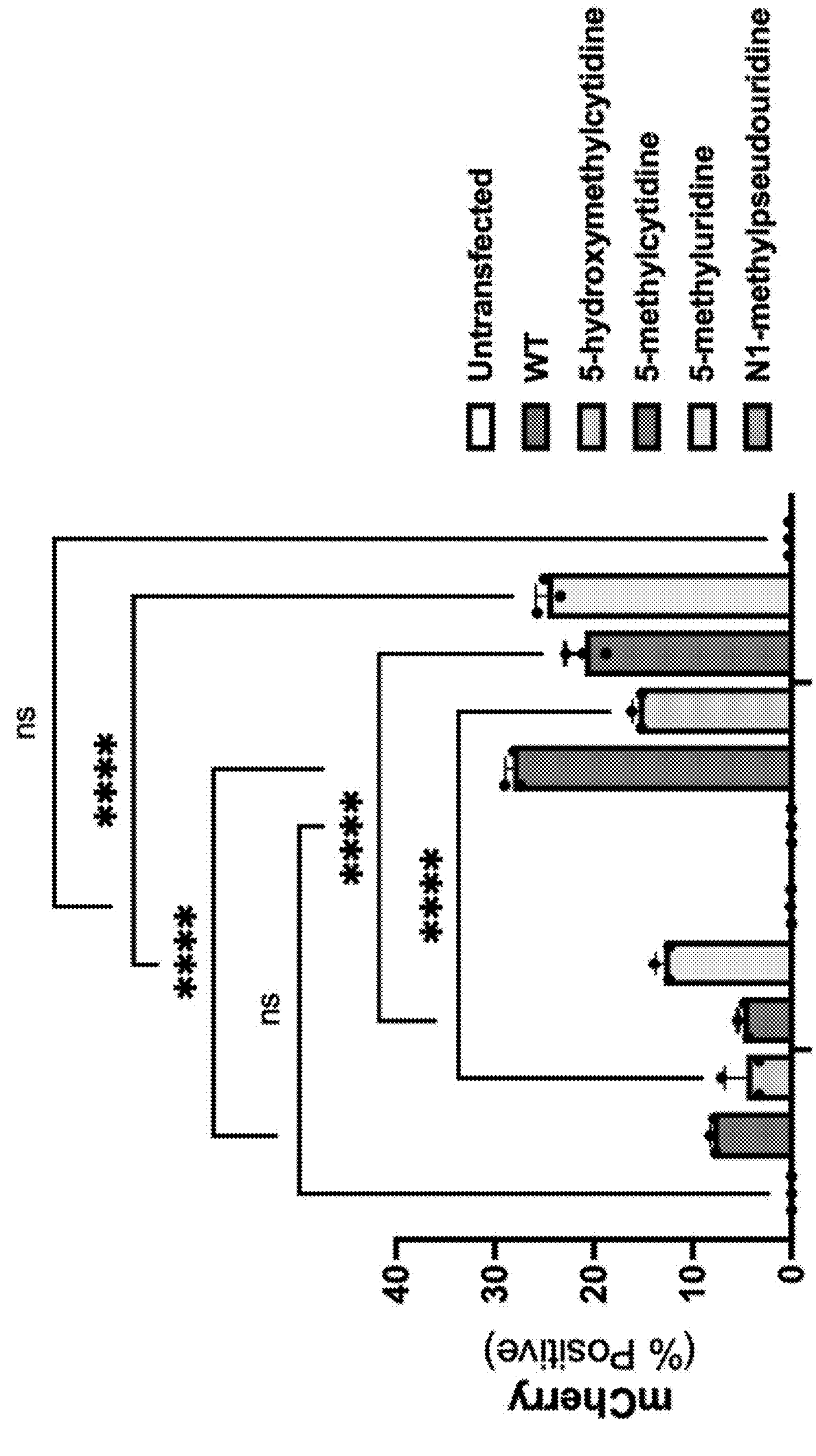
FIG. 45 depicts relative expression of a cargo protein, as measured by percent positive mCherry expression, from self-amplifying RNA with differing initiation nucleotides. This figure shows the Cap 1 structure in HEK293T cells. Left-right order of the bars in each group corresponds to top-down order in the legend.

Example 12: The Initiating Nucleotide is Critical for saRNA Expression Intensity This example demonstrates the unexpected result that the initiating nucleotide, the nucleotide directly 3' of the cap structure is critical for saRNA function when substituted with modified nucleotides. In this example, saRNA encoding an mCherry fluorescent reporter were synthesized as detailed in Example 10 save for the addition of cap analog. Select modified nucleotides, specifically, 5-methylcytidine, 5-methyluridine, 5-hydroxymethycytidine, and N1-methylpseudouridine were incorporated into the saRNA at 100% substitution. Both ATP initiated (Promoter seq: TAATACGACTCACTATAAT; SEQ ID NO: 1) and GTP initiated (Promoter seq: TAATACGACTCACTATAGAT; SEQ ID NO: 8) variants were synthesized with each listed modified nucleotide. All saRNA were enzymatically capped using Faustovirus Capping Enzyme (FCE) to achieve a cap 0 structure, according to manufacturer's protocols. 10 μg of each saRNA were further enzymatically modified to Cap 1 structure, according to manufacturer's protocols (NEW ENGLAND BIOLABS). HEK293T cells were plated at 80,000 cells/$cm^2$ and allowed to adhere overnight. Cells were transfected with 100 ng saRNA using MESSENGERMAX reagent; lipoplexes were prepared according to manufacturer's protocol (THERMO FISHER SCIENTIFIC). After 24 hours, cells were gently dissociated, and fluorescence was assessed via flow cytometry. The entire screen detailed in example 11 was repeated using ARCA capping instead of enzymatic capping. The transfection efficiencies were similar between ARCA and CLEANCAPAU capped constructs, but the expression intensity was markedly lower, indicating cap dependency to modified nucleotide efficacy and expression in saRNA (see e.g., FIG. 40-41). Cap 0, ATP-initiated saRNA, synthesized via enzymatic capping, expressed at significantly higher median fluorescent intensity compared to equivalent GTP-initiated constructs (see e.g., FIG. 42). The transfection efficiency of ATP-initiated vs GTP-initiated constructs was equivalent between modified nucleotides (see e.g., FIG. 43). Cap 1 saRNA displayed similar trends in median fluorescence intensity between ATP-initiated and GTP-initiated as Cap 0, with a decrease in the magnitude of differential (see e.g., FIG. 44). The cap 1 saRNA displayed increased transfection efficiency in the GTP-initiated constructs; however, the median expression intensity was decreased in across all modified nucleotides (see e.g., FIG. 45). In conclusion, this example demonstrates the unexpected result that initiating nucleotide is important for the function of saRNA with and without modified nucleotides. Additionally, this indicates that the reason for previous work not identifying modified nucleotides was a result of cap 0, GTP-initiated saRNA displaying low expression intensity.

Example 13: Suppression of Early Interferon Response in Human PBMCs

Figure 46A:
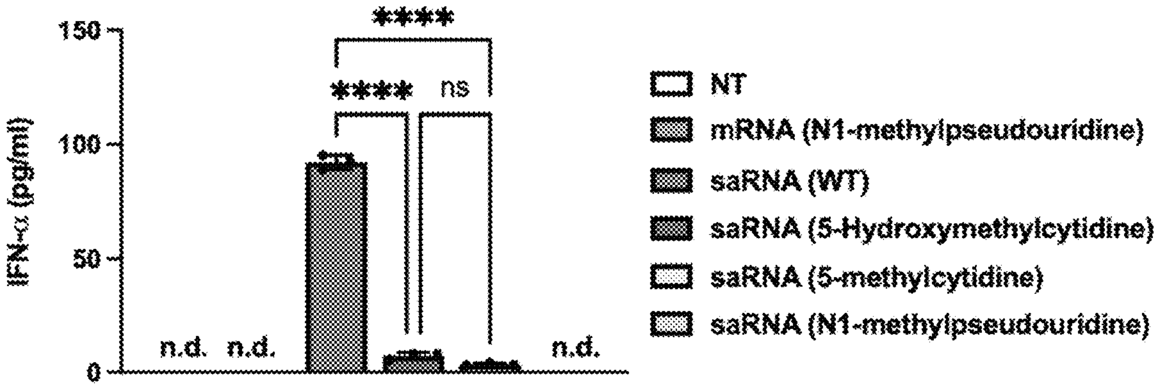
FIG. 46A-46B depict the protein level early interferon α and β response in human peripheral blood mononuclear cells (PBMCs) using Cap-1 and ATP-initiated constructs. PBMCs were exposed to RNA, either saRNA or traditional highly substituted mRNA, for 6 hours, and IFNα (all subtypes; see e.g., FIG. 46A) and IFNβ (see e.g., FIG. 46B) concentration was analyzed via ELISA. Cell culture supernatant was diluted 1:1 in reagent buffer. Left-right order of the bars corresponds to top-down order in the legend.
Figure 46B:
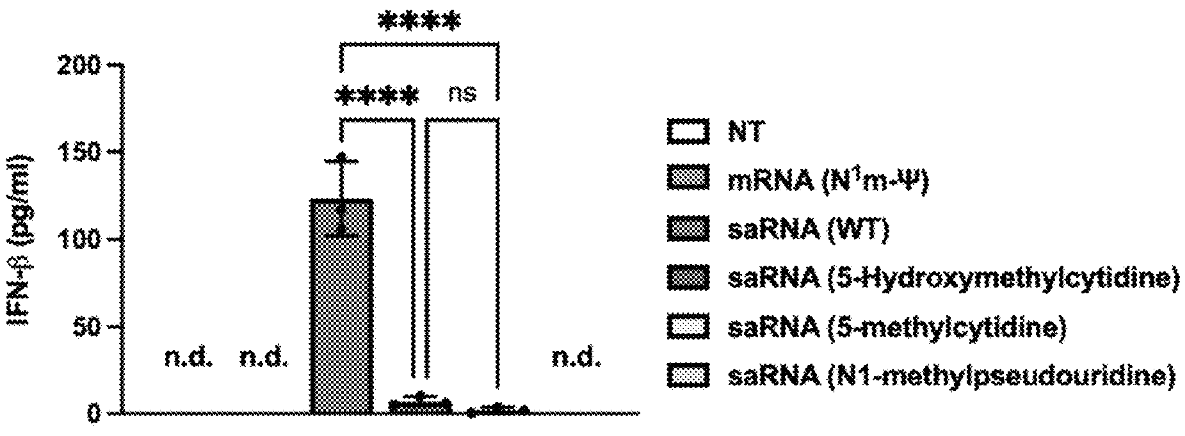
Figure 47A:
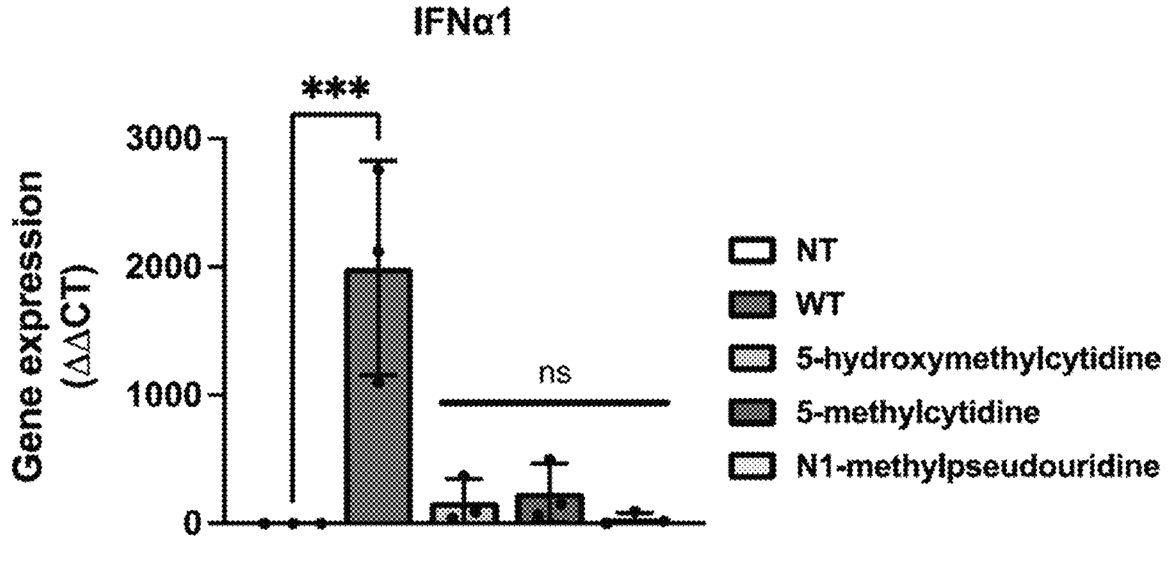
FIG. 47A-47B depict the transcriptional early interferon α and β response in human peripheral blood mononuclear cells using Cap-1 and ATP-initiated constructs. PBMCs were exposed to saRNA with wild-type nucleotides or with modified nucleotides, for 6 hours, and mRNA expression levels of IFNA1 (see e.g., FIG. 47A) and IFNB1 (see e.g., FIG. 47B) were measured via qPCR. Data represents transcriptional levels from three unique human donors dosed at 100 ng/1×$10^5$ cells. Left-right order of the bars corresponds to top-down order in the legend.
Figure 47B:
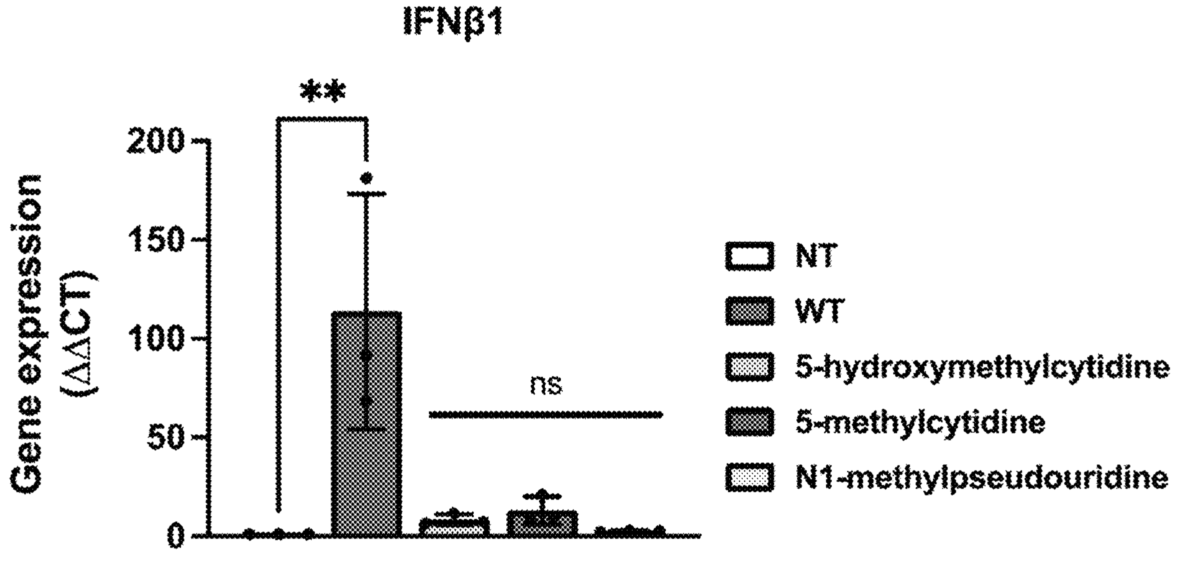

This example demonstrates the evasion of the early interferon response conferred to self-amplifying RNA through incorporation of modified nucleotides. In this example, PBMCs were isolated from apheresis collars, harvested from three unique human patients. Isolation was carried out according to manufacturer's protocol using SepMate™-50 columns containing LYMPHOPREP (STEMCELL TECHNOLOGIES). Isolated peripheral blood mononuclear cells (PBMCs) were either immediately used or stored in 90% Human AB serum+10% DMSO in a liquid nitrogen cryotank. PBMCs were rested overnight in Roswell Park Memorial Institute (RPMI) medium+10% fetal bovine serum (FBS)+1% penicillin and streptomycin (PS). Any monocytes that may have adhered to the tissue culture (TC) flask were gently dissociated using a sterile spatula. Individual donors were plated at 1 million cells/ml in 500 μl of complete media in 24 well plates. PBMCs were treated with 500 ng saRNA or mRNA, formulated in lipid nanoparticles (LNPs). Cells were cultured for 6 hours and 24 hours before assessing media and transcriptomic profiles of the given groups. The fully substituted self-amplifying RNA had a significantly lower elicited early interferon response than wild-type nucleotides (see e.g., FIG. 46 & FIG. 47). As a result, this example demonstrates that saRNA with 100% incorporation of modified nucleotides evades the early interferon response in human immune cells when compared to unmodified saRNA.

Example 14: Fully-Modified Self-Amplifying RNA as Vaccines

Figure 48:
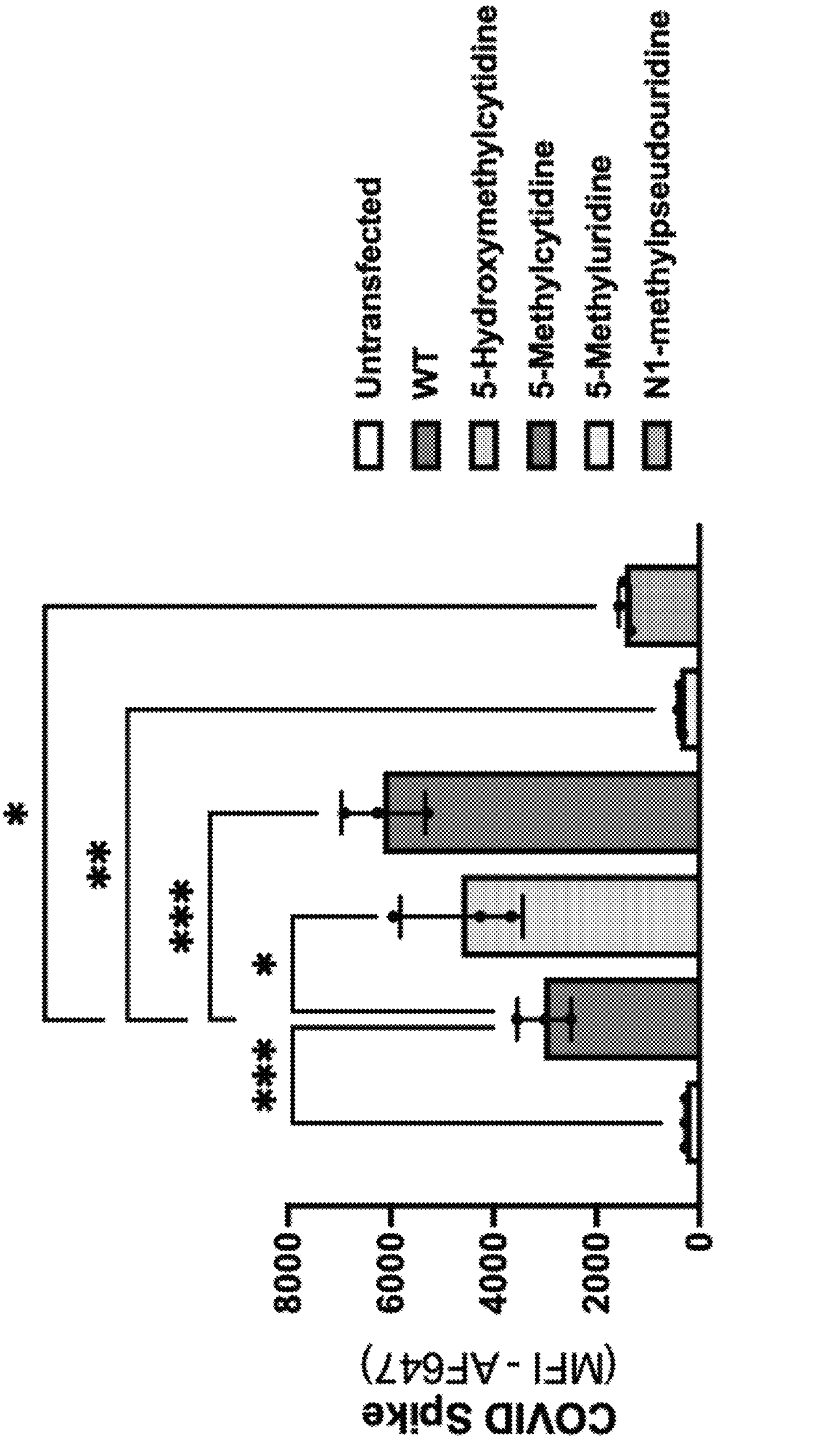
FIG. 48 depicts spike protein (Wuhan-1 variant) expression, as measured by MFI from a AF647 conjugated anti-spike antibody, from self-amplifying RNA in C2C12 mouse myoblast cells. The different modified nucleotides which are highly substituted are shown on the right of the figure. Left-right order of the bars corresponds to top-down order in the legend. Cap-1 and ATP-initiated saRNA constructs were used.
Figure 49:
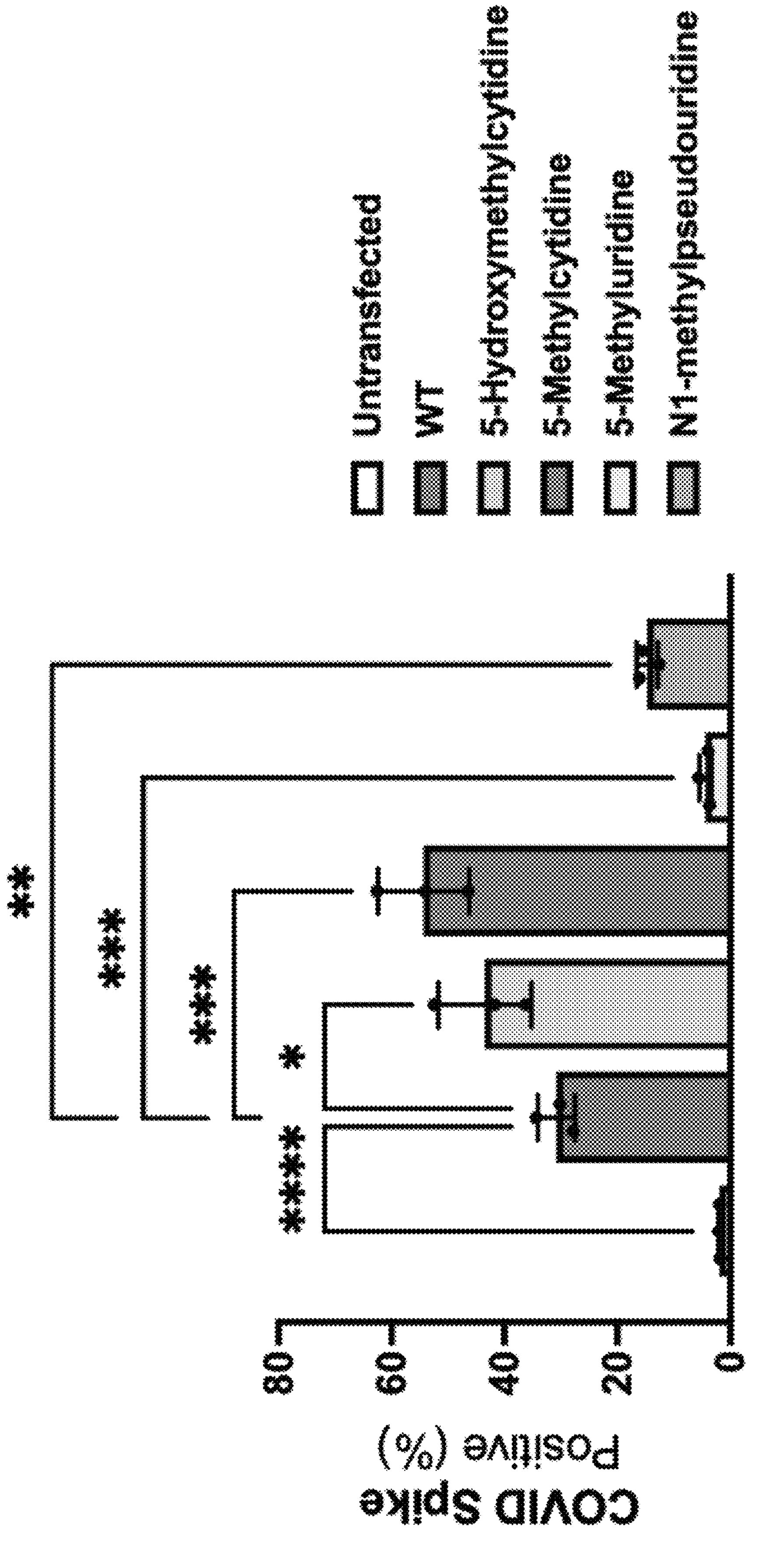
FIG. 49 depicts spike protein (Wuhan-1 variant) expression, as measured by percent positively expressing cells, from self-amplifying RNA in C2C12 mouse myoblast cells. The different modified nucleotides which are highly substituted are shown on the right of the figure. Left-right order of the bars corresponds to top-down order in the legend. Cap-1 and ATP-initiated saRNA constructs were used.

Self-amplifying RNA represents an attractive modality for vaccination as it can elicit a much more robust immune response with lower necessary dose than traditional non-amplifying RNA. Fully-substituted self-amplifying RNA is even more attractive as a modality compared to self-amplifying RNA produced with unmodified nucleotides, because a vaccine antigen of interest can be expressed more potently in a patient with a lower dose. A fully-substituted self-amplifying RNA encoding a stabilized variant of the SARS-CoV-2 spike protein was produced by IVT from a linearized plasmid template. Unique saRNA IVT reactions were run with 100% substitution of 5-methylcytidine, 5-hydroxymethylcytidine, 5-methyluridine, N1-methylpseudouridine, and wild-type nucleotides. It was encapsulated in lipid nanoparticles under aseptic conditions and LNP size and polydispersity were characterized via dynamic light scattering (DLS). LNPs were dialyzed under sterile conditions in sterile 1× phosphate buffered saline (PBS). After dialysis, loading of fully-substituted saRNA into LNPs was assessed via adding RNA-binding fluorescent dye to samples with and without lytic surfactant. Mouse myoblast cells, C2C12s, were plated in 96 well TC coated plates and allowed to adhere overnight. Cells were dosed with saRNA at 100 ng/well with and without full-substitution of modified nucleotides. Expression was assessed via direct flow cytometry with an ALEXAFLUOR700 conjugated mAb against the SARS-CoV-2 spike protein (see e.g., FIG. 48 & FIG. 49). Fully-modified self-amplifying RNA encoding for the SARS-CoV-2 spike expressed on a large population of cells demonstrating a higher transfection efficiency, as well as expressed more potently on the cells induced, demonstrating higher vaccine antigen production. In conclusion, this unexpected result demonstrates that highly-substituted saRNA is capable of over-expressing a vaccine antigen of interest at comparable or greater expression than wild-type saRNA.

A healthy patient is dosed with 100 ng of highly-substituted self-amplifying RNA via intramuscular injection of LNP. The fully modified saRNA transfects cell populations broadly and over-expresses the vaccine antigen compared to unmodified saRNA at the same dose. Immune cells in the healthy patient's body are activated by the expression of the viral antigen and induce an immunization response capable of recognizing the viral antigen and rapidly mounting a protective response after future exposure. An equivalent dose of highly-substituted saRNA results in a more robust immune response than unmodified saRNA.

Example 15: Cell Type Specific saRNA Expression Due to Modified Nucleotide

Figure 50:
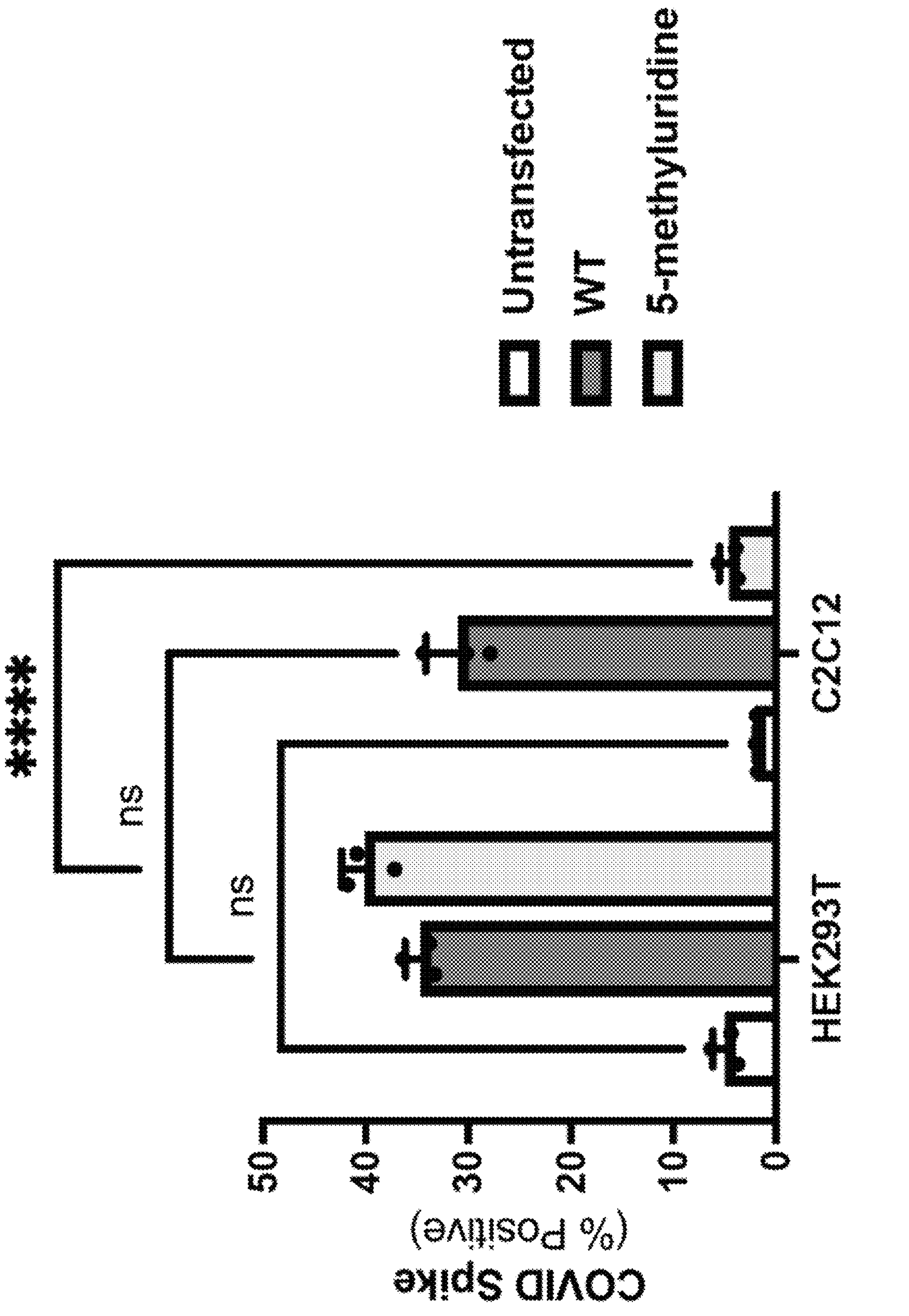
FIG. 50 depicts the cell type specific expression of a vaccine antigen from highly substituted self-amplifying RNA. This IVT was performed using a template with a T7 promoter using m7G(5')ppp(5')(2'OMeA)pU (CLEANCAP AU) as the 5' Cap. Left-right order of the bars in each group corresponds to top-down order in the legend.

This example demonstrates that a novel property of cell-type specific saRNA expression can be conferred via the selection of a given modified nucleotide. saRNA encoding a stabilized variant of the SARS-CoV-2 spike protein was produced by IVT with 100% substitution of 5-methyluridine for uridine, in a manner similar to previously described (see e.g., Example 11). HEK293T (immortalized human embryonic kidney) cells were plated at 80,000 cells/$cm^2$, and C2C12 (immortalized mouse myoblast) cells were plated at 25,000 cells/$cm^2$ and allowed to adhere overnight. Cells were treated with 100 ng of saRNA encapsulated in LNPs and incubated for 24 hours. Expression was determined via flow cytometry staining for the spike protein expressed on the surface of cells. 5-methyluridine saRNA expresses at comparable or greater levels in HEK293T cells, but it does not express in C2C12 cells (see e.g., FIG. 50). This unexpected result demonstrates the cell type specific expression conferred to saRNA via the selection of a specific modified nucleotide.

Figure 51A:
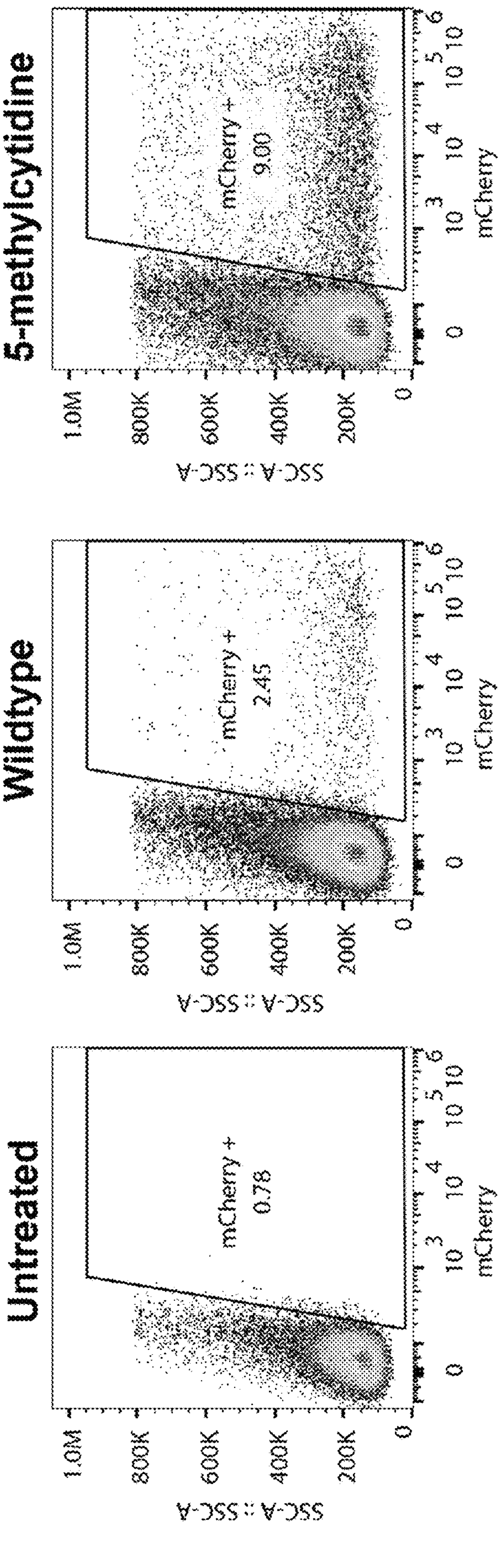
FIG. 51A-51C depicts the expression potentiation conferred by 100% substitution with 5-methylcytidine using Cap-1 and ATP-initiated saRNA constructs in human CD3+ T cells. Untreated cells are compared to saRNA encoding a fluorescent reporter protein, mCherry, with or without nucleotide modification.
Figure 51B:
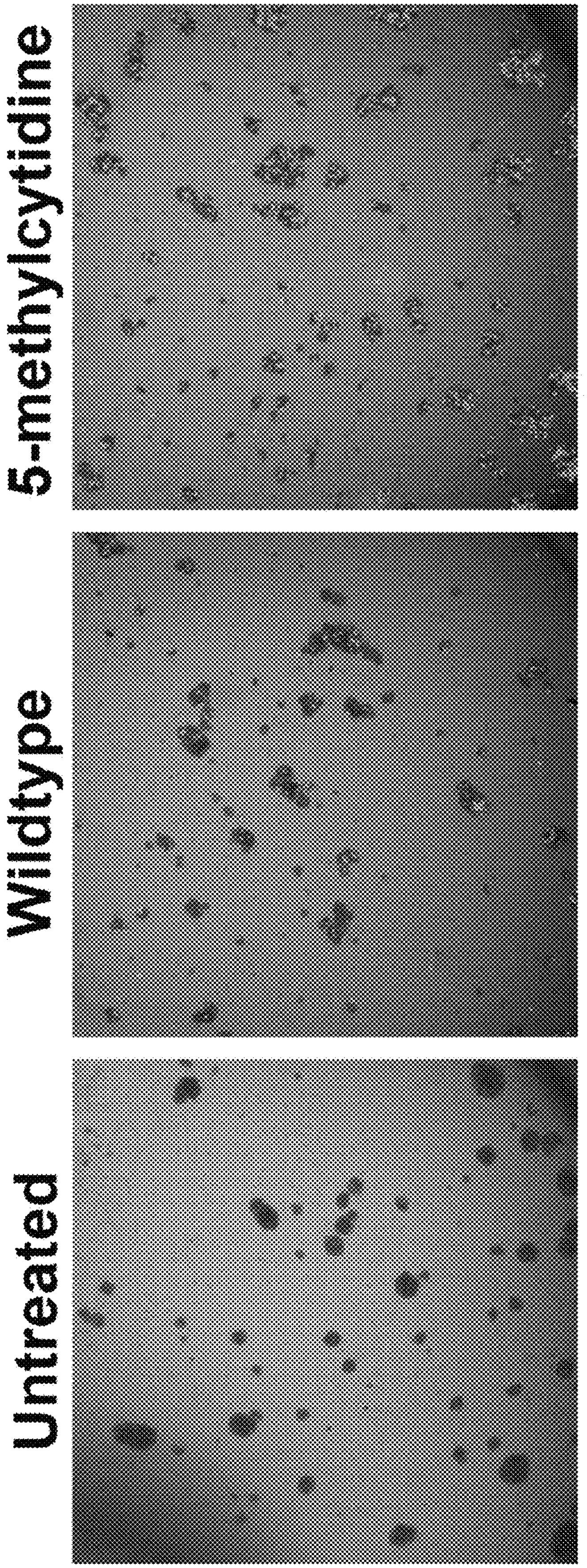
Figure 51C:
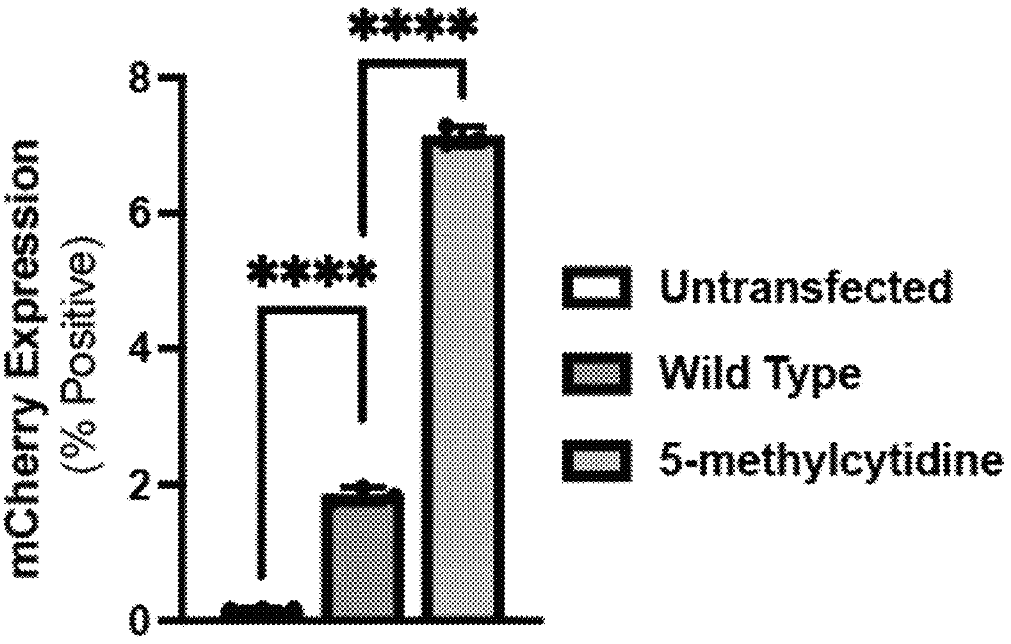
Figure 52:
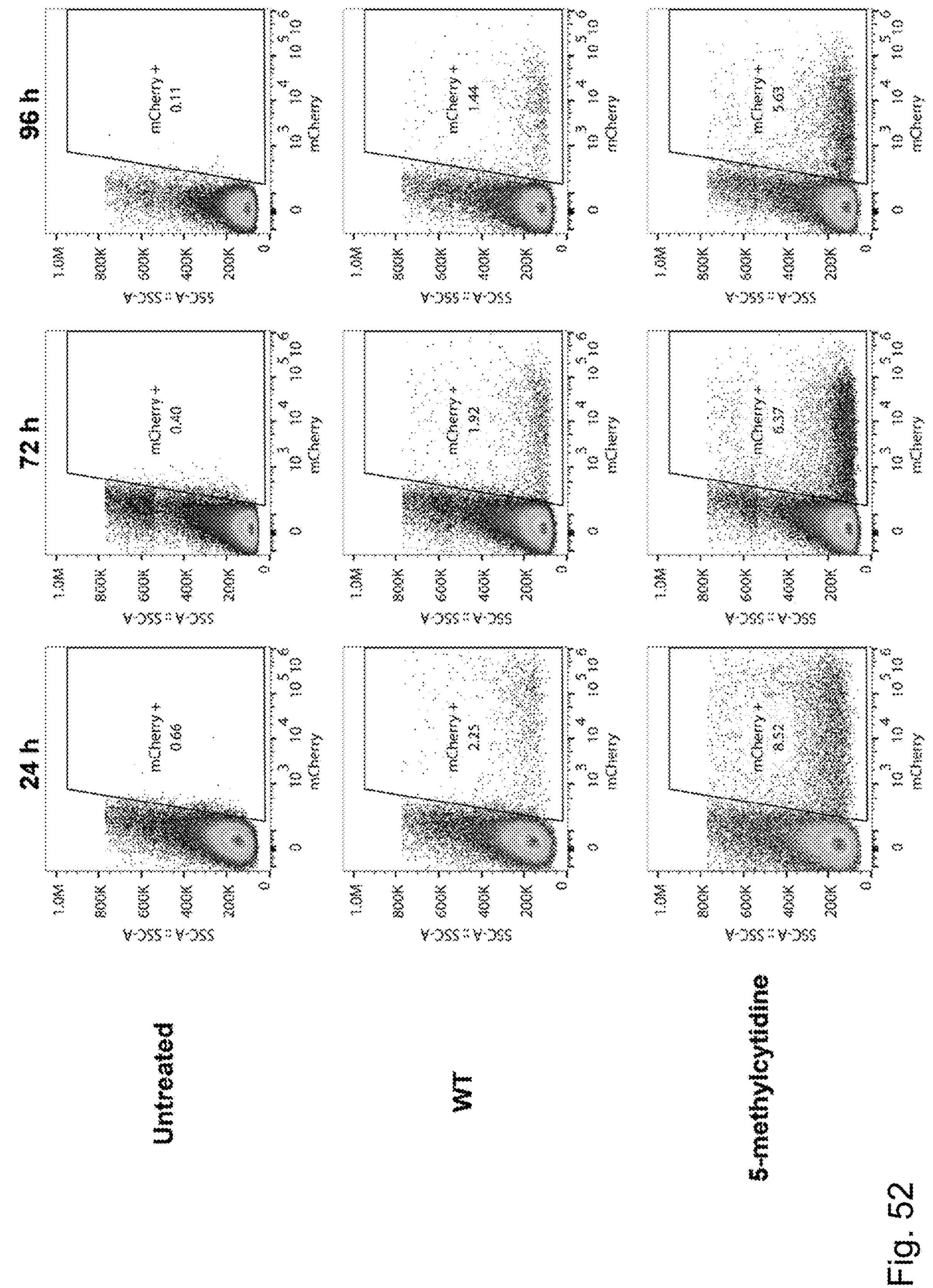
FIG. 52 depicts the prolonged and robust expression conferred by 100% substitution with 5-methylcytidine using Cap-1 and ATP-initiated saRNA constructs in human CD3+ T cells. Untreated cells are compared to saRNA encoding a fluorescent reporter protein, mCherry, with or without nucleotide modification and analyzed over time by flow cytometry.
Figure 53A:
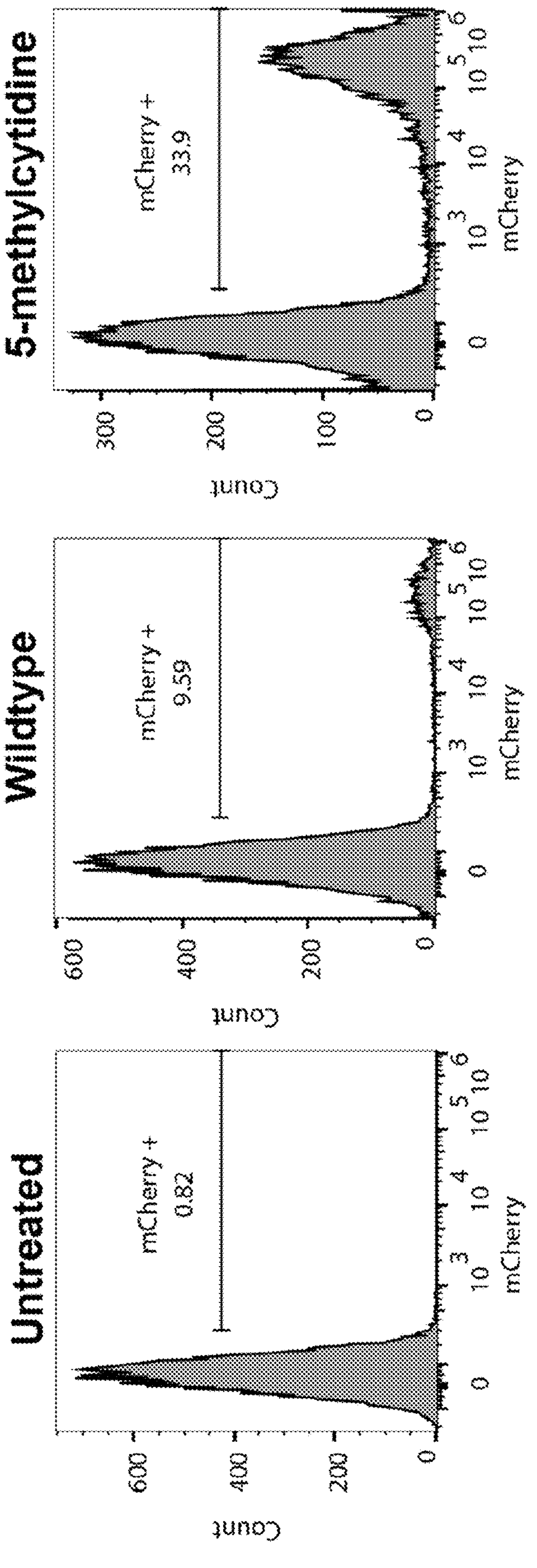
FIG. 53A-53C depicts the expression potentiation conferred by 100% substitution with 5-methylcytidine using Cap-1 and ATP-initiated saRNA constructs in Jurkat cells. Untreated cells are compared to saRNA encoding a fluorescent reporter protein, mCherry, with or without nucleotide modification.
Figure 53B:
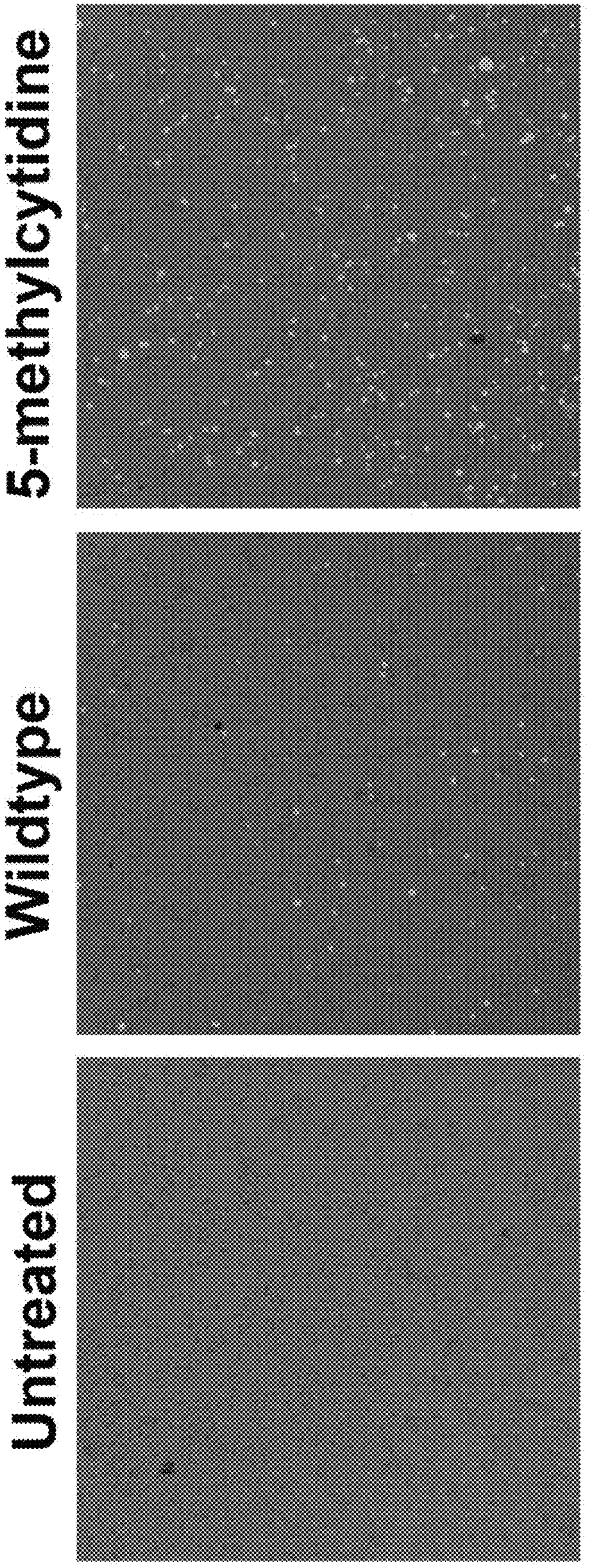
Figure 53C:
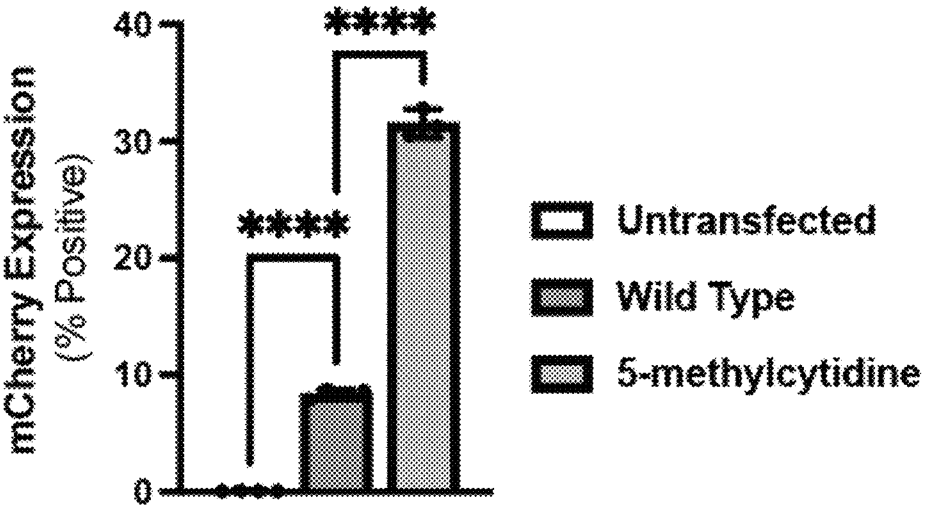
Figure 54A:
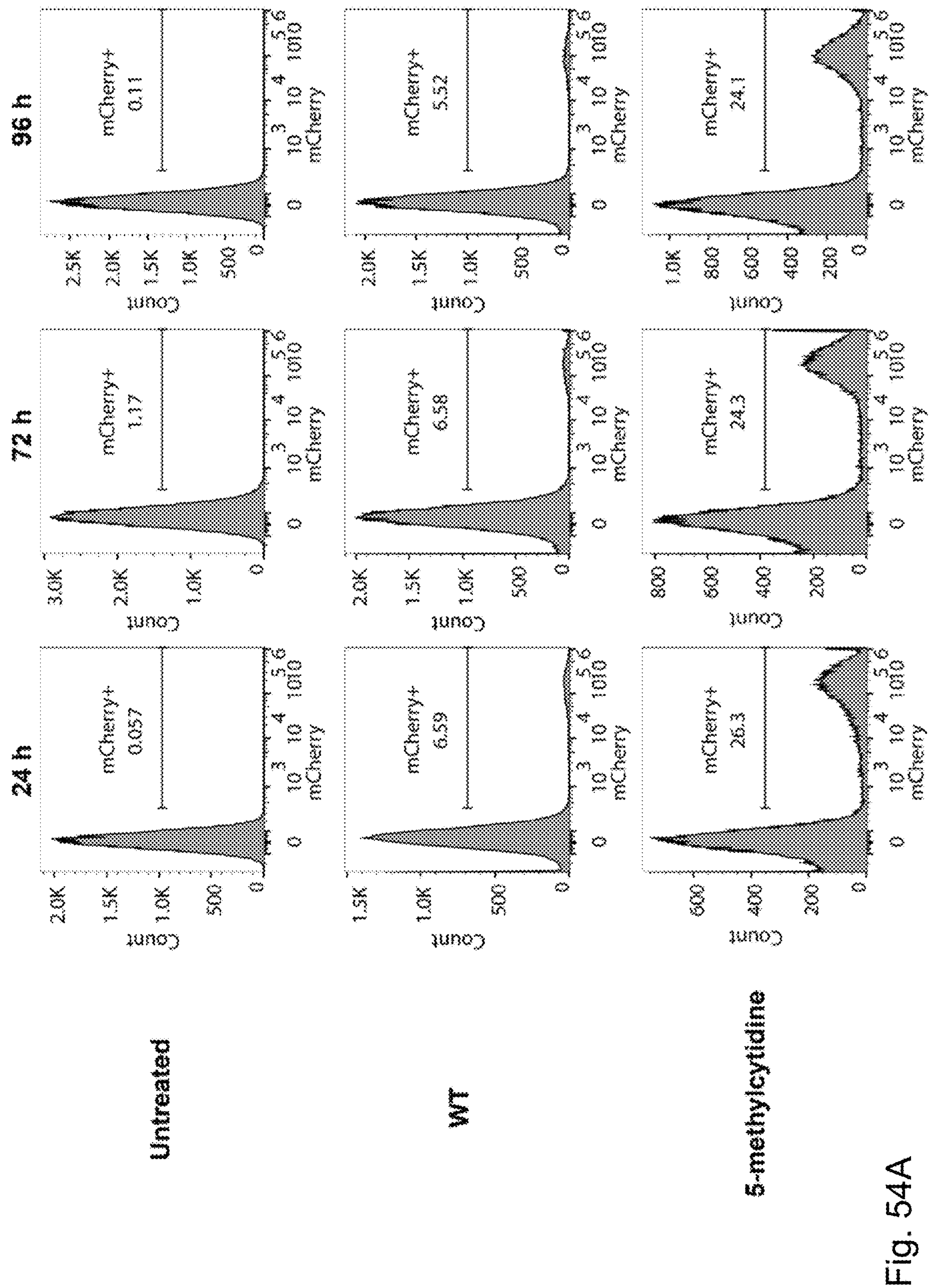
FIG. 54A-54B depicts the prolonged, robust expression conferred by 100% substitution with 5-methylcytidine using Cap-1 and ATP-initiated saRNA constructs in Jurkat cells. Untreated cells are compared to saRNA encoding a fluorescent reporter protein, mCherry, with or without nucleotide modification and analyzed over time by flow cytometry.
Figure 54B:
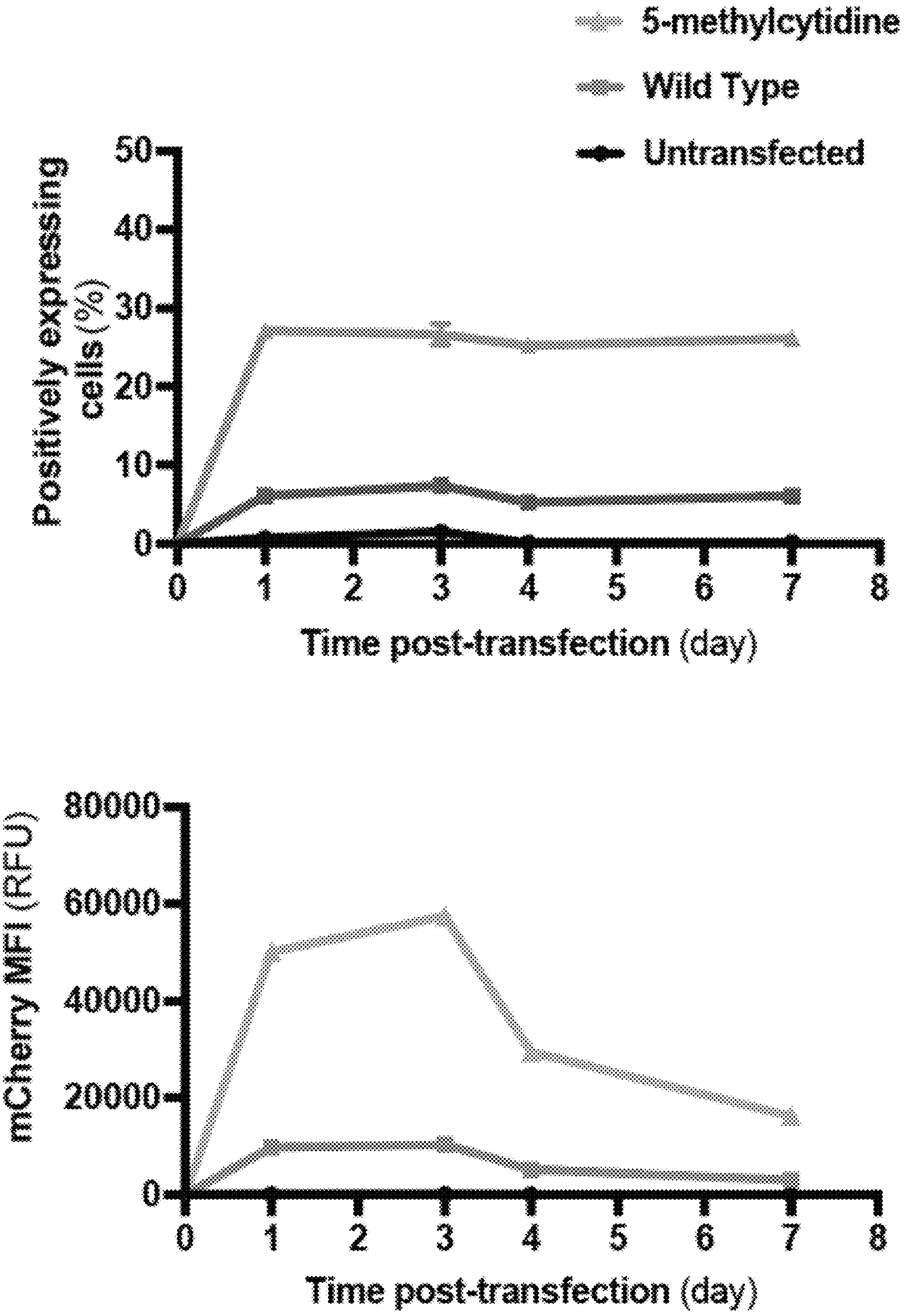
Figure 55:
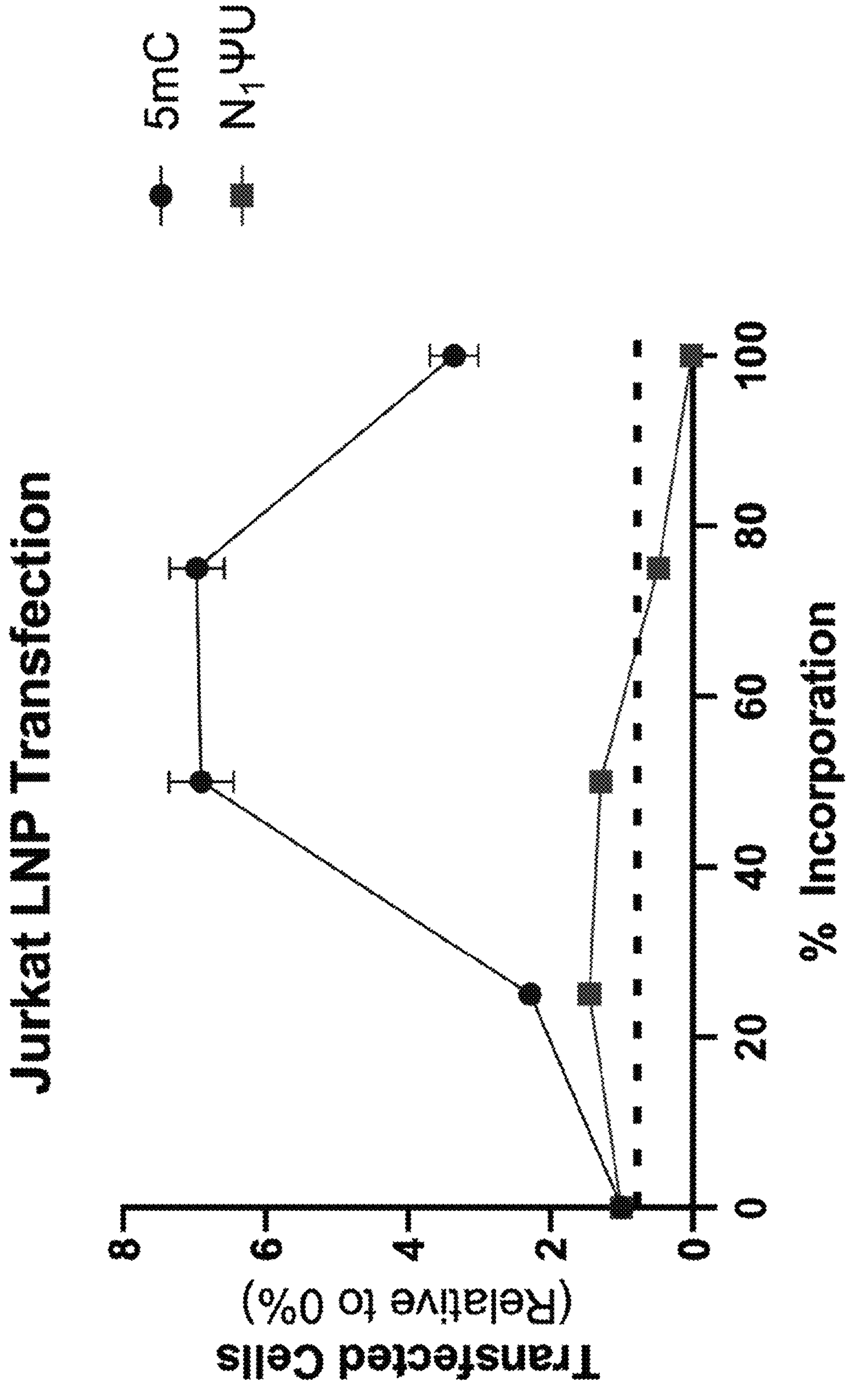
FIG. 55 depicts the impact of increasing substitution ratios ofNI-methylpseudouridine and 5-methylcytidine on Cap-1 and ATP-initiated saRNA efficacy in Jurkat cells. Transfection efficiency of saRNA encoding a fluorescent reporter protein synthesized with increasing % substitution of modified nucleotides. 0% substitution refers to unmodified saRNA.
Figure 56:
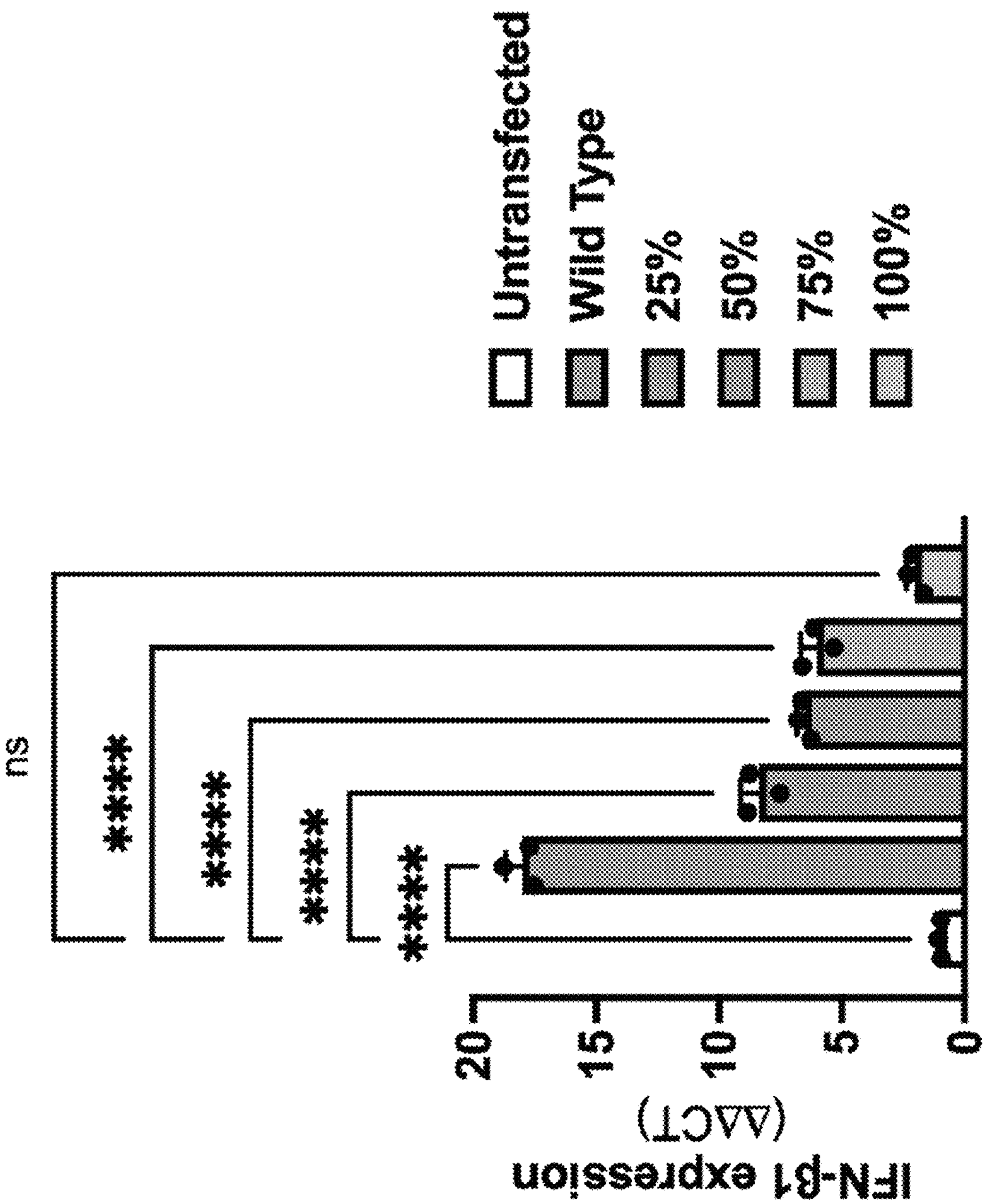
FIG. 56 depicts the impact of increasing substitution ratios of 5-methylcytidine on Cap-1 and ATP-initiated saRNA immunogenicity. Human PBMCs treated for 6 hours with saRNA loaded LNPs and then harvested for gene expression analysis. 0% substitution refers to unmodified saRNA. Left-right order of the bars corresponds to top-down order in the legend.

Example 16: Increased Expression of Highly-Substituted saRNA Compared to saRNA with Wild Type Nucleotides This example demonstrates the unexpected result that saRNA substituted at greater than 25% with modified nucleotides increases the expression of a cargo of interest. saRNA encoding a fluorescent reporter protein were synthesized via IVT from linearized plasmid with 100% (see e.g., FIG. 51-56), 75%, 50%, 25% or 0% (see e.g., FIG. 55-56) substitution of cytidine with 5-methylcytidine (see e.g., FIG. 51-56) or uridine with N1-methylpseudouridine (see e.g., FIG. 55-56). Jurkat cells were grown in RPMI+10% FBS+1% PS and maintained between $5\times10^5$ and $2\times10^6$ cells/ml. Prior to transfection, the cells were washed with PBS and plated in fresh RPMI at 250,000 cells/well. LNPs containing saRNA with or without modified nucleosides were added dropwise to cells in triplicate at 250 ng/well. After 24 hours, a portion of the cells were harvested for flow analysis. The remainder of the cells were maintained in culture and assayed by flow at additional time points. Primary human CD3+ T cells were isolated by negative selection from peripheral blood and grown in RPMI+10% FBS+1% PS supplemented with 50 U/mL of IL2. To activate the cells, CD3/CD28 DYNABEADS were added to the cells at a 2:1 bead to cell ratio for 48 hours. After activation, the DYNABEADS were removed and the T cells were allowed to recover for 24 hours before transfection. Primary T cells were washed with PBS and plated at 250K/well in RPMI+10% FBS supplemented with 50 U/mL IL2. To transfect, anti-CD3 conjugated LNPs were dosed in triplicate at 1 μg/well. CD3+ T cells treated with 5-methylcytidine substituted saRNA demonstrated significantly increased expression of the cargo of interest compared to unmodified saRNA (see e.g., FIG. 51). Additionally, CD3+ T cells demonstrated sustained expression of the cargo (see e.g., FIG. 52). Jurkat (immortalized human T lymphocyte) cells treated with 5-methylcytidine substituted saRNA demonstrated significantly increased expression of the cargo of interest compared to unmodified saRNA (see e.g., FIG. 53). Additionally, Jurkat cells demonstrated sustained expression of the cargo (see e.g., FIG. 54). Jurkat cells treated with 5-methylcytidine or N1-methylpseudouridine substituted saRNA at increasing ratios demonstrated a substitution-dependent activity. Increasing the nucleotide substitution percentage above 25% increased the expression of the cargo of interest with 5-methylcytidine, but decreased expression with N1-methylpseudouridine (see e.g., FIG. 55). The early interferon response, as determined by IFN-β1 gene expression in PBMCs, treated as previously described (see e.g., Example 13), demonstrated that 100% substitution was the only condition where gene expression was not significantly increased compared to the untransfected control cell population (see e.g., FIG. 56). In conclusion, the unexpected results of these experiments were the discovery of increased expression of the cargo of interest at substitution with 5-methylcytidine at substitution ratios greater than 25% in various cell types, over extended periods of time.

Example 17: Self-Amplifying CAR T Cells, Generated In Situ

Figure 57:
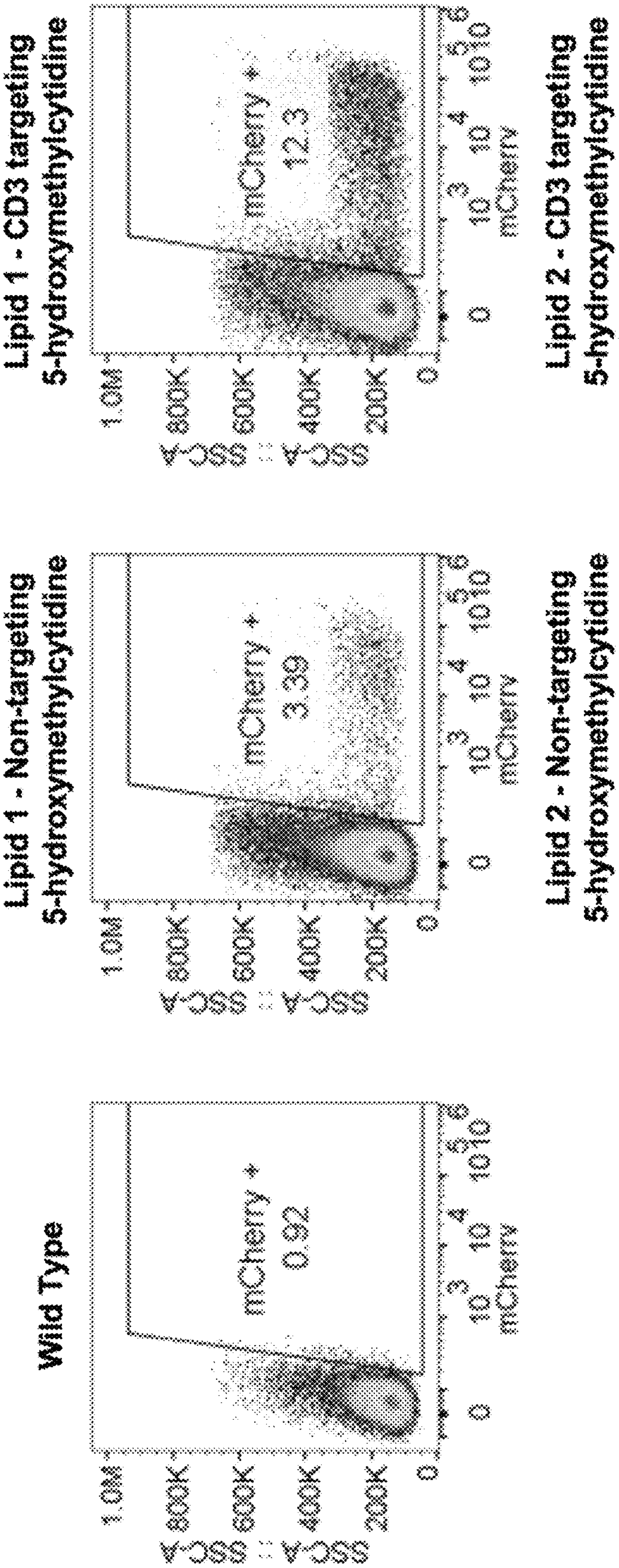
FIG. 57 depicts the increased expression of a chimeric antigen receptor conferred by 100% substitution with 5-methylcytidine of Cap-1 and ATP-initiated saRNA constructs in human CD3+ T cells. saRNA encoding a chimeric antigen receptor was delivered to CD3+ T cells via lipid nanoparticle synthesized with two different helper lipids with or without a CD3 targeting domain.

Self-amplifying RNA represents an attractive modality for long term expression of immunomodulatory therapies such as antibodies or chimeric antigen receptor T cells therapy. The expression of CAR is too short for sustained therapeutic effect when traditional mRNA is utilized and as a result, multiple injections are required. Additionally, the cell surface density of expressed CAR from traditional mRNA is often below therapeutic levels. Self-amplifying RNA extends the length of expression compared to non-replicating mRNA. However, self-amplifying RNA without nucleotide modification are difficult to transfect into the cell populations of interest, CD3+ T cells. They effectively do not take up self-amplifying RNA due to the early interferon immune response. Fully-modified saRNA allowed for transfection of larger cell populations to enable therapeutic effect. A fully-substituted self-amplifying RNA encoding an anti-CD19 chimeric antigen receptor with a mCherry fluorescent reporter was produced by IVT from a linearized plasmid template. It was encapsulated in lipid nanoparticles under aseptic conditions. Post insertion of a DSPE-PEG-anti-CD3 mAb complex was accomplished at room temperature and LNP size and polydispersity were characterized via dynamic light scattering. LNPs were dialyzed under sterile conditions in sterile 1×PBS. After dialysis, loading of fully-substituted saRNA into LNPs was assessed via adding RNA-binding fluorescent dye to samples with and without lytic surfactant. CD3+ T cells were selectively enriched from PBMCs, which were isolated from apheresis collars. Simultaneous isolation and enrichment was carried out using SepMate™-50 columns containing Lymphoprep™ and RosetteSep™ Human T Cell Enrichment Cocktail (STEMCELL TECHNOLOGIES). Isolated T cells were either immediately used or stored in 90% Human AB serum+10% DMSO in a liquid nitrogen cryotank. After thawing, T cells were rested overnight in T cell media and then plated at 1 million (M) cells/ml. T cells were activated prior to dosing with saRNA via LNPs at 100 ng/$1\times10^5$ T cells. Transfection was assessed via flow cytometry for mCherry as well as for cell surface expression of the CAR via direct flow cytometry with an anti-V5 antibody. Fully modified saRNA was capable of transfecting CD3+ T cells using multiple different ionizable lipids, with an increase in expression as a result of targeting (see e.g., FIG. 57). In conclusion, the unexpected result of this experiment is that saRNA 100% substituted with 5-methylcytidine for cytidine was able to transfect a larger population of cells and express anti-CD19 chimeric antigen receptor at higher levels than an equivalent dose of unmodified saRNA.

A cancer patient is intravenously injected with LNPs containing fully-modified saRNA encoding for a chimeric antigen receptor against an applicable target for their cancer. The LNPs are coupled with a targeting moiety to an immune cell of interest. Such an immune cell of interest includes, but is not limited to, T cells, NK cells, Macrophages, and B cells. In the event that CD3+ T cells are targeted, the fully-modified saRNA will transfect into the T cells, and begin expression of the CAR. Upon recognition of the target antigen of interest, the T cell will be stimulated to expand. As the T cell expands, the self-amplifying RNA will propagate throughout the T cell population with a lower rate of dilution that is seen in non-replicating RNA.

Example 18: Fully Modified saRNA Encoding for Protein Replacement Therapies

For conditions resulting from deficiencies of proteins or enzymes, replacement by messenger RNA is an attractive therapeutic option. The deficient protein or enzyme is expressed from the messenger RNA to improve the condition. The utilization of self-replicating RNA allows for decreased frequency of treatment. By enhancing the expression of the self-replicating RNA through the use of modified nucleotides, a similar therapeutic effect can be achieved with less frequent or lower doses.

Example 19: Highly Substituted Self-Amplifying RNA for Vaccination to Induce an Anti-Cancer Response This example details the use of highly substituted self-amplifying RNA as a mechanism to elicit a protective or therapeutic response against tumor antigens. To trigger a strong anti-cancer reaction, immunostimulatory vaccines encode neoantigens that come from patient-specific or tumor-specific mutations. Identification of patient-specific neoantigens involves sequencing a patient's tumor genome to detect mutations and predict which ones will lead to stable peptide-major histocompatibility complex (MHC) interactions. Identification of tumor-specific mutations involves sequencing a particular tumor derived from a conserved class of cancer across many patients to identified conserved mutations. Once the antigens are identified, highly substituted self-amplifying RNA is synthesized by in vitro transcription. For the case of multiple antigen vaccination, the highly substituted self-amplifying RNA is a polycistronic RNA or multiple monocistronic RNAs. The RNA is formulated into a pharmaceutical composition capable of transfection inside the body. Due to the highly substituted nature of the self-amplifying RNA, a lower dose is administered compared with unmodified self-replicating RNA or modified non-replicating RNA. To enhance efficacy of antigen RNA(s), the self-amplifying RNA can be co-administered with synergistic therapeutics (RNA, small-molecules, checkpoint inhibitors) to increase dendritic cell activation, antigen presentation, and T cell function. In conclusion, this example details the use of highly substituted self-amplifying RNA as a cancer vaccine.

Example 20: Complete Substitution with Modified Nucleotides Suppresses the Early Interferon Response and Increases the Potency of Self-Amplifying RNA Self-amplifying RNA (saRNA) can be used as vaccines and in situ therapeutics that permit protein expression for longer duration at lower doses, e.g., as compared to other RNA therapies. However, a major barrier to saRNA efficacy is the potent early interferon response triggered upon cellular entry, resulting in saRNA degradation and translational inhibition. Substitution of mRNA with modified nucleotides (modNTPs), such as N1-methylpseudouridine (N1mΨ), reduce the interferon response and enhance expression levels. Multiple attempts to use modNTPs in saRNA have been unsuccessful, leading to the conclusion that modNTPs are incompatible with saRNA, thus hindering further development. Here, contrary to the common dogma in the field, multiple modNTPs were identified that when incorporated into saRNA at 100% substitution confer immune evasion and enhance expression potency. Transfection efficiency enhances by roughly an order of magnitude in difficult-to-transfect cell types compared to unmodified saRNA, and interferon production reduces by >8 fold compared to unmodified saRNA in human peripheral blood mononuclear cells (PBMCs). Furthermore, expression of viral antigens were demonstrated in vitro, and significant protection was observed against lethal challenge with a mouse-adapted SARS-CoV-2 strain in vivo. A modified saRNA vaccine, at 100-fold lower dose than a modified mRNA vaccine, resulted in a statistically improved performance to unmodified saRNA and statistically equivalent performance to modified mRNA. This discovery considerably broadens the scope of self-amplifying RNA, permitting entry into previously impossible cell types, as well as the ability to apply saRNA technology to non-vaccine modalities such as cell therapy and protein replacement.

INTRODUCTION

The original discovery of the application of modified nucleotides (modNTPs) to mRNA by Karikó and Weissman revolutionized RNA medicine. This breakthrough permitted rapid development and deployment of mRNA vaccines against Severe acute respiratory syndrome coronavirus 2 (SARS-CoV-2), saving millions of lives. Chemically modified nucleotides enhance mRNA stability, transfection capability, and decrease immunogenicity. Without modNTPs, detection of exogenous RNA activates toll-like receptors (TLRs) and triggers the production of type I interferons, resulting in translational shutoff and systemic inflammation.

In the cytosol, retinoic acid-inducible gene 1 (RIG1) and RNA-dependent protein kinase (PKR) recognize RNA and trigger additional interferon production. Clinically approved mRNA vaccines utilize N1-methylpseudouridine (N1mΨF) to mitigate these responses and improve efficacy. Although effective, the inherent short half-life of mRNA necessitates a large dose to be effective, which increases risk of adverse side effects and limits accessibility. Therefore, efforts to further enhance the expression and durability of RNA-based medicine at lower doses has unlocked new therapeutic applications, improved tolerability, and expanded global access.

Self-amplifying RNAs (saRNAs) undergo replication and amplification, inside the cell, to afford robust and durable expression of an encoded cargo. saRNA are a platform capable of addressing the shortcomings of mRNA by decreasing the dose of vaccines and administration frequency of protein-encoding therapeutics. Decreasing doses mitigate vaccine related side effects and reduce the occurrence of rare but serious adverse events. Additionally, order-of-magnitude reductions in dose requirements significantly bolsters the manufacturing capacity to enhance production speed and democratize the distribution of vaccines against emerging pathogens. However, early clinical evidence from saRNA vaccine trials show decreased efficacy and reduced neutralizing antibody levels compared to mRNA; see e.g., Low et al., NPJ Vaccines, 2022. 7(1): p. 161, the content of which is incorporated herein by reference in its entirety. The early and intense activation of the type I interferon response induced by saRNA detection hinders replication and antigen expression; see e.g., Minnaert et al., Adv Drug Deliv Rev, 2021. 176: p. 113900; Zhong et al., Mol Ther, 2021. 29(4): p. 1370-1381; Ong et al., NPJ Vaccines, 2022. 7(1): p. 154; Pepini et al., J Immunol, 2017. 198(10): p. 4012-4024; the contents of each of which are incorporated herein by reference in their entireties. Strategies to decrease the immunogenicity of saRNA are urgently needed to permit further clinical development and translation.

Prior efforts to decrease the immunogenicity of saRNA focus largely on sequence evolution, co-expression of viral inhibitory proteins, and optimization of the delivery vehicle; see e.g., Li et al., Sci Rep, 2019. 9(1): p. 6932; Blakney et al., Mol Ther, 2021. 29(3): p. 1174-1185; Kimura et al., Mol Ther, 2023. 31(8): p. 2360-2375; the contents of each of which are incorporated herein by reference in their entireties. While useful in their respective applications, all prior approaches fail to achieve a universal method of mitigating the interferon response and improving saRNA expression. The best tools for such improvements are modNTPs. However, the current understanding of the field is that the incorporation of modNTPs into saRNA abrogates downstream efficacy, as reported by multiple independent groups; see e.g., Minnaert et al., Adv Drug Deliv Rev, 2021; Kairuz et al., Front Immunol, 2022. 13: p. 1018961; Voigt et al., NPJ Vaccines, 2022. 7(1): p. 136; Beissert et al., Mol Ther, 2020. 28(1): p. 119-128; Geall et al., RNA Containing Modified Nucleotides and Use Thereof in Vaccines 2010; Erasmus et al., Mol Ther Methods Clin Dev, 2020. 18: p. 402-414; the contents of each of which are incorporated herein by reference in their entireties. Thus, modified nucleotides are not currently viewed as a viable strategy to decrease immunogenicity.

A hypothesis for this observed incompatibility is the alteration of vital saRNA secondary structures; see e.g., Kairuz et al., Front Immunol, 2022. 13: p. 1018961; Helm, Nucleic Acids Res, 2006. 34(2): p. 721-33; the contents of each of which are incorporated herein by reference in their entireties. saRNAs traditionally utilize alphavirus sequences, replacing the structural genes with the genes encoding the cargo(s) of interest; see e.g., Bloom et al., Gene Ther, 2021. 28(3-4): p. 117-129; the contents of which are incorporated herein by reference in its entirety. The resulting synthetic construct encodes both an RdRp and the cargo(s) on the same RNA strand. Once expressed, the RdRp recognizes conserved sequence elements (CSEs) at the 5' and 3' ends to permit transcription of full-length copies of the entire saRNA construct. Later in its lifecycle, the RdRp complex also recognizes a sub-genomic promoter (SGP) to permit amplification of a truncated transcript encoding the cargo(s). The incorporation of modified nucleotides alters the stability or accessibility of specific base pairs, changes hydrogen bonding patterns, and/or shifts RNA hydrophobicity to stabilize or inhibit RNA-protein interactions; see e.g., Kierzek et al., Nat Commun, 2022. 13(1): p. 1271; Harcourt et al., Nature, 2017. 541(7637): p. 339-346; Davis, Nucleic Acids Res, 1995. 23(24): p. 5020-6; the contents of each of which are incorporated herein by reference in their entireties. Incorporating specific modNTPs, like N1mΨ may alter CSE or SGP structure and prevent effective RdRp recognition.

Described herein is the unexpected finding that several modified nucleotides at 100% substitution are compatible with saRNA and enhance its resulting in vitro and in vivo performance. A screen to identify modified modNTPs incorporated into a functional saRNA reporter system revealed two cytidine and one uridine modNTPs with activity greater than unmodified saRNA, while the vast majority of modNTPs, notably N1-methylpseudouridine (N1 mW), yielded minimal transfection. Modified saRNA resulted in a decreased type I interferon response in primary human peripheral blood mononuclear cells (PBMCs) and increased reporter expression in several cell lines. In a challenge study of SARS-CoV-2, the modified saRNA provided protection at significantly lower doses than modified mRNA and greater efficacy than unmodified saRNA.

Results

Described Herein is the Identification of Modified Nucleotides Capable of Maintaining saRNA Activity.

Figure 58A:
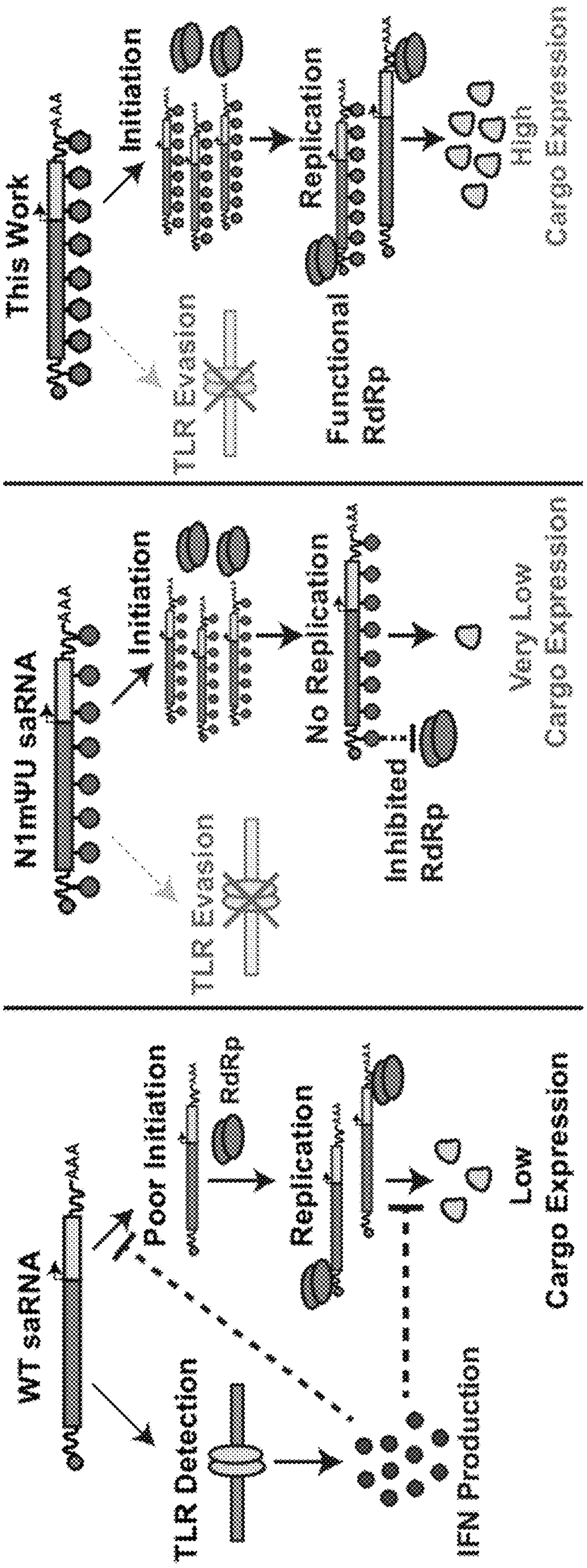
FIG. 58A-58I are a series of schematics and graphs showing the identification of modified nucleotides compatible with self-amplifying RNA and their in vitro bioactivity.
Figure 58B:
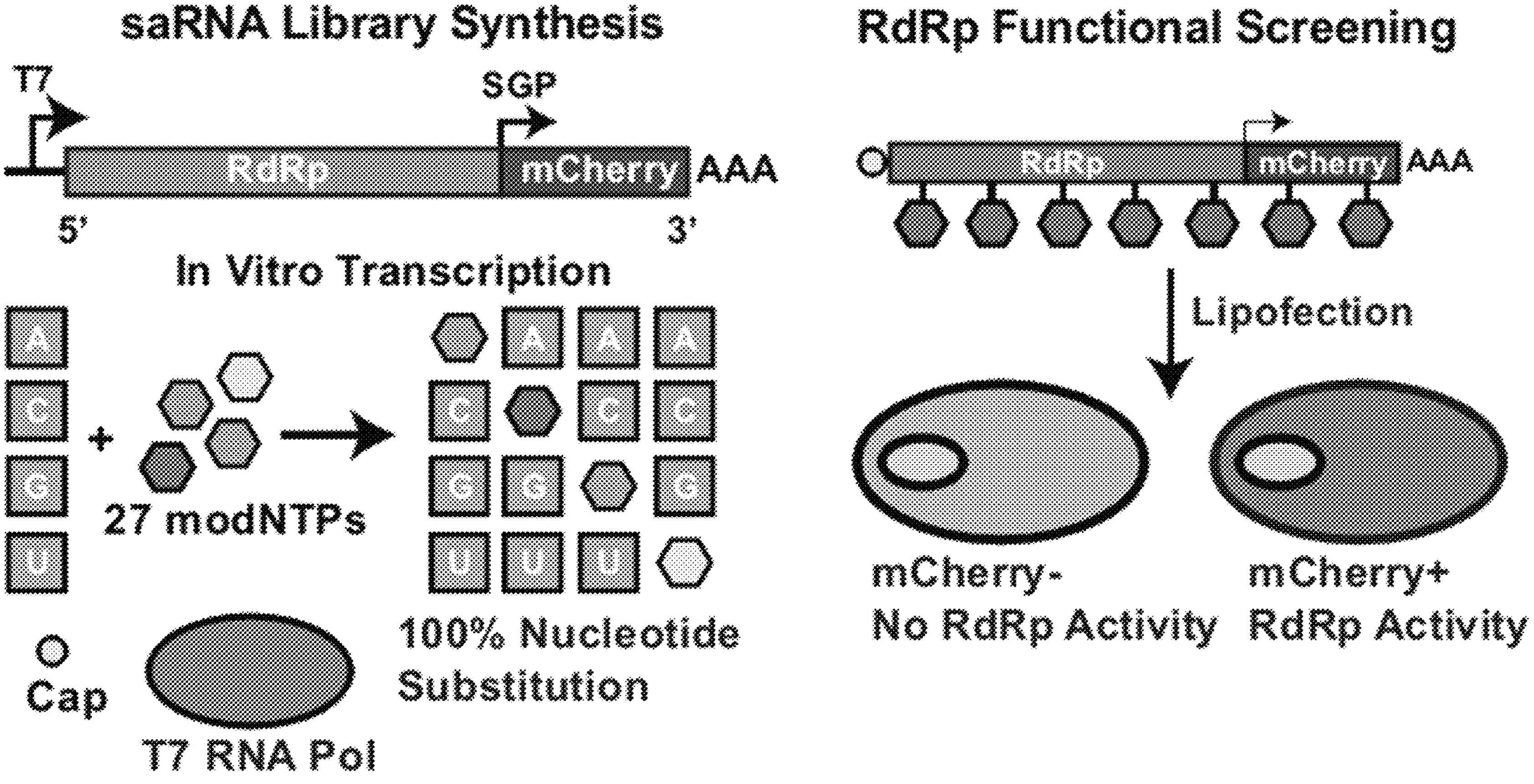
Figure 58C:
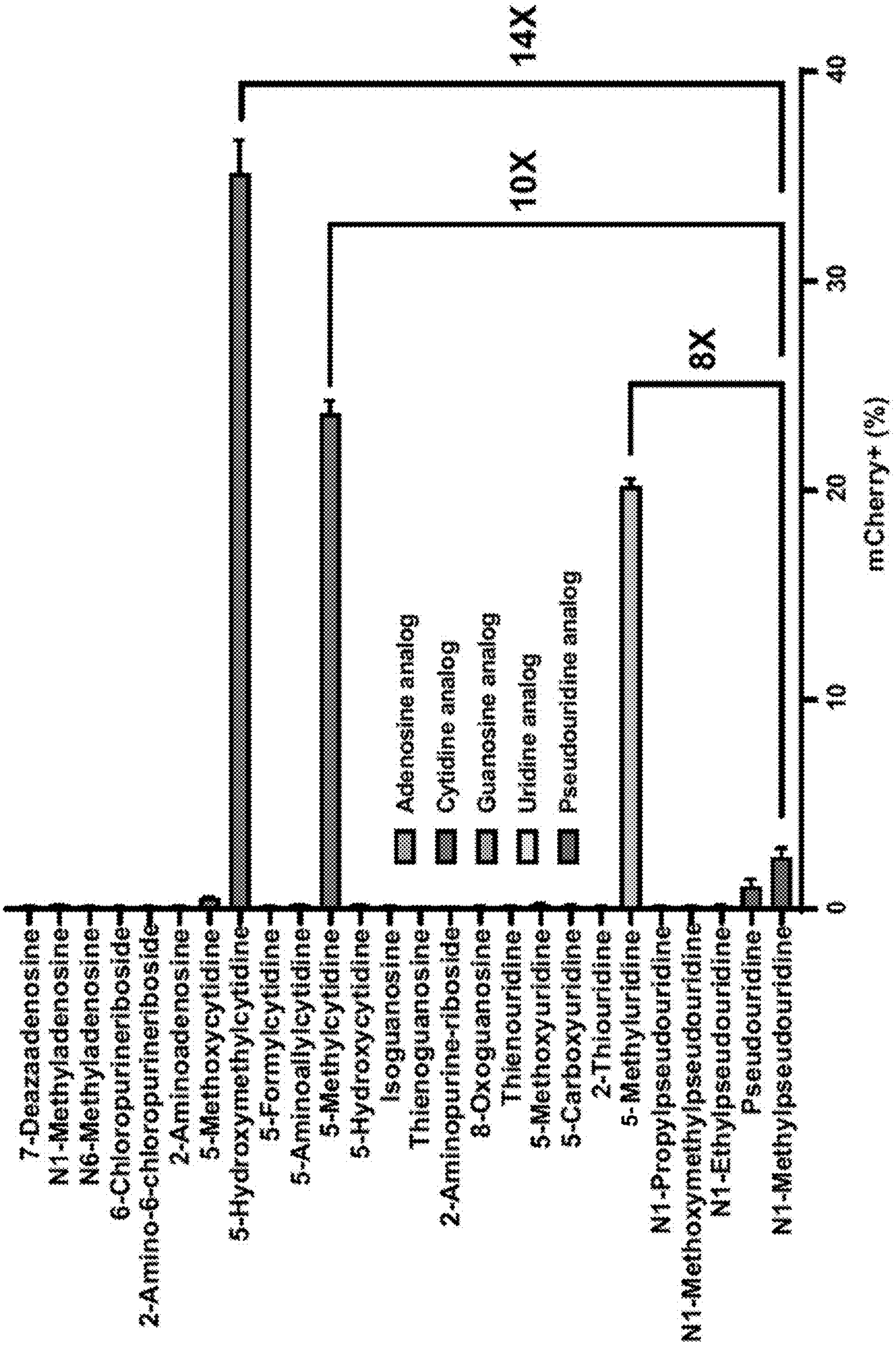
Figure 58D:
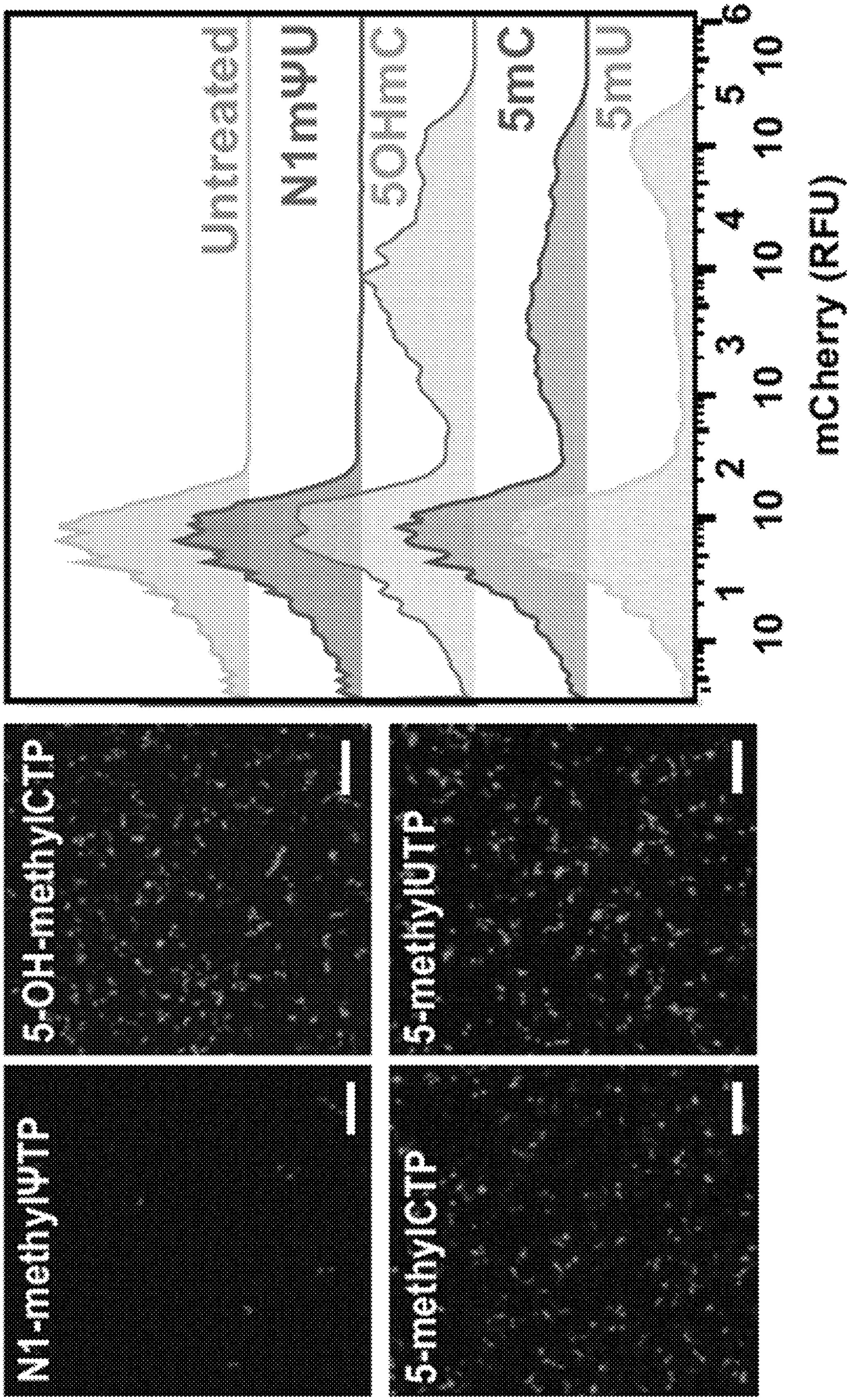
Figure 61A:
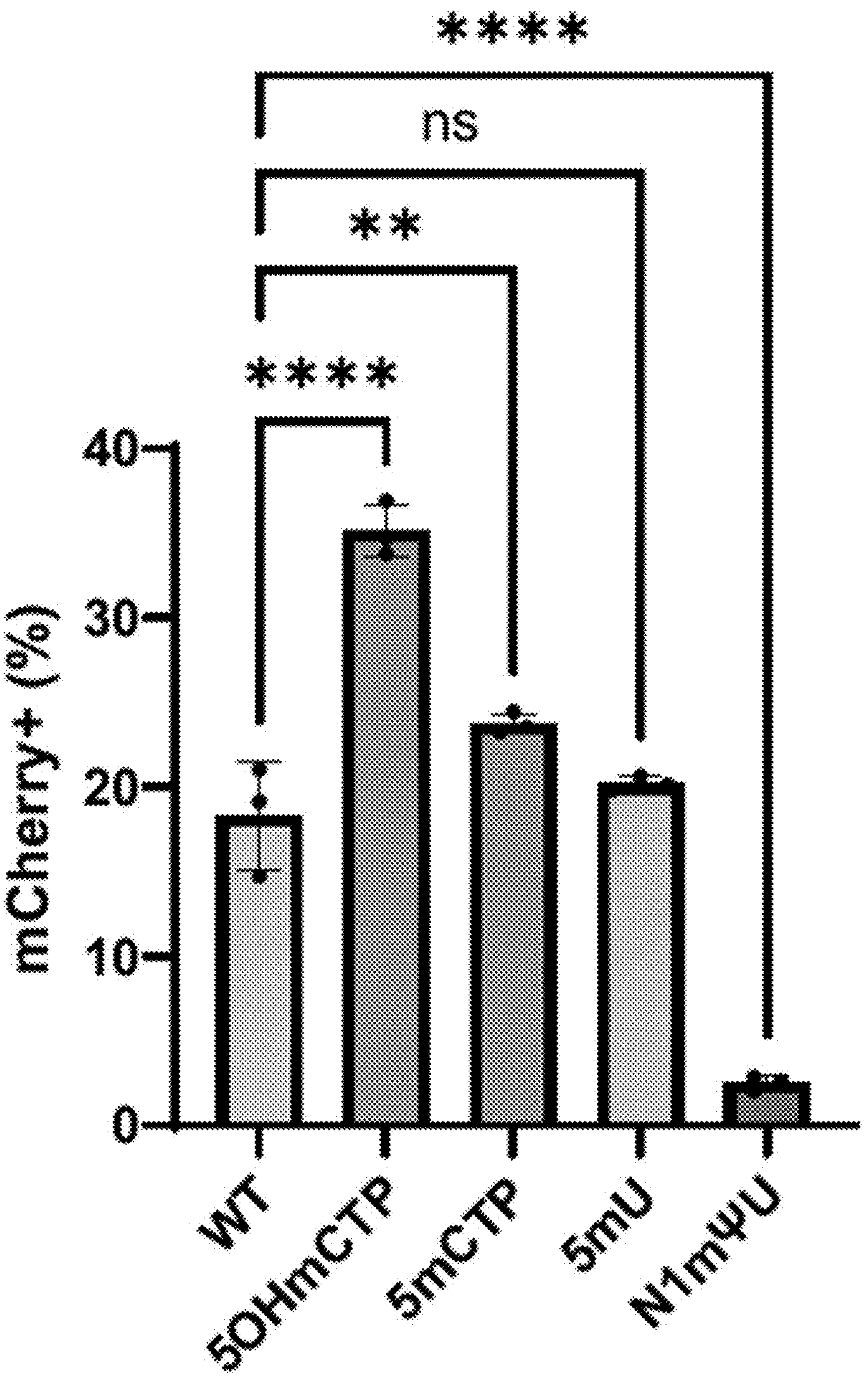
FIG. 61A-61D are a series of graphs, plots, and images showing testing of modified saRNAs.
Figure 61B:
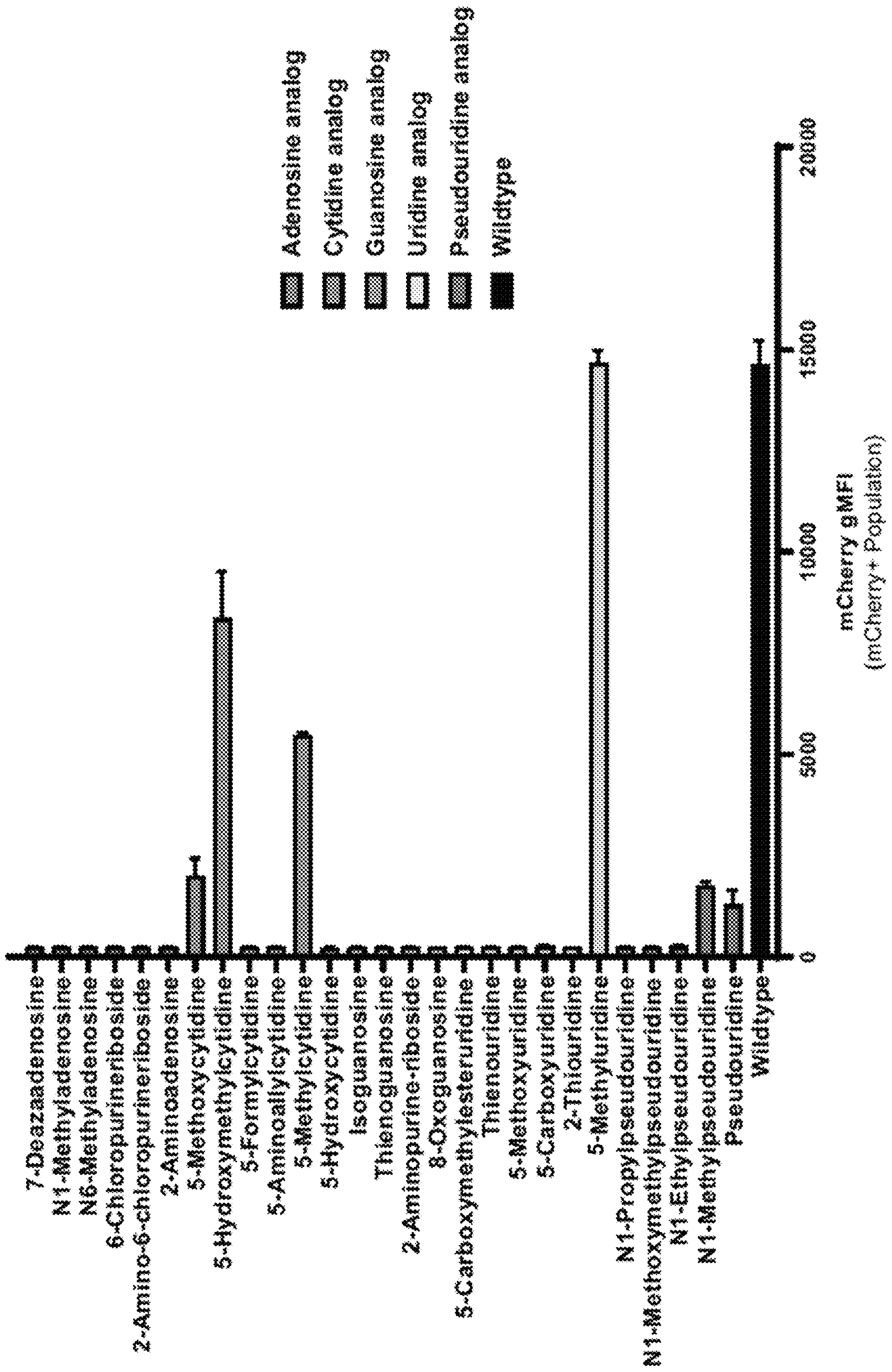
Figure 61C:
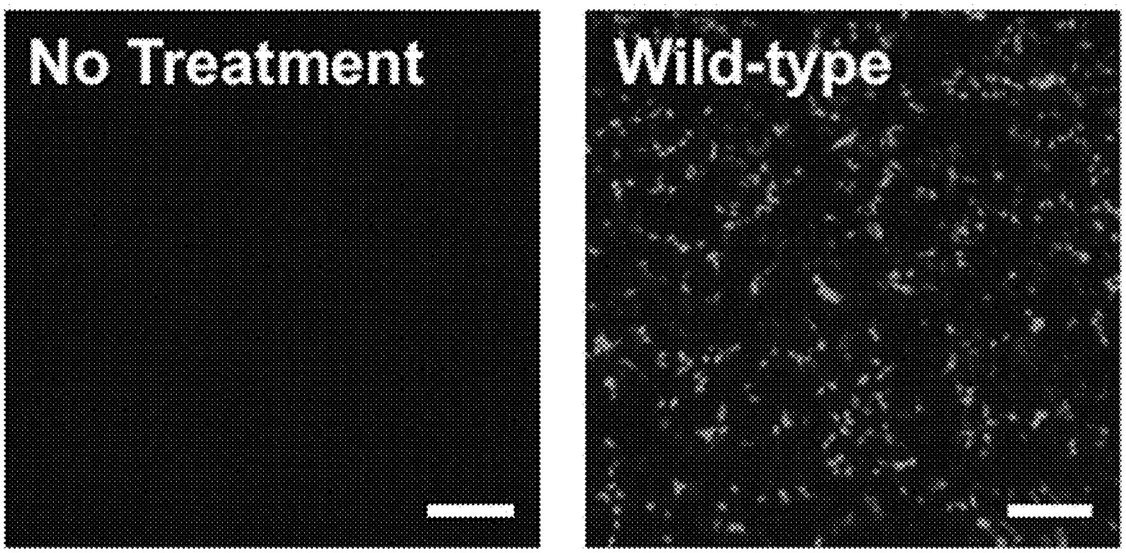
Figure 61D:
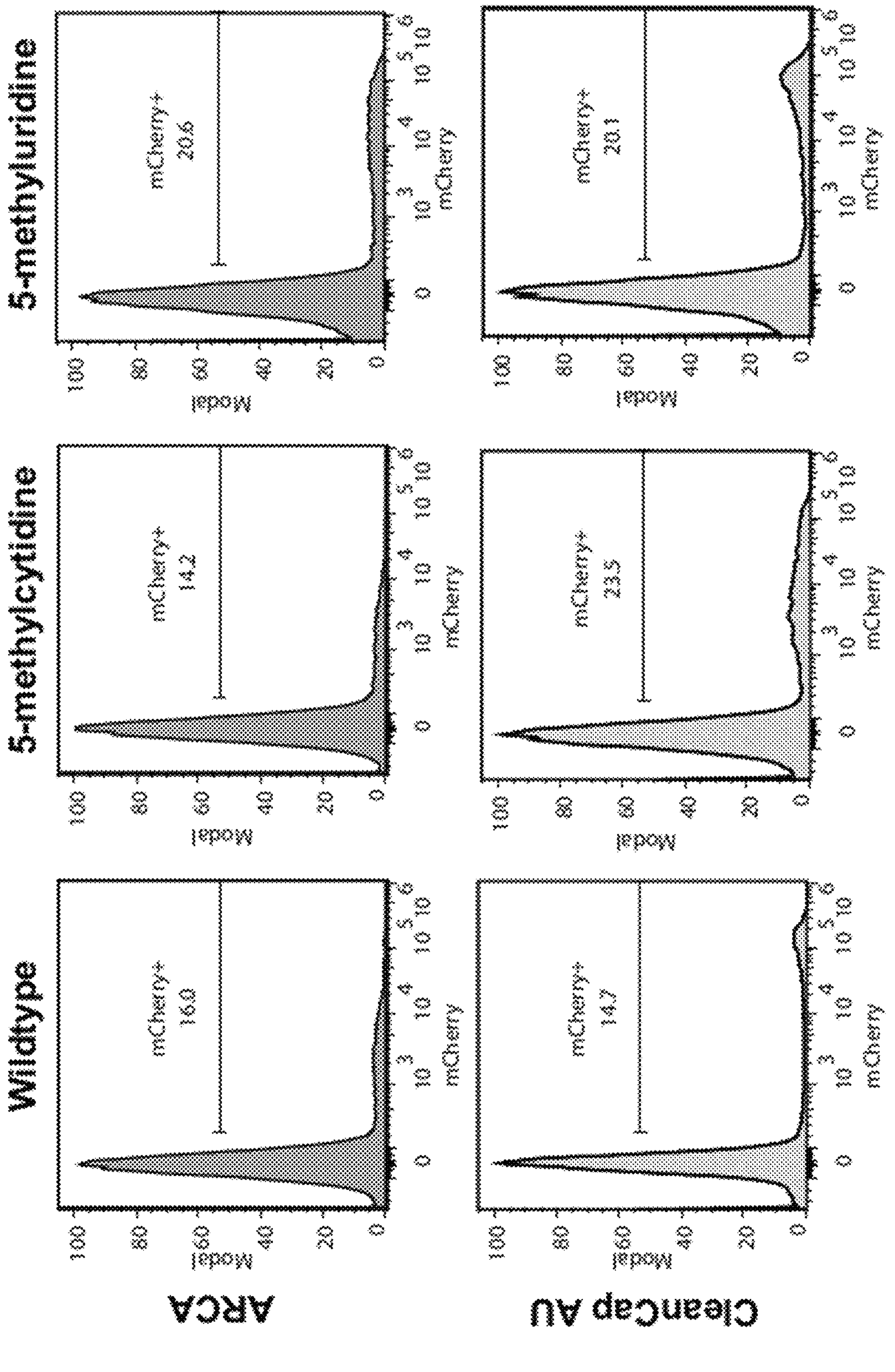

A library of saRNA constructs was synthesized through in vitro transcription (IVT), where all nucleotides were completely substituted with modified counterparts. To assess their functionality, these constructs encoded an mCherry reporter and were transfected into HEK293 cells by cationic lipofection (see e.g., FIG. 58B). Three modNTPs were identified that imparted significantly elevated transfection efficiencies compared to the N1-methylpseudouridine (N1 mW) modified construct that resulted in minimal transfection. Flow cytometry analysis (see e.g., FIG. 58C, 58D) and live cell microscopy (see e.g., FIG. 58D) revealed that constructs with complete substitution of 5-hydroxymethylcytidine (5OHmC), 5-methylcytidine (5mC), or 5-methyluridine (5mU) exhibited transfection efficiencies 14-fold, 10-fold, and 8-fold higher, respectively, in comparison to the N1mΨmodified construct. The transfection efficiencies for the identified modNTPs were equal to or greater than the wildtype unmodified control (see e.g., FIG. 61A). Notably, in the HEK293 cells transfected by lipofection for high-throughput screening, the mean cargo expression intensity was reduced compared to the wild-type construct for 5OHmC and 5mC (see e.g., FIG. 61B). Substitution with the identified modNTPs resulted in functional constructs when synthesized with Cap-0 structures (ARCA) or Cap-1 structures (CLEANCAP AU). However, a significant increase in expression intensity was observed when constructs contained a Cap-1 structure (see e.g., FIG. 61D).

Enhanced Expression Resulting from saRNA Modification was Observed Across Diverse Cell Types In Vitro.

Figure 58F:
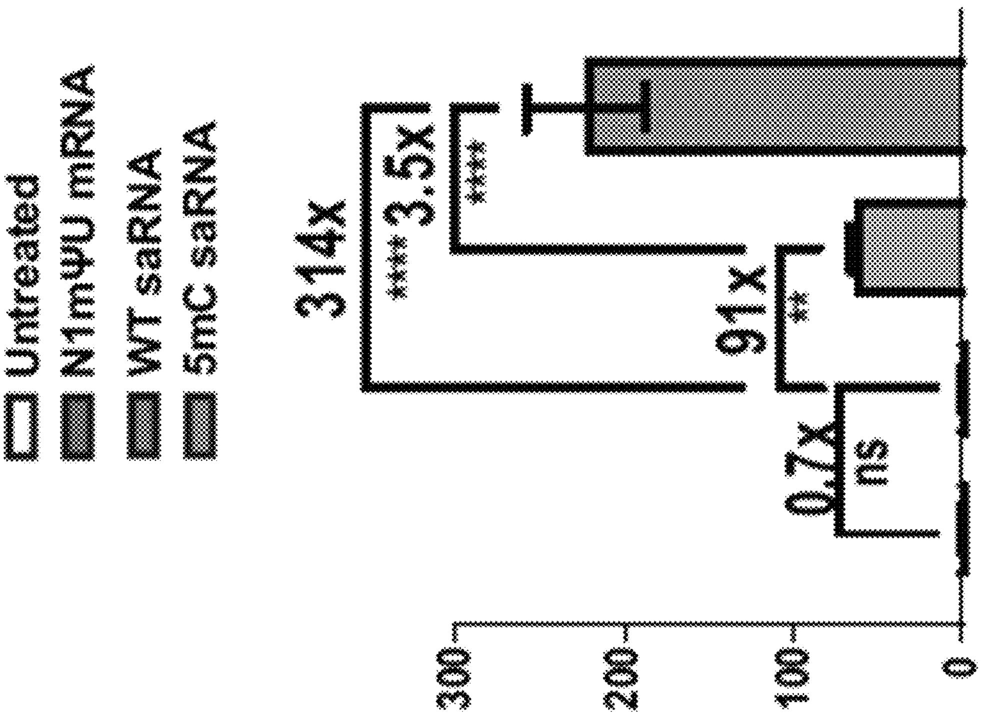
Figure 58E:
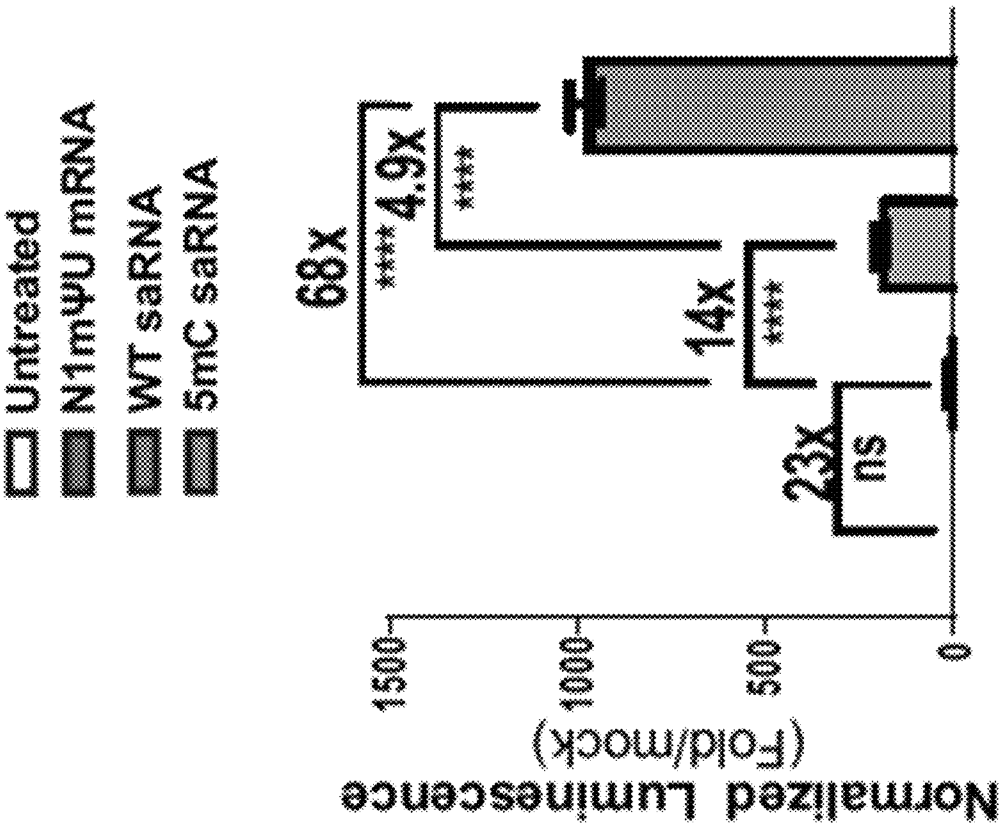
Figure 58H:
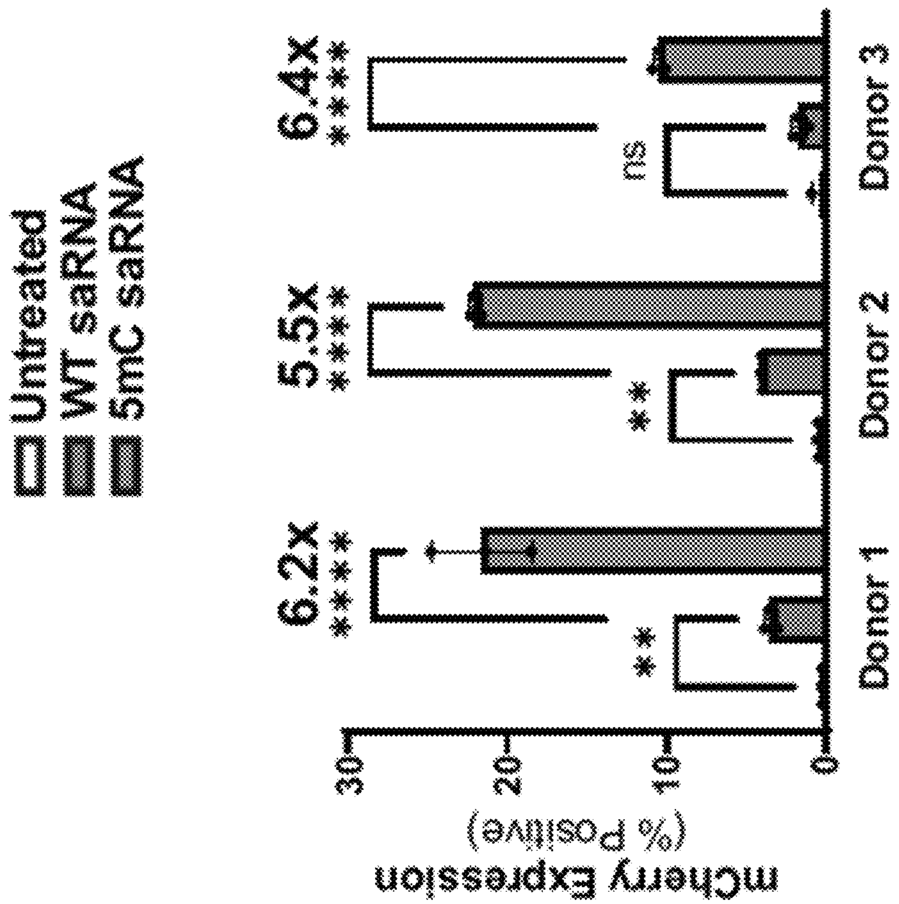
Figure 58G:
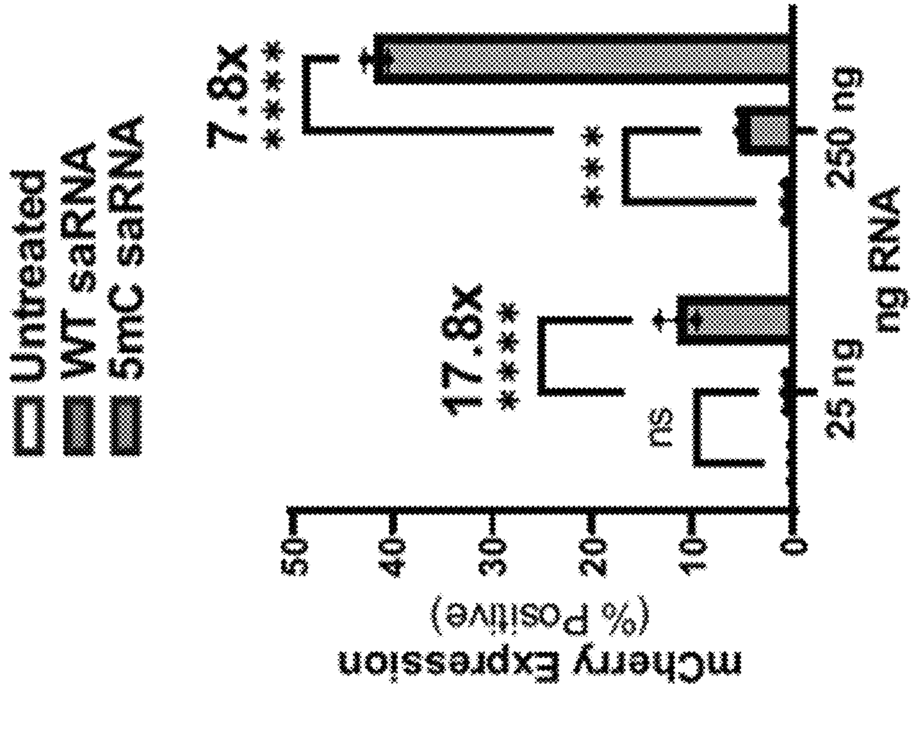
Figure 58I:
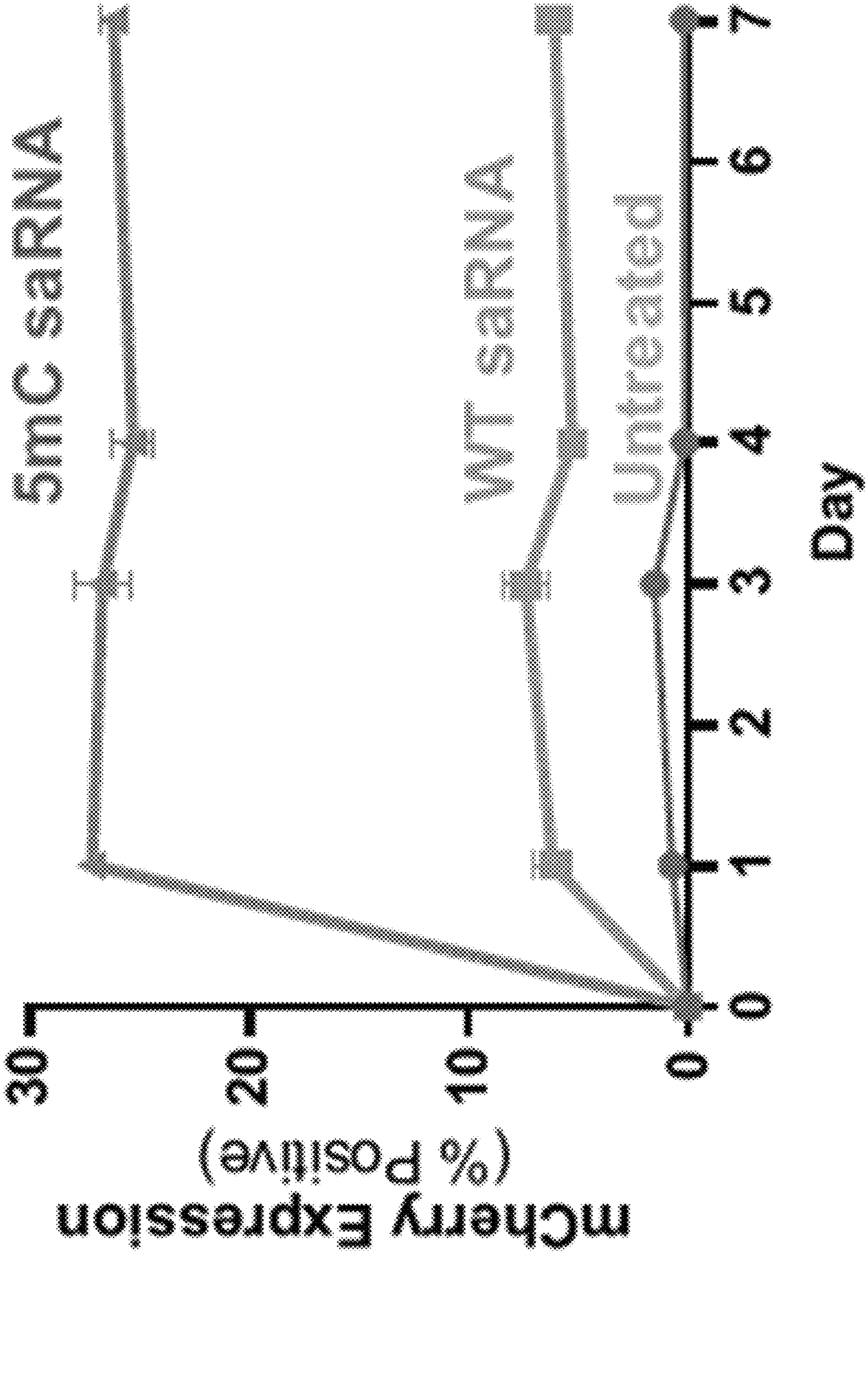
Figure 62A:
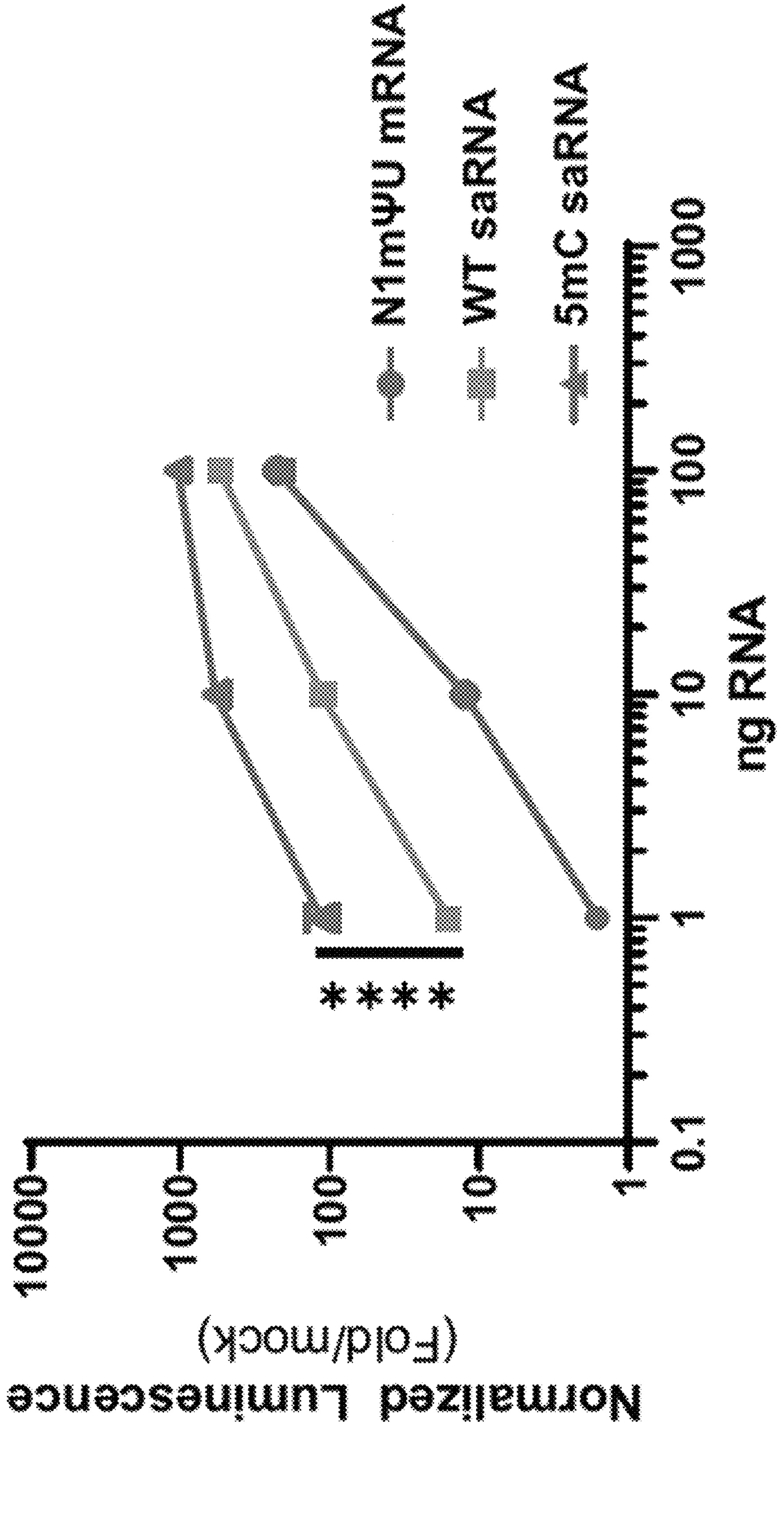
FIG. 62A-62E are a series of graphs and images showing testing of modified saRNAs.
Figure 62B:
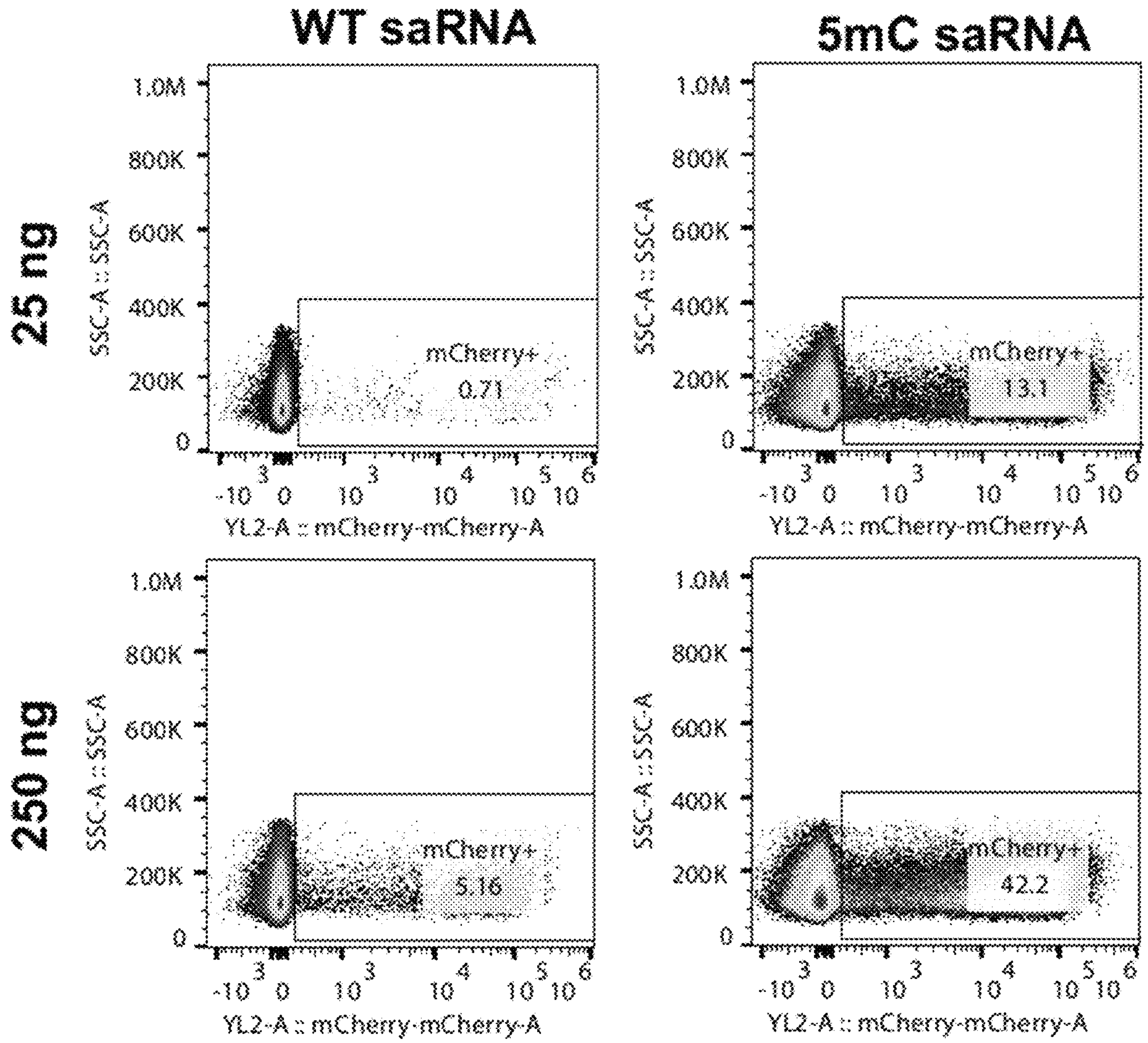
Figure 62C:
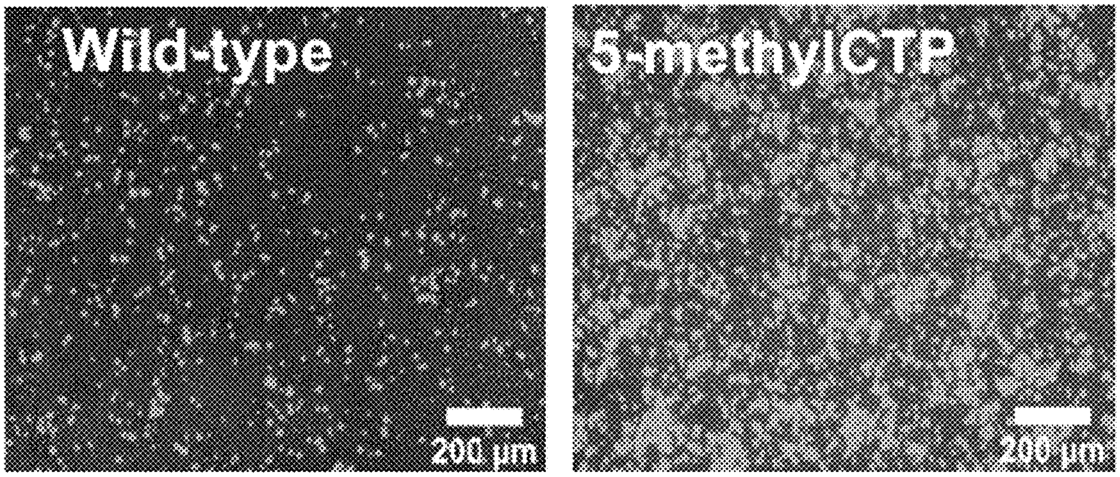
Figure 62D:
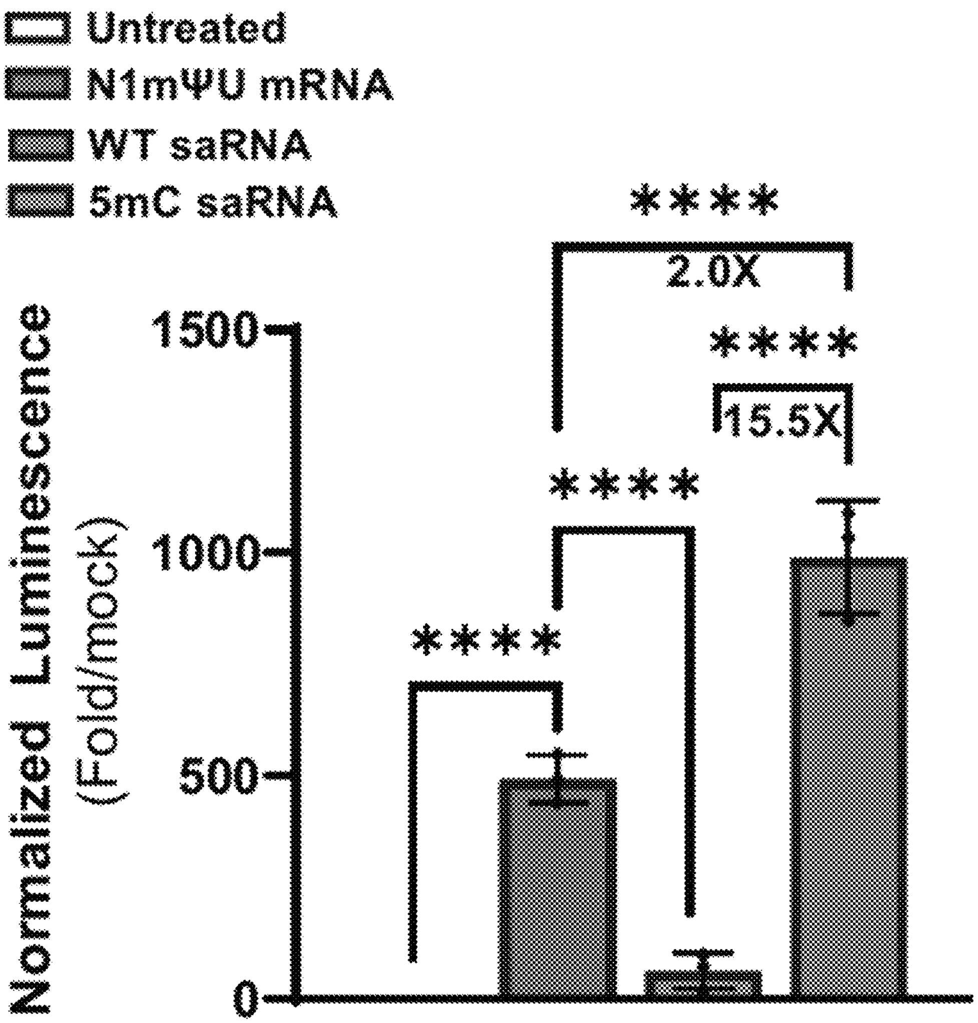
Figure 62E:
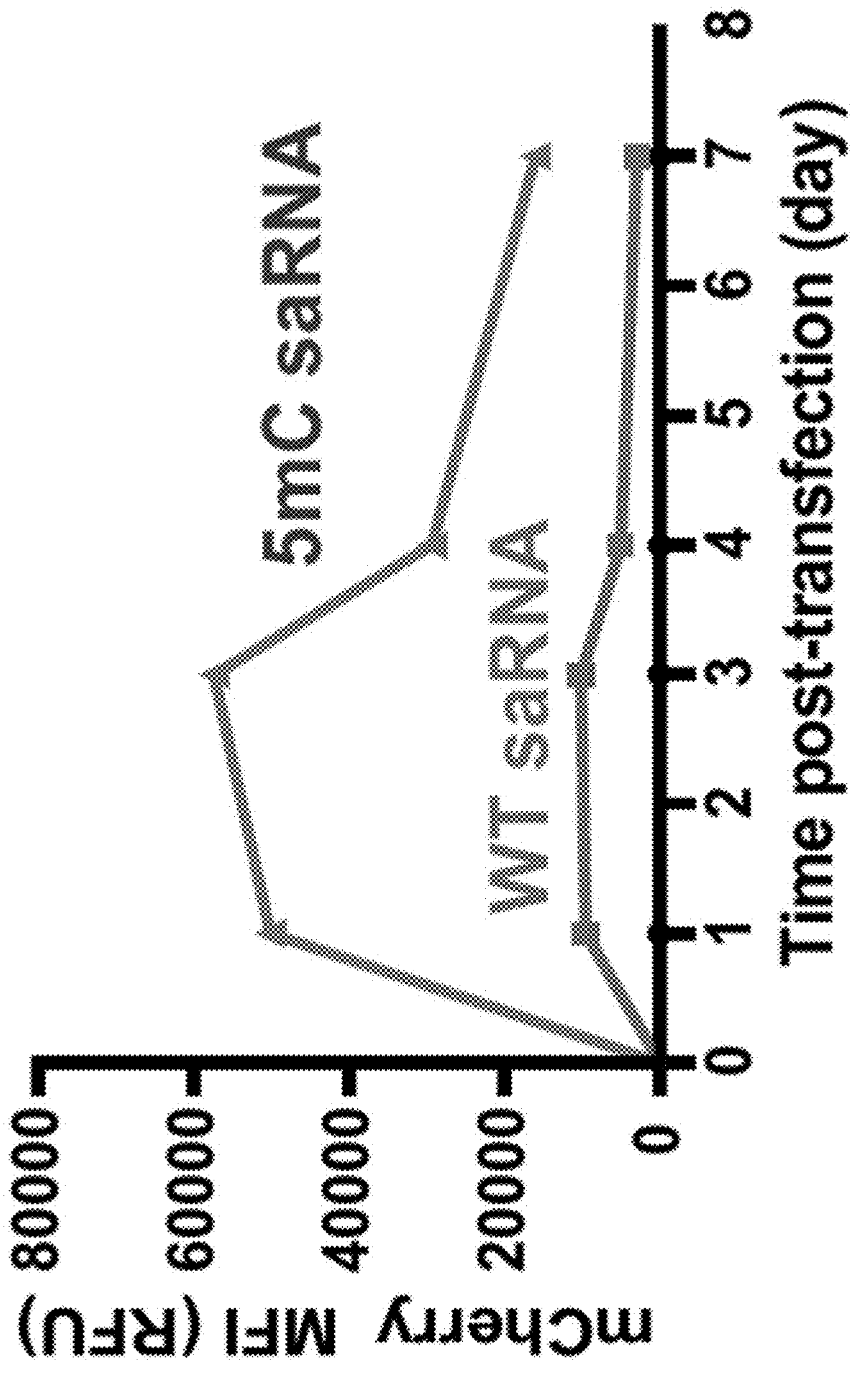
Figure 63A:
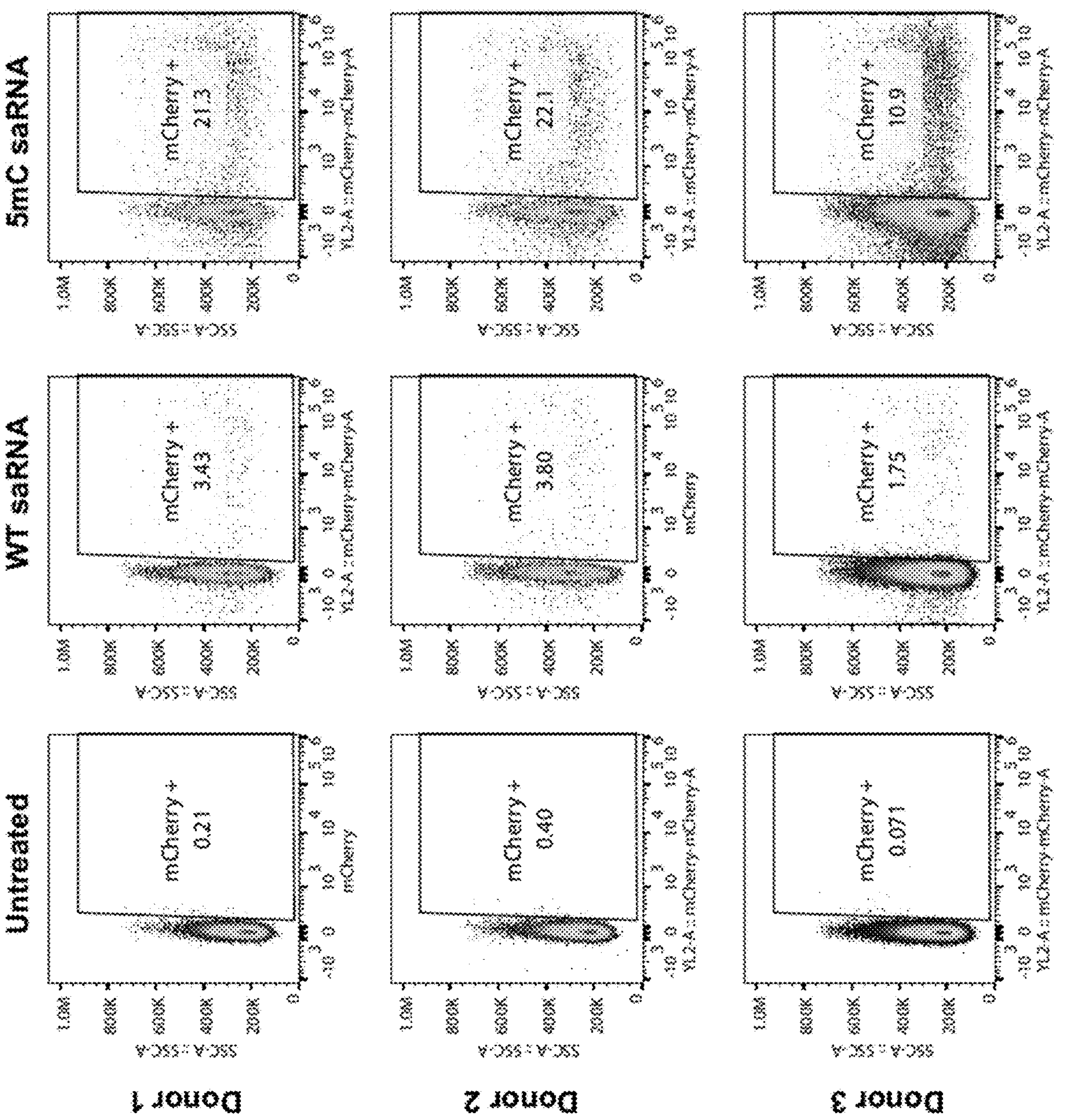
FIG. 63A-63B are a series of plots and images showing testing of modified saRNAs.
Figure 63B:
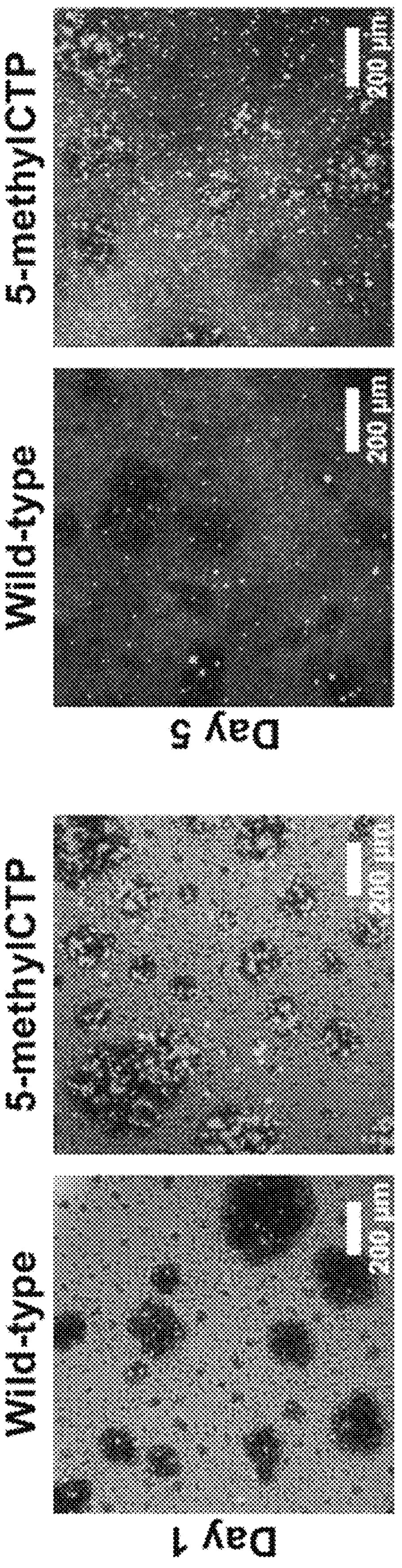

Following the demonstrated functionality of fully substituted saRNA, further investigations were conducted of the activity of the saRNA in vitro. To assess the overall protein expression resulting from transfection with WT saRNA, 5mC saRNA, and N1mΨmRNA, a luciferase-based reporter construct was employed. These constructs were loaded into lipid nanoparticles (LNPs). HEK293 and C2C12 cells were transfected with LNPs containing 10 ng of RNA. Notably, the 5mC modified saRNA exhibited a remarkable 4.9-fold increase in expression over WT saRNA, corresponding to a substantial 68-fold increase in expression over the N1mΨmRNA in HEK293 cells (see e.g., FIG. 58E). In C2C12 cells, a 3.5-fold increase in expression was observed for the 5mC modified saRNA, resulting in a 314-fold increase compared to the N1mΨmRNA, which resulted in limited expression at the low dosage administered (see e.g., FIG. 58F). A dose response experiment in HEK cells showed significantly improved expression at doses as low as 1 ng (see e.g., FIG. 62A). Next, transfection experiments were conducted with the modified saRNA in Jurkat T cells, a notoriously hard to transfect cell line by mRNA containing LNPs. To assess the expression profile at the individual cell level, an mCherry reporter was employed combined with flow cytometry analysis. A significant 17.8-fold improvement in transfection efficiency was observed at the lower dose of 25 ng, and a 7.8-fold enhancement was observed at the higher dose of 250 ng (see e.g., FIG. 58G, FIG. 62B, FIG. 62C). A similar expression profile was observed when the luciferase constructs were transfected at 250 ng (see e.g., FIG. 62D). In a time course study, the expression was durable over 7 days from the modified saRNA in Jurkat cells (see e.g., FIG. 58I, FIG. 62E). To assay the impact of fully substituted saRNA in primary cells, CD3+ T cells derived from three different human donors were treated with saRNA loaded-LNPs. All donors exhibited a 5-fold to 6-fold increase in transfection efficiency and significant expression of the mCherry reporter gene. This increase corresponded to approximately 1%-3% transfection efficiency for the wild-type (WT) saRNA and approximately 10-20% for the 5mC-modified saRNA (see e.g., FIG. 58H, FIG. 63A, FIG. 63B). The expression of the mCherry reporter was detected for at least 5 days (see e.g., FIG. 63B).

Reduced Interferon Response from Modified saRNA in Human PBMCs was Observed.

Figure 59A:
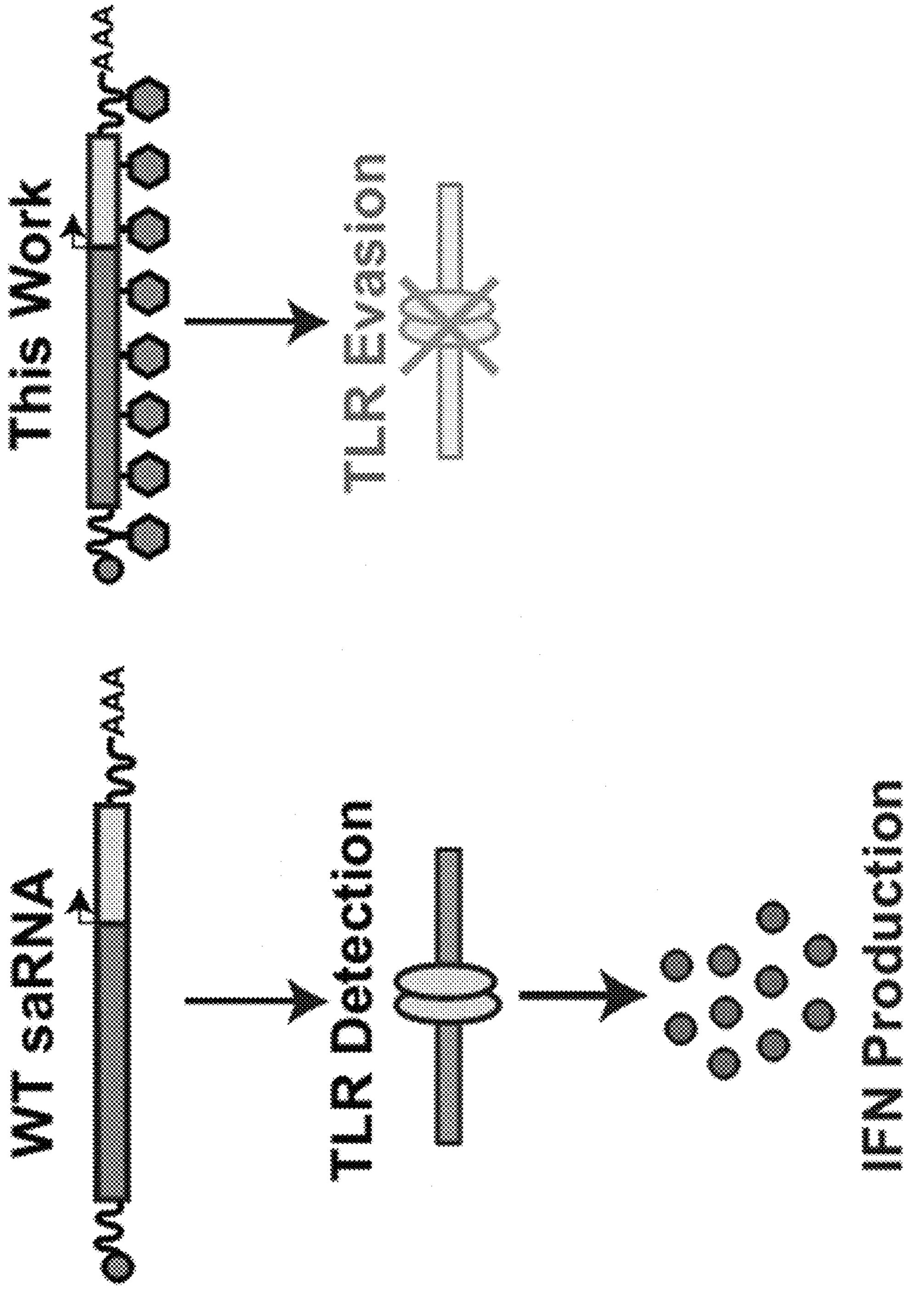
FIG. 59A-59G are a series of schematics and graphs showing the evaluation of immunogenicity of modified saRNA in human PBMCs.
Figure 59B:
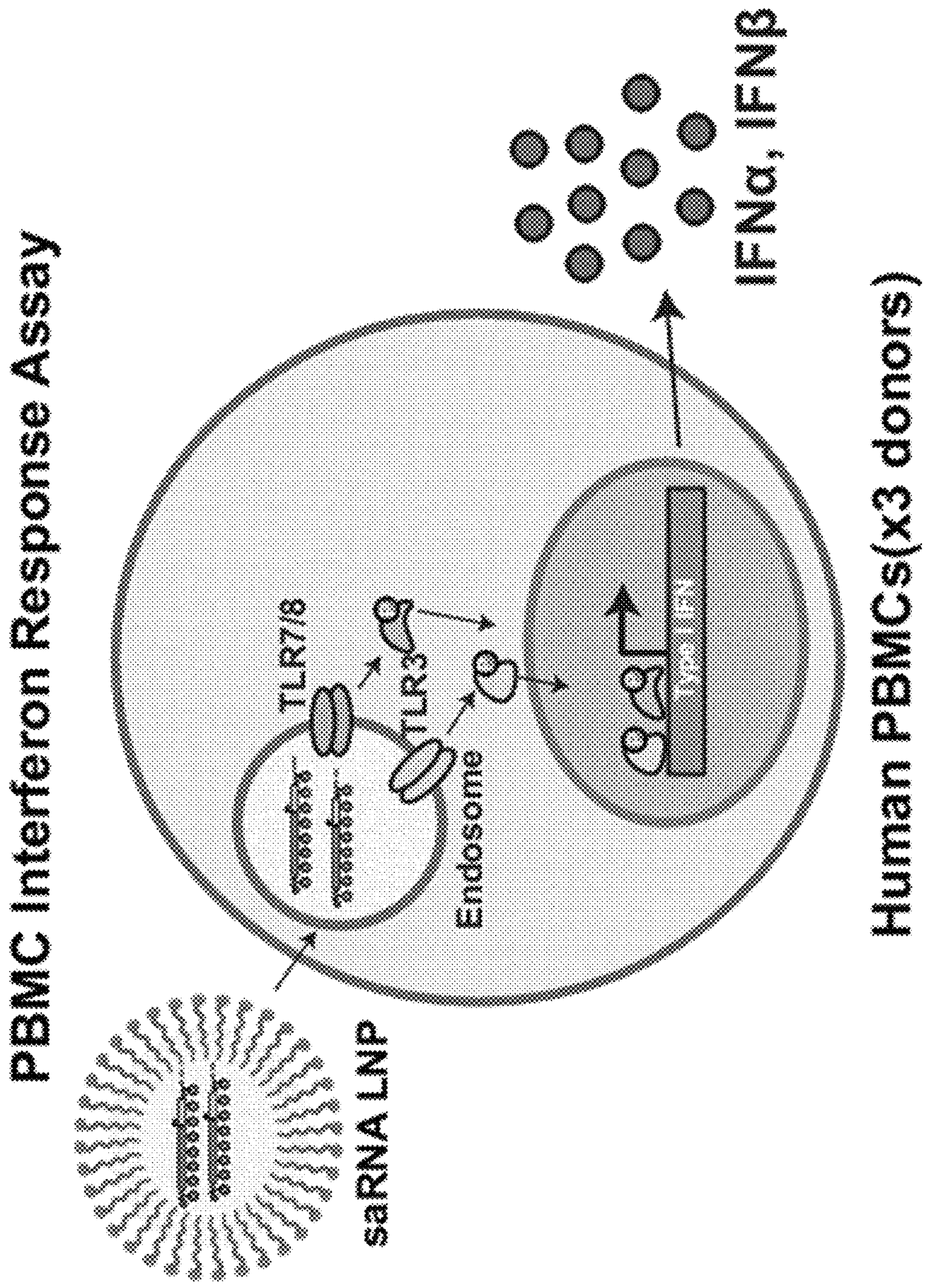
Figure 59D:
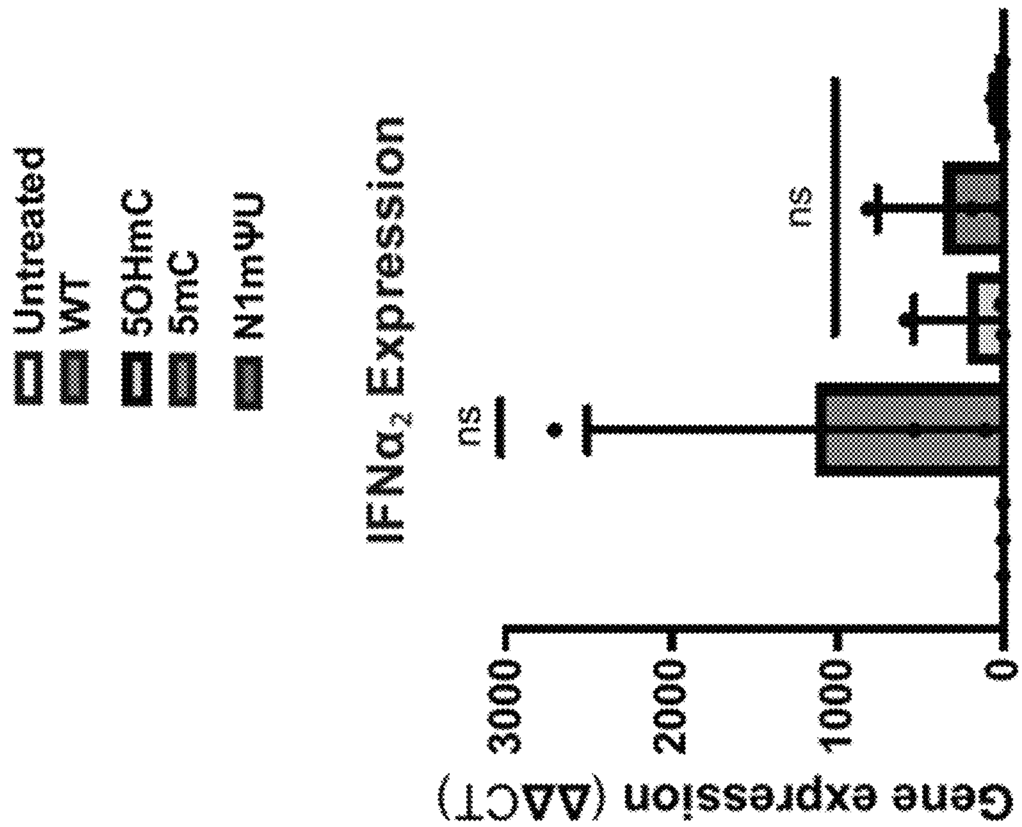
Figure 59C:
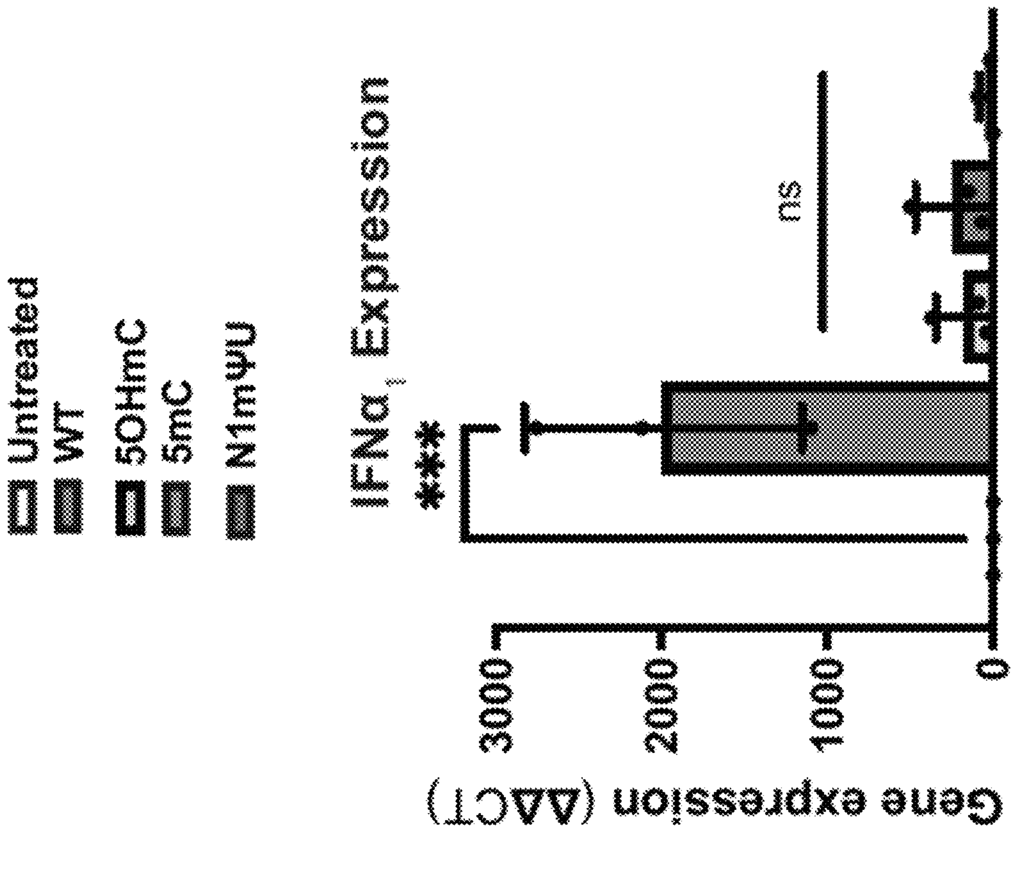
Figure 59F:
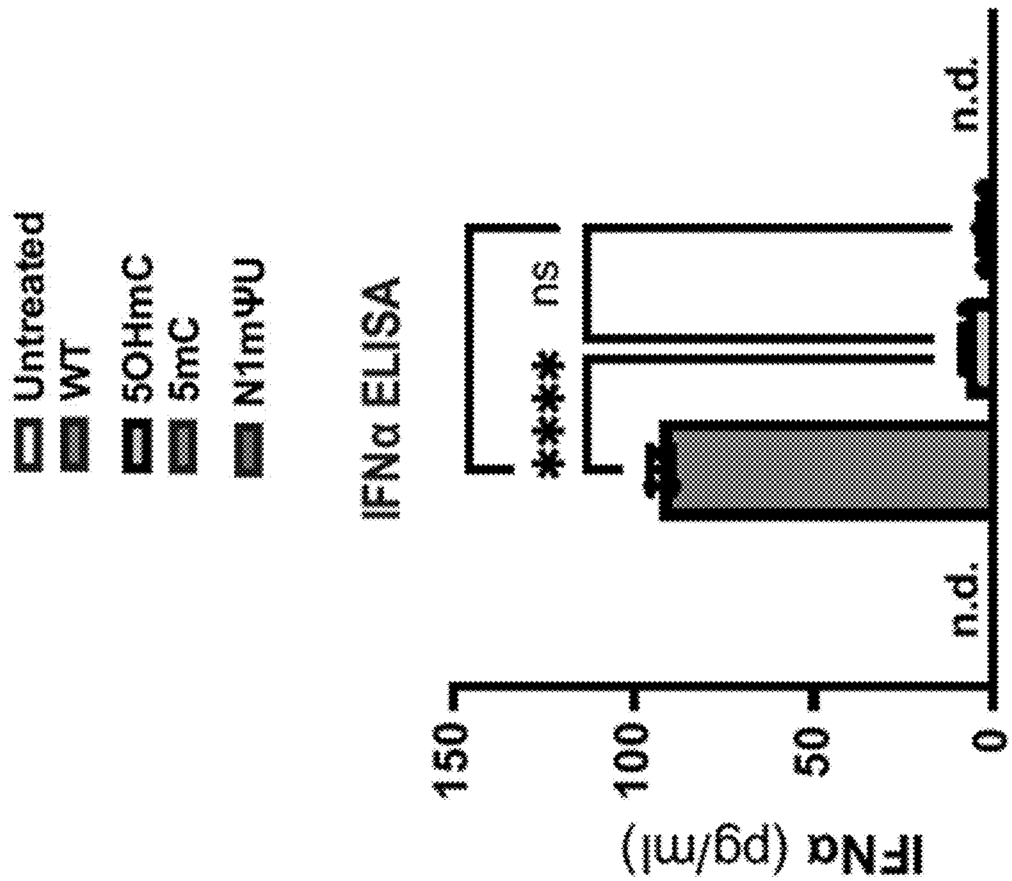
Figure 59E:
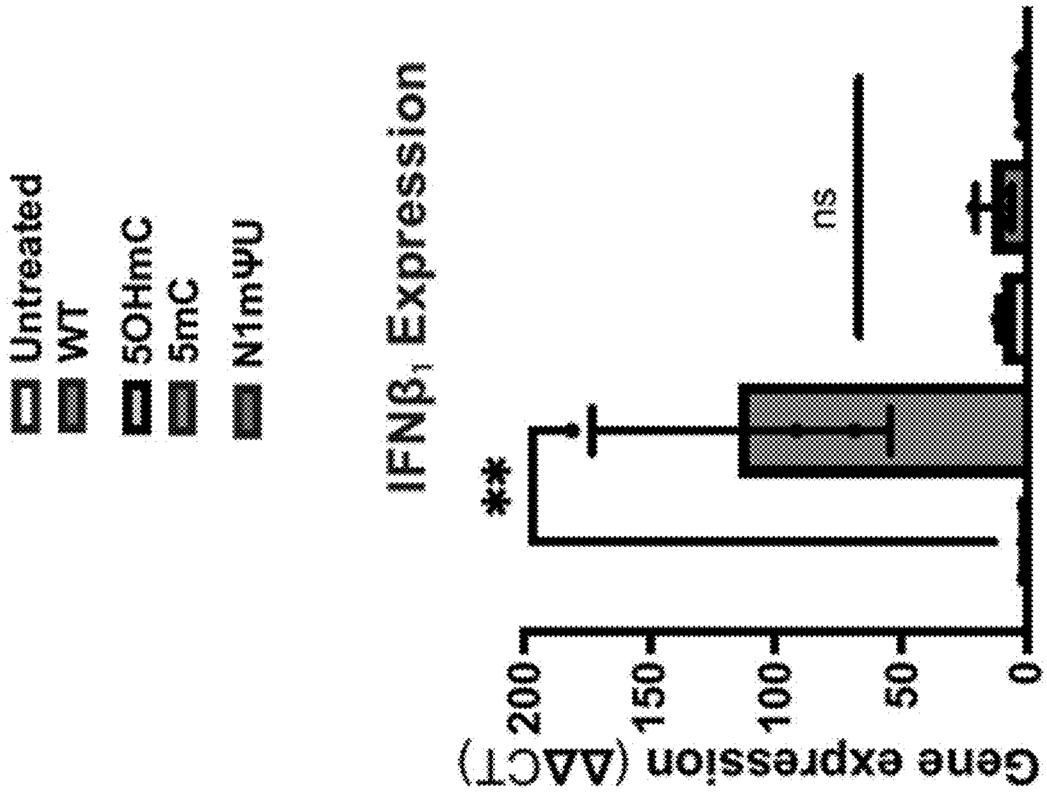
Figure 59G:
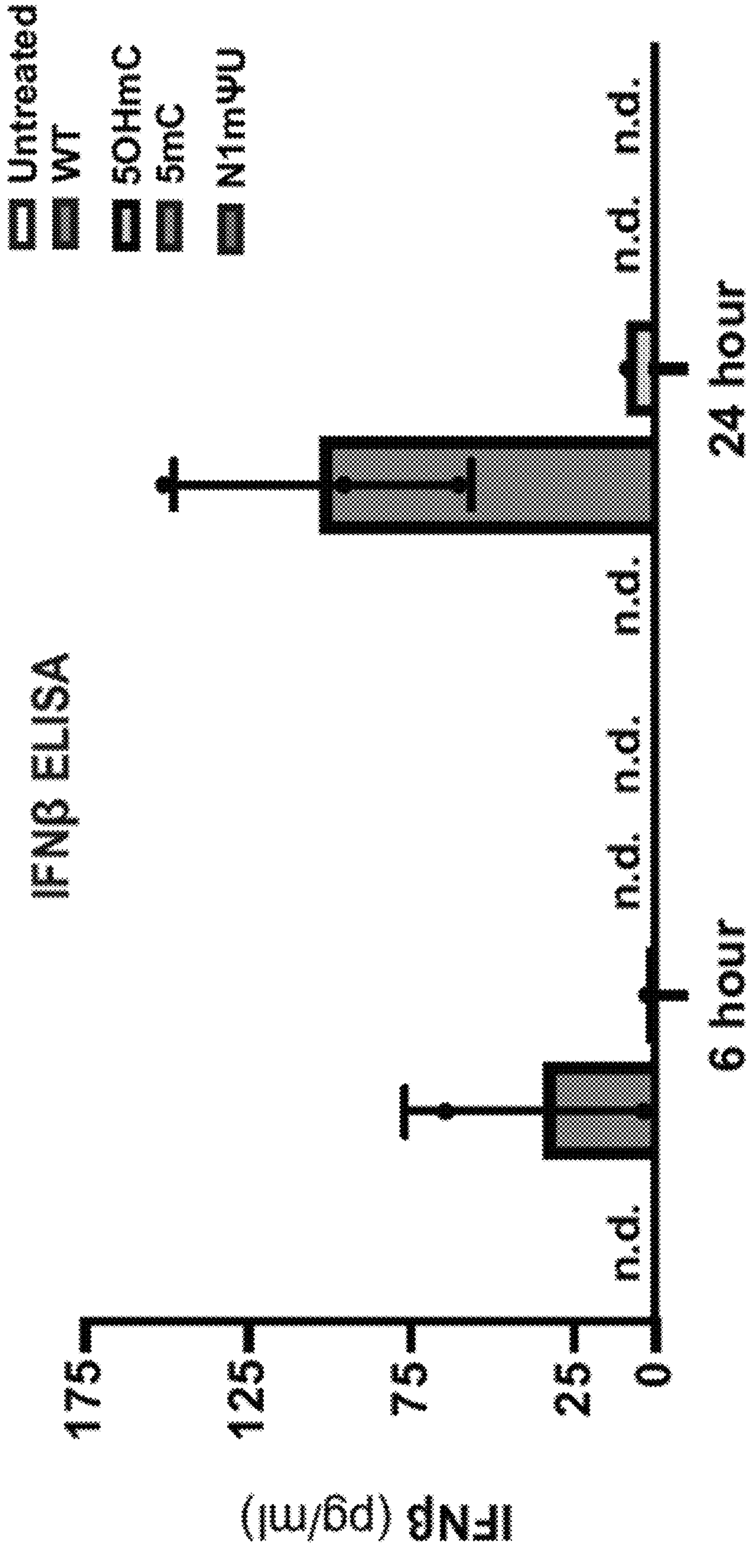

To characterize the interferon response caused by wild-type or modified saRNA, human peripheral blood mononuclear cells (PBMCs) from three distinct donors were cultured with lipid nanoparticles (LNPs) loaded with saRNA (see e.g., FIG. 59B). Gene expression analysis revealed that saRNA treatment induced a significant increase in the expression of early interferon-related genes, namely IFN-α1, IFN-α2, and IFN-β1, after 6 hours (see e.g., FIG. 59C-59E). However, when 5OHmC or 5mC are incorporated, there was a large reduction in the expression of these early IFN genes. Specifically, IFN-α1 and IFN-β1 exhibited a reduction of more than 8.5-fold, while IFN-α2 showed a reduction of over 3-fold. The saRNA containing N1mΨ afforded lower intensity and efficiency in expressing the reporter cargo (see e.g., FIG. 58C). The analysis of IFN-α subtypes in media from a single donor (see e.g., FIG. 59F) was consistent with the gene expression analysis. Additionally, a longitudinal analysis of human IFN-β in media indicated that modNTP saRNA effectively suppressed IFN-β expression. In all donors, no detectable expression of IFN-β was observed after 5mC and N1mΨ saRNA treatment, and only one donor exhibited detectable levels of IFN-β after 5OHmC saRNA treatment (see e.g., FIG. 59G).

Described Herein is the Development and Validation of a Low-Dose Modified saRNA SARS-CoV-2 Vaccine.

Figure 60A:
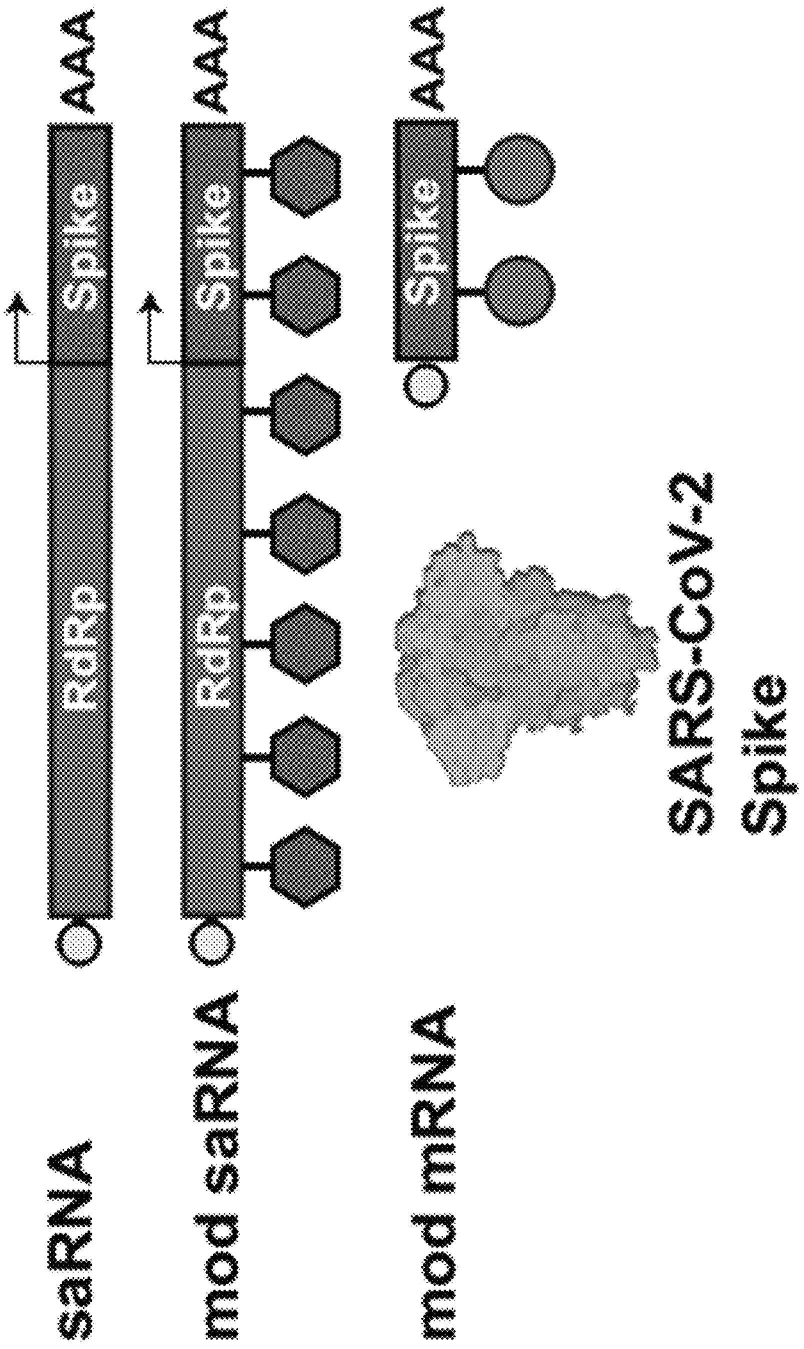
FIG. 60A-60H are a series of schematics and graphs showing the development and characterization of a fully modified saRNA vaccine against SARS-CoV-2.
Figure 60B:
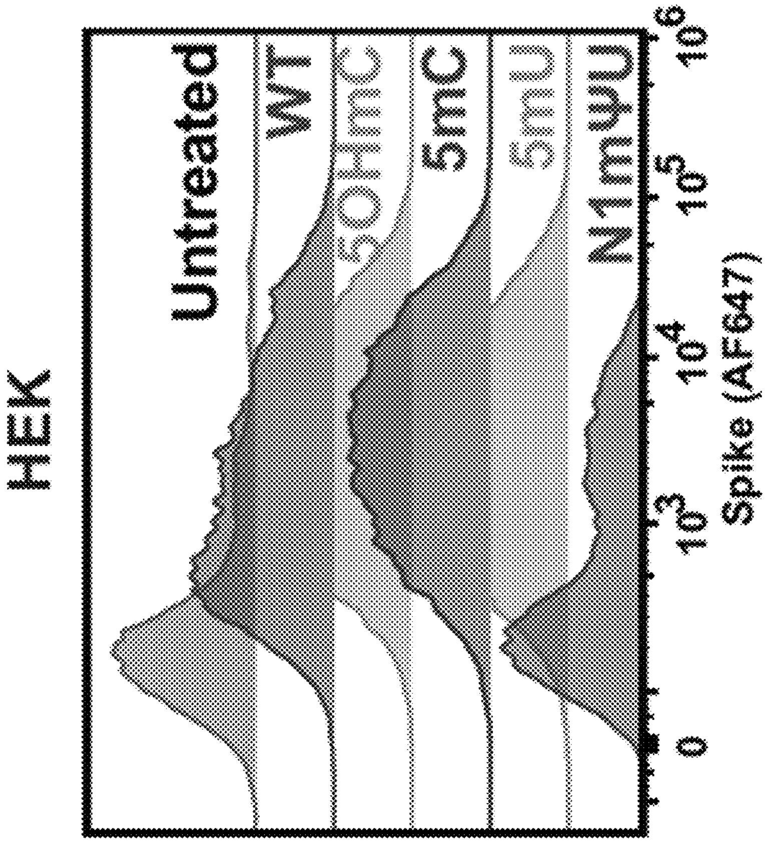
Figure 60C:
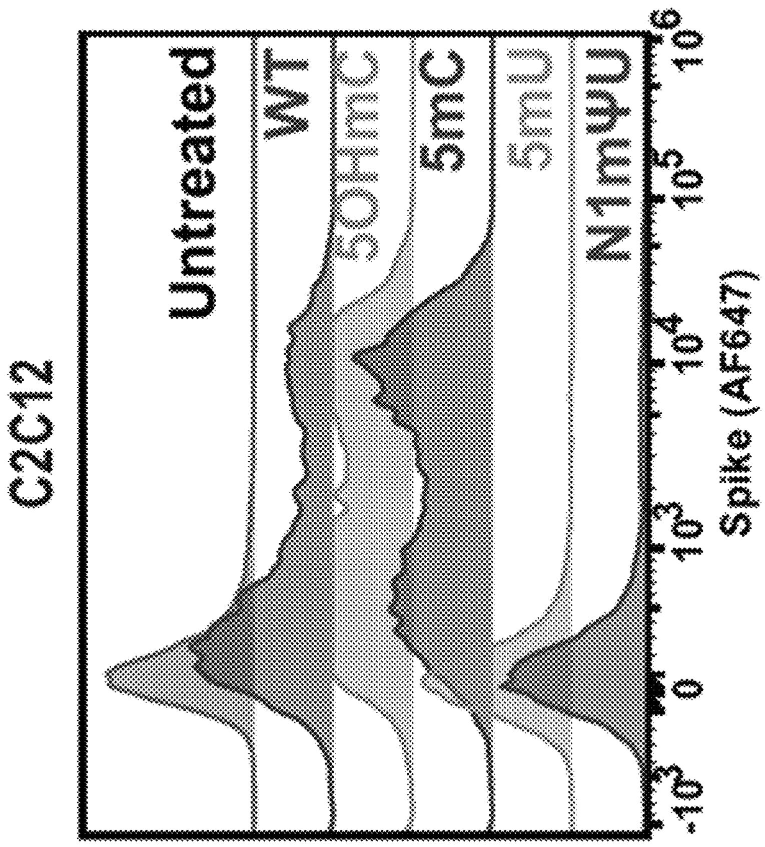
Figure 60D:
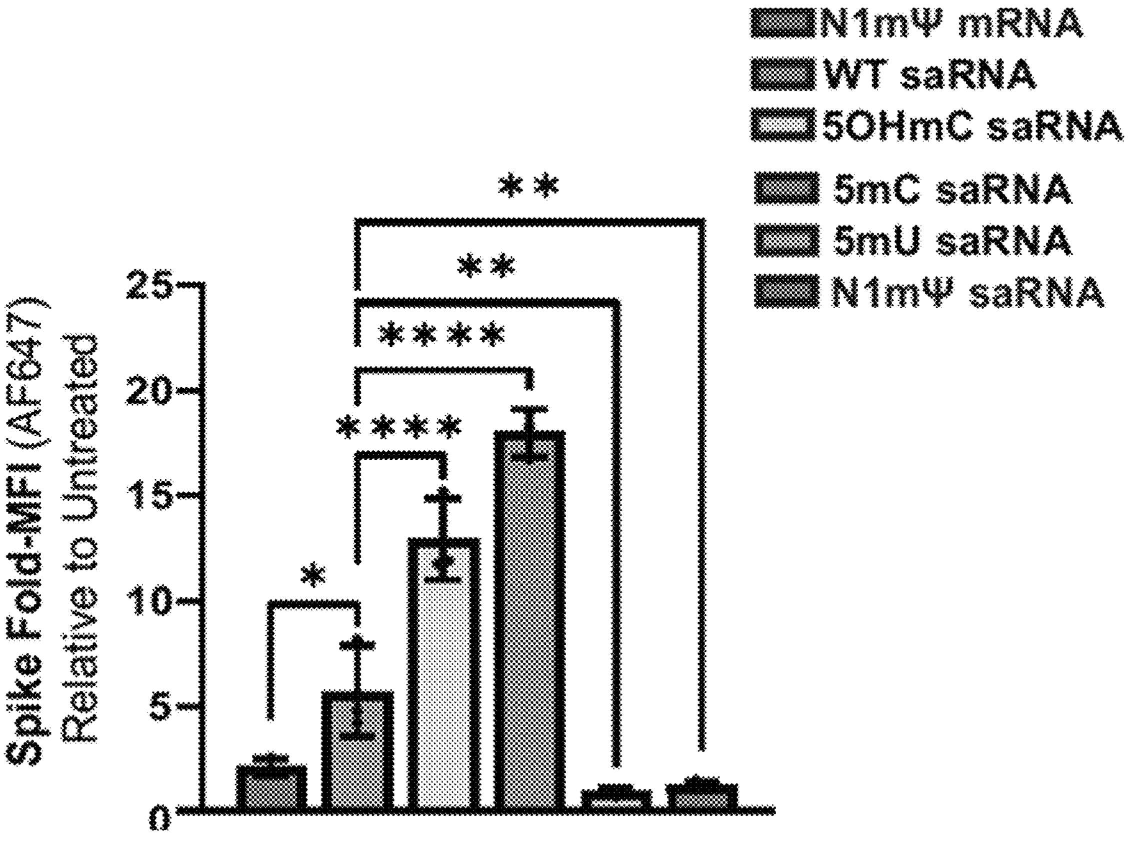
Figure 64A:
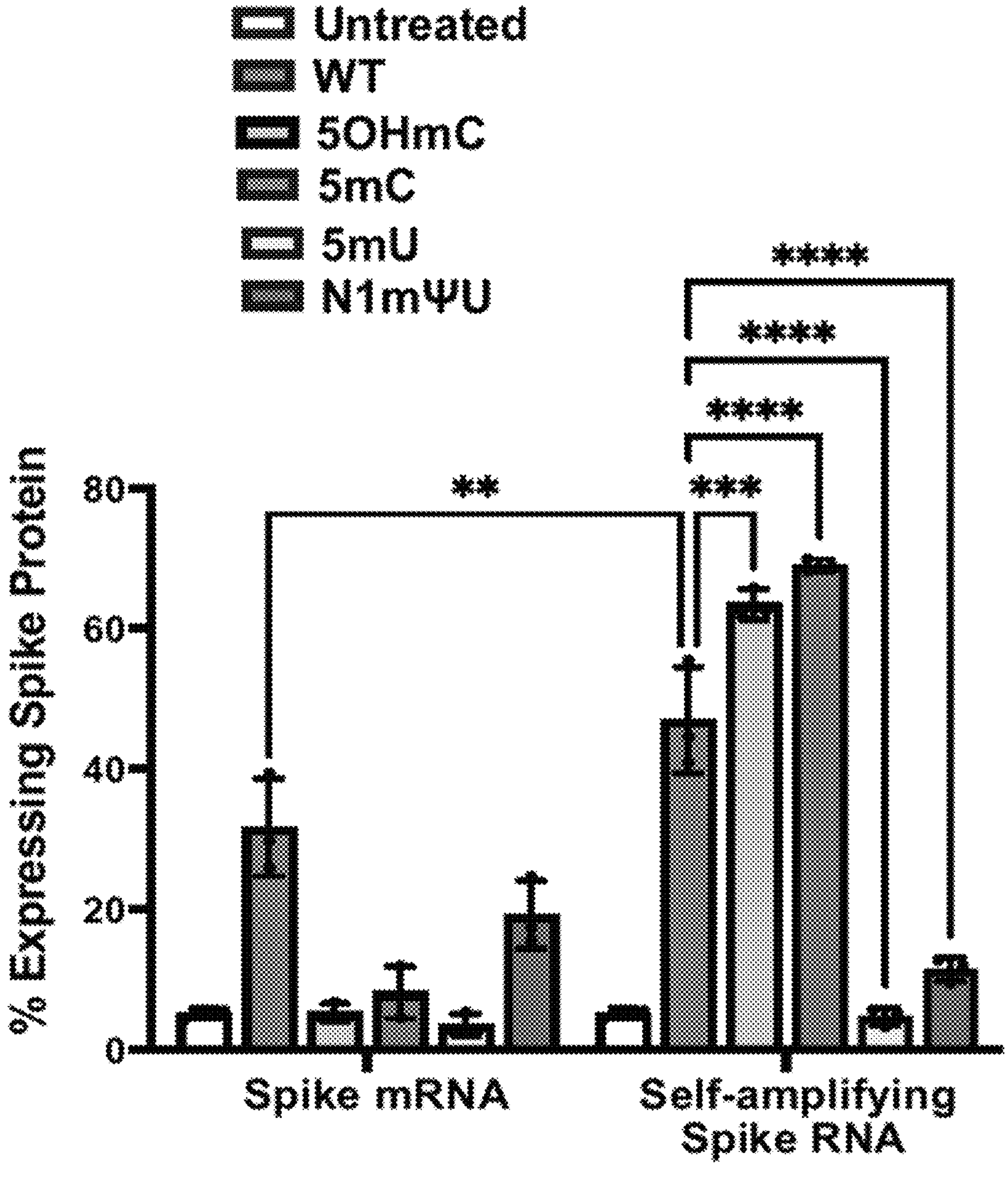
FIG. 64A-64D are a series of graphs showing testing of modified saRNAs as a SARS-CoV-2 vaccine.
Figure 64B:
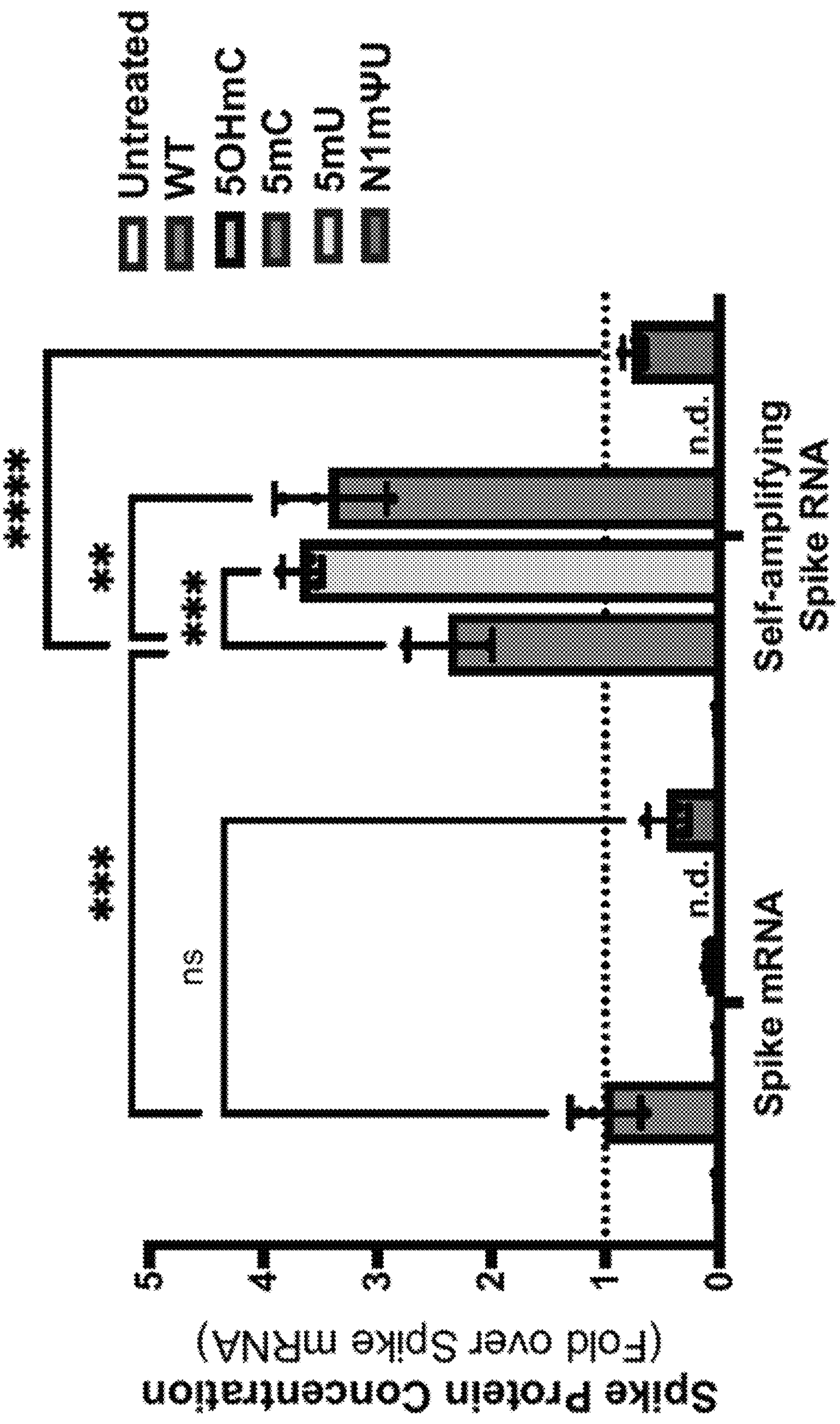
Figure 64C:
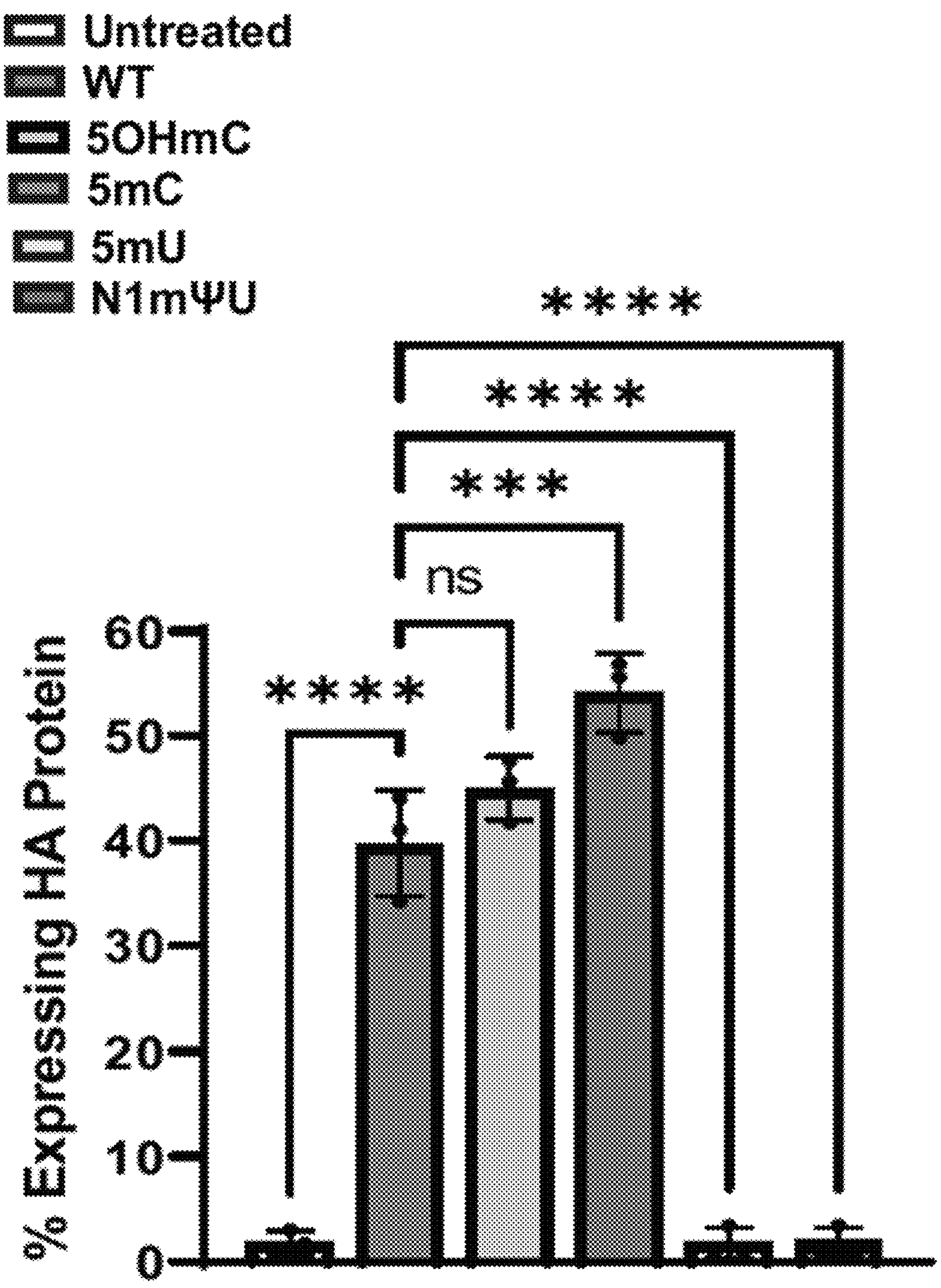
Figure 64D:
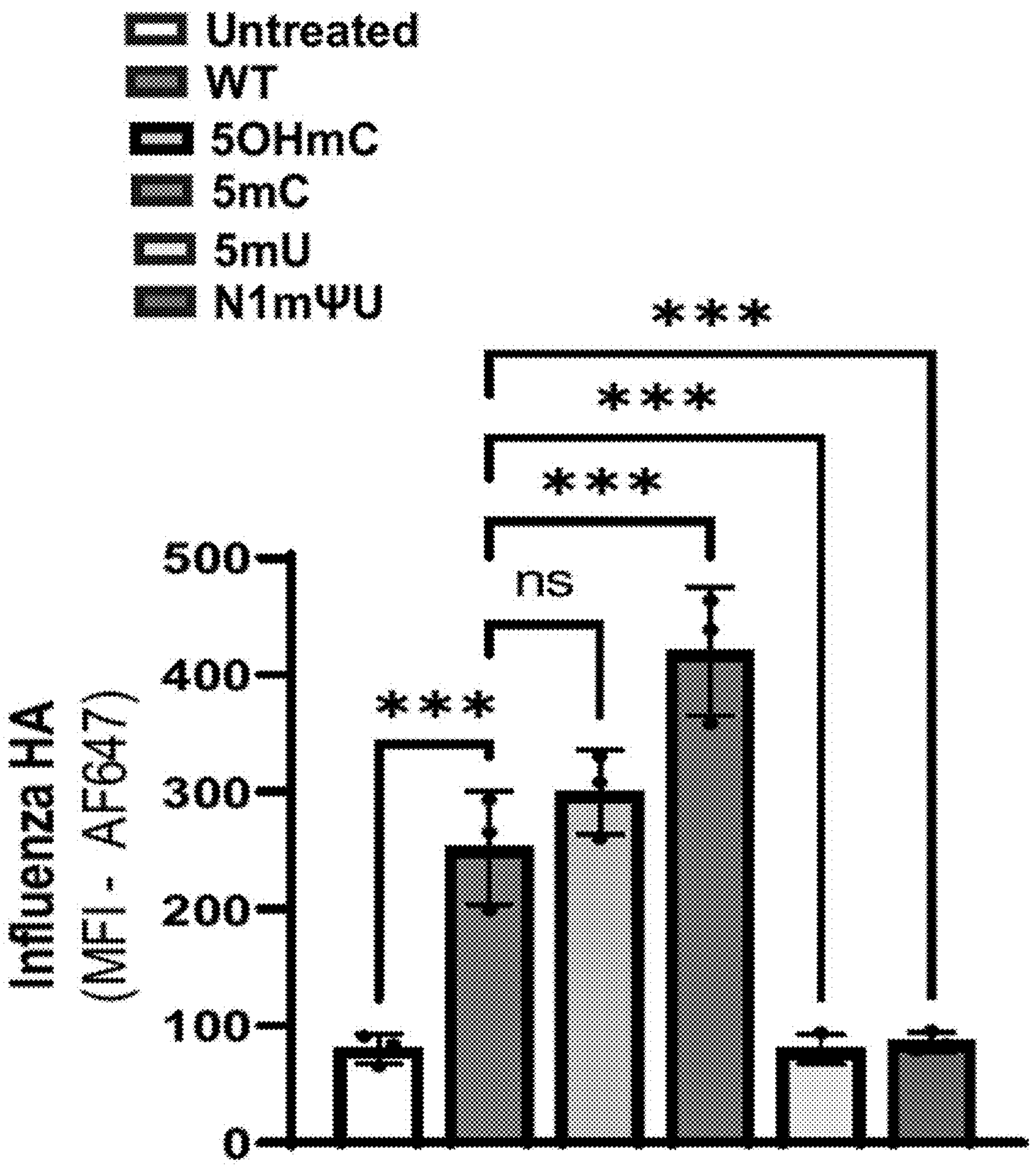

Next, non-replicating mRNA (Spike mRNA) and self-amplifying RNA (Spike saRNA) were generated encoding a K986P and V987P stabilized spike protein of SARS-CoV-2 derived from the Wuhan-1 strain (see e.g., FIG. 60A; see e.g., SEQ ID NOs: 21-22). The constructs were assembled by in vitro transcription. These RNAs were transfected into HEK and C2C12 cells via LNPs. In HEK cells, saRNA modified with 5OHmC, 5mC, and 5mU exhibited approximately twice the protein expression compared to wildtype saRNA, as assessed by flow cytometry (see e.g., FIG. 60B). Consistent with previous findings, N1mΨmodification of saRNA resulted in suppressed expression. In C2C12 cells, both 5OHmC and 5mC modifications significantly improved transfection efficiency, leading to approximately 2-fold higher protein expression than the unmodified saRNA construct and approximately 8-fold higher protein expression than N1mΨ modified non-replicating mRNA (see e.g., FIG. 60C, 60D, FIG. 64A). These findings were further supported by Enzyme Linked Immunosorbent Assay (ELISA) analysis, which confirmed enhanced protein expression for the modified saRNA constructs (see e.g., FIG. 64B). The 5mU modification did not result in protein expression in C2C12 cells. Similar in vitro experiments were performed to evaluate the expression of the flu hemagglutinin (HA) antigen, and an expression profile consistent with previous experiments was observed (see e.g., FIG. 64C+64D).

Figure 60E:
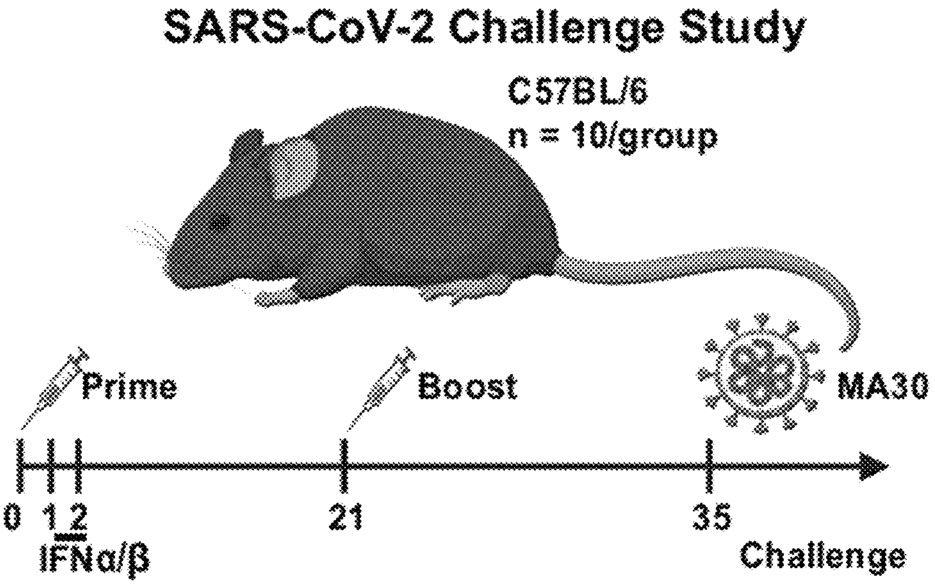
Figure 60F:
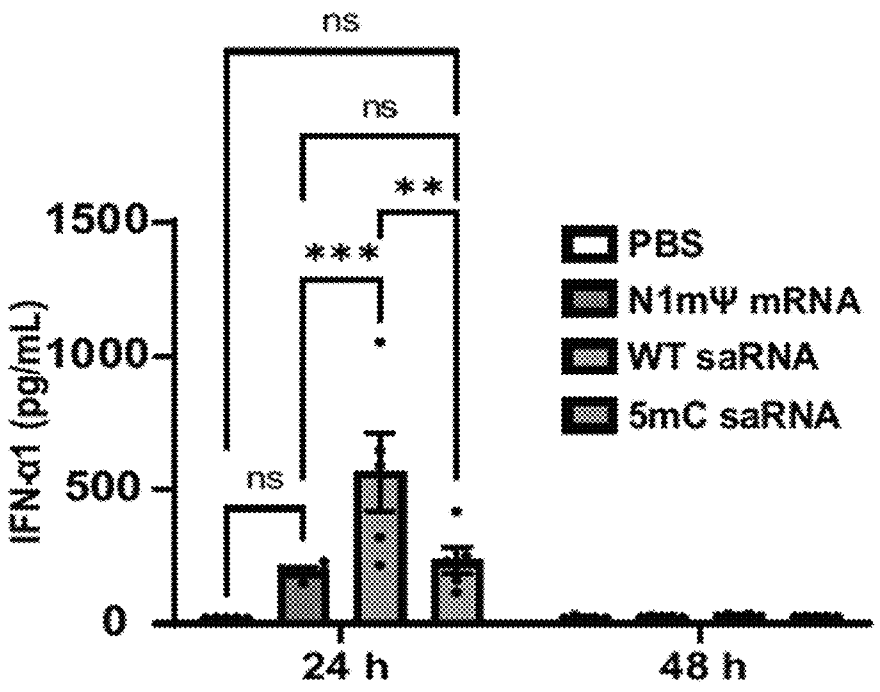
Figure 60G:
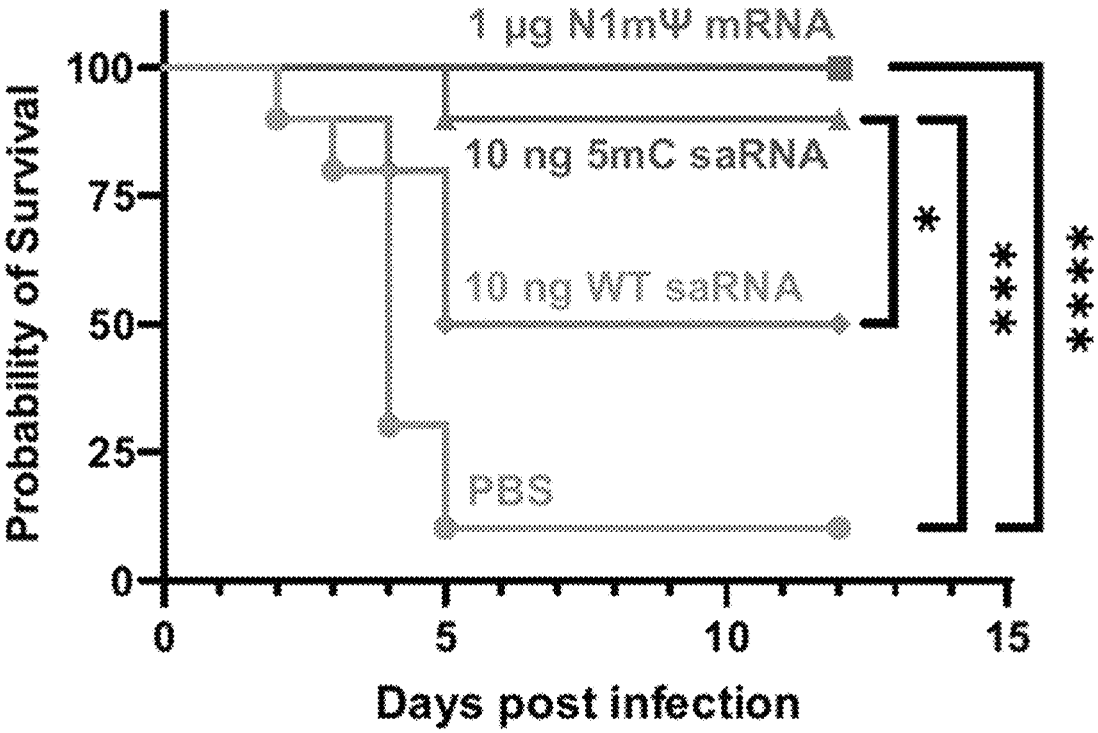
Figure 60H:
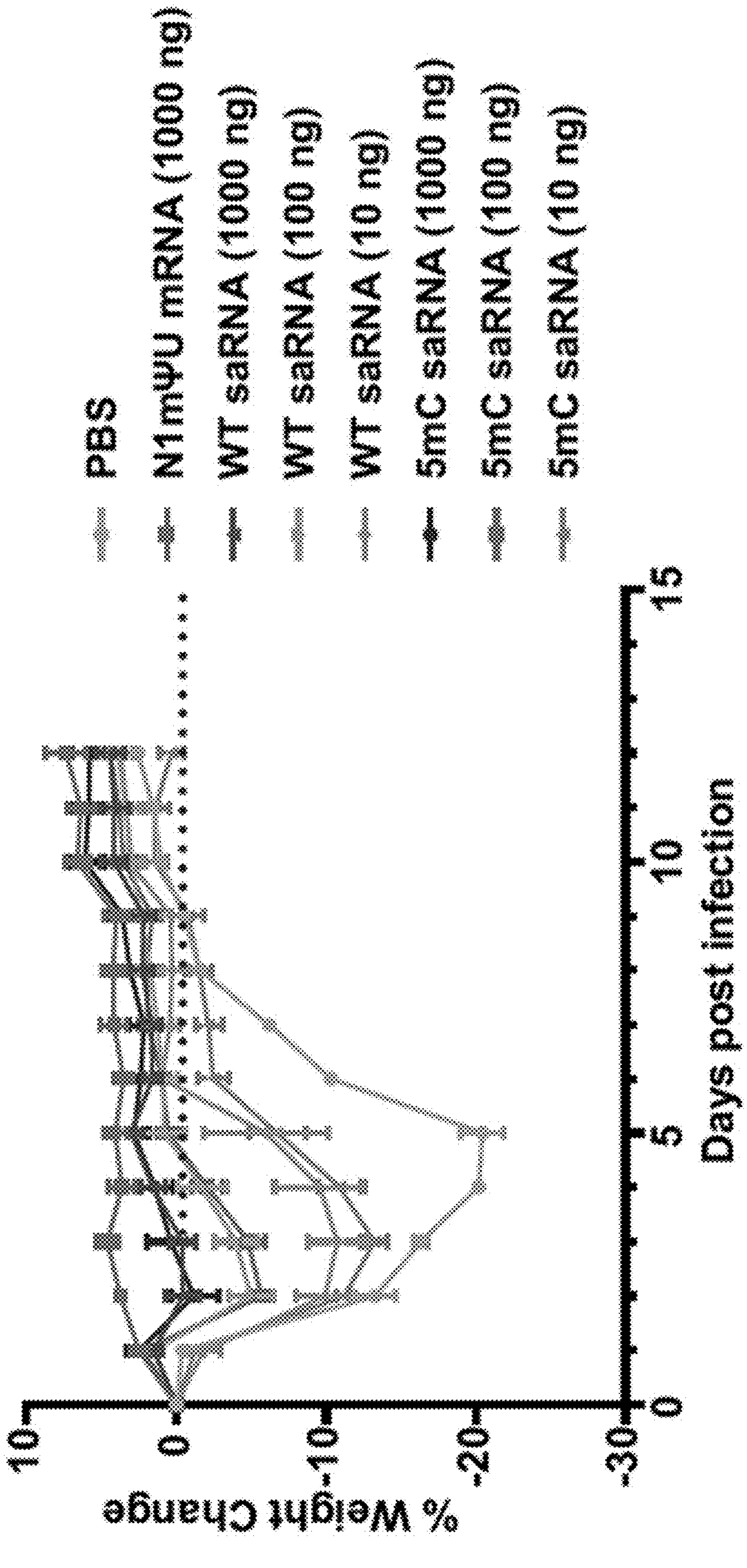
Figure 65A:
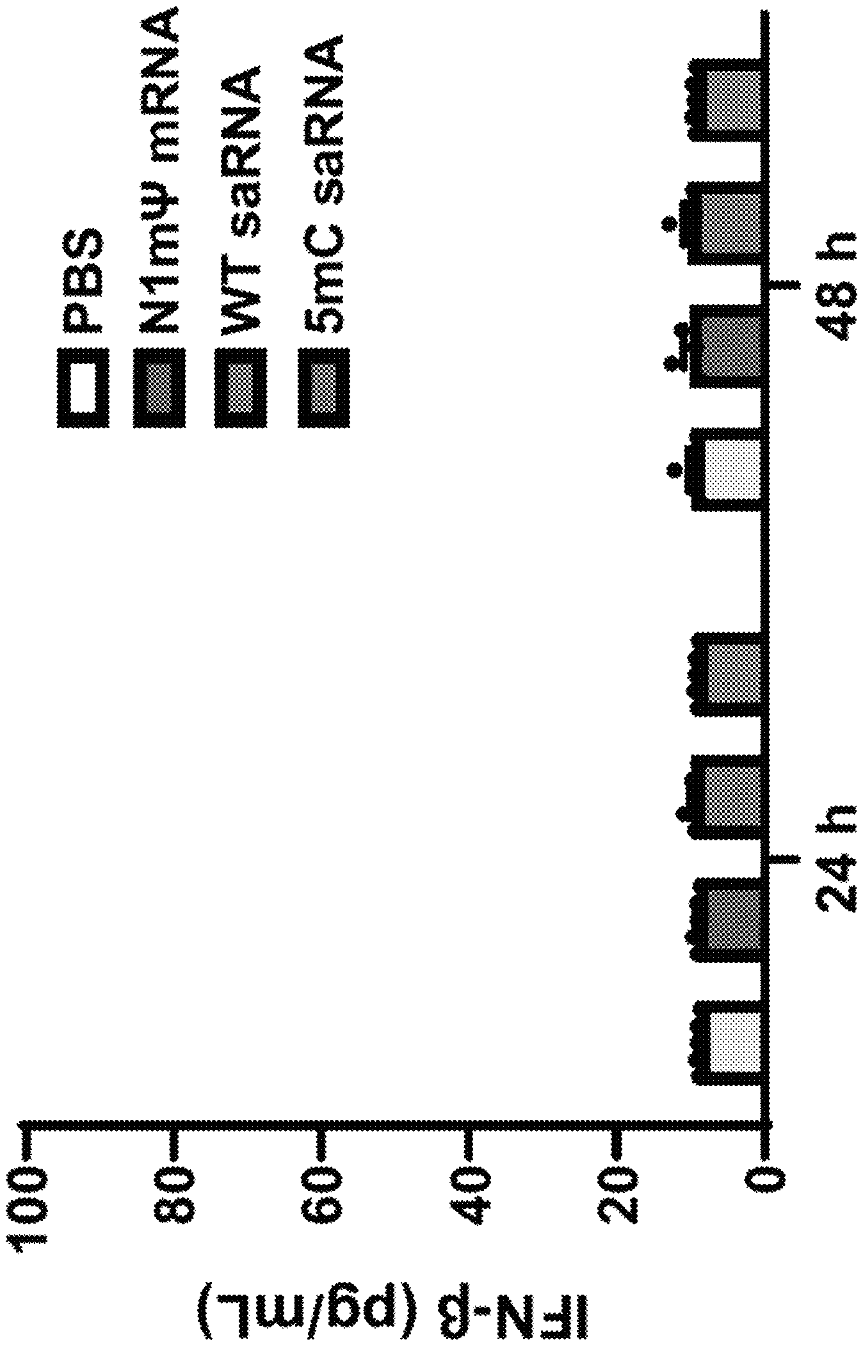
FIG. 65A-65B are a series of graphs and plots showing testing of modified saRNAs as a SARS-CoV-2 vaccine.
Figure 65B:
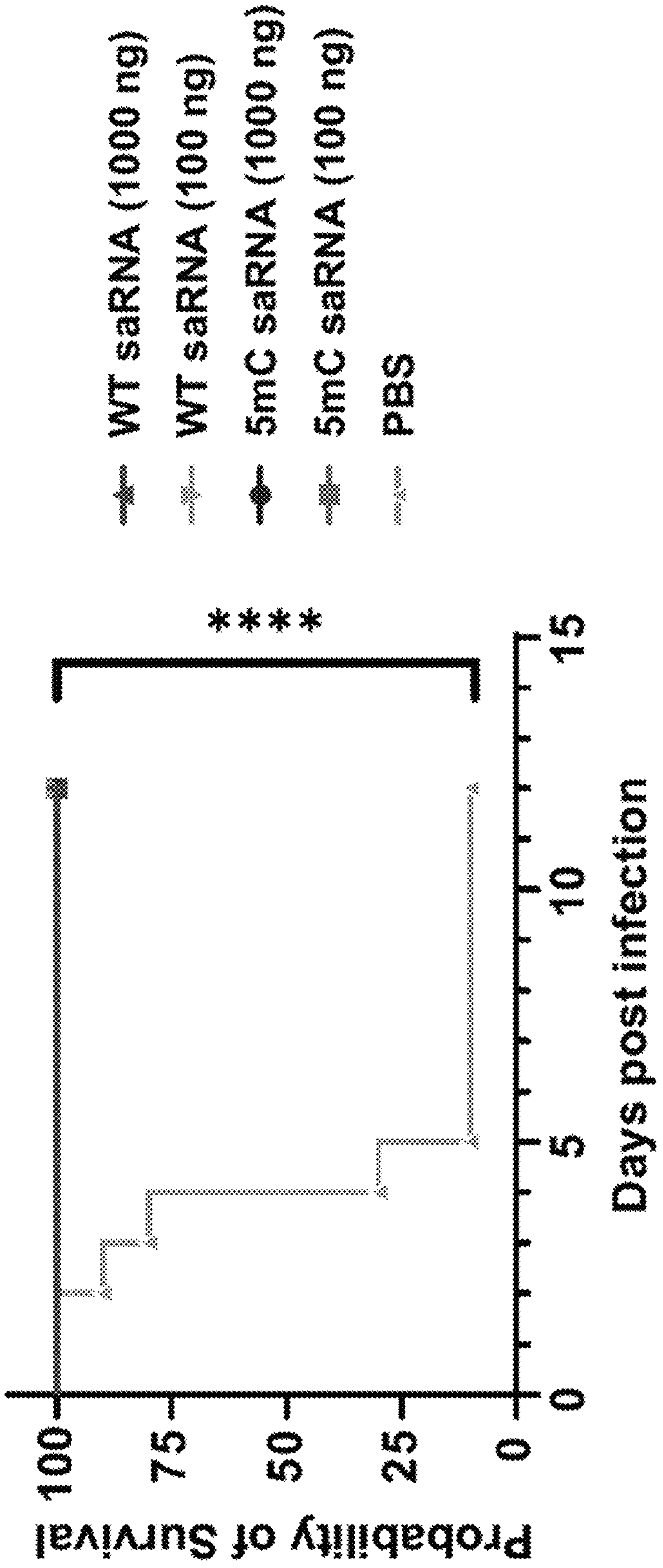
Figure 66B:
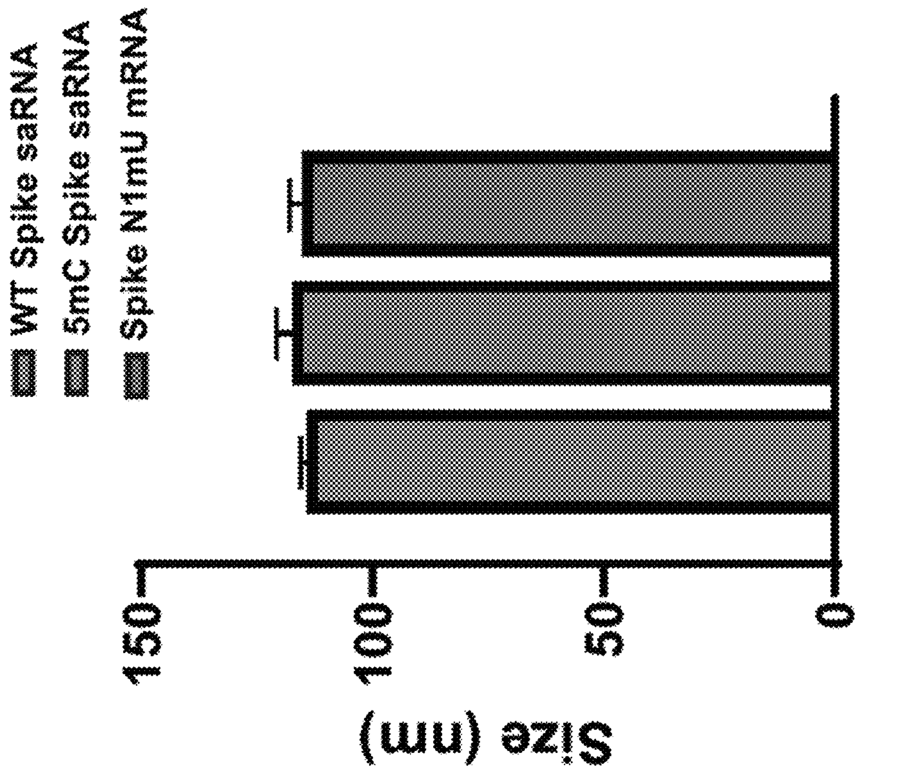
FIG. 66A-66D are a series of graphs showing testing of modified saRNAs as a SARS-CoV-2 vaccine.
Figure 66A:
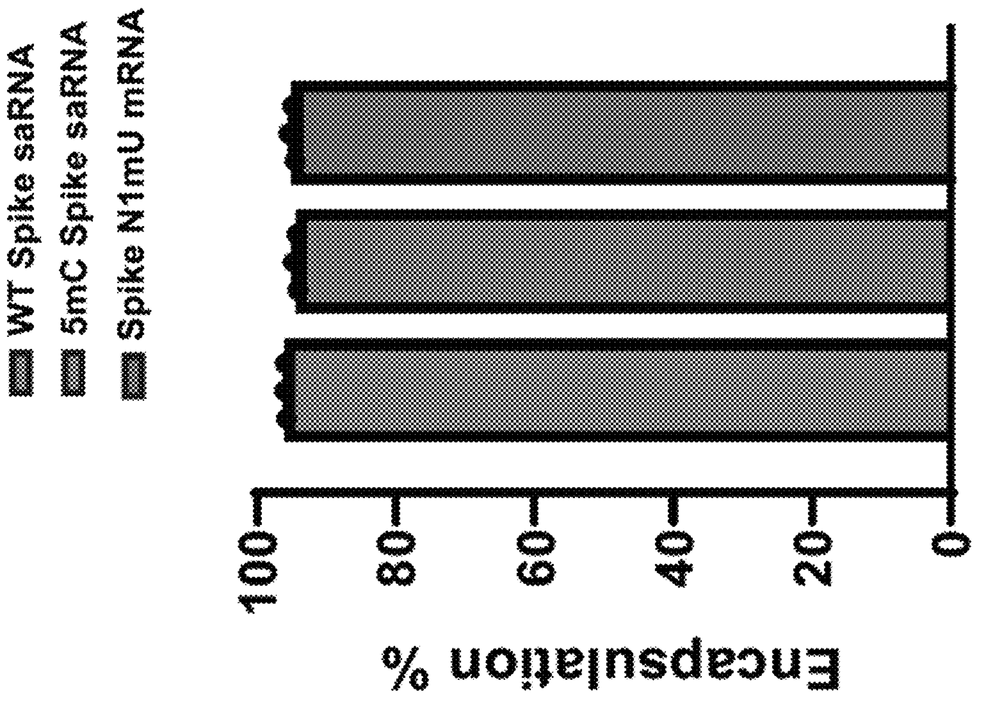
Figure 66D:
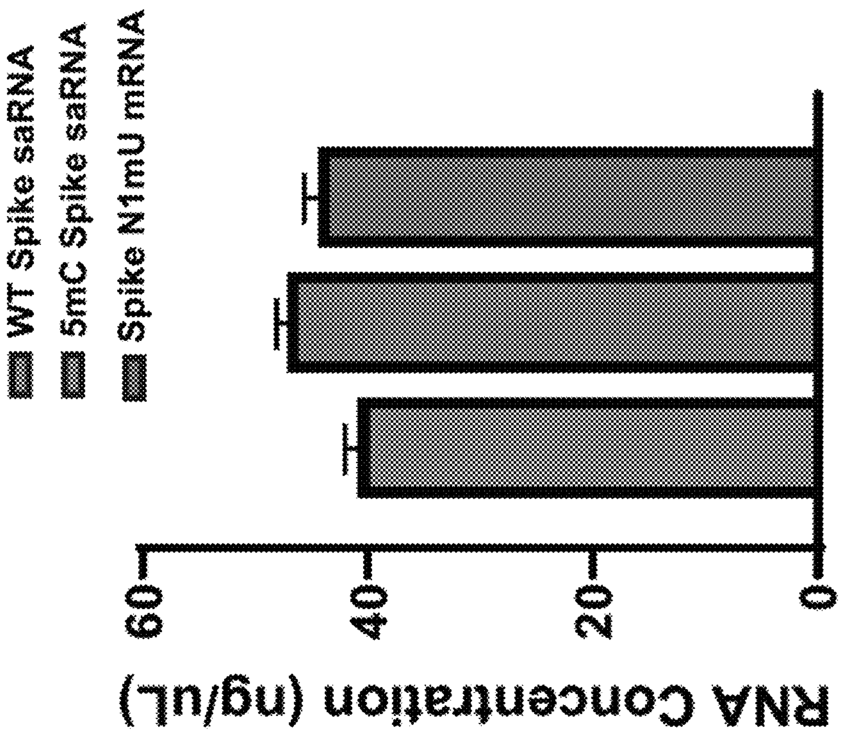
Figure 66C:
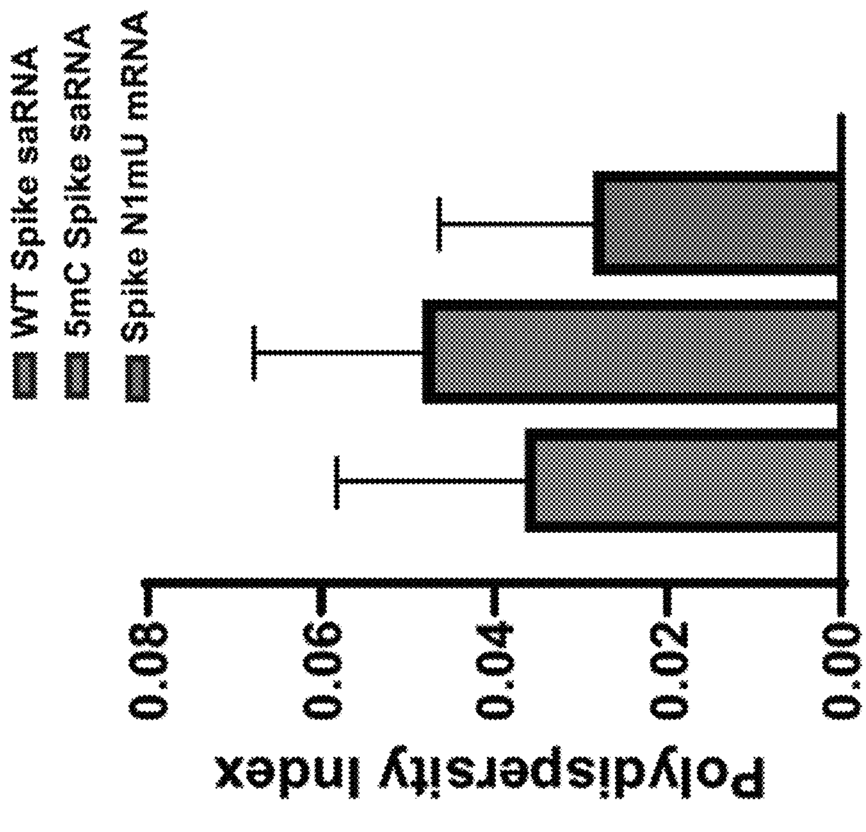
Figure 67A:
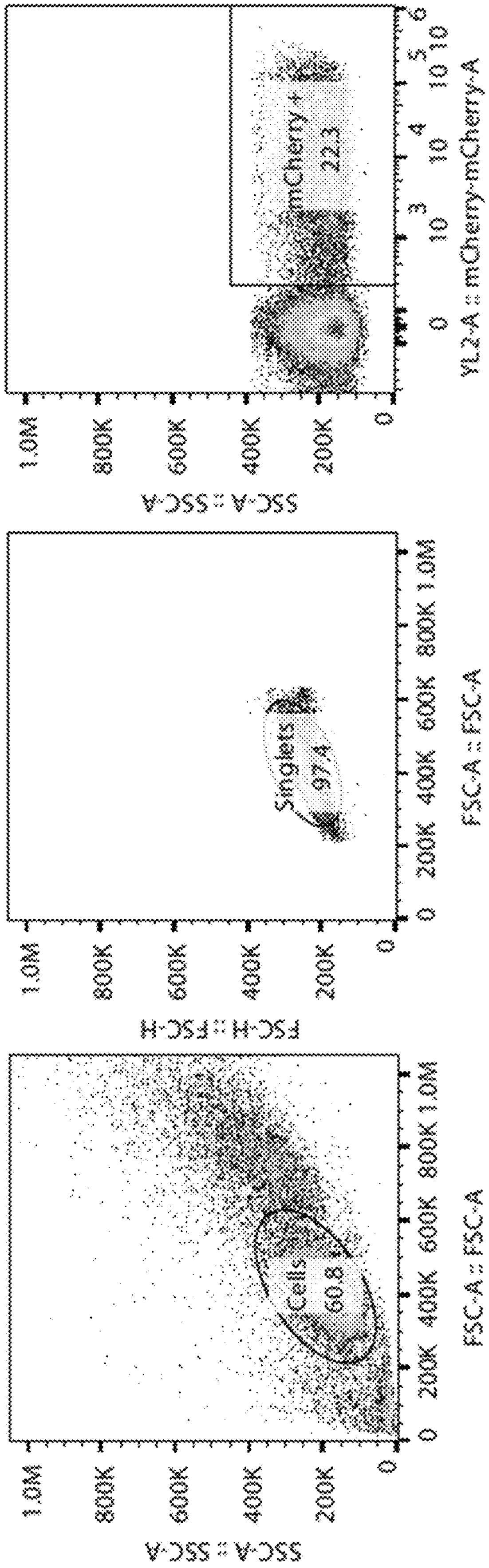
FIG. 67A-67D show flow cytometry gating strategies used in Example 20.
Figure 67B:
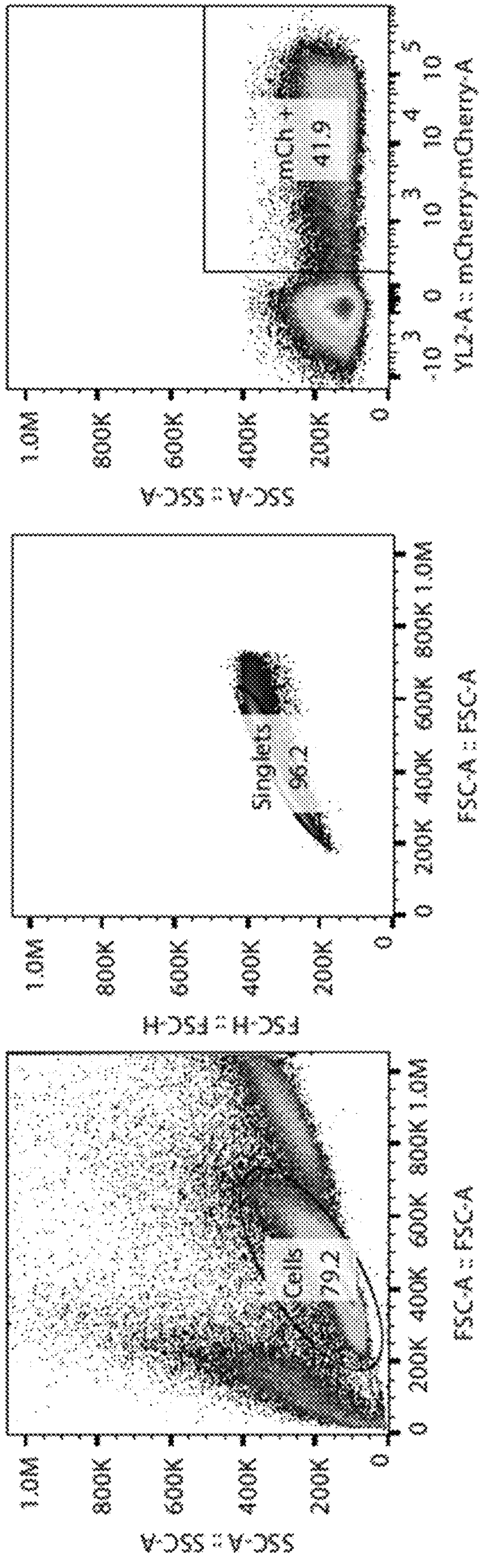
Figure 67C:
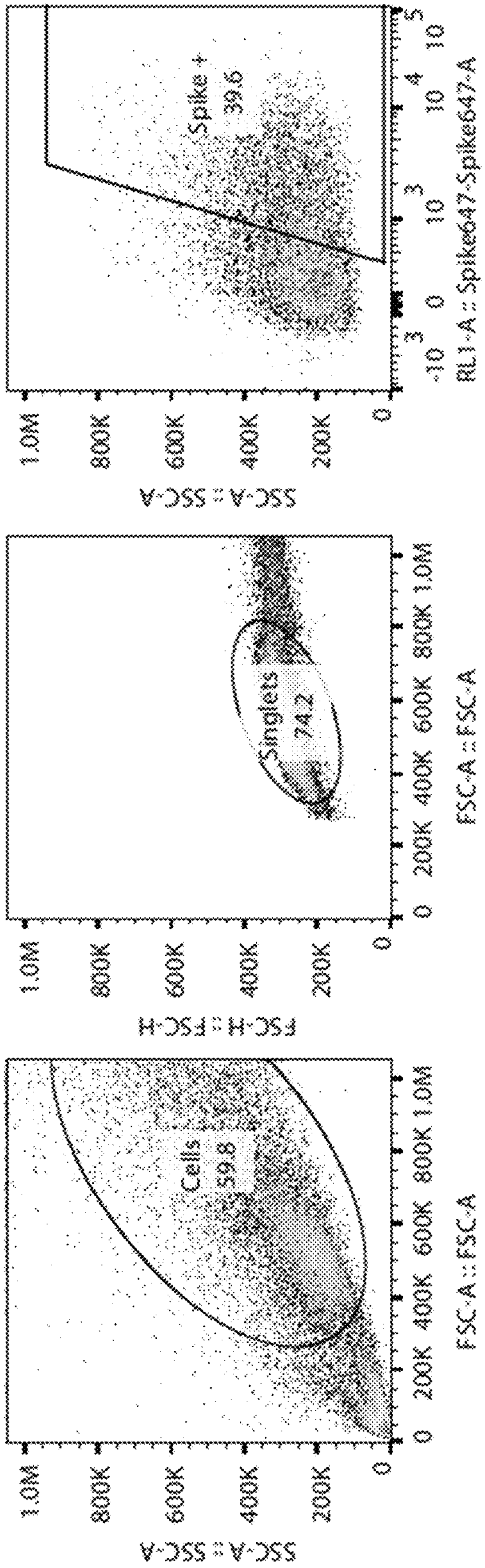
Figure 67D:
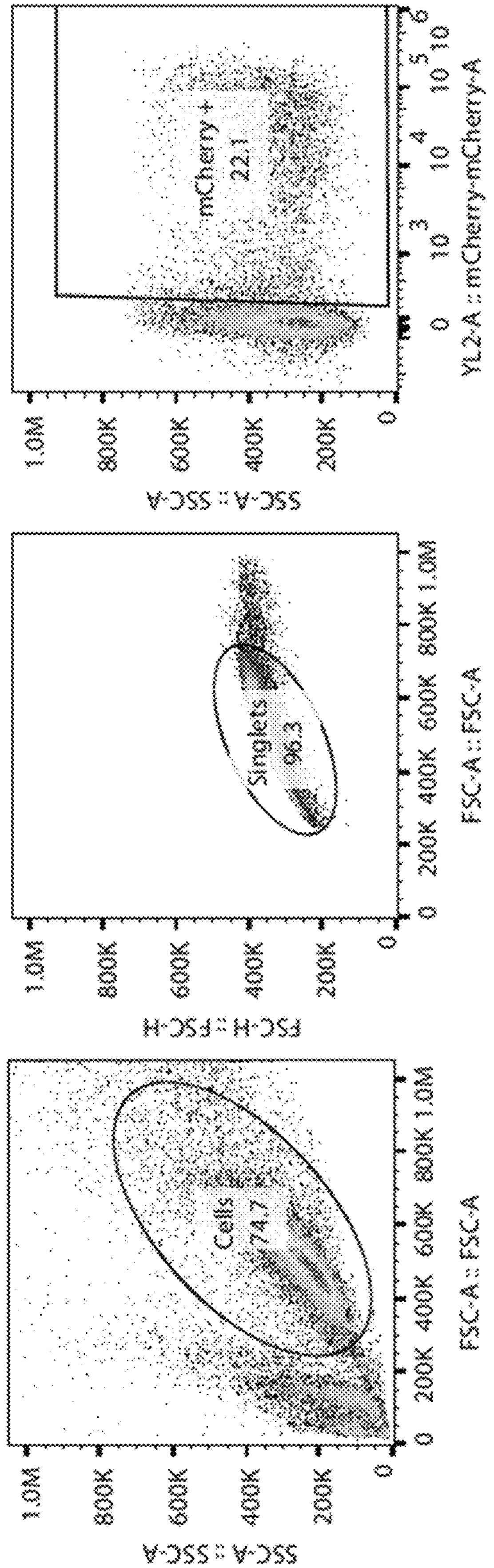

Following the successful antigen expression observed in vitro, the effectiveness of a modified saRNA vaccine was evaluated against SARS-CoV-2 infection. C57BL/6 mice (5 male and 5 female) were intramuscularly (i.m.) administered 10 ng, 100 ng, and 1000 ng of WT Spike saRNA or 5mC Spike and boosted at 35 days post initial vaccination (see e.g., FIG. 60E); assuming mouse weight of approximately 20 g, such doses equate to $5\times10^{-4}$ mg/kg, $5\times10^{-3}$ mg/kg, and $5\times10^{-2}$ mg/kg, respectively. As positive and negative controls, additional groups received 1000 ng of N1mΨ non-replicating mRNA or vehicle (PBS), respectively. To assess the early interferon response in mice, serum was collected from mice vaccinated with the 1000 ng dose at 24 hours and 48 hours. The mice vaccinated with WT saRNA exhibited significantly increased levels of serum IFN-α1 compared to N1mΨ or 5mC saRNA vaccinated mice. Conversely, mice receiving N1mΨ mRNA or 5mC saRNA displayed significantly reduced levels of serum IFN-α1, indicating a decrease in Toll-like receptor (TLR) signaling attributable to the modified nucleotides. By 48 hours post vaccination, IFN-α1 was no longer detectable in the serum of any mice (see e.g., FIG. 60F). Across all samples, IFN-β was not detectable at 24 hours or 48 hours (see e.g., FIG. 65A). On day 35, 14 days after the final vaccination, the mice were infected intranasally with $1\times10^5$ plaque-forming units (PFU) of mouse adapted SARS-CoV-2 (MA30); see e.g., Dinnon et al., Nature, 2020. 586(7830): p. 560-566, the content of which is incorporated herein by reference in its entirety. The mice vaccinated with either WT Spike saRNA or 5mC Spike saRNA at 100 ng and 1000 ng showed 100% survival and minimal weight loss (see e.g., FIG. 65B, FIG. 60H). However, mice receiving the 10 ng dose of WT Spike saRNA showed severe weight loss and 50% lethality. In contrast, mice vaccinated with the 10 ng dose of 5mC demonstrated only 10% lethality, a statistically significant improvement in survival compared to WT Spike saRNA (see e.g., FIG. 60G+60H).

DISCUSSION

As a technology, self-amplifying RNA permits lower dose vaccines and off-the-shelf, in situ, long-lasting, and non-integrating cell and gene therapies. Unfortunately, the clinical reality thus far paints a less encouraging picture. Despite success in preclinical models, saRNA vaccines show reduced seroconversion in human trials (see e.g., Low et al., 2022, supra). An analysis of gene expression in vaccinated humans reveals sharp activation of the innate immune system (see e.g., Ong et al., 2022, supra). Preclinical and clinical data also confirm that the early and intense interferon response inhibits antigen expression (see e.g., Minnaert et al., 2021, supra; Zong et al., 2021, supra; Pepini et al., 2017, supra; Zhong et al., Vaccines (Basel), 2019. 7(3); the contents of each of which are incorporated herein by reference in their entireties). A mechanism to evade the early interferon response and improve saRNA transfection, e.g., as shown by the modified saRNAs described herein, unlocks the true potential of the saRNA platform.

Prior strategies to enhance the efficacy of saRNA focus on reducing the innate immune response by optimizing the sequence, encoded cargo, and delivery vehicle. Evolved RdRp variants capable of decreasing the interferon response enhanced the anti-tumor efficacy of an IL2 encoding saRNA (see e.g., Ong et al., 2022, supra). Evolution of the RdRp sequence can affect performance in contexts beyond intratumoral immunotherapy. Co-expression of viral proteins that block the interferon response results in improved titers in a vaccine against Rabies virus (RABV) (see e.g., Blakney et al., 2021, supra). Without wishing to be bound by theory, it is expected that this strategy will enhance activity only in cell types lacking robust TLR sensing that are amenable to saRNA transfection. In the context of vaccination, the delayed interferon response resulting from cytosolic sensors likely has an adjunctive effect. For therapeutics, it can be desirable for saRNA constructs to evade TLR detection and to inhibit the downstream interferon response triggered by cytosolic sensors. In addition, a localizing cationic nanocarrier formulation (LION) limited the delivery of saRNA to the injection site and thereby decreased the systemic type I interferon response (see e.g., Kimura et al., 2023, supra). Dependency on the cationic delivery vehicle can pose challenges in achieving efficient delivery to specific tissue or cell types, potentially requiring higher doses, and thereby imposing constraints on its broader therapeutic applications. In sum, previous work demonstrates need for a universal approach to control the interferon response and improve saRNA translation.

One tool for suppression of the interferon response in non-replicating RNA therapeutics is the incorporation of modified nucleotides, as exemplified by N1mΨ modified mRNA. The current understanding in the field is that modified nucleotides (modNTPs) are incompatible with saRNA and that saRNA performance decreases proportional to incorporation percentage. In fact, multiple studies report the failure of modified saRNA, since the first discovery of the impact of modified nucleotides on mRNA (see e.g., Minnaert et al., 2021, supra; Kairuz et al., 2022, supra; Voigt et al., 2022, supra; Beissert et al., 2020, supra; Geall et al., 2010, supra; Erasmus et al., 2020, supra; Pollock et al., EClinicalMedicine, 2022. 44: p. 101262; Blakney et al., J Control Release, 2019. 304: p. 65-74; Papukashvili et al., Int J Mol Sci, 2022. 23(21); Kairuz et al., Pharmaceutics, 2023. 15(4); Deering et al., Expert Opin Drug Deliv, 2014. 11(6): p. 885-99; the contents of each of which are incorporated herein by reference in their entireties). It was hypothesized that modified nucleotides compatible with saRNA exist, considering the numerous RNA modifications observed in eukaryotic cells and their ubiquitous presence in RNA viruses; see e.g., Tong et al., Front Microbiol, 2022. 13: p. 845625, the content of which is incorporated herein by reference in its entirety.

Described herein is evidence of biologically active, fully substituted self-amplifying RNA containing 5OHmC, 5mC, or 5mU. These three modNTPs maintained saRNA activity at levels equal to or greater than an unmodified construct (see e.g., FIG. 58). These identified modified nucleotides significantly enhanced transfection efficiency in HEK293, C2C12, and Jurkat cells (see e.g., FIG. 58). This potentiation translated to transgenes in T cells (see e.g., FIG. 58) and vaccine antigens in muscle cells (see e.g., FIG. 60, FIG. 64). Significantly reduced expression of type I interferons occurred in transfected human PBMCs in vitro (see e.g., FIG. 59) and systemically in vivo (see e.g., FIG. 60). The significant reduction in serum IFN-α levels demonstrated diminished systemic immunogenicity, a factor frequently acknowledged as the primary remaining limitation associated with saRNA. Extensive in vitro and in vivo validation of a modNTP substituted saRNA vaccine candidate provided proof-of-concept for enhanced clinical efficacy. In a lethal challenge study, just 10 ng of modNTP substituted saRNA performed statistically better than unmodified saRNA, demonstrating the ability to use modified saRNA as an ultra-low dose vaccine platform (see e.g., FIG. 60). Studies presented in this work indicate that modified self-amplifying RNA are a platform technology capable of revolutionizing modem RNA therapeutics.

The discovery of modNTPs capable of maintaining saRNA functionality is a major step towards a deeper understanding of alphavirus transcriptional activity and control. Results here demonstrate that RdRp transcriptional activity is maintained with the incorporation of specific modNTPs but lost with modNTPs such as N1 mW. The observation of launch from fully modified saRNA means the two events are still occurring: (1) cap-dependent translation of the RdRp, and (2) the RdRp continues to recognize at least some of the conserved elements required for negative strand synthesis. Negative strand synthesis occurs intracellularly, and as a result, only wild type nucleotides will be incorporated into the new negative strand. Taking this and the results from N1 mW saRNA together indicate that modNTPs primarily impact RdRp-saRNA interaction, and not the initial cap-dependent translation event. Additionally, the compatibility of 5-methyluridine in HEK293 cells but not in C2C12 cells indicates a epitranscriptomic discrepancy and mechanism of cell-type specificity.

In conclusion, this work presents a significant advancement to the field of self-amplifying RNA, and RNA therapeutics more broadly. Described herein is an embodiment of fully substituted self-amplifying RNA with enhanced function, which goes against the thinking of the field. Modified nucleotides are shown herein to overcome the major barrier to successful translation of saRNA into the clinic, which is the early interferon response preventing launch and production of cargo proteins. This discovery considerably broadens the scope of self-amplifying RNA, permitting entry into previously impossible cell types, as well as the ability to apply saRNA technology to non-vaccine modalities such as cell therapy and protein replacement.

Materials and Methods

Template Design and Synthesis

All mRNA and saRNA templates described in this Example took the form of linearized plasmid DNA. All templates were generated from a plasmid encoding NSP1-4 of the Venezuela Equine Encephalitis virus under either a CLEANCAP AU (TRILINK BIOTECHNOLOGIES) compatible T7 promoter (Promoter seq: TAATACGACTCACTATAGAT; SEQ ID NO: 8) or a GTP/ARCA compatible T7 promoter (Promoter seq: TAATACGACTCACTATAGGAT; SEQ ID NO: 12). Antigen sequences are as follows: Influenza A Hemagglutinin (Influenza A virus (A/California/07/2009(H1N1)), NCBI Ref Seq: YP_009118626.1; see e.g., SEQ ID NO: 13), Human respiratory syncytial virus Fusion glycoprotein (Human respiratory syncytial virus (RSV) (subtype A, strain A2), GenBank: AQZ26655.1; see e.g., SEQ ID NO: 14) SARS-CoV-2 Spike (Wuhan-Hu-1, NCBI Ref Seq: YP_009724390.1; see e.g., SEQ ID NO: 15) with K986P and V987P stabilizing mutations (see e.g., SEQ ID NO: 16, SEQ ID NO: 22). Plasmids were cloned in DH5a *E. coli*. Plasmids were purified using ZymoPURE™II Plasmid Midiprep Kit (Zymo Research), linearized with MluI-HF for 3 hours at 37° C., and purified using QIAQUICK PCR Purification Kit (QIAGEN).

```
SEQ ID NO: 13, Influenza A Hemagglutinin (Influenza A virus
(A/California/07/2009(H1N1)), NCBI Ref Seq: YP_009118626.1,
566 amino acids (aa):
MKAILVVLLYTFATANADTLCIGYHANNSTDTVDTVLEKNVTVTHSVNLLEDKHNGKLCKLRG
VAPLHLGKCNIAGWILGNPECESLSTASSWSYIVETPSSDNGTCYPGDFIDYEELREQLSSVSSFER
FEIFPKTSSWPNHDSNKGVTAACPHAGAKSFYKNLIWLVKKGNSYPKLSKSYINDKGKEVLVLW
GIHHPSTSADQQSLYQNADAYVFVGSSRYSKKFKPEIAIRPKVRXXEGRMNYYWTLVEPGDKITF
EATGNLVVPRYAFAMERNAGSGIIISDTPVHDCNTTCQTPKGAINTSLPFQNIHPITIGKCPKYVKS
TKLRLATGLRNIPSIQSRGLFGAIAGFIEGGWTGMVDGWYGYHHQNEQGSGYAADLKSTQNAID
EITNKVNSVIEKMNTQFTAVGKEFNHLEKRIENLNKKVDDGFLDIWTYNAELLVLLENERTLDY
HDSNVKNLYEKVRSQLKNNAKEIGNGCFEFYHKCDNTCMESVKNGTYDYPKYSEEAKLNREEI
DGVKLESTRIYQILAIYSTVASSLVLVVSLGAISFWMCSNGSLQCRICI

SEQ ID NO: 14, Human respiratory syncytial virus Fusion glycopro-
tein
(Human respiratory syncytial virus (RSV) (subtype A, strain A2)),
GenBank: AQZ26655.1, 574 aa:
MELPILKANAISTILAAVTLCFASSQNITEEFYQSTCSAVSKGYLSALRTGWYTSVITIELSNIKENK
CNGTDAKVKLIKQELDKYKNAVTELQLLMQSTPAANSRARRELPRFMNYTLNNTKNTNVTLSK
KRKRRFLGFLLGVGSAIASGIAVSKVLHLEGEVNKIKSALLSTNKAVVSLSNGVSVLTSKVLDLK
NYIDKQLLPIVNKQSCSISNIETVIEFQQKNNRLLEITREFSVNAGVTTPVSTYMLTNSELLSLIND
MPITNDQKKLMSSNVQIVRQQSYSIMSIIKEEVLAYVVQLPLYGVIDTPCWKLHTSPLCTTNTKE
GSNICLTRTDRGWYCDNAGSVSFFPQAETCKVQSNRVFCDTMNSLTLPSEVNLCNIDIFNPKYDC
KIMTSKTDVSSSVITSLGAIVSCYGKTKCTASNKNRGIIKTFSNGCDYVSNKGVDTVSVGNTLYY
VNKQEGKSLYVKGEPIINFYDPLVFPSDEFDASISQVNEKINQSLAFIRKSDELLHNVNAGKSTTNI
MITTIIIVIIVILLALIAVGLLLYCKARSTPVTLSKDQLSGINNIAFSN

SEQ ID NO: 15, SARS-CoV-2 Spike, also referred to as a surface
glycoprotein, Wuhan-Hu-1, NCBI Ref Seq: YP_009724390.1, 1273 aa:
MFVFLVLLPLVSSQCVNLTTRTQLPPAYTNSFTRGVYYPDKVFRSSVLHSTQDLFLPFFSNVTWF
HAIHVSGTNGTKRFDNPVLPFNDGVYFASTEKSNIIRGWIFGTTLDSKTQSLLIVNNATNVVIKVC
EFQFCNDPFLGVYYHKNNKSWMESEFRVYSSANNCTFEYVSQPFLMDLEGKQGNFKNLREFVF
KNIDGYFKIYSKHTPINLVRDLPQGFSALEPLVDLPIGINITRFQTLLALHRSYLTPGDSSSGWTAG
AAAYYVGYLQPRTFLLKYNENGTITDAVDCALDPLSETKCTLKSFTVEKGIYQTSNFRVQPTESI
VRFPNITNLCPFGEVFNATRFASVYAWNRKRISNCVADYSVLYNSASFSTFKCYGVSPTKLNDLC
FTNVYADSFVIRGDEVRQIAPGQTGKIADYNYKLPDDFTGCVIAWNSNNLDSKVGGNYNYLYRL
FRKSNLKPFERDISTEIYQAGSTPCNGVEGFNCYFPLQSYGFQPTNGVGYQPYRVVVLSFELLHAP
ATVCGPKKSTNLVKNKCVNFNFNGLTGTGVLTESNKKFLPFQQFGRDIADTTDAVRDPQTLEILD
ITPCSFGGVSVITPGTNTSNQVAVLYQDVNCTEVPVAIHADQLTPTWRVYSTGSNVFQTRAGCLI
GAEHVNNSYECDIPIGAGICASYQTQTNSPRRARSVASQSIIAYTMSLGAENSVAYSNNSIAIPTNF
TISVTTEILPVSMTKTSVDCTMYICGDSTECSNLLLQYGSFCTQLNRALTGIAVEQDKNTQEVFAQ
VKQIYKTPPIKDFGGFNFSQILPDPSKPSKRSFIEDLLFNKVTLADAGFIKQYGDCLGDIAARDLIC
AQKFNGLTVLPPLLTDEMIAQYTSALLAGTITSGWTFGAGAALQIPFAMQMAYRENGIGVTQNV
LYENQKLIANQFNSAIGKIQDSLSSTASALGKLQDVVNQNAQALNTLVKQLSSNFGAISSVLNDIL
SRLDKVEAEVQIDRLITGRLQSLQTYVTQQLIRAAEIRASANLAATKMSECVLGQSKRVDFCGKG
YHLMSFPQSAPHGVVFLHVTYVPAQEKNFTTAPAICHDGKAHFPREGVFVSNGTHWFVTQRNF
YEPQIITTDNTFVSGNCDVVIGIVNNTVYDPLQPELDSFKEELDKYFKNHTSPDVDLGDISGINAS
VVNIQKEIDRLNEVAKNLNESLIDLQELGKYEQYIKWPWYIWLGFIAGLIAIVMVTIMLCCMTSC
CSCLKGCCSCGSCCKFDEDDSEPVLKGVKLHYT

SEQ ID NO: 16, SARS-CoV-2 Spike, Wuhan-Hu-1, NCBI Ref Seq:
YP_009724390.1) with K986P and V987P stabilizing mutations
(shown in bolded, double-underlined text):
MFVFLVLLPLVSSQCVNLTTRTQLPPAYTNSFTRGVYYPDKVFRSSVLHSTQDLFLPFFSNVTWF
HAIHVSGTNGTKRFDNPVLPFNDGVYFASTEKSNIIRGWIFGTTLDSKTQSLLIVNNATNVVIKVC
EFQFCNDPFLGVYYHKNNKSWMESEFRVYSSANNCTFEYVSQPFLMDLEGKQGNFKNLREFVF
KNIDGYFKIYSKHTPINLVRDLPQGFSALEPLVDLPIGINITRFQTLLALHRSYLTPGDSSSGWTAG
AAAYYVGYLQPRTFLLKYNENGTITDAVDCALDPLSETKCTLKSFTVEKGIYQTSNFRVQPTESI
VRFPNITNLCPFGEVFNATRFASVYAWNRKRISNCVADYSVLYNSASFSTFKCYGVSPTKLNDLC
FTNVYADSFVIRGDEVRQIAPGQTGKIADYNYKLPDDFTGCVIAWNSNNLDSKVGGNYNYLYRL
FRKSNLKPFERDISTEIYQAGSTPCNGVEGENCYFPLQSYGFQPTNGVGYQPYRVVVLSFELLHAP
ATVCGPKKSTNLVKNKCVNFNFNGLTGTGVLTESNKKFLPFQQFGRDIADTTDAVRDPQTLEILD
ITPCSFGGVSVITPGTNTSNQVAVLYQDVNCTEVPVAIHADQLTPTWRVYSTGSNVFQTRAGCLI
GAEHVNNSYECDIPIGAGICASYQTQTNSPRRARSVASQSIIAYTMSLGAENSVAYSNNSIAIPTNF
TISVTTEILPVSMTKTSVDCTMYICGDSTECSNLLLQYGSFCTQLNRALTGIAVEQDKNTQEVFAQ
```

-continued

VKQIYKTPPIKDFGGFNFSQILPDPSKPSKRSFIEDLLFNKVTLADAGFIKQYGDCLGDIAARDLIC
AQKFNGLTVLPPLLTDEMIAQYTSALLAGTITSGWTFGAGAALQIPFAMQMAYRFNGIGVTQNV
LYENQKLIANQFNSAIGKIQDSLSSTASALGKLQDVVNQNAQALNTLVKQLSSNFGAISSVLNDIL
SRLDPPEAEVQIDRLITGRLQSLQTYVTQQLIRAAEIRASANLAATKMSECVLGQSKRVDFCGKG
YHLMSFPQSAPHGVVFLHVTYVPAQEKNFTTAPAICHDGKAHFPREGVFVSNGTHWFVTQRNF
YEPQIITTDNTFVSGNCDVVIGIVNNTVYDPLQPELDSFKEELDKYFKNHTSPDVDLGDISGINAS
VVNIQKEIDRLNEVAKNLNESLIDLQELGKYEQYIKWPWYIWLGFIAGLIAIVMVTIMLCCMTSC
CSCLKGCCSCGSCCKFDEDDSEPVLKGVKLHYT

SEQ ID NO: 22, SARS-CoV-2 Spike with K986P and V987P stabilizing mutations (shown in bolded, double-underlined text):
MFVFLVLLPLVSSQCVNLTTRTQLPPAYTNSFTRGVYYPDKVFRSSVLHSTQDLFLPFFSNVTWF
HAIHVSGTNGTKRFDNPVLPFNDGVYFASTEKSNIIRGWIFGTTLDSKTQSLLIVNNATNVVIKVC
EFQFCNDPFLGVYYHKNNKSWMESEFRVYSSANNCTFEYVSQPFLMDLEGKQGNFKNLREFVF
KNIDGYFKIYSKHTPINLVRDLPQGFSALEPLVDLPIGINITRFQTLLALHRSYLTPGDSSSGWTAG
AAAYYVGYLQPRTFLLKYNENGTITDAVDCALDPLSETKCTLKSFTVEKGIYQTSNFRVQPTESI
VRFPNITNLCPFGEVFNATRFASVYAWNRKRISNCVADYSVLYNSASFSTFKCYGVSPTKLNDLC
FTNVYADSFVIRGDEVRQIAPGQTGKIADYNYKLPDDFTGCVIAWNSNNLDSKVGGNYNYLYRL
FRKSNLKPFERDISTEIYQAGSTPCNGVEGFNCYFPLQSYGFQPTNGVGYQPYRVVVLSFELLHAP
ATVCGPKKSTNLVKNKCVNFNFNGLTGTGVLTESNKKFLPFQQFGRDIADTTDAVRDPQTLEILD
ITPCSFGGVSVITPGTNTSNQVAVLYQDVNCTEVPVAIHADQLTPTWRVYSTGSNVFQTRAGCLI
GAEHVNNSYECDIPIGAGICASYQTQTNSPRAAASVASQSIIAYTMSLGAENSVAYSNNSIAIPTNF
TISVTTEILPVSMTKTSVDCTMYICGDSTECSNLLLQYGSFCTQLNRALTGIAVEQDKNTQEVFAQ
VKQIYKTPPIKDFGGFNFSQILPDPSKPSKRSFIEDLLFNKVTLADAGFIKQYGDCLGDIAARDLIC
AQKFNGLTVLPPLLTDEMIAQYTSALLAGTITSGWTFGAGAALQIPFAMQMAYRENGIGVTQNV
LYENQKLIANQFNSAIGKIQDSLSSTASALGKLQDVVNQNAQALNTLVKQLSSNFGAISSVLNDIL
SRLDPPEAEVQIDRLITGRLQSLQTYVTQQLIRAAEIRASANLAATKMSECVLGQSKRVDFCGKG
YHLMSFPQSAPHGVVFLHVTYVPAQEKNFTTAPAICHDGKAHFPREGVFVSNGTHWFVTQRNF
YEPQIITTDNTFVSGNCDVVIGIVNNTVYDPLQPELDSFKEELDKYFKNHTSPDVDLGDISGINAS
VVNIQKEIDRLNEVAKNLNESLIDLQELGKYEQYIKWPWYIWLGFIAGLIAIVMVTIMLCCMTSC
CSCLKGCCSCGSCC RNA Synthesis mRNA and saRNA was synthesized using MEGASCRIPT T7 Transcription kit (Invitrogen™, THERMOFISHER SCIENTIFIC) with 1 μg template and co-transcriptional capping using CLEANCAP AU (TRILINK BIOTECHNOLOGIES). For IVT with ARCA, a final concentration of 12 mM ARCA and 4 mM GTP was used. For ARCA experiments were a GTP analog was utilized, the modNTP was substituted completely to a final concentration of 4 mM. The modNTPs in all CLEANCAP AU IVT reactions were prepared according to manufacturer's protocol. IVT for 3 hours at 37° C. was followed by 10 min DNase treatment and 30 min post-transcriptional poly-adenylation using a Poly(A) Tailing Kit (Invitrogen™, THERMOFISHER SCIENTIFIC). saRNA was purified using MEGAclear™ Transcription Clean-up Kit (Invitrogen™ THERMOFISHER SCIENTIFIC) and eluted in DNase/RNase free $H_2O$ prior to storing at −80° C. The A260 of an equimolar, 1 mM mixture of all combinations of modNTPs and NTPs was empirically determined using a NANODROP2000 (THERMOFISHER SCIENTIFIC). The adjusted factor for each modNTP was used to calculate RNA concentration to ensure consistent delivery between modNTPs (see e.g., Table 1).

TABLE 1

Empirical determination of modified nucleotide absorbance conversion factors.

| Chemical Name | Base Analog | Mol Weight (g/mol) | Abs (260 nm) | Factor |
|---|---|---|---|---|
| 7-Deazaadenosine | Adenosine | 506.1 | 5.04 | 55.976 |
| N1-Methyladenosine | Adenosine | 521.2 | 15.369 | 39.399 |
| N6-Methyladenosine | Adenosine | 521.2 | 14.777 | 39.727 |
| 6-Chloropurineriboside | Adenosine | 526.6 | 17.481 | 38.430 |
| 2-Amino-6-chloropurineriboside | Adenosine | 541.6 | 11.482 | 42.280 |
| 2-Aminoadenosine | Adenosine | 522.2 | 14.523 | 39.880 |

TABLE 1-continued

Empirical determination of modified nucleotide absorbance conversion factors.

| Chemical Name | Base Analog | Mol Weight (g/mol) | Abs (260 nm) | Factor |
|---|---|---|---|---|
| Thienocytidine | Cytidine | 539.2 | *358.295 | n.d. |
| 5-Methoxycytidine | Cytidine | 513.2 | 13.912 | 34.580 |
| 5-Hydroxymethylcytidine | Cytidine | 513.1 | 14.618 | 34.140 |
| 5-Formylcytidine | Cytidine | 511.1 | 14.938 | 33.946 |
| 5-Aminoallylcytidine | Cytidine | 538.2 | 15.888 | 33.546 |
| 5-Methylcytidine | Cytidine | 497.1 | 15.01 | 33.847 |
| 5-Hydroxycytidine | Cytidine | 499.1 | 14.513 | 36.431 |
| Isoguanosine | Guanosine | 523.1 | 13.135 | 39.916 |
| Thienoguanosine | Guanosine | 539.2 | 11.774 | 41.100 |
| 2-Aminopurine-riboside | Guanosine | 507.2 | 10.584 | 42.112 |
| 8-Oxoguanosine | Guanosine | 539.1 | 13.191 | 39.951 |
| 5-Carboxy-methylesteruridine | Uridine | 542.1 | 23.333 | 33.266 |
| Thienouridine | Uridine | 542.2 | 15.559 | 36.017 |
| 5-Methoxyuridine | Uridine | 514.1 | 13.408 | 37.210 |
| 5-Carboxyuridine + A17 | Uridine | 528.1 | 16.619 | 35.437 |
| 2-Thiouridine | Uridine | 500.2 | 14.605 | 36.376 |
| Methyluridine | Uridine | 498.1 | 15.047 | 36.115 |
| N1-Propylpseudouridine | Uridine | 526.2 | 13.523 | 37.186 |
| N1-Methoxy-methylpseudouridine | Pseudouridine | 528.2 | 14.041 | 36.847 |
| N1-Ethylpseudouridine | Pseudouridine | 512.2 | 13.988 | 36.810 |
| N1-Methylpseudouridine | Pseudouridine | 498.1 | 14.557 | 36.396 |
| Pseudouridine | Pseudouridine | 484.1 | 14.861 | 36.160 |
| Wild type | — | | 13.865 | 38.288 |

Due to sample evaporation, as determined by significant increase in viscosity, thienocytidine concentration was hypothesized, without wishing to be bound by theory, to be >100 mM as listed. A wild-type absorbance factor was applied to thienocytidine $A_{260}$.
"N.d." indicates "not determined".

modNTP saRNA Screening in HEK293T

HEK293T cells were grown in DMEM+1 mM sodium pyruvate+10% FBS+1% PS, plated at 70,000cells/$cm^2$ in 96-well plates, and allowed to adhere overnight. mCherry saRNA was transfected using MESSENGERMAX according to manufacturer protocols (Invitrogen™, THERMOFISHER SCIENTIFIC). 24 hours later, cells were prepared for flow cytometry analysis of mCherry expression.

Cells were washed 1× in PBS, treated with 1×PBS+2 mM ethylenediaminetetraacetic acid (EDTA) for 5 mins, and then resuspended in fluorescence-activated cell sorting (FACS) Buffer (1×PBS+2% bovine serum albumin (BSA)). Data was acquired on the ATTUNE NXT (THERMO FISHER SCIENTIFIC) and analyzed on FLOWJO (version 10.8.1) Fluorescent microscopy of selected modNTPs was performed on a BIOTEK CYTATION 5 microscope prior to preparation for flow cytometry analysis.

LNP Formulation saRNA were encapsulated inside of LNPs with the following composition (mole percent): 50% (8-[(2-hydroxyethyl)[6-oxo-6-(undecyloxy)hexyl]amino]-octanoic acid, 1-octylnonyl ester [SM-102, CAYMAN]), 1.5% (1,2-dimyristoyl-rac-glycero-3-methoxypolyethylene glycol-2000 [DMG-PEG2K, AVANTI]), 10% (1 1,2-dioleoyl-sn-glycero-3-phosphoethanolamine [DOPE, AVANTI]), 38.5% cholesterol (AVANTI). All RNA was loaded at an N:P ratio of 10 (N:P ratio refers to the molar ratio of ionizable lipid nitrogen to oligonucleotide phosphate, and it represents the charge balance between the cationic tertiary amine of the ionizable cationic lipid and the anionic phosphate group in the oligonucleotide backbone). Prior to formulation, aqueous and lipid phases were separately sterile filtered through 0.22 μm filters. Formulation was performed in sterile conditions. After formulation, LNPs were dialyzed against sterile 1×PBS for 24 hours at 4° C. LNP morphology was characterized via dynamic light scattering (DLS) using a NANOBROOK OMNI (BROOKHAVEN INSTRUMENTS). Encapsulation efficiency was determined using the QUANTIFLUOR RNA System (PROMEGA). To transfect primary T cells, mAb-targeted LNPs were formulated via post-insertion of DSPE-PEG2K-maleimide coupled to anti-CD3 (Clone OKT3, BIOXCELL).

Expression Potentiation Assays

HEK and C2C12 cells were grown in Dulbecco's Modified Eagle Medium (DMEM)+10% FBS+1% PS and were passaged every three days. 24 hours prior to transfection, the cells were washed with PBS, trypsinized, and plated in fresh DMEM at 50,000 cells/well. LNPs containing mRNA or saRNA encoding luciferase were added dropwise to the cells in triplicate at 10 ng or 100 ng/well. After 24 hours, the luciferase expression was assayed using the BRIGHTGLO system (PROMEGA).

Jurkat cells were grown in RPMI+10% FBS+1% PS and maintained between $5\times10^5$ and $1\times10^6$ cells/ml. Prior to transfection, the cells were washed with PBS and plated in fresh RPMI at 250,000 cells/well. LNPs containing saRNA with or without modified nucleosides were added dropwise to cells in triplicate at 25 ng/well or 250 ng/well. After 24 hours, a portion of the cells were harvested for flow analysis. The remainder of the cells were maintained in culture and assayed by flow at additional time points.

Primary human CD3+ T cells were isolated by negative selection (T Cell Enrichment Cocktail, STEMCELL TECHNOLOGIES) from peripheral blood and were grown in RPMI+10% FBS+1% PS supplemented with 50 U/mL of IL2, 10 ng/mL IL7, 10 ng/mL IL15. To activate the cells, CD3/CD28 DYNABEADS were added to the cells at a 1:1 bead to cell ratio for 24 hours. After activation, the DYNABEADS were removed, and the T cells were rested for 24 hours before transfection. Primary T cells were washed with PBS and plated at 100K/well in RPMI+10% FBS supplemented with 50 U/mL IL2. For transfection, anti-CD3 conjugated LNPs were dosed in triplicate at 500 ng/well.

PBMC Early Interferon Response

Human Peripheral Blood Mononuclear Cells (PBMCs) were thawed and rested for 24 hours in RPMI+10% FBS+1% PS. 500,000 cells (1M/ml) were plated in a 24 well plate. 250 ng of saRNA encapsulated in LNPs, formulated as described above, was added dropwise to the PBMCs. After 6 or 24 hours, media was harvested by centrifugation and analyzed for interferon expression by ELISA. (Human IFN-alpha All Subtype QUANTIKINE ELISA—R&D SYSTEMS) (Human IFN-beta Duo Set ELISA R&D SYSTEMS). cDNA was generated using High-Capacity cDNA Reverse Transcription Kit (APPLIED BIOSYSTEMS), according to manufacturer's protocols. Quantitative polymerase chain reaction (qPCR) for specific genes was carried out using TAQMAN probes in TAQMAN advanced master mix (THERMO FISHER SCIENTIFIC). Ubiquitin C labeled with the fluorescent dye VIC™ (UBC-VIC) was multiplexed as the endogenous control for all qPCRs.

Animal Maintenance

All animal experiments described in this study were performed in accordance with protocols that were reviewed and approved by an Institutional Animal Care and Use and Committee. All mice were maintained in accredited facilities. Vaccination studies and replication-competent SARS-CoV-2 experiments were performed in a biosafety level 2 (BSL-2) and 3 laboratory (BSL-3).

Virus Production Cell Culture

VeroE6 cells were grown in Dulbecco's modified Eagle's medium (DMEM) (THERMOSCIENTIFIC, Waltham, MA, USA) supplemented with 10% (volume/volume percentage, v/v) heat-inactivated fetal bovine serum (FBS) (BIO-TECHNE, R&D SYSTEMS, Minneapolis, MN, USA) and 1% (v/v) penicillin streptomycin (P/S) (THERMOSCIENTIFIC, Waltham, MA, USA). A549-hACE2/hTMPRSS2 cell lines were maintained in DMEM containing 10% FBS and 1% PS supplemented with 2.5 ug/mL Puromycin and Blasticidin. All cell lines were maintained in a cell incubator at 37° C. with 5% $CO_2$.

SARS-CoV-2 Isolate Stock

All replication-competent SARS-CoV-2 experiments were performed in a BSL-3 facility at. The clinical isolate named 2019-nCoV/USA-WA1/2020 strain (NCBI accession number: MN985325) of SARS-CoV-2 was obtained from BEI RESOURCES (Manassas, VA, USA). SARS-CoV-2 MA30 and SARS-CoV-2 Delta variant were provided by other groups. Viral stocks were prepared and titered as described in Kenney et al., 2022, Cell Rep. 39(3): p. 110714, the content of which is incorporated herein by reference in its entirety.

Mouse Studies 8-10 weeks old male and female C57BL/6J mice were obtained from JACKSON LABORATORIES (Bar Harbor, ME, USA, Catalog #000664). In a BSL-2 and BSL-3 facility, mice were group-housed by sex in TECHNIPLAST green line individually ventilated cages (TECHNIPLAST, Buguggiate, Italy). The room was maintained with a 12:12 light cycle at 30-70% humidity.

Vaccination Studies

Mice were injected intramuscularly (I.M.) in the hind limb with 50 uL of PBS or LNPs containing 10 ng, 100 ng, or 1000 ng of mRNA or saRNA. At 24-hours and 48-hours post vaccination, serum was collected via submandibular bleeding from groups of five mice from the 1000 ng vaccinated groups for analysis of interferon response. At 28 days post vaccination, mice were administrated I.M. with a booster dose of PBS or vaccine (50 uL; similar dosage as primary vaccination). At day 35 post vaccination, mice were transferred into BSL-3 and challenged with MA30 virus.

SARS-CoV-2 Challenge Experiments

Vaccinated and boosted mice were intranasally inoculated with $1\times10^5$ PFU SARS-CoV-2 MA30 virus resuspended in 50 uL of 1×PBS. Mice were inoculated under 1%-3% isoflurane anesthesia. Infected mice were monitored and clinically scored for changes in weight, respiration, appearance, responsiveness and behavior over the course of 14-days post infection. Mice with a cumulative clinical score of 4 or 25% weight loss were euthanized.

Serum Preparation

Blood was collected at the designated time points via submandibular bleeding and serum was isolated by centrifuging blood in a benchtop centrifuge at 3500 revolutions per minute (RPM) for 10 minutes (min) at room temperature. Serum was then collected, transferred into a new EPPENDORF tube and stored at −80° C. for downstream analysis.

Antigen Production in C2C12 Cells

C2C12 cells were grown in DMEM+10% FBS+1% PS, plated at 25,000 cells/well in 96-well TC treated plates, and allowed to adhere overnight. LNPs containing mRNA or saRNA encoding for each antigen were added to cells in triplicate at 100 ng/well, except for HA which was dosed at 25 ng/well. After 24 hours cells were harvested for flow analysis using the following mAbs: SARS-CoV-2 Spike Protein (RBD) Human monoclonal (EBIOSCIENCES—Clone: P05Dhu-AF647 conjugated), Influenza A HIN1 (A/California/07/2009) Hemagglutinin, Rabbit polycloncal: (1:1000 dilution) (SINOBIOLOGICAL—Cat: 11085-T62-APC conjugated). Identical treatments were performed for ELISA confirmation. Cells for ELISA were washed twice in PBS and then resuspended in 1×PBS+0.1% TRITON X-100. Cells were freeze-thawed once before being thoroughly pipetted to ensure lysis and membrane disruption. ELISA was performed use antigen specific sandwich ELISA kits according to manufacturer's protocol (SINOBIOLOGICAL).

Serum Interferon Analysis

Serum interferon alpha and beta were analyzed by ELISA (LEGEND MAX™ Mouse IFN-j3 ELISA Kit-BIOLEGEND) (ELISA MAX™ Deluxe Set Mouse IFN-α1-BIOLEGEND).

TABLE 2

Summary of survival study statistics for group comparisons in FIG. 60 and FIG. 65. Log-rank (Mantel-Cox) test.

| Group 1 | Group 2 | P value |
|---|---|---|
| 10 ng WT saRNA | 10 ng 5 mC saRNA | 0.0497 |
| PBS | 10 ng 5 mC saRNA | 0.0001 |
| PBS | 1000 ng NimY mRNA | <0.0001 |
| PBS | 100 ng WT saRNA | <0.0001 |
| PBS | 100 ng 5 mC saRNA | <0.0001 |
| PBS | 1000 ng WT saRNA | <0.0001 |
| PBS | 1000 ng 5 mC saRNA | <0.0001 |

Figure 68:
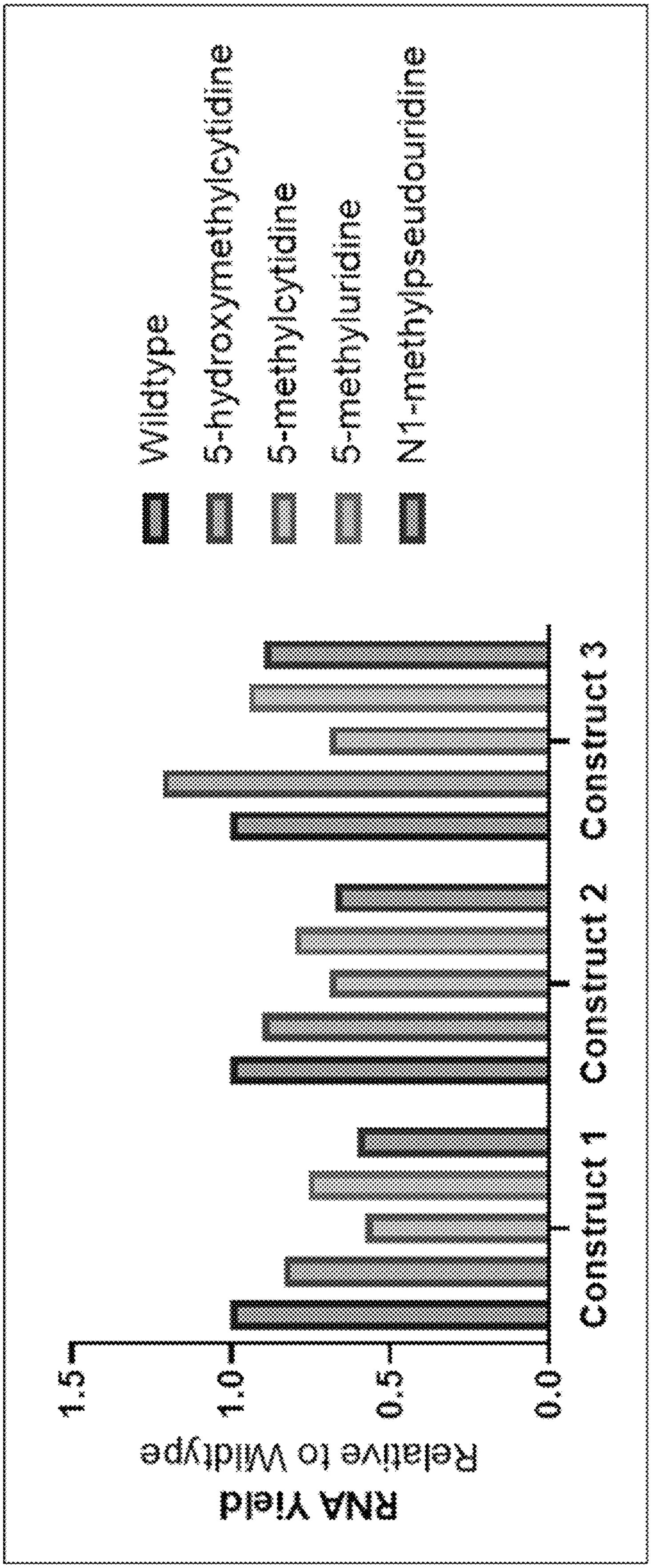
FIG. 68. shows yield of self-amplifying RNA constructs after in vitro transcription without modified nucleotides (wildtype) or 100% substitution of cytidine or uridine with 5-hydroxymethylcytidine, 5-methylcytidine or 5-methlyuridine, N1-methylpseudouridine respectively. Reported yields are relative to wildtype for each construct. Left-right order of the bars in each group corresponds to top-down order in the legend.

Example 21: Improved Yield of Self-Amplifying RNA with Complete Substitution of Cytidine for 5-Hydroxymethylcytdine This example demonstrates the unexpected finding that self-amplifying RNA synthesized with complete replacement of cytidine with 5-hydroxymethylcytidine resulted in greater yields than replacement of cytidine with 5-methylcytidine or replacement of uridine with 5-methyluridine or N1-methylspeudouridine. In this example, three different saRNA plasmid DNA templates were prepared containing the coding sequence of NSP1-4 of VEEV, and the SARS-CoV-2 Spike sequence (Construct 1), the RSV fusion protein sequence (Construct 2), or an mCherry fluorescent reporter sequence (Construct 3). The plasmids were cloned in DH5alpha *E. coli* and purified using a ZymoPURE™ 11 Plasmid Midiprep Kit (ZYMO RESEARCH). The promoter region was a CLEANCAP AU (TRILINK BIOTECHNOLOGIES) compatible T7 promoter (Promoter seq: TAATACGACTCACTATAAT; SEQ ID NO: 1). Plasmids were linearized with MluI-HF for 3 hours at 37° C., and linearized template was purified using QIAQUICK PCR PURIFICATION KIT (QIAGEN). saRNA was synthesized using MEGASCRIPT T7 TRANSCRIPTION KIT (INVITROGEN™, THERMOFISHER SCIENTIFIC) with 1p g template, co-transcriptional capping using CLEANCAP AU (final conc. 4 mM), and a 3 hour incubation (TRILINK BIOTECHNOLOGIES). The final concentration of all NTPs, either modified or unmodified, was 5 mM. IVT was followed by 10 min DNase treatment and 30 min post-transcriptional poly-adenylation using a Poly(A) Tailing Kit (INVITROGEN™, THERMOFISHER SCIENTIFIC). saRNA was purified using MEGACLEAR™ TRANSCRIPTION CLEAN-UP KIT (INVITROGEN™ THERMOFISHER SCIENTIFIC) and eluted in Dnase/Rnase free $H_2O$ prior to storing at −80° C. The A260 of all modNTPs was empirically determined using a NANODROP2000 (THERMOFISHER SCIENTIFIC). The adjusted factor for each modNTP was used to calculate RNA concentration after in vitro synthesis to adjust for discrepancies in quantification from inclusion of the different modifications. The complete substitution of cytidine for 5-methylcytidine resulted in a 34.8% lower RNA yield on average (see e.g., FIG. 68). Unexpectedly, the substitution of cytidine for 5-hydroxymethylcytidine resulted in only a 1.5% lower RNA yield on average. By comparison, complete substitution of uridine for 5-methyluridine resulted in a 16.5% lower RNA yield on average. Complete substitution of uridine for N1-methylspeudouridine resulted in a 27.6% lower RNA yield on average. In conclusion this example demonstrates the unexpected result that the complete substitution of cytidine with 5-hydroxymethylcytidine decreases the overall RNA yield less than by inclusion of other nucleotide modifications.

Figure 69:
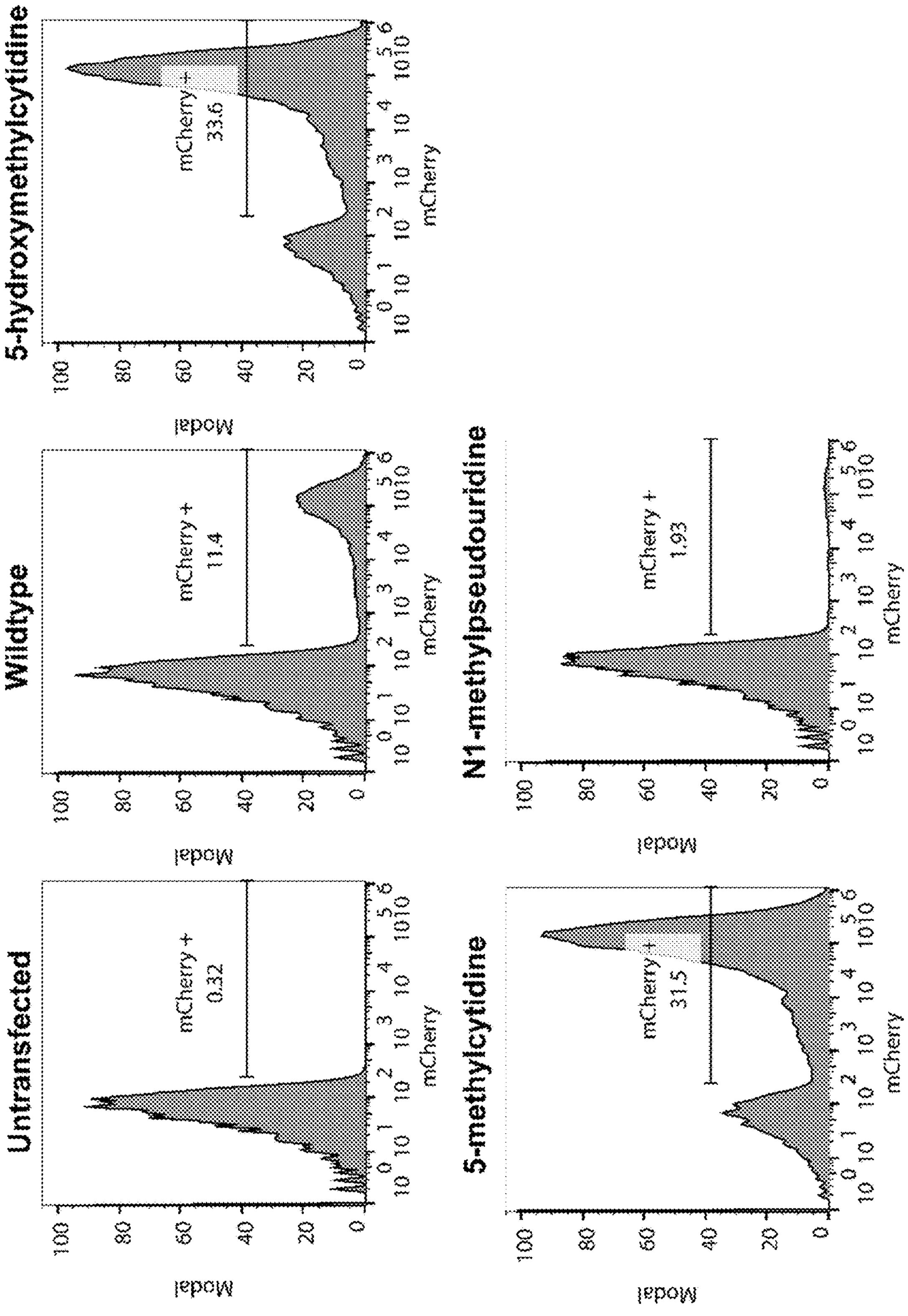
FIG. 69 is a series of flow cytometry results showing the distribution of mCherry expression 24 hours after LNP mediated transfection of Jurkat cells.

Example 22: Improved Transfection of Jurkat Cells Transfected with Self-Amplifying RNA with Complete Substitution of Cytidine for 5-Methylcytidine or 5-Hydroxymethylcytidine This example demonstrates the unexpected finding that self-amplifying RNA synthesized with complete replacement of cytidine with 5-hydroxymethylcytidine or 5-methylcytidine resulted in improved lipid nanoparticle (LNP) mediated transfection to Jurkat cells when compared with unmodified self-amplifying RNA. A self-amplifying RNA reporter encoding mCherry was synthesized by in vitro transcription saRNA was synthesized using MEGASCRIPT T7 TRANSCRIPTION KIT (INVITROGEN™, THERMOFISHER SCIENTIFIC) with 1 μg template, co-transcriptional capping using CLEANCAP AU (final conc. 4 mM), and a 3 hour incubation (TRILINK BIOTECHNOLOGIES). The final concentration of all NTPs, either modified or unmodified, was 5 mM. To synthesize wildtype saRNA, all of the nucleotides were unmodified. To synthesize 5-hydroxymethylctydine saRNA, 100% of cytidine was replaced by 5-hydroxymethylcytidine. To synthesize 5-methylcytidine saRNA, 100% of cytidine was replaced by 5-methylcytidine. To synthesize N1-methylpseudouridine, 100% of uridine was replaced by N1-methylpseudouridine. IVT was followed by 10 min Dnase treatment and 30 min post-transcriptional poly-adenylation using a Poly(A) Tailing Kit (INVITROGEN™, THERMOFISHER SCIENTIFIC). saRNA was purified using MEGAclear™ Transcription Clean-up Kit (INVITROGEN™ THERMOFISHER SCIENTIFIC) and eluted in Dnase/Rnase free $H_2O$ prior to storing at −80 degrees. The A260 of all modNTPs was empirically determined using a NANODROP2000 (THERMOFISHER SCIENTIFIC). The adjusted factor for each modNTP was used to ensure accurate loading of lipid nanoparticles (LNPs) with saRNA. Lipid nanoparticles comprised of an ionizable lipid (50 mol %), dioleoylphosphatidylethanolamine (DOPE) (10 mol %), cholesterol (38.5 mol %) and 1,2-dimyristoyl-rac-glycero-3-methoxypolyethylene glycol-2000 (DMG-PEG2K) (1.5 mol %) containing each saRNA construct were synthesized at a N:P ratio (the ratio of positively-chargeable polymer amine (N=nitrogen) groups to negatively-charged nucleic acid phosphate (P) groups) of 10. The resulting lipid nanoparticles were dialyzed in phosphate-buffered saline (PBS) for 24 hours. RNA encapsulation efficiency was determined using a QUANTIFLUOR assay (PROMEGA). Jurkat cells were grown in Roswell Park Memorial Institute (RPMI) RPMI medium+10% fetal bovine serum (FBS)+1% Penicillin/Streptomycin (PS) and maintained between $5\times10^5$ and $2\times10^6$ cells/ml. Prior to transfection, the cells were washed with PBS and plated in fresh RPMI at 100,000 cells/well. LNPs containing saRNA with or without modified nucleosides were added dropwise to cells in triplicate at 100 ng/well. After 24 hours, the cells were washed and prepared for flow cytometry. Flow cytometry analysis showed a significant enhancement in transfection efficiency for Jurkat cells transfected with 5-hydroxymethylcytidine or 5-methylcytidine substituted RNA, when compared with wildtype saRNA or N1-methylpseudouridine substituted saRNA (see e.g., FIG. 69). In conclusion, this unexpected result demonstrates that saRNA fully substituted with 5-hydroxymethylcytidine or 5-methylcytidine is capable of improved LNP mediated transfection and expression of a cargo protein, in contrast to unmodified saRNA or saRNA modified with other modified nucleotides such as N1-methylpseudouridine.

Figure 70:
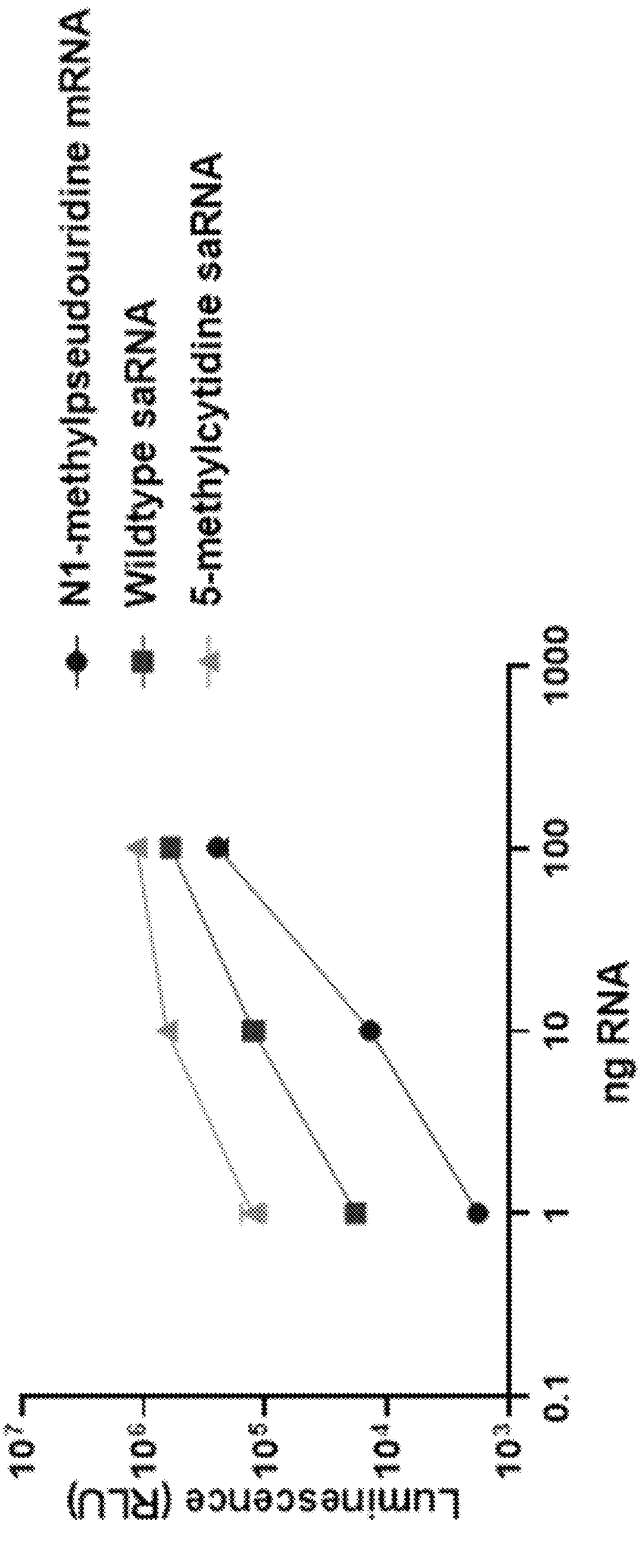
FIG. 70 shows an analysis of firefly luciferase reporter expression in HEK293-T cells transfected with LNPs containing N1-methylpseudouridine mRNA, unmodified (wildtype) saRNA, or 5-methylcytidine modified saRNA.

Example 23: Improved Protein Expression in Cells Transfected with Low Doses of Self-Amplifying RNA with Complete Substitution of Cytidine for 5-Methylcytidine This example demonstrates the unexpected finding that self-amplifying RNA synthesized with complete substitution of cytidine for 5-methylcytidine resulted in improved protein production by low dose LNP transfection. A self-amplifying (saRNA) or non-amplifying (mRNA) reporter constructs encoding firefly luciferase were synthesized by in vitro transcription. Both RNA constructs were synthesized using MEGASCRIPT T7 Transcription kit (INVITROGEN™, THERMOFISHER SCIENTIFIC) with 1p g template, co-transcriptional capping using CLEANCAP AU (final conc. 4 mM), and a 3 hour incubation (TRILINK BIOTECHNOLOGIES). The final concentration of all NTPs, either modified or unmodified, was 5 mM. To synthesize wildtype saRNA, all of the nucleotides were unmodified. To synthesize 5-methylcytidine saRNA, 100% of cytidine was replaced by 5-methylcytidine. To synthesize N1-methylpseudouridine mRNA, 100% of uridine was replaced by N1-methylpseudouridine. IVT was followed by 10 min Dnase treatment and 30 min post-transcriptional poly-adenylation using a Poly(A) Tailing Kit (INVITROGEN™, THERMOFISHER SCIENTIFIC). saRNA was purified using MEGACLEAR™ TRANSCRIPTION CLEAN-UP KIT (INVITROGEN™ THERMOFISHER SCIENTIFIC) and eluted in Dnase/RNase free $H_2O$ prior to storing at −80 degrees. The A260 of all modNTPs was empirically determined using a NANODROP2000 (THERMOFISHER SCIENTIFIC). The adjusted factor for each modNTP was used to ensure accurate loading of lipid nanoparticles with mRNA or saRNA. Lipid nanoparticles comprised of an ionizable lipid (50 mol %), DOPE (10 mol %), cholesterol (38.5 mol %) and DMG-PEG2K (1.5 mol %) containing each saRNA construct were synthesized at a N:P ratio of 10. The resulting lipid nanoparticles were dialyzed in PBS for 24 hours. The RNA encapsulation efficiency was determined using a QUANTIFLUOR assay (PROMEGA). 24 hours before transfection, 25K HEK293-T cells were plated in 200 μL of Dulbecco's Modified Eagle Medium (DMEM) containing 10% FBS and 1% P/S. For each construct, 100 ng, 10 ng, and 1 ng of RNA containing LNPs were added to wells in triplicate. To measure the production of the luciferase reporter protein, BRIGHTGLO reagent was added to the wells 24 hours after transfection. The luciferase signal was read with a spectrophotometer. Analysis of the luminescence signal showed that increased expression of the reporter occurred in cells transfected with 5-methylcytidine containing saRNA by comparison to expression from cells transfected with N1-methylpseudouridine containing mRNA or wildtype (unmodified) saRNA (see e.g., FIG. 70). Unexpectedly, the difference between the treatment groups was more pronounced as the dose of RNA administered was decreased (see e.g., Table 3A-3B). In conclusion this example demonstrates the unexpected result that saRNA modified with 5-methylcytidine shows improved expression over unmodified saRNA or modified mRNA and that the improved expression is more pronounced at lower doses.

TABLE 3A

Analysis of luciferase reporter expression in HEK cells. Expression is normalized to the level of expression of the N1-methylpseudouridine luciferase reporter at each dosage level.

| Dose | N1mU mRNA | WT saRNA | 5 mC saRNA |
|---|---|---|---|
| 1 ng | 1.00 | 2.41 | 4.63 |
| 10 ng | 1.00 | 9.13 | 46.87 |
| 100 ng | 1.00 | 9.98 | 70.55 |
| Average | 1.00 | 7.17 | 40.68 |

TABLE 3B

Analysis of luciferase reporter expression in HEK cells. Expression is normalized to the level of expression from the unmodified saRNA (WT saRNA) luciferase reporter at each dosage level.

| Dose | N1mU mRNA | WT saRNA | 5 mC saRNA |
|---|---|---|---|
| 1 ng | 0.10 | 1.00 | 7.07 |
| 10 ng | 0.11 | 1.00 | 5.13 |
| 100 ng | 0.42 | 1.00 | 1.92 |
| Average | 0.21 | 1.00 | 4.71 |

Figure 71:
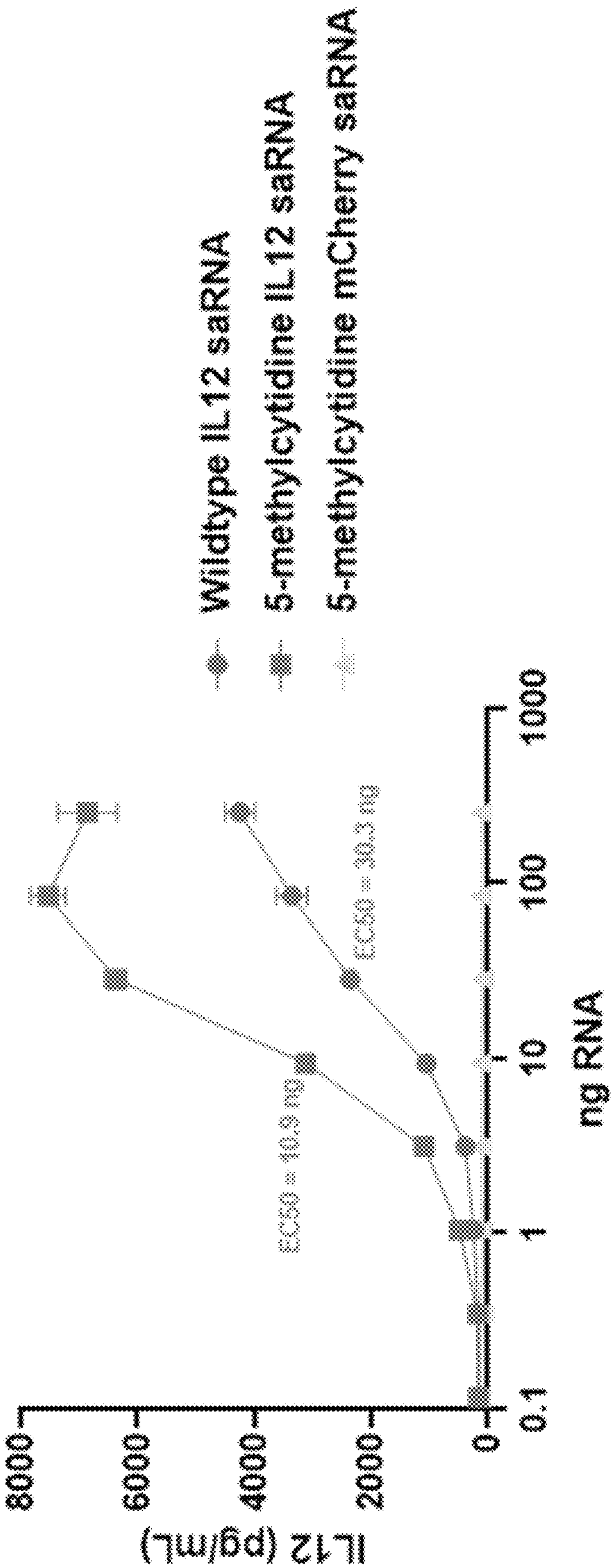
FIG. 71 shows an analysis of IL12 p70 expression in HEK293-T cells transfected with LNPs containing unmodified (wildtype) saRNA, or 5-methylcytidine modified saRNA.

Example 24: Improved Expression of Secreted Proteins in Cells Transfected with Self-Amplifying RNA with Complete Substitution of Cytidine by 5-Methylcytidine This example demonstrates the unexpected finding that self-amplifying RNA synthesized with complete replacement of cytidine for 5-methylcytidine results in improved production of a secreted protein, interleukin-12 (IL12). IL12 is a heterodimeric protein consisting of two chains, an alpha and beta chain. IL12 can be expressed in its active form as a monomeric protein by insertion of a linker between the two chains with an uninterrupted protein reading frame. A self-amplifying RNA reporter encoding this bioactive form of IL-12 was synthesized by in vitro transcription saRNA was synthesized using MEGASCRIPT T7 TRANSCRIPTION KIT (INVITROGEN™, THERMOFISHER SCIENTIFIC) with 1p g template, co-transcriptional capping using CLEANCAP AU (final conc. 4 mM), and a 3 hour incubation (TRILINK BIOTECHNOLOGIES). The final concentration of all NTPs, either modified or unmodified, was 5 mM. To synthesize wildtype saRNA, all of the nucleotides were unmodified. To synthesize 5-methylcytidine saRNA, 100% of cytidine was replaced by 5-methylcytidine. As a control, saRNA encoding mCherry was synthesized with complete substitution of cytidine for 5-methylcytidine. IVT was followed by 10 min DNase treatment and 30 min post-transcriptional poly-adenylation using a Poly(A) Tailing Kit (INVITROGEN™, THERMOFISHER SCIENTIFIC). saRNA was purified using MEGACLEAR™ TRANSCRIPTION CLEAN-UP KIT (INVITROGEN™ THERMOFISHER SCIENTIFIC) and eluted in DNase/RNase free $H_2O$ prior to storing at −80 degrees. The A260 of all modNTPs was empirically determined using a NANODROP2000 (THERMOFISHER SCIENTIFIC). The adjusted factor for each modNTP was used to ensure accurate loading of lipid nanoparticles with saRNA. Lipid nanoparticles comprised of an ionizable lipid (50 mol %), DOPE (10 mol %), cholesterol (38.5 mol %) and DMG-PEG2K (1.5 mol %) containing each saRNA construct were synthesized at a N:P ratio of 10. The resulting lipid nanoparticles were dialyzed in PBS for 24 hours. RNA encapsulation efficiency was determined using a QUANTIFLUOR assay (PROMEGA). 24 hours before transfection, 25K HEK293-T cells were plated in 200 uL of DMEM containing 10% FBS and 1% P/S. For each construct, an 8-point 3-fold serial dilution of the RNA containing LNPs was performed to dose cells at doses in the range of 250 ng to 0.11 ng. RNA containing LNPs were added to wells in triplicate. After 24 hours, supernatant from the transfected cells was harvested and analyzed by ELISA specific to IL-12 p70 (R&D SYSTEMS). Unexpectedly, the cells transfected with the 5-methylcytidine modified saRNA encoding IL12 resulted in greater IL12 secretion into the media than cells transfected by wildtype (unmodified saRNA) (see e.g., FIG. 71). The concentration necessary to achieve 50% of the maximum observed concentration of IL12 (EC50) for wildtype saRNA was 30.3 ng. Unexpectedly, the EC50 was decreased approximately 3-fold for the 5-methylcytidine modified saRNA to 10.9 ng.

In a therapeutic context, a cancer patient is injected intratumorally with 5mC modified saRNA encoding IL12 that is contained in a pharmaceutically acceptable delivery carrier. The administered dose is significantly less than the dose required for equivalent bioactivity from wildtype unmodified saRNA. The expression of IL12 occurs at bioactive levels for sufficient duration to recruit immune cells and result in tumor clearance. In conclusion, this example demonstrates the unexpected result that 5-methylcytidine substituted RNA resulted in improved expression of a secreted protein.

Example 25: Highly Substituted Self-Amplifying RNA for Expression of an Antibody or Antibody Fragment This example details the use of self-amplifying RNA (saRNA) with 100% substitution of cytidine for 5-methylcytidine or 5-hydroxymethylcytidine as a method to elicit a protective or therapeutic response against pathogens, cancer, or other biological agents that inflict disease. Self-amplifying RNA containing 5-hydroxymethylctydine or 5-methylcytidine is synthesized by in vitro transcription. The self-amplifying RNA encodes a monoclonal antibody, an antibody fragment, or multiple antibody fragments from different antibody clones. Distinct antibody fragments are linked together to form a hybrid molecule that can engage unique targets. The antibody or antibody fragments have specificity to a particular protein, nucleic acid, peptide, receptor, or other biological material. The expression of the antibody or antibody fragment from modified self-amplifying RNA transfected cells or tissue results in prophylactic neutralization of pathogens, clearing of cancer, or clearing of other biological agents that inflict disease. Alternatively, the expression of the antibody or antibody fragment results in stimulation or inhibition of a biological pathway that reduces disease burden. For prophylactic treatment against pathogens, a patient receiving an injection of 5-methylcytidine or 5-hydroxymethylcytidine modified saRNA encoding an antibody or antibody fragment results in neutralization of the suspected pathogen to prevent infectious disease. For clearing of cancer, the antibody or antibody fragment binds an extracellular receptor or protein with activity that drives proliferation. A hybrid molecule binds T cells and a marker on diseased cells or cells that inflict disease, resulting in targeted cytotoxicity of T cells against the diseased cells. The administration of the modified saRNA occurs intravenously, intradermally, subcutaneously, or preferably intramuscularly by delivery with a pharmaceutically acceptable delivery carrier. The expression of the antibody or antibody fragment occurs for longer and at higher levels when compared to an equivalent dose by modified messenger RNA or unmodified self-amplifying RNA.

Figure 72:
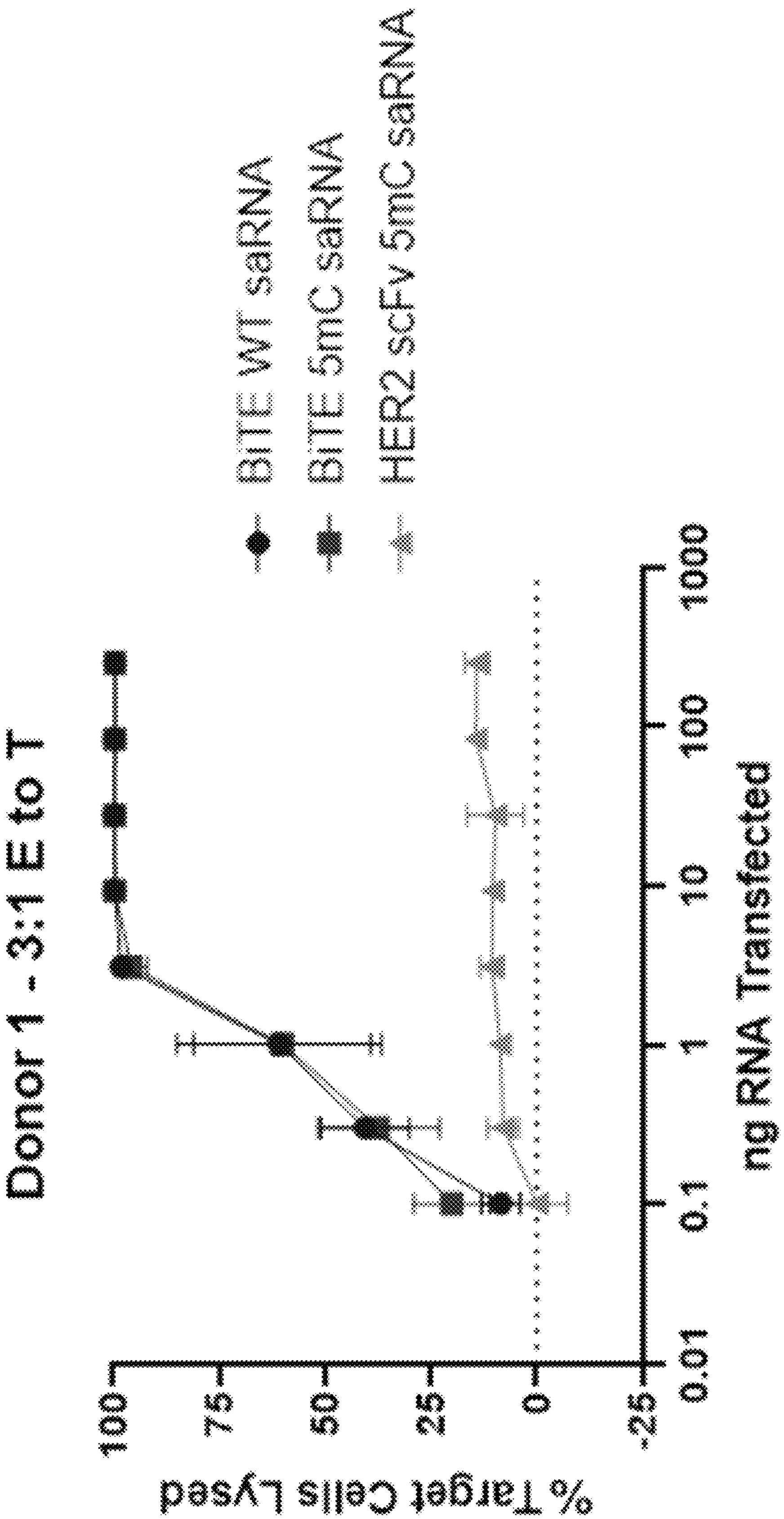
FIG. 72 shows target cell lysis of primary human T cells co-cultured with HER2 expressing Nalm6 cells and supernatant from C2C12 cells transfected with unmodified (WT) or 5-methylcytidine (5mC) modified saRNA encoding a HER2 bispecific T cell engager (BiTE).
Figure 73:
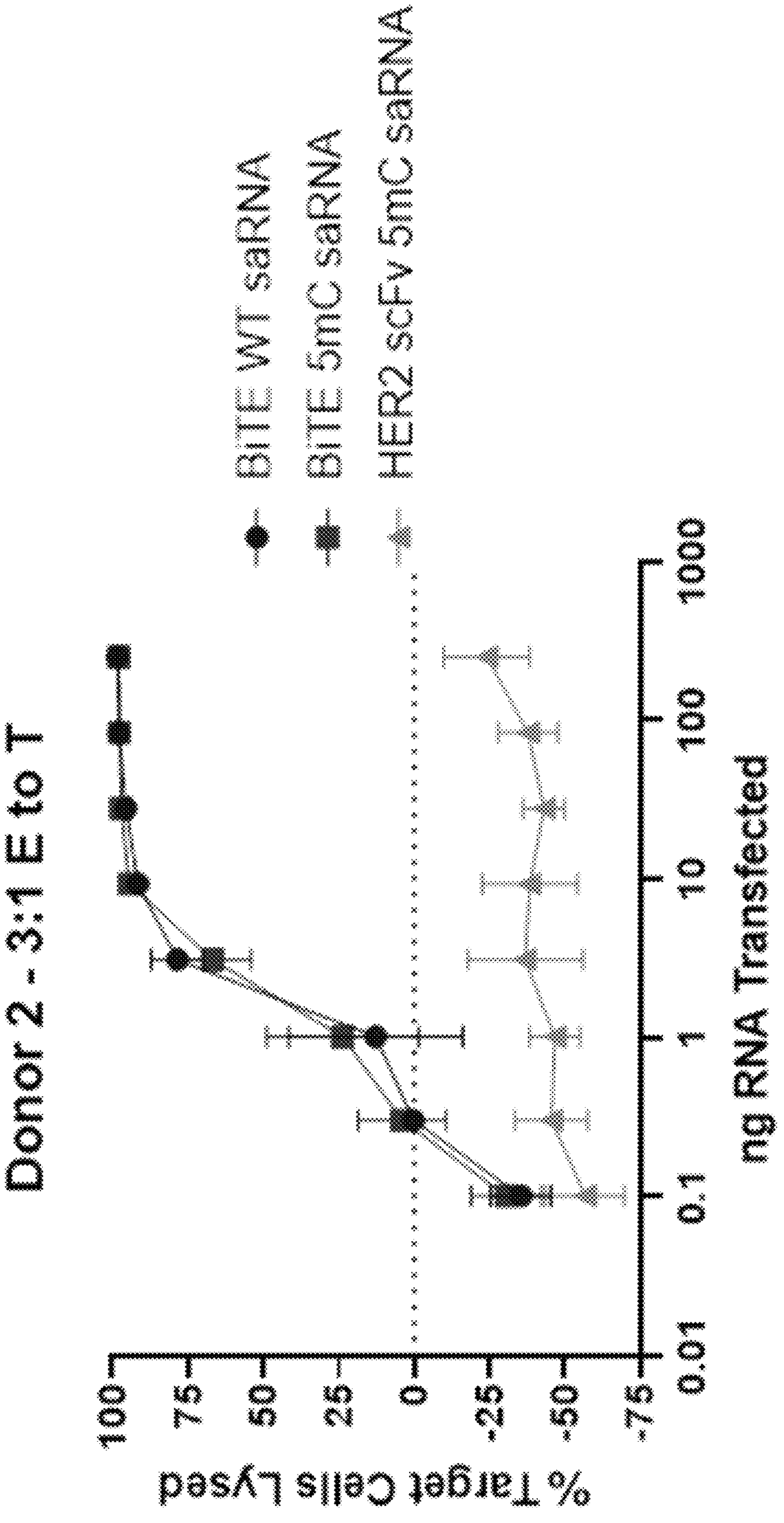
FIG. 73 shows target cell lysis of primary human T cells co-cultured with HER2 expressing Nalm6 cells and supernatant from C2C12 cells transfected with unmodified (WT) or 5-methylcytidine (5mC) modified saRNA encoding a HER2 bispecific T cell engager (BiTE).
Figure 74:
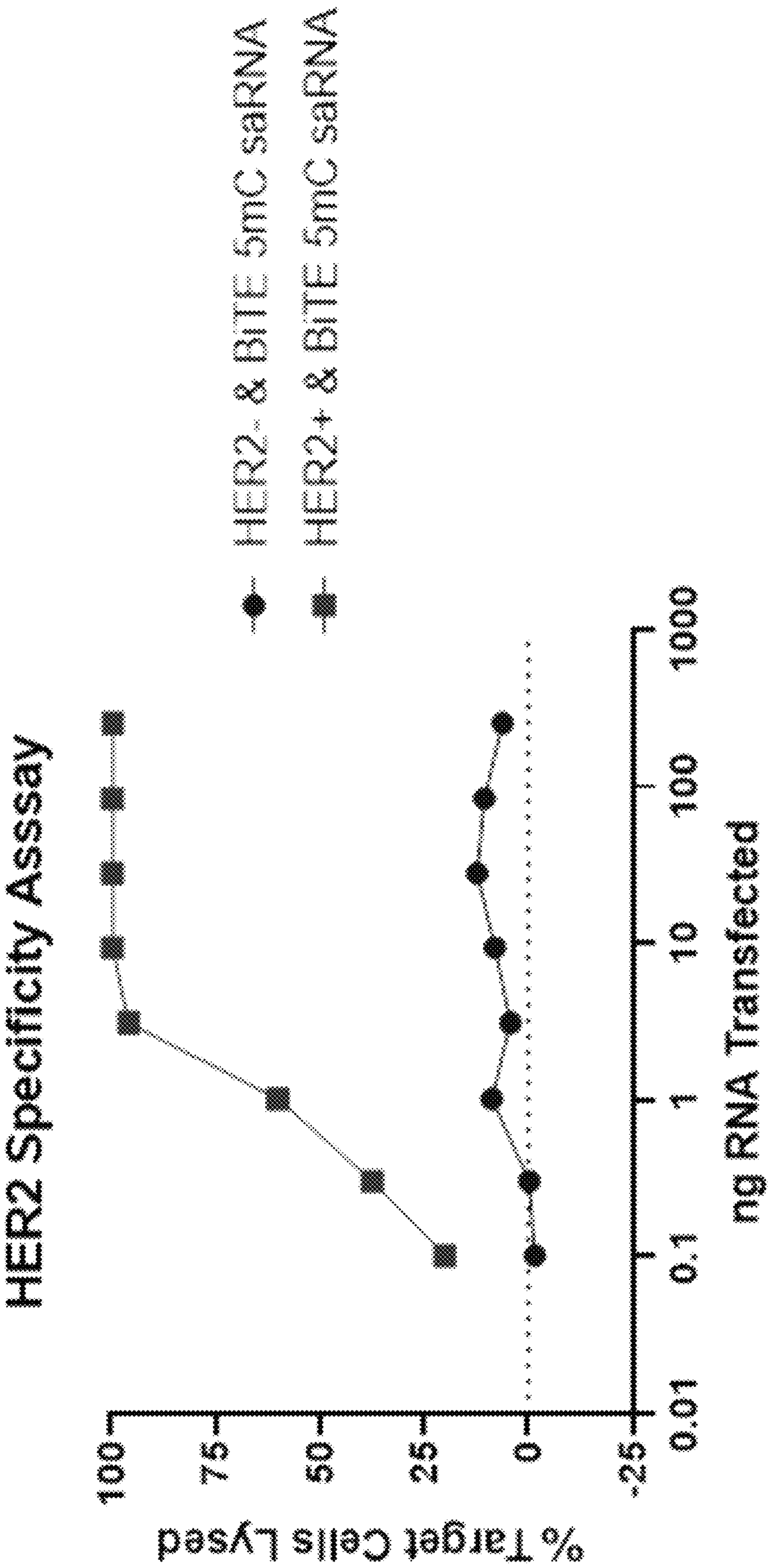
FIG. 74 shows target cell lysis of primary human T cells co-cultured with HER2 negative wildtype Nalm6 cells or HER2 expressing Nalm6 cells and supernatant from C2C12 cells transfected with unmodified (WT) or 5-methylcytidine (5mC) modified saRNA encoding a HER2 bispecific T cell engager (BiTE).

Example 26: Potent Secretion of a Bispecific T Cell Engager from Cells Transfected with Self-Amplifying RNA with Complete Substitution of Cytidine for 5-Methylcytidine This example demonstrates an unexpected result, when cells are transfected with self-amplifying RNA encoding a bispecific T cell engager, in which 5-methylcytidine replaces cytidine, production of a functional protein occurs at levels equal to or greater than the levels from unmodified self-amplifying RNA. A plasmid template containing the sequence of a self-amplifying RNA encoding a bispecific T cell engager (BiTE) targeting HER2 was generated by cloning. As a control, a self-amplifying RNA encoding a HER2 scFv was generated. Both RNA constructs were synthesized using MEGASCRIPT T7 TRANSCRIPTION KIT (INVITROGEN™, THERMOFISHER SCIENTIFIC) with 1 μg template, co-transcriptional capping using CLEANCAP AU (final conc. 4 mM), and a 3-hour incubation (TRILINK BIOTECHNOLOGIES). The final concentration of all NTPs, either modified or unmodified, was 5 mM. To synthesize wildtype saRNA, all of the nucleotides were unmodified. To synthesize 5-methylcytidine saRNA, 100% of cytidine was replaced by 5-methylcytidine. IVT was followed by 10 min DNase treatment and 30 min post-transcriptional poly-adenylation using a Poly(A) Tailing Kit (INVITROGEN™, THERMOFISHER SCIENTIFIC). saRNA was purified using MEGACLEAR™ TRANSCRIPTION CLEAN-UP KIT (TNVITROGEN™ THERMOFISHER SCIENTIFIC) and eluted in DNase/RNase free $H_2O$ prior to storing at −80 degrees. The A260 of all modNTPs was empirically determined using a NANODROP2000 (THERMOFISHER SCIENTIFIC). The adjusted factor for each modNTP was used to ensure accurate loading of lipid nanoparticles with mRNA or saRNA. Lipid nanoparticles comprised of an ionizable lipid (50 mol %), DOPE (10 mol %), cholesterol (38.5 mol %) and DMG-PEG2K (1.5 mol %) containing each saRNA construct were synthesized at a N:P ratio of 10. The resulting lipid nanoparticles were dialyzed in PBS for 24 hours. The RNA encapsulation efficiency was determined using a QUANTIFLUOR assay (PROMEGA). 24 hours before transfection, 25K C2C12 cells were plated in 200 μL of DMEM containing 10% FBS and 1% P/S. For each construct, an 8-point 3-fold serial dilution of the RNA containing LNPs was performed to dose cells at doses in the range of 250 ng to 0.11 ng. After 24 hours, supernatant was harvested from the cells. Primary human CD3+ T cells were isolated by negative selection from peripheral blood derived from two distinct donors and were grown in RPMI+10% FBS+1% PS supplemented with 50 U/mL of IL2, 10 ng/mL IL7, 10 ng/mL IL15. To activate the cells, CD3/CD28 Dynabeads were added to the cells at a 1:1 bead to cell ratio for 24 hours. After activation, the Dynabeads were removed, and the T cells were allowed to recover for 24 hours before transfection. Nalm6 cells do not express HER2 naturally. HER2-positive Nalm6 cells were generated by lentiviral transduction with a vector encoding the extracellular domain from the HER2 receptor. Primary T cells (75K/well) were washed with PBS and plated with HER2-negative or HER2-positive Nalm6 cells (25K/well) containing a luciferase reporter at 3:1 effector to target ratio in RPMI+10% FBS+1% PS. The supernatant from the transfected C2C12 were added to the co-culture at 1:10 dilution. After 24 hours, the luciferase signal from the target cells was measured by addition of BRIGHTGLO reagent (PROMEGA) and the signal was read from a spectrophotometer. The percentage of target cell lysis was calculated with the following formula: [(Target cell only signal) −(Target cell + T cell signal)]÷(Target cell signal)*100%. Unexpectedly, introduction of supernatant from C2C12 cells transfected with HER2 specific BiTE saRNA modified with 5mC led to target cell lysis in both donors, reaching levels equivalent to or surpassing those achieved with supernatant from cells transfected with HER2 specific BiTE unmodified saRNA (see e.g., FIG. 72 and FIG. 73). The observed target cell lysis was dependent on HER2 expression, since HER2 negative Nalm6 cells were not lysed by the addition of the supernatant containing the secreted bispecific T cell engager (see e.g., FIG. 74). In conclusion, this example demonstrates the unexpected result that 5-methylcytidine substituted RNA resulted in potent expression of a bispecific T cell engager at levels equal to or greater than the levels from unmodified RNA.

Figure 75:
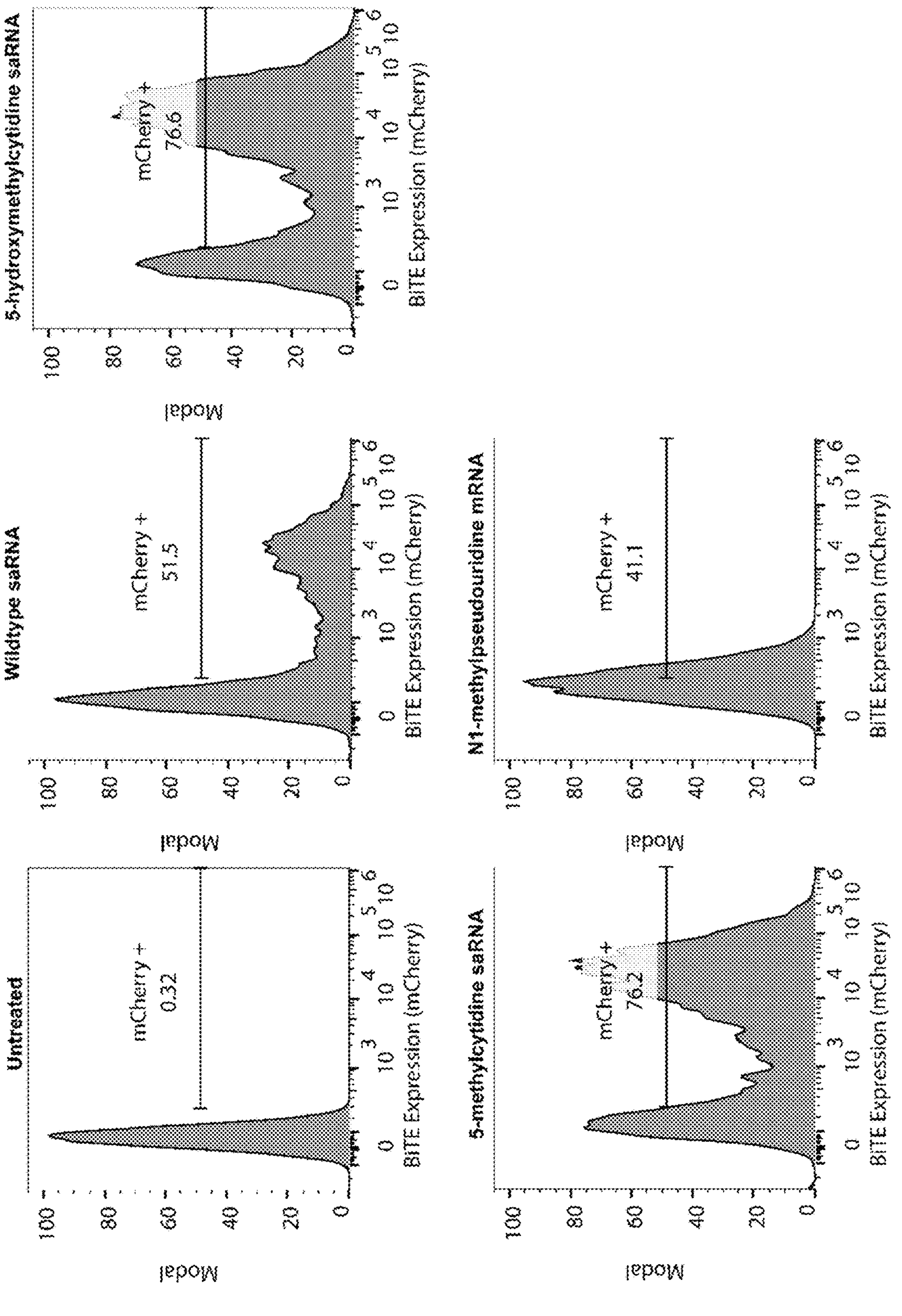
FIG. 75 is a series of flow cytometry results showing the distribution of the mCherry reporter expression 24 hours after LNP mediated transfection of C2C12 cells with an saRNA or mRNA encoding a HER2 bispecific antibody.
Figure 76:
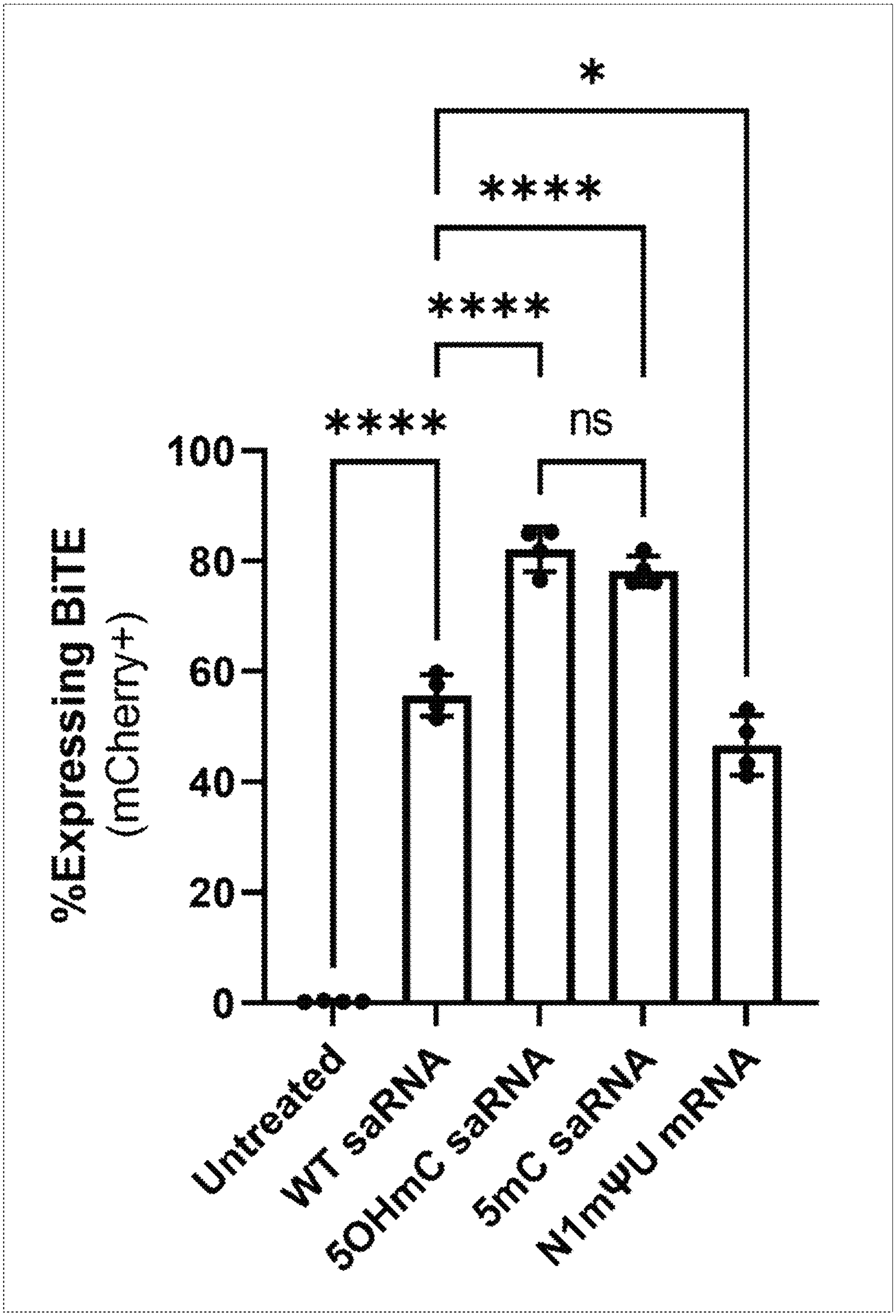
FIG. 76 shows the percentage of C2C12 cells transfected by LNPs containing the indicated RNA constructs. The percentage of cells expressing the encoded protein was determined by measurement of the mCherry reporter.
Figure 77:
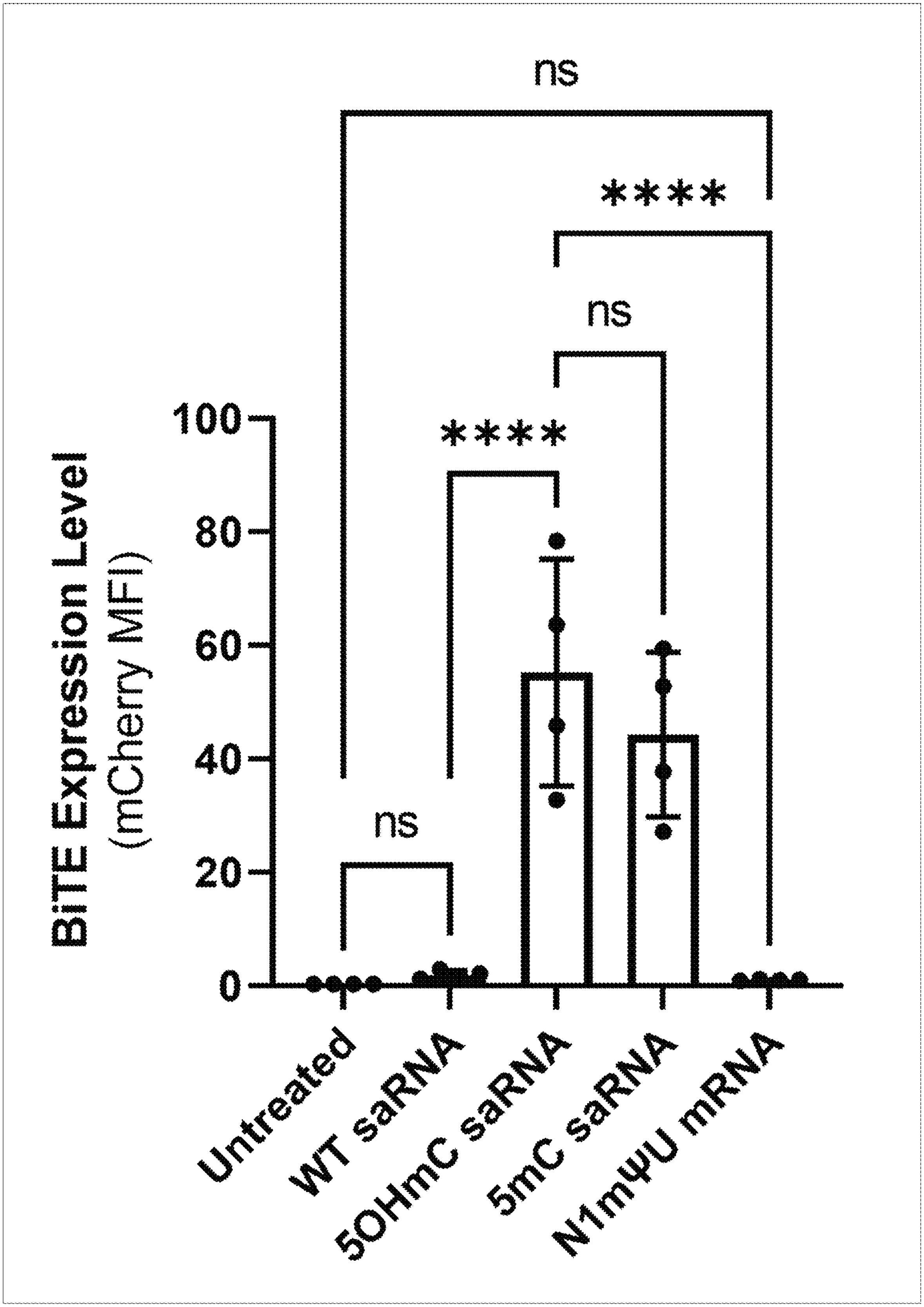
FIG. 77 shows relative expression of a bispecific T cell engager in C2C12 cells transfected by LNPs containing each RNA construct, as measured by median fluorescence intensity of an mCherry reporter.

Example 27: Improved Expression of a Bispecific T Cell Engager from Self-Amplifying RNA with Complete Substitution of 5-Hydroxymethylcytidine or 5-Methylcytidine This example demonstrates the unexpected finding that self-amplifying RNA encoding a bispecific T cell engager, with complete replacement of cytidine with 5-hydroxymethylcytidine or 5-methylcytidine, exhibits higher expression levels compared to unmodified self-amplifying RNA or mRNA modified with N1-methylspeudouridine. Plasmid templates containing the sequence of a self-amplifying RNA and a non-replicating mRNA encoding a bispecific T cell engager (BiTE) targeting HER2 and human CD3 and an mCherry reporter separated by a P2A sequence were generated by cloning. RNA was synthesized by in vitro transcription using the MEGASCRIPT T7 Transcription kit (INVITROGEN™, THERMOFISHER SCIENTIFIC) with 1 μg template, co-transcriptional capping using CLEANCAP AU (final conc. 4 mM), and a 3 hour incubation (TRILINK BIOTECHNOLOGIES). The final concentration of all NTPs, either modified or unmodified, was 5 mM. To synthesize wildtype saRNA (WT saRNA), all of the nucleotides were unmodified. To synthesize 5-hydroxymethylctydine saRNA (5OHmC saRNA), 100% of cytidine was replaced by 5-hydroxymethylcytidine. To synthesize 5-methylcytidine saRNA, 100% of cytidine was replaced by 5-methylcytidine (5mC saRNA). To synthesize N1-methylpseudouridine, 100% of uridine was replaced by N1-methylpseudouridine (N1mψU mRNA). IVT was followed by a 10 min DNase treatment and 30 min post-transcriptional poly-adenylation using a Poly(A) Tailing Kit (INVITROGEN™, THERMOFISHER SCIENTIFIC). The resulting RNA was purified using MEGACLEAR™ Transcription Clean-up Kit (INVITROGEN™ THERMOFISHER SCIENTIFIC) and eluted in DNase/RNase free $H_2O$ prior to storing at −80 degrees. The A260 of all modNTPs was empirically determined using a NANODROP2000 (THERMOFISHER SCIENTIFIC). The adjusted factor for each modNTP was used to ensure accurate loading of lipid nanoparticles with saRNA. Lipid nanoparticles comprised of an ionizable lipid (50 mol %), DOPE (10 mol %), cholesterol (38.5 mol %) and DMG-PEG2K (1.5 mol %) containing each RNA construct were synthesized at a N:P ratio of 10. The resulting lipid nanoparticles were dialyzed in PBS for 24 hours. RNA encapsulation efficiency was determined using a QUANTIFLUOR assay (PROMEGA). 24 hours before transfection, 40K C2C12 cells were plated in a 48 well containing 400 μL of DMEM prepared with 10% FBS and 1% P/S. Each RNA construct was transfected at a dose of 200 ng with 4 biological replicates. After 24 hours the expression of the bispecific T cell engager was determined by measurement of the mCherry reporter via flow cytometry. Viable cells were identified by staining with DAPI. In all conditions, the viability of the cells was >90%. Unexpectedly, flow cytometry analysis showed a significant enhancement in transfection efficiency for C2C12 cells transfected with 5-hydroxymethylcytidine or 5-methylcytidine substituted saRNA, when compared with wildtype saRNA or N1-methylpseudouridine substituted saRNA (see e.g., FIG. 75). The proportion of transfected viable cells was significantly enhanced for the saRNA containing complete substitution of 5-hydroxymethylcytidine or 5-methylcytidine when compared to the unmodified saRNA (see e.g., FIG. 76). The expression level was determined by measurement of the median fluorescence intensity of the mCherry reporter for the viable cell population. Unexpectedly, the expression levels were significantly greater for the 5-hydroxymethylcytidine or 5-methylcytidine modified saRNA when compared with the unmodified saRNA or N1-methylpseudouridine modified mRNA (see e.g., FIG. 77).

Figure 78:
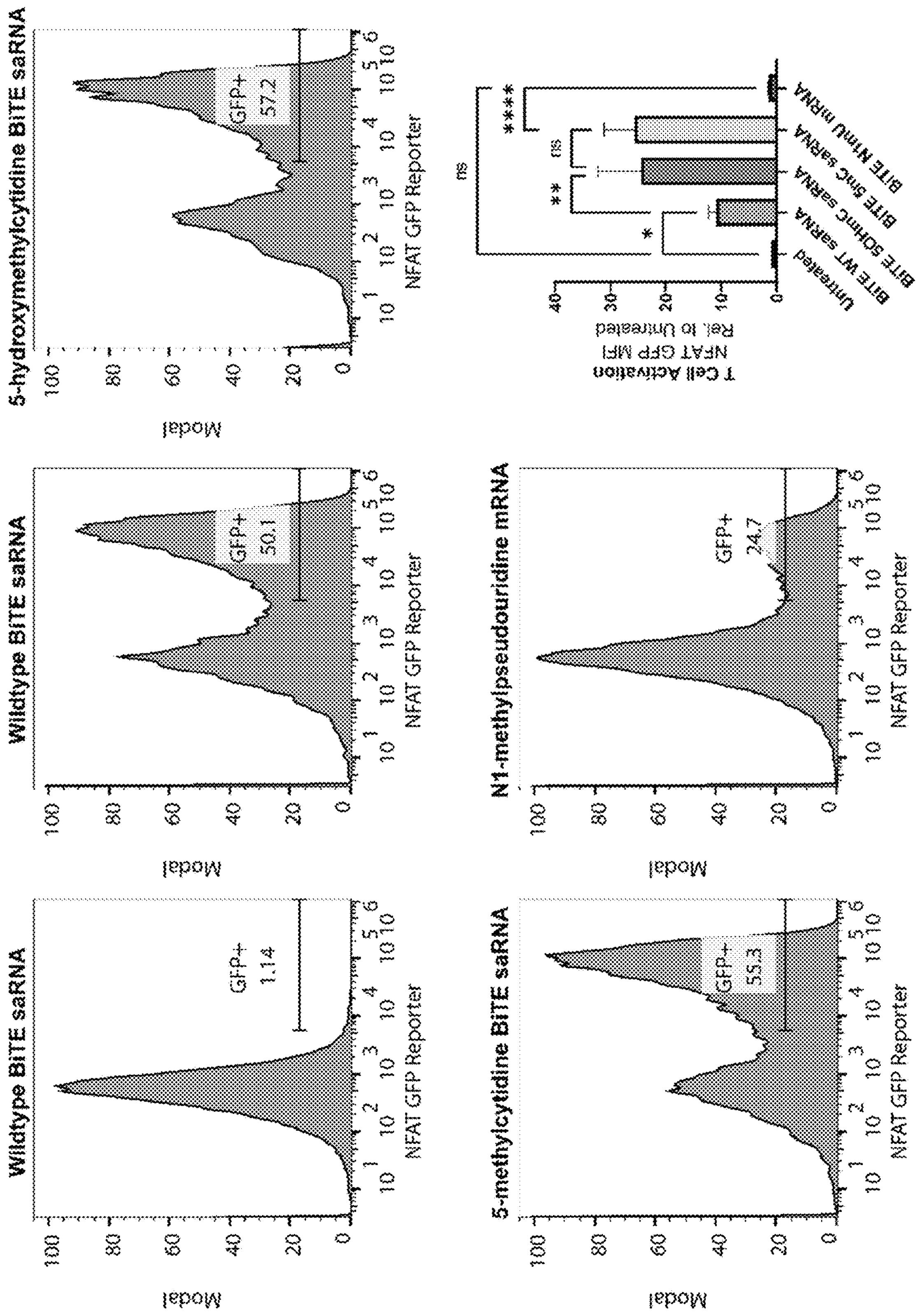
FIG. 78 is a series of flow cytometry data illustrating GFP expression in Jurkat cells harboring an NFAT GFP reporter, which were co-cultured with Nalm6 cells overexpressing HER2 and supernatant derived from C2C12 cells transfected with BiTE encoding saRNA or mRNA constructs.

To assess the bioactivity of the secreted bispecific T cell engager, a T cell activation experiment was conducted. In a 96-well plate, Jurkat T cells (125,000 cells per well) containing an NFAT GFP reporter were co-cultured with Nalm6 cells (25,000 cells per well) genetically modified to over-express HER2. The co-culture was maintained in a medium consisting of 200 µL RPMI with 10% FBS and 1% P/S. To this co-culture, 5 µL of supernatant collected 24 hours post-transfection of the C2C12 cells with the different RNA constructs encoding the HER2-CD3 BiTE and an mCherry reporter was introduced. After 24 hours of culture, the activation status of the Jurkat T cells was determined by measuring GFP expression by single-cell flow cytometry with an ATTUNE NXT instrument. The expression level of GFP was determined by measurement of the median fluorescence intensity of the GFP reporter for the viable Jurkat cell population. Unexpectedly, the conditions treated with supernatant from C2C12 cells transfected with saRNA fully substituted with 5-hydroxymethylcytidine or 5-methylcytidine exhibited the greatest GFP expression, indicating significant T cell activation that was greater than the activation resulting from treatment with supernatant of C2C12 cells transfected with unmodified saRNA or N1-methylpseudouridine modified mRNA (see e.g., FIG. 78). In conclusion, this unexpected result demonstrates that saRNA fully substituted with 5-hydroxymethylcytidine or 5-methylcytidine is capable of improved LNP mediated transfection and expression of a bispecific T cell engager, in contrast to unmodified saRNA or mRNA modified with N1-methylpseudouridine.

Figure 79:
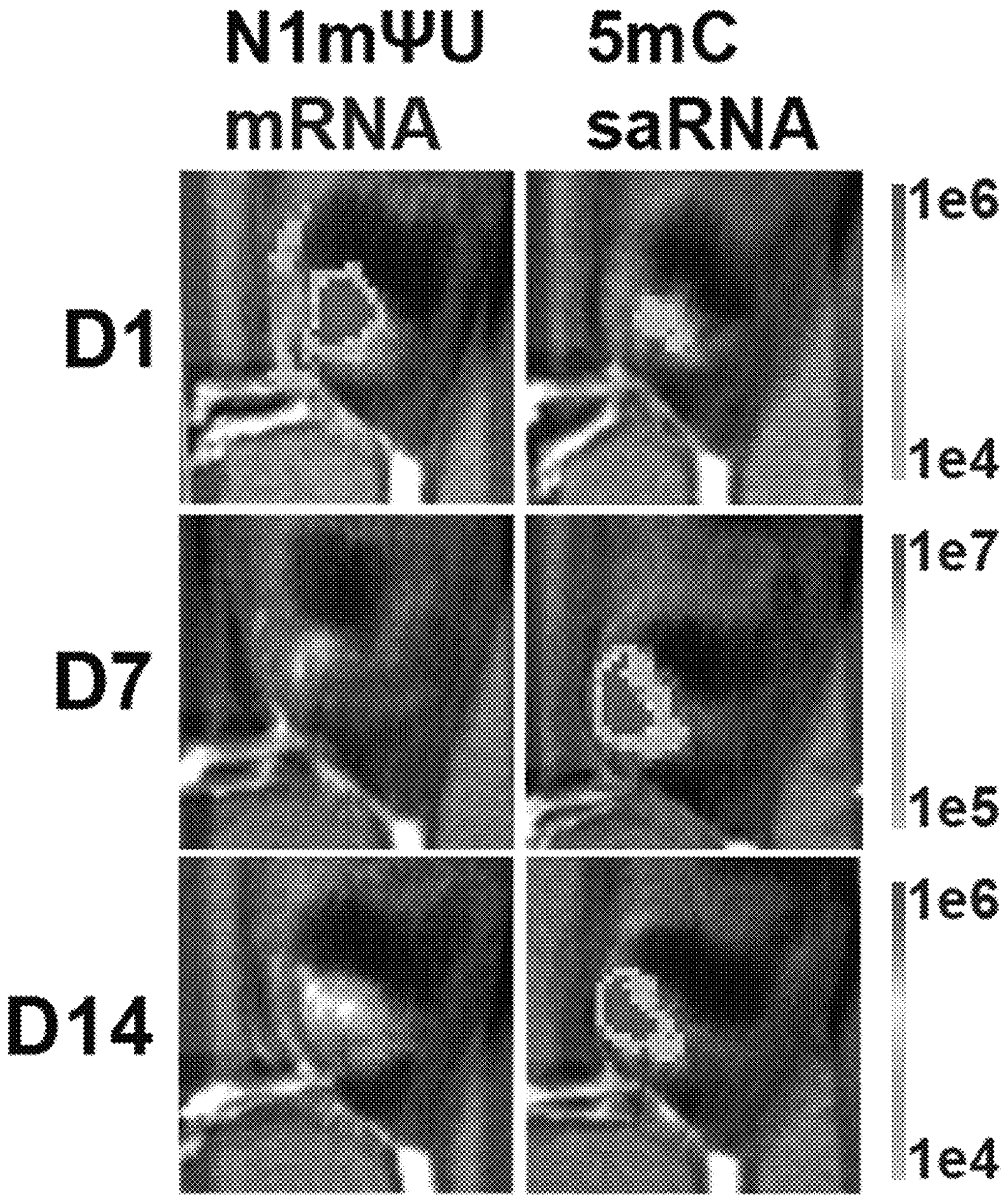
FIG. 79 shows representative bioluminescent images of mice at different time points after intramuscular injection with LNPs containing 2.5 μg of luciferase encoding N1mΨmRNA (left) or 5mC saRNA (right). Scale bar indicates radiance.
Figure 80:
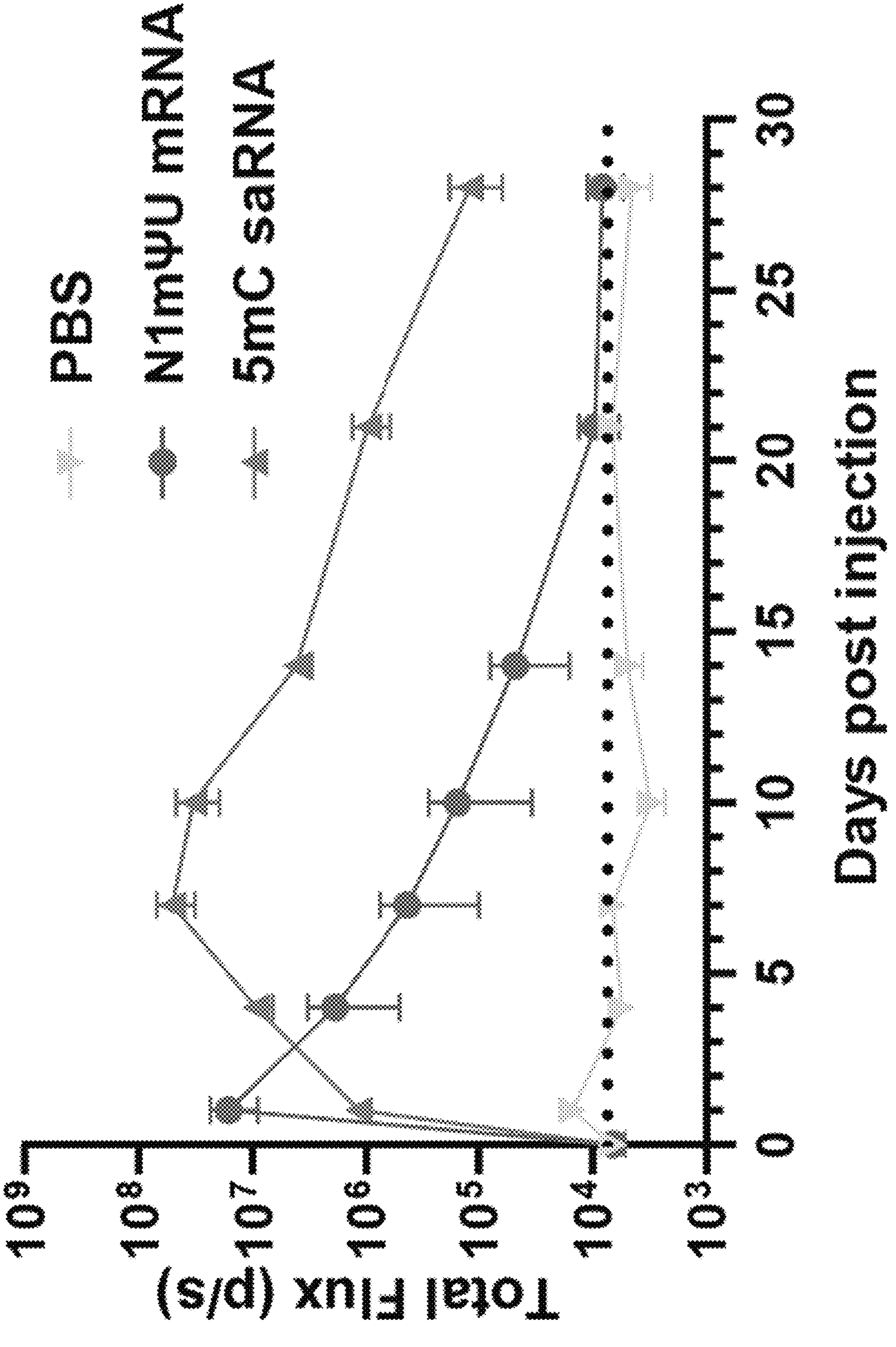
FIG. 80 shows total flux from BLI imaging of mice injected intramuscularly with LNPs containing 2.5 μg of luciferase encoding N1mΨ mRNA or 5mC saRNA (n=5 biological replicates). Dashed line indicates average signal for the PBS group over the duration of the study. Error bars indicate standard error mean.
Figure 81:
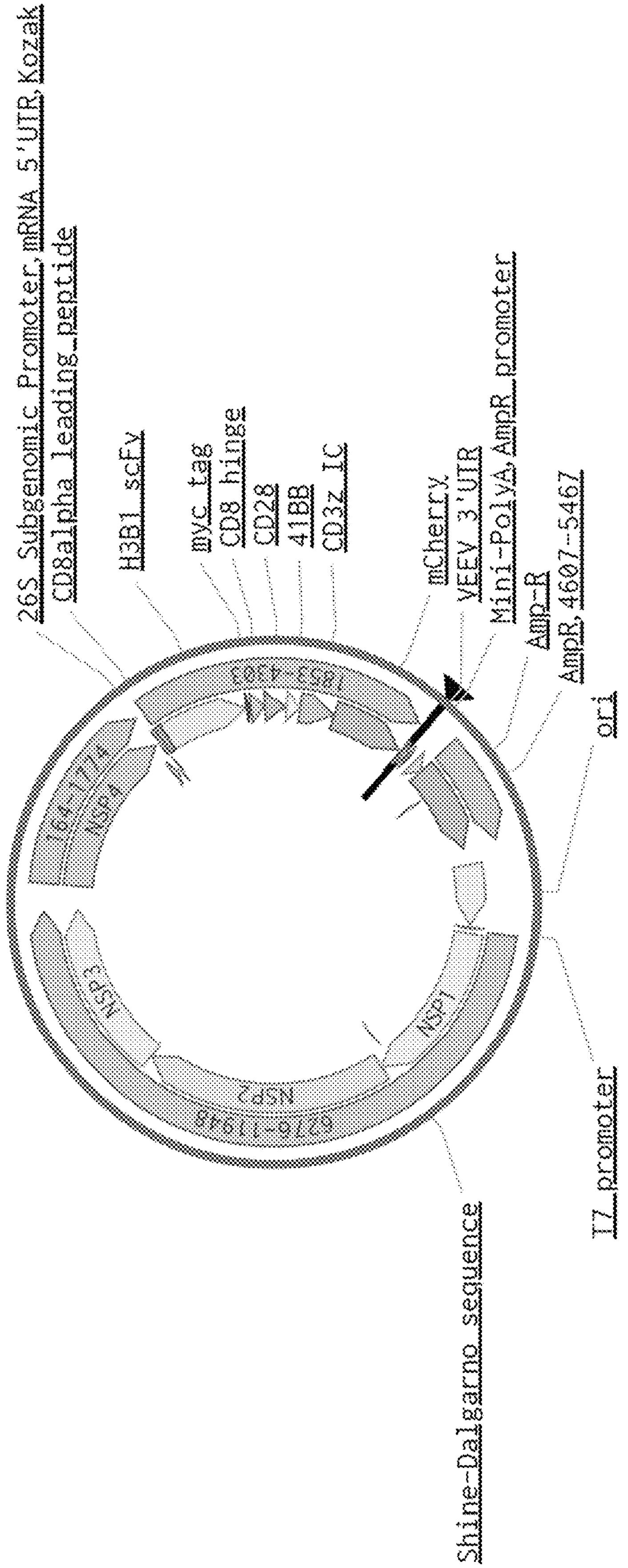
FIG. 81 is a schematic of the HER2 CAR saRNA plasmid.
Figure 82:
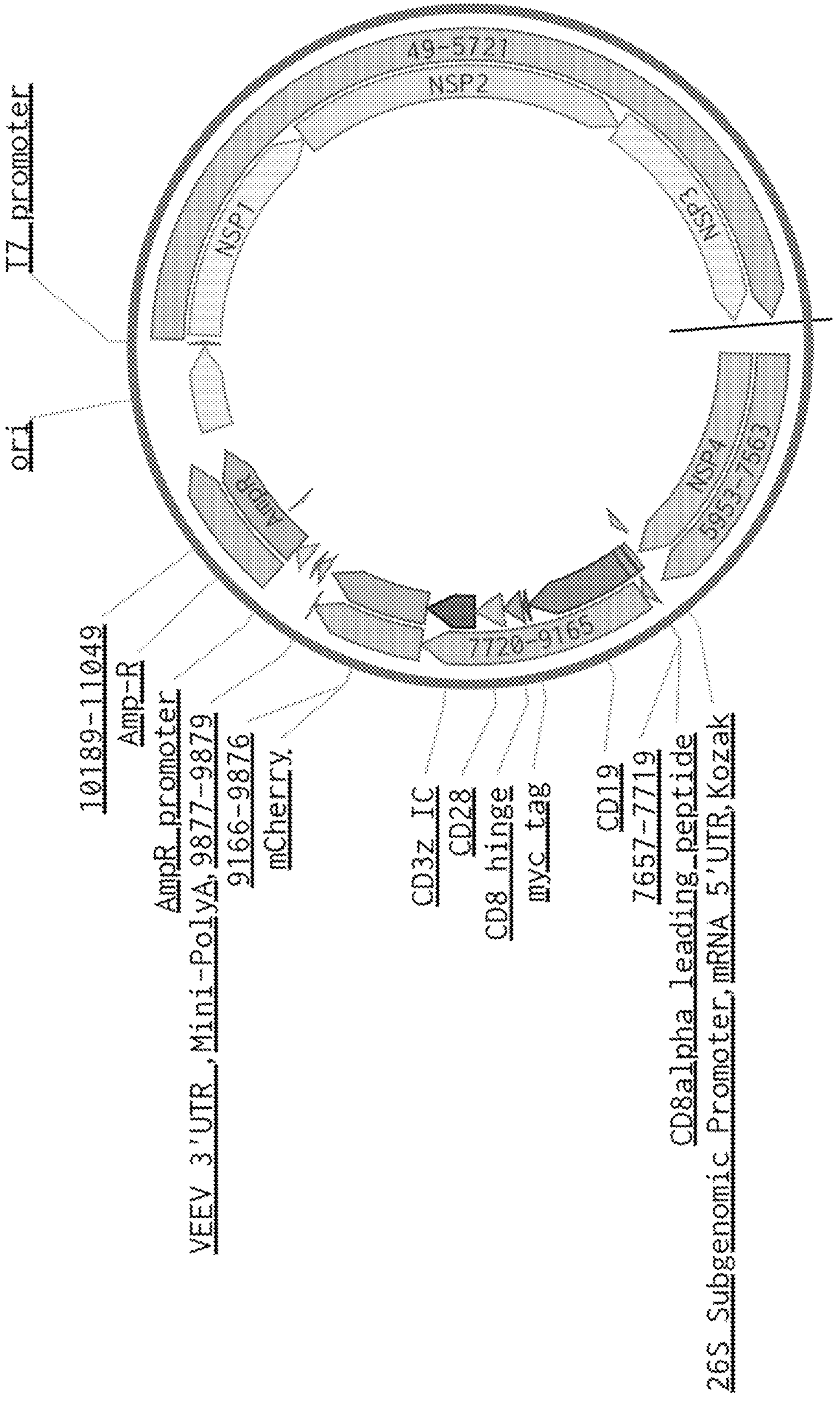
FIG. 82 is a schematic of the CD19 CAR saRNA plasmid.
Figure 83:
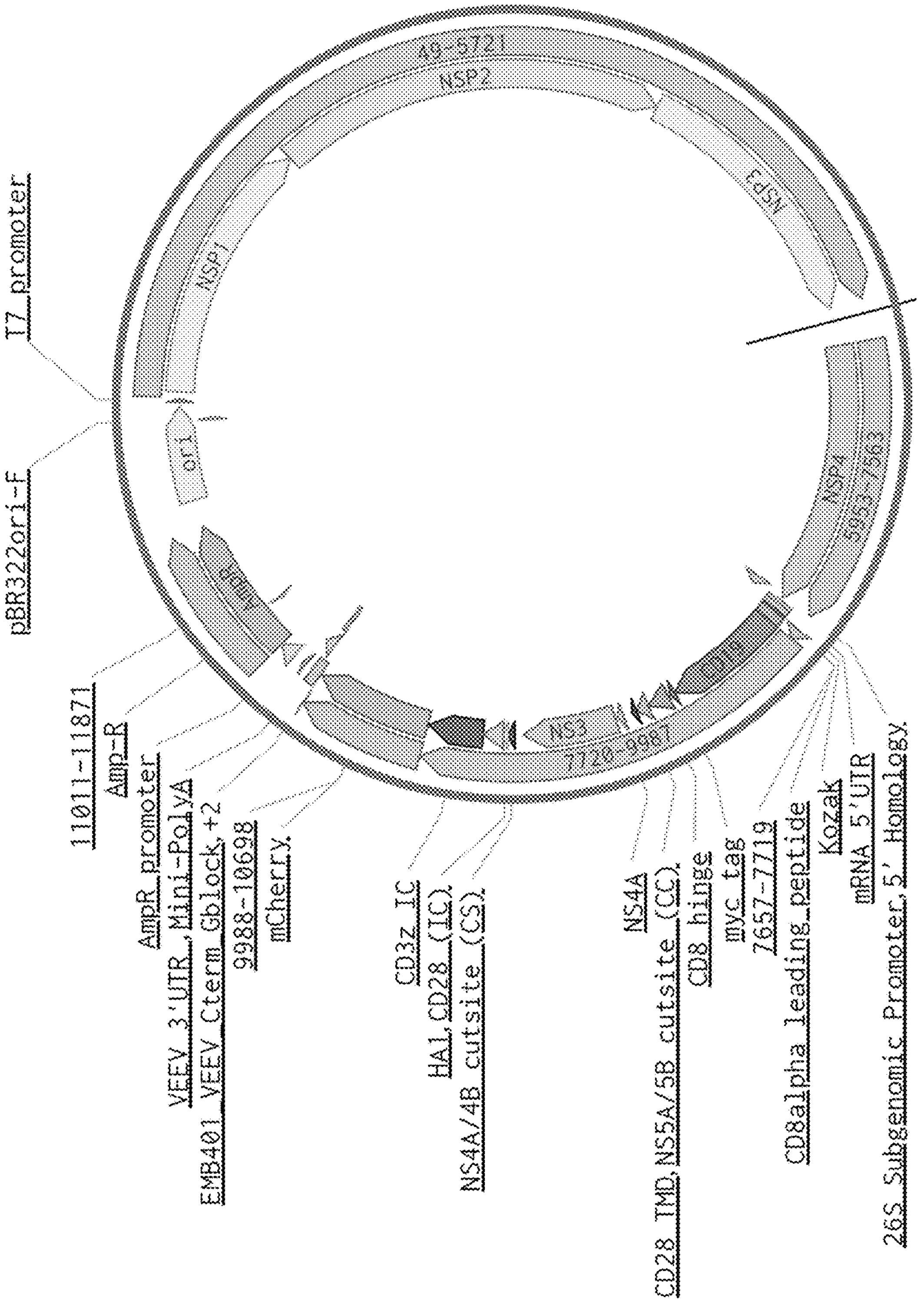
FIG. 83 is a schematic of the CD19 NS3 CAR saRNA plasmid.
Figure 84:
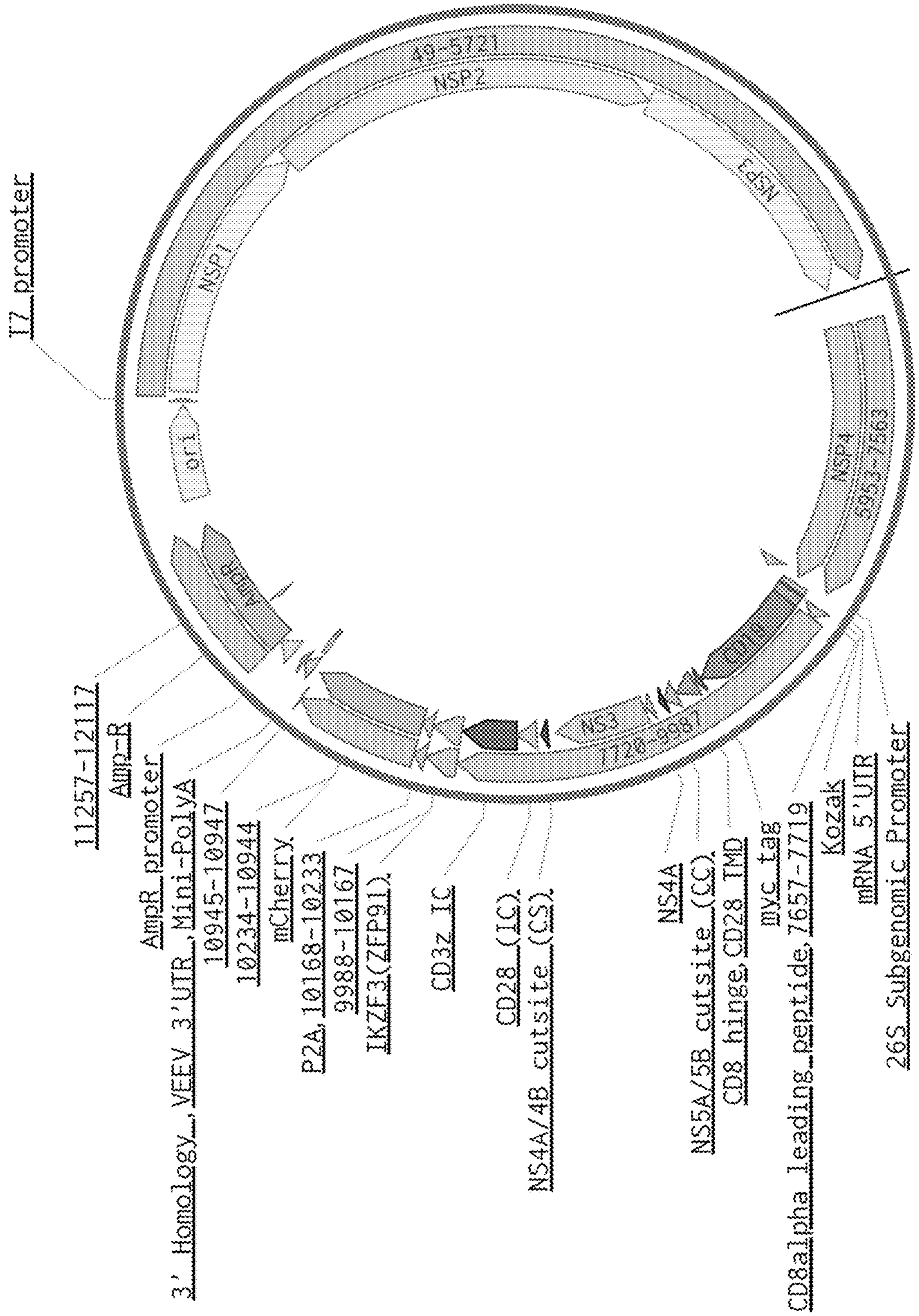
FIG. 84 is a schematic of the CD19 NS3-IKZF3 CAR saRNA plasmid.
Figure 85:
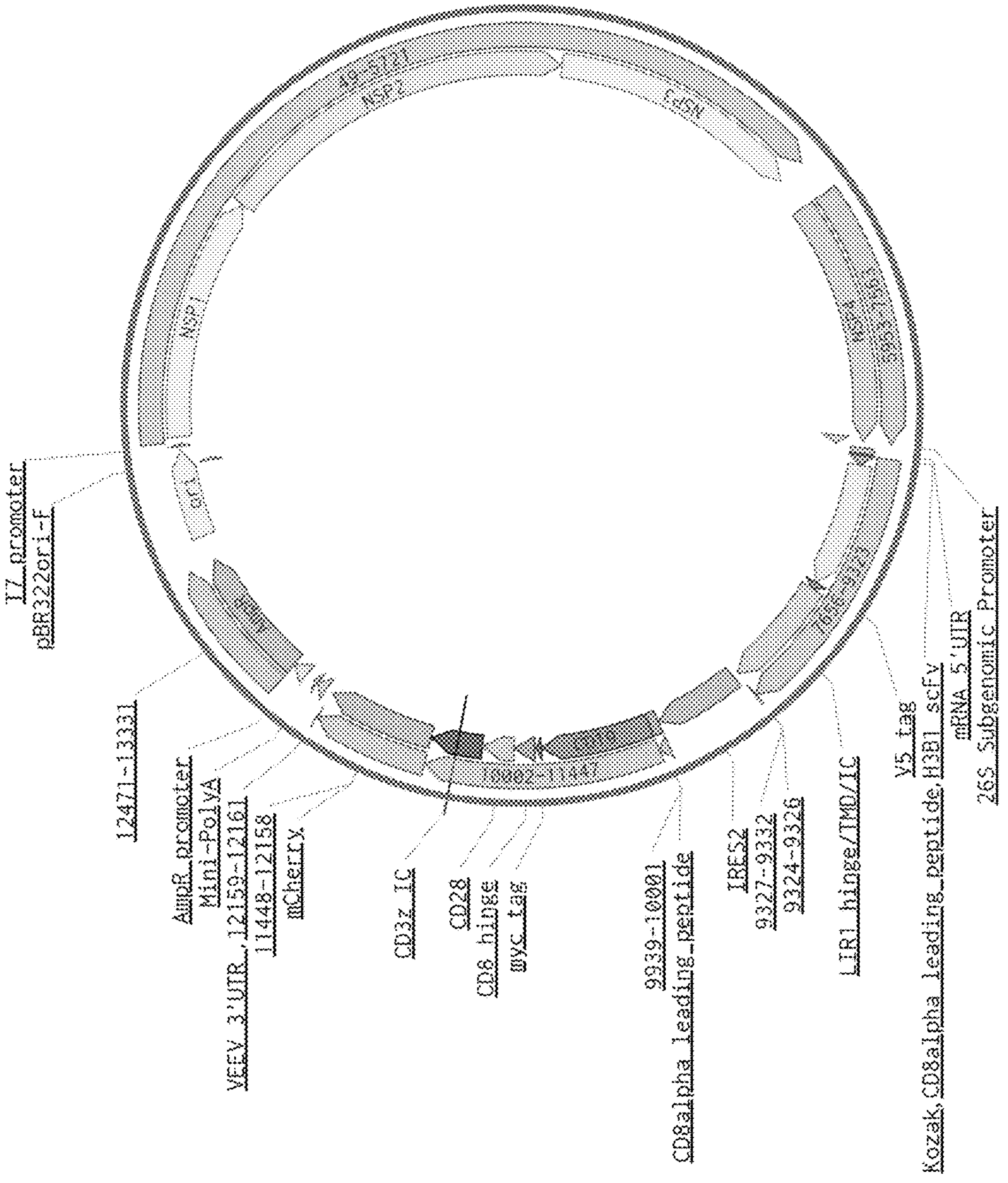
FIG. 85 is a schematic of the CD19 aCAR+HER2 iCAR saRNA plasmid.
Figure 86:
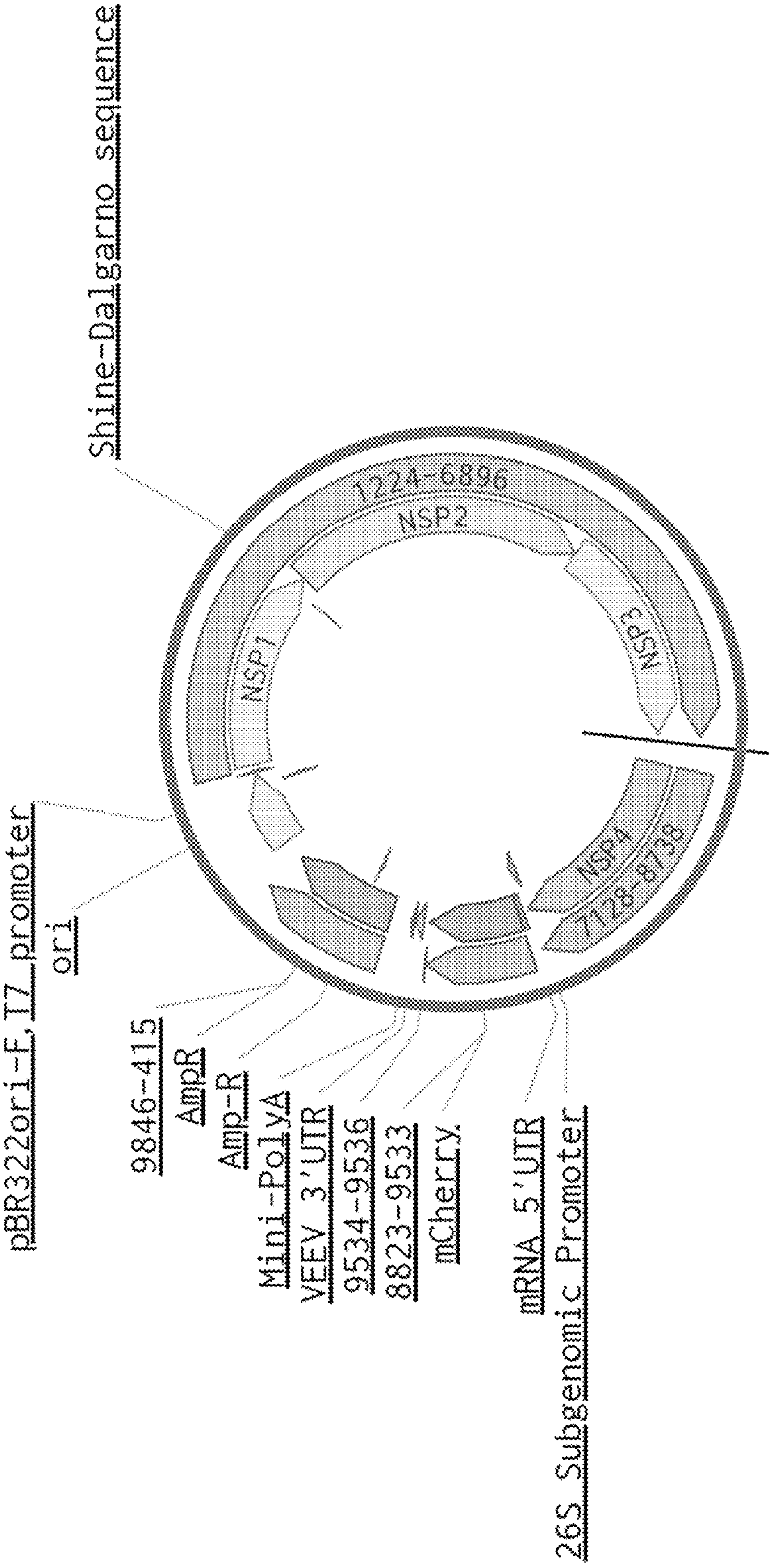
FIG. 86 is a schematic of the mCherry saRNA plasmid.
Figure 87:
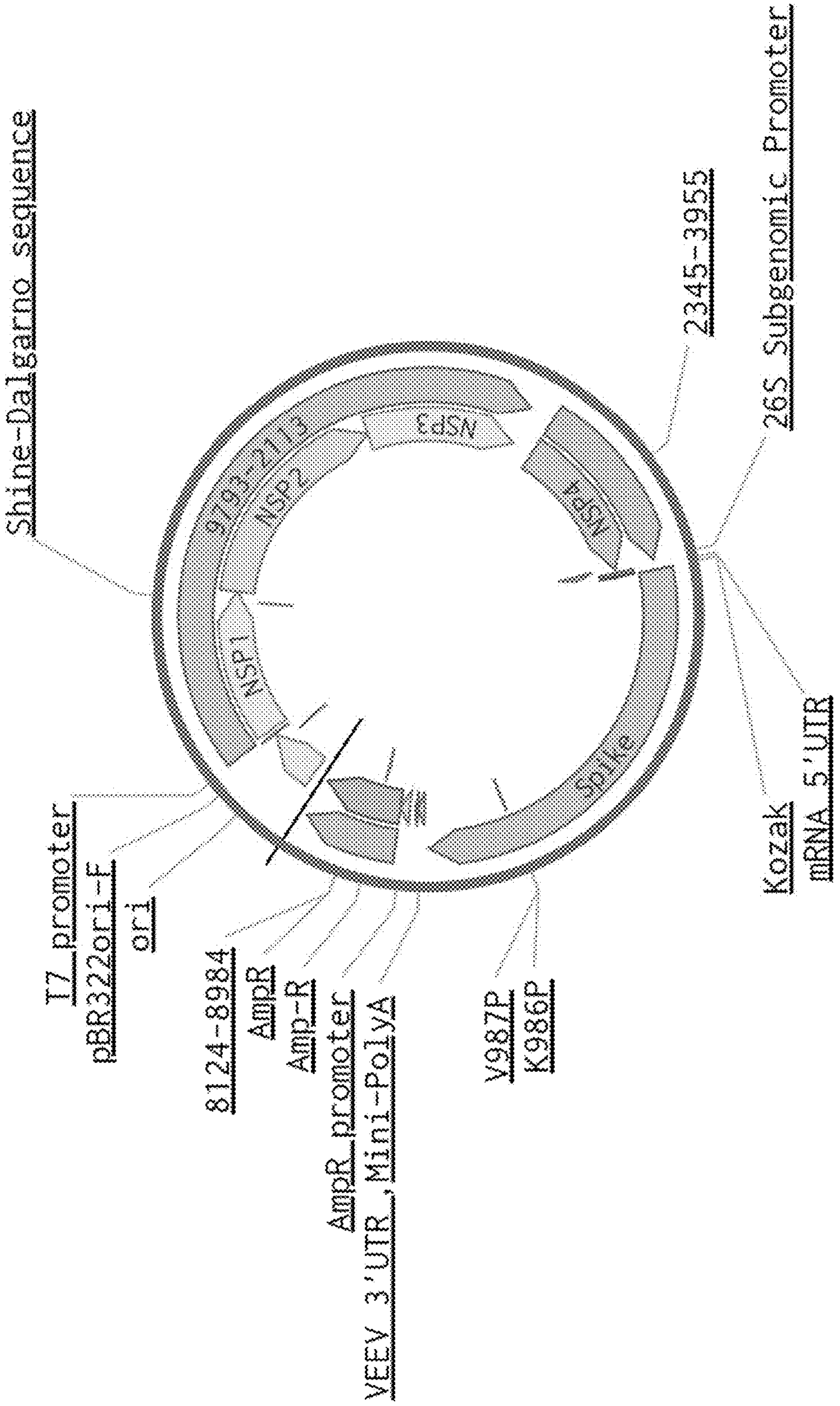
FIG. 87 is a schematic of the SARS-CoV-2 Spike saRNA plasmid.
Figure 88:
FIG. 88 is a schematic of the Influenza HA saRNA plasmid.
Figure 89:
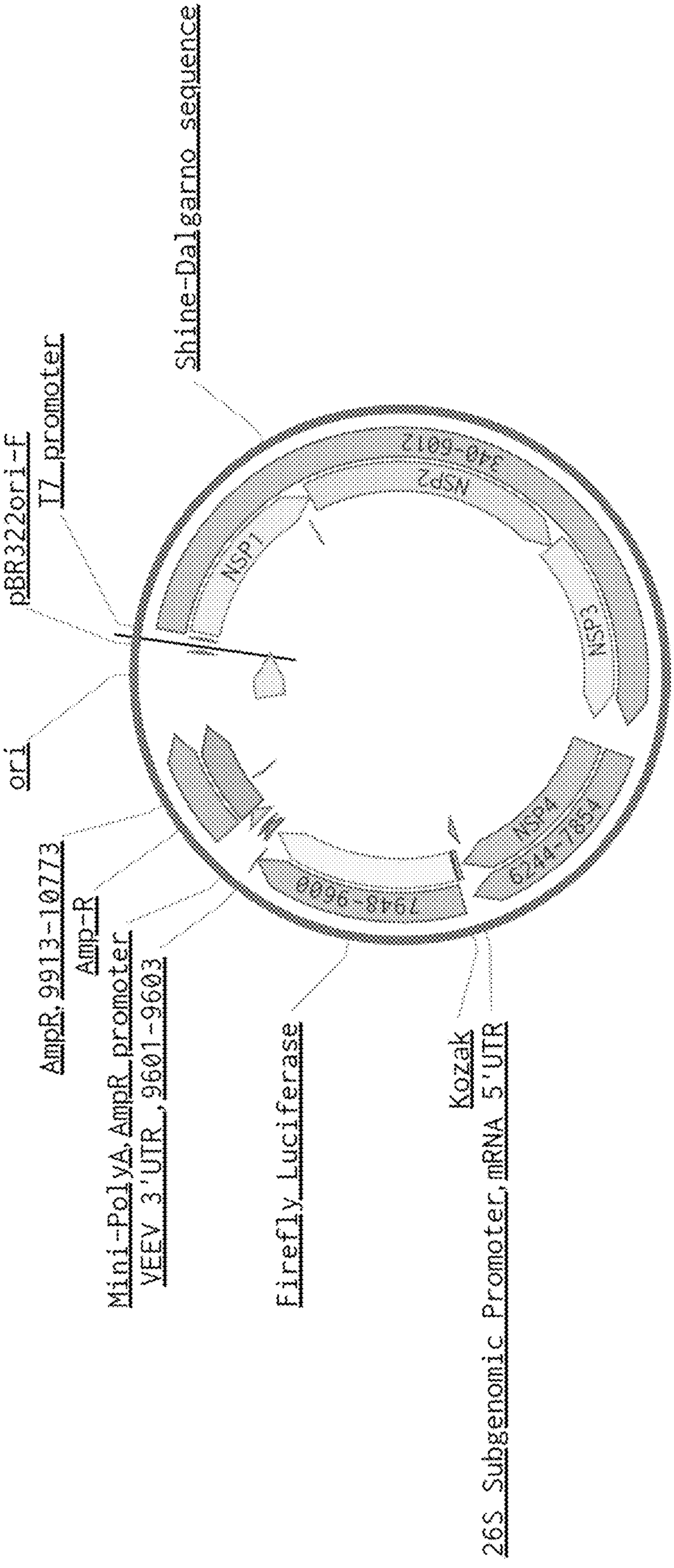
FIG. 89 is a schematic of the Firefly Luciferase saRNA plasmid.
Figure 90:
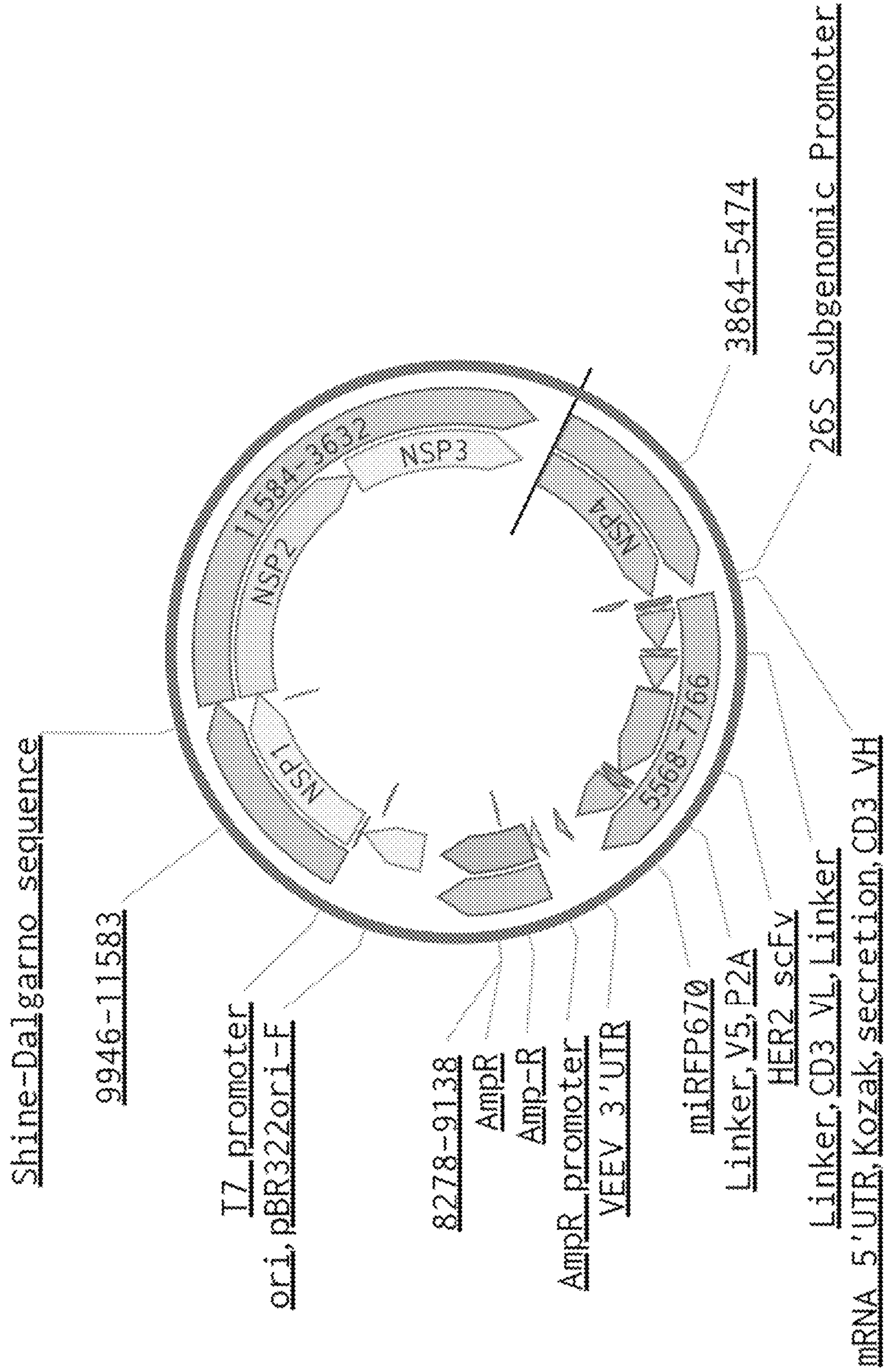
FIG. 90 is a schematic of the HER2 CD3 scFv BITE saRNA plasmid.
Figure 91:
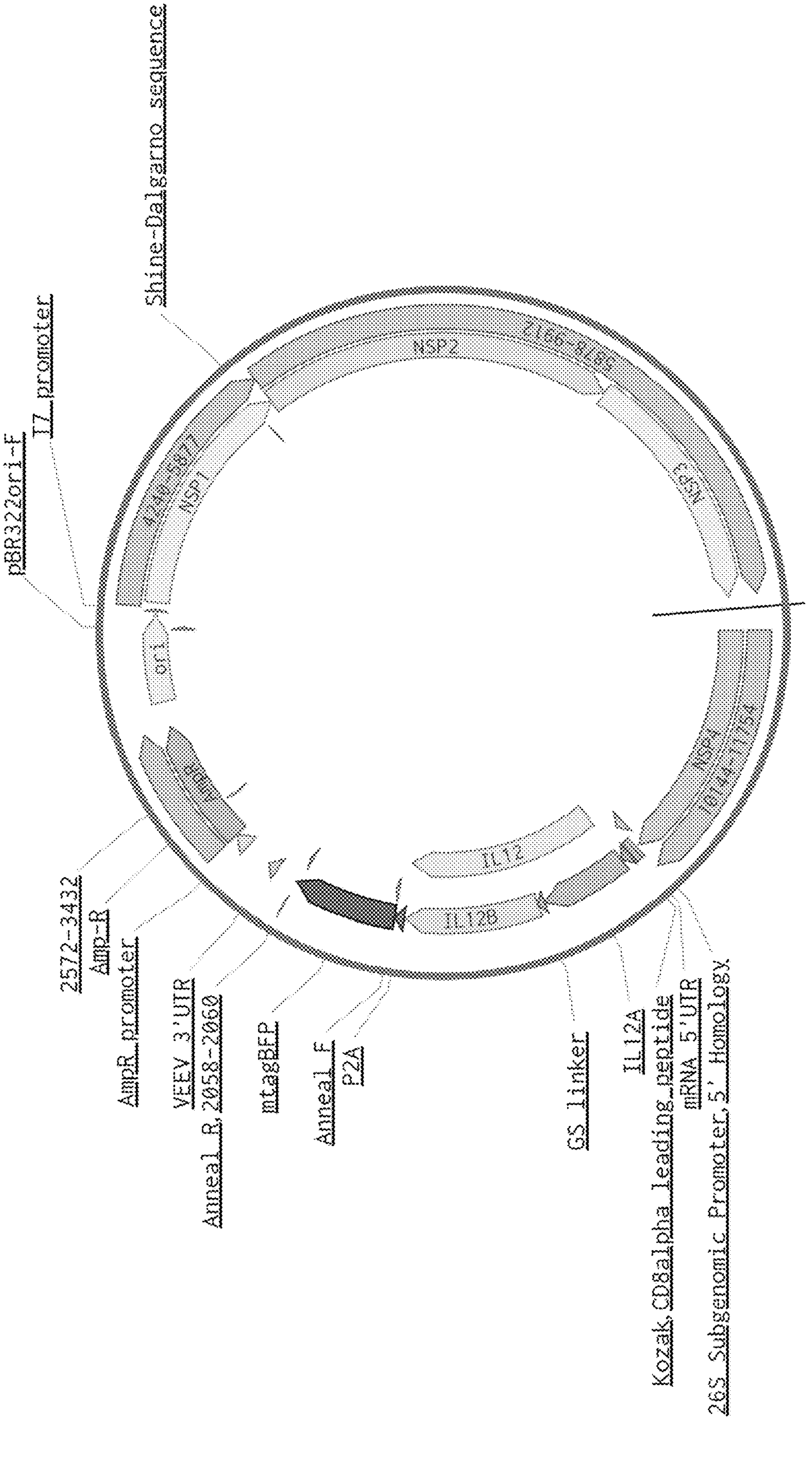
FIG. 91 is a schematic of the IL12 saRNA plasmid.

Example 28: Durable Expression from Self-Amplifying RNA with Complete Substitution of Cytidine for 5-Methylcytidine after Intramuscular Injection This example demonstrates the unexpected result that 5mC modified self-amplifying RNA results in robust and durable expression after intramuscular injection in vivo. A plasmid template containing the sequence of a self-amplifying RNA encoding firefly luciferase was generated by cloning. A plasmid template containing the sequence of a non-replicating RNA encoding firefly luciferase was utilized as a control. Both RNA constructs were synthesized using MEGASCRIPT T7 Transcription kit (INVITROGEN™, THERMOFISHER SCIENTIFIC) with 1 µg template, co-transcriptional capping using CLEANCAP AU (final conc. 4 mM), and a 3-hour incubation (TRILINK BIOTECHNOLOGIES). The final concentration of all NTPs, either modified or unmodified, was 5 mM. To synthesize 5-methylcytidine saRNA (5mC saRNA), 100% of cytidine was replaced by 5-methylcytidine. To synthesize N1-methylpseudouridine non-replicating mRNA (N1mψU mRNA), 100% of uridine was replaced by N1-methylspeudouridine. IVT was followed by 10 min DNase treatment and 30 min post-transcriptional poly-adenylation using a Poly(A) Tailing Kit (INVITROGEN™, THERMOFISHER SCIENTIFIC). saRNA was purified using MEGACLEAR™ Transcription Clean-up Kit (INVITROGEN™ THERMOFISHER SCIENTIFIC) and eluted in DNase/RNase free $H_2O$ prior to storing at −80 degrees. The A260 of all modNTPs was empirically determined using a NANODROP2000 (THERMOFISHER SCIENTIFIC). The adjusted factor for each modNTP was used to ensure accurate loading of lipid nanoparticles with mRNA or saRNA. Lipid nanoparticles comprised of an ionizable lipid (50 mol %), DOPE (10 mol %), cholesterol (38.5 mol %) and DMG-PEG2K (1.5 mol %) containing each RNA construct were synthesized at a NP ratio of 10. The resulting lipid nanoparticles were dialyzed in PBS for 24 hours. The LNP synthesis process was conducted under sterile conditions. The RNA encapsulation efficiency was determined using a QUANTIFLUOR assay (PROMEGA). 6-week-old female C57BL/6 mice (n=5/group) were intramuscularly administered LNPs containing 2.5 µg of 5mC saRNA or N1mU mRNA encoding firefly luciferase in 50 µL of PBS. After 24 hours, 200 µL of D-luciferin (15 mg/mL) was administered by intraperitoneal injection. The mice were anesthetized with 2% isoflurane. The resulting bioluminescent signal was measured with an IVIS SPECTRUM instrument at 10 minutes post luciferin injection. This procedure was repeated at 3 days, 7 days, 10 days, 14 days, 21 days, 28 days post LNP administration. The mRNA group exhibited a greater total flux at 24 hours (see e.g., FIG. 79). Unexpectedly, the group administered saRNA modified with 100% 5-methylcytidine substitution showed a consistent increase in signal, reaching peak expression 7 days after the initial injection, which was four times greater than the peak expression of the mRNA group (see e.g., FIG. 80). The 5mC modified saRNA group displayed significantly prolonged expression, maintaining an average signal above the background observed in the PBS treated group throughout the entire 28-day study duration (see e.g., FIG. 80). In conclusion, this example demonstrates the unexpected result that 5-methylcytidine substituted RNA results in robust and durable protein expression after intramuscular injection in vivo.

Example 29: Exemplary Sequences

FIGS. 81-91 contain schematics of exemplary vectors and templates used for in vitro transcription of the RNA constructs from the described examples. Additionally, this example includes: DNA sequences of the generic backbone (VEEV saRNA template; see e.g., SEQ ID NO: 2), amino acid sequences of the VEEV replicase (nsp1-4) (see e.g., SEQ ID NO: 4, SEQ ID NO: 23), DNA sequence of an exemplary mCherry encoding saRNA (Exemplary mCherry saRNA template; see e.g., SEQ ID NO: 5), RNA sequence of an exemplary mCherry saRNA with cytidine substitution (see e.g., SEQ ID NO: 6), RNA sequence of an exemplary mCherry saRNA with uridine substitution (see e.g., SEQ ID NO: 7), exemplary SARS-CoV-2 saRNA vaccine sequence (see e.g., SEQ ID NO: 21), and exemplary SARS-CoV-2 spike protein (see e.g., SEQ ID NO: 22).

```
SEQ ID NO: 2, VEEV saRNA Template, Sequence Type: DNA; T7 promoter double-
underlined (beginning of sequence; taatacgactcactata, SEQ ID NO: 3), AflII cut site
dotted-underlined (cttaag), NdeI cut site bolded (catatg). Cargo is inserted into
the backbone at the AflII and NdeI sites.
taatacgactcactataatgggcggcgcatgagagaagcccagaccaattacctacccaaaatggagaaagttcacgttgacatcgaggaaga
cagcccattcctcagagctttgcagcggagcttcccgcagtttgaggtagaagccaagcaggtcactgataatgaccatgctaatgccagagc
gttttcgcatctggcttcaaaactgatcgaaacggaggtggacccatccgacacgatccttgacattggaagtgcgcccgcccgcagaatgta
ttctaagcacaagtatcattgtatctgtccgatgagatgtgcggaagatccggacagattgtataagtatgcaactaagctgaagaaaaactg
taaggaaataactgataaggaattggacaagaaaatgaaggagctggccgccgtcatgagcgaccctgacctggaaactgagactatgtgcct
ccacgacgacgagtcgtgtcgctacgaagggcaagtcgctgtttaccaggatgtatacgcggttgacggaccgacaagtctctatcaccaagc
caataagggagttagagtcgcctactggataggctttgacaccaccccttttatgtttaagaacttggctggagcatatccatcatactctac
```

-continued caactgggccgacgaaaccgtgttaacggctcgtaacataggcctatgcagctctgacgttatggagcggtcacgtagagggatgtccattct
tagaaagaagtatttgaaaccatccaacaatgttctattctctgttggctcgaccatctaccacgagaagagggacttactgaggagctggca
cctgccgtctgtatttcacttacgtggcaagcaaaattacacatgtcggtgtgagactatagttagttgcgacgggtacgtcgttaaaagaat
agctatcagtccaggcctgtatgggaagccttcaggctatgctgctacgatgcaccgcgagggattcttgtgctgcaaagtgacagacacatt
gaacggggagagggtctcttttcccgtgtgcacgtatgtgccagctacattgtgtgaccaaatgactggcatactggcaacagatgtcagtgc
ggacgacgcgcaaaaactgctggttgggctcaaccagcgtatagtcgtcaacggtcgcacccagagaaacaccaataccatgaaaaattacct
tttgcccgtagtggcccaggcatttgctaggtgggcaaaggaatataaggaagatcaagaagatgaaaggccactaggactacgagatagaca
gttagtcatggggtgttgttgggcttttagaaggcacaagataacatctatttataagcgcccggatacccaaaccatcatcaaagtgaacag
cgatttccactcattcgtgctgcccaggataggcagtaacacattggagatcgggctgagaacaagaatcaggaaaatgttagaggagcacaa
ggagccgtcacctctcattaccgccgaggacgtacaagaagctaagtgcgcagccgatgaggctaaggaggtgcgtgaagccgaggagttgcg
cgcagctctaccacctttggcagctgatgttgaggagcccactctggaggcagacgtcgacttgatgttacaagaggctggggccggctcagt
ggagacacctcgtggcttgataaaggttaccagctacgatggcgaggacaagatcggctcttacgctgtgctttctccgcaggctgtactcaa
gagtgaaaaattatcttgcatccaccctctcgctgaacaagtcatagtgataacacactctggccgaaaagggcgttatgccgtggaaccata
ccatggtaaagtagtggtgccagagggacatgcaatacccgtccaggactttcaagctctgagtgaaagtgccaccattgtgtacaacgaacg
tgagttcgtaaacaggtacctgcaccatattgccacacatggaggagcgctgaacactgatgaagaatattacaaaactgtcaagcccagcga
gcacgacggcgaatacctgtacgacatcgacaggaaacagtgcgtcaagaaagaactagtcactgggctagggctcacaggcgagctggtgga
tcctcccttccatgaattcgcctacgagagtctgagaacacgaccagccgctccttaccaagtaccaaccataggggtgtatggcgtgccagg
atcaggcaagtctggcatcattaaaagcgcagtcaccaaaaaagatctagtggtgagcgccaagaaagaaaactgtgcagaaattataaggga
cgtcaagaaaatgaaagggctggacgtcaatgccagaactgtggactcagtgctcttgaatggatgcaaacaccccgtagagaccctgtatat
tgacgaagcttttgcttgtcatgcaggtactctcagagcgctcatagccattataagacctaaaaaggcagtgctctgcggggatcccaaaca
gtgcggtttttttaacatgatgtgcctgaaagtgcattttaaccacgagatttgcacacaagtcttccacaaaagcatctctcgccgttgcac
taaatctgtgacttcggtcgtctcaaccttgttttacgacaaaaaaatgagaacgacgaatccgaaagagactaagattgtgattgacactac
cggcagtaccaaacctaagcaggacgatctcattctcacttgtttcagagggggtgaagcagttgcaaatagattacaaaggcaacgaaata
atgacggcagctgcctctcaagggctgacccgtaaaggtgtgtatgccgttcggtacaaggtgaatgaaaatcctctgtacgcacccacctca
gaacatgtgaacgtcctactgacccgcacggaggaccgcatcgtgtggaaaacactagccggcgacccatggataaaaacactgactgccaag
taccctgggaatttcactgccacgatagaggagtggcaagcagagcatgatgccatcatgaggcacatcttggagagaccggaccctaccgac
gtcttccagaataaggcaaacgtgtgttgggccaaggctttagtgccggtgctgaagaccgctggcatagacatgaccactgaacaatggaac
actgtggattattttgaaacggacaaagctcactcagcagagatagtattgaaccaactatgcgtgaggttctttggactcgatctggactcc
ggtctattttctgcacccactgttccgttatccattaggaataatcactgggataactccccgtcgcctaacatgtacgggctgaataaagaa
gtggtccgtcagctctctcgcaggtacccacaactgcctcgggcagttgccactggaagagtctatgacatgaacactggtacactgcgcaat
tatgatccgcgcataaacctagtacctgtaaacagaagactgcctcatgctttagtcctccaccataatgaacacccacagagtgacttttct
tcattcgtcagcaaattgaagggcagaactgtcctggtggtcggggaaaagttgtccgtcccaggcaaaatggttgactggttgtcagaccgg
cctgaggctaccttcagagctcggctggatttaggcatcccaggtgatgtgcccaaatatgacataatatttgttaatgtgaggaccccatat
aaataccatcactatcagcagtgtgaagaccatgccattaagcttagcatgttgaccaagaaagcttgtctgcatctgaatcccggcggaacc
tgtgtcagcataggttatggttacgctgacagggccagcgaaagcatcattggtgctatagcgcggcagttcaagttttcccgggtatgcaaa
ccgaaatcctcacttgaagagacggaagttctgtttgtattcattgggtacgatcgcaaggcccgtacgcacaattcttacaagctttcatca
accttgaccaacatttatacaggttccagactccacgaagccggatgtgcaccctcatatcatgtggtgcgaggggatattgccacggccacc
gaaggagtgattataaatgctgctaacagcaaaggacaacctggcggaggggtgtgcggagcgctgtataagaaattcccggaaagcttcgat
ttacagccgatcgaagtaggaaaagcgcgactggtcaaaggtgcagctaaacatatcattcatgccgtaggaccaaacttcaacaaagtttcg
gaggttgaaggtgacaaacagttggcagaggcttatgagtccatcgctaagattgtcaacgataacaattacaagtcagtagcgattccactg
ttgtccaccggcatcttttccgggaacaaagatcgactaacccaatcattgaaccatttgctgacagctttagacaccactgatgcagatgta
gccatatactgcagggacaagaaatgggaaatgactctcaaggaagcagtggctaggagagaagcagtggaggagatatgcatatccgacgac
tcttcagtgacagaacctgatgcagagctggtgagggtgcatccgaagagttctttggctggaaggaagggctacagcacaagcgatggcaaa
actttctcatatttggaagggaccaagtttcaccaggcggccaaggatatagcagaaattaatgccatgtggcccgttgcaacggaggccaat
gagcaggtatgcatgtatatcctcggagaaagcatgagcagtattaggtcgaaatgccccgtcgaagagtcggaagcctccacaccacctagc
acgctgccttgcttgtgcatccatgccatgactccagaaagagtacagcgcctaaaagcctcacgtccagaacaaattactgtgtgctcatcc
tttccattgccgaagtatagaatcactggtgtgcagaagatccaatgctcccagcctatattgttctcaccgaaagtgcctgcgtatattcat
ccaaggaagtatctcgtggaaacaccaccggtagacgagactccggagccatcggcagagaaccaatccacagaggggacacctgaacaacca
ccacttataaccgaggatgagaccaggactagaacgcctgagccgatcatcatcgaagaggaagaagaggatagcataagtttgctgtcagat
ggcccgacccaccaggtgctgcaagtcgaggcagacattcacgggccgccctctgtatctagctcatcctggtccattcctcatgcatccgac
tttgatgtggacagtttatccatacttgacaccctggagggagctagcgtgaccagcggggcaacgtcagccgagactaactcttacttcgca
aagagtatggagtttctggcgcgaccggtgcctgcgcctcgaacagtattcaggaaccctccacatcccgctccgcgcacaagaacaccgtca
cttgcacccagcagggcctgctcgagaaccagcctagtttccaccccgccaggcgtgaatagggtgatcactagagaggagctcgaggcgctt
accccgtcacgcactcctagcaggtcggtctcgagaaccagcctggtctccaacccgccaggcgtaaatagggtgattacaagagaggagttt
gaggcgttcgtagcacaacaacaatgacggtttgatgcgggtgcatacatcttttcctccgacaccggtcaagggcatttacaacaaaaatca
gtaaggcaaacggtgctatccgaagtggtgttggagaggaccgaattggagatttcgtatgccccgcgcctcgaccaagaaaaagaagaatta
ctacgcaagaaattacagttaaatcccacacctgctaacagaagcagataccagtccaggaaggtggagaacatgaaagccataacagctaga
cgtattctgcaaggcctagggcattatttgaaggcagaaggaaaagtggagtgctaccgaaccctgcatcctgttcctttgtattcatctagt
gtgaaccgtgccttttcaagccccaaggtcgcagtggaagcctgtaacgccatgttgaaagagaactttccgactgtggcttcttactgtatt
attccagagtacgatgcctatttggacatggttgacggagcttcatgctgcttagacactgccagtttttgccctgcaaagctgcgcagcttt
ccaaagaaacactcctatttggaacccacaatacgatcggcagtgccttcagcgatccagaacacgctccagaacgtcctggcagctgccaca
aaaagaaattgcaatgtcacgcaaatgagagaattgcccgtattggattcggcggcctttaatgtggaatgcttcaagaaatatgcgtgtaat
aatgaatattgggaaacgtttaaagaaaaccccatcaggcttactgaagaaaacgtggtaaattacattaccaaattaaaaggaccaaaagct
gctgctcttttttgcgaagacacataatttgaatatgttgcaggacataccaatggacaggtttgtaatggacttaaagagagacgtgaaagtg
actccaggaacaaaacatactgaagaacggcccaaggtacaggtgatccaggctgccgatccgctagcaacagcgtatctgtgcggaatccac
cgagagctggttaggagattaaatgcggtcctgcttccgaacattcatacactgtttgatatgtcggctgaagactttgacgctattatagcc
gagcacttccagcctggggattgtgttctggaaactgacatcgcgtcgtttgataaaagtgaggacgacgccatggctctgaccgcgttaatg
attctggaagacttaggtgtggacgcagagctgttgacgctgattgaggcggctttcggcgaaatttcatcaatacatttgcccactaaaact
aaatttaaattcggagccatgatgaaatctggaatgttcctcacactgtttgtgaacacagtcattaacattgtaatcgcaagcagagtgttg
agagaacggctaaccggatcaccatgtgcagcattcattggagatgacaatatcgtgaaaggagtcaaatcggacaaattaatggcagacagg
tgcgccacctggttgaatatggaagtcaagattatagatgctgtggtgggcgagaaagcgccttatttctgtggagggtttattttgtgtgac
tccgtgaccggcacagcgtgccgtgtggcagacccccctaaaaaggctgtttaagcttggcaaacctctggcagcagacgatgaacatgatgat
gacaggagaagggcattgcatgaagagtcaacacgctggaaccgagtgggtattctttcagagctgtgcaaggcagtagaatcaaggtatgaa
accgtaggaacttccatcatagttatggccatgactactctagctagcagtgttaaatcattcagctacctgagaggggcccctataactctc
tacggctaacctgaatggactacgacatagtctagtccgccaagtctagcaggagagtcccgacctccaggagagaccagggccaccCTTAAG
CATATGgaattggcaagctgcttacatagaactcgcggcgattggcatgccgccttaaaattttatttatttttcttttcttttccgaat
cggattttgtttttaatatttcaaaaaaaaaaaaaaaaaaaaaaaaaa -continued SEQ ID NO: 4, first portion of VEEV Replicase (nsp1-4) Protein Sequence; Sequence Type: Amino Acid; Star indicates stop codon; can be encoded by nucleotides 62-5701 of SEQ ID NO: 2 (or a codon-optimized version of nucleotides 62-5701 of SEQ ID NO: 2)

MEKVHVDIEEDSPFLRALQRSFPQFEVEAKQVTDNDHANARAFSHLASKLIETEVDPSDTILDIGS
APARRMYSKHKYHCICPMRCAEDPDRLYKYATKLKKNCKEITDKELDKKMKELAAVMSDPDL
ETETMCLHDDESCRYEGQVAVYQDVYAVDGPTSLYHQANKGVRVAYWIGFDTTPFMFKNLAG
AYPSYSTNWADETVLTARNIGLCSSDVMERSRRGMSILRKKYLKPSNNVLFSVGSTIYHEKRDLL
RSWHLPSVFHLRGKQNYTCRCETIVSCDGYVVKRIAISPGLYGKPSGYAATMHREGFLCCKVTD
TLNGERVSFPVCTYVPATLCDQMTGILATDVSADDAQKLLVGLNQRIVVNGRTQRNTNTMKNY
LLPVVAQAFARWAKEYKEDQEDERPLGLRDRQLVMGCCWAFRRHKITSIYKRPDTQTIIKVNSD
FHSFVLPRIGSNTLEIGLRTRIRKMLEEHKEPSPLITAEDVQEAKCAADEAKEVREAEELRAALPPL
AADVEEPTLEADVDLMLQEAGAGSVETPRGLIKVTSYDGEDKIGSYAVLSPQAVLKSEKLSCIHP
LAEQVIVITHSGRKGRYAVEPYHGKVVVPEGHAIPVQDFQALSESATIVYNEREFVNRYLHHIAT
HGGALNTDEEYYKTVKPSEHDGEYLYDIDRKQCVKKELVTGLGLTGELVDPPFHEFAYESLRTR
PAAPYQVPTIGVYGVPGSGKSGIIKSAVTKKDLVVSAKKENCAEIIRDVKKMKGLDVNARTVDS
VLLNGCKHPVETLYIDEAFACHAGTLRALIAIIRPKKAVLCGDPKQCGFFNMMCLKVHFNHEICT
QVFHKSISRRCTKSVTSVVSTLFYDKKMRTTNPKETKIVIDTTGSTKPKQDDLILTCFRGWVKQL
QIDYKGNEIMTAAASQGLTRKGVYAVRYKVNENPLYAPTSEHVNVLLTRTEDRIVWKTLAGDP
WIKTLTAKYPGNFTATIEEWQAEHDAIMRHILERPDPTDVFQNKANVCWAKALVPVLKTAGID
MTTEQWNTVDYFETDKAHSAEIVLNQLCVRFFGLDLDSGLFSAPTVPLSIRNNHWDNSPSPNMY
GLNKEVVRQLSRRYPQLPRAVATGRVYDMNTGTLRNYDPRINLVPVNRRLPHALVLHHNEHPQ
SDFSSFVSKLKGRTVLVVGEKLSVPGKMVDWLSDRPEATFRARLDLGIPGDVPKYDIIFVNVRTP
YKYHHYQQCEDHAIKLSMLTKKACLHLNPGGTCVSIGYGYADRASESIIGAIARQFKFSRVCKPK
SSLEETEVLFVFIGYDRKARTHNSYKLSSTLTNIYTGSRLHEAGCAPSYHVVRGDIATATEGVIIN
AANSKGQPGGGVCGALYKKFPESFDLQPIEVGKARLVKGAAKHIIHAVGPNFNKVSEVEGDKQL
AEAYESIAKIVNDNNYKSVAIPLLSTGIFSGNKDRLTQSLNHLLTALDTTDADVAIYCRDKKWEM
TLKEAVARREAVEEICISDDSSVTEPDAELVRVHPKSSLAGRKGYSTSDGKTFSYLEGTKFHQAA
KDIAEINAMWPVATEANEQVCMYILGESMSSIRSKCPVEESEASTPPSTLPCLCIHAMTPERVQRL
KASRPEQITVCSSFPLPKYRITGVQKIQCSQPILFSPKVPAYIHPRKYLVETPPVDETPEPSAENQST
EGTPEQPPLITEDETRTRTPEPIIIEEEEEDSISLLSDGPTHQVLQVEADIHGPPSVSSSSWSIPHASDF
DVDSLSILDTLEGASVTSGATSAETNSYFAKSMEFLARPVPAPRTVFRNPPHPAPRTRTPSLAPSR
ACSRTSLVSTPPGVNRVITREELEALTPSRTPSRSVSRTSLVSNPPGVNRVITREEFEAFVAQQQ*

SEQ ID NO: 23, second portion of VEEV Replicase (nsp1-4) Protein Sequence; Sequence Type: Amino Acid; Star indicates stop codon; can be encoded by nucleotides 5702-7543 of SEQ ID NO: 2 (or a codon-optimized version of nucleotides 5702-7543 of SEQ ID NO: 2)

RFDAGAYIFSSDTGQGHLQQKSVRQTVLSEVVLERTELEISYAPRLDQEKEELLRKKLQLNPTPA
NRSRYQSRKVENMKAITARRILQGLGHYLKAEGKVECYRTLHPVPLYSSSVNRAFSSPKVAVEA
CNAMLKENFPTVASYCIIPEYDAYLDMVDGASCCLDTASFCPAKLRSFPKKHSYLEPTIRSAVPS
AIQNTLQNVLAAATKRNCNVTQMRELPVLDSAAFNVECFKKYACNNEYWETFKENPIRLTEEN
VVNYITKLKGPKAAALFAKTHNLNMLQDIPMDRFVMDLKRDVKVTPGTKHTEERPKVQVIQAA
DPLATAYLCGIHRELVRRLNAVLLPNIHTLFDMSAEDFDAIIAEHFQPGDCVLETDIASFDKSEDD
AMALTALMILEDLGVDAELLTLIEAAFGEISSIHLPTKTKFKFGAMMKSGMFLTLFVNTVINIVIA
SRVLRERLTGSPCAAFIGDDNIVKGVKSDKLMADRCATWLNMEVKIIDAVVGEKAPYFCGGFIL
CDSVTGTACRVADPLKRLFKLGKPLAADDEHDDDRRRALHEESTRWNRVGILSELCKAVESRYE
TVGTSIIVMAMTTLASSVKSFSYLRGAPITLYG*

SEQ ID NO: 5, Exemplary mCherry saRNA Template Sequence; Sequence Type: DNA; T7 promoter double-underlined (taatacgactcactata, SEQ ID NO: 3), AflII cut site dotted-underlined (cttaag), mCherry sequence bolded, NdeI cut site zigzag-underlined (catatg)

taatacgactcactataatgggggcgcatgagagaagcccagaccaattacctacccaaaatggagaaagttcacgttgacatcgaggaagac
agcccattcctcagagctttgcagcggagcttcccgcagtttgaggtagaagccaagcaggtcactgataatgaccatgctaatgccagagcg
ttttcgcatctggcttcaaaactgatcgaaacggaggtggacccatccgacacgatccttgacattggaagtgcgcccgcccgcagaatgtat
tctaagcacaagtatcattgtatctgtccgatgagatgtgcggaagatccggacagattgtataagtatgcaactaagctgaagaaaaactgt
aaggaaataactgataaggaattggacaagaaaatgaaggagctggccgccgtcatgagcgaccctgacctggaaactgagactatgtgcctc
cacgacgacgagtcgtgtcgctacgaagggcaagtcgctgtttaccaggatgtatacgcggttgacggaccgacaagtctctatcaccaagcc
aataagggagttagagtcgcctactggataggctttgacaccaccccttttatgtttaagaacttggctggagcatatccatcatactctacc
aactgggccgacgaaaccgtgttaacggctcgtaacataggcctatgcagctctgacgttatggagcggtcacgtagagggatgtccattctt
agaaagaagtatttgaaaccatccaacaatgttctattctctgttggctcgaccatctaccacgagaagagggacttactgaggagctggcac
ctgccgtctgtatttcacttacgtggcaagcaaaattacacatgtcggtgtgagactatagttagttgcgacgggtacgtcgttaaaagaata
gctatcagtccaggcctgtatgggaagccttcaggctatgctgctacgatgcaccgcgagggattcttgtgctgcaaagtgacagacacattg
aacggggagagggtctcttttcccgtgtgcacgtatgtgccagctacattgtgtgaccaaatgactggcatactggcaacagatgtcagtgcg
gacgacgcgcaaaaactgctggttgggctcaaccagcgtatagtcgtcaacggtcgcacccagagaaacaccaataccatgaaaaattacctt
ttgcccgtagtggcccaggcatttgctaggtgggcaaaggaatataaggaagatcaagaagatgaaaggccactaggactacgagatagacag
ttagtcatggggtgttgttgggcttttagaaggcacaagataacatctatttataagcgcccggatacccaaaccatcatcaaagtgaacagc
gatttccactcattcgtgctgcccaggataggcagtaacacattggagatcgggctgagaacaagaatcaggaaaatgttagaggagcacaag
gagccgtcacctctcattaccgccgaggacgtacaagaagctaagtgcgcagccgatgaggctaaggaggtgcgtgaagccgaggagttgcgc
gcagctctaccacctttggcagctgatgttgaggagcccactctggaggcagacgtcgacttgatgttacaagaggctggggccggctcagtg
gagacacctcgtggcttgataaaggttaccagctacgatggcgaggacaagatcggctcttacgctgtgctttctccgcaggctgtactcaag
agtgaaaaattatcttgcatccaccctctcgctgaacaagtcatagtgataacacactctggccgaaaagggcgttatgccgtggaaccatac
catggtaaagtagtggtgccagagggacatgcaatacccgtccaggactttcaagctctgagtgaaagtgccaccattgtgtacaacgaacgt
gagttcgtaaacaggtacctgcaccatattgccacacatggaggagcgctgaacactgatgaagaatattacaaaactgtcaagcccagcgag
cacgacggcgaatacctgtacgacatcgacaggaaacagtgcgtcaagaaagaactagtcactgggctagggctcacaggcgagctggtggat
cctcccttccatgaattcgcctacgagagtctgagaacacgaccagccgctccttaccaagtaccaaccataggggtgtatggcgtgccagga
tcaggcaagtctggcatcattaaaagcgcagtcaccaaaaaagatctagtggtgagcgccaagaaagaaaactgtgcagaaattataagggac
gtcaagaaaatgaaagggctggacgtcaatgccagaactgtggactcagtgctcttgaatggatgcaaacaccccgtagagaccctgtatatt
gacgaagcttttgcttgtcatgcaggtactctcagagcgctcatagccattataagacctaaaaaggcagtgctctgcggggatcccaaacag
tgcggtttttttaacatgatgtgcctgaaagtgcattttaaccacgagatttgcacacaagtcttccacaaaagcatctctcgccgttgcact
aaatctgtgacttcggtcgtctcaaccttgttttacgacaaaaaaatgagaacgacgaatccgaaagagactaagattgtgattgacactacc
ggcagtaccaaacctaagcaggacgatctcattctcacttgtttcagagggggtgaagcagttgcaaatagattacaaaggcaacgaaataa
tgacggcagctgcctctcaagggctgacccgtaaaggtgtgtatgccgttcggtacaaggtgaatgaaaatcctctgtacgcacccacctcag -continued aacatgtgaacgtcctactgacccgcacggaggaccgcatcgtgtggaaaacactagccggcgacccatggataaaaacactgactgccaagt
accctgggaatttcactgccacgatagaggagtggcaagcagagcatgatgccatcatgaggcacatcttggagagaccggaccctaccgacg
tcttccagaataaggcaaacgtgtgttgggccaaggctttagtgccggtgctgaagaccgctggcatagacatgaccactgaacaatggaaca
ctgtggattattttgaaacggacaaagctcactcagcagagatagtattgaaccaactatgcgtgaggttctttggactcgatctggactccg
gtctattttctgcacccactgttccgttatccattaggaataatcactgggataactccccgtcgcctaacatgtacgggctgaataaagaag
tggtccgtcagctctctcgcaggtacccacaactgcctcgggcagttgccactggaagagtctatgacatgaacactggtacactgcgcaatt
atgatccgcgcataaacctagtacctgtaaacagaagactgcctcatgctttagtcctccaccataatgaacacccacagagtgacttttctt
cattcgtcagcaaattgaagggcagaactgtcctggtggtcggggaaaagttgtccgtcccaggcaaaatggttgactggttgtcagaccggc
ctgaggctaccttcagagctcggctggatttaggcatcccaggtgatgtgcccaaatatgacataatatttgttaatgtgaggaccccatata
aataccatcactatcagcagtgtgaagaccatgccattaagcttagcatgttgaccaagaaagcttgtctgcatctgaatcccggcggaacct
gtgtcagcataggttatggttacgctgacagggccagcgaaagcatcattggtgctatagcgcggcagttcaagttttcccgggtatgcaaac
cgaaatcctcacttgaagagacggaagttctgtttgtattcattgggtacgatcgcaaggcccgtacgcacaattcttacaagctttcatcaa
ccttgaccaacatttatacaggttccagactccacgaagccggatgtgcaccctcatatcatgtggtgcgaggggatattgccacggccaccg
aaggagtgattataaatgctgctaacagcaaaggacaacctggcggaggggtgtgcggagcgctgtataagaaattcccggaaagcttcgatt
tacagccgatcgaagtaggaaaagcgcgactggtcaaaggtgcagctaaacatatcattcatgccgtaggaccaaacttcaacaaagtttcgg
aggttgaaggtgacaaacagttggcagaggcttatgagtccatcgctaagattgtcaacgataacaattacaagtcagtagcgattccactgt
tgtccaccggcatcttttccgggaacaaagatcgactaacccaatcattgaaccatttgctgacagctttagacaccactgatgcagatgtag
ccatatactgcagggacaagaaatgggaaatgactctcaaggaagcagtggctaggagagaagcagtggaggagatatgcatatccgacgact
cttcagtgacagaacctgatgcagagctggtgagggtgcatccgaagagttctttggctggaaggaagggctacagcacaagcgatggcaaaa
ctttctcatatttggaagggaccaagtttcaccaggcggccaaggatatagcagaaattaatgccatgtggcccgttgcaacggaggccaatg
agcaggtatgcatgtatatcctcggagaaagcatgagcagtattaggtcgaaatgccccgtcgaagagtcggaagcctccacaccacctagca
cgctgccttgcttgtgcatccatgccatgactccagaaagagtacagcgcctaaaagcctcacgtccagaacaaattactgtgtgctcatcct
ttccattgccgaagtatagaatcactggtgtgcagaagatccaatgctcccagcctatattgttctcaccgaaagtgcctgcgtatattcatc
caaggaagtatctcgtggaaacaccaccggtagacgagactccggagccatcggcagagaaccaatccacagaggggacacctgaacaaccac
cacttataaccgaggatgagaccaggactagaacgcctgagccgatcatcatcgaagaggaagaagaggatagcataagtttgctgtcagatg
gcccgacccaccaggtgctgcaagtcgaggcagacattcacgggccgccctctgtatctagctcatcctggtccattcctcatgcatccgact
ttgatgtggacagtttatccatacttgacaccctggagggagctagcgtgaccagcggggcaacgtcagccgagactaactcttacttcgcaa
agagtatggagtttctggcgcgaccggtgcctgcgcctcgaacagtattcaggaaccctccacatcccgctccgcgcacaagaacaccgtcac
ttgcacccagcagggcctgctcgagaaccagcctagtttccaccccgccaggcgtgaatagggtgatcactagagaggagctcgaggcgctta
ccccgtcacgcactcctagcaggtcggtctcgagaaccagcctggtctccaacccgccaggcgtaaatagggtgattacaagagaggagtttg
aggcgttcgtagcacaacaacaatgacggtttgatgcgggtgcatacatctttttcctccgacaccggtcaagggcatttacaacaaaaatcag
taaggcaaacggtgctatccgaagtggtgttggagaggaccgaattggagatttcgtatgccccgcgcctcgaccaagaaaaagaagaattac
tacgcaagaaattacagttaaatcccacacctgctaacagaagcagataccagtccaggaaggtggagaacatgaaagccataacagctagac
gtattctgcaaggcctagggcattatttgaaggcagaaggaaaagtggagtgctaccgaaccctgcatcctgttcctttgtattcatctagtg
tgaaccgtgccttttcaagccccaaggtcgcagtggaagcctgtaacgccatgttgaaagagaactttccgactgtggcttcttactgtatta
ttccagagtacgatgcctatttggacatggttgacggagcttcatgctgcttagacactgccagttttttgccctgcaaagctgcgcagctttc
caaagaaacactcctatttggaacccacaatacgatcggcagtgccttcagcgatccagaacacgctccagaacgtcctggcagctgccacaa
aaagaaattgcaatgtcacgcaaatgagagaattgcccgtattggattcggcggcctttaatgtggaatgcttcaagaaatatgcgtgtaata
atgaatattgggaaacgtttaaagaaaaccccatcaggcttactgaagaaaacgtggtaaattacattaccaaattaaaaggaccaaaagctg
ctgctctttttgcgaagacacataatttgaatatgttgcaggacataccaatggacaggtttgtaatggacttaaagagagacgtgaaagtga
ctccaggaacaaaacatactgaagaacggcccaaggtacaggtgatccaggctgccgatccgctagcaacagcgtatctgtgcggaatccacc
gagagctggttaggagattaaatgcggtcctgcttccgaacattcatacactgtttgatatgtcggctgaagactttgacgctattatagccg
agcacttccagcctggggattgtgttctggaaactgacatcgcgtcgtttgataaaagtgaggacgacgccatggctctgaccgcgttaatga
ttctggaagacttaggtgtggacgcagagctgttgacgctgattgaggcggctttcggcgaaatttcatcaatacatttgcccactaaaacta
aatttaaattcggagccatgatgaaatctggaatgttcctcacactgtttgtgaacacagtcattaacattgtaatcgcaagcagagtgttga
gagaacggctaaccggatcaccatgtgcagcattcattggagatgacaatatcgtgaaaggagtcaaatcggacaaattaatggcagacaggt
gcgccacctggttgaatatggaagtcaagattatagatgctgtggtgggcgagaaagcgccttatttctgtggagggtttattttgtgtgact
ccgtgaccggcacagcgtgccgtgtggcagacccccctaaaaaggctgtttaagcttggcaaacctctggcagcagacgatgaacatgatgatg
acaggagaagggcattgcatgaagagtcaacacgctggaaccgagtgggtattctttcagagctgtgcaaggcagtagaatcaaggtatgaaa
ccgtaggaacttccatcatagttatggccatgactactctagctagcagtgttaaatcattcagctacctgagaggggcccctataactctct
acggctaacctgaatggactacgacatagtctagtccgccaagtctagcaGGAGAgtcccgacctccaggagagaccagggccacccttaag
cttaagATGGTGAGCAAGGGCGAGGAGGATAACATGGCCATCATCAAGGAGTTCATGCGCTTCAAG
GTGCACATGGAGGGCTCCGTGAACGGCCACGAGTTCGAGATCGAGGGCGAGGGCGAG
GGCCGCCCCTACGAGGGCACCCAGACCGCCAAGCTGAAGGTGACCAAGGGTGGCCCC
CTGCCCTTCGCCTGGGACATCCTGTCCCCTCAGTTCATGTACGGCTCCAAGGCCTACGT
GAAGCACCCCGCCGACATCCCCGACTACTTGAAGCTGTCCTTCCCCGAGGGCTTCAAG
TGGGAGCGCGTGATGAACTTCGAGGACGGCGGCGTGGTGACCGTGACCCAGGACTCC
TCCCTGCAGGACGGCGAGTTCATCTACAAGGTGAAGCTGCGCGGCACCAACTTCCCCT
CCGACGGCCCCGTAATGCAGAAGAAGACCATGGGCTGGGAGGCCTCCTCCGAGCGGA
TGTACCCCGAGGACGGCGCCCTGAAGGGCGAGATCAAGCAGAGGCTGAAGCTGAAGG
ACGGCGGCCACTACGACGCTGAGGTCAAGACCACCTACAAGGCCAAGAAGCCCGTGCA
GCTGCCCGGCGCCTACAACGTCAACATCAAGTTGGACATCACCTCCCACAACGAGGAC
TACACCATCGTGGAACAGTACGAACGCGCCGAGGGCCGCCACTCCACCGGCGGCATG
GACGAGCTGTACAAGTAATAAcatatggaattggcaagctgcttacatagaactcgcggcgattggcatgccgccttaaaatttttatttat
tttttcttttcttttccgaatcggatttttgtttttaatatttcaaaaaaaaaaaaaaaaaaaaaaaaaa SEQ ID NO: 6, Exemplary mCherry saRNA Sequence with Cytidine Substitution; Sequence Type: RNA; AflII cut site dotted-underlined (nuuaag), mCherry sequence bolded, NdeI cut site zigzag-underlined (nauaug); n indicates cytidine, 5-methylcytidine, or 5-hydroxymethylcytidine:

augggnggngnaugagagaagnnnagannaauuannuannnaaaaauggagaaaguunanguuganaungaggaaganagnnnauunnu
nagagnuuugnagnggagnuunnngnaguuugagguagaagnnaagnagguunanugauaaugannaugnuaaugnnagagnguuuun
gnaunuggnuunaaaanugaungaaanggagguggannnaunnganangaunnuuganauuggaagugngnnngnnngnagaaugua
uunuaagnanaaguaunauuguaunugunngaugagaugugnggaagaunnggangagauuguauaaguaugnaanuaagnugaagaaa
aanuguaaggaaauaanugauaaggaauugganaagaaaaugaaggagnuggnngnngunaugagngannnugannuggaaanugaga
nuaugugnnunnangangangagagungugungnuangaagggnaagungnuguuunnaggauguauangngguuganggannganaa
gununuaunannaagnnaauaagggaguuagagungnnuanuggauaggnuuuganannannnnuuuuauguuuaagaanuuggnug
gagnauaunnaunauaunuannaanugggnngangaaanngug uuaanggnunguaanauaggnnuaugnagnunuganguuaugg
agnggunanguagagggaugunnauunuuagaaagaaguauuugaaannaunnaanaauguunuauunuuguuggnunganna unu
annangagaagagggganuuanugaggagnuggnannugnngunuguauuunanuuanguggnaagnaaaauuananaugunggugug
aganuauaguuaguugngangggguangunguuaaaagaauagnuaunagunnaggnnuguaugggaagnnuunaggnuaugnugnua -continued ngaugnanngngagggauunuugugnugnaaaguganaganauugaanggggagagggunuuuunnngugugnanguaugugn
naguanauuguguganaaauganuggnauanuggnaanagaugunagugnggangangngnaaaaanugnugguugggnunaann
agnguauagungunaanggungnannnagagaaananaauannaugaaaauuannuuuugnnnguaguggnnnaggnauuugnuag
gugggnaaaggaauauaaggaagaunaagaagaugaaaggnnanuagganuangagauaganaguuagunaugggguguuguugggnu
uuuagaaggnanaagauaanaunuauuuauaagngnnnggauannnaaannaunaunaaagugaanagngauuunnanunauungugn
ugnnnaggauaggnaguaananauuggagaungggnugagaanaagaaunaggaaaauguuagaggagnanaaggagnngunannunu
nauuanngnngagganguanaagaagnuaagugngnagnngaugaggnuaaggaggugngugaagnngaggaguugngngnagnunu
annannuuuggnagnugauguugaggagnnnanunuggaggnagangunganuugauguuanaagaggnuggggnnggnunagugga
ganannunguggnuugauaaagguuannagnuangauggngagganaagaunggnunuuangnugugnuuununngnaggnuguanu
naagagugaaaaauuaunuugnaunnannnunungnugaanaagunauagugauaanananunuggnngaaaagggnguuaugnngug
gaannauannaugguaaaguaguggugnnagaggganaugnaauannngunnagganuuunaagnunugagugaaagugnnannauug
uguanaangaangugaguunguaaanagguannugnannauauugnnananauggaggagngnugaananugaugaagaauauuanaa
aanugunaagnnnagngagnanganggngaauannuguanganaunganaggaaanagugngunaagaaagaanuagunanugggnua
gggnunanaggngagnugguggaunnunnnuunnaugaauungnnuangagagunugagaananganna gnngnunnuuannaagua
nnaannauaggggguguauggngugnnaggaunaggnaagunuggnaunauuaaaagngnagunannaaaaaagaunuagugguga gng
nnaagaaagaaaanugugnagaaauuauaagggangunaagaaaaugaaagggnuggangunaaugnnagaanuguggan unagugnu
nuugaauggaugnaaanannnguagagannnuguauauugangaagnuuuugnuugunaugnagguanununagagngnunauagn
nauuauaagannuaaaaaggnagugnunugngggg aunnnaaanagugngguuuuuuuaanaugaugugnnugaaagugnauuuuaan
nangagauuugnananaagunuunnanaaaagnaunununngnnguugnanuaaaunuguganuunggungununaannuuguuuuan
ganaaaaaaaugagaangangaaunngaaagaganuaagauugugauugananuannggnaguannaaannuaagnaggangaununau
ununanuuguuunagagggugggugaagnaguugnaaauagauuanaaaggnaangaaauaaugangg nagnugnnununaagggnug
annnguaaaggugug uaugnnguungguanaaggugaaugaaaaunnunuguangnannnannunagaanaugugaangunnuanug
annngnanggaggan ngnaunguguggaaaananuagnnggngannnauggauaaaaananuganugnnaaguannnugggaauuuna
nugnnangauagaggaguggnaagnagagnaugaugnnaunaugaggnanaunuuggagagannggannnuannganguuunnaga
auaaggnaaanguguguuggg nnaaggnuuuagugnnggugnugaagannngnuggnauaganaugannanugaanaauggaananug
uggauuauuuugaaangganaaagnunanunagnagagauaguauugaannaanuaugngugagguunuuugganungaunugganu
nnggunuauuuunugnannnanuguunnguuaunnauuaggaauaaunanugggauaanunnnngungnnuaanauguangggnuga
auaaagaaguggunngunagnununungnagguannnanaanugnnungggnaguugnnanuggaagagunuauganaugaananug
guananugngnaauuaugaunngngnauaaannuaguannuguaaanagaaganugnnunaugnuuuagunnunnannauaaugaana
nnnanagaguganuuuunuunauungunagnaaauugaagggnagaanugunnugguggunggggaaaaguugunngunnnaggnaa
aaugguuganugguugunagannggnnugaggnuannuunagagnunggnuggauuuaggnaunnnaggugaugugnnnaaauauga
nauaauauuuguuaaugugaggannnnauauaaauannaunanuaunagnagugugaagannaugnnauuaagnuuagnauguugann
aagaaagnuugunugnaunugaaunnnggnggaannugugunagnauagguuaugguuangnuganagggnnagngaaagnaunauu
ggugnuauagngnggnaguunaaguuuunnngggu augnaaanngaaaunnunanuugaagagangg aaguunuguuuguauunauu
ggguangaungnaaggnnnguangnanaauunuuanaagnuuunaunaannuugannaanauuuauanagguunnaganunnangaag
nnggaugugnannnunauaunauguggugngaggggauauugnnanggnnanngaaggagugauuauaaaugnugnuaanagnaaag
ganaannuggnggaggggugugnggagngnuguauaagaaauunnnggaaagnuungauuuanagnngaungaaguaggaaaagngn
ganuggunaaaggugnagnuaaanauaunauunaugnnguaggannaaanuunaanaaaguuunggagguugaagguganaaanaguu
ggnagaggnuuaugagunnaungnuaagauugunaangauaanaauuanaagunaguagngauunnanuguugunnanngg naunuu
uunngggaanaaagaunganuaannnaaunauugaannauuugnuganagnuuuaganannanugaugnagauguagnnauauanugn
aggganaagaaaugggaaauganununaaggaagnaguggnuaggagagaagnaguggaggagauaugnauaunnganganunuunag
uganagaannugaugnagagnuggugagggugnaunngaagaguunuuuggnuggaaggaagggnuanagnanaagngauggnaaaan
uuununauauuuggaagggannaaguuunannaggnggnnaaggauauagnagaaauuaaugnnauguggnnnguugnaanggaggn
naaugagnagguaugnauguauaunnunggagaaagnaugagnaguauuaggungaaaugnnnngungaagagunggaagnnunnana
nnannuagnangnugnnuugnuugugnaunnaugnnauganunnagaaagaguanagngnnuaaaagnnunangunnagaanaaauua
nugugugnunaunnuuunnauugnngaaguauagaaunanuggugugnagaagaunnaaugnunnnagnnuauauuguunun anng a
aagugnnugnguauauunaunnaaggaaguaunu nguggaaananannanngguagangaganunnggagnnaunggnagagaannaaun
nanagaggggganannugaanaannannanuuauaanngaggaugagannagganuagaangnnugagnngaunaunaungaagaggaa
gaagaggauagnauaaguuugnugunagauggnnnganunnannaggugnugnaagungaggnaganauunangggnngnnnunugua
unuagnunaunnuggunnauunnunaugnaunnganuuugauguggana guuuaunnauanuuganannnuggagggagnuagngug
annagnggggnaangunagnngaganuaanunuuanuungnaaagaguauggaguuunuggngnganngg ugnnugngnnungaana
guauunaggaannnunnanaunnngnunngngnanaagaananngunanuugnannnagnagggnnugnungagaannagnnuaguu
unnannnngnnaggngugaauagggugaunanuagagaggagnungaggngnuuannnngunangnanunnuagnaggungg unung
agaannagnnuggunun naannngnnaggnguaaauagggugauuanaagagaggaguuugaggnguunguagnanaanaanaaugan
gguuugaugngggugnauanaunuuuunnunnganannggunaagggnauuuanaanaaaaaunaguaaggnaaanggugnuaunng
aaguggug uuggagaggann gaauuggagauuunguaugnnnngngnnunganna agaaaaagaagaauuanuangnaagaaauuana
guuaaaunnnanannugnuaanagaagnagauannagunnaggaagguggagaanaugaaagnnauaanagnuaganguauunugnaa
ggnnuagggnauuauuugaaggnagaaggaaaaguggagugnuanngaannnugnaunnuguunnuuuguauunaunuagugugaan
ngugnnuuuunaagnnnnaaggungnaguggaagnnuguaangnnauguugaaagagagaanuuunnganuguggnuunuuanuguauu
auunnagaguangaugnnuauuuggaaugguuganggagnuunaugnugnuuaganaanugnnaguuuuugnnnugnaaagnugngn
agnuuunnaaagagaaananunnuauuuggaannnanaauangaunggnagugnnuunagngaunnagaanangnunnagaangunnugg
nagnugnnanaaaaagaaauugnaaugunangnaaaugagagaauugnnnguauuggauunggnggnnuuuaaauguggaaugnuunaa
gaaauaugnguguaauaaugaauauugggaaanguuuaaagaaaannnnaunaggnuuanugaagaaaanggugguaaaauuanauuanna
aauuaaaaggannaaaagnugnugnunuuuuugngaaganananauaauuugaauauguugnaggana uannaauggana gguuuguaau
gganuuaaagagagagangugaaaguganunnaggaanaaaanauanugaagaaanggnnnaagguanaggugaunnaggnugnngaunng
nuagnaanagnguaunugugnggaaunnanngagagnugguuaggagauuaaaugnggunnugnuunngaananunauananuguuu
gauaugunggnugaaganuuugangnuauuauagnngagnanuunnagnnuggggauugugu unuggaaanuganaungngunguuu
gauaaaagugaggangangnnauggnunugannngnguuaaugauuuggaaganuuaggugugganggnagagnuguuganngnugauu
gaggnggnuuunggngaaauuunaunaaunanauuugnnnanuaaaanuaaauuuaaauungggagnnaugaugaaaunuggaauguunn
unananuguuugugaananagunauuaanauuguaaungnaagnagaguguugagagaanggnuaannggaunannaugugnagnauu
nauuggagaugana aauaungugaaaggagunaaaunggana aauuaauggnaganaggugngnnannugguugaauauggaagunaag
auuauagaugnuguggugggngagaaagngnnuuauuunuguggagggguuuauuuugugugananungugan nggnanagngugnng
uguggnagannnnnuaaaaaggnugugu uuaagnuuggnaaannunuggnagnagangaugaanaugaugauganaggagaagggnauug
naugaagagunaanangnuggaanngagugggguauunuuunagagnugugnaaggnaguagaaunaagguaugaaannguaggaanuu
nnaunauaguuauggnnauganuanunuagnuagnaguguuaaaunauunagnuannugagaggggnnnnuauaanununuanggnu
aannugaaugganuanganauagunuagunngnnaagunuagnaGGAGAgunnnganunnaggagagannagggnnannnuuaa
gnuuaagAUGGUGAGNAAGGGNGAGGAGGAUAANAUGGNNAUNAUNAAGGAGUUNAUGN
GNUUNAAGGUGNANAUGGAGGGNUNNGUGAANGGNNANGAGUUNGAGAUNGAGGGNG
AGGGNGAGGGNNGNNNNUANGAGGGNANNNAGANNGNNAAGNUGAAGGUGANNAAGG
GUGGNNNNNUGNNNUUNGNNUGGGANAUNNUGUNNNNUNAGUUNAUGUANGGNUNNA
AGGNNUANGUGAAGNANNNNGNNGANAUNNNNGANUANUUGAAGNUGUNNUUNNNNG

-continued

AGGGNUUNAAGUGGGAGNGNGUGAUGAANUUNGAGGANGGNGGNGUGGUGANNGUG
ANNNAGGANUNNUNNNUGNAGGANGGNGAGUUNAUNUANAAGGUGAAGNUGNGNGGN
ANNAANUUNNNNUNNGANGGNNNNGUAAUGNAGAAGAAGANNAUGGGNUGGGAGGNN
UNNUNNGAGNGGAUGUANNNNGAGGANGGNGNNNUGAAGGGNGAGAUNAAGNAGAGG
NUGAAGNUGAAGGANGGNGGNNANUANGANGNUGAGGUNAAGANNANNUANAAGGNN
AAGAAGNNNGUGNAGNUGNNNGGNGNNUANAANGUNAANAUNAAGUUGGANAUNANN
UNNNANAANGAGGANUANANNAUNGUGGAANAGUANGAANGNGNNGAGGGNNGNNAN
UNNANNGGNGGNAUGGANGAGNUGUANAAGUAAUAAnauauggaauuggnaagnugnuuanauagaanu
ngnggngauuggnaugnngnnuuaaaauuuuauuuuauuuuuunuuuunuuuunngaaunggauuuuguuuuuaauauuunaaaaa
aaaaaaaaaaaaaaaaaaaaa SEQ ID NO: 7, Exemplary mCherry saRNA Sequence with Uridine Substitution; Sequence Type: RNA; AflII cut site dotted-underlined (cnnaag), mCherry sequence bolded, NdeI cut site zigzag-underlined (canang); n indicates uridine, 5-methyluridine, or 5-hydroxymethyluridine:

angggcggcgcangagagaagcccagaccaannaccnacccaaaanggagaaagnncacgnngacancgaggaagacagcccannccncag
agcnnngcagcggagcnncccgcagnnngaggnagaagccaagcaggncacnganaangaccangcnaangccagagcgnnnncgcancn
ggcnncaaaacngancgaaacggaggnggacccanccgacacganccnngacanngg aagngcgcccgcccgcagaangnanncnaagca
caagnancanngnancngnccgangagangngcggaaganccggacagannngnanaagnangcaacnaagcngaagaaaaacngnaagga
aanaacnganaaggaannggacaagaaaangaaggagcnggccgccgncangagcgacccngaccnggaaacngagacnangngccncca
cgacgacgagncgngncgcnacgaagggcaagncgcngnnnaccaggangnanacgcggnngacggaccgacaagncncnancaccaagc
caanaagggagnnagagncgccnacnggan aggcnnngacaccaccccnnnnangnnnaagaacnnggcnggagcananccancanacnc
naccaacngggccgacgaaaccgngnnaacggcncgnaacanaggccnangcagcncngacgnnanggagcggncacgnagagggangnc
cannc nnagaaagaagnannngaaaccanccaacaangnncnanncncngnnggcncgaccancnaccacgagaagagggacnnacngag
gagcnggcaccngccgncngnannncacnnacgnggcaagcaaaannacacangncggngngagacnanagnnagnngcgacgggnacg
ncgnnaaaagaanagcnancagnccaggccngnangggaagccnncaggcnangcngcnacgangcaccgcgagggannc nngngcngc
aaagngacagacacanngaacggggagagggncncnnnnccgngngcacgnangngccagcnacanngngngaccaaangacnggcan
acnggcaacagangncagngcggacgacgcgcaaaaacngcnggnngggcncaaccagcgnanagncgncaacggncgcacccagagaaa
caccaanaccangaaaaannaccnnnngcccgnagnggcccaggcannngcnaggngggcaaaggaananaaggaagancaagaaganga
aaggccacnaggacnacgaganagacagnnagncanggggngnngnngggcnnnnagaaggcacaaganaacancnannnanaagcgcc
cgganacccaaaccancancaaagngaacagcgannnccacncanncgngcngcccagganaggcagnaacacannggagancgggcnga
gaacaagaancaggaaaangnnagaggagcacaaggagccgncaccncncannaccgccgaggacgnacaagaagcnaagngcgcagccga
ngaggcnaaggaggngcgngaagccgaggagnngcgcgcagcncnaccaccnnnggcagcngangnngaggagcccacncnggaggcag
acgncgacnngangnnacaagaggcnggggccggcncagnggagacaccncgnggcnnganaaaggnnaccagcnacganggcgaggac
aagancggcncnnacgcngngcnnncnccgcaggcngnacncaagagngaaaaannancnngcanccacccncncgcngaacaagncana
gnganaacacacncnggccgaaaagggcgnnangccgnggaaccanaccanggnaaagnagnggngccagagggacangcaanacccgnc
caggacnnncaagcncngagngaaagngccaccanngngnacaacgaacgngagnncgnaaacaggnaccngcaccananngccacacan
ggaggagcgcngaacacngangaagaanannacaaaacngncaagcccagcgagcacgacggcgaanaccngnacgacancgacaggaaac
agngcgncaagaaagaacnagncacngggcnagggcncacaggcgagcnggnggancc ncccnnccangaanncgccnacgagagncnga
gaacacgaccagccgcnccnnaccaagnaccaaccanaggggngnanggcgngccaggancaggcaagncnggcancannaaaagcgcag
ncaccaaaaaagancnagnggngagcgccaagaaagaaaacngngcagaaannanaagggacgncaagaaaangaaagggcnggacgncaa
ngccagaacngnggacncagngcncnngaanggangcaaacaccccgnagagacccngnananngacgaagcnnnngcnngncangcag
gnacncncagagcgcncanagccannanaagaccnaaaaaggcagngcncngcggggancccaaacagngcggnnnnnnnaacangangn
gccngaaagngcannnnaaccacgagannngcacacaagncnnccacaaaagcancncncgccgnngcacnaaancngngacnncggncg
ncncaaccnngnnnnacgacaaaaaaangagaacgacgaanccgaaagagacnaagannngnganngacacnaccggcagnaccaaaccnaa
gcaggacgancncanncncacnngnnncagagggngggngaagcagnngcaaanagannacaaaggcaacgaaanaangacggcagcngc
cncncaagggcngacccgnaaaggngngnangccgnncggnacaaggngaangaaaanccncngnacgcacccaccncagaacangngaa
cgnccnacngacccgcacggaggaccgcancgngnggaaaacacnagccggcgacccangganaaaaacacngacngccaagnacccnggg
aannncacngccacganagaggagnggcaagcagagcangangccancangaggcacancnnggagagaccggacccnaccgacgncnnc
cagaanaaggcaaacgngngnngggccaaggcnnnagngccggngcngaagaccgcnggcanagacangaccacngaacaanggaacacn
gnggannannnngaaacggacaaagcncacncagcagaganagnanngaaccaacnangcgngaggnncnnnggacncgancnggacnc
cggncnannnncngcacccacngnnccgnnanccannaggaanaancacngggganaacnccccgncgccnaacangnacgggcngaanaa
agaagnggnccgncagcncncncgcaggnacccacaacngccncgggcagnngccacnggaagagncnangacangaacacnggnacacn
gcgcaannanganccgcgcanaaaccnagnaccngnaaacagaagacngccncangcnnnagnccnccaccanaangaacacccacagagn
gacnnnncnncanncgncagcaaanngaagggcagaacngnccnggnggncggggaaaagnngnccgncccaggcaaaanggnngacng
gnngncagaccggccngaggcnaccnncagagcncggcnggannnaggcancccaggngangngcccaaanangacanaanannngnna
angngaggaccccananaaanaccancacnancagcagngngaagaccangccannaagcnnagcangnngaccaagaaagcnngncngc
ancngaancccggcggaaccngngncagcanaggnnanggnnacgcngacagggccagcgaaagcancanngg ngcnanagcgcggcag
nncaagnnnncccgggnangcaaaccgaaanccncacnngaagagacggaagnncngnnngnanncanngggnacgancgcaaggcccg
nacgcacaannc nnacaagcnnncancaaccnngaccaacannnanacaggnnccagacnccacgaagccggangngcacccncanancan
gnggngcgaggggananngccacggccaccgaaggagngannanaaangcngcnaacagcaaaggacaaccnggcggaggggngngcgg
agcgcngnanaagaaannc ccggaaagcnncgannnacagccgancgaagnaggaaaagcgcgacnggncaaaggngcagcnaaacanan
canncangccgnaggaccaaacnncaacaaagnnncggaggnngaaggngacaaacagnnggcagaggcnnangagnccancgcnaagan
ngncaacganaacaannacaagncagnagcganncc acngnngnccaccggcancnnnnccgggaacaaagancgacnaacccaancann
gaaccannngcngacagcnnnagacaccacngangcagangnagccananacngcagggacaagaaanggg aaangacncncaaggaagc
agnggcnaggagagaagcagnggaggaganangcananccgacgacncnncagngacagaaccngangcagagcnggngagggngcanc
cgaagagnncnnnggcnggaaggaagggcnacagcacaagcganggcaaaacnnncncanannnggaagggaccaagnnncaccaggcgg
ccaagganaagcagaaannaangccangnggcccgnngcaacggaggccaangagcaggnangcangnananccncggagaaagcanga
gcagnannaggncgaaangccccgncgaagagncggaagccnccacaccaccnagcacgcngccnngcnngngcanccangccangacnc
cagaaagagnacagcgccnaaaagccncacgnccagaacaaannacngngngcncanccnnnccanngccgaagnanagaancacnggng
ngcagaaganccaangcncccagccnananngnncncaccgaaagngccngcgnananncanccaaggaagnancncgnggaaacaccac
cggnagacgagacnccggagccancggcagagaaccaanccacagaggggacaccngaacaaccaccacnnanaaccgaggangagaccag
gacnagaacgccngagccgancancancgaagaggaagaagagganagcanaagnnngcngncaganggcccgacccaccaggngcngca
agncgaggcagacannc acgggccgcccncngnancnagcncancnggnccannccncangcanccgacnnngangnggacagnnnanc
canacnngacacccnggagggagcnagcgngaccagcggggcaacgncagccgagacnaacncnnacnncgcaaagagnanggagnnncn
ggcgcgaccggngccngcgccncgaacagnanncaggaacccnccacancccgcnccgcgcacaagaacaccgncacnngcacccagcagg
gccngcncgagaaccagccnagnnnccaccccgccaggcgngaanagggngancacnagagaggagcncgaggcgcnnaccccgncacgc
acnccnagcaggncggncncgagaaccagccnggncnccaacccgccaggcgnaaanagggngannacaagagaggagnnngaggcgnnc
gnagcacaacaacaangacggnnngangcgggngcanacancnnnnccnccgacaccggncaagggcannnacaacaaaaancagnaagg
caaacggngcnanccgaagnggngnnggagaggaccgaannggagannncgnangccccgcgccncgaccaagaaaaagaagaannacna
cgcaagaaannacagnnaaancccacaccngcnaacagaagcaganaccagnccaggaaggnggagaacangaaagccanaacagcnagac -continued gnanncngcaaggccnagggcannannngaaggcagaaggaaaagnggagngcnaccgaacccngcanccngnnccnnngnanncancn
agngngaaccgngccnnnncaagccccaaggncgcagnggaagccngnaacgccangnngaaagagaacnnnccgacngnggcnncnnac
ngnannanncccagagnacgangccnannnggacanggnngacggagcnncangcngcnnagacacngccagnnnnngcccngcaaagcn
gcgcagcnnnccaaagaaacacnccnannnggaacccacaanacgancggcagngccnncagcganccagaacacgcnccagaacgnccng
gcagcngccacaaaaagaaanngcaangncacgcaaangagagaanngcccgnannggannccggcggccnnnaangnggaangcnncaag
aaanangcgngnaanaangaananngggaaacgnnnaaagaaaaccccancaggcnnacngaagaaaacgnggnaaannacannaccaaa
nnaaaaggaccaaaagcngcngcncnnnnngcgaagacacanaannngaanangnngcaggacanaccaanggacaggnnngnaanggac
nnaaagagagagacgngaaagngacnccaggaacaaaacanacngaagaacggcccaaggnacaggnganccaggcngccganccgcnagcaa
cagcgnancngngcggaanccaccgagagcnggnnaggagannaaangcggnccngcnnccgaacanncanacacngnnnganangncg
gcngaagacnnngacgcnannanagccgagcacnnccagccngggganngngnncnggaaacngacancgcgncgnnnganaaaagnga
ggacgacgccanggcncngaccgcgnnaanganncnggaagacnnaggngnggacgcagagcngnngacgcnganngaggggcnnncg
gcgaaannncancaanacannngcccacnaaaacnaaannnaaanncggagccangangaaancnggaangnnccncacacngnnngnga
acacagncannaacanngnaancgcaagcagagngnngagagaacggcnaaccggancaccangngcagcanncanngganganacaana
ncgngaaaggagncaaancggacaaannaanggcagacaggngcgccaccnggnngaananggaagncaagannanagangcngnggng
ggcgagaaagcgccnnannncngnggagggnnnannnngngngacnccgngaccggcacagcgngccgngnggcagacccccnaaaaag
gcngnnnaagcnnggcaaaccncnggcagcagacgangaacanganganggacaggagaagggcanngcangaagagncaacacgcnggaa
ccgagngggnanncnnncagagcngngcaaggcagnagaancaaggnangaaaccgnaggaacnnccancanagnnanggccangacnac
ncnagcnagcagngnnaaancanncagcnaccngagaggggccccnanaacncncnacggcnaaccngaanggacnacgacanagncnag
nccgccaagncnagcaGGAGAgncccgaccnccaggagagaccagggccacccnnaagcnnaagANGGNGAGCAAGGGC
GAGGAGGANAACANGGCCANCANCAAGGAGNNCANGCGCNNCAAGGNGCACANGGAG
GGCNCCGNGAACGGCCACGAGNNCGAGANCGAGGGCGAGGGCGAGGGCCGCCCCNAC
GAGGGCACCCAGACCGCCAAGCNGAAGGNGACCAAGGGNGGCCCCCNGCCCNNCGCC
NGGGACANCCNGNCCCCNCAGNNCANGNACGGCNCCAAGGCCNACGNGAAGCACCCC
GCCGACANCCCCGACNACNNGAAGCNGNCCNNCCCCGAGGGCNNCAAGNGGGAGCGC
GNGANGAACNNCGAGGACGGCGGCGNGGNGACCGNGACCCAGGACNCCNCCCNGCAG
GACGGCGAGNNCANCNACAAGGNGAAGCNGCGCGGCACCAACNNCCCCNCCGACGGC
CCCGNAANGCAGAAGAAGACCANGGGCNGGGAGGCCNCCNCCGAGCGGANGNACCCC
GAGGACGGCGCCCNGAAGGGCGAGANCAAGCAGAGGCNGAAGCNGAAGGACGGCGG
CCACNACGACGCNGAGGNCAAGACCACCNACAAGGCCAAGAAGCCCGNGCAGCNGCC
CGGCGCCNACAACGNCAACANCAAGNNGGACANCACCNCCCACAACGAGGACNACACC
ANCGNGGAACAGNACGAACGCGCCGAGGGCCGCCACNCCACCGGCGGCANGGACGAG
CNGNACAAGNAANAAcanangggaanngcaagcngcnnacanagaacncgcggcganngcangccgccnnaaaannnnna
nnnnannnnnnnnnnnnnccgaancggannnngnnnnnaananmncaaaaaaaaaaaaaaaaaaaaaaaaaa The saRNAs described herein can self-replicate due to inclusion of conserved sequence elements (CSEs) located on the 5' and 3' ends of the RNA in combination with protein machinery (RNA-dependent RNA polymerase or RdRp) encoded by the coding sequences for nsp1-4. The saRNA can also include amplification of a sub-genomic RNA, e.g., encoding the cargo of interest, from a subgenomic promoter (SGP) that is recognized by the RdRp. As such, the exemplary saRNAs described herein can comprise at least the following domains: nsp1-4 (see e.g., nucleotides 62-5701 of SEQ ID NO: 2 and nucleotides 5702-7543 of SEQ ID NO: 2, which translate to SEQ ID NO: 4 and SEQ ID NO: 23, respectively); 3' CSE; 5' CSE; and/or a SGP.

The conserved 3'-conserved sequence element (3' CSE) is encoded in the 3' UTR and is dependent on the viral machinery (e.g., nsP1-4) used in the saRNA. For VEEV, the 3' CSE is in the 3' UTR sequence and can comprise: catgccgccttaaaatttttattttatttttcttttcttttccgaatcggatttgtttttaatatttc, SEQ ID NO: 9 (see e.g., nucleotides 7673-7742 of SEQ ID NO: 2).

The conserved 5' sequence element (5' CSE) is contained in the nsp1 coding sequence and is 51 nt. The 5' CSE is also dependent on viral machinery (e.g., nsP1-4) used to generate the saRNA. For VEEV, the 5' CSE can comprise: aagcaggtcactgataatgaccatgctaatgccagagcgttttcgcatctg, SEQ ID NO: 10 (see e.g., nucleotides 149-199 of SEQ ID NO: 2).

The subgenomic promoter (SGP) is located at the end of nsp4 and contains sequences within and after the coding sequence of nsp4. This is also dependent on viral machinery (e.g., nsP1-4) used to generate the saRNA. The sequence for the SGP in VEEV can comprise:

agcttggcaaacctctggcagcagacgatgaacatgatgatgacaggag
aagggcattgcatgaagagtcaacacgctggaaccgagtgggtattctt
tcagagctgtgcaaggcagtagaatcaaggtatgaaaccgtaggaactt
ccatcatagttatggccatgactactctagctagcagtgttaaatcatt
cagctacctgagaggggcccctataactctctacggctaacctgaatgg
actacgacatagtctagtccgccaag, (see e.g., nucleotides 7308-7578 of SEQ ID NO: 2).

SEQ ID NO: 21, Exemplary SARS-CoV-2 saRNA vaccine sequence; spike sequence bolded
(aa 7599-11384 of SEQ ID NO: 21)
atgggcggcgcatgagagaagcccagaccaattacctacccaaaatggagaaagttcacgttgacatcgaggaagacagcccattcctcagag
ctttgcagcggagcttcccgcagtttgaggtagaagccaagcaggtcactgataatgaccatgctaatgccagagcgttttcgcatctggctt
caaaactgatcgaaacggaggtggacccatccgacacgatccttgacattggaagtgcgcccgcccgcagaatgtattctaagcacaagtatc
attgtatctgtccgatgagatgtgcggaagatccggacagattgtataagtatgcaactaagctgaagaaaaactgtaaggaaataactgata
aggaattggacaagaaaatgaaggagctggccgccgtcatgagcgaccctgacctggaaactgagactatgtgcctccacgacgacgagtcgt
gtcgctacgaagggcaagtcgctgtttaccaggatgtatacgcggttgacggaccgacaagtctctatcaccaagccaataagggagttagag
tcgcctactggataggctttgacaccacccctttttatgtttaagaacttggctggagcatatccatcatactctaccaactgggccgacgaaa
ccgtgttaacggctcgtaacataggcctatgcagctctgacgttatggagcggtcacgtagagggatgtccattcttagaaagaagtatttga
aaccatccaacaatgttctattctctgttggctcgaccatctaccacgagaagagggacttactgaggagctggcacctgccgtctgtatttc
acttacgtggcaagcaaaattacacatgtcggtgtgagactatagttagttgcgacgggtacgtcgttaaaagaatagctatcagtccaggcc
tgtatgggaagccttcaggctatgctgctacgatgcaccgcgagggattcttgtgctgcaaagtgacagacacattgaacggggagagggtct
cttttcccgtgtgcacgtatgtgccagctacattgtgtgaccaaatgactggcatactggcaacagatgtcagtgcggacgacgcgcaaaaac
tgctggttgggctcaaccagcgtatagtcgtcaacggtcgcacccagagaaacaccaataccatgaaaaattacctttgcccgtagtggccc
aggcatttgctaggtgggcaaaggaatataaggaagatcaagaagatgaaaggccactaggactacgagatagacagttagtcatggggtgtt -continued gttgggcttttagaaggcacaagataacatctatttataagcgcccggatacccaaaccatcatcaaagtgaacagcgatttccactcattcg
tgctgcccaggataggcagtaacacattggagatcggggctgagaacaagaatcaggaaaatgttagaggagcacaaggagccgtcacctctca
ttaccgccgaggacgtacaagaagctaagtgcgcagccgatgaggctaaggaggtgcgtgaagccgaggagttgcgcgcagctctaccacctt
tggcagctgatgttgaggagcccactctggaggcagacgtcgacttgatgttacaagaggctggggccggctcagtggagacacctcgtggct
tgataaaggttaccagctacgatggcgaggacaagatcggctcttacgctgtgctttctccgcaggctgtactcaagagtgaaaaattatctt
gcatccaccctctcgctgaacaagtcatagtgataacacactctggccgaaaagggcgttatgccgtggaaccataccatggtaaagtagtgg
tgccagagggacatgcaatacccgtccaggactttcaagctctgagtgaaagtgccaccattgtgtacaacgaacgtgagttcgtaaacaggt
acctgcaccatattgccacacatggaggagcgctgaacactgatgaagaatattacaaaactgtcaagcccagcgagcacgacggcgaatacc
tgtacgacatcgacaggaaacagtgcgtcaagaaagaactagtcactgggctagggctcacaggcgagctggtggatcctcccttccatgaat
tcgcctacgagagtctgagaacacgaccagccgctccttaccaagtaccaaccatagggggtgtatggcgtgccaggatcaggcaagtctggca
tcattaaaagcgcagtcaccaaaaaagatctagtggtgagcgccaagaaagaaaactgtgcagaaattataagggacgtcaagaaaatgaaag
ggctggacgtcaatgccagaactgtggactcagtgctcttgaatggatgcaaacaccccgtagagaccctgtatattgacgaagcttttgctt
gtcatgcaggtactctcagagcgctcatagccattataagacctaaaaaggcagtgctctgcggggatcccaaacagtgcggtttttttaaca
tgatgtgcctgaaagtgcattttaaccacgagatttgcacacaagtcttccacaaaagcatctctcgccgttgcactaaatctgtgacttcgg
tcgtctcaaccttgttttacgacaaaaaaatgagaacgacgaatccgaaagagactaagattgtgattgacactaccggcagtaccaaaccta
agcaggacgatctcattctcacttgtttcagagggggggtgaagcagttgcaaatagattacaaaggcaacgaaataatgacggcagctgcctc
tcaagggctgacccgtaaaggtgtgtatgccgttcggtacaaggtgaatgaaaatcctctgtacgcacccacctcagaacatgtgaacgtcct
actgacccgcacggaggaccgcatcgtgtggaaaacactagccggcgacccatggataaaaacactgactgccaagtaccctgggaatttcac
tgccacgatagaggagtggcaagcagagcatgatgccatcatgaggcacatcttggagagaccggaccctaccgacgtcttccagaataaggc
aaacgtgtgttgggccaaggctttagtgccggtgctgaagaccgctggcatagacatgaccactgaacaatggaacactgtggattattttga
aacggacaaagctcactcagcagagatagtattgaaccaactatgcgtgaggttctttggactcgatctggactccggtctattttctgcacc
cactgttccgttatccattaggaataatcactgggataactccccgtcgcctaacatgtacgggctgaataaagaagtggtccgtcagctctc
tcgcaggtacccacaactgcctcgggcagttgccactggaagagtctatgacatgaacactggtacactgcgcaattatgatccgcgcataaa
cctagtacctgtaaacagaagactgcctcatgctttagtcctccaccataatgaacacccacagagtgactttcttcattcgtcagcaaatt
gaagggcagaactgtcctggtggtcggggaaaagttgtccgtcccaggcaaaatggttgactggttgtcagaccggcctgaggctaccttcag
agctcggctggatttaggcatcccaggtgatgtgcccaaatatgacataatatttgttaatgtgaggaccccatataaataccatcactatca
gcagtgtgaagaccatgccattaagcttagcatgttgaccaagaaagcttgtctgcatctgaatcccggcggaacctgtgtcagcataggtta
tggttacgctgacagggccagcgaaagcatcattggtgctatagcgcggcagttcaagttttcccgggtatgcaaaccgaaatcctcacttga
agagacggaagttctgtttgtattcattgggtacgatcgcaaggcccgtacgcacaattcttacaagctttcatcaaccttgaccaacattta
tacaggttccagactccacgaagccggatgtgcaccctcatatcatgtggtgcgaggggatattgccacggccaccgaaggagtgattataaa
tgctgctaacagcaaaggacaacctggcggaggggtgtgcggagcgctgtataagaaattcccggaaagcttcgatttacagccgatcgaagt
aggaaaagcgcgactggtcaaaggtgcagctaaacatatcattcatgccgtaggaccaaacttcaacaaagtttcggaggttgaaggtgacaa
acagttggcagaggcttatgagtccatcgctaagattgtcaacgataacaattacaagtcagtagcgattccactgttgtccaccggcatctt
ttccgggaacaaagatcgactaacccaatcattgaaccatttgctgacagctttagacaccactgatgcagatgtagccatatactgcaggga
caagaaatgggaaatgactctcaaggaagcagtggctaggagagaagcagtggaggagatatgcatatccgacgactcttcagtgacagaacc
tgatgcagagctggtgagggtgcatccgaagagttctttggctggaaggaagggctacagcacaagcgatggcaaaactttctcatatttgga
agggaccaagtttcaccaggcggccaaggatatagcagaaattaatgccatgtggcccgttgcaacggaggccaatgagcaggtatgcatgta
tatcctcggagaaagcatgagcagtattaggtcgaaatgccccgtcgaagagtcggaagcctccacaccacctagcacgctgccttgcttgtg
catccatgccatgactccagaaagagtacagcgcctaaaagcctcacgtccagaacaaattactgtgtgctcatcctttccattgccgaagta
tagaatcactggtgtgcagaagatccaatgctcccagcctatattgttctcaccgaaagtgcctgcgtatattcatccaaggaagtatctcgt
ggaaacaccaccggtagacgagactccggagccatcggcagagaaccaatccacagaggggacacctgaacaaccaccacttataaccgagga
tgagaccaggactagaacgcctgagccgatcatcatcgaagaggaagaagaggatagcataagtttgctgtcagatggcccgacccaccaggt
gctgcaagtcgaggcagacattcacgggccgccctctgtatctagctcatcctggtccattcctcatgcatccgactttgatgtggacagttt
atccatacttgacaccctggagggagctagcgtgaccagcggggcaacgtcagccgagactaactcttacttcgcaaagagtatggagtttct
ggcgcgaccggtgcctgcgcctcgaacagtattcaggaaccctccacatcccgctccgcgcacaagaacaccgtcacttgcacccagcagggc
ctgctcgagaaccagcctagtttccaccccgccaggcgtgaatagggtgatcactagagaggagctcgaggcgcttaccccgtcacgcactcc
tagcaggtcggtctcgagaaccagcctggtctccaacccgccaggcgtaaatagggtgattacaagagaggagtttgaggcgttcgtagcaca
acaacaatgacggtttgatgcgggtgcatacatcttttcctccgacaccggtcaagggcatttacaacaaaaatcagtaaggcaaacggtgct
atccgaagtggtgttggagaggaccgaattggagatttcgtatgccccgcgcctcgaccaagaaaaagaagaattactacgcaagaaattaca
gttaaatcccacacctgctaacagaagcagataccagtccaggaaggtggagaacatgaaagccataacagctagacgtattctgcaaggcct
agggcattatttgaaggcagaaggaaaagtggagtgctaccgaaccctgcatcctgttcctttgtattcatctagtgtgaaccgtgccttttc
aagccccaaggtcgcagtggaagcctgtaacgccatgttgaaagagaactttccgactgtggcttcttactgtattattccagagtacgatgc
ctatttggacatggttgacggagcttcatgctgcttagacactgccagtttttgccctgcaaagctgcgcagctttccaaagaaacactccta
tttggaacccacaatacgatcggcagtgccttcagcgatccagaacacgctccagaacgtcctggcagctgccacaaaaagaaattgcaatgt
cacgcaaatgagagaattgcccgtattggattcggcggcctttaatgtggaatgcttcaagaaatatgcgtgtaataatgaatattgggaaac
gtttaaagaaaaccccatcaggcttactgaagaaaacgtggtaaattacattaccaaattaaaaggaccaaaagctgctgctctttttgcgaa
gacacataatttgaatatgttgcaggacataccaatggacaggtttgtaatggacttaaagagagacgtgaaagtgactccaggaacaaaaca
tactgaagaacggcccaaggtacaggtgatccaggctgccgatccgctagcaacagcgtatctgtgcggaatccaccgagagctggttaggag
attaaatgcggtcctgcttccgaacattcatacactgtttgatatgtcggctgaagactttgacgctattatagccgagcacttccagcctgg
ggattgtgttctggaaactgacatcgcgtcgtttgataaaagtgaggacgacgccatggctctgaccgcgttaatgattctggaagacttagg
tgtggacgcagagctgttgacgctgattgaggcggctttcggcgaaatttcatcaatacatttgcccactaaaactaaatttaaattcggagc
catgatgaaatctggaatgttcctcacactgtttgtgaacacagtcattaacattgtaatcgcaagcagagtgttgagagaacggctaaccgg
atcaccatgtgcagcattcattggagatgacaatatcgtgaaaggagtcaaatcggacaaattaatggcagacaggtgcgccacctggttgaa
tatggaagtcaagattatagatgctgtggtgggcgagaaagcgccttatttctgtggagggtttattttgtgtgactccgtgaccggcacagc
gtgccgtgtggcagacccccctaaaaaggctgtttaagcttggcaaacctctggcagcagacgatgaacatgatgatgacaggagaagggcatt
gcatgaagagtcaacacgctggaaccgagtgggtattctttcagagctgtgcaaggcagtagaatcaaggtatgaaaccgtaggaacttccat
catagttatggccatgactactctagctagcagtgttaaatcattcagctacctgagaggggcccctataactctctacggctaacctgaatg
gactacgacatagtctagtccgccaagtctagcaggagagtcccgacctccaggagagaccagggccacccttaaggccgccaccatgtttgt
gttcttggtgttgcttccactggtcagttcccaatgcgttaatctcaccacccgaactcaactcccacccgcatatacaaattccttcaccag
aggagtgtactatcctgacaaagtgtttcggtcaagtgtcctccactctactcaggacctctttctgcctttcttttctaacgttacatggtt
tcatgcaatccatgtgtctgggacaaacggcaccaaacgcttcgacaaccctgtattgccattcaatgatggggtgtactttgcctccacaga
gaaatccaacatcattcgaggatggattttcgggactactctggactcaaagacacagagcctgctgatcgttaacaacgccacaaacgttgt
catcaaagtgtgcgaattccagttttgcaatgatcccttcctgggagtgtactatcacaagaataacaagtcctggatggagagcgaatttcg
ggtctacagcagcgcaaacaactgcaccttcgagtacgtgagtcaaccctttctgatggacctggaagggaaacagggaaacttcaagaacct
gagagagtttgtctttaagaacatcgacggctattttaagatctatagtaagcatacgcctatcaacctggtaagggatcttccccagggctt
ttcagccctggaacctttggttgacttgcctattggtatcaatatcaccagatttcagacccttctggcattgcatcggtcttatcttactcc
aggtgattcctcctccgggtggactgccggcgccgctgcctactatgtcggctatctgcaaccaagaacgttcctgctcaagtacaacgaaaa
cggcactattacggatgctgttgattgtgccctggaccctctgtctgagactaaatgcaccctcaagagctttaccgttgagaaggggattta
ccaaaccagtaatttccgggtccaacccaccgaaagcattgtgcggttcccaaatatcaccaatctgtgtccctttggcgaagtgttcaatgc
tacaaggtttgcttctgtgtacgcatggaataggaaacgcatctccaattgtgtcgctgattactccgtgctgtacaattccgcctctttctc
aaccttcaagtgttatggcgtttcacctaccaaacttaacgacctgtgcttcactaatgtgtatgccgactcttttgtgatacgaggcgatga

-continued

```
agtgagacagattgcaccagggcagaccggcaaaattgccgactacaactacaagcttccagatgactttaccggatgtgttattgcatggaa
ctcaaacaatctggattccaaggtgggtggcaactataactacctgtatagactgttcaggaaatccaacctgaaaccattcgagcgagatat
aagcacagaaatctaccaggctggaagtacgccctgcaacggcgtggaagggttcaactgctacttcccattgcagagttacggattccagcc
tacaaacggggggttaccaaccctatcgtgtcgtagtcctgagttttgagctcctccatgccccagccacagtctgtggccccaagaaaagc
accaatctggtgaagaacaaatgcgtgaactttaactttaacggactcacaggaaccggcgtattgacggagagtaacaagaagttcctgcca
ttccagcagttcggtcgcgatattgccgacactaccgacgctgtccgagatccccagacattggagattcttgatatcacaccctgtagtttc
ggcggagtgagcgtgattacgcccggaaccaataccagcaatcaggttgccgtcctgtatcaggacgtgaattgcaccgaggtacctgtcgcc
atccacgctgaccaacttacacccacatggcgagtatattccaccggctccaacgtctttcagacacgtgctggatgtctgatcggtgcagaa
cacgttaataatagctacgagtgtgatatccccatcggtgctggaatatgcgcctcttatcaaactcaaaccaactctcctagggcggcagct
agtgtagcatcccaaagtatcattgcctacacaatgagcctcggtgctgagaattctgtcgcctacagcaacaactccattgctatccctact
aacttcacaatcagtgtgacaactgaaattctgcccgtatctatgaccaaaacaagcgttgactgcaccatgtacatctgtggcgattctacc
gaatgtagcaatctcctcctgcaatacggatcattctgcactcagctgaatcgtgccctcacaggtattgcagttgagcaggacaagaatacg
caggaagtgtttgcccaggtgaagcaaatctacaaaactccacccataaaagactttggcggattcaatttctcacagatcctgcccgatccc
tcaaaaccctccaagcgtagctttatcgaggatctgctcttcaacaaggtaaccctcgcagatgccggtttcatcaagcagtatggcgattgt
ctgggagacatcgccgctcgggacctgatctgtgcacagaagttcaatggactgaccgtgctgcctcccttgctgaccgacgagatgatagcc
caatacactagcgccctgctggccggcaccatcacttctgggtggacattcggagctggcgctgcccttcagattccttttgctatgcagatg
gcctaccgctttaacggcatcggtgtgacacaaaacgttctgtatgaaaaccagaaactcatcgccaaccagttcaacagtgctatcggtaag
atacaggatagcctgtcatccactgccagcgcattgggaaagttgcaggatgtagtgaaccagaatgcccaggcacttaacaccctggtgaaa
cagctctcttcaaattttggtgccatttctagcgtgctgaatgacatactgagccggttggaccctccggaggctgaagtgcagattgatagg
ctgataactgggcgccttcagtctcttcagacctatgtgacccagcagctcatccgcgctgctgaaattcgcgcatccgctaacctggcagca
accaaaatgtccgagtgtgtgctgggtcagtctaagagagtggactttgcgggaaggggtatcacctgatgtcttttcctcagtctgcaccc
catggtgtggtctttctgcacgtgacttatgtcccagctcaggaaaagaacttcactacagccccagccatctgccacgatggaaagcccac
tttcccagggaaggcgtattcgtgtccaatggtactcattggttcgtcactcagagaaatttctacgagccccagattataaccactgacaat
acatttgtatccggcaattgtgatgtggttatcgggattgtgaataatactgtttacgatcctttgcagccagagctggactccttcaaggag
gagcttgacaaatatttaagaatcacacatcacctgacgtcgacctcggagatatttcaggaatcaatgcttccgtggtcaatattcagaag
gagatagacaggctgaatgaggttgccaagaacctcaacgagtctctgatcgatctgcaggagttgggcaagtacgaacagtatatcaaatgg
ccatggtacatttggcttgggttcattgctgggctgatagctatcgtcatggtgacaattatgttgtgttgcatgacatcctgctgtagttgt
ctgaagggctgctgctcatgcggcagctgttgctaacatatggaattggcaagctgcttacatagaactcgcggcgattggcatgccgcctta
aaattttatttatttttcttttcttttccgaatcggatttgtttttaatatttcaaaaaaaaaaaaaaaaaaaaaaaaa
```

SEQ ID NO: 22, Exemplary SARS-CoV-2 spike protein encoded by SEQ ID NO: 21:

```
MFVFLVLLPLVSSQCVNLTTRTQLPPAYTNSFTRGVYYPDKVFRSSVLHSTQDLFLPFFSNVTWF
HAIHVSGTNGTKRFDNPVLPFNDGVYFASTEKSNIIRGWIFGTTLDSKTQSLLIVNNATNVVIKVC
EFQFCNDPFLGVYYHKNNKSWMESEFRVYSSANNCTFEYVSQPFLMDLEGKQGNFKNLREFVF
KNIDGYFKIYSKHTPINLVRDLPQGFSALEPLVDLPIGINITRFQTLLALHRSYLTPGDSSSGWTAG
AAAYYVGYLQPRTFLLKYNENGTITDAVDCALDPLSETKCTLKSFTVEKGIYQTSNFRVQPTESI
VRFPNITNLCPFGEVFNATRFASVYAWNRKRISNCVADYSVLYNSASFSTFKCYGVSPTKLNDLC
FTNVYADSFVIRGDEVRQIAPGQTGKIADYNYKLPDDFTGCVIAWNSNNLDSKVGGNYNYLYRL
FRKSNLKPFERDISTEIYQAGSTPCNGVEGFNCYFPLQSYGFQPTNGVGYQPYRVVVLSFELLHAP
ATVCGPKKSTNLVKNKCVNFNFNGLTGTGVLTESNKKFLPFQQFGRDIADTTDAVRDPQTLEILD
ITPCSFGGVSVITPGTNTSNQVAVLYQDVNCTEVPVAIHADQLTPTWRVYSTGSNVFQTRAGCLI
GAEHVNNSYECDIPIGAGICASYQTQTNSPRAAASVASQSIIAYTMSLGAENSVAYSNNSIAIPTNF
TISVTTEILPVSMTKTSVDCTMYICGDSTECSNLLLQYGSFCTQLNRALTGIAVEQDKNTQEVFAQ
VKQIYKTPPIKDFGGFNFSQILPDPSKPSKRSFIEDLLFNKVTLADAGFIKQYGDCLGDIAARDLIC
AQKFNGLTVLPPLLTDEMIAQYTSALLAGTITSGWTFGAGAALQIPFAMQMAYRFNGIGVTQNV
LYENQKLIANQFNSAIGKIQDSLSSTASALGKLQDVVNQNAQALNTLVKQLSSNFGAISSVLNDIL
SRLDPPEAEVQIDRLITGRLQSLQTYVTQQLIRAAEIRASANLAATKMSECVLGQSKRVDFCGKG
YHLMSFPQSAPHGVVFLHVTYVPAQEKNFTTAPAICHDGKAHFPREGVFVSNGTHWFVTQRNF
YEPQIITTDNTFVSGNCDVVIGIVNNTVYDPLQPELDSFKEELDKYFKNHTSPDVDLGDISGINAS
VVNIQKEIDRLNEVAKNLNESLIDLQELGKYEQYIKWPWYIWLGFIAGLIAIVMVTIMLCCMTSC
CSCLKGCCSCGSCC
```

Figure 92:
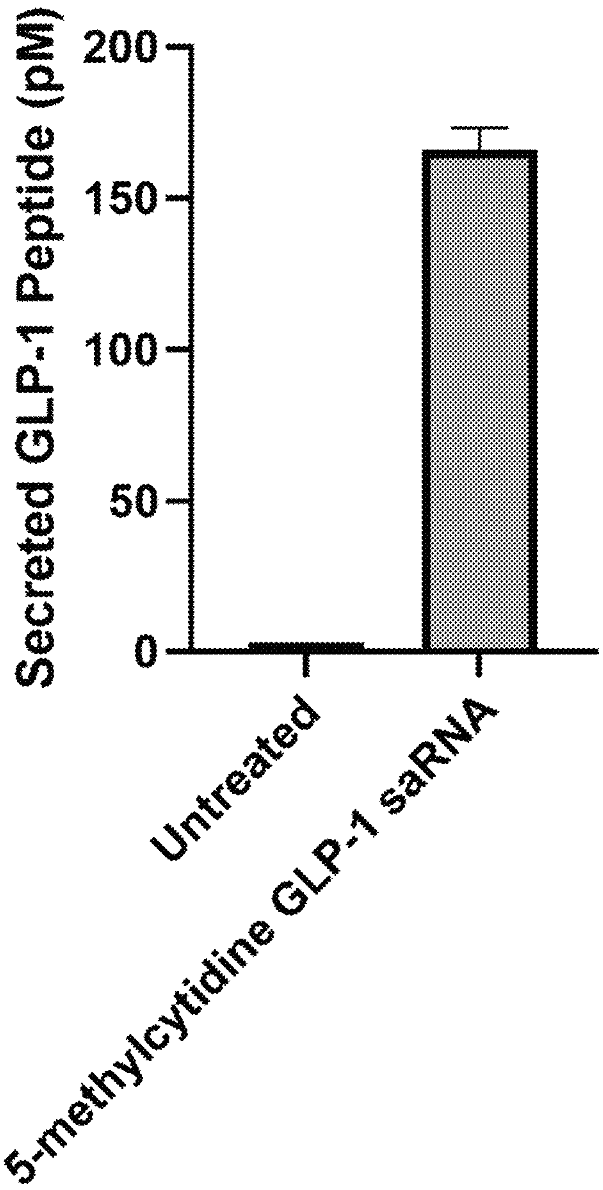
FIG. 92 is a bar graph showing the detection of bioactive GLP-1 peptide (amino acids 7-37) in the supernatant of HEK293 cells transfected with 5-methylcytidine substituted self-amplifying RNA.

Example 30: Expression of a Bioactive GLP-1 Peptide from Self-Amplifying RNA Synthesized with Complete Substitution of 5-Methylcytidine This example demonstrates the unexpected finding that self-amplifying RNA encoding a GLP-1 peptide, with complete replacement of cytidine with 5-methylcytidine, allows for expression of the peptide in its bioactive form. Plasmid templates containing the sequence of a self-amplifying RNA encoding the bioactive form ofglucagon-like peptide-1 (GLP-1) (amino acids 7-37, HAEGTFTSDVSSYLEGQAAKEFIAWLVRGRG, SEQ ID NO: 17) after an endogenous insulin secretion signal (MALWMRLLPLLALLALWGPDPAAA, SEQ ID NO: 18) and a furin cleavage site (RGRR, SEQ ID NO: 19) were generated by cloning. RNA was synthesized by in vitro transcription using the MEGAscript T7 Transcription kit (Invitrogen™, THERMOFISHER SCIENTIFIC) with 1p g template, co-transcriptional capping using CLEANCAP AU (final conc. 4 mM), and a 3 hour incubation (TRILINK BIOTECHNOLOGIES). The final concentration of all NTPs was 5 mM. To synthesize 5-methylcytidine saRNA, 100% of cytidine was replaced by 5-methylcytidine (5mC saRNA). IVT was followed by a 10 min DNase treatment and 30 min post-transcriptional poly-adenylation using a Poly(A) Tailing Kit (Invitrogen™, THERMOFISHER SCIENTIFIC). The resulting RNA was purified using MEGAclear™ Transcription Clean-up Kit (Invitrogen™ THERMOFISHER SCIENTIFIC) and eluted in DNase/RNase free $H_2O$ prior to storing at −80° C. degrees. The A260 of all modNTPs was empirically determined using a NANODROP2000 (THERMOFISHER SCIENTIFIC). 100,000 HEK293T cells were plated in a 12 well plate overnight in 400 μL of DMEM+10% FBS+1% P/S+50 μM Dipeptidyl peptidase-4 (DPP4) inhibitor. The cells were transfected with 0.5 μg of 5-methylcytidine substituted saRNA encoding GLP-1 by MESSENGERMAX transfection (THERMOFISHER SCIENTIFIC). After 24 hours, supernatant was harvested from the cells. To detect the presence of bioactive GLP-1, the Glucagon Like Peptide-1 (Active) ELISA kit (#EGLP-35K, SIGMA-ALDRICH) was utilized following the manufacturer's protocol. Unexpectedly, the cells transfected with 5-methylcytidine modified self-amplifying RNA encoding GLP-1 produced bioactive GLP-1 peptide at a level of 166 pM (see e.g., FIG. 92).

What is claimed herein is:

1. A self-amplifying RNA (saRNA) comprising at least 25% modified nucleotides, wherein the modified nucleotides comprise a pyrimidine nucleoside phosphate with a moiety on carbon 5 of the pyrimidine, wherein the moiety is selected from the group consisting of methyl, ethyl, propyl, trifluoromethyl, hydroxymethyl, hydroxyethyl, and hydroxypropyl functional groups, and at least one cargo of interest.

2. The saRNA of claim 1, wherein the modified nucleotides comprise 5-methylcytidine, 5-methyluridine, 5-hydroxymethyluridine, 5-hydroxymethylcytidine or a combination thereof.

3. The saRNA of claim 1, wherein the saRNA expresses the cargo at a level greater than or equal to that of a corresponding saRNA with less than 25% modified nucleotides.

4. The saRNA of claim 1, wherein the level of substitution of the modified nucleotides is: 25%-50%; 51%-75%; 75%-99%; 99.1%-99.9%; or 100%.

5. The saRNA of claim 1, wherein the initiating nucleotide comprises:

(a) an adenosine or adenosine analog, and wherein the initiating nucleotide of the saRNA is methylated at the 2'O position of the ribose (Cap1);

(b) an adenosine or adenosine analog, and wherein the initiating nucleotide and the subsequent nucleotide of the saRNA are both methylated at the 2'O position of the ribose (Cap2);

(c) a guanosine or guanosine analog, and wherein the initiating nucleotide of the saRNA is methylated at the 2'O position of the ribose (Cap1); or (d) a guanosine or guanosine analog, and wherein the initiating nucleotide and the subsequent nucleotide of the saRNA are both methylated at the 2'O position of the ribose (Cap2).

6. The saRNA of claim 1 comprising from 5' to 3':

(a) a 5' cap;

(b) non-structural protein 1 (nsp1), non-structural protein 2 (nsp2), non-structural protein 3 (nsp3), and/or non-structural protein 4 (nsp4), each derived from at least one virus;

(c) a subgenomic promoter (SGP) derived from at least one virus;

(d) 5' untranslated region (UTR) derived from at least one virus;

(e) the at least one cargo of interest;

(f) a 3' untranslated region (UTR) derived from at least one virus; and (g) a poly-A tail.

7. The saRNA of claim 1, further comprising at least one 5' conserved sequence element (CSE) and/or 3' at least one conserved sequence element (CSE) derived from at least one virus.

8. The saRNA of claim 6, wherein the at least one virus is an alphavirus.

9. The saRNA of claim 6, wherein the at least one virus is selected from the group consisting of: Venezuela Equine Encephalitis Virus (VEEV), Semliki Forest Virus (SFV), Sindbis Virus (SIN), Chikungunya Virus (CHIKV), Eastern Equine Encephalitis Virus (EEEV), Mayaro Virus (MAYV), Getah Virus (GETV), Ross River Virus (RRV), Una Virus (UNAV), Middleburg Virus (MIDV), O'anyong nyong virus (ONNV), Barmah Forest Virus (BFV), Mucambo Virus (MUCV), Tonate Virus (TONV), Everglades Virus (EVEV), Rio Negro Virus (RNV), Turnip Rosette Virus (TROV), Highlands J Virus (HJV), Western Equine Encephalitis Virus (WEEV), Fig Mosaic Emaravirus (FMV), Aura Virus (AURAV), Kunjin Virus (KUN), Measles virus (MV), Coronavirus (CoV), Rabies virus (RABV), and Vesicular Stomatitis virus (VSV).

10. The saRNA of claim 1, wherein the cargo comprises a chimeric antigen receptor (CAR) comprising an extracellular domain that specifically binds to an antigen of interest.

11. The saRNA of claim 10, wherein the antigen of interest for the CAR is selected from the group consisting of: CD19, CD22, CD30, b-cell maturation antigen (BCMA), disialoganglioside GD2, human estrogen receptor 2 (HER2), G protein-coupled receptor 87 (GPR87), Fibroblast Activator Protein (FAP), CD20, receptor tyrosine kinase-like orphan receptor 1 (ROR1), carcinoembryonic antigen (CEA), mesothelin (MSLN), prostate-specific membrane antigen (PSMA), epidermal growth factor receptor variant III (EGFRvIII), Interleukin 13 receptor alpha 2 (IL13Rα2), and natural killer group 2 member D (NKG2D).

12. The saRNA of claim 10, wherein the CAR is selected from the group consisting of:

(a) a conventional CAR;

(b) an ON-CAR;

(c) an OFF-CAR system;

(d) an ON/OFF-CAR;

(e) an inhibitory CAR; or (f) a split, universal, programmable and reconfigurable (SUPRA) CAR system.

13. The saRNA of claim 1, wherein the cargo comprises a ligand, a cell surface receptor, a transcription factor, a cytokine, a chemokine, an enzyme, and/or an antibody or fragment thereof.

14. The saRNA of claim 13, wherein the antibody is a bispecific antibody.

15. The saRNA of claim 1, wherein the cargo comprises a bispecific T cell engager (BiTE).

16. The saRNA of claim 1, wherein the cargo comprises at least one non-coding RNA selected from the group consisting of siRNA, shRNA, and microRNA.

17. The saRNA of claim 1, wherein the cargo comprises at least one vaccine-associated antigen comprising at least one protein encoded by a genome of a virus.

18. The saRNA of claim 17, wherein the virus is selected from the group consisting of: Rift valley fever, Crimean-Congo haemorrhagic fever, Lassa fever, Chikungunya Virus (CHIKV), Nipah Virus (NiV), respiratory syncytial virus (RSV), Ebola virus, Marburg virus, West Nile virus, Venezuela equine encephalitis, yellow fever virus, Japanese encephalitis virus, western equine encephalitis virus, eastern equine encephalitis, cytomegalovirus (CMV), human immunodeficiency virus (HIV), influenza virus, Zika virus, middle eastern respiratory syndrome coronavirus (MERS-CoV), severe acute respiratory syndrome coronavirus (SARS-CoV), severe acute respiratory syndrome coronavirus 2 (SARS-CoV-2), human papillomavirus (HPV), herpes virus, rotavirus, varicella-zoster virus (VZV), dengue virus, hepatitis A virus, hepatitis B virus, rubella virus, poliovirus, and rabies virus.

19. The saRNA of claim 1, wherein the cargo comprises at least one transcription factor selected from the group consisting of Octamer-Binding Transcription Factor 3 (Oct3, Oct4), Sex-Determining Region Y (SRY)-Box Transcription Factor 2 (Sox2), Kruppel-Like Factor 4 (Klf4), and cellular myelocytomatosis oncogene (c-Myc).

20. The saRNA of claim 1, wherein the cargo comprises at least one growth factor and/or cytokine selected from the group consisting of platelet-derived growth factor (PDGF), erythropoietin (EPO), vascular endothelial growth factor (VEGF), transforming growth factor-β1 (TGF-β1), fibroblast growth factor (FGF), human relaxin-2 (RLX2), alpha-melanocyte-stimulating hormone (alpha-MSH), insulin-like growth factor-I (IGF-I), epidermal growth factor (EGF), nerve growth factor (NGF), granulocyte-monocyte colony-stimulating factor (GMCSF), Thrombopoietin (TPO), Bone morphogenic protein (BMP), hepatocyte growth factor (HGF), growth/differentiation factor (GDF), a Neurotrophin, migration stimulating factor (MSF), and sarcoma growth factor (SGF); or wherein the cargo comprises one or both of Pappalysin-A1 (PAPPA1) and Pappalysin-A2 (PAPPA2).

21. The saRNA of claim 1, wherein the cargo comprises at least one interleukin and/or a cognate receptor(s) of the interleukin and/or receptor sub-units for the interleukin, wherein the interleukin is selected from the group consisting of IL-2, IL-4, IL-7, IL-10, IL-12, IL-13, and IL-15.

22. The saRNA of claim 1, wherein the cargo comprises at least one enzyme with antioxidant activity, wherein the enzyme is selected from the group consisting of phospholipid hydroperoxide glutathione peroxidase, superoxide dismutase-1, superoxide dismutase-2, Bruton's tyrosine kinase, adenosine deaminase, and ecto-nucleoside triphosphate diphosphydrolase.

23. The saRNA of claim 1, wherein the cargo comprises glucagon-like peptide-1 (GLP-1) or a fragment thereof.

24. A self-amplifying RNA (saRNA) comprising from 5' to 3':

(a) a 5' cap;

(b) non-structural protein 1 (nsp1), non-structural protein 2 (nsp2), non-structural protein 3 (nsp3), and/or non-structural protein 4 (nsp4), each derived from at least one virus;

(c) a subgenomic promoter (SGP) derived from at least one virus;

(d) a 5' untranslated region (UTR) derived from at least one virus;

(e) at least one cargo of interest;

(f) a 3' untranslated region (UTR) derived from at least one virus; and (g) a poly-A tail.

25. A nucleic acid, vector, or cell encoding or comprising the saRNA of claim 1.

26. A pharmaceutical composition comprising the saRNA of claim 1 and a pharmaceutically acceptable carrier.

27. A method of expressing at least one cargo of interest in a cell, the method comprising contacting the cell with the saRNA of claim 1.

28. The method of claim 27, the method further comprising contacting the cell with at least one input to control the fate or function of the cell.

29. A method of expressing at least one cargo in a subject in need thereof, the method comprising administering to the subject an effective amount of the pharmaceutical composition of claim 26.

30. The method of claim 29, the method further comprising administering to the subject at least one input to control the fate or function of at least one cell in the subject.

* * * * *

SEQUENCE LISTING

```
Sequence total quantity: 23
SEQ ID NO: 1            moltype = DNA  length = 19
FEATURE                 Location/Qualifiers
source                  1..19
                        mol_type = other DNA
                        organism = synthetic construct
SEQUENCE: 1
taatacgact cactataat                                               19

SEQ ID NO: 2            moltype = DNA  length = 7768
FEATURE                 Location/Qualifiers
source                  1..7768
                        mol_type = other DNA
                        organism = synthetic construct
SEQUENCE: 2
taatacgact cactataatg ggcggcgcat gagagaagcc cagaccaatt acctacccaa  60
aatggagaaa gttcacgttg acatcgagga agacagccca ttcctcagag ctttgcagcg  120
gagcttcccg cagtttgagg tagaagccaa gcaggtcact gataatgacc atgctaatgc  180
cagagcgttt tcgcatctgg cttcaaaact gatcgaaacg gaggtggacc catccgacac  240
gatccttgac attggaagtg cgcccgcccg cagaatgtat tctaagcaca agtatcattg  300
tatctgtccg atgagatgtg cggaagatcc ggacagattg tataagtatg caactaagct  360
gaagaaaaac tgtaaggaaa taactgataa ggaattggac aagaaaatga aggagctggc  420
cgccgtcatg agcgaccctg acctggaaac tgagactatg tgcctccacg acgacgagtc  480
gtgtcgctac gaagggcaag tcgctgttta ccaggatgta tacgcggttg acggaccgac  540
aagtctctat caccaagcca ataagggagt tagagtcgcc tactggatag gctttgacac  600
cacccctttt atgtttaaga acttggctgg agcatatcca tcatactcta ccaactgggc  660
cgacgaaacc gtgttaacgg ctcgtaacat aggcctatgc agctctgacg ttatggagcg  720
gtcacgtaga gggatgtcca ttcttagaaa gaagtatttg aaaccatcca acaatgttct  780
attctctgtt ggctcgacca tctaccacga gaagagggac ttactgagga gctggcacct  840
gccgtctgta tttcacttac gtggcaagca aaattacaca tgtcggtgtg agactatagt  900
tagttgcgac gggtacgtcg ttaaaagaat agctatcagt ccaggcctgt atgggaagcc  960
ttcaggctat gctgctacga tgcaccgcga gggattcttg tgctgcaaag tgacagacac  1020
attgaacggg gagagggtct cttttcccgt gtgcacgtat gtgccagcta cattgtgtga  1080
ccaaatgact ggcatactgg caacagatgt cagtgcggac gacgcgcaaa aactgctggt  1140
tgggctcaac cagcgtatag tcgtcaacgg tcgcacccag agaaacacca ataccatgaa  1200
aaattacctt ttgcccgtag tggcccaggc atttgctagg tgggcaaagg aatataagga  1260
agatcaagaa gatgaaaggc cactaggact acgagataga cagttagtca tggggtgttg  1320
ttgggctttt agaaggcaca agataacatc tatttataag cgcccggata cccaaaccat  1380
catcaaagtg aacagcgatt tccactcatt cgtgctgccc aggataggca gtaacacatt  1440
ggagatcggg ctgagaacaa gaatcaggaa aatgttagag gagcacaagg agccgtcacc  1500
tctcattacc gccgaggacg tacaagaagc taagtgcgca gccgatgagg ctaaggaggt  1560
gcgtgaagcc gaggagttgc gcgcagctct accacctttg gcagctgatg ttgaggagcc  1620
cactctggag gcagacgtcg acttgatgtt acaagaggct ggggccggct cagtggagac  1680
acctcgtggc ttgataaagg ttaccagcta cgatggcgag gacaagatcg gctcttacgc  1740
tgtgctttct ccgcaggctg tactcaagag tgaaaaatta tcttgcatcc accctctcgc  1800
tgaacaagtc atagtgataa cacactctgg ccgaaaaggg cgttatgccg tggaaccata  1860
ccatggtaaa gtagtggtgc cagagggaca tgcaataccc gtccaggact ttcaagctct  1920
gagtgaaagt gccaccattg tgtacaacga acgtgagttc gtaaacaggt acctgcacca  1980
tattgccaca catggaggag cgctgaacac tgatgaagaa tattacaaaa ctgtcaagcc  2040
cagcgagcac gacggcgaat acctgtacga catcgacagg aaacagtgcg tcaagaaaga  2100
actagtcact gggctagggc tcacaggcga gctggtggat cctcccttcc atgaattcgc  2160
ctacgagagt ctgagaacac gaccagccgc tccttaccaa gtaccaacca taggggtgta  2220
tggcgtgcca ggatcaggca agtctggcat cattaaaagc gcagtcacca aaaaagatct  2280
agtggtgagc gccaagaaag aaaactgtgc agaaattata agggacgtca agaaaatgaa  2340
agggctggac gtcaatgcca gaactgtgga ctcagtgctc ttgaatggat gcaaacaccc  2400
cgtagagacc ctgtatattg acgaagcttt tgcttgtcat gcaggtactc tcagagcgct  2460
catagccatt ataagaccta aaaaggcagt gctctgcggg gatcccaaac agtgcggttt  2520
ttttaacatg atgtgcctga aagtgcattt taaccacgag atttgcacac aagtcttcca  2580
caaaagcatc tctcgccgtt gcactaaatc tgtgacttcg gtcgtctcaa ccttgtttta  2640
cgacaaaaaa atgagaacga cgaatccgaa agagactaag attgtgattg acactaccgg  2700
cagtaccaaa cctaagcagg acgatctcat tctcacttgt ttcagagggt gggtgaagca  2760
gttgcaaata gattacaaag gcaacgaaat aatgacggca gctgcctctc aagggctgac  2820
ccgtaaaggt gtgtatgccg ttcggtacaa ggtgaatgaa aatcctctgt acgcacccac  2880
ctcagaacat gtgaacgtcc tactgacccg cacggaggac cgcatcgtgt ggaaaacact  2940
agccggcgac ccatggataa aaacactgac tgccaagtac cctgggaatt tcactgccac  3000
gatagaggag tggcaagcag agcatgatgc catcatgagg cacatcttgg agagaccgga  3060
ccctaccgac gtcttccaga ataaggcaaa cgtgtgttgg gccaaggctt tagtgccggt  3120
gctgaagacc gctggcatag acatgaccac tgaacaatgg aacactgtgg attattttga  3180
aacggacaaa gctcactcag cagagatagt attgaaccaa ctatgcgtga ggttctttgg  3240
actcgatctg gactccggtc tattttctgc acccactgtt ccgttatcca ttaggaataa  3300
tcactgggat aactccccgt cgcctaacat gtacgggctg aataaagaag tggtccgtca  3360
gctctctcgc aggtacccac aactgcctcg ggcagttgcc actggaagag tctatgacat  3420
gaacactggt acactgcgca attatgatcc gcgcataaac ctagtacctg taaacagaag  3480
actgcctcat gctttagtcc tccaccataa tgaacaccca cagagtgact tttcttcatt  3540
cgtcagcaaa ttgaagggca gaactgtcct ggtggtcggg gaaaagttgt ccgtcccagg  3600
caaaatggtt gactggttgt cagaccggcc tgaggctacc ttcagagctc ggctggattt  3660
aggcatccca ggtgatgtgc ccaaatatga cataatattt gttaatgtga ggaccccata  3720
taaataccat cactatcagc agtgtgaaga ccatgccatt aagcttagca tgttgaccaa  3780
```

-continued

```
gaaagcttgt ctgcatctga atcccggcgg aacctgtgtc agcataggtt atggttacgc  3840
tgacagggcc agcgaaagca tcattggtgc tatagcgcgg cagttcaagt tttcccgggt  3900
atgcaaaccg aaatcctcac ttgaagagac ggaagttctg tttgtattca ttgggtacga  3960
tcgcaaggcc cgtacgcaca attcttacaa gctttcatca accttgacca acatttatac  4020
aggttccaga ctccacgaag ccggatgtgc accctcatat catgtggtgc gaggggatat  4080
tgccacggcc accgaaggag tgattataaa tgctgctaac agcaaaggac aacctggcgg  4140
aggggtgtgc ggagcgctgt ataagaaatt cccggaaagc ttcgatttac agccgatcga  4200
agtaggaaaa gcgcgactgg tcaaaggtgc agctaaacat atcattcatg ccgtaggacc  4260
aaacttcaac aaagtttcgg aggttgaagg tgacaaacag ttggcagagg cttatgagtc  4320
catcgctaag attgtcaacg ataacaatta caagtcagta gcgattccac tgttgtccac  4380
cggcatcttt tccgggaaca aagatcgact aacccaatca ttgaaccatt tgctgacagc  4440
tttagacacc actgatgcag atgtagccat atactgcagg gacaagaaat gggaaatgac  4500
tctcaaggaa gcagtggcta ggagagaagc agtggaggag atatgcatat ccgacgactc  4560
ttcagtgaca gaacctgatg cagagctggt gagggtgcat ccgaagagtt ctttggctgg  4620
aaggaagggc tacagcacaa gcgatggcaa aactttctca tatttggaag ggaccaagtt  4680
tcaccaggcg gccaaggata tagcagaaat taatgccatg tggcccgttg caacggaggc  4740
caatgagcag gtatgcatgt atatcctcgg agaaagcatg agcagtatta ggtcgaaatg  4800
ccccgtcgaa gagtcggaag cctccacacc acctagcacg ctgccttgct tgtgcatcca  4860
tgccatgact ccagaaagag tacagcgcct aaaagcctca cgtccagaac aaattactgt  4920
gtgctcatcc tttccattgc cgaagtatag aatcactggt gtgcagaaga tccaatgctc  4980
ccagcctata ttgttctcac cgaaagtgcc tgcgtatatt catccaagga agtatctcgt  5040
ggaaacacca ccggtagacg agactccgga gccatcggca gagaaccaat ccacagaggg  5100
gacacctgaa caaccaccac ttataaccga ggatgagacc aggactagaa cgcctgagcc  5160
gatcatcatc gaagaggaag aagaggatag cataagtttg ctgtcagatg gcccgaccca  5220
ccaggtgctg caagtcgagg cagacattca cgggccgccc tctgtatcta gctcatcctg  5280
gtccattcct catgcatccg actttgatgt ggacagttta tccatacttg acaccctgga  5340
gggagctagc gtgaccagcg gggcaacgtc agccgagact aactcttact tcgcaaagag  5400
tatggagttt ctggcgcgac cggtgcctgc gcctcgaaca gtattcagga accctccaca  5460
tcccgctccg cgcacaagaa caccgtcact tgcacccagc agggcctgct cgagaaccag  5520
cctagtttcc accccgccag gcgtgaatag ggtgatcact agagaggagc tcgaggcgct  5580
taccccgtca cgcactccta gcaggtcggt ctcgagaacc agcctggtct ccaacccgcc  5640
aggcgtaaat agggtgatta caagagagga gtttgaggcg ttcgtagcac aacaacaatg  5700
acggtttgat gcgggtgcat acatcttttc ctccgacacc ggtcaagggc atttacaaca  5760
aaaatcagta aggcaaacgg tgctatccga agtggtgttg gagaggaccg aattggagat  5820
ttcgtatgcc ccgcgcctcg accaagaaaa agaagaatta ctacgcaaga aattacagtt  5880
aaatcccaca cctgctaaca gaagcagata ccagtccagg aaggtggaga acatgaaagc  5940
cataacagct agacgtattc tgcaaggcct agggcattat ttgaaggcag aaggaaaagt  6000
ggagtgctac cgaaccctgc atcctgttcc tttgtattca tctagtgtga accgtgcctt  6060
ttcaagcccc aaggtcgcag tggaagcctg taacgccatg ttgaaagaga actttccgac  6120
tgtggcttct tactgtatta ttccagagta cgatgcctat ttggacatgg ttgacggagc  6180
ttcatgctgc ttagacactg ccagtttttg ccctgcaaag ctgcgcagct ttccaaagaa  6240
acactcctat ttggaaccca caatacgatc ggcagtgcct tcagcgatcc agaacacgct  6300
ccagaacgtc ctggcagctg ccacaaaaag aaattgcaat gtcacgcaaa tgagagaatt  6360
gcccgtattg gattcggcgg cctttaatgt ggaatgcttc aagaaatatg cgtgtaataa  6420
tgaatattgg gaaacgttta aagaaaaccc catcaggctt actgaagaaa acgtggtaaa  6480
ttacattacc aaattaaaag gaccaaaagc tgctgctctt tttgcgaaga cacataattt  6540
gaatatgttg caggacatac caatggacag gtttgtaatg gacttaaaga gagacgtgaa  6600
agtgactcca ggaacaaaac atactgaaga acggcccaag gtacaggtga tccaggctgc  6660
cgatccgcta gcaacagcgt atctgtgcgg aatccaccga gagctggtta ggagattaaa  6720
tgcggtcctg cttccgaaca ttcatacact gtttgatatg tcggctgaag actttgacgc  6780
tattatagcc gagcacttcc agcctgggga ttgtgttctg gaaactgaca tcgcgtcgtt  6840
tgataaaagt gaggacgacg ccatggctct gaccgcgtta atgattctgg aagacttagg  6900
tgtggacgca gagctgttga cgctgattga ggcggctttc ggcgaaattt catcaataca  6960
tttgcccact aaaactaaat ttaaattcgg agccatgatg aaatctggaa tgttcctcac  7020
actgtttgtg aacacagtca ttaacattgt aatcgcaagc agagtgttga gagaacggct  7080
aaccggatca ccatgtgcag cattcattgg agatgacaat atcgtgaaag gagtcaaatc  7140
ggacaaatta atggcagaca ggtgcgccac ctggttgaat atggaagtca agattataga  7200
tgctgtggtg ggcgagaaag cgccttattt ctgtggaggg tttatttgt gtgactccgt  7260
gaccggcaca gcgtgccgtg tggcagaccc cctaaaaagg ctgtttaagc ttggcaaacc  7320
tctggcagca gacgatgaac atgatgatga caggagaagg gcattgcatg aagagtcaac  7380
acgctggaac cgagtgggta ttctttcaga gctgtgcaag gcagtagaat caaggtatga  7440
aaccgtagga acttccatca tagttatggc catgactact ctagctagca gtgttaaatc  7500
attcagctac ctgagagggg cccctataac tctctacggc taacctgaat ggactacgac  7560
atagtctagt ccgccaagtc tagcaggaga gtcccgacct ccaggagaga ccagggccac  7620
ccttaagcat atggaattgg caagctgctt acatagaact cgcggcgatt ggcatgccgc  7680
cttaaaattt ttattttatt ttttctttc ttttccgaat cggattttgt ttttaatatt  7740
tcaaaaaaaa aaaaaaaaaa aaaaaaaa                                    7768
```

```
SEQ ID NO: 3            moltype = DNA  length = 17
FEATURE                 Location/Qualifiers
source                  1..17
                        mol_type = other DNA
                        organism = synthetic construct
SEQUENCE: 3
taatacgact cactata                                                17
```

```
SEQ ID NO: 4            moltype = AA  length = 1879
FEATURE                 Location/Qualifiers
source                  1..1879
```

```
                         mol_type = protein
                         organism = Venezuelan equine encephalitis virus
SEQUENCE: 4
MEKVHVDIEE DSPFLRALQR SFPQFEVEAK QVTDNDHANA RAFSHLASKL IETEVDPSDT  60
ILDIGSAPAR RMYSKHKYHC ICPMRCAEDP DRLYKYATKL KKNCKEITDK ELDKKMKELA  120
AVMSDPDLET ETMCLHDDES CRYEGQVAVY QDVYAVDGPT SLYHQANKGV RVAYWIGFDT  180
TPFMFKNLAG AYPSYSTNWA DETVLTARNI GLCSSDVMER SRRGMSILRK KYLKPSNNVL  240
FSVGSTIYHE KRDLLRSWHL PSVFHLRGKQ NYTCRCETIV SCDGYVVKRI AISPGLYGKP  300
SGYAATMHRE GFLCCKVTDT LNGERVSFPV CTYVPATLCD QMTGILATDV SADDAQKLLV  360
GLNQRIVVNG RTQRNTNTMK NYLLPVVAQA FARWAKEYKE DQEDERPLGL RDRQLVMGCC  420
WAFRRHKITS IYKRPDTQTI IKVNSDFHSF VLPRIGSNTL EIGLRTRIRK MLEEHKEPSP  480
LITAEDVQEA KCAADEAKEV REAEELRAAL PPLAADVEEP TLEADVDLML QEAGAGSVET  540
PRGLIKVTSY DGEDKIGSYA VLSPQAVLKS EKLSCIHPLA EQVIVITHSG RKGRYAVEPY  600
HGKVVVPEGH AIPVQDFQAL SESATIVYNE REFVNRYLHH IATHGGALNT DEEYYKTVKP  660
SEHDGEYLYD IDRKQCVKKE LVTGLGLTGE LVDPPFHEFA YESLRTRPAA PYQVPTIGVY  720
GVPGSGKSGI IKSAVTKKDL VVSAKKENCA EIIRDVKKMK GLDVNARTVD SVLLNGCKHP  780
VETLYIDEAF ACHAGTLRAL IAIIRPKKAV LCGDPKQCGF FNMMCLKVHF NHEICTQVFH  840
KSISRRCTKS VTSVVSTLFY DKKMRTTNPK ETKIVIDTTG STKPKQDDLI LTCFRGWVKQ  900
LQIDYKGNEI MTAAASQGLT RKGVYAVRYK VNENPLYAPT SEHVNVLLTR TEDRIVWKTL  960
AGDPWIKTLT AKYPGNFTAT IEEWQAEHDA IMRHILERPD PTDVFQNKAN VCWAKALVPV  1020
LKTAGIDMTT EQWNTVDYFE TDKAHSAEIV LNQLCVRFFG LDLDSGLFSA PTVPLSIRNN  1080
HWDNSPSPNM YGLNKEVVRQ LSRRYPQLPR AVATGRVYDM NTGTLRNYDP RINLVPVNRR  1140
LPHALVLHHN EHPQSDFSSF VSKLKGRTVL VVGEKLSVPG KMVDWLSDRP EATFRARLDL  1200
GIPGDVPKYD IIFVNVRTPY KYHHYQQCED HAIKLSMLTK KACLHLNPGG TCVSIGYGYA  1260
DRASESIIGA IARQFKFSRV CKPKSSLEET EVLFVFIGYD RKARTHNSYK LSSTLTNIYT  1320
GSRLHEAGCA PSYHVVRGDI ATATEGVIIN AANSKGQPGG GVCGALYKKF PESFDLQPIE  1380
VGKARLVKGA AKHIIHAVGP NFNKVSEVEG DKQLAEAYES IAKIVNDNNY KSVAIPLLST  1440
GIFSGNKDRL TQSLNHLLTA LDTTDADVAI YCRDKKWEMT LKEAVARREA VEEICISDDS  1500
SVTEPDAELV RVHPKSSLAG RKGYSTSDGK TFSYLEGTKF HQAAKDIAEI NAMWPVATEA  1560
NEQVCMYILG ESMSSIRSKC PVEESEASTP PSTLPCLCIH AMTPERVQRL KASRPEQITV  1620
CSSFPLPKYR ITGVQKIQCS QPILFSPKVP AYIHPRKYLV ETPPVDETPE PSAENQSTEG  1680
TPEQPPLITE DETRTRTPEP IIIEEEEEDS ISLLSDGPTH QVLQVEADIH GPPSVSSSSW  1740
SIPHASDFDV DSLSILDTLE GASVTSGATS AETNSYFAKS MEFLARPVPA PRTVFRNPPH  1800
PAPRTRTPSL APSRACSRTS LVSTPPGVNR VITREELEAL TPSRTPSRSV SRTSLVSNPP  1860
GVNRVITREE FEAFVAQQQ                                              1879

SEQ ID NO: 5             moltype = DNA  length = 8488
FEATURE                  Location/Qualifiers
source                   1..8488
                         mol_type = other DNA
                         organism = synthetic construct
SEQUENCE: 5
taatacgact cactataatg ggcggcgcat gagagaagcc cagaccaatt acctacccaa  60
aatggagaaa gttcacgttg acatcgagga agacagccca ttcctcagag ctttgcagcg  120
gagcttcccg cagtttgagg tagaagccaa gcaggtcact gataatgacc atgctaatgc  180
cagagcgttt tcgcatctgg cttcaaaact gatcgaaacg gaggtggacc catccgacac  240
gatccttgac attggaagtg cgcccgcccg cagaatgtat tctaagcaca agtatcattg  300
tatctgtccg atgagatgtg cggaagatcc ggacagattg tataagtatg caactaagct  360
gaagaaaaac tgtaaggaaa taactgataa ggaattggac aagaaaatga aggagctggc  420
cgccgtcatg agcgaccctg acctggaaac tgagactatg tgcctccacg acgacgagtc  480
gtgtcgctac gaagggcaag tcgctgttta ccaggatgta tacgcggttg acggaccgac  540
aagtctctat caccaagcca ataagggagt tagagtcgcc tactggatag gctttgacac  600
caccccttt atgtttaaga acttggctgg agcatatcca tcatactcta ccaactgggc  660
cgacgaaacc gtgttaacgg ctcgtaacat aggcctatgc agctctgacg ttatggagcg  720
gtcacgtaga gggatgtcca ttcttagaaa gaagtatttg aaaccatcca acaatgttct  780
attctctgtt ggctcgacca tctaccacga gaagagggac ttactgagga gctggcacct  840
gccgtctgta tttcacttac gtggcaagca aaattacaca tgtcggtgtg agactatagt  900
tagttgcgac gggtacgtcg ttaaaagaat agctatcagt ccaggcctgt atgggaagcc  960
ttcaggctat gctgctacga tgcaccgcga gggattcttg tgctgcaaag tgacagacac  1020
attgaacggg gagagggtct cttttcccgt gtgcacgtat gtgccagcta cattgtgtga  1080
ccaaatgact ggcatactgg caacagatgt cagtgcggac gacgcgcaaa aactgctggt  1140
tgggctcaac cagcgtatag tcgtcaacgg tcgcacccag agaaacacca ataccatgaa  1200
aaattacctt ttgcccgtag tggcccaggc atttgctagg tgggcaaagg aatataagga  1260
agatcaagaa gatgaaaggc cactaggact acgagataga cagttagtca tggggtgttg  1320
ttgggctttt agaaggcaca agataacatc tatttataag cgcccggata cccaaaccat  1380
catcaaagtg aacagcgatt tccactcatt cgtgctgccc aggataggca gtaacacatt  1440
ggagatcggg ctgagaacaa gaatcaggaa aatgttagag gagcacaagg agccgtcacc  1500
tctcattacc gccgaggacg tacaagaagc taagtgcgca gccgatgagg ctaaggaggt  1560
gcgtgaagcc gaggagttgc gcgcagctct accacctttg gcagctgatg ttgaggagcc  1620
cactctggag gcagacgtcg acttgatgtt acaagaggct ggggccggct cagtggagac  1680
acctcgtggc ttgataaagg ttaccagcta cgatggcgag gacaagatcg gctcttacgc  1740
tgtgctttct ccgcaggctg tactcaagag tgaaaaatta tcttgcatcc accctctcgc  1800
tgaacaagtc atagtgataa cacactctgg ccgaaaaggg cgttatgccg tggaaccata  1860
ccatggtaaa gtagtggtgc cagagggaca tgcaataccc gtccaggact ttcaagctct  1920
gagtgaaagt gccaccattg tgtacaacga acgtgagttc gtaaacaggt acctgcacca  1980
tattgccaca catggaggag cgctgaacac tgatgaagaa tattacaaaa ctgtcaagcc  2040
cagcgagcac gacggcgaat acctgtacga catcgacagg aaacagtgcg tcaagaaaga  2100
actagtcact gggctagggc tcacaggcga gctggtggat cctcccttcc atgaattcgc  2160
ctacgagagt ctgagaacac gaccagccgc tccttaccaa gtaccaacca taggggtgta  2220
```

-continued

```
tggcgtgcca ggatcaggca agtctggcat cattaaaagc gcagtcacca aaaaagatct  2280
agtggtgagc gccaagaaag aaaactgtgc agaaattata agggacgtca agaaaatgaa  2340
agggctggac gtcaatgcca gaactgtgga ctcagtgctc ttgaatggat gcaaacaccc  2400
cgtagagacc ctgtatattg acgaagcttt tgcttgtcat gcaggtactc tcagagcgct  2460
catagccatt ataagaccta aaaaggcagt gctctgcggg gatcccaaac agtgcggttt  2520
ttttaacatg atgtgcctga aagtgcattt taaccacgag atttgcacac aagtcttcca  2580
caaaagcatc tctcgccgtt gcactaaatc tgtgacttcg gtcgtctcaa ccttgtttta  2640
cgacaaaaaa atgagaacga cgaatccgaa agagactaag attgtgattg acactaccgg  2700
cagtaccaaa cctaagcagg acgatctcat tctcacttgt ttcagagggt gggtgaagca  2760
gttgcaaata gattacaaag gcaacgaaat aatgacggca gctgcctctc aagggctgac  2820
ccgtaaaggt gtgtatgccg ttcggtacaa ggtgaatgaa aatcctctgt acgcacccac  2880
ctcagaacat gtgaacgtcc tactgacccg cacggaggac cgcatcgtgt ggaaaacact  2940
agccggcgac ccatggataa aaacactgac tgccaagtac cctgggaatt tcactgccac  3000
gatagaggag tggcaagcag agcatgatgc catcatgagg cacatcttgg agagaccgga  3060
ccctaccgac gtcttccaga ataaggcaaa cgtgtgttgg gccaaggctt tagtgccggt  3120
gctgaagacc gctggcatag acatgaccac tgaacaatgg aacactgtgg attattttga  3180
aacggacaaa gctcactcag cagagatagt attgaaccaa ctatgcgtga ggttctttgg  3240
actcgatctg gactccggtc tattttctgc acccactgtt ccgttatcca ttaggaataa  3300
tcactgggat aactccccgt cgcctaacat gtacgggctg aataaagaag tggtccgtca  3360
gctctctcgc aggtacccac aactgcctcg ggcagttgcc actggaagag tctatgacat  3420
gaacactggt acactgcgca attatgatcc gcgcataaac ctagtacctg taaacagaag  3480
actgcctcat gctttagtcc tccaccataa tgaacaccca cagagtgact tttcttcatt  3540
cgtcagcaaa ttgaagggca gaactgtcct ggtggtcggg gaaaagttgt ccgtcccagg  3600
caaaatggtt gactggttgt cagaccggcc tgaggctacc ttcagagctc ggctggattt  3660
aggcatccca ggtgatgtgc ccaaatatga cataatattt gttaatgtga ggaccccata  3720
taaataccat cactatcagc agtgtgaaga ccatgccatt aagcttagca tgttgaccaa  3780
gaaagcttgt ctgcatctga atcccggcgg aacctgtgtc agcataggtt atggttacgc  3840
tgacagggcc agcgaaagca tcattggtgc tatagcgcgg cagttcaagt tttcccgggt  3900
atgcaaaccg aaatcctcac ttgaagagac ggaagttctg tttgtattca ttgggtacga  3960
tcgcaaggcc cgtacgcaca attcttacaa gctttcatca accttgacca acatttatac  4020
aggttccaga ctccacgaag ccggatgtgc accctcatat catgtggtgc gaggggatat  4080
tgccacggcc accgaaggag tgattataaa tgctgctaac agcaaaggac aacctggcgg  4140
aggggtgtgc ggagcgctgt ataagaaatt cccggaaagc ttcgatttac agccgatcga  4200
agtaggaaaa gcgcgactgg tcaaaggtgc agctaaacat atcattcatg ccgtaggacc  4260
aaacttcaac aaagtttcgg aggttgaagg tgacaaacag ttggcagagg cttatgagtc  4320
catcgctaag attgtcaacg ataacaatta caagtcagta gcgattccac tgttgtccac  4380
cggcatcttt tccgggaaca aagatcgact aacccaatca ttgaaccatt tgctgacagc  4440
tttagacacc actgatgcag atgtagccat atactgcagg gacaagaaat gggaaatgac  4500
tctcaaggaa gcagtggcta ggagagaagc agtggaggag atatgcatat ccgacgactc  4560
ttcagtgaca gaacctgatg cagagctggt gagggtgcat ccgaagagtt ctttggctgg  4620
aaggaagggc tacagcacaa gcgatggcaa aactttctca tatttggaag ggaccaagtt  4680
tcaccaggcg gccaaggata tagcagaaat taatgccatg tggcccgttg caacggaggc  4740
caatgagcag gtatgcatgt atatcctcgg agaaagcatg agcagtatta ggtcgaaatg  4800
ccccgtcgaa gagtcggaag cctccacacc acctagcacg ctgccttgct tgtgcatcca  4860
tgccatgact ccagaaagag tacagcgcct aaaagcctca cgtccagaac aaattactgt  4920
gtgctcatcc tttccattgc cgaagtatag aatcactggt gtgcagaaga tccaatgctc  4980
ccagcctata ttgttctcac cgaaagtgcc tgcgtatatt catccaagga agtatctcgt  5040
ggaaacacca ccggtagacg agactccgga gccatcggca gagaaccaat ccacagaggg  5100
gacacctgaa caaccaccac ttataaccga ggatgagacc aggactagaa cgcctgagcc  5160
gatcatcatc gaagaggaag aagaggatag cataagtttg ctgtcagatg gcccgaccca  5220
ccaggtgctg caagtcgagg cagacattca cgggccgccc tctgtatcta gctcatcctg  5280
gtccattcct catgcatccg actttgatgt ggacagttta tccatacttg acaccctgga  5340
gggagctagc gtgaccagcg gggcaacgtc agccgagact aactcttact tcgcaaagag  5400
tatggagttt ctggcgcgac cggtgcctgc gcctcgaaca gtattcagga accctccaca  5460
tcccgctccg cgcacaagaa caccgtcact tgcacccagc agggcctgct cgagaaccag  5520
cctagtttcc accccgccag gcgtgaatag ggtgatcact agagaggagc tcgaggcgct  5580
taccccgtca cgcactccta gcaggtcggt ctcgagaacc agcctggtct ccaacccgcc  5640
aggcgtaaat agggtgatta caagagagga gtttgaggcg ttcgtagcac aacaacaatg  5700
acggtttgat gcgggtgcat acatcttttc ctccgacacc ggtcaagggc atttacaaca  5760
aaaatcagta aggcaaacgg tgctatccga agtggtgttg gagaggaccg aattggagat  5820
ttcgtatgcc ccgcgcctcg accaagaaaa agaagaatta ctacgcaaga aattacagtt  5880
aaatcccaca cctgctaaca gaagcagata ccagtccagg aaggtggaga acatgaaagc  5940
cataacagct agacgtattc tgcaaggcct agggcattat ttgaaggcag aaggaaaagt  6000
ggagtgctac cgaaccctgc atcctgttcc tttgtattca tctagtgtga accgtgcctt  6060
ttcaagcccc aaggtcgcag tggaagcctg taacgccatg ttgaaagaga actttccgac  6120
tgtggcttct tactgtatta ttccagagta cgatgcctat ttggacatgg ttgacggagc  6180
ttcatgctgc ttagacactg ccagtttttg ccctgcaaag ctgcgcagct ttccaaagaa  6240
acactcctat ttggaaccca caatacgatc ggcagtgcct tcagcgatcc agaacacgct  6300
ccagaacgtc ctggcagctg ccacaaaaag aaattgcaat gtcacgcaaa tgagagaatt  6360
gcccgtattg gattcggcgg cctttaatgt ggaatgcttc aagaaatatg cgtgtaataa  6420
tgaatattgg gaaacgttta aagaaaaccc catcaggctt actgaagaaa acgtggtaaa  6480
ttacattacc aaattaaaag gaccaaaagc tgctgctctt tttgcgaaga cacataattt  6540
gaatatgttg caggacatac caatggacag gtttgtaatg gacttaaaga gagacgtgaa  6600
agtgactcca ggaacaaaac atactgaaga acggcccaag gtacaggtga tccaggctgc  6660
cgatccgcta gcaacagcgt atctgtgcgg aatccaccga gagctggtta ggagattaaa  6720
tgcggtcctg cttccgaaca ttcatacact gtttgatatg tcggctgaag actttgacgc  6780
tattatagcc gagcacttcc agcctgggga ttgtgttctg gaaactgaca tcgcgtcgtt  6840
tgataaaagt gaggacgacg ccatggctct gaccgcgtta atgattctgg aagacttagg  6900
tgtggacgca gagctgttga cgctgattga ggcggctttc ggcgaaattt catcaataca  6960
```

-continued tttgcccact aaaactaaat ttaaattcgg agccatgatg aaatctggaa tgttcctcac 7020
actgtttgtg aacacagtca ttaacattgt aatcgcaagc agagtgttga gagaacggct 7080
aaccggatca ccatgtgcag cattcattgg agatgacaat atcgtgaaag gagtcaaatc 7140
ggacaaatta atggcagaca ggtgcgccac ctggttgaat atggaagtca agattataga 7200
tgctgtggtg ggcgagaaag cgccttattt ctgtggaggg tttattttgt gtgactccgt 7260
gaccggcaca gcgtgccgtg tggcagaccc cctaaaaagg ctgtttaagc ttggcaaacc 7320
tctggcagca gacgatgaac atgatgatga caggagaagg gcattgcatg aagagtcaac 7380
acgctggaac cgagtgggta ttctttcaga gctgtgcaag gcagtagaat caaggtatga 7440
aaccgtagga acttccatca tagttatggc catgactact ctagctagca gtgttaaatc 7500
attcagctac ctgagagggg cccctataac tctctacggc taacctgaat ggactacgac 7560
atagtctagt ccgccaagtc tagcaggaga gtcccgacct ccaggagaga ccagggccac 7620
ccttaagctt aagatggtga gcaagggcga ggaggataac atggccatca tcaaggagtt 7680
catgcgcttc aaggtgcaca tggagggctc cgtgaacggc cacgagttcg agatcgaggg 7740
cgagggcgag ggccgcccct acgagggcac ccagaccgcc aagctgaagg tgaccaaggg 7800
tggcccccctg cccttcgcct gggacatcct gtcccctcag ttcatgtacg gctccaaggc 7860
ctacgtgaag caccccgccg acatccccga ctacttgaag ctgtccttcc ccgagggctt 7920
caagtgggag cgcgtgatga acttcgagga cggcggcgtg gtgaccgtga cccaggactc 7980
ctccctgcag gacggcgagt tcatctacaa ggtgaagctg cgcggcacca acttcccctc 8040
cgacggcccc gtaatgcaga agaagaccat gggctgggag gcctcctccg agcggatgta 8100
ccccgaggac ggcgccctga agggcgagat caagcagagg ctgaagctga aggacggcgg 8160
ccactacgac gctgaggtca agaccaccta caaggccaag aagcccgtgc agctgcccgg 8220
cgcctacaac gtcaacatca agttggacat cacctcccac aacgaggact acaccatcgt 8280
ggaacagtac gaacgcgccg agggccgcca ctccaccggc ggcatggacg agctgtacaa 8340
gtaataacat atggaattgg caagctgctt acatagaact cgcggcgatt ggcatgccgc 8400
cttaaaattt ttattttatt ttttcttttc ttttccgaat cggattttgt ttttaatatt 8460
tcaaaaaaaa aaaaaaaaaa aaaaaaaa 8488

SEQ ID NO: 6 moltype = RNA length = 8471
FEATURE Location/Qualifiers
source 1..8471
mol_type = other RNA
organism = synthetic construct
misc_difference 1..8471
note = n indicates cytidine, 5-methylcytidine, or 5-hydroxymethylcytidine
SEQUENCE: 6
atgggnggng natgagagaa gnnnaganna attanntann naaaatggag aaagttnang 60
ttganatnga ggaaganagn nnattnntna gagntttgna gnggagnttn nngnagtttg 120
aggtagaagn naagnaggtn antgataatg annatgntaa tgnnagagng ttttngnatn 180
tggnttnaaa antgatngaa anggaggtgg annnatnnga nangatnntt ganattggaa 240
gtgngnnngn nngnagaatg tattntaagn anaagtatna ttgtatntgt nngatgagat 300
gtgnggaaga tnngganaga ttgtataagt atgnaantaa gntgaagaaa aantgtaagg 360
aaataantga taaggaattg ganaagaaaa tgaaggagnt ggnngnngtn atgagngann 420
ntganntgga aantgagant atgtgnntnn anganganga gtngtgtngn tangaagggn 480
aagtngntgt ttannaggat gtatangngg ttganggann ganaagtntn tatnannaag 540
nnaataaggg agttagagtn gnntantgga taggntttga nannannnnt tttatgttta 600
agaanttggn tggagnatat nnatnatant ntannaantg ggnngangaa anngtgttaa 660
nggntngtaa nataggnnta tgnagntntg angttatgga gnggtnangt agagggatgt 720
nnattnttag aaagaagtat ttgaaannat nnaanaatgt tntattntnt gttggntnga 780
nnatntanna ngagaagagg ganttantga ggagntggna nntgnngtnt gtatttnant 840
tangtggnaa gnaaaattan anatgtnggt gtgagantat agttagttgn gangggtang 900
tngttaaaag aatagntatn agtnnaggnn tgtatgggaa gnnttnaggn tatgntgnta 960
ngatgnanng ngagggattn ttgtgntgna aagtganaga nanattgaan ggggagaggg 1020
tntnttttnn ngtgtgnang tatgtgnnag ntanattgtg tgannaaatg antggnatan 1080
tggnaanaga tgtnagtgng gangangngn aaaaantgnt ggttgggntn aannagngta 1140
tagtngtnaa nggtngnann nagagaaana nnaatannat gaaaaattan nttttgnnng 1200
tagtggnnna ggnatttgnt aggtgggnaa aggaatataa ggaagatnaa gaagatgaaa 1260
ggnnantagg antangagat aganagttag tnatggggtg ttgttgggnt tttagaaggn 1320
anaagataan atntatttat aagngnnngg atannnaaan natnatnaaa gtgaanagng 1380
atttnnantn attngtgntg nnnaggatag gnagtaanan attggagatn gggntgagaa 1440
naagaatnag gaaaatgtta gaggagnana aggagnngtn anntntnatt anngnngagg 1500
angtanaaga agntaagtgn gnagnngatg aggntaagga ggtgngtgaa gnngaggagt 1560
tgngngnagn tntannannt ttggnagntg atgttgagga gnnnantntg gaggnagang 1620
tnganttgat gttanaagag gntggggnng gntnagtgga ganannttngt ggnttgataa 1680
aggttannag ntangatggn gagganaaga tnggntntta ngntgtgntt tntnngnagg 1740
ntgtantnaa gagtgaaaaa ttatnttgna tnnannntnt ngntgaanaa gtnatagtga 1800
taananantn tggnngaaaa gggngttatg nngtggaann atannatggt aaagtagtgg 1860
tgnnagaggg anatgnaata nnngtnnagg antttnaagn tntgagtgaa agtgnnanna 1920
ttgtgtanaa ngaangtgag ttngtaaana ggtanntgna nnatattgnn ananatggag 1980
gagngntgaa nantgatgaa gaatattana aaantgtnaa gnnnagngag nanganggng 2040
aatanntgta nganatngan aggaaaanagt gngtnaagaa agaantagtn antgggntag 2100
ggntnanagg ngagntggtg gatnntnnnt tnnatgaatt ngnntangag agtntgagaa 2160
nangannagn ngntnnttan naagtannaa nnatagggggt gtatggngtg nnaggatnag 2220
gnaagtntgg natnattaaa agngnagtna nnaaaaaaga tntagtggtg agngnnaaga 2280
aagaaaantg tgnagaaatt ataagggang tnaagaaaat gaaagggntg gangtnaatg 2340
nnagaantgt ggantnagtg ntnttgaatg gatgnaaana nnnngtagag annntgtata 2400
ttgangaagn ttttgnttgt natgnaggta ntntnagagn gntnatagnn attataagan 2460
ntaaaaaggn agtgntntgn ggggatnnna aanagtgngg tttttttaan atgatgtgnn 2520
tgaaagtgna ttttaannan gagatttgna nanaagtntt nnanaaaagn atntntngnn 2580

-continued

```
gttgnantaa atntgtgant tnggtngtnt naannttgtt ttanganaaa aaaatgagaa  2640
ngangaatnn gaaagagant aagattgtga ttganantan nggnagtann aaanntaagn  2700
aggangatnt nattntnant tgtttnagag ggtgggtgaa gnagttgnaa atagattana  2760
aaggnaanga aataatgang gnagntgnnt ntnaagggnt gannngtaaa ggtgtgtatg  2820
nngttnggta naaggtgaat gaaaatnntn tgtangnann nanntnagaa natgtgaang  2880
tnntantgan nngnanggag ganngnatng tgtggaaaan antagnnggn gannnatgga  2940
taaaaanant gantgnnaag tannntggga atttnantgn nangatagag gagtggnaag  3000
nagagnatga tgnnatnatg aggnanatnt tggagagann ggannntann gangtnttnn  3060
agaataaggn aaangtgtgt tgggnnaagg ntttagtgnn ggtgntgaag anngntggna  3120
taganatgan nantgaanaa tggaanantg tggattattt tgaaanggan aaagntnant  3180
nagnagagat agtattgaan naantatgng tgaggttntt tggantngat ntggantnng  3240
gtntattttn tgnannnant gttnngttat nnattaggaa taatnantgg gataantnnn  3300
ngtngnntaa natgtanggg ntgaataaag aagtggtnng tnagntntnt ngnaggtann  3360
nanaantgnn tngggnagtt gnnantggaa gagtntatga natgaanant ggtanantgn  3420
gnaattatga tnngngnata aanntagtan ntgtaaanag aagantgnnt natgntttag  3480
tnntnnanna taatgaanan nnanagagtg anttttnttn attngtnagn aaattgaagg  3540
gnagaantgt nntggtggtn ggggaaaagt tgtnngtnnn aggnaaaatg gttgantggt  3600
tgtnaganng gnntgaggnt annttnagag ntnggntgga tttaggnatn nnaggtgatg  3660
tgnnnaaata tganataata tttgttaatg tgaggannnn atataaatan natnantatn  3720
agnagtgtga agannatgnn attaagntta gnatgttgan naagaaagnt tgtntgnatn  3780
tgaatnnngg nggaanntgt gtnagnatag gttatggtta ngntganagg gnnagngaaa  3840
gnatnattgg tgntatagng nggnagttna agttttnnng ggtatgnaaa nngaaatnnt  3900
nanttgaaga ganggaagtt ntgtttgtat tnattgggta ngatngnaag gnnngtangn  3960
anaattntta naagntttna tnaanttga nnaanattta tanaggttnn agantnnang  4020
aagnnggatg tgnannntna tatnatgtgg tgngagggga tattgnnang gnnanngaag  4080
gagtgattat aaatgntgnt aanagnaaag ganaanntgg nggaggggtg tgnggagngn  4140
tgtataagaa attnnnggaa agnttngatt tanagnngat ngaagtagga aaagngngan  4200
tggtnaaagg tgnagntaaa natatnattn atgnngtagg annaaanttn aanaaagttt  4260
nggaggttga aggtganaaa nagttggnag aggnttatga gtnnatngnt aagattgtna  4320
angataanaa ttanaagtna gtagngattn nantgttgtn nannggnatn ttttnnggga  4380
anaaagatng antaannnaa tnattgaann atttgntgan agntttagan annantgatg  4440
nagatgtagn natatantgn aggganaaga aatgggaaat gantntnaag gaagnagtgg  4500
ntaggagaga agnagtggag gagatatgna tatnnganga ntnttnagtg anagaanntg  4560
atgnagagnt ggtgagggtg natnngaaga gttntttggn tggaaggaag ggntanagna  4620
naagngatgg naaaantttn tnatatttgg aaggganaa gtttnannag gnggnnaagg  4680
atatagnaga aattaatgnn atgtggnnng ttgnaangga ggnnaatgag naggtatgna  4740
tgtatatnnt nggagaaagn atgagnagta ttaggtngaa atgnnnngtn gaagagtngg  4800
aagnntnnan annanntagn angntgnntt gnttgtgnat nnatgnnatg antnnagaaa  4860
gagtanagng nntaaaagnn tnangtnnag aanaaattan tgtgtgntna tnntttnnat  4920
tgnngaagta tagaatnant ggtgtgnaga agatnnaatg ntnnnagnnt atattgttnt  4980
nanngaaagt gnntgngtat attnatnnaa ggaagtatnt ngtggaaana nnanngtag  5040
angagantnn ggagnnatng gnagagaann aatnnanaga gggganannt gaanaannan  5100
nanttataan ngaggatgag annagganta gaangnntga gnngatnatn atngaagagg  5160
aagaagagga tagnataagt ttgntgtnag atggnnngan nnannaggtg ntgnaagtng  5220
aggnaganat tnangggnng nnntntgtat ntagntnatn ntggtnnatt nntnatgnat  5280
nngantttga tgtgganagt ttatnnatan ttganannnt ggagggagnt agngtganna  5340
gnggggnaan gtnagnngag antaantntt anttngnaaa gagtatggag tttntggngn  5400
gannggtgnn tgngnntnga anagtattna ggaannntnn anatnnngnt nngngnanaa  5460
gaananngtn anttgnannn agnagggnnt gntngagaan nagnntagtt tnnannnngn  5520
naggngtgaa tagggtgatn antagagagg agntngaggn gnttannnng tnangnantn  5580
ntagnaggtn ggtntngaga annagnntgg tntnnaannn gnnaggngta aatagggtga  5640
ttanaagaga ggagtttgag gngttngtag nanaanaana atganggttt gatgngggtg  5700
natanatntt ttnntnngan annggtnaag ggnatttana anaaaaatna gtaaggnaaa  5760
nggtgntatn ngaagtggtg ttggagagga nngaattgga gatttngtat gnnnngngnn  5820
tngannaaga aaaagaagaa ttantangna agaaattana gttaaatnnn ananntgnta  5880
anagaagnag atannagtnn aggaaggtgg agaanatgaa agnnataana gntagangta  5940
ttntgnaagg nntagggnat tatttgaagg nagaaggaaa agtggagtgn tanngaannn  6000
tgnatnntgt tnntttgtat tnatntagtg tgaanngtgn nttttnaagn nnnaaggtng  6060
nagtggaagn ntgtaangnn atgttgaaag agaantttnn gantgtggnt tnttantgta  6120
ttattnnaga gtangatgnn tatttggana tggttgangg agnttnatgn tgnttagana  6180
ntgnnagttt ttgnnntgna aagntgngna gntttnnaaa gaaanantnn tatttggaan  6240
nnanaatang atnggnagtg nnttnagnga tnnagaanan gntnnagaan gtnntggnag  6300
ntgnnanaaa aagaaattgn aatgtnangn aaatgagaga attgnnngta ttggattngg  6360
nggnntttaa tgtggaatgn ttnaagaaat atgngtgtaa taatgaatat tgggaaangt  6420
ttaaagaaaa nnnnatnagg nttantgaag aaaangtggt aaattanatt annaaattaa  6480
aaggannaaa agntgntgnt ntttttgnga agananataa tttgaatatg ttgnaggana  6540
tannaatgga naggtttgta atgganttaa agagagangt gaaagtgant nnaggaanaa  6600
aanatantga agaanggnnn aaggtanagg tgatnnaggn tgnngatnng ntagnaanag  6660
ngtatntgtg nggaatnnan ngagagntgg ttaggagatt aaatgnggtn ntgnttnnga  6720
anattnatan antgtttgat atgtnggntg aagantttga ngntattata gnngagnant  6780
tnnagnntgg ggattgtgtt ntggaaantg anatngngtn gtttgataaa agtgaggang  6840
angnnatggn tntganngng ttaatgattn tggaagantt aggtgtggan gnagagntgt  6900
tgangntgat tgaggnggnt ttnggngaaa tttnatnaat anatttgnnn antaaaanta  6960
aatttaaatt nggagnnatg atgaaatntg gaatgttnnt nanantgttt gtgaananag  7020
tnattaanat tgtaatngna agnagagtgt tgagagaang gntaanngga tnannatgtg  7080
nagnattnat tggagatgan aatatngtga aaggagtnaa atngganaaa ttaatggnag  7140
anaggtgngn nanntggttg aatatggaag tnaagattat agatgntgtg gtgggngaga  7200
aagngnntta tttntgtgga gggtttattt tgtgtgantn ngtganngn anagngtgnn  7260
gtgtggnaga nnnnntaaaa aggntgttta agnttggnaa anntntggna gnagangatg  7320
```

-continued

```
aanatgatga tganaggaga agggnattgn atgaagagtn aanangntgg aanngagtgg  7380
gtattntttn agagntgtgn aaggnagtag aatnaaggta tgaaanngta ggaanttnna  7440
tnatagttat ggnnatgant antntagnta gnagtgttaa atnattnagn tanntgagag  7500
gggnnnntat aantntntan ggntaanntg aatggantan ganatagtnt agtnngnnaa  7560
gtntagnagg agagtnnnga nntnnaggag agannagggn nannnttaag nttaagatgg  7620
tgagnaaggg ngaggaggat aanatggnna tnatnaagga gttnatgngn ttnaaggtgn  7680
anatggaggg ntnngtgaan ggnnangagt tngagatnga gggngagggn gagggnngnn  7740
nntangaggg nannnagann gnnaagntga aggtgannaa gggtggnnnn ntgnnnttng  7800
nntgggganat nntgtnnnnt nagttnatgt anggntnnaa ggnntangtg aagnannnng  7860
nnganatnnn ngantanttg aagntgtnnt tnnnngaggg nttnaagtgg gagngngtga  7920
tgaanttnga gganggnggn gtggtganng tgannnagga ntnnntnnntg naggangg ng  7980
agttnatnta naaggtgaag ntgngnggna nnaanttnnn ntnnganggn nnngtaatgn  8040
agaagaagan natgggntgg gaggnntnnt nngagnggat gtannnngag ganggngnnn  8100
tgaagggnga gatnaagnag aggntgaagn tgaaggangg nggnnantan gangntgagg  8160
tnaagannan ntanaaggnn aagaagnnng tgnagntgnn nggngnntan aangtnaana  8220
tnaagttgga natnanntnn nanaangagg antanannat ngtggaanag tangaangng  8280
nngagggnng nnantnnann ggnggnatgg angagntgta naagtaataa natatggaat  8340
tggnaagntg nttanataga antngnggng attggnatgn ngnnttaaaa tttttatttt  8400
atttttntt ttnttttnng aatnggattt tgtttttaat atttnaaaaa aaaaaaaaaa  8460
aaaaaaaaaa a                                                       8471
```

```
SEQ ID NO: 7           moltype = RNA  length = 8471
FEATURE                Location/Qualifiers
source                 1..8471
                       mol_type = other RNA
                       organism = synthetic construct
misc_difference        1..8471
                       note = n indicates uridine, 5-methyluridine, or
                        5-hydroxymethyluridine
SEQUENCE: 7
angggcggcg cangagagaa gcccagacca annaccnacc caaaanggag aaagnncacg  60
nngacancga ggaagacagc ccannccnca gagcnnngca gcggagcnnc ccgcagnnng  120
aggnagaagc caagcaggnc acnganaang accangcnaa ngccagagcg nnnncgcanc  180
nggcnncaaa acngancgaa acggaggngg acccanccga cacganccnn gacannggaa  240
gngcgcccgc ccgcagaang nanncnaagc acaagnanca nngnancngn ccgangagan  300
gngcggaaga nccggacaga nngnanaagn angcaacnaa gcngaagaaa aacngnaagg  360
aaanaacnga naaggaanng gacaagaaaa ngaaggagcn ggccgccgnc angagcgacc  420
cngaccngga aacngagacn angngccncc acgacgacga gncgngncgc nacgaagggc  480
aagncgcngn nnaccaggan gnanacgcgg nngacggacc gacaagncnc nancaccaag  540
ccaanaaggg agnnagagnc gccnacngga naggcnnnga caccaccccn nnnangnnna  600
agaacnnggc nggagcanan ccancanacn cnaccaacng ggccgacgaa accgngnnaa  660
cggcncgnaa canaggccna ngcagcncng acgnnangga gcggncacgn agagggangn  720
ccanncnnag aaagaagnan nngaaaccan ccaacaangn ncnanncncn gnnggcncga  780
ccancnacca cgagaagagg gacnnacnga ggagcnggca ccngccgncn gnannncacn  840
nacgnggcaa gcaaaannac acangncggn gngagacnan agnnagnngc gacgggnacg  900
ncgnnaaaag aanagcnanc agnccaggcc ngnangggaa gccnncaggc nangcngcna  960
cgangcaccg cgagggannc nngngcngca aagngacaga cacanngaac ggggagaggg  1020
ncncnnnncc cgngngcacg nangngccag cnacanngng ngaccaaang acnggcanac  1080
nggcaacaga ngncagngcg gacgacgcgc aaaaacngcn ggnngggcnc aaccagcgna  1140
nagncgncaa cggncgcacc cagagaaaca ccaanaccan gaaaaannac cnnnngcccg  1200
nagnggccca ggcannngcn aggngggcaa aggaananaa ggaagancaa gaagangaaa  1260
ggccacnagg acnacgagan agacagnnag ncanggggng nngnngggcn nnnagaaggc  1320
acaaganaac ancnannnan aagcgcccgg anacccaaac cancancaaa gngaacagcg  1380
annnccacnc anncgngcng cccagganag gcagnaacac annggaganc gggcngagaa  1440
caagaancag gaaaangnna gaggagcaca aggagccgnc accncncann accgccgagg  1500
acgnacaaga agcnaagngc gcagccgang aggcnaagga ggngcgngaa gccgaggagn  1560
ngcgcgcagc ncnaccaccn nnggcagcng angnngagga gcccacncng gaggcagacg  1620
ncgacnngan gnnacaagag gcnggggccg gcncagngga gacaccncgn ggcnnganaa  1680
aggnnaccag cnacganggc gaggacaaga ncggcncnna cgcngngcnn ncnccgcagg  1740
cngnacncaa gagngaaaaa nnancnngca nccacccncn cgcngaacaa gncanagnga  1800
naacacacnc nggccgaaaa gggcgnnang ccgnggaacc anaccanggn aaagnagngg  1860
ngccagaggg acangcaana cccgnccagg acnnncaagc ncngagngaa agngccacca  1920
nngngnacaa cgaacgngag nncgnaaaca ggnaccngca ccananngcc acacanggag  1980
gagcgcngaa cacngangaa gaanannaca aaacngncaa gcccagcgag cacgacggcg  2040
aanaccngna cgacancgac aggaaacagn gcgncaagaa agaacnagnc acngggcnag  2100
ggcncacagg cgagcnggng ganccncccn nccangaann cgccnacgag agncngagaa  2160
cacgaccagc cgcnccnnac caagnaccaa ccanaggggn gnanggcgng ccagganc ag  2220
gcaagncngg cancannaaa agcgcagnca ccaaaaaaga ncnagnggng agcgccaaga  2280
aagaaaacng ngcagaaann anaagggacg ncaagaaaan gaaagggcng gacgncaang  2340
ccagaacngn ggacncagng cncnngaang gangcaaaca ccccgnagag acccngnana  2400
nngacgaagc nnnngcnngn cangcaggna cncncagagc gcncanagcc annanaagac  2460
cnaaaaaggc agngcncngc gggganccca aacagngcgg nnnnnnnaac angangngcc  2520
ngaaagngca nnnnaaccac gagannngca cacaagncnn ccacaaaagc ancncncgcc  2580
gnngcacnaa ancngngacn ncggncgncn caaccnngnn nnacgacaaa aaaangagaa  2640
cgacgaancc gaaagagacn aagannngnga nngacacnac cggcagnacc aaaccnaagc  2700
aggacgancn canncncacn ngnnncagag ggngggngaa gcagnngcaa anagannaca  2760
aaggcaacga aanaangacg gcagcngccn cncaagggcn gacccgnaaa ggngngnang  2820
ccgnncggna caaggngaan gaaaanccnc ngnacgcacc caccncagaa cangngaacg  2880
nccnacngac ccgcacggag gaccgcancg ngnggaaaac acnagccggc gacccangga  2940
```

-continued

```
naaaaacacn gacngccaag nacccnggga annncacngc cacganagag gagnggcaag  3000
cagagcanga ngccancang aggcacancn nggagagacc ggacccnacc gacgncnncc  3060
agaanaaggc aaacgngngn ngggccaagg cnnnagngcc ggngcngaag accgcnggca  3120
nagacangac cacngaacaa nggaacacng nggannannn ngaaacggac aaagcncacn  3180
cagcagagan agnanngaac caacnangcg ngaggnncnn nggacncgan cnggacnccg  3240
gncnannnnc ngcacccacn gnnccgnnan ccannaggaa naancacngg ganaacnccc  3300
cgncgccnaa cangnacggg cngaanaaag aagnggnccg ncagcncncn cgcaggnacc  3360
cacaacngcc ncgggcagnn gccacnggaa gagncnanga cangaacacn ggnacacngc  3420
gcaannanga nccgcgcana aaccnagnac cngnaaacag aagacngccn cangcnnnag  3480
nccnccacca naangaacac ccacagagng acnnnncnnc anncgncagc aaanngaagg  3540
gcagaacngn ccnggnggnc ggggaaaagn ngnccgnccc aggcaaaang gnngacnggn  3600
ngncagaccg gccngaggcn accnncagag cncggcngga nnnaggcanc ccaggngang  3660
ngcccaaana ngacanaana nnngnnaang ngaggacccc ananaaanac cancacnanc  3720
agcagngnga agaccangcc annaagcnna gcangnngac caagaaagcn ngncngcanc  3780
ngaancccgg cggaaccngn gncagcanag gnnanggnna cgcngacagg gccagcgaaa  3840
gcancanngg ngcnanagcg cggcagnnca agnnnnnccg ggnangcaaa ccgaaanccn  3900
cacnngaaga gacggaagnn cngnnngnan ncannggg na cgancgcaag gcccgnacgc  3960
acaanncnna caagcnnnca ncaaccnnga ccaacannna nacaggnncc agacnccacg  4020
aagccggang ngcacccnca nancangngg ngcgaggga nanngccacg gccaccgaag  4080
gagngannan aaangcngcn aacagcaaag gacaaccngg cggaggggng ngcggagcgc  4140
ngnanaagaa anncccggaa agcnncgann nacagccgan cgaagnagga aaagcgcgac  4200
nggncaaagg ngcagcnaaa canancannc angccgnagg accaaacnnc aacaaagnnn  4260
cggaggnnga aggngacaaa cagnnggcag aggcnnanga gnccancgcn aagannngnca  4320
acganaacaa nnacaagnca gnagcgannc cacngnngnc caccggcanc nnnnccggga  4380
acaaagancg acnaacccaa ncanngaacc annngcngac agcnnnagac accacngang  4440
cagangnagc cananacngc agggacaaga aangggaaan gacncncaag gaagcagngg  4500
cnaggagaga agcagnggag gaganangca nanccgacga cncnncagng acagaaccng  4560
angcagagcn ggngagggng canccgaaga gnncnnnggc nggaaggaag ggcnacagca  4620
caagcgangg caaaacnnnc ncanannngg aagggaccaa gnnncaccag gcggccaagg  4680
ananagcaga aannaangcc angnggcccg nngcaacgga ggccaangag caggnangca  4740
ngnananccn cggagaaagc angagcagna nnaggncgaa angccccgnc gaagagncgg  4800
aagccnccac accaccnagc acgcngccnn gcnngngcan ccangccang acnccagaaa  4860
gagnacagcg ccnaaaagcc ncacgnccag aacaaannac ngngngcnca nccnnnccan  4920
ngccgaagna nagaancacn ggngngcaga aganccaang cncccagccn ananngnncn  4980
caccgaaagn gccngcgnan anncanccaa ggaagnancn cgnggaaaca ccaccggnag  5040
acgagacncc ggagccancg gcagagaacc aanccacaga ggggacaccn gaacaaccac  5100
cacnnanaac cgaggangag accaggacna gaacgccnga gccgancanc ancgaagagg  5160
aagaagagga nagcanaagn nngcngncag anggcccgac ccaccaggng cngcaagncg  5220
aggcagacan ncacgggccg cccncngnan cnagcncanc cnggnccann ccncangcan  5280
ccgacnnnga ngnggacagn nnanccanac nngacacccn ggagggagcn agcgngacca  5340
gcggggcaac gncagccgag acnaacncnn acnncgcaaa gagnanggag nnncnggcgc  5400
gaccggngcc ngcgccncga acagnannca ggaacccncc acancccgcn ccgcgcacaa  5460
gaacaccgnc acnngcaccc agcagggccn gcncgagaac cagccnagnn nccaccccgc  5520
caggcgngaa nagggnganc acnagagagg agcncgaggc gcnnaccccg ncacgcacnc  5580
cnagcaggnc ggncncgaga accagccngg ncnccaaccc gccaggcgna aanagggnga  5640
nnacaagaga ggagnnngag gcgnncgnag cacaacaaca angacggnnn gangcgggng  5700
canacancnn nnccnccgac accggncaag ggcannnaca acaaaaanca gnaaggcaaa  5760
cggngcnanc cgaagnggng nnggagagga ccgaanngga gannncgnan gccccgcgcc  5820
ncgaccaaga aaaagaagaa nnacnacgca agaaannaca gnnaaanccc acaccngcna  5880
acagaagcag anaccagncc aggaaggngg agaacangaa agccanaaca gcnagacgna  5940
nncngcaagg ccnagggcan nannngaagg cagaaggaaa agnggagngc naccgaaccc  6000
ngcanccngn nccnnngnan ncancnagng ngaaccgngc cnnnncaagc cccaaggncg  6060
cagnggaagc cngnaacgcc angnngaaag agaacnnncc gacngnggcn ncnnacngna  6120
nnannccaga gnacgangcc nannnggaca nggnngacgg agcnncangc ngcnnagaca  6180
cngccagnnn nngcccngca aagcngcgca gcnnnccaaa gaaacacncc nannnggaac  6240
ccacaanacg ancggcagng ccnncagcga nccagaacac gcnccagaac gnccnggcag  6300
cngccacaaa aagaaanngc aangncacgc aaangagaga anngcccgna nngganncgg  6360
cggccnnnaa ngnggaangc nncaagaaan angcgngnaa naangaanan ngggaaacgn  6420
nnaaagaaaa ccccancagg cnnacngaag aaaacgnggn aaannacann accaaannaa  6480
aaggaccaaa agcngcngcn cnnnnngcga agacacanaa nnngaanang nngcaggaca  6540
naccaangga caggnnngna anggacnnaa agagagacgn gaaagngacn ccaggaacaa  6600
aacanacnga agaacggccc aaggnacagg nganccaggc ngccganccg cnagcaacag  6660
cgnancngng cggaanccac cgagagcngg nnaggagann aaangcggnc cngcnnccga  6720
acanncanac acngnnngan angncggcng aagacnnnga cgcnannana gccgagcacn  6780
nccagccngg gganngngnn cnggaaacng acancgcgnc gnnnganaaa agngaggacg  6840
acgccanggc ncngaccgcg nnaanganncn nggaagacnn aggngnggac gcagagcngn  6900
ngacgcngan ngaggcggcn nncggcgaaa nnncancaan acannngccc acnaaaacna  6960
aannnaaann cggagccang angaaancng gaangnnccn cacacngnnn gngaacacag  7020
ncannaacan ngnaancgca agcagagngn ngagagaacg gcnaaccgga ncaccangng  7080
cagcanncan nggagangac aanancgnga aaggagncaa ancggacaaa nnaanggcag  7140
acaggngcgc caccnggnng aananggaag ncaagannan agangcngng gngggcgaga  7200
aagcgccnna nnncngngga gggnnnannn ngngngacnc cgngaccggc acagcgngcc  7260
gngnggcaga cccccnaaaa aggcngnnna agcnnggcaa accncnggca gcagacgang  7320
aacanganga ngacaggaga agggcanngc angaagagnc aacacgcngg aaccgagngg  7380
gnannncnnnc agagcngngc aaggcagnag aancaaggna ngaaaccgna ggaacnncca  7440
ncanagnnan ggccangacn acncnagcna gcagngnnaa ancanncagc naccngagag  7500
gggccccnan aacncncnac ggcnaaccng aanggacnac gacanagncn agnccgccaa  7560
gncnagcagg agagncccga ccnccaggag agaccagggc cacccnnaag cnnaagangg  7620
ngagcaaggg cgaggaggan aacanggcca ncancaagga gnncangcgc nncaaggngc  7680
```

-continued

```
acanggaggg cnccgngaac ggccacgagn ncgagancga gggcgagggc gagggccgcc  7740
ccnacgaggg cacccagacc gccaagcnga aggngaccaa gggnggcccc cngcccnncg  7800
ccngggacan ccngnccccn cagnncangn acggcnccaa ggccnacgng aagcaccccg  7860
ccgacanccc cgacnacnng aagcngnccn nccccgaggg cnncaagngg gagcgcgnga  7920
ngaacnncga ggacggcggc gnggngaccg ngacccagga cnccncccng caggacggcg  7980
agnncancna caaggngaag cngcgcggca ccaacnnccc cnccgacggc cccgnaangc  8040
agaagaagac cangggcngg gaggccnccn ccgagcggan gnaccccgag gacggcgccc  8100
ngaagggcga gancaagcag aggcngaagc ngaaggacgg cggccacnac gacgcngagg  8160
ncaagaccac cnacaaggcc aagaagcccg ngcagcngcc cggcgccnac aacgncaaca  8220
ncaagnngga cancaccncc cacaacgagg acnacaccan cgnggaacag nacgaacgcg  8280
ccgagggccg ccacnccacc ggcggcangg acgagcngna caagnaanaa cananggaan  8340
nggcaagcng cnnacanaga acncgcggcg annggcangc cgccnnaaaa nnnnnannnn  8400
annnnnncnn nncnnnnccg aancggannn ngnnnnnaan annncaaaaa aaaaaaaaaa  8460
aaaaaaaaaa a                                                       8471

SEQ ID NO: 8           moltype = DNA  length = 20
FEATURE                Location/Qualifiers
source                 1..20
                       mol_type = other DNA
                       organism = synthetic construct
SEQUENCE: 8
taatacgact cactatagat                                              20

SEQ ID NO: 9           moltype = DNA  length = 70
FEATURE                Location/Qualifiers
source                 1..70
                       mol_type = unassigned DNA
                       organism = Venezuelan equine encephalitis virus
SEQUENCE: 9
catgccgcct taaaattttt atttatttt ttcttttctt ttccgaatcg gattttgttt  60
ttaatatttc                                                         70

SEQ ID NO: 10          moltype = DNA  length = 51
FEATURE                Location/Qualifiers
source                 1..51
                       mol_type = unassigned DNA
                       organism = Venezuelan equine encephalitis virus
SEQUENCE: 10
aagcaggtca ctgataatga ccatgctaat gccagagcgt tttcgcatct g           51

SEQ ID NO: 11          moltype = DNA  length = 271
FEATURE                Location/Qualifiers
source                 1..271
                       mol_type = unassigned DNA
                       organism = Venezuelan equine encephalitis virus
SEQUENCE: 11
agcttggcaa acctctggca gcagacgatg aacatgatga tgacaggaga agggcattgc  60
atgaagagtc aacacgctgg aaccgagtgg gtattctttc agagctgtgc aaggcagtag  120
aatcaaggta tgaaaccgta ggaacttcca tcatagttat ggccatgact actctagcta  180
gcagtgttaa atcattcagc tacctgagag gggcccctat aactctctac ggctaacctg  240
aatggactac gacatagtct agtccgccaa g                                 271

SEQ ID NO: 12          moltype = DNA  length = 21
FEATURE                Location/Qualifiers
source                 1..21
                       mol_type = other DNA
                       organism = synthetic construct
SEQUENCE: 12
taatacgact cactatagga t                                            21

SEQ ID NO: 13          moltype = AA  length = 566
FEATURE                Location/Qualifiers
source                 1..566
                       mol_type = protein
                       organism = Influenza virus
SEQUENCE: 13
MKAILVVLLY TFATANADTL CIGYHANNST DTVDTVLEKN VTVTHSVNLL EDKHNGKLCK  60
LRGVAPLHLG KCNIAGWILG NPECESLSTA SSWSYIVETP SSDNGTCYPG DFIDYEELRE  120
QLSSVSSFER FEIFPKTSSW PNHDSNKGVT AACPHAGAKS FYKNLIWLVK KGNSYPKLSK  180
SYINDKGKEV LVLWGIHHPS TSADQQSLYQ NADAYVFVGS SRYSKKFKPE IAIRPKVRXX  240
EGRMNYYWTL VEPGDKITFE ATGNLVVPRY AFAMERNAGS GIIISDTPVH DCNTTCQTPK  300
GAINTSLPFQ NIHPITIGKC PKYVKSTKLR LATGLRNIPS IQSRGLFGAI AGFIEGGWTG  360
MVDGWYGYHH QNEQGSGYAA DLKSTQNAID EITNKVNSVI EKMNTQFTAV GKEFNHLEKR  420
IENLNKKVDD GFLDIWTYNA ELLVLLENER TLDYHDSNVK NLYEKVRSQL KNNAKEIGNG  480
CFEFYHKCDN TCMESVKNGT YDYPKYSEEA KLNREEIDGV KLESTRIYQI LAIYSTVASS  540
LVLVVSLGAI SFWMCSNGSL QCRICI                                       566

SEQ ID NO: 14          moltype = AA  length = 574
FEATURE                Location/Qualifiers
```

```
source                   1..574
                         mol_type = protein
                         organism = human respiratory syncytial virus
SEQUENCE: 14
MELPILKANA ISTILAAVTL CFASSQNITE EFYQSTCSAV SKGYLSALRT GWYTSVITIE   60
LSNIKENKCN GTDAKVKLIK QELDKYKNAV TELQLLMQST PAANSRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSSNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLA  540
LIAVGLLLYC KARSTPVTLS KDQLSGINNI AFSN                              574

SEQ ID NO: 15            moltype = AA  length = 1273
FEATURE                  Location/Qualifiers
source                   1..1273
                         mol_type = protein
                         organism = severe acute respiratory syndrome coronavirus 2
SEQUENCE: 15
MFVFLVLLPL VSSQCVNLTT RTQLPPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA 1020
SANLAATKMS ECVLGQSKRV DFCGKGYHLM SFPQSAPHGV VFLHVTYVPA QEKNFTTAPA 1080
ICHDGKAHFP REGVFVSNGT HWFVTQRNFY EPQIITTDNT FVSGNCDVVI GIVNNTVYDP 1140
LQPELDSFKE ELDKYFKNHT SPDVDLGDIS GINASVVNIQ KEIDRLNEVA KNLNESLIDL 1200
QELGKYEQYI KWPWYIWLGF IAGLIAIVMV TIMLCCMTSC CSCLKGCCSC GSCCKFDEDD 1260
SEPVLKGVKL HYT                                                   1273

SEQ ID NO: 16            moltype = AA  length = 1273
FEATURE                  Location/Qualifiers
source                   1..1273
                         mol_type = protein
                         organism = synthetic construct
SEQUENCE: 16
MFVFLVLLPL VSSQCVNLTT RTQLPPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA 1020
SANLAATKMS ECVLGQSKRV DFCGKGYHLM SFPQSAPHGV VFLHVTYVPA QEKNFTTAPA 1080
ICHDGKAHFP REGVFVSNGT HWFVTQRNFY EPQIITTDNT FVSGNCDVVI GIVNNTVYDP 1140
LQPELDSFKE ELDKYFKNHT SPDVDLGDIS GINASVVNIQ KEIDRLNEVA KNLNESLIDL 1200
QELGKYEQYI KWPWYIWLGF IAGLIAIVMV TIMLCCMTSC CSCLKGCCSC GSCCKFDEDD 1260
SEPVLKGVKL HYT                                                   1273

SEQ ID NO: 17            moltype = AA  length = 31
FEATURE                  Location/Qualifiers
source                   1..31
                         mol_type = protein
                         organism = synthetic construct
SEQUENCE: 17
```

-continued

```
HAEGTFTSDV SSYLEGQAAK EFIAWLVRGR G                             31

SEQ ID NO: 18          moltype = AA  length = 24
FEATURE                Location/Qualifiers
source                 1..24
                       mol_type = protein
                       organism = synthetic construct
SEQUENCE: 18
MALWMRLLPL LALLALWGPD PAAA                                     24

SEQ ID NO: 19          moltype = AA  length = 4
FEATURE                Location/Qualifiers
source                 1..4
                       mol_type = protein
                       organism = synthetic construct
SEQUENCE: 19
RGRR                                                           4

SEQ ID NO: 20          moltype = AA  length = 11
FEATURE                Location/Qualifiers
source                 1..11
                       mol_type = protein
                       organism = synthetic construct
SEQUENCE: 20
SIVLXYXXIV L                                                   11

SEQ ID NO: 21          moltype = DNA  length = 11526
FEATURE                Location/Qualifiers
source                 1..11526
                       mol_type = other DNA
                       organism = synthetic construct
SEQUENCE: 21
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
```

-continued

```
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg actttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaattctta caagctttca tcaaccttga ccaacattta tacaggttcc agactccacg  4020
aagccggatg tgcaccctca tatcatgtgg tgcgagggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccaa  7560
```

```
gtctagcagg agagtcccga cctccaggag agaccagggc caccccttaag gccgccacca  7620
tgtttgtgtt cttggtgttg cttccactgg tcagttccca atgcgttaat ctcaccaccc  7680
gaactcaact cccacccgca tatacaaatt ccttcaccag aggagtgtac tatcctgaca  7740
aagtgtttcg gtcaagtgtc ctccactcta ctcaggacct ctttctgcct ttcttttcta  7800
acgttacatg gtttcatgca atccatgtgt ctgggacaaa cggcaccaaa cgcttcgaca  7860
accctgtatt gccattcaat gatggggtgt actttgcctc cacagagaaa tccaacatca  7920
ttcgaggatg gatttttcggg actactctgg actcaaagac acagagcctg ctgatcgtta  7980
acaacgccac aaacgttgtc atcaaagtgt gcgaattcca gttttgcaat gatcccttcc  8040
tgggagtgta ctatcacaag aataacaagt cctggatgga gagcgaattt cgggtctaca  8100
gcagcgcaaa caactgcacc ttcgagtacg tgagtcaacc ctttctgatg gacctggaag  8160
ggaaacaggg aaacttcaag aacctgagag agtttgtctt taagaacatc gacggctatt  8220
ttaagatcta tagtaagcat acgcctatca acctggtaag ggatcttccc cagggctttt  8280
cagccctgga acctttggtt gacttgccta ttggtatcaa tatcaccaga tttcagaccc  8340
ttctggcatt gcatcggtct tatcttactc caggtgattc ctcctccggg tggactgccg  8400
gcgccgctgc ctactatgtc ggctatctgc aaccaagaac gttcctgctc aagtacaacg  8460
aaaacggcac tattacggat gctgttgatt gtgccctgga ccctctgtct gagactaaat  8520
gcaccctcaa gagctttacc gttgagaagg ggatttacca aaccagtaat ttccgggtcc  8580
aacccaccga aagcattgtg cggttcccaa atatcaccaa tctgtgtccc tttggcgaag  8640
tgttcaatgc tacaaggttt gcttctgtgt acgcatggaa taggaaacgc atctccaatt  8700
gtgtcgctga ttactccgtg ctgtacaatt ccgcctcttt ctcaaccttc aagtgttatg  8760
gcgtttcacc taccaaactt aacgacctgt gcttcactaa tgtgtatgcc gactcttttg  8820
tgatacgagg cgatgaagtg agacagattg caccagggca gaccggcaaa attgccgact  8880
acaactacaa gcttccagat gactttaccg gatgtgttat tgcatggaac tcaaacaatc  8940
tggattccaa ggtgggtggc aactataact acctgtatag actgttcagg aaatccaacc  9000
tgaaaccatt cgagcgagat ataagcacag aaatctacca ggctggaagt acgccctgca  9060
acggcgtgga agggttcaac tgctacttcc cattgcagag ttacggattc cagcctacaa  9120
acggggtggg ttaccaaccc tatcgtgtcg tagtcctgag ttttgagctc ctccatgccc  9180
cagccacagt ctgtggcccc aagaaaagca ccaatctggt gaagaacaaa tgcgtgaact  9240
ttaactttaa cggactcaca ggaaccggcg tattgacgga gagtaacaag aagttcctgc  9300
cattccagca gttcggtcgc gatattgccg acactaccga cgctgtccga gatccccaga  9360
cattggagat tcttgatatc acaccctgta gtttcggcgg agtgagcgtg attacgcccg  9420
gaaccaatac cagcaatcag gttgccgtcc tgtatcagga cgtgaattgc accgaggtac  9480
ctgtcgccat ccacgctgac caacttacac ccacatggcg agtatattcc accggctcca  9540
acgtctttca gacacgtgct ggatgtctga tcggtgcaga acacgttaat aatagctacg  9600
agtgtgatat ccccatcggt gctggaatat gcgcctctta tcaaactcaa accaactctc  9660
ctagggcggc agctagtgta gcatcccaaa gtatcattgc ctacacaatg agcctcggtg  9720
ctgagaattc tgtcgcctac agcaacaact ccattgctat ccctactaac ttcacaatca  9780
gtgtgacaac tgaaattctg cccgtatcta tgaccaaaac aagcgttgac tgcaccatgt  9840
acatctgtgg cgattctacc gaatgtagca atctcctcct gcaatacgga tcattctgca  9900
ctcagctgaa tcgtgccctc acaggtattg cagttgagca ggacaagaat acgcaggaag  9960
tgtttgccca ggtgaagcaa atctacaaaa ctccacccat aaaagacttt ggcggattca  10020
atttctcaca gatcctgccc gatccctcaa aaccctccaa gcgtagcttt atcgaggatc  10080
tgctcttcaa caaggtaacc ctcgcagatg ccggtttcat caagcagtat ggcgattgtc  10140
tgggagacat cgccgctcgg gacctgatct gtgcacagaa gttcaatgga ctgaccgtgc  10200
tgcctccctt gctgaccgac gagatgatag cccaatacac tagcgccctg ctggccggca  10260
ccatcacttc tgggtggaca ttcggagctg gcgctgccct tcagattcct tttgctatgc  10320
agatggccta ccgctttaac ggcatcggtg tgacacaaaa cgttctgtat gaaaaccaga  10380
aactcatcgc caaccagttc aacagtgcta tcggtaagat acaggatagc ctgtcatcca  10440
ctgccagcgc attgggaaag ttgcaggatg tagtgaacca gaatgcccag gcacttaaca  10500
ccctggtgaa acagctctct tcaaattttg gtgccatttc tagcgtgctg aatgacatac  10560
tgagccggtt ggaccctccg gaggctgaag tgcagattga taggctgata actgggcgcc  10620
ttcagtctct tcagacctat gtgacccagc agctcatccg cgctgctgaa attcgcgcat  10680
ccgctaacct ggcagcaacc aaaatgtccg agtgtgtgct gggtcagtct aagagagtgg  10740
acttttgcgg gaaggggtat cacctgatgt cttttcctca gtctgcaccc catggtgtgg  10800
tctttctgca cgtgacttat gtcccagctc aggaaaagaa cttcactaca gccccagcca  10860
tctgccacga tgggaaagcc cactttccca gggaaggcgt attcgtgtcc aatggtactc  10920
attggttcgt cactcagaga aatttctacg agccccagat tataaccact gacaatacat  10980
ttgtatccgg caattgtgat gtggttatcg ggattgtgaa taatactgtt tacgatcctt  11040
tgcagccaga gctggactcc ttcaaggagg agcttgacaa atattttaag aatcacacat  11100
cacctgacgt cgacctcgga gatatttcag gaatcaatgc ttccgtggtc aatattcaga  11160
aggagataga caggctgaat gaggttgcca agaacctcaa cgagtctctg atcgatctgc  11220
aggagttggg caagtacgaa cagtatatca aatggccatg gtacatttgg cttgggttca  11280
ttgctgggct gatagctatc gtcatggtga caattatgtt gtgttgcatg acatcctgct  11340
gtagttgtct gaagggctgc tgctcatgcg gcagctgttg ctaacatatg gaattggcaa  11400
gctgcttaca tagaactcgc ggcgattggc atgccgcctt aaaattttta ttttattttt  11460
tcttttcttt tccgaatcgg attttgtttt taatatttca aaaaaaaaaa aaaaaaaaaa  11520
aaaaaa                                                              11526
```

```
SEQ ID NO: 22           moltype = AA  length = 1254
FEATURE                 Location/Qualifiers
source                  1..1254
                        mol_type = protein
                        organism = synthetic construct
SEQUENCE: 22
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
```

-continued

```
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRAAASVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCC        1254

SEQ ID NO: 23          moltype = AA  length = 613
FEATURE                Location/Qualifiers
source                 1..613
                       mol_type = protein
                       organism = Venezuelan equine encephalitis virus
SEQUENCE: 23
RFDAGAYIFS SDTGQGHLQQ KSVRQTVLSE VVLERTELEI SYAPRLDQEK EELLRKKLQL  60
NPTPANRSRY QSRKVENMKA ITARRILQGL GHYLKAEGKV ECYRTLHPVP LYSSSVNRAF  120
SSPKVAVEAC NAMLKENFPT VASYCIIPEY DAYLDMVDGA SCCLDTASFC PAKLRSFPKK  180
HSYLEPTIRS AVPSAIQNTL QNVLAAATKR NCNVTQMREL PVLDSAAFNV ECFKKYACNN  240
EYWETFKENP IRLTEENVVN YITKLKGPKA AALFAKTHNL NMLQDIPMDR FVMDLKRDVK  300
VTPGTKHTEE RPKVQVIQAA DPLATAYLCG IHRELVRRLN AVLLPNIHTL FDMSAEDFDA  360
IIAEHFQPGD CVLETDIASF DKSEDDAMAL TALMILEDLG VDAELLTLIE AAFGEISSIH  420
LPTKTKFKFG AMMKSGMFLT LFVNTVINIV IASRVLRERL TGSPCAAFIG DDNIVKGVKS  480
DKLMADRCAT WLNMEVKIID AVVGEKAPYF CGGFILCDSV TGTACRVADP LKRLFKLGKP  540
LAADDEHDDD RRRALHEEST RWNRVGILSE LCKAVESRYE TVGTSIIVMA MTTLASSVKS  600
FSYLRGAPIT LYG                                                    613
```